(12) United States Patent
Desbordes et al.

(10) Patent No.: US 11,219,214 B2
(45) Date of Patent: Jan. 11, 2022

(54) BENZOSULTAMS AND ANALOGUES AND THEIR USE AS FUNGICIDES

(71) Applicant: Bayer CropScience Aktiengesellschaft, Monheim am Rhein (DE)

(72) Inventors: Philippe Desbordes, Lyons (FR); Christophe Dubost, Charbonnieres les bains (FR); Jeremy Dufour, Lyons (FR); Mathieu Gourgues, Lyons (FR); Philipp Holstein, Lyons (FR); Virginie Lempereur, Lyons (FR); Frederic Miege, Lyons (FR); Philippe Rinolfi, Chatillon D Azergues (FR); Vincent Rodeschini, Mions (FR); Valerie Toquin, Saint-Romain-au-Mont-d'Or (FR); Francois Villalba, Albigny-sur-Saone (FR); Ulrike Wachendorff-Neumann, Neuwied (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 16/913,862

(22) Filed: Jun. 26, 2020

(65) Prior Publication Data
US 2020/0323211 A1  Oct. 15, 2020

Related U.S. Application Data

(62) Division of application No. 16/314,641, filed as application No. PCT/EP2017/066510 on Jul. 3, 2017, now Pat. No. 10,736,321.

(30) Foreign Application Priority Data

Jul. 4, 2016 (EP) .................... 16290128
Dec. 22, 2016 (EP) .................... 16290247

(51) Int. Cl.
| | | |
|---|---|---|
| A01N 43/42 | (2006.01) | |
| A01N 43/60 | (2006.01) | |
| C07D 215/18 | (2006.01) | |
| C07D 241/44 | (2006.01) | |
| A01N 43/84 | (2006.01) | |
| A01N 43/72 | (2006.01) | |
| C07D 281/06 | (2006.01) | |
| C07D 417/10 | (2006.01) | |

(52) U.S. Cl.
CPC ............ *A01N 43/84* (2013.01); *A01N 43/72* (2013.01); *C07D 281/06* (2013.01); *C07D 417/10* (2013.01)

(58) Field of Classification Search
CPC ...... A01N 43/42; A01N 43/60; C07D 215/18; C07D 241/44
See application file for complete search history.

(56) References Cited

U.S. PATENT DOCUMENTS

| | | |
|---|---|---|
| 3,303,190 A | 2/1967 | Loev |
| 3,303,191 A | 2/1967 | Loev |
| 2010/0331306 A1 | 12/2010 | Bui et al. |

FOREIGN PATENT DOCUMENTS

| | | |
|---|---|---|
| EP | 1334999 A2 | 8/2003 |
| EP | 2711361 A1 | 3/2014 |
| JP | H09288338 A | 11/1997 |
| JP | 2007001944 A | 1/2007 |
| JP | 2008088139 A | 4/2008 |
| JP | 2014221747 A | 11/2014 |
| JP | 2017001998 A | 1/2017 |
| WO | 9205164 A1 | 4/1992 |
| WO | 9834929 A1 | 8/1998 |
| WO | 9911253 A1 | 3/1999 |
| WO | 9911264 A1 | 3/1999 |
| WO | 9066163 A1 | 11/2000 |
| WO | 0172725 A1 | 10/2001 |
| WO | 0187881 A1 | 11/2001 |
| WO | 2004014388 A1 | 2/2004 |
| WO | 2008073956 A2 | 6/2008 |
| WO | 2010065717 A1 | 6/2010 |
| WO | 2012085852 A1 | 6/2012 |
| WO | 2013012681 A1 | 1/2013 |
| WO | 2013034758 A1 | 3/2013 |
| WO | 2013170186 A1 | 11/2013 |

OTHER PUBLICATIONS

PCT International Search Report for PCT/EP2017/066510, dated Sep. 12, 2017.
Moutrille C. et al: "A new approach for the ortho-substitution of anilines and for the synthesis of indolines", Tetrahedron Letters, vol. 45, No. 24, (Jul. 6, 2004), pp. 4631-4634, XP027330684.
Porter N. A. et al: "Penultimate Group Effects in Free Radical Telomerizations of Acrylamides", TETRAHEDRON, vol. 52, No. 12, (Mar. 18, 1996), pp. 4181-4198, XP004104219.
Wojciechowski K: "[1,5] hydrogen shift in aza-ortho-xylylenes generated from 3-alkyl-2,1-benzisothiazoline2,2-dioxides", TETRAHEDRON, vol. 49, No. 44, 1993, pp. 10017-10026, XP055318874.
Wojciechowski K: "New Synthesis of 2-Phenylindene Derivatives", Synthetic Communications, vol. 23, No. 17, (Sep. 1993), pp. 2415-2422, XP055319002.
Martinez C. et al: "Towards Uniform Iodine Catalysis: Intramolecular C—H Amination of Arenes under Visible Light", Chemistry—A European Journal, vol. 22, No. 29, (Jun. 15, 2016), pp. 9929-9932, XP055319091.
Grosheva D. S. et al.: "A Route to Benzo-Annelated delta-Sultams through Michael Cyclization", European Journal of Organic Chemistry, vol. 2015, No. 6, (Feb. 15, 2015), pp. 1355-1363, XP055319097.

(Continued)

*Primary Examiner* — Brenda L Coleman
(74) *Attorney, Agent, or Firm* — McBee Moore & Vanik IP, LLC

(57) ABSTRACT

The present disclosure relates to fungicidal active compounds, more specifically to benzosultams and analogues thereof, processes and, intermediates for their preparation and use thereof as fungicidal active compound, particularly in the form of fungicide compositions. The present disclosure also relates to methods for the control of phytopathogenic fungi of plants using these compounds or compositions comprising thereof.

1 Claim, No Drawings

(56) References Cited

OTHER PUBLICATIONS

Jeon MK et al: "A solid-phase synthetic method for 3,4-dihydro-IH-2,I-benzothiazin-4-one 2,2-dioxide derivatives", TETRAHEDRON, vol. 64, No. 38, (Sep. 15, 2008), pp. 9060-9072, XP023902249.
Musser J. H. et al: "N-(arylmethoxyphenyl)-sulfonamides", Journal of Medicinal Chemistry, vol. 32, No. 6, (Jun. 1989), pp. 1176-1183, XP002300915.
Grombein C M et al.: "Heteroatom insertion into 3,4-dihydro-IH-quinolin-2-ones leads to potent and selective inhibitors of human and rat aldosterone synthase", European Journal of Medicinal Chemistry, vol. 90, (Jan. 27, 2015), pp. 788-796, XP055319106.
Shafiq M. et al.: "Synthesis and Antifungal Activity of Halogen-Substituted 2,I-Benzothiazine-2,2-dioxide Derivatives", Asian Journal of Chemistry, vol. 23, No. 5, (2011), pp. 2101-2105, XP055319125.
Abramovitch R A et al: "The decomposition of beta-phenethylsulfonyl azides. Solution chemistry and flash vacuum pyrolysis", Journal of the American Chemical Society, vol. 103, No. 6, (Mar. 1981), pp. 1525-1533, XP055319276.
Database Chemcats [Online] Chemical Abstracts; (May 26, 2016), "6-fluoro-3,4-dihydro-1H-2lambda6,I-benzot hiazine-2,2,4-trione", XP002764452.
Database Chemcats [Online] Chemical Abstracts; Apr. 7, 2016 (Apr. 7, 2016), "K08.703.865", XP002764453,.
Abramovitch R A et al: "Solution and flash vacuum pyrolyses of 3-arylpropanesulfonyl and 2-(aryloxy) ethanesulfonyl azides. Synthesis of 7- and 8-membered sultams", The Journal of Organic Chemistry, vol. 49, No. 17, (Aug. 1984), pp. 3114-3121, XP055319449.
Database Chemcats [Online] 2016,11 A30.311.01511, XP002764454, Database accession No. 0476104585 abstract.
Ukrainets IV et al: "2,1-Benzothiazine 2,2-dioxides 10*. Reaction of alkyl 1-R-4-hydroxy-2,2-dioxo-1N-2[lambda]6,I-be nzothiazine-3-carboxylates withIH-1,2,4-triazol-5-amine", Chemistry of Heterocyclic Compounds, vol. 51, nN. 1 (Jan. 2015), pp. 97-101, XP055400748.
Buckingham F et al: "Oxidative fluorination of N-arylsulfonamides", Journal of Fluorine Chemistry, vol. 180, (Dec. 2015), pp. 33-39, XP029304147.
Volovenko Y et al: "N-a I kyl-4-chl oro-IH-benzo [c] [1,2] thi azi ne-3-carbaldehyde-2,2-dioxides—New functional benzothiazine derivatives", Journal of Heterocyclic Chemistry, vol. 44, No. 6 (Nov. 2007), pp. 1413-1419 XP055401437.
Blondet D et al: "A convenient synthesis of 3,4-dihydro-2,2-dioxide 5-hydroxy-2,I-benzothiazine", Tetrahedron Letters, vol. 35, No. 18, (May 2, 1994), pp. 2911-2912, XP055401438.

BENZOSULTAMS AND ANALOGUES AND THEIR USE AS FUNGICIDES

CROSS-REFERENCE TO RELATED APPLICATIONS

This application is a division of U.S. application Ser. No. 16/314,641, filed Dec. 31, 2018, which is a National Stage entry of International Application No. PCT/EP2017/066510, filed Jul. 3, 2017, which claims priority to European Patent Applications No. 16290128.4, filed Jul. 4, 2016, and 16290247.2, filed Dec. 22, 2016. The disclosure of the priority applications are incorporated in their entirety herein by reference.

FIELD

The present disclosure relates to fungicidal active compounds, more specifically to benzosultams and analogues thereof, processes and intermediates for their preparation and use thereof as fungicidal active compounds, particularly in the form of fungicide compositions. The present disclosure also relates to methods for the control of phytopathogenic fungi of plants using these compounds or compositions comprising thereof.

DESCRIPTION OF RELATED ART

In Japanese patent application JP-2014/221747, certain nitrogen-containing heterocyclic compounds are generically embraced in a broad disclosure of numerous compounds of the following formula:

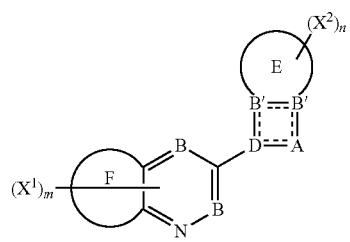

wherein E and F represent a 5- to 7-membered ring, B represents C or N, B' can represent C, D can represent N and A represents a 1 to 3 atoms linker. However, JP-2014/221747 does not disclose nor suggest providing compounds wherein D-A contains a N—SO$_2$ group as a multivalent organic group.

In Japanese patent application JP-2008/088139, certain 3-substituted quinolines are generically embraced in a broad disclosure of numerous compounds of the following formula:

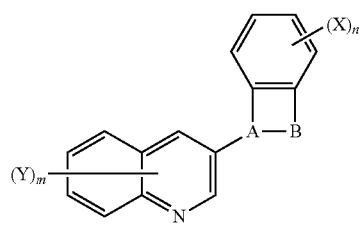

wherein A-B represents a multivalent organic group included in the list consisting of C=NC(R$^1$)(R$^2$), NC(O)C(R$^1$)(R$^2$), C=NC(R$^1$)(R$^2$)O, and C=NSO$_2$ wherein R$^1$ and R$^2$ can independently represent among various groups, a halogen atom, an optionally substituted alkyl group, a hydroxyl group or an optionally substituted alkoxy group. However, JP-2008/088139 does not disclose nor suggest providing compounds wherein A-B contains a N—SO$_2$ group.

In Japanese patent application JP-2007/001944, certain 3,4-dihydro-1,3'-biquinolin-2-ones are generically embraced in a broad disclosure of numerous compounds of the following formula:

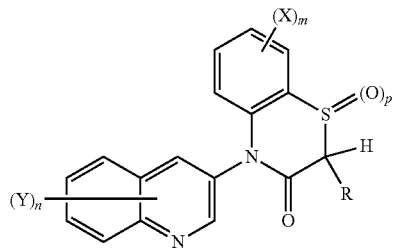

wherein R$^a$, R$^b$, R$^c$ and R$^d$ can independently represent, among various groups, a hydrogen atom, a halogen atom, an optionally substituted alkyl group, an optionally substituted alkenyl group, an optionally substituted alkynyl group, an optionally substituted aryl group, a hydroxyl group or an optionally substituted alkoxy group. However, JP-2007/001944 does not disclose nor suggest providing compounds wherein the cyclic amide function is replaced by a cyclic sulfonamide function.

In Japanese patent application JP-2017/001998, certain 3-substituted quinolines are generically embraced in a broad disclosure of numerous compounds of the following formula:

wherein R can independently represent, a hydrogen atom or an optionally substituted alkyl group. However, JP-2017/001998 does not disclose nor suggest providing compounds wherein the cyclic amide function is replaced by a cyclic sulfonamide function.

In international patent application WO-2008/073956 certain monoamine reuptake inhibitors cyclic sulfonamide derivatives are generically embraced in a broad disclosure of numerous compounds of the following formula:

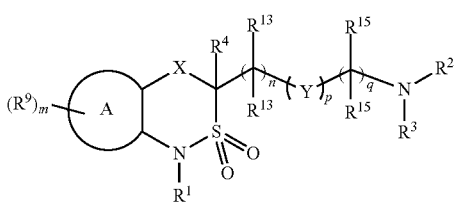

wherein A can represent an optionally substituted phenyl ring, X can represent $C(R^{11})_2$, $N(R^{12})$, O, S(O), $SO_2$ wherein $R^{11}$ can represent, among various groups, a hydrogen atom, a halogen atom or an optionally substituted alkyl group and $R^{12}$ can represent, among various groups, a hydrogen atom or an optionally substituted alkyl group and $R^1$ can represent an optionally substituted heteroaryl group such as pyridyl and quinolyl among others. However, WO-2008/073956 does not disclose nor suggest any fungicidal activities for such compounds.

Nowadays, environmental and economic demands are continuously increasing with regard for instance to the spectrum of action, toxicity, selectivity, application rate, formation of residues, and preparation processes of fungicides. Some pathogens have also been found to develop resistance to used fungicides. Therefore, in agriculture, there is a continuous need to provide new fungicide compounds that may answer these environmental and economic requirements and/or alleviate the problems associated with pathogens resistance.

SUMMARY

Accordingly, the present invention provides benzosultams and analogues thereof as described herein below that may be used as microbicide, preferably as fungicide.

Active Ingredients

The present invention provides compounds of formula (I)

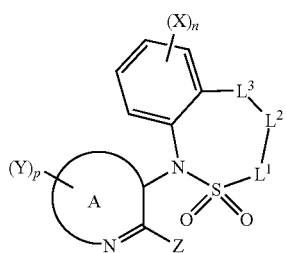

(I)

wherein
- A is a partially saturated or unsaturated fused bicyclic 9-, 10- or 11-membered heterocyclyl ring comprising at least 1 nitrogen atom and from 0 to 4 more heteroatoms independently selected in the list consisting of N, O and S;
- Z is selected from the group consisting of hydrogen atom, halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, hydroxyl, $C_1$-$C_8$-alkoxy, $C_1$-$C_8$-halogenoalkoxy comprising up to 9 halogen atoms that can be the same or different, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, cyano and nitro, wherein each of Z is optionally substituted;
- n is 0, 1, 2, 3 or 4;
- p is 0, 1, 2, 3, 4 or 5;
- X is independently selected from the group consisting of halogen atom, $C_1$-$C_8$-alkyl, $C_1$-$C_8$-halogenoalkyl comprising up to 9 halogen atoms that can be the same or different, $C_2$-$C_8$-alkenyl, $C_2$—C-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, hydroxyl, $C_1$-$C_8$-alkoxy, $C_1$-$C_8$-halogenoalkoxy comprising up to 9 halogen atoms that can be the same or different, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, $C_1$-$C_6$-trialkylsilyl-$C_1$-$C_6$-alkyl, cyano and nitro, wherein each of X is optionally substituted;
- Y is independently selected from the group consisting of halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, hydroxyl, $C_1$-$C_8$-alkoxy, $C_1$-$C_8$-halogenoalkoxy comprising up to 9 halogen atoms that can be the same or different, aryl, heterocyclyl, formyl, $C_1$-$C_8$-alkylcarbonyl, (hydroxyimino)$C_1$-$C_8$-alkyl, carboxyl, ($C_1$-$C_8$-alkoxyimino)$C_1$-$C_8$-alkyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, cyano and nitro, wherein each of Y is optionally substituted;
- $L^1$ is $CR^{1a}R^{1b}$ wherein:
  - $R^{1a}$ and $R^{1b}$ are independently selected from the group consisting of hydrogen atom, halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, aryl, aryl-$C_1$-$C_8$-alkyl, heterocyclyl, heterocyclyl-$C_1$-$C_8$-alkyl, hydroxyl, $C_1$-$C_8$-alkoxy and $C_1$-$C_8$-halogenoalkoxy comprising up to 9 halogen atoms that can be the same or different, wherein each of $R^{1a}$ and $R^{1b}$ is optionally substituted, or $R^{1a}$ and $R^{1b}$ together with the carbon atom to which they are linked form a 3-, 4-, 5- or 6-membered, saturated or partially saturated, optionally substituted, carbocycle or heterocycle comprising at least 1 heteroatom selected in the list consisting of N, O and S, or $R^{1a}$ and $R^{1b}$ together with the carbon atom to which they are linked form an unsubstituted or substituted, saturated or partially unsaturated, bicyclo$[m^1,m^2,0]$-$C_6$-$C_{11}$-alkyl wherein $m^2 \geq 1$ and $m^1+m^2=4$ to 9, or $R^{1a}$ and $R^{1b}$ together with the carbon atom to which they are linked form an unsubstituted or substituted, saturated or partially unsaturated, heterobicyclo$[m^1,m^2,0]$-$C_6$-$C_{11}$-alkyl comprising from 1 to 4 heteroatoms independently selected in the list consisting of N, O and S, wherein $m^2 \geq 1$ and $m^1+m^2=4$ to 9, or $R^{1a}$ and $R^{1b}$ together with the carbon atom to which they are linked form an unsubstituted or substituted, saturated or partially unsaturated, spiro$[n^1,n^2]$-$C_5$-$C_{11}$-alkyl wherein $n^1 \geq 2$ and $n^1+n^2=4$ to 10, or $R^{1a}$ and $R^{1b}$ together with the carbon atom to which they are linked form an unsubstituted or substituted, saturated or partially unsaturated, heterospiro$[n^1,n^2]$-$C_5$-$C_{11}$-alkyl comprising from 1 to 4 heteroatoms independently selected in the list consisting of N, O and S, wherein $n^1 \geq 2$ and $n^1+n^2=4$ to 10, or $R^{1a}$ and $R^{1b}$ together with the carbon atom to which they are linked form an unsubstituted or substituted methylidene group;

$L^2$ is a direct bond, $CR^{2a}R^{2b}$, $C(=O)$, O, $NR^{2c}$, $C=N-OR^{2d}$, S, S(O) or $SO_2$ wherein $R^{2a}$ and $R^{2b}$ are independently selected from the group consisting of hydrogen atom, halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, aryl, aryl-$C_1$-$C_8$-alkyl, heterocyclyl, heterocyclyl-$C_1$-$C_8$-alkyl, hydroxyl, $C_1$-$C_8$-alkoxy, $C_1$-$C_8$-halogenoalkoxy comprising up to 9 halogen atoms that can be the same or different, $C_2$-$C_8$-alkenyloxy, $C_2$-$C_8$-halogenoalkenyloxy comprising up to 9 halogen atoms that can be the same or different, $C_3$-$C_8$-alkynyloxy, $C_3$-$C_8$-halogenoalkynyloxy comprising up to 9 halogen atoms that can be the same or different, $C_3$-$C_7$-cycloalkoxy, $C_3$-$C_7$-halogenocycloalkoxy comprising up to 9 halogen atoms that can be the same or different, $C_3$-$C_7$-cycloalkyl-$C_1$-$C_8$-alkoxy, aryloxy, aryl-$C_1$-$C_8$-alkoxy, heterocyclyloxy, heterocyclyl-$C_1$-$C_8$-alkoxy and partially saturated or unsaturated fused bicyclic 9-, 10- or 11-membered heterocyclyl-$C_1$-$C_8$-alkoxy comprising from 1 to 5 heteroatoms independently selected in the list consisting of N, O and S, wherein each of $R^{2a}$ and $R^{2b}$ is optionally substituted, or $R^{2a}$ and $R^{2b}$ together with the carbon atom to which they are linked form an unsubstituted or substituted 3-, 4-, 5- or 6-membered, saturated or partially saturated, carbocycle or heterocycle comprising at least 1 heteroatom selected in the list consisting of N, O and S, or $R^{2a}$ and $R^{2b}$ together with the carbon atom to which they are linked form an unsubstituted or substituted, saturated or partially unsaturated, bicyclo$[m^1,m^2,0]$-$C_6$-$C_{11}$-alkyl wherein $m^2 \geq 1$ and $m^1+m^2=4$ to 9, or $R^{2a}$ and $R^{2b}$ together with the carbon atom to which they are linked form an unsubstituted or substituted, saturated or partially unsaturated, heterobicyclo$[m^1,m^2,0]$-$C_6$-$C_{11}$-alkyl comprising from 1 to 4 heteroatoms independently selected in the list consisting of N, O and S, wherein $m^2 \geq 1$ and $m^1+m^2=4$ to 9, or $R^{2a}$ and $R^{2b}$ together with the carbon atom to which they are linked form an unsubstituted or substituted, saturated or partially unsaturated, spiro$[n^1,n^2]$-$C_5$-$C_{11}$-alkyl wherein $n^1 \geq 2$ and $n^1+n^2=4$ to 10, or $R^{2a}$ and $R^{2b}$ together with the carbon atom to which they are linked form an unsubstituted or substituted, saturated or partially unsaturated, heterospiro$[n^1,n^2]$-$C_5$-$C_{11}$-alkyl comprising from 1 to 4 heteroatoms independently selected in the list consisting of N, O and S, wherein $n^1 \geq 2$ and $n^1+n^2=4$ to 10, or $R^{2a}$ and $R^{2b}$ together with the carbon atom to which they are linked form an unsubstituted or substituted methylidene group;

$R^{2c}$ is selected from the group consisting of hydrogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_3$-$C_8$-alkynyl, $C_3$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, formyl, $C_1$-$C_8$-alkylcarbonyl, $C_1$-$C_8$-halogenoalkylcarbonyl comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylsulfonyl, $C_1$-$C_8$-halogenoalkylsulfonyl comprising up to 9 halogen atoms that can be the same or different, arylsulfonyl, aryl, aryl-$C_1$-$C_8$-alkyl, heterocyclyl and heterocyclyl-$C_1$-$C_8$-alkyl, wherein each of $R^{2c}$ is optionally substituted;

$R^{2d}$ is selected from the group consisting of hydrogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_3$-$C_8$-alkynyl, $C_3$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, aryl, aryl-$C_1$-$C_8$-alkyl, heterocyclyl and heterocyclyl-$C_1$-$C_8$-alkyl, wherein each of $R^{2d}$ is optionally substituted;

$L^3$ is a direct bond, $CR^{3a}R^{3b}$, $C(=O)$, O, $NR^{3c}$, $C=N-OR^{3d}$, S, S(O) or $SO_2$ provided that $L^2$-$L^3$ do not represent a peroxo group [O—O], wherein $R^{3a}$ and $R^{3b}$ are independently selected from the group consisting of hydrogen atom, halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, aryl, aryl-$C_1$-$C_8$-alkyl, heterocyclyl, heterocyclyl-$C_1$-$C_8$-alkyl, hydroxyl, $C_1$-$C_8$-alkoxy, $C_1$-$C_8$-halogenoalkoxy comprising up to 9 halogen atoms that can be the same or different, $C_2$-$C_8$-alkenyloxy, $C_2$-$C_8$-halogenoalkenyloxy comprising up to 9 halogen atoms that can be the same or different, $C_3$-$C_8$-alkynyloxy, $C_3$-$C_8$-halogenoalkynyloxy comprising up to 9 halogen atoms that can be the same or different, $C_3$-$C_7$-cycloalkoxy, $C_3$-$C_7$-halogenocycloalkoxy comprising up to 9 halogen atoms that can be the same or different, $C_3$-$C_7$-cycloalkyl-$C_1$-$C_8$-alkoxy, aryloxy, aryl-$C_1$-$C_8$-alkoxy, heterocyclyloxy, heterocyclyl-$C_1$-$C_8$-alkoxy and partially saturated or unsaturated fused bicyclic 9-, 10- or 11-membered heterocyclyl-$C_1$-$C_8$-alkoxy comprising from 1 to 5 heteroatoms independently selected in the list consisting of N, O and S, wherein each of $R^{3a}$ and $R^{3b}$ is optionally substituted, or wherein $R^{3a}$ and $R^{3b}$ together with the carbon atom to which they are linked form an unsubstituted or substituted 3-, 4-, 5- or 6-membered, saturated or partially saturated, carbocycle or heterocycle comprising at least 1 heteroatom selected in the list consisting of N, O and S, or $R^{3a}$ and $R^{3b}$ together with the carbon atom to which they are linked form an unsubstituted or substituted, saturated or partially unsaturated, bicyclo[$m^1$,$m^2$,0]-$C_6$-$C_{11}$-alkyl wherein $m^2 \geq 1$ and $m^1+m^2=4$ to 9, or $R^{3a}$ and $R^{3b}$ together with the carbon atom to which they are linked form a unsubstituted or substituted, saturated or partially unsaturated, heterobicyclo[$m^1$,$m^2$,0]-$C_6$-$C_{11}$-alkyl comprising from 1 to 4 heteroatoms independently selected in the list consisting of N, O and S, wherein $m^2 \geq 1$ and $m^1+m^2=4$ to 9, or $R^{3a}$ and $R^{3b}$ together with the carbon atom to which they are linked form an unsubstituted or substituted, saturated or partially unsaturated, spiro[$n^1$,$n^2$]-$C_5$-$C_{11}$-alkyl wherein $n^1 \geq 2$ and $n^1+n^2=4$ to 10, or $R^{3a}$ and $R^{3b}$ together with the carbon atom to which they are linked form an unsubstituted or substituted, saturated or partially unsaturated, heterospiro[$n^1$,$n^2$]-$C_5$-$C_{11}$-alkyl comprising from 1 to 4 heteroatoms independently selected in the list consisting of N, O and S, wherein $n^1 \geq 2$ and $n^1+n^2=4$ to 10, or $R^{3a}$ and $R^{3b}$ together with the carbon atom to which they are linked form an unsubstituted or substituted methylidene group;

$R^{3c}$ is selected from the group consisting of hydrogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_3$—C-alkynyl, $C_3$—C-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, formyl, $C_1$-$C_8$-alkylcarbonyl, $C_1$-$C_8$-halogenoalkylcarbonyl comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylsulfonyl, $C_1$-$C_8$-halogenoalkylsulfonyl comprising up to 9 halogen atoms that can be the same or different, arylsulfonyl, aryl, aryl-$C_1$-$C_8$-alkyl, heterocyclyl and heterocyclyl-$C_1$-$C_8$-alkyl, wherein each of $R^{3c}$ is optionally substituted;

$R^{3d}$ is selected from the group consisting of hydrogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_3$-$C_8$-alkynyl, $C_3$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, aryl, aryl-$C_1$-$C_8$-alkyl, heterocyclyl and heterocyclyl-$C_1$-$C_8$-alkyl, wherein each of $R^{3d}$ is optionally substituted;

as well as their salts, N-oxides, metal complexes, metalloid complexes and optically active isomers or geometric isomers, provided that the compound of formula (I) is not:
  3-(3-chloropropyl)-1-(quinolin-3-yl)-1H-4,2,1-benzoxathiazine 2,2-dioxide [1033629-42-3],
  3-[2,2-dioxido-1-(quinolin-3-yl)-1H-4,2,1-benzoxathiazin-3-yl]-N-methylpropan-1-amine [1033628-19-1], and
  3-[2,2-dioxido-1-(quinolin-3-yl)-1H-4,2,1-benzoxathiazin-3-yl]-N-methylpropan-1-amine dihydrochloride [1033625-98-7].

DETAILED DESCRIPTION OF A PREFERRED EMBODIMENT

As used herein, when a variable (e.g. X, Y or Z) is said to be "optionally substituted", it is understood that this applies to moieties containing carbon-hydrogen bonds, wherein the hydrogen atom is substituted by the corresponding substituents and not to moieties such as hydrogen, halogen, CN or the like. The variable may be substituted with one or more substituents that may be identical or different. The expression "one or more substituents" refers to a number of substituents that ranges from one to the maximum number of substituents possible based on the number of available bonding sites, provided that the conditions of stability and chemical feasibility are met. The one or more substituents of the substituted variable may be independently selected from the group consisting of halogen atom, nitro, hydroxyl, cyano, amino, sulfanyl, pentafluoro-$\lambda^6$-sulfanyl, formyl, carbamoyl, carbamate, $C_1$-$C_8$-alkyl, tri($C_1$-$C_8$-alkyl)silyl, $C_3$-$C_7$-cycloalkyl, $C_1$-$C_8$-halogenoalkyl having 1 to 5 halogen atoms, $C_3$-$C_7$-halogenocycloalkyl having 1 to 5 halogen atoms, $C_2$-$C_8$-alkenyl, $C_2$-$C_8$-alkynyl, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl and $C_1$-$C_8$-halogenoalkylsulfonyl having 1 to 5 halogen atoms.

As used herein, halogen means fluorine, chlorine, bromine or iodine; formyl means —C(=O)H; carboxy means —C(=O)OH; carbonyl means —C(=O)—; carbamoyl means —C(=O)NH$_2$; triflyl means —SO$_2$—CF$_3$; SO represents a sulfoxide group; SO$_2$ represents a sulfone group; heteroatom means sulfur, nitrogen or oxygen; a methylidene group means the diradical =CH$_2$; aryl typically means phenyl or naphthyl. Unless provided differently, the term "heterocyclyl" such as used in the expression "unsubstituted or substituted heterocyclyl" means, an unsaturated, saturated or partially saturated 5- to 7-membered ring, preferably a 5- to 6-membered ring, comprising from 1 to 4 heteroatoms independently selected in the list consisting of N, O and S. The term "heterocyclyl" as used herein encompasses heteroaryl. The term "membered" as used herein in the expression "9-, 10- or 11-membered heterocyclyl ring" or "5- to 6-membered ring" designates the number of skeletal atoms that constitutes the ring.

As used herein, the expression "partially saturated or unsaturated fused bicyclic 9-, 10- or 11-membered heterocyclyl ring" designates fused bicyclic ring systems comprising a saturated ring fused with an unsaturated ring or two fused unsaturated rings, the bicyclic ring system being constituted from 9 to 11 skeletal atoms.

As used herein, an alkyl group, an alkenyl group and an alkynyl group as well as moieties containing these terms, can be linear or branched.

As used herein, the term "carbocycle" designates a hydrocarbon ring.

When an amino group or the amino moiety of any other amino-containing group is substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino group or piperidinyl group.

Any of the compounds of the present invention can exist in one or more optical or chiral isomer forms depending on the number of asymmetric centres in the compound. The invention thus relates equally to all optical isomers and racemic or scalemic mixtures thereof (the term "scalemic" denotes a mixture of enantiomers in different proportions) and to mixtures of all possible stereoisomers, in all proportions. The diastereoisomers and/or the optical isomers can be separated according to methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans) of the substituents of the chain or ring. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

When a compound of the invention can be present in tautomeric form, such a compound is understood herein above and herein below also to include, where applicable, corresponding tautomeric forms, even when these are not specifically mentioned in each case.

Compounds of formula (I) are herein referred to as "active ingredient(s)".

In the above formula (I), Z may be preferably selected from the group consisting of hydrogen atom, halogen atom, unsubstituted or substituted C$_1$-C$_6$-alkyl, C$_1$-C$_6$-halogenoalkyl comprising up to 9 halogen atoms that can be the same or different, unsubstituted or substituted C$_1$-C$_6$-alkoxy, C$_1$-C$_6$-halogenoalkoxy comprising up to 9 halogen atoms that can be the same or different and cyano, more preferably Z is a hydrogen atom, an unsubstituted or substituted C$_1$-C$_6$-alkyl (e.g. a methyl group) or a C$_1$-C$_6$-halogenoalkyl comprising up to 9 halogen atoms that can be the same or different.

In the above formula (I), X may be preferably independently selected from the group consisting of halogen atom, unsubstituted or substituted C$_1$-C$_6$-alkyl, C$_1$-C$_6$-halogenoalkyl comprising up to 9 halogen atoms that can be the same or different, unsubstituted or substituted C$_2$-C$_8$-alkenyl, unsubstituted or substituted C$_2$-C$_8$-alkynyl, unsubstituted or substituted C$_3$-C$_7$-cycloalkyl, hydroxyl, unsubstituted or substituted C$_1$-C$_6$-alkoxy, C$_1$-C$_6$-halogenoalkoxy comprising up to 9 halogen atoms that can be the same or different, unsubstituted or substituted aryl, unsubstituted or substituted heterocyclyl, unsubstituted or substituted C$_1$-C$_6$-alkylcarbonyl, unsubstituted or substituted C$_1$-C$_6$-trialkylsilyl-C$_1$-C$_6$-alkyl and unsubstituted or substituted C$_1$-C$_6$-trialkylsilyl, more preferably X is a halogen atom (a chlorine atom, a bromine atom or a fluorine atom), an unsubstituted or substituted C$_1$-C$_6$-alkyl (e.g. a methyl group), a C$_1$-C$_6$-halogenoalkyl comprising up to 9 halogen atoms that can be the same or different (e.g. a trifluoromethyl group), an unsubstituted or substituted C$_1$-C$_6$-alkoxy (e.g. a methoxy group), an unsubstituted or substituted C$_1$-C$_6$-halogenoalkoxy (e.g. a trifluoromethoxy group) or a trimethylsilyl group.

In the above formula (I), n is preferably 0, 1, 2 or 3, more preferably 0 or 1.

In the above formula (I), Y may be preferably independently selected from the group consisting of halogen atom, unsubstituted or substituted C$_1$-C$_6$-alkyl, C$_1$-C$_6$-halogenoalkyl comprising up to 9 halogen atoms that can be the same or different, unsubstituted or substituted C$_3$-C$_7$-cycloalkyl, hydroxyl, unsubstituted or substituted C$_1$-C$_6$-alkoxy, C$_1$-C$_6$-halogenoalkoxy comprising up to 9 halogen atoms that can be the same or different, unsubstituted or substituted C$_1$-C$_6$-alkoxycarbonyl, formyl and cyano, more preferably Y is a halogen atom, an unsubstituted or substituted C$_1$-C$_6$-alkyl, a C$_1$-C$_6$-halogenoalkyl comprising up to 9 halogen atoms that can be the same or different (e.g. trifluoromethyl) or a cyano.

In the above formula (I), p is preferably 0, 1 or 2.

In the above formula (I), $R^{1a}$ and $R^{1b}$, or $R^{2a}$ and $R^{2b}$, or $R^{3a}$ and $R^{3b}$, together with the carbon atom to which they are linked may form a 3-, 4-, 5- or 6-membered, saturated or partially saturated, optionally substituted, carbocycle or heterocycle comprising at least 1 heteroatom selected in the list consisting of N, O and S. Examples of 3-, 4-, 5- or 6-membered, saturated or partially saturated, optionally substituted, carbocycle include cyclopropyl, cyclopentyl, cyclohexyl, cyclopropenyl, cyclopentenyl and cyclohexenyl.

Examples of 3-, 4-, 5- or 6-membered, saturated or partially saturated, optionally substituted, heterocycle include oxiranyl, aziridinyl, tetrahydrofuranyl, tetrahydrothienyl, pyrrolidinyl, dihydrofuryl, dihydrothienyl, pyrrolidinyl, piperidinyl, dioxanyl, tetrahydropyranyl, hexahydropyridazinyl, hexahydropyrimidinyl and piperazinyl.

In the above formula (I), $R^{1a}$ and $R^{1b}$, or $R^{2a}$ and $R^{2b}$, or $R^{3a}$ and $R^{3b}$, together with the carbon atom to which they are linked may form an unsubstituted or substituted, saturated or partially unsaturated, bicyclo[$m^1$, $m^2$,0]-$C_6$-$C_{11}$-alkyl wherein $m^2 \geq 1$ and $m^1 + m^2 = 4$ to 9. Examples of these include indane and decalin.

In the above formula (I), $R^{1a}$ and $R^{1b}$, or $R^{2a}$ and $R^{2b}$, or $R^{3a}$ and $R^{3b}$, together with the carbon atom to which they are linked may form an unsubstituted or substituted, saturated or partially unsaturated, spiro[$n^1$,$n^2$]-$C_5$-$C_{11}$-alkyl comprising from 1 to 4 heteroatoms independently selected in the list consisting of N, O and S, wherein $n^1 \geq 2$ and $n^1 + n^2 = 4$ to 10. Examples of these include spiro-[2,2]pentane and spiro-[2,3]hexane. In the above formula (I), $R^{1a}$ and $R^{1b}$, or $R^{2a}$ and $R^{2b}$, or $R^{3a}$ and $R^{3b}$, together with the carbon atom to which they are linked may form an unsubstituted or substituted, saturated or partially unsaturated, heterospiro[$n^1$,$n^2$]-$C_5$-$C_{11}$-alkyl comprising from 1 to 4 heteroatoms independently selected in the list consisting of N, O and S, wherein $n^1 \geq 2$ and $n^1 + n^2 = 4$ to 10. An example of these includes 2-oxaspiro[3,3]heptane.

In the above formula (I), $R^{1a}$ and $R^{1b}$ may be preferably independently selected from the group consisting of hydrogen atom, halogen atom, unsubstituted or substituted $C_1$-$C_6$-alkyl, unsubstituted or substituted $C_2$-$C_6$-alkenyl, unsubstituted or substituted $C_2$-$C_6$-halogenoalkenyl, unsubstituted or substituted $C_2$-$C_6$-alkynyl, unsubstituted or substituted $C_3$-$C_7$-cycloalkyl, unsubstituted or substituted $C_3$-$C_7$-cycloalkyl-$C_1$-$C_6$-alkyl, unsubstituted or substituted aryl, unsubstituted or substituted heterocyclyl-$C_1$-$C_6$-alkyl, unsubstituted or substituted heterocyclyl, and unsubstituted or substituted aryl-$C_1$-$C_8$-alkyl, or $R^{1a}$ and $R^{1b}$ together with the carbon atom to which they are linked may preferably
- form a 3-, 4-, 5- or 6-membered, saturated or partially saturated, optionally substituted, carbocycle or heterocycle comprising at least 1 heteroatom selected in the list consisting of N, O and S, or
- form an unsubstituted or substituted, saturated or partially unsaturated, bicyclo[$m^1$, $m^2$,0]-$C_6$-$C_{11}$-alkyl wherein $m^2 \geq 1$ and $m^1 + m^2 = 4$ to 9, or
- form an unsubstituted or substituted, saturated or partially unsaturated, heterobicyclo[$m^1$, $m^2$,0]-$C_6$-$C_{11}$-alkyl comprising from 1 to 4 heteroatoms independently selected in the list consisting of N, O and S, wherein $m^2 \geq 1$ and $m^1 + m^2 = 4$ to 9, or
- form an unsubstituted or substituted, saturated or partially unsaturated, spiro[$n^1$,$n^2$]-$C_5$-$C_{11}$-alkyl wherein $n^1 \geq 2$ and $n^1 + n^2 = 4$ to 10, or
- form an unsubstituted or substituted, saturated or partially unsaturated, heterospiro[$n^1$,$n^2$]-$C_6$-$C_{11}$-alkyl comprising from 1 to 4 heteroatoms independently selected in the list consisting of N, O and S, wherein $n^1 \geq 2$ and $n^1 + n^2 = 4$ to 10.

In the above formula (I), more preferably $R^{1a}$ and $R^{1b}$ are each independently a hydrogen atom, an unsubstituted or substituted $C_1$-$C_6$-alkyl (e.g. methyl group), or $R^{1a}$ and $R^{1b}$ together form a 3-, 4-, 5- or 6-membered, saturated or partially saturated, optionally substituted, carbocycle (e.g. cyclopropyl, cyclobutyl, cyclopentyl, cyclohexyl, cyclopentenyl), or an unsubstituted or substituted, saturated or partially unsaturated, spiro[$n^1$,$n^2$]-$C_5$-$C_{11}$-alkyl wherein $n^1 \geq 2$ and $n^1 + n^2 = 4$ to 10 (e.g. spiro-[2,2]pentane).

In the above formula (I), $L^2$ is preferably a direct bond, O, C(=O), S, $CR^{2a}R^{2b}$ or C=N—$OR^{2d}$ with $R^{2a}$, $R^{2b}$ and $R^{2d}$ as described herein.

When present, $R^{2a}$ and $R^{2b}$ are preferably independently a hydrogen atom, a halogen atom, a hydroxyl, an unsubstituted or substituted $C_1$-$C_6$-alkoxy, an unsubstituted or substituted $C_1$-$C_6$-alkyl, an unsubstituted or substituted aryl, a hydroxyl, an unsubstituted or substituted $C_2$-$C_8$-alkenyloxy, an unsubstituted or substituted $C_3$-$C_8$-alkynyloxy, an unsubstituted or substituted aryl-$C_1$-$C_6$-alkoxy, an unsubstituted or substituted heterocyclyl-$C_1$-$C_6$-alkoxy or an unsubstituted or substituted partially saturated or unsaturated fused bicyclic 9-, 10- or 11-membered heterocyclyl-$C_1$-$C_6$-alkoxy comprising from 1 to 5 heteroatoms independently selected in the list consisting of N, O and S. In some preferred embodiments, $R^{2a}$ and $R^{2b}$ together with the carbon atom to which they are linked may also form an unsubstituted or substituted methylidene group.

Examples of unsubstituted or substituted aryl-$C_1$-$C_6$-alkoxy include unsubstituted or substituted phenyl-$C_1$-$C_6$-alkoxy wherein the phenyl group may be substituted by one or more group selected from the group consisting of unsubstituted or substituted $C_1$-$C_6$-alkyl, cyano, halogen, unsubstituted or substituted $C_1$-$C_6$-alkylsulfonyl, unsubstituted or substituted $C_1$-$C_6$-alkylsulfanyl unsubstituted or substituted aryl (e.g. phenyl, naphthyl), unsubstituted or substituted arylcarbonyl, unsubstituted or substituted $C_1$-$C_6$-alkoxy, $C_1$-$C_6$-halogenoalkoxy, unsubstituted or substituted aryloxy and unsubstituted or substituted aryl-$C_1$-$C_6$-alkoxy. Examples of unsubstituted or substituted heterocyclyl-$C_1$-$C_6$-alkoxy include unsubstituted or substituted thiazolyl-$C_1$-$C_6$-alkoxy and unsubstituted or substituted furanyl-$C_1$-$C_6$-alkoxy.

Examples of unsubstituted or substituted partially saturated or unsaturated fused bicyclic 9-, 10- or 11-membered heterocyclyl-$C_1$-$C_6$-alkoxy comprising from 1 to 5 heteroatoms independently selected in the list consisting of N, O and S include unsubstituted or substituted indazolyl-$C_1$-$C_6$-alkoxy and unsubstituted or substituted benzoxazolyl-$C_1$-$C_6$-alkoxy.

When present, $R^{2a}$ and $R^{2b}$ are more preferably independently a hydrogen atom, a halogen atom (e.g. fluorine atom), a hydroxyl, an unsubstituted or substituted $C_1$-$C_6$-alkyl (e.g. a methyl group), an unsubstituted or substituted aryl (e.g. unsubstituted or substituted phenyl), an unsubstituted or substituted $C_1$-$C_6$-alkoxy (e.g. a methoxy group), an unsubstituted or substituted aryloxy, an unsubstituted or substituted aryl-$C_1$-$C_6$-alkoxy (e.g. unsubstituted or substituted benzyloxy), an unsubstituted or substituted $C_2$-$C_8$-alkenyloxy (e.g. allyloxy), an unsubstituted or substituted $C_3$-$C_8$-alkynyloxy (e.g. propynyloxy), an unsubstituted or substituted aryl-$C_1$-$C_6$-alkoxy (e.g. unsubstituted or substituted phenyl-$C_1$-$C_6$-alkoxy or unsubstituted or substituted naphthalenyl-$C_1$-$C_6$-alkoxy), an unsubstituted or substituted heterocyclyl-$C_1$-$C_6$-alkoxy, an unsubstituted or substituted partially saturated or unsaturated fused bicyclic 9-, 10- or 11-membered heterocyclyl-$C_1$-$C_6$-alkoxy comprising from 1 to 5 heteroatoms independently selected in the list consisting of N, O and S, or $R^{2a}$ and $R^{2b}$ together with the carbon atom to which they are linked form an unsubstituted or substituted methylidene group.

When present, $R^{2d}$ is preferably a hydrogen atom, an unsubstituted or substituted $C_1$-$C_6$-alkyl, an unsubstituted or substituted $C_2$-$C_6$-alkenyl or an unsubstituted or substituted aryl-$C_1$-$C_6$-alkyl.

In the above formula (I), $L^3$ is preferably a direct bond, $CR^{3a}R^{3b}$ or $NR^{3c}$ with $R^{3a}$, $R^{3b}$ and $R^{3c}$ as described herein, more preferably $L^3$ is a direct bond.

When present, $R^{3a}$ and $R^{3b}$ are preferably independently a hydrogen atom, a halogen atom, a hydroxyl, an unsubstituted or substituted $C_1$-$C_8$-alkoxy or an unsubstituted or substituted $C_1$-$C_6$-alkyl, more preferably a hydrogen atom or a methyl group.

When present, $R^3$ is preferably a hydrogen atom or an unsubstituted or substituted $C_1$-$C_6$-alkyl.

In some embodiments, the active ingredients are compounds of formula (I) wherein:
- Y is independently selected from the group consisting of halogen atom, unsubstituted or substituted $C_1$-$C_6$-alkyl, $C_1$-$C_6$-halogenoalkyl comprising up to 9 halogen atoms that can be the same or different, unsubstituted or substituted $C_3$-$C_7$-cycloalkyl, hydroxyl, unsubstituted or substituted $C_1$-$C_6$-alkoxy, $C_1$-$C_6$-halogenoalkoxy comprising up to 9 halogen atoms that can be the same or different, unsubstituted or substituted $C_1$-$C_6$-alkoxycarbonyl, formyl and cyano;
- Z is selected from the group consisting of hydrogen atom, halogen atom, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano;
- A, $L^1$, $L^2$, $L^3$, X, n and p are as defined above.

Some preferred compounds according to the invention are compounds of formula (I) wherein A is selected in the list consisting of:

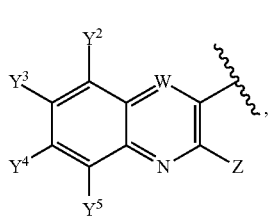
(A¹)

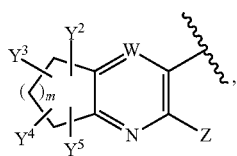
(A²)

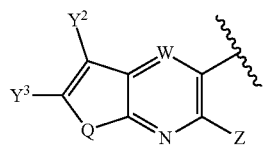
(A³)

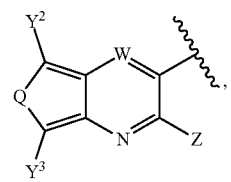
(A⁴)

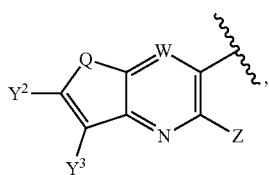
(A⁵)

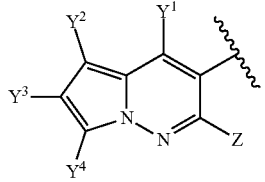
(A⁶)

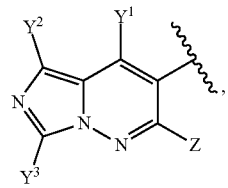
(A⁷)

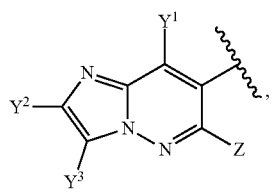
(A⁸)

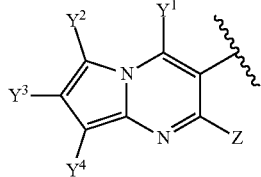
(A⁹)

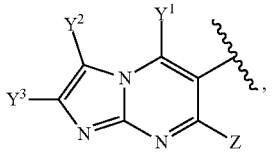
(A¹⁰)

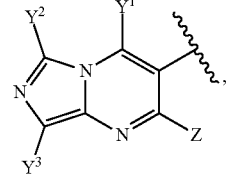
(A¹¹)

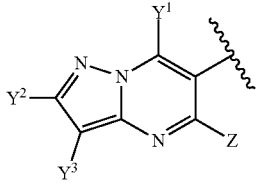
(A¹²)

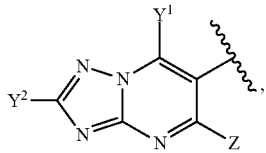
(A¹³)

(A¹⁴)

(A¹⁵)

(A¹⁶)

(A¹⁷)

(A¹⁸) and (A¹⁹)

wherein:
W is $CY^1$ or N;
T is $CY^4$ or N;
Q is O, S or $NY^6$ with $Y^6$ being a hydrogen atom or an unsubstituted or substituted $C_1$-$C_8$-alkyl;
$Y^1$, $Y^2$, $Y^3$, $Y^4$ and $Y^5$ are independently a hydrogen atom or Y as disclosed above, preferably, $Y^1$, $Y^2$, $Y^3$, $Y^4$ and $Y^5$ are independently selected from the group consisting of hydrogen atom, halogen atom, unsubstituted or substituted $C_1$-$C_6$-alkyl, $C_1$-$C_6$-halogenoalkyl comprising up to 9 halogen atoms that can be the same or different, unsubstituted or substituted $C_3$-$C_7$-cycloalkyl, hydroxyl, unsubstituted or substituted $C_1$-$C_6$-alkoxy, $C_1$-$C_6$-halogenoalkoxy comprising up to 9 halogen atoms that can be the same or different, unsubstituted or substituted $C_1$-$C_6$-alkoxycarbonyl, formyl and cyano;
Z is as disclosed above, preferably Z is selected from the group consisting of hydrogen atom, halogen atom, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano;
m is 1, 2 or 3; and
n, X, $L^1$, $L^2$ and $L^3$ are as disclosed herein.

In the above formula (I), A is more preferably selected from the group consisting of $A^1$, $A^2$, $A^3$, $A^5$, $A^9$, $A^{10}$, $A^{12}$, $A^{13}$, $A^{14}$, $A^{16}$, $A^{17}$, $A^{18}$ and $A^{19}$ as herein disclosed, even more preferably $A^1$ or $A^2$.

In some embodiments, the compounds of the invention are compounds of formula (I) wherein A is $A^1$, and W, $Y^1$ to $Y^5$, Z, X, $L^1$, $L^2$, $L^3$ and n are as described above.

Some preferred compounds according to the invention are compounds of formula (I) wherein A is a heterocycle of formula ($A^1$) wherein:
W is $CY^1$ or N;
$Y^1$ to $Y^5$ are independently a hydrogen atom, a fluorine atom, a chlorine atom, a methyl group or a trifluoromethyl group;
Z is a hydrogen atom or a methyl group;
$L^1$, $L^2$, $L^3$, X and n are as defined above,
preferably $L^2$ is $CR^{2a}R^{2b}$, O, C(=O) or a direct bond, with $CR^{2a}R^{2b}$ as defined above, preferably $L^3$ is a direct bond, preferably n is 0 or 1, and preferably X is a bromine atom, chlorine atom, a fluorine atom, a methyl group, a trifluoromethyl group, a methoxy group or a trifluoromethoxy group. In these embodiments, $R^{1a}$ is preferably a hydrogen atom, an unsubstituted or a substituted $C_1$-$C_6$-alkyl or an unsubstituted or substituted aryl-$C_1$-$C_8$-alkyl, more preferably a hydrogen atom, a methyl group or a benzyl group; and/or $R^{1b}$ is preferably a hydrogen atom, an unsubstituted or a substituted $C_1$-$C_6$-alkyl or an unsubstituted or substituted aryl-$C_1$-$C_8$-alkyl, more preferably a hydrogen atom, a methyl group or a benzyl group; or $R^{1a}$ and $R^{1b}$ together with the carbon atom to which they are linked, form an unsubstituted or substituted $C_3$-$C_7$-cycloalkyl, more preferably an unsubstituted or substituted cyclopropyl or an unsubstituted or substituted cyclobutyl; and/or $R^{2a}$ is preferably a hydrogen atom, a hydroxyl, an unsubstituted or substituted $C_1$-$C_8$-alkoxy, an unsubstituted or substituted $C_1$-$C_6$-alkyl, a halogen atom, an unsubstituted or substituted aryl-$C_1$-$C_8$-alkoxy, an unsubstituted or substituted heterocyclyl-$C_1$-$C_8$-alkoxy, an unsubstituted or substituted partially saturated or unsaturated fused bicyclic 9-, 10- or 11-membered heterocyclyl-$C_1$-$C_8$-alkoxy comprising from 1 to 5 heteroatoms independently selected in the list consisting of N, O and S, more preferably a hydrogen, a hydroxyl a methoxy group, a methyl group or a fluorine atom, and/or $R^{2b}$ is preferably a hydrogen atom, a hydroxyl, an unsubstituted or substituted $C_1$-$C_8$-alkoxy, an unsubstituted or substituted $C_1$-$C_6$-alkyl, a halogen atom, an unsubstituted or substituted aryl-$C_1$-$C_8$-alkoxy, an unsubstituted or substituted heterocyclyl-$C_1$-$C_8$-alkoxy, an unsubstituted or substituted partially saturated or unsaturated fused bicyclic 9-, 10- or 11-membered heterocyclyl-$C_1$-$C_8$-alkoxy comprising from 1 to 5 heteroatoms independently selected in the list consisting of N, O and S, more preferably a hydrogen, a hydroxyl, a methoxy group, a methyl group or a fluorine atom; or $R^{2a}$ and $R^{2b}$ together with the carbon atom to which they are linked form an unsubstituted or substituted methylidene group.

Some preferred compounds according to the invention are compounds of formula (Ia)

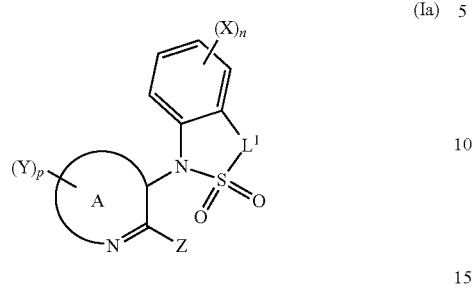

wherein:
- A is a partially saturated or unsaturated fused bicyclic 9-, 10- or 11-membered heterocyclyl ring comprising at least 1 nitrogen atom and from 0 to 4 more heteroatoms independently selected in the list consisting of N, O and S, preferably A is selected in the list consisting of $A^1$ to $A^{19}$ as disclosed above, more preferably A is $A^1$;
- $L^1$ is $CR^{1a}R^{1b}$ wherein $R^{1a}$ and $R^{1b}$ are as disclosed above, preferably $R^{1a}$ and $R^{1b}$ are independently selected from the group consisting of hydrogen atom, halogen atom, unsubstituted or substituted $C_1$-$C_6$-alkyl, unsubstituted or substituted $C_2$-$C_6$-alkenyl, unsubstituted or substituted $C_2$-$C_6$-halogenoalkenyl, unsubstituted or substituted $C_2$-$C_6$-alkynyl, unsubstituted or substituted $C_3$-$C_7$-cycloalkyl, unsubstituted or substituted $C_3$-$C_7$-cycloalkyl-$C_1$-$C_6$-alkyl, unsubstituted or substituted aryl, unsubstituted or substituted heterocyclyl-$C_1$-$C_6$-alkyl, unsubstituted or substituted heterocyclyl, and unsubstituted or substituted aryl-$C_1$-$C_8$-alkyl, or $R^{1a}$ and $R^{1b}$ together with the carbon atom to which they are linked:
  - form a 3-, 4-, 5- or 6-membered, saturated or partially saturated, optionally substituted, carbocycle or heterocycle comprising at least 1 heteroatom selected in the list consisting of N, O and S, or
  - form an unsubstituted or substituted, saturated or partially unsaturated, bicyclo[$m^1$, $m^2$,0]-$C_6$-$C_{11}$-alkyl wherein $m^2 \geq 1$ and $m^1+m^2=4$ to 9, or
  - form an unsubstituted or substituted, saturated or partially unsaturated, heterobicyclo[$m^1$, $m^2$,0]-$C_6$-$C_{11}$-alkyl comprising from 1 to 4 heteroatoms independently selected in the list consisting of N, O and S, wherein $m^2 \geq 1$ and $m^1+m^2=4$ to 9, or
  - form an unsubstituted or substituted, saturated or partially unsaturated, spiro[$n^1$,$n^2$]-$C_5$-$C_{11}$-alkyl wherein $n^1 \geq 2$ and $n^1+n^2=4$ to 10, or
  - form an unsubstituted or substituted, saturated or partially unsaturated, heterospiro[$n^1$,$n^2$]-$C_5$-$C_{11}$-alkyl comprising from 1 to 4 heteroatoms independently selected in the list consisting of N, O and S, wherein $n^1 \geq 2$ and $n^1+n^2=4$ to 10, or
  - form an unsubstituted or substituted methylidene group,
- n is 0, 1, 2 or 3, preferably 0 or 1;
- p is 0, 1 or 2;
- Z is as disclosed above, preferably Z is selected from the group consisting of hydrogen atom, halogen atom, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano, more preferably Z is a hydrogen atom, an unsubstituted or substituted $C_1$-$C_6$-alkyl (e.g. a methyl group) or a $C_1$-$C_6$-halogenoalkyl comprising up to 9 halogen atoms that can be the same or different;
- X is as disclosed above, preferably X is independently selected from the group consisting of halogen atom, unsubstituted or substituted $C_1$-$C_6$-alkyl, $C_1$-$C_6$-halogenoalkyl comprising up to 9 halogen atoms that can be the same or different, unsubstituted or substituted $C_2$-$C_8$-alkenyl, unsubstituted or substituted $C_2$-$C_8$-alkynyl, unsubstituted or substituted $C_3$-$C_7$-cycloalkyl, hydroxyl, unsubstituted or substituted $C_1$-$C_6$-alkoxy, $C_1$-$C_6$-halogenoalkoxy comprising up to 9 halogen atoms that can be the same or different, unsubstituted or substituted aryl, unsubstituted or substituted heterocyclyl, unsubstituted or substituted $C_1$-$C_6$-alkylcarbonyl, unsubstituted or substituted $C_1$-$C_6$-trialkylsilyl-$C_1$-$C_6$-alkyl and unsubstituted or substituted $C_1$-$C_6$-trialkylsilyl, more preferably X is a halogen atom (a chlorine atom, a bromine atom or a fluorine atom), an unsubstituted or substituted $C_1$-$C_6$-alkyl (e.g. a methyl group), a $C_1$-$C_6$-halogenoalkyl comprising up to 9 halogen atoms that can be the same or different (e.g. a trifluoromethyl group), an unsubstituted or substituted $C_1$-$C_6$-alkoxy (e.g. a methoxy group), an unsubstituted or substituted $C_1$-$C_6$-halogenoalkoxy (e.g. a trifluoromethoxy group) or a trimethylsilyl group;
- Y is as disclosed above, preferably Y is independently selected from the group consisting of halogen atom, unsubstituted or substituted $C_1$-$C_6$-alkyl, $C_1$-$C_6$-halogenoalkyl comprising up to 9 halogen atoms that can be the same or different, unsubstituted or substituted $C_3$-$C_7$-cycloalkyl, hydroxyl, unsubstituted or substituted $C_1$-$C_6$-alkoxy, $C_1$-$C_6$-halogenoalkoxy comprising up to 9 halogen atoms that can be the same or different, unsubstituted or substituted $C_1$-$C_6$-alkoxycarbonyl, formyl and cyano, more preferably Y is a halogen atom, an unsubstituted or substituted $C_1$-$C_6$-alkyl, a $C_1$-$C_6$-halogenoalkyl comprising up to 9 halogen atoms that can be the same or different (e.g. trifluoromethyl) or a cyano.

Some preferred compounds according to the invention are compounds of formula (Ib)

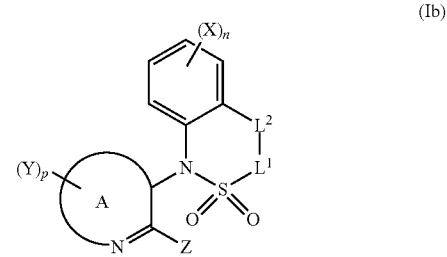

wherein:
- A is a partially saturated or unsaturated fused bicyclic 9-, 10- or 11-membered heterocyclyl ring comprising at least 1 nitrogen atom and from 0 to 4 more heteroatoms independently selected in the list consisting of N, O and S, preferably A is selected in the list consisting of $A^1$ to $A^{19}$ as disclosed above, more preferably A is $A^1$;
- $L^1$ is $CR^{1a}R^{1b}$ wherein $R^{1a}$ and $R^{1b}$ are as disclosed above, preferably $R^{1a}$ and $R^{1b}$ are independently selected from the group consisting of hydrogen atom, halogen atom, unsubstituted or substituted $C_1$-$C_6$-alkyl, unsubstituted or substituted $C_2$-$C_6$-alkenyl, unsubstituted or substituted $C_2$-$C_6$-halogenoalkenyl, unsubstituted or substituted $C_2$-$C_6$-alkynyl, unsubstituted or substituted $C_3$-$C_7$-cycloalkyl, unsubstituted or substituted $C_3$-$C_7$-cycloalkyl-$C_1$-$C_6$-alkyl, unsubstituted or substituted aryl, unsubstituted or substituted heterocyclyl-$C_1$-$C_6$-alkyl, unsubstituted or substituted heterocyclyl, and unsubstituted or substituted aryl-$C_1$-$C_8$-alkyl, or $R^{1a}$ and $R^{1b}$ together with the carbon atom to which they are linked:
- form a 3-, 4-, 5- or 6-membered, saturated or partially saturated, optionally substituted, carbocycle or heterocycle comprising at least 1 heteroatom selected in the list consisting of N, O and S, or
- form an unsubstituted or substituted, saturated or partially unsaturated, bicyclo[$m^1$, $m^2$,0]-$C_6$-$C_{11}$-alkyl wherein $m^2 \geq 1$ and $m^1+m^2=4$ to 9, or form an unsubstituted or substituted, saturated or partially unsaturated, heterobicyclo[$m^1$, $m^2$,0]-$C_6$-$C_{11}$-alkyl comprising from 1 to 4 heteroatoms independently selected in the list consisting of N, O and S, wherein $m^2 \geq 1$ and $m^1+m^2=4$ to 9, or
- form an unsubstituted or substituted, saturated or partially unsaturated, spiro[$n^1$,$n^2$]-$C_5$-$C_{11}$-alkyl wherein $n^1 \geq 2$ and $n^1+n^2=4$ to 10, or
- form an unsubstituted or substituted, saturated or partially unsaturated, heterospiro[$n^1$,$n^2$]-$C_5$-$C_{11}$-alkyl comprising from 1 to 4 heteroatoms independently selected in the list consisting of N, O and S, wherein $n^1 \geq 2$ and $n^1+n^2=4$ to 10, or
- form an unsubstituted or substituted methylidene group;

$L^2$ is $CR^{2a}R^{2b}$, $C(=O)$, O, $NR^{2c}$, $C=N-OR^{2d}$, S, S(O) or $SO_2$ with $R^{2a}$, $R^{2b}$, $R^{2c}$ and $R^{2d}$ as described herein, preferably $L^2$ is O, $C(=O)$, S, $CR^{2a}R^{2b}$ or $C=N-OR^{2d}$ with $R^{2a}$, $R^{2b}$ and $R^{2d}$ as described herein, preferably $R^{2a}$ and $R^{2b}$ are independently a hydrogen atom, a halogen atom, a hydroxyl, an unsubstituted or substituted $C_1$-$C_6$-alkoxy, an unsubstituted or substituted $C_1$-$C_6$-alkyl, an unsubstituted or substituted aryl, a hydroxyl, an unsubstituted or substituted $C_2$-$C_8$-alkenyloxy, an unsubstituted or substituted $C_3$-$C_8$-alkynyloxy, an unsubstituted or substituted aryl-$C_1$-$C_6$-alkoxy, an unsubstituted or substituted heterocyclyl-$C_1$-$C_6$-alkoxy or an unsubstituted or substituted, partially saturated or unsaturated, fused bicyclic 9-, 10- or 11-membered heterocyclyl-$C_1$-$C_6$-alkoxy comprising from 1 to 5 heteroatoms independently selected in the list consisting of N, O and S, or $R^{2a}$ and $R^{2b}$ together with the carbon atom to which they are linked form an unsubstituted or substituted methylidene group, preferably $R^{2d}$ is a hydrogen atom, an unsubstituted or substituted $C_1$-$C_6$-alkyl, an unsubstituted or substituted $C_2$-$C_6$-alkenyl or an unsubstituted or substituted aryl-$C_1$-$C_6$-alkyl;

n is 0, 1, 2 or 3, preferably 0 or 1;

p is 0, 1 or 2;

Z is as disclosed above, preferably Z is selected from the group consisting of hydrogen atom, halogen atom, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano, more preferably Z is a hydrogen atom, an unsubstituted or substituted $C_1$-$C_6$-alkyl (e.g. a methyl group) or a $C_1$-$C_6$-halogenoalkyl comprising up to 9 halogen atoms that can be the same or different;

X is as disclosed above, preferably X is independently selected from the group consisting of halogen atom, unsubstituted or substituted $C_1$-$C_6$-alkyl, $C_1$-$C_6$-halogenoalkyl comprising up to 9 halogen atoms that can be the same or different, unsubstituted or substituted $C_2$-$C_8$-alkenyl, unsubstituted or substituted $C_2$-$C_8$-alkynyl, unsubstituted or substituted $C_3$-$C_7$-cycloalkyl, hydroxyl, unsubstituted or substituted $C_1$-$C_6$-alkoxy, $C_1$-$C_6$-halogenoalkoxy comprising up to 9 halogen atoms that can be the same or different, unsubstituted or substituted aryl, unsubstituted or substituted heterocyclyl, unsubstituted or substituted $C_1$-$C_6$-alkylcarbonyl, unsubstituted or substituted $C_1$-$C_6$-trialkylsilyl-$C_1$-$C_6$-alkyl and unsubstituted or substituted $C_1$-$C_6$-trialkylsilyl, more preferably X is a halogen atom (a chlorine atom, a bromine atom or a fluorine atom), an unsubstituted or substituted $C_1$-$C_6$-alkyl (e.g. a methyl group), a $C_1$-$C_6$-halogenoalkyl comprising up to 9 halogen atoms that can be the same or different (e.g. a trifluoromethyl group), an unsubstituted or substituted $C_1$-$C_6$-alkoxy (e.g. a methoxy group), an unsubstituted or substituted $C_1$-$C_6$-halogenoalkoxy (e.g. a trifluoromethoxy group) or a trimethylsilyl group;

Y is as disclosed above, preferably Y is independently selected from the group consisting of halogen atom, unsubstituted or substituted $C_1$-$C_6$-alkyl, $C_1$-$C_6$-halogenoalkyl comprising up to 9 halogen atoms that can be the same or different, unsubstituted or substituted $C_3$-$C_7$-cycloalkyl, hydroxyl, unsubstituted or substituted $C_1$-$C_6$-alkoxy, $C_1$-$C_6$-halogenoalkoxy comprising up to 9 halogen atoms that can be the same or different, unsubstituted or substituted $C_1$-$C_6$-alkoxycarbonyl, formyl and cyano, more preferably Y is a halogen atom, an unsubstituted or substituted $C_1$-$C_6$-alkyl, a $C_1$-$C_6$-halogenoalkyl comprising up to 9 halogen atoms that can be the same or different (e.g. trifluoromethyl) or a cyano.

In some embodiments, compounds according to the invention are compounds of formula (Ib) wherein $R^{2a}$ and $R^{2b}$ are independently a hydrogen atom, a halogen atom (e.g. fluorine atom), a hydroxyl, an unsubstituted or substituted $C_1$-$C_6$-alkyl (e.g. a methyl group), an unsubstituted or substituted aryl (e.g. unsubstituted or substituted phenyl), an unsubstituted or substituted $C_1$-$C_6$-alkoxy (e.g. a methoxy group), an unsubstituted or substituted aryloxy, an unsubstituted or substituted aryl-$C_1$-$C_6$-alkoxy (e.g. unsubstituted or substituted benzyloxy), an unsubstituted or substituted $C_2$-$C_8$-alkenyloxy (e.g. allyloxy), an unsubstituted or substituted $C_3$-$C_8$-alkynyloxy (e.g. propynyloxy), an unsubstituted or substituted aryl-$C_1$-$C_6$-alkoxy (e.g. unsubstituted or substituted phenyl-$C_1$-$C_6$-alkoxy or unsubstituted or substituted naphthalenyl-$C_1$-$C_6$-alkoxy), an unsubstituted or substituted heterocyclyl-$C_1$-$C_6$-alkoxy, an unsubstituted or substituted partially saturated or unsaturated fused bicyclic 9-, 10- or 11-membered heterocyclyl-$C_1$-$C_6$-alkoxy comprising from 1 to 5 heteroatoms independently selected in the list consisting of N, O and S, or $R^{2a}$ and $R^{2b}$ together with the carbon atom to which they are linked form an unsubstituted or substituted methylidene group.

The above mentioned preferences with regard to A, $L^1$, $L^2$, $L^3$, n, p, X, Y and Z can be combined in various manners. These combinations of preferred features thus provide sub-classes of compounds according to the invention. Examples of such sub-classes of preferred compounds according to the invention are:
- preferred features of A with one or more preferred features of $L^1$, $L^2$, $L^3$, n, p, X, Y and Z;
- preferred features of $L^1$ with one or more preferred features of A, $L^2$, $L^3$, n, p, X, Y and Z;

preferred features of $L^2$ with one or more preferred features of A, $L^1$, $L^3$, n, p, X, Y and Z;

preferred features of $L^3$ with one or more preferred features of A, $L^1$, $L^2$, n, p, X, Y and Z;

preferred features of n with one or more preferred features of A, $L^1$, $L^2$, $L^3$, p, X, Y and Z;

preferred features of p with one or more preferred features of A, $L^1$, $L^2$, $L^3$, n, X, Y and Z;

preferred features of X with one or more preferred features of A, $L^1$, $L^2$, $L^3$, n, p, Y and Z;

preferred features of Y with one or more preferred features of A, $L^1$, $L^2$, $L^3$, n, p, X and Z;

preferred features of Z with one or more preferred features of A, $L^1$, $L^2$, $L^3$, n, p, X and Y.

In these combinations of preferred features of the substituents of the compounds according to the invention, the said preferred features can also be selected among the more preferred features of each of A, $L^1$, $L^2$, $L^3$, n, p, X, Y and Z so as to form most preferred subclasses of compounds according to the invention.

Processes for the Preparation of the Active Ingredients

The present invention also relates to processes for the preparation of compounds of formula (I).

Compound of formula (I) or one of its salts as herein-defined can be prepared by a process P1 which comprises the step of reacting a compound of formula (II) or one of its salts with a compound of formula (III) as illustrated by the following reaction scheme:

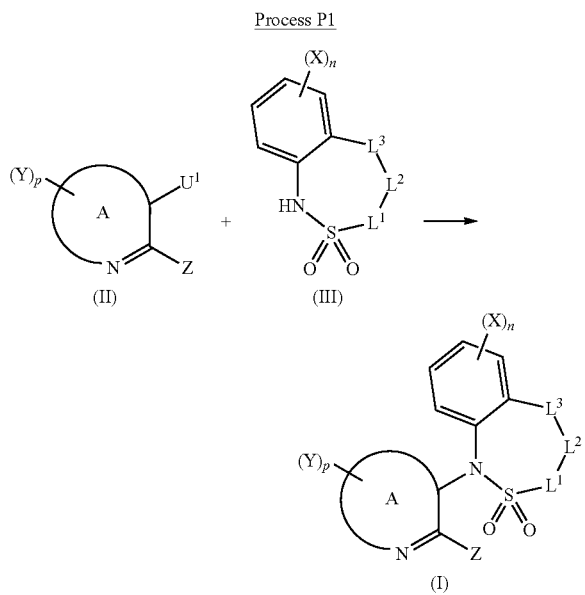

wherein A, n, p, X, Y, Z, $L^1$, $L^2$ and $L^3$ are as herein-defined and $U^1$ is a fluorine atom, a bromine atom, a chlorine atom, an iodine atom, a mesyl group, a tosyl group or a triflyl group.

Process P1 can be performed in the presence of a transition metal catalyst such as a metal salt or complex, and if appropriate in the presence of a ligand; if appropriate in the presence of a base and if appropriate in the presence of a solvent.

Suitable metal derivatives for this purpose are transition metal such as palladium or copper.

Suitable palladium salts or complexes for this purpose are for example, palladium chloride, palladium acetate, tetrakis (triphenylphosphine)palladium(0), bis(dibenzylideneacetone)palladium(0), tris(dibenzylideneacetone)dipalladium (0), bis(triphenylphosphine)palladium(II) dichloride, [1,1'-bis(diphenylphosphino)ferrocene]dichloropalladium(II), bis (cinnamyl)dichlorodipalladium(II), bis(allyl)-dichlorodipalladium(II) or [1,1'-Bis(di-tert-butylphosphino) ferrocene]dichloropalladium(II).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropylbiphenyl 2-dicyclohexylphosphino-2',4',6'-triisopropylbiphenyl, 2-dicyclohexylphosphino-2,6'-dimethoxybiphenyl, 2-dicyclohexylphosphino-2',6'-diisopropoxybiphenyl, triphenylphosphine, tris-(o-tolyl)phosphine, sodium 3-(diphenylphosphino)benzenesulfonate, tris-2-(methoxyphenyl)phosphine, 2,2'-bis(diphenylphosphino)-1,1'-binaphthyl, 1,4-bis(diphenylphosphino)butane, 1,2-bis(diphenylphosphino) ethane, 1,4-bis(dicyclohexylphosphino) butane, 1,2-bis(dicyclohexylphosphino)-ethane, 2-(dicyclohexylphosphino)-2'-(N,N-dimethylamino)-biphenyl, 1,1'-bis(diphenylphosphino)-ferrocene, (R)-(–)-1-[(S)-2-diphenylphosphino)ferrocenyl]ethyldicyclohexylphosphine, tris-(2,4-tert-butyl-phenyl)phosphite, di(1-adamantyl)-2-morpholinophenylphosphine or 1,3-bis(2,4,6-trimethylphenyl)imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

Suitable copper salts or complexes and their hydrates for this purpose are for example, copper metal, copper(I) iodide, copper(I) chloride, copper(I) bromide, copper(II) chloride, copper(II) bromide, copper(II) oxide, copper(I) oxide, copper(II) acetate, copper(I) acetate, copper(I) thiophene-2-carboxylate, copper(I) cyanide, copper(II) sulfate, copper (II) bis(2,2,6,6-tetramethyl-3,5-heptanedionate), copper(II) trifluoromethanesulfonate, tetrakis(acetonitrile)copper(I) hexafluorophosphate, tetrakis(acetonitrile)-copper(I)tetrafluoroborate.

It is also possible to generate a copper complex in the reaction mixture by separate addition to the reaction of a copper salt and a ligand or salt, such as ethylenediamine, N,N-dimethylethylenediamine, N,N'-dimethylethylenediamine, rac-trans-1,2-diaminocyclohexane, rac-trans-N,N'-dimethylcyclohexane-1,2-diamine, 1,1'-binaphthyl-2,2'-diamine, N,N,N',N'-tetramethylethylenediamine, proline, N,N-dimethylglycine, quinolin-8-ol, pyridine, 2-aminopyridine, 4-(dimethylamino)pyridine, 2,2'-bipyridyl, 2,6-di(2-pyridyl)pyridine, 2-picolinic acid, 2-(dimethylaminomethyl)-3-hydroxypyridine, 1,10-phenanthroline, 3,4,7,8-tetramethyl-1,10-phenanthroline, 2,9-dimethyl-1,10-phenanthroline, 4,7-dimethoxy-1,10-phenanthroline, N,N'-bis[(E)-pyridin-2-ylmethylidene]cyclohexane-1,2-diamine, N-[(E)-phenylmethylidene], N-[(E)-phenylmethylidene]-cyclohexanamine, 1,1,1-tris(hydroxymethyl)ethane, ethylene glycol, 2,2,6,6-tetramethylheptane-3,5-dione, 2-(2,2-dimethylpropanoyl)cyclohexanone, acetylacetone, dibenzoylmethane, 2-(2-methylpropanoyl)cyclohexanone, biphenyl-2-yl(di-tert-butyl)phosphane, ethylenebis-(diphenylphosphine), N,N-diethylsalicylamide, 2-hydroxybenzaldehyde oxime, oxo[(2,4,6-trimethylphenyl)amino]acetic acid or 1H-pyrrole-2-carboxylic acid.

It is also advantageous to choose the appropriate catalyst and/or ligand from commercial catalogues such as "Metal Catalysts for Organic Synthesis" by Strem Chemicals or from reviews (Chemical Society Reviews (2014), 43, 3525, Coordination Chemistry Reviews (2004), 248, 2337 and references therein).

Suitable bases for carrying out process P1 can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkaline earth metal, alkali metal or ammonium fluorides such as potassium fluoride, caesium fluoride or tetrabutylammonium fluoride; alkaline earth metal or alkali metal carbonates, such as sodium carbonate, potassium carbonate, potassium bicarbonate, sodium bicarbonate or caesium carbonate; alkali metal or alkaline earth metal acetates, such as sodium acetate, lithium acetate, potassium acetate or calcium acetate; alkali metal alcoholates, such as potassium tert-butoxide or sodium tert-butoxide; alkali metal phosphates, such as tri-potassium phosphate; tertiary amines, such as trimethylamine, triethylamine, tributylamine, N,N-dimethylaniline, N,N-dicyclohexylmethylamine, N,N-diisopropylethylamine, N-methylpiperidine, N,N-dimethylaminopyridine, diazabicyclooctane (DABCO), diazabicyclononene (DBN) or diazabicycloundecene (DBU); and also aromatic bases, such as pyridine, picolines, lutidines or collidines.

Suitable solvents for carrying out process P1 can be customary inert organic solvents. Preference is given to using, optionally halogenated, aliphatic, alicyclic or aromatic hydrocarbons, such as petroleum ether, pentane, hexane, heptane, cyclohexane, methylcyclohexane, benzene, toluene, xylene or decalin; chlorobenzene, dichlorobenzene, dichloromethane, chloroform, carbon tetrachloride, 1,2-dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2 (1H)-pyrimidinone; esters, such as methyl acetate or ethyl acetate, sulfoxides, such as dimethyl sulfoxide, or sulfones, such as sulfolane; and a mixture thereof.

Process P1 may be performed in an inert atmosphere such as argon or nitrogen atmosphere. When carrying out process P1, 1 mole or an excess of compound of formula (III) and from 1 to 5 moles of base can be employed per mole of compound of formula (II). When palladium salts or complexes are used, from 0.01 to 20 mole percent of a palladium complex can be employed per mole of compound of formula (II). When copper salts or complexes are used, from 0.01 to 200 mole percent of a copper complex can be employed per mole of compound of formula (II). It is also possible to employ the reaction components in other ratios. Work-up is carried out by known methods.

A derivative of formula (III) or one of its salts can be prepared by a process P2 which comprises the deprotection of a derivative of formula (IV) as illustrated by the following reaction scheme:

Process P2

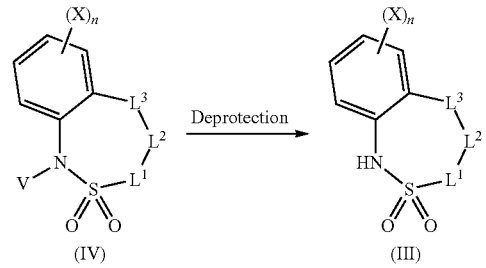

wherein n, X, $L^1$, $L^2$ and $L^3$ are as herein-defined and V represents a benzyl group, a 4-methoxybenzyl group, an allyl group, an unsubstituted or substituted $C_1$-$C_6$-alkylsulfonyl such as a trifluoromethylsulfonyl, an unsubstituted or substituted phenylsulfonyl, such as a tolylsulfonyl, an unsubstituted or substituted $C_1$-$C_6$-alkoxycarbonyl, such as a tert-butoxycarbonyl, an unsubstituted or substituted benzyloxycarbonyl or an allyloxycarbonyl.

Process P2 can be carried out according to known processes for removing protecting groups (Greene's Protective Groups in Organic Synthesis; Peter G. M. Wuts; Wiley; Fifth Edition; 2014; 895-1194).

For example, tert-butoxycarbonyl and benzyloxycarbonyl protecting groups can be removed in an acidic medium (for example with hydrochloric acid or trifluoroacetic acid). Benzylic protecting groups can be removed hydrogenolytically with hydrogen in the presence of a catalyst (for example palladium on activated carbon).

Compounds of formula (IV) can be prepared according to known processes (The Chemistry of Functional Groups—The Chemistry of sulphonic acids, esters and their derivatives; Saul Patai, Avi Rappoport; Wiley-Interscience; 1991; 851-878).

Alternatively, a derivative of formula (III) or one of its salts can be prepared by a process P3 which comprises the deprotection of a derivative of formula (V) as illustrated by the following reaction scheme Process P3

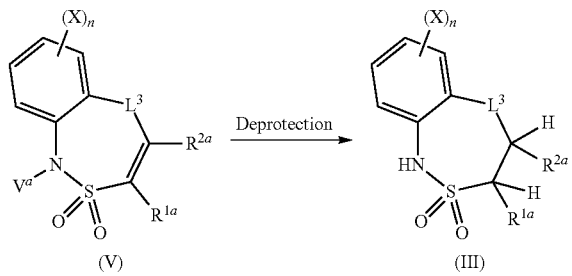

wherein n, X, $R^{1a}$, $R^{2a}$ and $L^3$ are as herein-defined provided that $R^{1a}$ is not a hydroxyl group and that $R^{2a}$ is not a hydroxyl group and $V^a$ represents a benzyl group, a 4-methoxybenzyl group or an unsubstituted or substituted benzyloxycarbonyl.

Process P3 can be carried out according to known processes for removing protecting groups (Greene's Protective Groups in Organic Synthesis; Peter G. M. Wuts; Wiley; Fifth Edition; 2014; 895-1194) such as hydrogenation with hydrogen in the presence of a catalyst (for example palladium on activated carbon).

Compounds of formula (V) can be prepared according to known processes such as a ring closing metathesis (Tetrahedron Letters (2008), 49, 3677-3681).

Compound of formula (I) or one of its salts as herein-defined can be prepared by a process P4 from a compound of formula (VI) or one of its salts by an intermolecular cyclisation reaction as illustrated by the following reaction scheme:

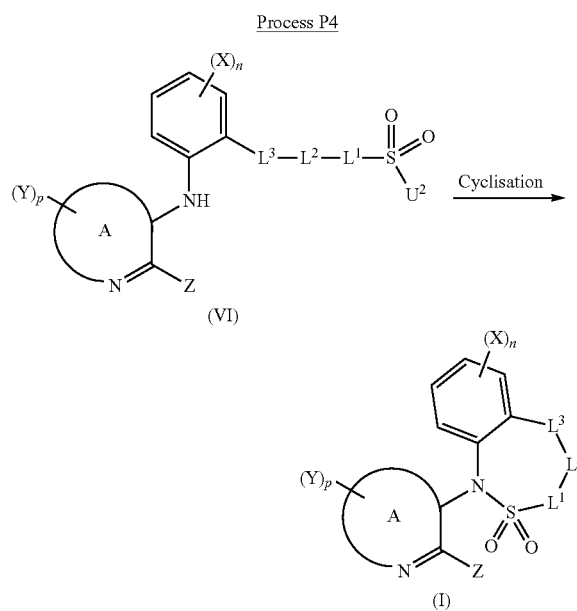

wherein A, $L^1$, $L^2$, $L^3$, n, p, X, Y and Z are as herein-defined and $U^2$ is a chlorine atom or a fluorine atom. If appropriate process P4 can be performed in the presence of a base and if appropriate in the presence of a solvent, preferably under anhydrous conditions.

Suitable solvents for carrying out process P4 are not particularly limited. They can be customary inert organic solvents as long as it is not dissolving the compound to react therewith or exhibit any particular interaction therewith. Preference is given to using, optionally halogenated, aliphatic, alicyclic or aromatic hydrocarbons, such as petroleum ether, pentane, hexane, heptane, cyclohexane, methylcyclohexane, benzene, toluene, xylene, decalin, ISOPAR™ E or ISOPAR™ G, chlorobenzene, dichlorobenzene, dichloromethane, chloroform, carbon tetrachloride, 1,2-dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2(1H)-pyrimidinone; esters, such as methyl acetate or ethyl acetate, sulfoxides, such as dimethyl sulfoxide, or sulfones, such as sulfolane; and a mixture thereof.

Suitable bases for carrying out process P4 can be inorganic and organic bases which are customary for such reactions such as the bases disclosed in connection with process P1. Other suitable bases for carrying out process P4 according to the invention can be amides or organometallic derivatives. Preference is given to alkali metal amides, such as sodium amide or potassium amide; organic amides, such as lithium diisopropylamine (LDA), lithium tetramethylpiperidide, lithium hexamethyldisilazane (LiHMDS), potassium hexamethyldisilazane (KHMDS) or sodium hexamethyldisilazane (NaHMDS); organolithium derivatives, such as methyllithium, phenyllithium, n-butyllithium, sec-butyllithium, iso-butyllithium or tert-butyllithium.

When carrying out process P4, from 1 to 5 moles of base can be employed per mole of compound of formula (VI). It is also possible to employ the reaction components in other ratios. Work-up is carried out by known methods.

Compound of formula (VI) or one of its salts as herein-defined can be prepared by a process P5 from a compound of formula (VII) or one of its salts by a halogenation reaction as illustrated by the following reaction scheme:

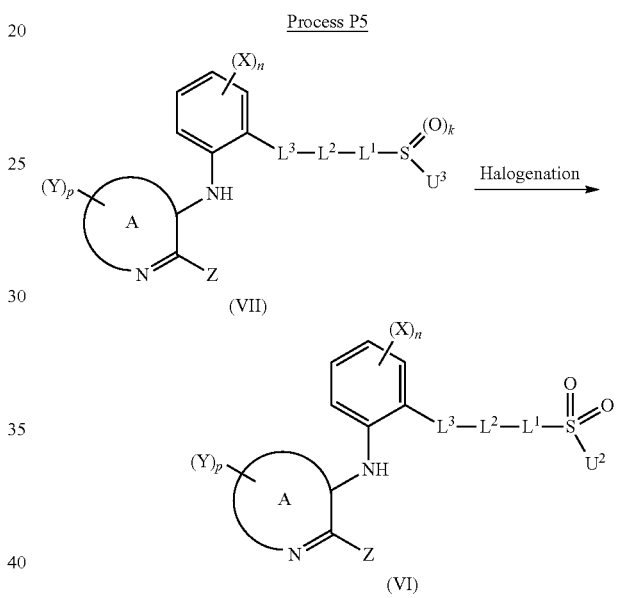

wherein A, $L^1$, $L^2$, $L^3$, n, p, X, Y, Z and $U^2$ are as herein-defined, k is 0, 1 or 2 and $U^3$ is, when k=0, a hydrogen atom, a hydroxyl group, a chlorine atom, an unsubstituted or substituted $C_1$-$C_6$-alkylcarbonyl or an unsubstituted or substituted $C_1$-$C_6$-alkylsulfanyl, when k=1, a hydroxyl group, a chlorine atom or a fluorine atom and when k=2, a hydroxyl group.

Process P5 can be carried out according to known processes (The Chemistry of Functional Groups—The Chemistry of sulphonic acids, esters and their derivatives; Saul Patai, Avi Rappoport; Wiley-Interscience; 1991; 351-399).

Once obtained following process P5, compounds of formula (VI) can directly cyclize to yield compounds of formula (I).

Compounds of formula (VII) can be prepared according to known processes (The Chemistry of Functional Groups—The Chemistry of sulphonic acids, esters and their derivatives; Saul Patai, Avi Rappoport; Wiley-Interscience; 1991; 351-399; The Chemistry of Functional Groups—The Chemistry of sulphenic acids, esters and their derivatives; Saul Patai; Wiley-Interscience; 1990; 187-292; The Chemistry of Functional Groups—The Chemistry of the thiol group, Part 1; Saul Patai; Wiley-Interscience; 1974; 163-270; The Chemistry of Functional Groups—The Chemistry of sulphinic acids, esters and their derivatives; Saul Patai; Wiley-Interscience; 1990; 185-216 and 577-602).

Compound of formula (I) or one of its salts as herein-defined can be prepared by a process P6 from a compound of formula (VIII) or one of its salts by an intermolecular cyclisation reaction:

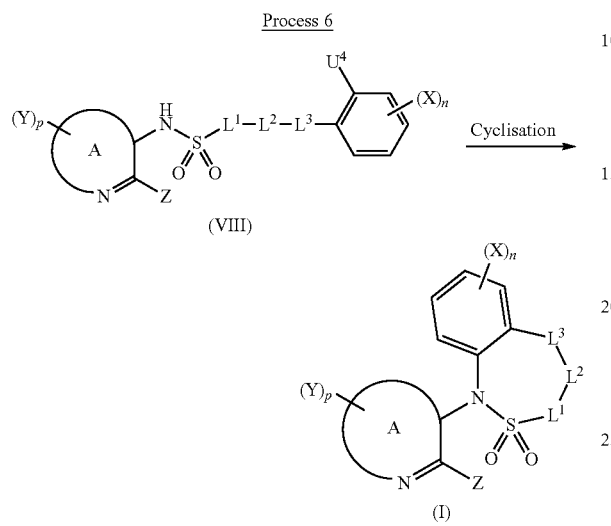

wherein A, n, p, X, Y, Z, $L^1$, $L^2$ and $L^3$ are as herein-defined and $U^4$ is a bromine atom, a chlorine atom, an iodine atom, a mesyl group, a tosyl group, a triflyl group or a fluorine atom.

Process P6 can be performed in the presence of a transition metal catalyst such as palladium and if appropriate in the presence of a phosphine ligand or a N-heterocyclic carbene ligand; or copper and if appropriate in the presence of a ligand; and if appropriate in the presence of a base and if appropriate in the presence of a solvent.

When $U^4$ is a bromine atom, a chlorine atom, an iodine atom, a mesyl group, a tosyl group or a triflyl group, process P6 can be carried out in the presence of a catalyst, such as a metal salt or complex. Suitable metal derivatives for this purpose are transition metal such as palladium or copper.

When $U^4$ is a chlorine atom or a fluorine atom, process P6 can be carried out in the sole presence of a base.

Suitable metal salt or complex can be as disclosed in connection with process P1.

Suitable bases for carrying out process P6 can be inorganic and organic bases which are customary for such reactions, such as for instance the bases disclosed in connection with process P1.

Suitable solvents for carrying out process P6 can be customary inert organic solvents, such as for instance the solvents disclosed in connection with process P1.

Process P6 may be performed in an inert atmosphere such as argon or nitrogen atmosphere. When carrying out process P6, from 1 to 5 moles of base can be employed per mole of compound of formula (VIII). When palladium salts or complexes are used, from 0.01 to 20 mole percent of a palladium complex can be employed per mole of compound of formula (VIII). When copper salts or complexes are used, from 0.01 to 200 mole percent of a copper complex can be employed per mole of compound of formula (VIII). It is also possible to employ the reaction components in other ratios. Work-up is carried out by known methods.

Compounds of formula (VIII) can be prepared according to known processes (The Chemistry of Functional Groups—The Chemistry of sulphonic acids, esters and their derivatives; Saul Patai, Avi Rappoport; Wiley-Interscience; 1991; 351-399).

Compound of formula (Id) or one of its salts as herein-defined can be prepared by a process P7 which comprises the step of reacting a compound of formula (Ic) or one of its salts with a compound of formula (IX) as illustrated by the following reaction scheme:

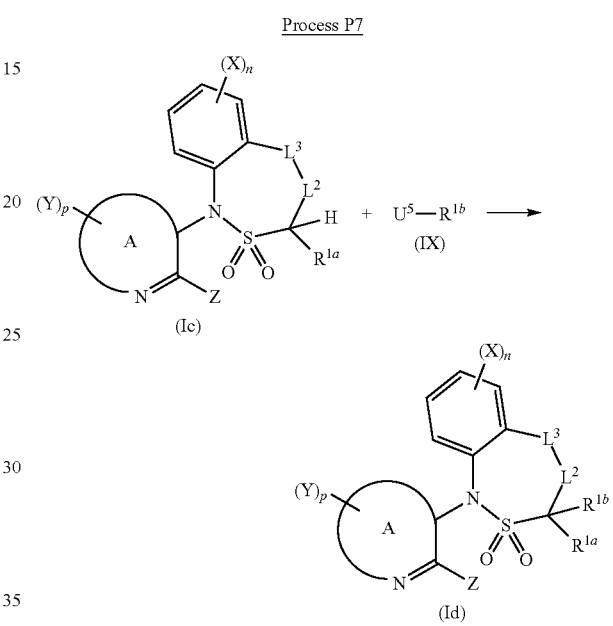

wherein A, n, p, X, Y, Z, $L^2$, $L^3$, $R^{1a}$ and $R^{1b}$ are as herein-defined provided that $R^{1b}$ is not a hydrogen atom, and $U^5$ is a bromine atom, a chlorine atom, an iodine atom, a mesyl group or a tosyl group.

If appropriate, process P7 can be performed in the presence of a base and if appropriate in the presence of a solvent.

Suitable solvents for carrying out process P7 are not particularly limited. They can be customary inert organic solvents as long as it is not dissolving the compound to react therewith or exhibit any particular interaction therewith. Suitable solvents can be for instance the solvents disclosed in connection with process P4.

Suitable bases for carrying out process P7 can be inorganic and organic bases which are customary for such reactions, such as for instance the bases disclosed in connection with processes P1 and P4.

When carrying out process P7, 1 mole or an excess of compound of formula (X) and from 1 to 5 moles of base can be employed per mole of compound of formula (Ic). It is also possible to employ the reaction components in other ratios. Work-up is carried out by known methods.

Compounds of formula (Ic) or one of its salts can be prepared according to process P1.

Compounds of formula (Ie) or one of its salts wherein $R^{1a}$ and $R^{1b}$ together with the carbon atom to which they are linked form a 3-, 4-, 5- or 6-membered, saturated or partially saturated, optionally substituted, carbocycle or heterocycle comprising at least 1 heteroatom selected in the list consisting of N, O and S, or form an unsubstituted or substituted saturated or partially unsaturated bicyclo[$m^1$, $m^2$,0]-$C_6$-$C_{11}$- alkyl wherein $m^2 \geq 1$ and $m^1+m^2=4$ to 9, or form a unsubstituted or substituted saturated or partially unsaturated heterobicyclo[$m^1$, $m^2$,0]-$C_6$-$C_{11}$-alkyl comprising from 1 to 4 heteroatoms independently selected in the list consisting of N, O and S, wherein $m^2 \geq 1$ and $m^1+m^2=4$ to 9, or form an unsubstituted or substituted, saturated or partially unsaturated, spiro[$n^1$,$n^2$]-$C_5$-$C_{11}$-alkyl wherein $n^1 \geq 2$ and $n^1+n^2=4$ to 10, or form an unsubstituted or substituted, saturated or partially unsaturated, heterospiro[$n^1$,$n^2$]-$C_5$-$C_{11}$-alkyl comprising from 1 to 4 heteroatoms independently selected in the list consisting of N, O and S, wherein $n^1 \geq 2$ and $n^1+n^2=4$ to 10, can be prepared by reaction of a compound of formula (I) wherein $R^{1a}$ and $R^{1b}$ are both hydrogen atoms with a compound of formula $U^5$—$R^{1b}$—$R^{1a}$—$U^{5'}$ wherein $U^5$ and $U^{5'}$ are independently a bromine atom, a chlorine atom, an iodine atom, a mesyl group or a tosyl group according to the conditions described for process P7.

Compound of formula (If) or one of its salts as herein-defined can be prepared by a process P8 from a compound of formula (X) or one of its salts by an intramolecular cyclisation reaction as illustrated by the following reaction scheme:

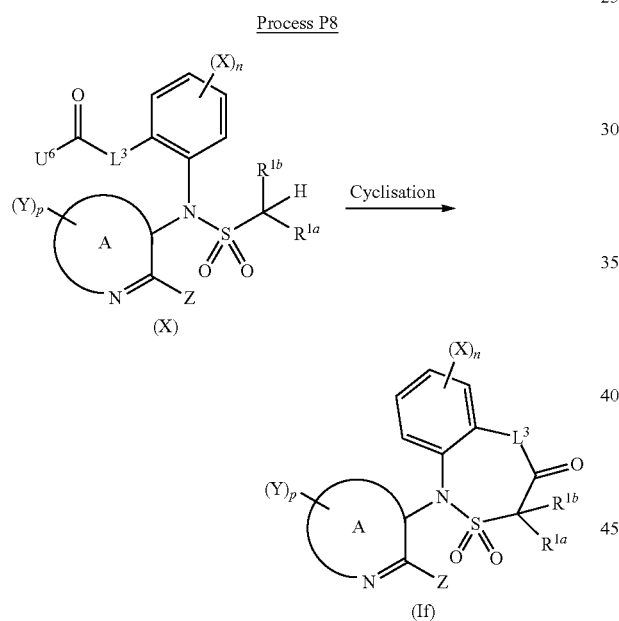

wherein A, n, p, X, Y, Z, $R^{1a}$ and $R^{1b}$ are as herein-defined, $L^3$ is a direct bond, C(=O) or $CR^{3a}R^{3b}$ with $R^{3a}$ and $R^{3b}$ as herein defined and $U^6$ is a leaving group such as an unsubstituted or substituted $C_1$-$C_6$-alkoxy, an unsubstituted or substituted di-$C_1$-$C_8$-alkylamino or an unsubstituted or substituted N—[$C_1$-$C_6$-alkoxy]-$C_1$-$C_6$-alkylamino.

If appropriate process P8 can be performed in the presence of a base and if appropriate in the presence of a solvent, preferably under anhydrous conditions.

Suitable solvents for carrying out process P8 are not particularly limited. They can be customary inert organic solvents as long as it is not dissolving the compound to react therewith or exhibit any particular interaction therewith, such as for instance the solvents disclosed in connection with process P4.

Suitable bases for carrying out process P8 can be inorganic and organic bases which are customary for such reactions, such as for instance the bases disclosed in connection with processes P1 and P4.

When carrying out process P8, from 1 to 5 moles of base can be employed per mole of compound of formula (X). It is also possible to employ the reaction components in other ratios. Work-up is carried out by known methods.

Compound of formula (X) or one of its salts as herein-defined can be prepared by a process P9 which comprises the step of reacting a compound of formula (XI) or one of its salts:

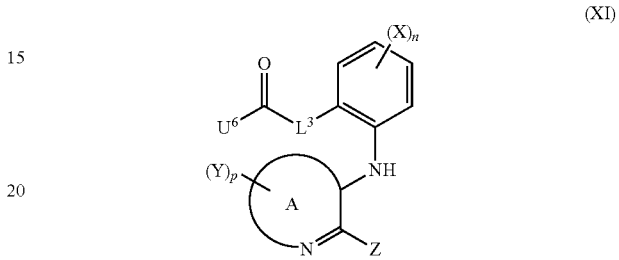

wherein A, n, p, X, Y and Z are as herein-defined, $L^3$ represents a bond, C(=O) or $CR^{3a}R^{3b}$ and $R^{3a}$ and $R^{3b}$ are herein defined and $U^6$ represents a leaving group such as an unsubstituted or substituted $C_1$-$C_6$-alkoxy, an unsubstituted or substituted di-$C_1$-$C_8$-alkylamino or an unsubstituted or substituted N—[$C_1$-$C_6$-alkoxy]-$C_1$-$C_6$-alkylamino; with a derivative of formula (XIIa) or a derivative of formula (XIIb):

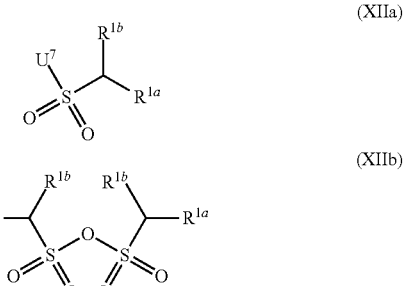

wherein $R^{1a}$ and $R^{1b}$ are as herein-defined and $U^7$ is a fluorine atom or a chlorine atom.

If appropriate process P9 can be performed in the presence of a base and if appropriate in the presence of a solvent, preferably under anhydrous conditions.

Suitable solvents for carrying out process P9 are not particularly limited. They can be customary inert organic solvents as long as it is not dissolving the compound to react therewith or exhibit any particular interaction therewith, such as for instance the solvents disclosed in connection with process P4.

Suitable bases for carrying out process P9 can be inorganic and organic bases which are customary for such reactions, such as for instance the bases disclosed in connection with processes P1 and P4.

When carrying out process P9, 1 mole or an excess of compound of formula (XIIa) or (XIIb) and from 1 to 5 moles of base can be employed per mole of compound of formula (XI). It is also possible to employ the reaction components in other ratios. Work-up is carried out by known methods.

Compound of formula (XI) or one of its salts as herein-defined can be prepared by a process P10 which comprises the step of reacting a compound of formula (II) or one of its salts with a compound of formula (XIII) as illustrated by the following reaction scheme:

Process P10

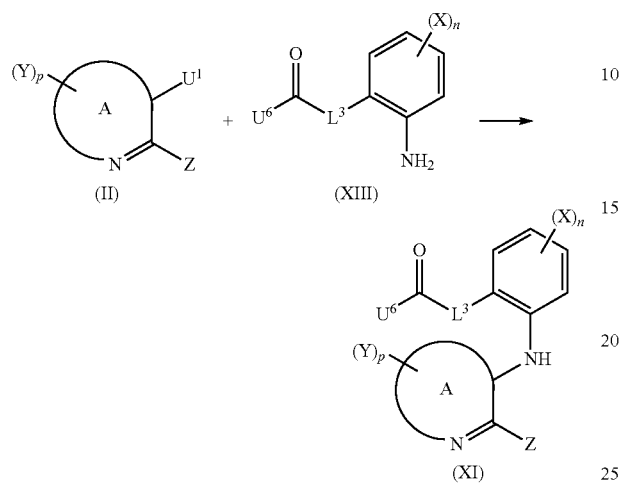

wherein A, n, p, X, Y, Z, $L^1$, $L^2$ are as herein-defined, $L^3$ represents a bond, C(=O) or $CR^{3a}R^{3b}$ and $R^{3a}$ and $R^{3b}$ are herein defined, $U^1$ is a fluorine atom, a bromine atom, a chlorine atom, an iodine atom, a mesyl group, a tosyl group or a triflyl group and $U^6$ represents a leaving group such as an unsubstituted or substituted $C_1$-$C_6$-alkoxy, an unsubstituted or substituted di-$C_1$-$C_8$-alkylamino or an unsubstituted or substituted N—[$C_1$-$C_6$-alkoxy]-$C_1$-$C_6$-alkylamino.

Process P10 can be carried out with the similar reactions conditions than the ones disclosed in process P1.

Compound of formula (Ih) or one of its salts as herein-defined can be prepared by a process P11 from a compound of formula (Ig) or one of its salts by a chlorination reaction as illustrated by the following reaction scheme:

Process P11

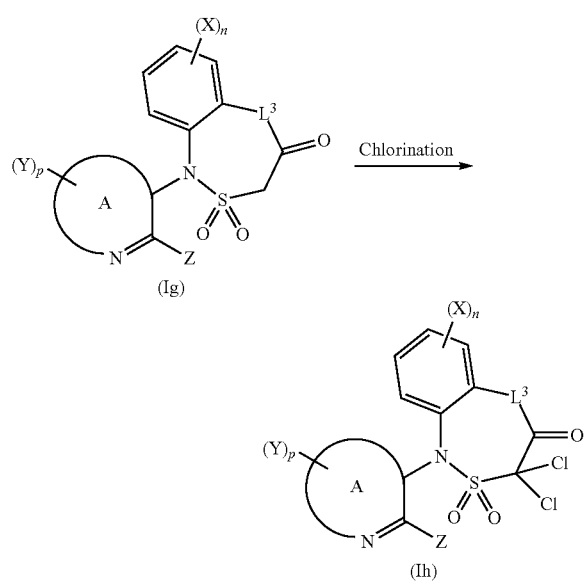

wherein A, n, p, X, Y and Z are as herein-defined, $L^3$ is a direct bond or $CR^{3a}R^{3b}$ with $R^{3a}$ and $R^{3b}$ as herein defined.

Process P11 can be carried out according to known processes (Asian Journal of Chemistry (2011), 23, 2101-2105).

Compound of formula (Ii) or one of its salts as herein-defined can be prepared by a process P12 from a compound of formula (If) or one of its salts by a fluorination reaction as illustrated by the following reaction scheme:

Process P12

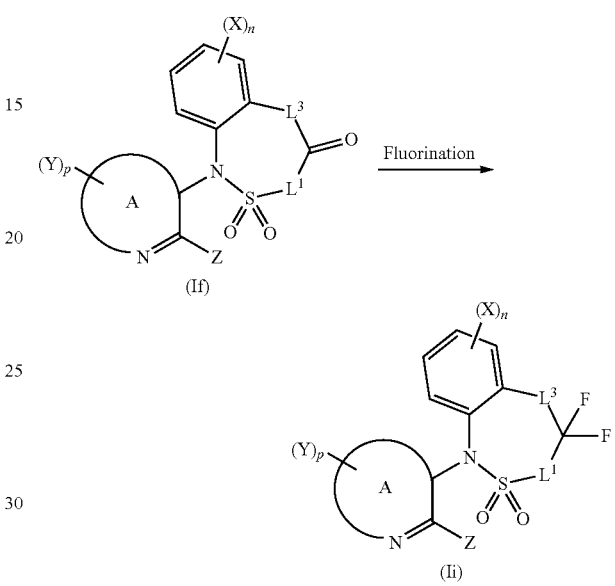

wherein A, n, p, X, Y, Z, $L^1$ and $R^{1b}$ are as herein-defined, $L^3$ is a direct bond or $CR^{3a}R^{3b}$ with $R^{3a}$ and $R^{3b}$ as herein defined.

Process P12 can be performed in the presence of a fluorinating agent and if appropriate in the presence of a solvent.

Suitable fluorinating agents for carrying out process P12 are not particularly limited provided they are used for fluorination. Examples of fluorinating agents include sulfur fluorides such as sulfur tetrafluoride, diehtylaminosulfurtrifluoride, morpholinosulfur trifluoride, bis(2-methoxyethyl) aminosulfur trifluoride, 2,2-difluoro-1,3-dimethylimidazolidine or 4-tert-butyl-2,6-dimethylphenylsulfur trifluoride, Suitable solvents for carrying out process P12 are not particularly limited. They can be customary inert organic solvents as long as it is not dissolving the compound to react therewith or exhibit any particular interaction therewith. Suitable solvents can be for instance the solvents disclosed in connection with process P4.

When carrying out process P12, 1 to 20 moles of fluorinating agent can be employed per mole of compound of formula (If). It is also possible to employ the reaction components in other ratios. Work-up is carried out by known methods.

Compounds of formula (If) or one of its salts can be prepared according to process P8.

Compound of formula (Ik) or one of its salts as herein-defined can be prepared by a process P13 from a compound of formula (Ij) or one of its salts by a fluorination reaction as illustrated by the following reaction scheme:

Process P13

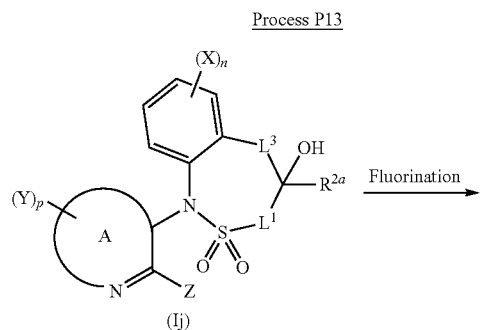

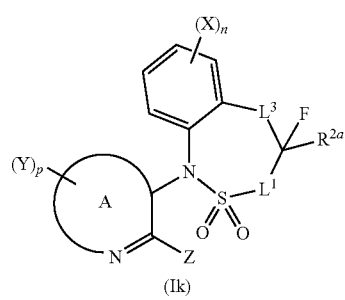

wherein A, n, p, X, Y, Z, $L^1$ and $R^{2a}$ are as herein-defined, $L^3$ is a direct bond, $C(=O)$ or $CR^{3a}R^{3b}$ with $R^{3a}$ and $R^{3b}$ as herein defined.

Process P13 can be carried out with the similar reactions conditions than the ones disclosed in process P12.

Compounds of formula (j) or one of its salts can be prepared from a compound of formula (If) or one of its salts with classical functional group interconversion methods known by the person skilled in the art such as reductions or additions of an organometallic reagent.

Compound of formula (Im) or one of its salts as herein-defined can be prepared from a compound of formula (Ij) or one of its salts by classical methods known by the person skilled in the art such as alkylations, nucleophilic aromatic substitutions or transition metal-catalyzed reactions.

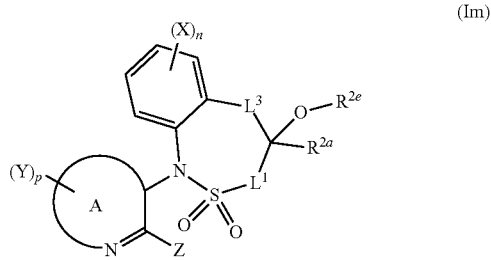

wherein A, n, p, X, Y, Z, $L^1$, $R^{2a}$ and $R^{3e}$ are as herein-defined, $L^3$ is a direct bond, $C(=O)$ or $CR^{3a}R^{3b}$ with $R^{3a}$ and $R^{3b}$ as herein defined.

Compound of formula (In) or one of its salts as herein-defined can be prepared from a compound of formula (Ij) or one of its salts by classical methods known by the person skilled in the art such as hydroxylamine or O-substituted hydroxylamine condensations.

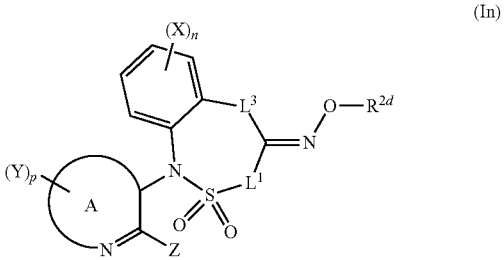

wherein A, n, p, X, Y, Z and $R^{2d}$ are as herein-defined, $L^3$ is a direct bond, $C(=O)$ or $CR^{3a}R^{3b}$ with $R^{3a}$ and $R^{3b}$ as herein defined.

The corresponding N-oxides of compounds of formula (I) can be prepared by classical oxidation methods known by the person skilled in the art.

Processes P1, P2, P3, P4, P5, P6, P7, P8, P9, P10, P11, P12 and P13 are generally carried out under atmospheric pressure. It is also possible to operate under elevated or reduced pressure.

When carrying out processes P1, P2, P3, P4, P5, P6, P7, P8, P9, P10, P11, P12 and P13, the reaction temperatures can be varied within a relatively wide range. In general, these processes are carried out at temperatures from −78° C. to 200° C., preferably from −78° C. to 150° C. A way to control the temperature for the processes is to use microwave technology.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, crystallization or distillation, from any impurities that may still be present.

The compounds of formula (I) can be prepared according to the general processes of preparation described above and by classical functional group interconversion methods known by the person skilled in the art. It will nevertheless be understood that, on the basis of his general knowledge and of available publications, the skilled worker will be able to adapt the methods according to the specifics of each compound, which it is desired to synthesize.

Intermediates for the Preparation of the Active Ingredients

The present invention also relates to intermediates for the preparation of compounds of formula (I).

Thus, the present invention relates to compounds of formula (IIIa) and (IVa) as well as their acceptable salts:

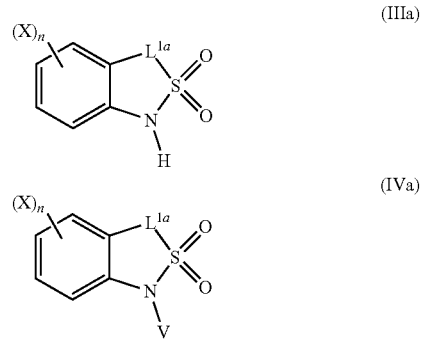

wherein:

X and n are as herein-defined;

$L^1a$ represents $CR^{1a}R^{1b}$ with $R^{1a}$ and $R^{1b}$ as herein defined provided that at least one of $R^{1a}$ or $R^{1b}$ is not a hydrogen atom; and V is a benzyl group, a 4-methoxybenzyl group, an allyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl or an allyloxycarbonyl;

provided that the compound of formula (IIIa) or (IVa) does not represent:

4-chloro-3-fluoro-1,3-dihydro-2,1-benzothiazol-7-amine 2,2-dioxide [1503771-33-2],
4-chloro-3-fluoro-7-nitro-1,3-dihydro-2,1-benzothiazole 2,2-dioxide [1503771-32-1],
3-(2,2-dioxido-1,3-dihydro-2,1-benzothiazol-3-yl)propanenitrile [736178-12-4],
5-(3-chlorophenyl)-1H-spiro[2,1-benzothiazole-3,1'-cyclohexane] 2,2-dioxide [304681-96-7],
4-chloro-1H-spiro[2,1-benzothiazole-3,1'-cyclopentan]-7-amine 2,2-dioxide [221010-70-4],
4-chloro-7-nitro-1H-spiro[2,1-benzothiazole-3,1'-cyclopentane] 2,2-dioxide [221010-67-9],
4-chloro-1H-spiro[2,1-benzothiazole-3,1'-cyclopentane] 2,2-dioxide [221010-65-7],
4-chloro-3,3-dimethyl-1,3-dihydro-2,1-benzothiazol-7-amine 2,2-dioxide [220973-37-5],
4-chloro-3,3-dimethyl-7-nitro-1,3-dihydro-2,1-benzothiazole 2,2-dioxide [220973-36-4],
4-chloro-3-propyl-1,3-dihydro-2,1-benzothiazol-7-amine 2,2-dioxide [220973-33-1],
4-chloro-7-nitro-3-propyl-1,3-dihydro-2,1-benzothiazole 2,2-dioxide [220973-32-0],
4-chloro-3-propyl-1,3-dihydro-2,1-benzothiazole 2,2-dioxide [220973-31-9],
4-chloro-3-methyl-1,3-dihydro-2,1-benzothiazol-7-amine 2,2-dioxide [220973-29-5],
4-chloro-3-methyl-7-nitro-1,3-dihydro-2,1-benzothiazole 2,2-dioxide [220973-27-3],
4-chloro-3-methyl-1,3-dihydro-2,1-benzothiazole 2,2-dioxide [220973-26-2],
3,3-diphenyl-1,3-dihydro-2,1-benzothiazole 2,2-dioxide [176684-30-3],
3-phenyl-1,3-dihydro-2,1-benzothiazole 2,2-dioxide [176684-29-0],
3,3-dimethyl-1,3-dihydro-2,1-benzothiazole 2,2-dioxide [176684-28-9],
3-methyl-1,3-dihydro-2,1-benzothiazole 2,2-dioxide [176684-27-8],
3-(1-benzyl-2,2-dioxido-1,3-dihydro-2,1-benzothiazol-3-yl)propanenitrile [736178-15-7],
1-benzyl-3,3-dimethyl-4-nitro-1,3-dihydro-2,1-benzothiazole 2,2-dioxide [155243-23-5],
1-benzyl-5-methyl-6-nitro-1',3'-dihydro-1H-spiro[2,1-benzothiazole-3,2'-indene] 2,2-dioxide [153431-67-5],
1-allyl-4-chloro-1H-spiro[2,1-benzothiazole-3,1-cyclopentane] 2,2-dioxide [221010-64-6],
1-allyl-4-chloro-3-fluoro-3-methyl-1,3-dihydro-2,1-benzothiazol-7-amine 2,2-dioxide [220973-39-7],
1-allyl-4-chloro-3,3-dimethyl-7-nitro-1,3-dihydro-2,1-benzothiazole 2,2-dioxide [220973-35-3],
1-allyl-4-chloro-3-propyl-1,3-dihydro-2,1-benzothiazole 2,2-dioxide [220973-30-8],
1-allyl-4-chloro-3-methyl-1,3-dihydro-2,1-benzothiazole 2,2-dioxide [220973-25-1],
1-allyl-4-chloro-3-fluoro-7-nitro-1,3-dihydro-2,1-benzothiazole 2,2-dioxide [220973-22-8], and
1,3-diallyl-4-nitro-1,3-dihydro-2,1-benzothiazole 2,2-dioxide [155243-30-4].

The following compound of formula (IIIa) or (IVa) wherein X and n are as herein-defined, $L^{1a}$ is $CR^{1a}R^{1b}$ with $R^{1a}$ and $R^{1b}$ as herein defined provided that at least one of $R^{1a}$ or $R^{1b}$ is a not hydrogen atom and V is a benzyl group, a 4-methoxybenzyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl or an allyloxycarbonyl, is also mentioned in chemical databases and/or suppliers' databases but without any references or information which enable this to be prepared and separated:

5-bromo-2',3',5',6'-tetrahydro-1H-spiro[2,1-benzothiazole-3,4'-pyran] 2,2-dioxide [1251001-33-8].

The present invention also relates to compounds of formula (IIIb1) and (IVb1) as well as their acceptable salts:

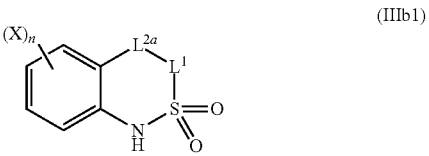

(IIIb1)

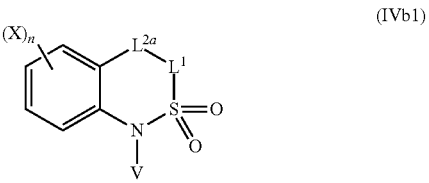

(IVb1)

wherein:

X, n and $L^1$ are as herein-defined;

$L^{2a}$ is C(=O) or $CR^{2a}R^{2b}$ with $R^{2a}$ and $R^{2b}$ as herein defined provided that at least one of $R^{2a}$ or $R^{2b}$ is not a hydrogen atom; and V is a benzyl group, a 4-methoxybenzyl group, an allyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl or allyloxycarbonyl, provided that the compound of formula (IIIb1) or (IVb1) does not represent:

1H-2,1-benzothiazin-4(3H)-one 2,2-dioxide [7117-28-4],
6-bromo-1H-2,1-benzothiazin-4(3H)-one 2,2-dioxide [13568-93-9],
6-iodo-1H-2,1-benzothiazin-4(3H)-one 2,2-dioxide [658709-22-9],
6-fluoro-1H-2,1-benzothiazin-4(3H)-one 2,2-dioxide [1708370-70-0],
6-methoxy-1H-2,1-benzothiazin-4(3H)-one 2,2-dioxide [364614-33-5],
4-oxo-3,4-dihydro-1H-2,1-benzothiazine-7-carboxylic acid 2,2-dioxide [577971-78-9],
6-nitro-1H-2,1-benzothiazin-4(3H)-one 2,2-dioxide [143184-89-8],
6-(trifluoromethyl)-1H-2,1-benzothiazin-4(3H)-one 2,2-dioxide [13581-98-1],
6-(pyridin-3-yl)-1H-2,1-benzothiazin-4(3H)-one 2,2-dioxide [1644658-85-4],
4-methyl-3,4-dihydro-1H-2,1-benzothiazine 2,2-dioxide [76653-05-9], 4-phenyl-3,4-dihydro-1H-2,1-benzothiazine 2,2-dioxide [3192-11-8],
1-benzyl-1H-2,1-benzothiazin-4(3H)-one 2,2-dioxide [31846-95-4],
1-benzyl-6-bromo-1H-2,1-benzothiazin-4(3H)-one 2,2-dioxide [1644658-88-7],
1-benzyl-3-ethyl-1H-2,1-benzothiazin-4(3H)-one 2,2-dioxide [1064656-49-0],
1-benzyl-3,3-dibromo-1H-2,1-benzothiazin-4(3H)-one 2,2-dioxide [1308887-75-3],
1-benzyl-3,3-dichloro-1H-2,1-benzothiazin-4(3H)-one 2,2-dioxide [1308887-76-4],
1-benzyl-6-(pyridin-3-yl)-1H-2,1-benzothiazin-4(3H)-one 2,2-dioxide [1644658-89-8],
1-benzyl-3-phenyl-1H-2,1-benzothiazin-4(3H)-one 2,2-dioxide [1064656-60-5],
1-benzyl-6-methyl-3-phenyl-1H-2,1-benzothiazin-4(3H)-one 2,2-dioxide [1064657-04-0],
1-benzyl-8-methyl-3-phenyl-1H-2,1-benzothiazin-4(3H)-one 2,2-dioxide [1064657-24-4],
1-benzyl-3-(4-fluorophenyl)-1H-2,1-benzothiazin-4(3H)-one 2,2-dioxide [1064656-69-4],
1-benzyl-3-(4-chlorophenyl)-1H-2,1-benzothiazin-4(3H)-one 2,2-dioxide [1064656-74-1],
1-benzyl-6-chloro-3-phenyl-1H-2,1-benzothiazin-4(3H)-one 2,2-dioxide [1064657-08-4],
1-benzyl-6-methoxy-3-phenyl-1H-2,1-benzothiazin-4(3H)-one 2,2-dioxide [1064656-92-3],
1-benzyl-7-chloro-3-phenyl-1H-2,1-benzothiazin-4(3H)-one 2,2-dioxide [1064657-18-6],
1-benzyl-3-(4-nitrophenyl)-1H-2,1-benzothiazin-4(3H)-one 2,2-dioxide [1064656-82-1],
1-benzyl-8-methoxy-3-phenyl-1H-2,1-benzothiazin-4(3H)-one 2,2-dioxide [1064657-21-1],
1-benzyl-3-[4-(trifluoromethyl)phenyl]-1H-2,1-benzothiazin-4(3H)-one 2,2-dioxide [1064656-79-6],
1-benzyl-3-(2-nitrophenyl)-1H-2,1-benzothiazin-4-ol 2,2-dioxide [1064656-64-9],
1-(4-methoxybenzyl)-1H-2,1-benzothiazin-4(3H)-one 2,2-dioxide and [1260918-17-9],
1-(4-methoxybenzyl)-3-phenyl-1H-2,1-benzothiazin-4(3H)-one 2,2-dioxide [1064656-86-5],
1-benzyl-4-(4-fluorophenyl)-7-methoxy-3,4-dihydro-1H-2,1-benzothiazine 2,2-dioxide [1957224-47-3],
1-allyl-3,3-dimethyl-6-(methylsulfanyl)-3,4-dihydro-1H-2,1-benzothiazin-4-ol 2,2-dioxide [374920-02-2],
1-(4-methoxybenzyl)-3-phenyl-1H-2,1-benzothiazin-4(3H)-one 2,2-dioxide [1064656-86-5],
1-allyl-1H-2,1-benzothiazin-4(3H)-one 2,2-dioxide [1222434-90-3],
1-allyl-7-bromo-1H-2,1-benzothiazin-4(3H)-one 2,2-dioxide [1418316-00-3],
1-allyl-6-(methylsulfanyl)-1H-2,1-benzothiazin-4(3H)-one 2,2-dioxide [374919-40-1],
1-allyl-3,3-dimethyl-6-(methylsulfanyl)-1H-2,1-benzothiazin-4(3H)-one 2,2-dioxide [374919-43-4],
methyl 1-allyl-4-oxo-3,4-dihydro-1H-2,1-benzothiazine-8-carboxylate 2,2-dioxide [1418315-98-6],
(3Z)-1-allyl-7-bromo-3-[(dimethylamino)methylene]-1H-2,1-benzothiazin-4(3H)-one 2,2-dioxide [1418316-02-5],
methyl 1-allyl-4-hydroxy-1H-2,1-benzothiazine-3-carboxylate 2,2-dioxide [1492047-40-1], and
1-allyl-4-hydroxy-N-(4H-1,2,4-triazol-3-yl)-1H-2,1-benzothiazine-3-carboxamide 2,2-dioxide [1673590-81-2].

The following compounds of formula (IIIb1) or (IVb1) wherein X, n and L¹ are as herein-defined, L$^{2a}$ is C(=O) or CR$^{2a}$R$^{2b}$ with R$^{2a}$ and R$^{2b}$ as herein defined provided that at least one of R$^{2a}$ or R$^{2b}$ is not a hydrogen atom and V is a benzyl group, a 4-methoxybenzyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl or an allyloxycarbonyl, are also mentioned in chemical databases and/or suppliers' databases but without any references or information which enable these to be prepared and separated:

1-benzyl-6-chloro-1H-2,1-benzothiazin-4(3H)-one 2,2-dioxide [1255783-37-9],
1-benzyl-7-chloro-1H-2,1-benzothiazin-4(3H)-one 2,2-dioxide [219864-33-2],
(3Z)-1-benzyl-3-[(dimethylamino)methylene]-1H-2,1-benzothiazin-4(3H)-one 2,2-dioxide [1255790-83-0], and
(3Z)-1-benzyl-7-chloro-3-[(dimethylamino)methylene]-1H-2,1-benzothiazin-4(3H)-one 2,2-dioxide [219864-37-6], and
1-allyl-6-bromo-1H-2,1-benzothiazin-4(3H)-one 2,2-dioxide [1222407-84-2].

The present invention also relates to compounds of formula (IIIb2) and (IVb2) as well as their acceptable salts:

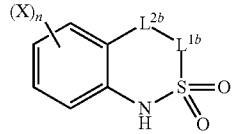

(IIIb2)

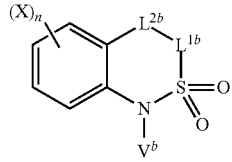

(IVb2)

wherein:
X and n are as herein-defined;
L¹ is CR$^{1a}$R$^{1b}$ with R$^{1a}$ and R$^{1b}$ as herein defined provided that at least one of R$^{1a}$ or R$^{1b}$ is not a hydrogen atom;
L$^{2b}$ is O, S, S(O), SO$_2$, NR$^{2c}$ with NR$^{2c}$ as herein defined; and
V$^b$ is a benzyl group, a 4-methoxybenzyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl or an allyloxycarbonyl; provided that the compound of formula (IIIb2) or (IVb2) does not represent:

3-(3-chloropropyl)-1H-2,4,1-benzodithiazine 2,2-dioxide [1033629-43-4],
3-(3-chloropropyl)-7-phenyl-1H-4,2,1-benzoxathiazine 2,2-dioxide [1033629-36-5],
7-chloro-3-(3-chloropropyl)-1H-4,2,1-benzoxathiazine 2,2-dioxide [1033629-33-2],
3-(3-chloropropyl)-6-methoxy-1H-4,2,1-benzoxathiazine 2,2-dioxide [1033629-30-9],
3-(3-chloropropyl)-6-methyl-1H-4,2,1-benzoxathiazine 2,2-dioxide [1033629-27-4],
3-(3-chloropropyl)-7-methyl-1H-4,2,1-benzoxathiazine 2,2-dioxide [1033629-24-1],
3-(3-chloropropyl)-8-methyl-1H-4,2,1-benzoxathiazine 2,2-dioxide [1033629-21-8], 3-(3-chloropropyl)-8-fluoro-1H-4,2,1-benzoxathiazine 2,2-dioxide [1033629-18-3],
3-(3-chloropropyl)-5-fluoro-1H-4,2,1-benzoxathiazine 2,2-dioxide [1033629-15-0],
3-(3-chloropropyl)-6-fluoro-1H-4,2,1-benzoxathiazine 2,2-dioxide [1033629-12-7],
6-chloro-3-(3-chloropropyl)-1H-4,2,1-benzoxathiazine 2,2-dioxide [1033629-10-5],
3-(3-chloropropyl)-7-fluoro-1H-4,2,1-benzoxathiazine 2,2-dioxide [1033629-07-0],
3-(3-chloropropyl)-1H-4,2,1-benzoxathiazine 2,2-dioxide [1033628-91-9],
3-(3-chloropropyl)-1-(4-methoxybenzyl)-1H-4,2,1-benzoxathiazine 2,2-dioxide [1033628-90-8],
3-[1-(4-methoxybenzyl)-2,2-dioxido-1H-4,2,1-benzoxathiazin-3-yl]propan-1-ol [1033628-89-5], and
3-allyl-1-(4-methoxybenzyl)-1H-4,2,1-benzoxathiazine 2,2-dioxide [1033628-88-4].

The present invention also relates to compounds of formula (IIIc) an (IVc) as well as their acceptable salts:

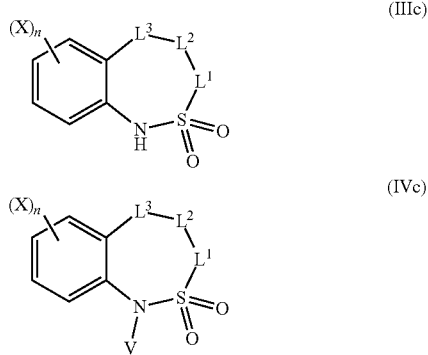

wherein:
X, n, $L^1$, $L^2$ and $L^3$ are as herein-defined provided that $L^2$ is not a direct bond, $L^3$ is not a direct bond or $NR^{3c}$; and
V is a benzyl group, a 4-methoxybenzyl group, an allyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl or an allyloxycarbonyl;
provided that the compound of formula (IIIc) does not represent:
8-chloro-3,4-dihydro-1H-5,2,1-benzoxathiazepine 2,2-dioxide [90245-52-6],
1,3,4,5-tetrahydro-2,1-benzothiazepine 2,2-dioxide-thallium (1:1) [90220-55-6],
3,4-dihydro-1H-5,2,1-benzoxathiazepine 2,2-dioxide [90220-51-2],
6,9-dichloro-1,3,4,5-tetrahydro-2,1-benzothiazepine 2,2-dioxide [90220-50-1],
6-chloro-1,3,4,5-tetrahydro-2,1-benzothiazepine 2,2-dioxide [90220-49-8],
7,9-dimethyl-1,3,4,5-tetrahydro-2,1-benzothiazepine 2,2-dioxide [90220-47-6],
5,5-dimethyl-1,3,4,5-tetrahydro-2,1-benzothiazepine 2,2-dioxide [90220-46-5],
5-methyl-1,3,4,5-tetrahydro-2,1-benzothiazepine 2,2-dioxide [90220-45-4], and
1,3,4,5-tetrahydro-2,1-benzothiazepine 2,2-dioxide [80639-72-1], The followings compounds of formula (IIIc) or (IVc) wherein X, n, $L^1$, $L^2$ and $L^3$ are as herein-defined and V is a benzyl group, a 4-methoxybenzyl group, an allyl group, an unsubstituted or substituted $C_1$-$C_6$-alkylsulfonyl, a trifluoromethylsulfonyl, an unsubstituted or substituted phenylsulfonyl, an unsubstituted or substituted $C_1$-$C_6$-alkoxycarbonyl, an unsubstituted or substituted benzyloxycarbonyl or an allyloxycarbonyl, are also mentioned in chemical databases and/or suppliers' databases but without any references or information which enable these to be prepared and separated:
1-allyl-1,3,4,5-tetrahydro-2,1,5-benzothiadiazepine 2,2-dioxide [1896790-15-0].

The present invention also relates to compounds of formula (V) as well as their acceptable salts:

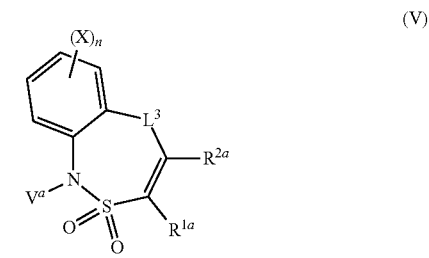

wherein:
X, n, $R^{1a}$, $R^{2a}$ and $L^3$ are as herein-defined provided that $R^{1a}$ is not a hydroxyl group and that $R^{2a}$ is not a hydroxyl group; and
$V^a$ represents a benzyl group, a 4-methoxybenzyl group or an unsubstituted or substituted benzyloxycarbonyl.

The present invention also relates to compounds of formula (Via) and (Via) as well as their salts:

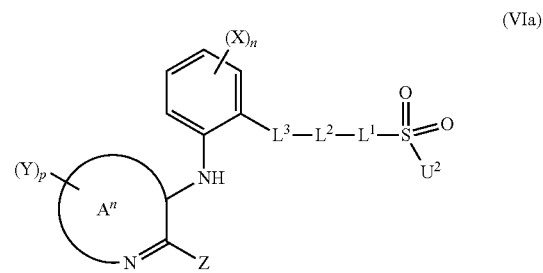

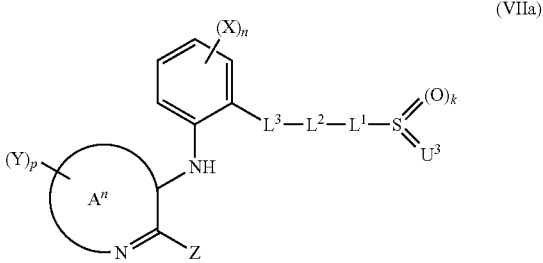

wherein:
X, Y, Z, n, p, $L^1$, $L^2$ and $L^3$ are as herein-defined;
$A^n$ is selected in the list consisting of $A^1$ to $A^{19}$ as herein-defined;
k is 0, 1 or 2;
$U^2$ is a chlorine atom or a fluorine atom; and $U^3$ is, when k=0, a hydrogen atom, hydroxyl group, a chlorine atom, an unsubstituted or substituted $C_1$-$C_6$-alkyl-carbonyl or an unsubstituted or substituted $C_1$-$C_6$-alkylsulfanyl, when k=1, a hydroxyl group, a chlorine atom or a fluorine atom and when k=2, a hydroxyl group.

The present invention also relates to compounds of formula (VIIa) as well as their salts:

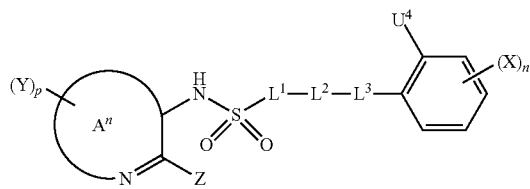

(VIIIa)

wherein:
X, Y, Z, n, p, $L^1$, $L^2$ and $L^3$ are as herein-defined;
$A^n$ is selected in the list consisting of $A^1$ to $A^{19}$ as herein-defined; and
$U^4$ is a fluorine atom, a chlorine atom, a bromine atom, an iodine atom, a mesyl group, a tosyl group, a mesyl group or a triflyl group.

The followings compounds of formula (VIIa) wherein X, Y, Z, n, p, $L^1$, $L^2$ and $L^3$ are as herein-defined, An is selected in the list consisting of $A^1$ to $A^{19}$ and $U^4$ is a fluorine atom, a chlorine atom, a bromine atom, an iodine atom, a mesyl group, a tosyl group or a triflyl group are also mentioned in chemical databases and/or suppliers' databases but without any references or information which enable these to be prepared and separated:
1-(2,6-difluorophenyl)-N-(quinoxalin-2-yl)methanesulfonamide [1808755-71-6],
1-(2-chlorophenyl)-N-(quinolin-3-yl)methanesulfonamide [1791294-94-4],
1-(2,5-difluorophenyl)-N-(2-methylpyrazolo[1,5-a]pyrimidin-6-yl)methanesulfonamide [1795299-90-9], and
1-(2-chlorophenyl)-N-(1H-imidazo[4,5-b]pyridin-6-yl)methanesulfonamide [1795388-97-4].

The present invention also relates to compounds of formula (Xa) as well as their salts

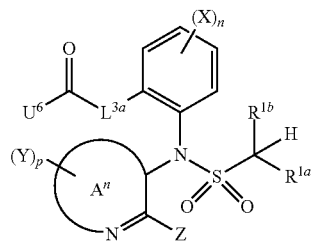

(Xa)

wherein:
n, p, X, Y, Z, $R^{1a}$ and $R^{1b}$ are as herein-defined;
$A^n$ is selected in the list consisting of $A^1$ to $A^{19}$ as herein-defined;
$L^{3a}$ is a direct bond, C(=O) or $CR^{3a}R^{3b}$ with $R^{3a}$ and $R^{3b}$ as herein defined; and
$U^6$ is an unsubstituted or substituted $C_1$-$C_6$-alkoxy, an unsubstituted or substituted di-$C_1$-$C_8$-alkylamino or an unsubstituted or substituted N—[$C_1$-$C_6$-alkoxy]-$C_1$-$C_6$-alkylamino.

The present invention also relates to compounds of formula (IIa) as well as their salts:

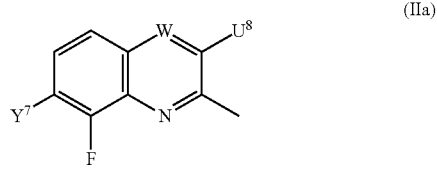

(IIa)

wherein:
W is CH or N;
$Y^7$ is a hydrogen atom or a fluorine atom; and
$U^8$ is a fluorine atom, a bromine atom, a chlorine atom, an iodine atom, a hydroxyl group, an amino group, a mesyl group, a tosyl group or a triflyl group, provided that the compound of formula (IIa) does not represent:
3-bromo-8-fluoro-2-methylquinoline [1259519-95-3],
8-fluoro-2-methylquinolin-3-ol [1314012-55-9],
8-fluoro-2-methylquinolin-3-amine [1259519-93-1],
7,8-difluoro-2-methylquinolin-3-ol [1314012-50-4],
5-fluoro-3-methylquinoxalin-2(1H)-one [1426822-07-2],
2-chloro-5-fluoro-3-methylquinoxaline [1426822-08-3], and
2-chloro-5,6-difluoro-3-methylquinoxaline [1415018-73-3].

The following compound of formula (IIa) wherein $Y^7$ is a hydrogen atom or a fluorine atom and $U^8$ is a fluorine atom, a bromine atom, a chlorine atom, an iodine atom, a hydroxyl group, an amino group, a mesyl group, a tosyl group or a triflyl group is also mentioned in chemical databases and/or suppliers' databases but without any references or information which enable these to be prepared and separated:
7,8-difluoro-2-methylquinolin-3-amine [2092336-33-7],
The present invention also relates to compounds of formula (IIb) as well as their salts:

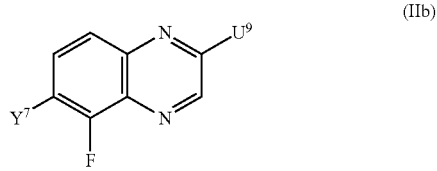

(IIb)

wherein:
$Y^7$ is a hydrogen atom or a fluorine atom; and
$U^9$ is a fluorine atom, a bromine atom, a chlorine atom, an iodine atom, a hydroxyl group, an amino group, a mesyl group, a tosyl group or a triflyl group, provided that the compound of formula (IIb) does not represent:
5-fluoroquinoxalin-2(1H)-one [55687-16-6],
5-fluoroquinoxalin-2-amine [1895170-02-1],
2-chloro-5-fluoroquinoxaline [55687-09-7],
5,6-difluoroquinoxalin-2(1H)-one [917343-50-1], and
2-chloro-5,6-difluoroquinoxaline [1384067-26-8].

Compositions and Formulations

The present invention further relates to a composition, in particular a composition for controlling unwanted microorganisms, comprising one or more compounds of formula (I). The composition is preferably is a fungicidal composition.

The composition typically comprises one or more compounds of formula (I) and one or more acceptable carriers, in particular one or more agriculturally acceptable carriers.

A carrier is a natural or synthetic, organic or inorganic substance with which the active ingredients are mixed or combined for better applicability, in particular for better application to plants, plant parts or seeds. The carrier, which may be solid or liquid, is generally inert.

Examples of suitable solid carriers include, but are not limited to, ammonium salts, natural rock flours, such as kaolins, clays, talc, chalk, quartz, attapulgite, montmorillonite or diatomaceous earth, and synthetic rock flours, such as finely divided silica, alumina and silicates. Examples of typically useful solid carriers for preparing granules include, but are not limited to, crushed and fractionated natural rocks such as calcite, marble, pumice, sepiolite and dolomite, synthetic granules of inorganic and organic flours and granules of organic material such as paper, sawdust, coconut shells, maize cobs and tobacco stalks.

Examples of suitable liquid carriers include, but are not limited to, water, polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone cyclohexanone), esters (including fats and oils) and (poly)ethers, unsubstituted and substituted amines, amides (such as dimethylformamide), lactams (such as N-alkylpyrrolidones) and lactones, sulphones and sulphoxides (such as dimethyl sulphoxide). The carrier may also be a liquefied gaseous extender, i.e. liquid which is gaseous at standard temperature and under standard pressure, for example aerosol propellants such as halohydrocarbons, butane, propane, nitrogen and carbon dioxide.

The composition may further comprise one or more acceptable auxiliaries which are customary for formulating compositions (e.g. agrochemical compositions), such as one or more surfactants.

Examples of suitable surfactants include emulsifiers and/ or foam formers, dispersants or wetting agents having ionic or nonionic properties, or mixtures thereof. Examples thereof are salts of polyacrylic acid, salts of lignosulphonic acid, salts of phenolsulphonic acid or naphthalenesulphonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. A surfactant is typically used when the active ingredient and/or the carrier is insoluble in water and the application is made with water. Then, the amount of surfactants typically ranges from 5 to 40% by weight of the composition.

Further examples of auxiliaries which are customary for formulating agrochemical compositions include water repellent, siccatives, binder (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone, polyvinyl acetate, polyvinyl alcohol and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes and nutrients (including trace nutrients, such as salts of iron, manganese, boron, copper, cobalt, molybdenum and zinc), protective colloids, thixotropic substances, penetrants, sequestering agents and complex formers.

The choice of the carriers and/or auxiliaries will depend on the intended mode of application of the composition and/or on the physical properties of the active ingredient(s).

The compositions may be formulated in the form of any customary formulations, such as solutions (e.g aqueous solutions), emulsions, wettable powders, water- and oil-based suspensions, powders, dusts, pastes, soluble powders, soluble granules, granules for broadcasting, suspoemulsion concentrates, natural products impregnated with the active ingredient(s), synthetic substances impregnated with the active ingredient(s), fertilizers and also microencapsulations in polymeric substances. In the formulation of the composition, the active ingredient may be present in suspended, emulsified or dissolved form.

The compositions may be ready-for-use compositions, i.e. the compositions can be directly applied to the plant or seed by a suitable device, such as a spraying or dusting device. Alternatively, the compositions may be in the form of commercial concentrates which have to be diluted, preferably with water, prior to use.

The compositions can be prepared in conventional manners, for example by mixing the active ingredient(s) with one or more carriers and/or one or more suitable auxiliaries, such as disclosed herein above.

The compositions contain generally from 0.05 to 99% by weight, from 0.01 to 98% by weight, preferably from 0.1 to 95% by weight, more preferably from 0.5 to 90% by weight, most preferably from 10 to 70% by weight of the active ingredient or mixture thereof.

The compositions described above can be used for controlling unwanted microorganisms. The compositions may be applied to the microorganisms and/or in their habitat.

The compounds of formula (I) can be used as such or in formulations thereof. They can also be mixed or used in combination with known fungicides, bactericides, acaricides, nematicides, insecticides or mixtures thereof. The use of known fungicides, bactericides, acaricides, nematicides or insecticides, may allow to broaden the activity spectrum or to prevent development of resistance. Examples of known fungicides, insecticides, acaricides, nematicides or bactericides are disclosed in Pesticide Manual, 14th ed.

The compounds of formula (I) can also be mixed or used in combination with other known active agents, such as herbicides, or with fertilizers, growth regulators, safeners and/or semiochemicals.

Thus, in some embodiments, the composition further comprises an additional active agent selected from fungicides, bactericides, acaricides, nematicides, insecticides, herbicides, fertilizers, growth regulators, safeners, semiochemicals and mixtures thereof.

Methods and Uses

The compounds of formula (I) have potent microbicidal activity. Thus, the compounds of formula (I) or compositions comprising thereof can be used for controlling unwanted microorganisms, such as fungi and bacteria. They can be particularly useful in crop protection—they control microorganisms that cause plants diseases—or in the protection of timber, storage goods or various materials, as described in more details herein below. More specifically, the compounds of formula (I) or compositions comprising thereof can be used to protect seeds, germinating plants, emerged seedlings, plants, plant parts, fruits and the soil in which the plants grow from unwanted microorganisms.

The term "control" or "controlling" as used herein encompasses curative and protective control of unwanted microorganisms. The unwanted microorganisms may be pathogenic bacteria or pathogenic fungi, more specifically phytopathogenic bacteria or phytopathogenic fungi. As detailed herein below, these phytopathogenic microorganism are the causal agents of a broad spectrum of plants diseases More specifically, the compounds of the formula (I) or compositions comprising thereof can be used as fungicide. In particular, they can useful in crop protection, for example for the control of unwanted fungi, such as Plasmodiophoromycetes, Oomycetes, Chytridiomycetes, Zygomycetes, Ascomycetes, Basidiomycetes and Deuteromycetes.

The compounds of the formula (I) or compositions comprising thereof can also be used as bactericide. In particular, they can be used in crop protection, for example for the control unwanted bacteria, such as Pseudomonadaceae, Rhizobiaceae, Enterobacteriaceae, Corynebacteriaceae and Streptomycetaceae.

Therefore, the present invention also relates to a method for controlling unwanted phytopathogenic microorganisms, such as fungi and bacteria, comprising the step of applying one or more compound of formula (I) or a composition comprising thereof to the microorganisms and/or in their habitat.

More specifically, the present invention relates to curative or protective methods for controlling unwanted microorganisms, more specifically phytopathogenic fungi, which comprises the step of applying one or more compound of formula (I) or a composition comprising thereof to the seeds, the plants, the plant parts, the fruit or the soil in which the plants grow.

Typically, when the compounds of formula (I) or the compositions comprising thereof are intended to be used in curative or protective methods for controlling phytopathogenic fungi, an effective and non-phytotoxic amount of one or more compounds of formula (I) or a composition comprising thereof, is typically applied to the plant, plant part, fruit, seed or soil in which the plants grow. The expression "effective and non-phytotoxic amount" means an amount that is sufficient to control or destroy the fungi present or liable to appear on the cropland and that does not entail any appreciable symptom of phytotoxicity for said crops. Such an amount can vary within a wide range depending on the fungus to be controlled, the type of crop, the climatic conditions and the compounds of formula (I). This amount can be determined by systematic field trials that are within the capabilities of a person skilled in the art.

The term "treatment" as used herein refers to the step of applying one or more compound of formula (I) or a composition comprising thereof to the plants, plant parts, fruits, seeds or soil that need(s) to be protected or cured.

Plants and Plant Parts

All plants and plant parts can be treated in accordance with the methods of the invention.

Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and the plant cultivars which are protectable and non-protectable by plant breeders' rights.

Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds. Plants which can be treated in accordance with the methods of the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

In some preferred embodiments, wild plant species and plant cultivars, or those obtained by conventional biological breeding methods, such as crossing or protoplast fusion, and also parts thereof, are treated in accordance with the methods of the invention.

In some other preferred embodiments, transgenic plants and plant cultivars obtained by genetic engineering methods, if appropriate in combination with conventional methods (Genetically Modified Organisms), and parts thereof are treated in accordance with the methods of the invention. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The methods according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi-technology or microRNA—miRNA—technology). A heterologous gene that is located in the genome is also called a transgene. A transgene that is defined by its particular location in the plant genome is called a transformation or transgenic event.

Plants and plant cultivars which can be treated by the above disclosed methods include all plants which have genetic material which impart particularly advantageous, useful traits to these plants (whether obtained by breeding and/or biotechnological means).

Plants and plant cultivars which can be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which can be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which can be treated by the above disclosed methods include those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability. Plants and plant cultivars which can be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which can be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which can be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect resistance. Plants and plant cultivars (obtained by plant biotechnology methods such as genetic engineering) which can be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which can be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which can be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which can be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics. Plants and plant cultivars (obtained by plant biotechnology methods such as genetic engineering) which can be treated by the above disclosed methods include plants and plant cultivars, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering. Plants and plant cultivars (obtained by plant biotechnology methods such as genetic engineering) which can be treated by the above disclosed methods include plants and plant cultivars, such as Tobacco plants, with altered post-translational protein modification patterns.

Pathogens and Diseases

The methods disclosed above can be used to control microorganisms, in particular phytopathogenic fungi, causing diseases, such as:

diseases caused by powdery mildew pathogens, such as *Blumeria* species (e.g. *Blumeria graminis*), *Podosphaera* species (e.g. *Podosphaera leucotricha*), *Sphaerotheca* species (e.g. *Sphaerotheca fuliginea*), *Uncinula* species (e.g. *Uncinula necator*);

diseases caused by rust disease pathogens, such as *Gymnosporangium* species (e.g. *Gymnosporangium sabinae*), *Hemileia* species (e.g. *Hemileia vastatrix*), *Phakopsora* species (e.g. *Phakopsora pachyrhizi* or *Phakopsora meibomiae*), *Puccinia* species (e.g. *Puccinia recondita*, *Puccinia graminis* or *Puccinia striiformis*), *Uromyces* species (e.g. *Uromyces appendiculatus*);

diseases caused by pathogens from the group of the Oomycetes, such as *Albugo* species (e.g. *Albugo candida*), *Bremia* species (e.g. *Bremia lactucae*), *Peronospora* species (e.g. *Peronospora pisi* or *P. brassicae*), *Phytophthora* species (e.g. *Phytophthora infestans*), *Plasmopara* species (e.g. *Plasmopara viticola*), *Pseudoperonospora* species (e.g. *Pseudoperonospora humuli* or *Pseudoperonospora cubensis*), *Pythium* species (e.g. *Pythium ultimum*);

leaf blotch diseases and leaf wilt diseases caused, for example, by *Alternaria* species (e.g. *Alternaria solani*), *Cercospora* species (e.g. *Cercospora beticola*), *Cladiosporium* species (e.g. *Cladiosporium cucumerinum*), *Cochliobolus* species (e.g. *Cochliobolus sativus* (conidial form: *Drechslera*, syn: *Helminthosporium*) or *Cochliobolus miyabeanus*), *Colletotrichum* species (e.g. *Colletotrichum lindemuthanium*), *Cycloconium* species (e.g. *Cycloconium oleaginum*), *Diaporthe* species (e.g. *Diaporthe citri*), *Elsinoe* species (e.g. *Elsinoe fawcettii*), *Gloeosporium* species (e.g. *Gloeosporium laeticolor*), *Glomerella* species (e.g. *Glomerella cingulate*), *Guignardia* species (e.g. *Guignardia bidwelli*), *Leptosphaeria* species (e.g. *Leptosphaeria maculans*), *Magnaporthe* species (e.g. *Magnaporthe grisea*), *Microdochium* species (e.g. *Microdochium nivale*), *Mycosphaerella* species (e.g. *Mycosphaerella graminicola, Mycosphaerella arachidicola* or *Mycosphaerella fijiensis*), *Phaeosphaeria* species (e.g. *Phaeosphaeria nodorum*), *Pyrenophora* species (e.g. *Pyrenophora teres* or *Pyrenophora tritici repentis*), *Ramularia* species (e.g. *Ramularia collo-cygni* or *Ramularia areola*), *Rhynchosporium* species (e.g. *Rhynchosporium secalis*), *Septoria* species (e.g. *Septoria apii* or *Septoria lycopersici*), *Stagonospora* species (e.g. *Stagonospora nodorum*), *Typhula* species (e.g. *Typhula incarnate*), *Venturia* species (e.g. *Venturia inaequalis*), root and stem diseases caused, for example, by *Corticium* species (e.g. *Corticium graminearum*), *Fusarium* species (e.g. *Fusarium oxysporum*), *Gaeumannomyces* species, (e.g. *Gaeumannomyces graminis*), *Plasmodiophora* species, (e.g. *Plasmodiophora brassicae*), *Rhizoctonia* species, (e.g. *Rhizoctonia solani*), *Sarocladium* species, (e.g. *Sarocladium oryzae*), *Sclerotium* species, (e.g. *Sclerotium oryzae*), *Tapesia* species, (e.g. *Tapesia acuformis*), *Thielaviopsis* species, (e.g. *Thielaviopsis basicola*);

ear and panicle diseases (including corn cobs) caused, for example, by *Alternaria* species, (e.g. *Alternaria* spp.), *Aspergillus* species (e.g. *Aspergillus flavus*), *Cladosporium* species (e.g. *Cladosporium cladosporioides, Claviceps* species (e.g. *Claviceps purpurea*), *Fusarium* species, (e.g. *Fusarium culmorum*), *Gibberella* species (e.g. *Gibberella zeae*), *Monographella* species, (e.g. *Monographella nivalis*), *Stagnospora* species, (e.g. *Stagnospora nodorum*);

diseases caused by smut fungi, for example *Sphacelotheca* species (e.g. *Sphacelotheca reiliana*), *Tilletia* species (e.g. *Tilletia caries* or *Tilletia controversa*), *Urocystis* species (e.g. *Urocystis occulta*), *Ustilago* species (e.g. *Ustilago nuda*);

fruit rot caused, for example, by *Aspergillus* species (e.g. *Aspergillus flavus*), *Botrytis* species (e.g. *Botrytis cinerea*), *Penicillium* species (e.g. *Penicillium expansum* or *Penicillium purpurogenum*), *Rhizopus* species (e.g. *Rhizopus stolonifer*), *Sclerotinia* species (e.g. *Sclerotinia sclerotiorum*), *Verticilium* species (e.g. *Verticilium alboatrum*);

seed- and soil-borne rot and wilt diseases, and also diseases of seedlings, caused, for example, by *Alternaria* species (e.g. *Alternaria brassicicola*), *Aphanomyces* species (e.g. *Aphanomyces euteiches*), *Ascochyta* species (e.g. *Ascochyta lentis*), *Aspergillus* species (e.g. *Aspergillus flavus*), *Cladosporium* species (e.g. *Cladosporium herbarum*), *Cochliobolus* species (e.g. *Cochliobolus sativus* (conidial form: *Drechslera, Bipolaris* Syn: *Helminthosporium*)), *Colletotrichum* species (e.g. *Colletotrichum coccodes*), *Fusarium* species (e.g. *Fusarium culmorum*), *Gibberella* species (e.g. *Gibberella zeae*), *Macrophomina* species (e.g. *Macrophomina phaseolina*), *Microdochium* species (e.g. *Microdochium nivale*), *Monographella* species (e.g. *Monographella nivalis*), *Penicillium* species (e.g. *Penicillium expansum*), *Phoma* species (e.g. *Phoma* lingam), *Phomopsis* species (e.g. *Phomopsis sojae*), *Phytophthora* species (e.g. *Phytophthora cactorum*), *Pyrenophora* species (e.g. *Pyrenophora graminea*), *Pyricularia* species (e.g. *Pyricularia oryzae*), *Pythium* species (e.g. *Pythium ultimum*), *Rhizoctonia* species (e.g. *Rhizoctonia solani*), *Rhizopus* species (e.g. *Rhizopus oryzae*), *Sclerotium* species (e.g. *Sclerotium rolfsii*), *Septoria* species (e.g. *Septoria nodorum*), *Typhula* species (e.g. *Typhula incarnate*), *Verticillium* species (e.g. *Verticillium dahlia*);

cancers, galls and witches' broom caused, for example, by *Nectria* species (e.g. *Nectria galligena*); wilt diseases caused, for example, by *Monilinia* species (e.g. *Monilinia laxa*);

deformations of leaves, flowers and fruits caused, for example, by *Exobasidium* species (e.g. *Exobasidium vexans*), *Taphrina* species (e.g. *Taphrina deformans*);

degenerative diseases in woody plants, caused, for example, by *Esca* species (e.g. *Phaeomoniella chlamydospora, Phaeoacremonium aleophilum* or *Fomitiporia mediterranea*), *Ganoderma* species (e.g. *Ganoderma boninense*);

diseases of flowers and seeds caused, for example, by *Botrytis* species (e.g. *Botrytis cinerea*); diseases of plant tubers caused, for example, by *Rhizoctonia* species (e.g. *Rhizoctonia solani*), *Helminthosporium* species (e.g. *Helminthosporium solani*);

diseases caused by bacterial pathogens, for example *Xanthomonas* species (e.g. *Xanthomonas campestris* pv. *Oryzae*), *Pseudomonas* species (e.g. *Pseudomonas syringae* pv. *Lachrymans*), *Erwinia* species (e.g. *Erwinia amylovora*).

Seed Treatment

The method for controlling unwanted microorganisms may be used to protect seeds from phytopathogenic microorganisms, such as fungi.

The term "seed(s)" as used herein include dormant seed, primed seed, pregerminated seed and seed with emerged roots and leaves.

Thus, the present invention also relates to a method for protecting seeds and/or crops from unwanted microorganisms, such as bacteria or fungi, which comprises the step of treating the seeds with one or more compounds of formula (I) or a composition comprising thereof. The treatment of seeds with the compound(s) of formula (I) or a composition comprising thereof not only protects the seeds from phytopathogenic microorganisms, but also the germinating plants, the emerged seedlings and the plants after emergence.

The seeds treatment may be performed prior to sowing, at the time of sowing or shortly thereafter.

When the seeds treatment is performed prior to sowing (e.g. so-called on-seed applications), the seeds treatment may be performed as follows: the seeds may be placed into a mixer with a desired amount of compound(s) of formula (I) or a composition comprising thereof (either as such or after dilution), the seeds and the compound(s) of formula (I) or the composition comprising thereof are mixed until a homogeneous distribution on seeds is achieved. If appropriate, the seeds may then be dried.

The invention also relates to seeds treated with one or more compounds of formula (I) or a composition comprising thereof. As said before, the use of treated seeds allows not only protecting the seeds before and after sowing from unwanted microorganisms, such as phytopathogenic fungi, but also allows protecting the germinating plants and young seedlings emerging from said treated seeds. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant.

Therefore, the present invention also relates to a method for protecting seeds, germinating plants and emerged seedlings, more generally to a method for protecting crop from phytopathogenic microorganisms, which comprises the step of using seeds treated by one or more compounds of formula (I) or a composition comprising thereof.

Preferably, the seed is treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pre-germinated seeds, or seeds sown on nursery trays, tapes or paper.

The amount of compound(s) of formula (I) or composition comprising thereof applied to the seed is typically such that the germination of the seed is not impaired, or that the resulting plant is not damaged. This must be ensured particularly in case the active ingredients would exhibit phytotoxic effects at certain application rates. The intrinsic phenotypes of transgenic plants should also be taken into consideration when determining the amount of compound(s) of formula (I) or composition comprising thereof to be applied to the seed in order to achieve optimum seed and germinating plant protection with a minimum amount of compound(s) of formula (I) or composition comprising thereof being employed.

As indicated above, the compounds of the formula (I) can be applied, as such, directly to the seeds, i.e. without the use of any other components and without having been diluted, or a composition comprising the compounds of formula (I) can be applied. Preferably, the compositions are applied to the seed in any suitable form. Examples of suitable formulations include solutions, emulsions, suspensions, powders, foams, slurries or combined with other coating compositions for seed, such as film forming materials, pelleting materials, fine iron or other metal powders, granules, coating material for inactivated seeds, and also ULV formulations. The formulations may be ready-to-use formulations or may be concentrates that need to be diluted prior to use.

These formulations are prepared in a known manner, for instance by mixing the active ingredient or mixture thereof with customary additives, for example customary extenders and solvents or diluents, dyes, wetting agents, dispersants, emulsifiers, preservatives, secondary thickeners, antifoams, adhesives, gibberellins, and also water.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1. Useful wetting agents which may be present in the seed dressing formulations are all substances which promote wetting and which are conventionally used for the formulation of active agrochemical ingredients. Usable with preference are alkylnaphthalenesulphonates, such as diisopropyl- or diisobutylnaphthalenesulphonates. Useful dispersants and/or emulsifiers which may be present in the seed dressing formulations are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates. Antifoams which may be present in the seed dressing formulations are all foam-inhibiting substances conventionally used for the formulation of active agrochemical ingredients. Silicone antifoams and magnesium stearate can be used with preference. Preservatives which may be present in the seed dressing formulations are all substances usable for such purposes in agrochemical compositions. Examples include dichlorophene and benzyl alcohol hemiformal. Secondary thickeners which may be present in the seed dressing formulations are all substances usable for such purposes in agrochemical compositions. Preferred examples include cellulose derivatives, acrylic acid derivatives, xanthan, modified clays and finely divided silica. Adhesives which may be present in the seed dressing formulations are all customary binders usable in seed dressing products. Preferred examples include polyvinylpyrrolidone, polyvinyl acetate, polyvinyl alcohol and tylose. The compounds of the formula (I) and the compositions comprising thereof are suitable for protecting seeds of any plant variety which is used in agriculture, in greenhouses, in forests or in horticulture. More particularly, the seed is that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice. The compounds of formula (I) or the compositions comprising thereof can be used for treating transgenic seeds, in particular seeds of plants capable of expressing a protein which acts against pests, herbicidal damage or abiotic stress, thereby increasing the protective effect. Synergistic effects may also occur in interaction with the substances formed by expression.

Application

The active ingredient(s) can be applied as such, in the form of their formulations or in the use forms prepared from said formulations when these are not ready-to-use.

The application to the plant, plant part, fruit, seed or soil is accomplished in a customary manner, for example by watering, spraying, atomizing, broadcasting, dusting, foaming, spreading-on and the like. The active ingredients may also be applied by the ultra-low volume method or be injected into the soil.

The effective and non-phytotoxic amount of compounds of formula (I) or of a composition comprising thereof which is applied to the plant, plant part, fruit, seed or soil will depend on various factors, such as the compound/composition employed, the subject of the treatment (plant, plant part, fruit, seed or soil), the type of treatment (dusting, spraying, seed dressing), the purpose of the treatment (prophylactic or therapeutic) and the type of microorganisms.

When compounds of formula (I) are used as fungicides, the application rates can vary within a relatively wide range, depending on the kind of application. For instance, when compounds of formula (I) are used in the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). When compounds of formula (I) are used in the treatment of seeds, the application rate may range from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed. When compounds of formula (I) are used in the treatment of soil, the application rate may range from 0.1 to 10 000 g/ha, preferably from 1 to 5000 g/ha.

These application rates are merely by way of example and are not limiting for the purposes of the invention.

Mycotoxins

In addition, the compounds of the formula (I) or compositions comprising thereof can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The compounds of the formula (I) and compositions comprising thereof can be used in the protection of materials, for instance industrial materials, from attack and destruction by microorganisms, such as fungi.

The terms "industrial materials" as used herein designate inanimate materials that may be used in industry. Examples of industrial materials include, but are not limited to, adhesives, glues, paper, wallpaper, board/cardboard, textiles, carpets, leather, wood, fibers, tissues, paints, plastic articles, cooling lubricants, heat transfer fluids and other materials which can be infected with or destroyed by microorganisms. Preferred industrial materials include adhesives, sizes, paper and card, leather, wood, paints, cooling lubricants and heat transfer fluids, more preferably wood. The compounds of the formula (I) and compositions comprising thereof may prevent adverse effects, such as rotting, decay, discoloration or formation of mould.

Further materials that can be protected by the compounds and compositions of the present invention include parts of production plants and buildings which may be impaired by the proliferation of microorganisms, for example cooling-water circuits, cooling and heating systems and ventilation and air-conditioning units.

In addition, the compounds of the formula (I) and compositions comprising thereof can be used to protect objects which come into contact with saltwater or brackish water, especially hulls, screens, nets, buildings, moorings and signaling systems, from fouling. Therefore, the compounds of the formula (I) and compositions comprising thereof can be used as antifouling agent, alone or in combinations with other active ingredients.

The compounds of the formula (I) and compositions comprising thereof may also be used to treat wood, in particular to treat wood against fungal diseases liable to grow on or inside timber. The term "timber" designates all types and species of wood and all types of construction timber, for example solid wood, high-density wood, laminated wood, and plywood. An exemplary method for treating timber comprises the step of contacting one or more compounds of formula (I) or a composition comprising thereof with the timber. The contacting step may be performed by direct application, spraying, dipping, injection or any other suitable means.

The compounds of the formula (I) and compositions comprising thereof can also be used for protecting storage goods. The terms "storage goods" as used herein designate natural substances of vegetable or animal origin or processed products thereof for which long-term protection is desired. Examples of storage goods of vegetable origin that can be protected include plants or plant parts, such as stems, leaves, tubers, seeds, fruits and grains. They can be protected in a freshly harvested state or after being processed, such as by (pre)drying, moistening, comminuting, grinding, pressing and/or roasting. Examples of storage goods of animal origin include hides, leather, furs and hairs. The compounds of the formula (I) or compositions comprising thereof may prevent adverse effects, such as rotting, decay, discoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp.,

*Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

Aspects of the present teaching may be further understood in light of the following examples, which should not be construed as limiting the scope of the present teaching in any way.

EXAMPLES

In analogy to the examples disclosed herein below and according to the general description of the processes herein disclosed, the compounds of formula (I) shown in table 1a have been obtained.

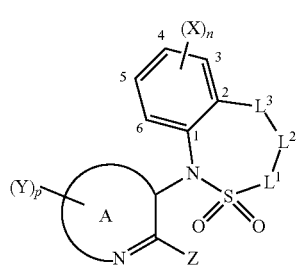

(I)

In table 1a, unless otherwise specified, M+H (Apcl+) means the molecular ion peak plus 1 a.m.u. (atomic mass unit) as observed in mass spectroscopy via positive atmospheric pressure chemical ionisation.

In table 1a, the log P values were determined in accordance with EEC Directive 79/831 Annex V.A8 by HPLC (High Performance Liquid Chromatography) on a reversed-phase column (C 18), using the method described below:

Method A: temperature: 40° C.; mobile phases: 0.1% aqueous formic acid and acetonitrile; linear gradient from 10% acetonitrile to 95% acetonitrile;

Method B: temperature: 40° C.; mobile phases: 0.001 molar ammonium acetate solution in water and acetonitrile; linear gradient from 10% acetonitrile to 95% acetonitrile;

Method C: temperature: 55° C.; mobile phases: 0.1% aqueous formic acid and acetonitrile; linear gradient from 10% acetonitrile to 95% acetonitrile.

If more than one Log P value is available within the same method, all the values are given and separated by ";".

Calibration was carried out using unbranched alkan-2-ones (comprising 3 to 16 carbon atoms) with known log P values (determination of the log P values by the retention times using linear interpolation between two successive alkanones). Iambda-max-values were determined using UV-spectra from 200 nm to 400 nm and the peak values of the chromatographic signals.

In table 1a, the point of attachment of the $(X)_n$ residue to the phenyl ring is based on the above numbering of the phenyl ring.

TABLE 1A

| Example | (X)n | L1 | L2 | L3 | A/Z group | M + H | logP | log P Method |
|---|---|---|---|---|---|---|---|---|
| I.001 | | spiro-cyclopropyl | — | — | 8-fluoroquinolin-3-yl | 341 | 3.02 | A |
| I.002 | | CH(Me) | — | — | quinolin-3-yl | 311 | 2.70 | A |
| I.003 | | CH(Me) | — | — | 8-fluoro-quinolin-3-yl | 329 | 2.76 | A |
| I.004 | | spiro-cyclopentyl | — | — | 8-fluoro-quinolin-3-yl | 367 | 3.38 | A |
| I.005 | | spiro-indanyl | — | — | 8-fluoro-quinolin-3-yl | | 3.97 | A |
| I.006 | | spiro-cyclohexyl | — | — | 8-fluoro-quinolin-3-yl | 383 | 3.88 | A |
| I.007 | | C(Me)2 | — | — | quinolin-3-yl | 371 | 2.98 | A |
| I.008 | | spiro-cyclobutyl | — | — | quinolin-3-yl | 383 | 3.21 | A |

TABLE 1A-continued

| Example | (X)n | L1 | L2 | L3 | (structure) | M + H | logP | log P Method |
|---|---|---|---|---|---|---|---|---|
| I.009 | | 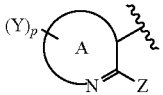 | — | — | quinolin-3-yl | 397 | 3.51 | A |
| I.010 | |  | — | — | quinolin-3-yl | 395 | 3.33 | A |
| I.011 | |  | — | — | quinolin-3-yl | 411 | 3.84 | A |
| I.012 | | CH(i-Pr) | — | — | quinolin-3-yl | 339 | 3.40 | A |
| I.013 | |  | — | — | quinolin-3-yl | 323 | 2.82 | A |
| I.014 | |  | — | — | quinolin-3-yl | | 3.94 | A |
| I.015 | | C(Me)2 | — | — | 8-fluoro-quinolin-3-yl | 343 | 3.05 | A |
| I.016 | | 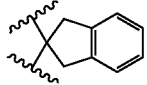 | — | — | 8-fluoro-quinolin-3-yl | 355 | 3.26 | A |
| I.017 | |  | — | — | 8-fluoro-quinolin-3-yl | 369 | 3.56 | A |
| I.018 | | CH2 | — | — | 8-fluoro-quinolin-3-yl | 315 | 2.46 | A |
| I.019 | | CH2 | — | — | quinolin-3-yl | 343 | 2.40 | A |
| I.020 | | CH(i-Pr) | — | — | 8-fluoro-quinolin-3-yl | 357 | 3.46 | A |
| I.021 | | CH2 | — | — | 7,8-difluoro-quinolin-3-yl | 333 | 2.88 | A |
| I.022 | |  | — | — | 7,8-difluoro-quinolin-3-yl | 359 | 3.31 | A |
| I.023 | | C(Me)2 | — | — | 7,8-difluoro-quinolin-3-yl | 361 | 3.33 | A |
| I.024 | |  | — | — | 7,8-difluoro-quinolin-3-yl | 373 | 3.55 | A |
| I.025 | | CH2 | — | — | 5,6-difluoro-quinoxalin-2-yl | 334 | 2.94 | A |

TABLE 1A-continued

| Example | (X)n | L1 | L2 | L3 | (Y)p-A-N=Z | M + H | logP | log P Method |
|---|---|---|---|---|---|---|---|---|
| I.026 | | CH-N(Me)2 | — | — | 8-fluoro-quinolin-3-yl | 370 | 3.15 | B |
| I.027 | | C(Me)2 | — | — | 5,6-difluoro-quinoxalin-2-yl | 362 | 3.55 | A |
| I.028 | | CH2 | — | — | 7,8-difluoro-2-methyl-quinolin-3-yl | 347 | 3.00 | A |
| I.029 | | C(Me)2 | — | — | 7,8-difluoro-2-methylquinolin-3-yl | 375 | 4.18 | A |
| I.030 | | cyclopropyl-spiro | — | — | 7,8-difluoro-2-methylquinolin-3-yl | 373 | 3.44 | A |
| I.031 | | cyclobutyl-spiro | — | — | 7,8-difluoro-2-methylquinolin-3-yl | 387 | 3.85 | A |
| I.032 | | bicyclopropyl | — | — | 7,8-difluoro-2-methylquinolin-3-yl | 399 | 3.87; 3.94 | A |
| I.033 | | bicyclopropyl | — | — | 7,8-difluoro-quinolin-3-yl | 385 | 3.71 | A |
| I.034 | | CH2 | — | — | 2-methyl-quinolin-3-yl | 311 | 2.37 | A |
| I.035 | | bicyclopropyl | — | — | 2-methyl-quinolin-3-yl | 363 | 3.35; 3.44 | A |
| I.036 | | cyclopropyl-spiro | — | — | 2-methyl-quinolin-3-yl | 337 | 2.86 | A |
| I.037 | | C(Me)2 | — | — | 2-methyl-quinolin-3-yl | 339 | 3.00 | A |
| I.038 | | cyclobutyl-spiro | — | — | 2-methyl-quinolin-3-yl | 351 | 3.25 | A |
| I.039 | 3-F | CH2 | — | — | 8-fluoro-quinolin-3-yl | 333 | 2.71 | A |
| I.040 | 3-F | C(Me)2 | — | — | 8-fluoro-quinolin-3-yl | 361 | 3.44 | A |
| I.041 | | CH(Bn) | — | — | 8-fluoro-quinolin-3-yl | 405 | 3.83 | A |
| I.042 | | CH2 | — | — | quinoxalin-2-yl | 298 | 2.66 | A |
| I.043 | | cyclobutyl-spiro | — | — | quinoxalin-2-yl | 338 | 3.44 | A |
| I.044 | | C(Me)2 | — | — | quinoxalin-2-yl | 326 | 3.17 | A |

TABLE 1A-continued

| Example | (X)n | L1 | L2 | L3 | (Y)p–A(N=Z) | M + H | logP | log P Method |
|---|---|---|---|---|---|---|---|---|
| I.045 | | 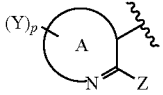 | — | — | quinoxalin-2-yl | 324 | 3.11 | A |
| I.046 | | CH2 | — | — | 5-fluoro-quinoxalin-2-yl | 316 | 2.8 | A |
| I.047 | |  | — | — | 5,6-difluoro-quinoxalin-2-yl | 360 | 3.48 | A |
| I.048 | |  | — | — | 5,6-difluoro-quinoxalin-2-yl | 374 | 3.78 | A |
| I.049 | | C(Me)2 | — | — | 5,6-difluoro-3,8-dimethyl-quinoxalin-2-yl | 390 | 4.11 | A |
| I.050 | | C(Me)2 | — | — | 5-fluoro-quinoxalin-2-yl | 344 | 3.31 | A |
| I.051 | | C(Me)2 | — | — | 5,6-difluoro-3-methyl-quinoxalin-2-yl | 376 | 3.58 | A |
| I.052 | 4-OMe | CH2 | — | — | 7,8-difluoro-2-methyl-quinolin-3-yl | 377 | 2.95 | A |
| I.053 | 4-Me | CH2 | — | — | 7,8-difluoro-2-methyl-quinolin-3-yl | 361 | 3.39 | A |
| I.054 | | C(Me)2 | — | — | 8-fluoro-4-methyl-quinolin-3-yl | 357 | 3.20 | A |
| I.055 | | C(Me)2 | — | — | 8-fluoro-2-methyl-quinolin-3-yl | 357 | 3.26 | A |
| I.056 | | C(Me)2 | — | — | 8-fluoro-2,4-dimethyl-quinolin-3-yl | 371 | 3.42 | A |
| I.057 | | C(Me)2 | — | — | 8-fluoro-2,4,7-trimethyl-quinolin-3-yl | 385 | 3.75 | A |
| I.058 | | C(Me)2 | — | — | 8-fluoro-6-methyl-quinolin-3-yl | 357 | 3.52 | A |
| I.059 | | C(Me)2 | — | — | 4-cyclopropyl-7,8-difluoro-quinolin-3-yl | | 3.88 | A |
| I.060 | 3-Br | CH2 | — | — | 8-fluoro-quinolin-3-yl | 393 | 3.11 | A |
| I.061 | | C(Me)2 | — | — | 8-fluoro-1-oxidoquinolin-1-ium-3-yl | 359 | 2.08 | A |
| I.062 | 4-OMe | C(Me)2 | — | — | 7,8-difluoro-2-methyl-quinolin-3-yl | 405 | 3.51 | A |
| I.063 | 3-OMe | CH2 | — | — | 8-fluoro-quinolin-3-yl | 345 | 2.84 | A |
| I.064 | 3-Me | CH2 | — | — | 8-fluoro-quinolin-3-yl | 329 | 2.84 | A |
| I.065 | 4-Me | C(Me)2 | — | — | 7,8-difluoro-2-methyl-quinolin-3-yl | 389 | 3.87 | A |
| I.066 | 4-OMe |  | — | — | 7,8-difluoro-2-methyl-quinolin-3-yl | | 3.44 | A |

TABLE 1A-continued

| Example | (X)n | L1 | L2 | L3 | (Y)p-A-N=Z | M + H | logP | log P Method |
|---|---|---|---|---|---|---|---|---|
| I.067 | 4-Me | 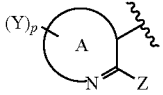 | — | — | 7,8-difluoro-2-methyl-quinolin-3-yl | 387 | 3.75 | A |
| I.068 | 3-Me |  | — | — | 8-fluoro-quinolin-3-yl | 355 | 3.23 | A |
| I.069 | 3-OMe | C(Me)2 | — | — | 8-fluoro-quinolin-3-yl | 373 | 3.44 | A |
| I.070 | | C(Me)2 | — | — | 8-chloro-6-cyano-quinolin-3-yl | | 3.39 | A |
| I.071 | | C(Me)2 | — | — | pyrido[2,3-b]pyrazin-7-yl | | 1.90 | A |
| I.072 | | C(Me)2 | — | — | 5H-pyrrolo[2,3-b]pyrazin-2-yl | | 2.05 | A |
| I.073 | | C(Me)2 | — | — | furo[3,2-b]pyridin-6-yl | | 2.49 | A |
| I.074 | | C(Me)2 | — | — | 1,8-naph-thyridin-3-yl | | 1.92 | A |
| I.075 | | C(Me)2 | — | — | 8-chloro-quinolin-3-yl | | 3.39 | A |
| I.076 | | C(Me)2 | — | — | [1,2,4]triazolo[1,5-a]pyrimidin-6-yl | | 1.76 | A |
| I.077 | | C(Me)2 | — | — | thieno[2,3-b]pyridin-5-yl | | 3.04 | A |
| I.078 | | C(Me)2 | — | — | 7,8-dichloro-quinolin-3-yl | | 3.97 | A |
| I.079 | | C(Me)2 | — | — | 5,8-difluoro-quinolin-3-yl | | 3.22 | A |
| I.080 | | C(Me)2 | — | — | 6,8-difluoro-quinolin-3-yl | | 3.24 | A |
| I.081 | | C(Me)2 | — | — | 6-formyl-quinolin-3-yl | | 2.72 | A |
| I.082 | | C(Me)2 | — | — | 7,8-dimethoxy-quinolin-3-yl | | 2.62 | A |
| I.083 | | C(Me)2 | — | — | 3,4-dihydro-2H-pyrano[2,3-b]pyridin-6-yl | | 2.43 | A |
| I.084 | | C(Me)2 | — | — | 5-methyl-5H-pyrrolo[2,3-b]pyrazin-2-yl | | 2.52 | A |
| I.085 | | C(Me)2 | — | — | 5-methyl-5H-pyrrolo[2,3-b]pyrazin-3-yl | | 2.45 | A |
| I.086 | | C(Me)2 | — | — | 6-cyano-quinolin-3-yl | | 2.91 | A |
| I.087 | | C(Me)2 | — | — | 6,7-dihydro-5H-cyclopenta[b]pyridin-3-yl | | 2.54 | A |
| I.088 | | C(Me)2 | — | — | 5,6,7,8-tetra-hydroquinolin-3-yl | | 2.54 | A |
| I.089 | | C(Me)2 | — | — | 8-methyl-quinolin-3-yl | | 3.69 | A |
| I.090 | | C(Me)2 | — | — | 1,5-naphthyridin-3-yl | | 2.20 | A |
| I.091 | | C(Me)2 | — | — | 1-methyl-1H-pyrrolo[2,3-b]pyridin-5-yl | | 2.87 | A |
| I.092 | | C(Me)2 | — | — | 1-methyl-1H-pyrrolo[3,2-b]pyridin-6-yl | | 1.65 | A |
| I.093 | | C(Me)2 | — | — | pyrrolo[1,2-a]pyrimidin-3-yl | 314 | 2.60 | A |
| I.094 | 3-Br | C(Me)2 | — | — | 8-fluoro-quinolin-3-yl | 421 | 3.85 | A |
| I.095 | 5-F | CH2 | — | — | 8-fluoro- | 333 | 2.66 | A |

TABLE 1A-continued

| Example | (X)n | L1 | L2 | L3 | (Y)p-A-N=Z | M + H | logP | log P Method |
|---|---|---|---|---|---|---|---|---|
| I.096 | 4-Me | CH2 | — | — | 8-fluoro-quinolin-3-yl | 329 | 2.82 | A |
| I.097 | 5-F | 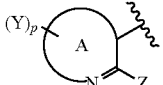 | — | — | 8-fluoro-quinolin-3-yl | 359 | 3.09 | A |
| I.098 | 4-Br | CH2 | — | — | 8-fluoro-quinolin-3-yl | 393 | 3.13 | A |
| I.099 | | C(Me)2 | — | — | 8-fluoro-5-methyl-quinolin-3-yl | 357 | 3.41 | A |
| I.100 | | C(Me)2 | — | — | 6-chloro-8-fluoroquinolin-3-yl | 377 | 3.81 | A |
| I.101 | | C(Me)2 | — | — | 8-fluoro-7-methylquinolin-3-yl | 357 | 3.44 | A |
| I.102 | | C(Me)2 | — | — | 8-(trifluoromethyl)quinolin-3-yl | 393 | 3.92 | A |
| I.103 | | C(Me)2 | — | — | 8-cyano-quinolin-3-yl | 350 | 3.04 | A |
| I.104 | | C(Me)2 | — | — | 7-chloro-8-fluoro-quinolin-3-yl | 377 | 3.74 | A |
| I.105 | | C(Me)2 | — | — | 6,7-difluoro-quinolin-3-yl | 361 | 3.50 | A |
| I.106 | 4-Me | C(Me)2 | — | — | 8-fluoro-quinolin-3-yl | 357 | 3.48 | A |
| I.107 | 5-F | C(Me)2 | — | — | 8-fluoro-quinolin-3-yl | 361 | 3.23 | B |
| I.108 | 4-Me |  | — | — | 8-fluoro-quinolin-3-yl | 355 | 3.35 | A |
| I.109 | |  | — | — | 8-fluoro-quinolin-3-yl | 367 | 3.51 | A |
| I.110 | | C(Et)2 | — | — | 8-fluoro-quinolin-3-yl | 371 | 3.78 | A |
| I.111 | |  | — | — | 8-fluoro-quinolin-3-yl | 385 | 2.90 | A |
| I.112 | | 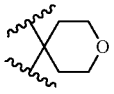 | — | — | 8-fluoro-quinolin-3-yl | 381 | 3.87 | A |
| I.113 | |  | — | — | 8-fluoro-quinolin-3-yl | 397 | 2.71 | A |
| I.114 | 3-(2-trimethyl-silylethyn-1-yl) | CH2 | — | — | 8-fluoro-quinolin-3-yl | 411 | 4.85 | A |
| I.115 | 4-Cl | CH2 | — | — | 8-fluoro-quinolin-3-yl | 349 | 3.02 | A |
| I.116 | 4-F | C(Me)2 | — | — | 8-fluoro-quinolin-3-yl | 361 | 3.19 | A |

TABLE 1A-continued

| Example | (X)n | L1 | L2 | L3 | 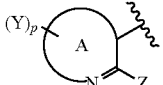 | M + H | logP | log P Method |
|---|---|---|---|---|---|---|---|---|
| I.117 | 4-Cl | C(Me)2 | — | — | 8-fluoro-quinolin-3-yl | 377 | 3.62 | A |
| I.118 | 3-Si(Me)3 | C(Me)2 | — | — | 8-fluoro-quinolin-3-yl | 415 | 4.60 | A |
| I.119 | 3-Cl | CH2 | — | — | 8-fluoro-quinolin-3-yl | 349 | 3.06 | A |
| I.120 | 3-OCF3 | CH2 | — | — | 8-fluoro-quinolin-3-yl | 399 | 3.42 | A |
| I.121 | 3-CF3 | CH2 | — | — | 8-fluoro-quinolin-3-yl |  | 3.23 | A |
| I.122 |  | C(Me)2 | — | — | 5,7-difluoro-quinolin-3-yl | 361 | 3.57 | A |
| I.123 |  |  | — | — | 8-fluoro-quinolin-3-yl | 369 | 3.59 | A |
| I.124 |  | 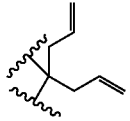 [SMILES: *C(*)(CC=C)CC=C] | — | — | 8-fluoro-quinolin-3-yl | 395 | 4.06 | A |
| I.125 | 5-Cl | C(Me)2 | — | — | 8-fluoro-quinolin-3-yl | 377 | 3.59 | A |
| I.126 | 3-ethynyl | C(Me)2 | — | — | 8-fluoro-quinolin-3-yl | 367 | 3.48 | A |
| I.127 | 3-(2-trimethyl-silylethyn-1-yl) | C(Me)2 | — | — | 8-fluoro-quinolin-3-yl | 439 | 5.42 | A |
| I.128 | 3-ethynyl | CH2 | — | — | 8-fluoro-quinolin-3-yl | 339 | 2.85 | A |
| I.129 | 3-(prop-1-en-2-yl) | C(Me)2 | — | — | 8-fluoro-quinolin-3-yl | 383 | 3.92 | A |
| I.130 |  | 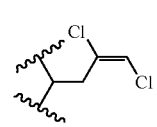(1) | — | — | 8-fluoro-quinolin-3-yl |  | 3.79 | A |
| I.131 | 4-Br | C(Me)2 | — | — | 8-fluoro-quinolin-3-yl | 421 | 3.70 | A |
| I.132 |  | C(Me)(4-NO2-Ph) | — | — | 8-fluoro-quinolin-3-yl | 450 | 3.70 | A |
| I.133 |  | 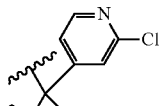 | — | — | 8-fluoro-quinolin-3-yl | 440 | 3.35 | A |
| I.134 | 3-cyclopropyl | C(Me)2 | — | — | 8-fluoro-quinolin-3-yl | 383 | 3.78 | A |
| I.135 | 3-Ph | CH2 | — | — | 8-fluoro-quinolin-3-yl | 391 | 3.74 | A |
| I.136 | 3-(6-chloropyridin-3-yl) | CH2 | — | — | 8-fluoro-quinolin-3-yl | 426 | 3.23 | A |
| I.137 | 5-Me | CH2 | — | — | 8-fluoro-quinolin-3-yl | 329 | 2.78 | A |
| I.138 | 5-Me | C(Me)2 | — | — | 8-fluoro-quinolin-3-yl | 357 | 3.32 | A |
| I.139 | 3-Si(Me)3 | CH(Me) | — | — | 8-fluoro-quinolin-3-yl | 401 | 4.37 | A |

TABLE 1A-continued

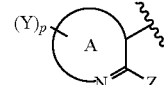

| Example | (X)n | L1 | L2 | L3 | Z | M + H | logP | log P Method |
|---|---|---|---|---|---|---|---|---|
| I.140 | 3-(6-chloropyridin-3-yl) | C(Me)2 | — | — | 8-fluoro-quinolin-3-yl | 454 | 3.60 | A |
| I.141 | 4-OMe | C(Me)2 | — | — | 8-fluoro-quinolin-3-yl | 373 | 3.13 | A |
| I.142 | 4-OMe | CH2 | — | — | 8-fluoro-quinolin-3-yl | 345 | 2.63 | A |
| I.143 | 3-Cl | C(Me)2 | — | — | 8-fluoro-quinolin-3-yl | 377 | 3.63 | A |
| I.144 | 3-OCF3 | C(Me)2 | — | — | 8-fluoro-quinolin-3-yl | 427 | 3.94 | A |
| I.145 | 3-CF3 | C(Me)2 | — | — | 8-fluoro-quinolin-3-yl | 411 | 3.76 | A |
| I.146 | 3-(1-ethoxy-ethen-1-yl) | C(Me)2 | — | — | 8-fluoro-quinolin-3-yl | 413 | 4.05 | A |
| I.147 | 4-CF3 | CH2 | — | — | 8-fluoro-quinolin-3-yl | 383 | 3.25 | A |
| I.148 | 3-C(O)Me | C(Me)2 | — | — | 8-fluoro-quinolin-3-yl | 385 | 3.11 | A |
| I.149 | 3-Ph | C(Me)2 | — | — | 8-fluoro-quinolin-3-yl | 419 | 4.34 | A |
| I.150 |  | CH2 | — | — | 2,4-bis(difluoromethyl)quinolin-3-yl | 397 | 3.39 | A |
| I.151 | 4-CF3 | C(Me)2 | — | — | 8-fluoro-quinolin-3-yl | 411 | 3.79 | A |
| I.152 | 6-Cl | CH2 | — | — | 8-fluoro-quinolin-3-yl | 349 | 2.70 | A |
| I.153 | 6-Me | CH2 | — | — | 8-fluoro-quinolin-3-yl | 329 | 2.71 | A |
| I.154 | 6-Me | C(Me)2 | — | — | 8-fluoro-quinolin-3-yl | 357 | 3.12 | A |
| I.155 |  | CH2 | CH2 | — | quinolin-3-yl |  | 2.30 | C |
| I.156 |  | C(Me)2 | C=O | — | quinolin-3-yl |  | 2.93 | C |
| I.157 |  | C(Me)2 | CH2 | — | quinolin-3-yl |  | 2.83 | C |
| I.158 |  | CH(Me) | CH2 | — | quinolin-3-yl |  | 2.58 | C |
| I.159 |  | CH2 | C=O | — | quinolin-3-yl |  | 2.28 | C |
| I.160 |  | CH2 | CH2 | — | 7,8-difluoro-quinolin-3-yl |  | 2.66 | C |
| I.161 |  | C(Me)2 | CH2 | — | 1-oxidoquinolin-1-ium-3-yl |  | 2.00 | C |
| I.162 |  | CH(Me) | CH2 | — | 1-oxidoquinolin-1-ium-3-yl |  | 1.80 | C |
| I.163 |  | C(Me)2 | CF2 | — | quinolin-3-yl |  | 3.25 | C |
| I.164 | 4-F | CH2 | C=O | — | quinolin-3-yl |  | 2.46 | C |
| I.165 |  | C(Me)2 | CH2 | — | 7,8-difluoro-quinolin-3-yl |  | 3.17 | C |
| I.166 |  | CH2 | C(Me)2 | — | quinolin-3-yl |  | 2.88 | C |
| I.167 |  |  | CH2 | — | quinolin-3-yl |  | 2.71 | C |
| I.168 |  | CH2 | C=O | — | quinoxalin-2-yl |  | 2.39 | C |
| I.169 |  | C(Me)2 | CH2 | — | 7,8-difluoro-1-oxidoquinolin-1-ium-3-yl |  | 2.40 | C |
| I.170 |  | C(Me)2 | C=O | — | quinoxalin-2-yl |  | 3.16 | C |
| I.171 |  | CH(Me) | C=O | — | quinolin-3-yl |  | 2.63 | C |
| I.172 |  | C(Me)2 | C(Me)2 | — | quinolin-3-yl |  | 3.85 | C |
| I.173 |  | CH(Me) | C(Me)2 | — | quinolin-3-yl |  | 3.57 | C |
| I.174 | 4-Cl | C(Me)2 | CH2 | — | quinolin-3-yl |  | 3.37 | C |
| I.175 | 4-Cl | CH2 | CH2 | — | quinolin-3-yl |  | 2.77 | C |
| I.176 | 4-Cl | CH(Me) | CH2 | — | quinolin-3-yl |  | 3.09 | C |
| I.177 |  | C(Me)2 | CF2 | — | quinoxalin-2-yl |  | 3.51 | C |
| I.178 | 4-F | C(Me)2 | CF2 | — | quinolin-3-yl |  | 3.39 | C |
| I.179 | 4-F | C(Me)2 | C=O | — | quinolin-3-yl |  | 3.14 | C |

TABLE 1A-continued

| Example | (X)n | L1 | L2 | L3 | (Y)p-A-N=Z | M + H | logP | log P Method |
|---|---|---|---|---|---|---|---|---|
| I.180 |  | (cyclopropyl) | C=O | — | quinolin-3-yl |  | 2.77 | C |
| I.181 |  | C(Me)2 | CH2 | — | 3-methyl-quinoxalin-2-yl |  | 3.26 | C |
| I.182 |  | C(Me)2 | CH2 | — | quinoxalin-2-yl |  | 3.03 | C |
| I.183 |  | CH2 | C=O | — | 7-fluoro-8-methoxyquinolin-3-yl |  | 2.47 | C |
| I.184 |  | CH2 | C=O | — | 8-fluoro-7-methoxyquinolin-3-yl |  | 2.34 | C |
| I.185 |  | CH2 | CH2 | — | 7,8-difluoro-2-methylquinolin-3-yl |  | 2.80 | C |
| I.186 |  | CH2 | C=O | — | 7,8-difluoro-quinolin-3-yl |  | 2.61 | C |
| I.187 |  | C(Me)2 | CH2 | — | 2-chloro-7,8-difluoroquinolin-3-yl |  | 3.71 | C |
| I.188 |  | C(Me)2 | CH2 | — | 4-chloro-7,8-difluoroquinolin-3-yl |  | 3.60 | C |
| I.189 |  | C(Me)2 | C=O | — | 7,8-difluoro-quinolin-3-yl |  | 3.21 | C |
| I.190 | 4-F | (cyclopropyl) | C=O | — | quinolin-3-yl |  | 2.95 | C |
| I.191 |  | C(Me)2 | CH2 | — | 7,8-difluoro-2-methylquinolin-3-yl |  | 3.43 | C |
| I.192 | 4-F | CH(Me) | C(Me)2 | — | quinolin-3-yl |  | 3.19 | C |
| I.193 | 4-F | CH2 | C(Me)2 | — | quinolin-3-yl |  | 2.98 | C |
| I.194 | 4-F | C(Me)2 | CH2 | — | quinolin-3-yl |  | 2.91 | C |
| I.195 | 4-F | CH2 | CH2 | — | quinolin-3-yl |  | 2.39 | C |
| I.196 |  | C(Me)2 | O | — | 7,8-difluoro-quinolin-3-yl |  | 3.25 | C |
| I.197 |  | C(Me)2 | O | — | quinolin-3-yl |  | 2.95 | C |
| I.198 |  | CH(Me) | O | — | quinolin-3-yl |  | 2.72 | C |
| I.199 |  | CH2 | O | — | quinolin-3-yl |  | 2.43 | C |
| I.200 |  | C(Me)2 | CF2 | — | 7-fluoro-8-methoxyquinolin-3-yl |  | 3.37 | C |
| I.201 |  | C(Me)2 | CF2 | — | 8-fluoro-7-methoxyquinolin-3-yl |  | 3.24 | C |
| I.202 |  | C(Me)2 | CH(OH) | — | 7,8-difluoro-quinolin-3-yl |  | 2.57 | C |
| I.203 |  | C(Me)2 | C=O | — | 7-fluoro-8-methoxyquinolin-3-yl |  | 3.11 | C |
| I.204 |  | C(Me)2 | C=O | — | 8-fluoro-7-methoxyquinolin-3-yl |  | 2.94 | C |
| I.205 |  | (cyclopentyl) | C=O | — | quinolin-3-yl |  | 3.42 | C |
| I.206 |  | C(Me)2 | CF2 | — | 7,8-difluoro-quinolin-3-yl |  | 3.51 | C |
| I.207 | 4-F | C(Me)2 | C(Me)2 | — | quinolin-3-yl |  | 3.46 | C |
| I.208 | 4-F | CH(Me) | CH2 | — | quinolin-3-yl |  | 2.70 | C |

TABLE 1A-continued

| Example | (X)n | L1 | L2 | L3 | [A ring with (Y)p, N, Z] | M + H | logP | log P Method |
|---|---|---|---|---|---|---|---|---|
| I.209 | | C(Me)2 | 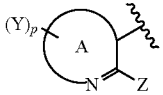 | — | quinolin-3-yl | | 3.02 | C |
| I.210 | | CH2 |  | — | quinolin-3-yl | | 2.14 | C |
| I.211 | | C(Me)2 | CMe(F) | — | quinolin-3-yl | | 3.29 | C |
| I.212 | | C(Me)2 | CMe(OMe) | — | quinolin-3-yl | | 2.94 | C |
| I.213 | | C(Me)2 | CMe(OH) | — | quinolin-3-yl | | 2.46 | C |
| I.214 | | C(Me)2 | CH(OMe) | — | quinolin-3-yl | | 3.03 | C |
| I.215 | | C(Me)2 | CH(OH) | — | quinolin-3-yl | | 2.22 | C |
| I.216 | | C(Me)2 | CH(F) | — | quinolin-3-yl | | 3.02 | C |
| I.217 | 4-F | C(Me)2 | O | — | 1-oxidoquinolin-1-ium-3-yl | | 2.21 | C |
| I.218 | | CH2 | O | — | quinoxalin-2-yl | | 2.58 | C |
| I.219 | | C(Me)2 | 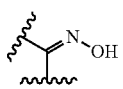 | — | 7,8-difluoro-quinolin-3-yl | | 3.34 | C |
| I.220 | 4-F | C(Me)2 | O | — | quinolin-3-yl | | 3.09 | C |
| I.221 | 4-F | CH2 | O | — | quinolin-3-yl | | 2.56 | C |
| I.222 | 4-F | CH2 | CH2 | — | 1-oxidoquinolin-1-ium-3-yl | | 1.72 | C |
| I.223 | 4-F | CH2 | O | — | 1-oxidoquinolin-1-ium-3-yl | | 1.83 | C |
| I.224 | | CH2 | O | — | 7,8-difluoro-quinolin-3-yl | | 2.72 | C |
| I.225 | | C(Me)2 | CMe(F) | — | 7,8-difluoro-quinolin-3-yl | | 3.60 | C |
| I.226 | | C(Me)2 | CMe(OMe) | — | 7,8-difluoro-quinolin-3-yl | | 3.32 | C |
| I.227 | | C(Me)2 | CMe(OH) | — | 7,8-difluoro-quinolin-3-yl | | 2.93 | C |
| I.228 | | C(Me)2 | CH(F) | — | 7,8-difluoro-quinolin-3-yl | | 3.30 | C |
| I.229 | | C(Me)2 | CH(OMe) | — | 7,8-difluoro-quinolin-3-yl | | 3.35 | C |
| I.230 | | C(Me)2 | O | — | 5,6-difluoro-quinoxalin-2-yl | | 4.66 | C |
| I.231 | | C(Me)2 | CH2 | — | 5,6-difluoro-quinoxalin-2-yl | | 3.32 | C |
| I.232 | | C(Me)2 | O | — | quinoxalin-2-yl | | 4.41 | C |
| I.233 | 4-F | CH(Me) | O | — | quinolin-3-yl | | 2.87 | C |
| I.234 | 4-F | CH(Me) | CH2 | — | 1-oxidoquinolin-1-ium-3-yl | | 1.93 | C |
| I.235 | 4-F | C(Me)2 | CH2 | — | 1-oxidoquinolin-1-ium-3-yl | | 2.09 | C |
| I.236 | 4-F | CH(Et) | CH2 | — | quinolin-3-yl | | 3.04 | C |
| I.237 | 4-F | CH(Et) | CH2 | — | 1-oxidoquinolin-1-ium-3-yl | | 2.23 | C |
| I.238 | 4-F | CH(Me) | O | — | 1-oxidoquinolin-1-ium-3-yl | | 2.07 | C |
| I.239 | | CCl2 | C=O | — | quinolin-3-yl | | 3.49 | C |
| I.240 | | CH2 | 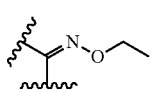 [SMILES: *C(*)=NOCC] | — | quinolin-3-yl | | 3.38 | C |
| I.241 | | CH2 | 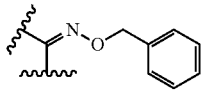 [SMILES: *C(*)=NOCc1ccccc1] | — | quinolin-3-yl | | 3.94 | C |

TABLE 1A-continued

| Example | (X)n | L1 | L2 | L3 | 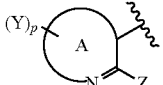 | M + H | logP | log P Method |
|---|---|---|---|---|---|---|---|---|
| I.242 | 4-F | CH2 | 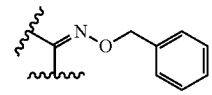 [SMILES: *C(*)=NOCc1ccccc1] | — | quinolin-3-yl | | 4.09 | C |
| I.243 | | C(Me)2 | CH(Me) | — | 5,6-difluoro-quinoxalin-2-yl | | 3.62 | C |
| I.244 | | C(Me)2 | CH(Me) | — | 7,8-difluoro-quinolin-3-yl | | 3.44 | C |
| I.245 | | CH2 | 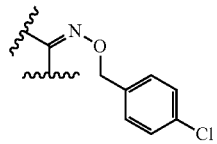 [SMILES: *C(*)=NOCc1ccc(Cl)cc1] | — | quinolin-3-yl | | 4.34 | C |
| I.246 | | CH2 | 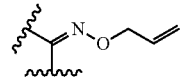 | — | quinolin-3-yl | | 3.47 | C |
| I.247 | | CH2 | 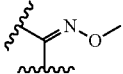 | — | quinolin-3-yl | | 2.98 | C |
| I.248 | | CH2 | 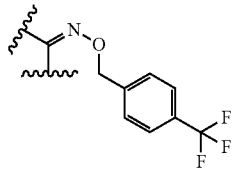 [SMILES: *C(*)=NOCc1ccc(C(F)(F)F)cc1] | — | quinolin-3-yl | | 4.40 | C |
| I.251 | | C(Me)2 | CMe(OMe) | — | 6-(trifluoro-methyl)pyridin-3-yl | | 3.34 | C |
| I.252 | | C(Me)2 | CMe(OMe) | — | 1-methyl-1H-pyrrolo[2,3-b]pyridin-5-yl | | 2.86 | C |
| I.253 | | C(Me)2 | CMe(OMe) | — | thieno[2,3-b]pyridin-5-yl | | 3.06 | C |
| I.254 | | C(Me)2 | CMe(OMe) | — | 8-methyl-quinolin-3-yl | | 3.72 | C |
| I.255 | | C(Me)2 | CMe(OMe) | — | pyrazolo[1,5-a]pyrimidin-6-yl | | 2.30 | C |
| I.256 | | C(Me)2 | CMe(OMe) | — | 2-methylimidazo[1,2-a]pyrimidin-6-yl | | 1.34 | C |
| I.257 | | C(Me)2 | CMe(OMe) | — | 1-methyl-1H-pyrrolo[3,2-b]pyridin-6-yl | | 1.91 | C |
| I.258 | | C(Me)2 | CMe(OMe) | — | 5-oxo-5,6-dihydro-1,6-naphthyridin-3-yl | | 1.79 | C |
| I.259 | | C(Me)2 |  | — | 5-methyl-5H-pyrrolo[2,3-b]pyrazin-3-yl | | 2.59 | C |
| I.260 | | C(Me)2 | CMe(OMe) | — | 8-fluoro-6-methyl quinolin-3-yl | | 3.44 | C |
| I.261 | | C(Me)2 | CMe(OMe) | — | 5-methyl-5H-pyrrolo[2,3-b]pyrazin-2-yl | | 2.63 | C |
| I.262 | | C(Me)2 | CMe(OMe) | — | 6-cyano-quinolin-3-yl | | 2.98 | C |

TABLE 1A-continued

|  |  |  |  |  | (Y)p—A—Z, N |  |  | log P |
|---|---|---|---|---|---|---|---|---|
| Example | (X)n | L1 | L2 | L3 |  | M + H | logP | Method |
| I.263 |  | C(Me)2 | CMe(OMe) | — | 8-chloro-6-cyanoquinolin-3-yl |  | 3.51 | C |
| I.264 |  | C(Me)2 | CMe(OMe) | — | 5-methyl-5H-pyrrolo[2,3-b]pyrazin-3-yl |  | 2.55 | C |
| I.265 |  | C(Me)2 | CMe(OMe) | — | 3-fluoropyrazolo[1,5-a]pyrimidin-6-yl |  | 2.70 | C |
| I.266 |  | C(Me)2 | CMe(OMe) | — | 1,8-naphthyridin-3-yl |  | 1.95 | C |
| I.267 |  | C(Me)2 | CMe(OMe) | — | 6,7-dihydro-5H-cyclopenta[b]pyridin-3-yl |  | 2.52 | C |
| I.269 |  | C(Me)2 | CMe(OMe) | — | 3-methyl-3H-imidazo[4,5-b]pyridin-6-yl |  | 1.86 | C |
| I.270 |  | C(Me)2 | CMe(OMe) | — | furo[3,2-b]pyridin-6-yl |  | 2.53 | C |
| I.271 |  | C(Me)2 | CMe(OMe) | — | pyrido[2,3-b]pyrazin-7-yl |  | 1.96 | C |
| I.273 |  | C(Me)2 | CMe(OMe) | — | 2-methylpyrazolo[1,5-a]pyrimidin-6-yl |  | 2.54 | C |
| I.274 |  | C(Me)2 | CMe(OMe) | — | 5,6,7,8-tetrahydroquinolin-3-yl |  | 2.37 | C |
| I.277 |  | C(Me)2 | CMe(OMe) | — | pyrrolo[1,2-a]pyrimidin-3-yl |  | 2.64 | C |
| I.278 |  | C(Me)2 | CMe(OMe) | — | 3,4-dihydro-2H-pyrano[2,3-b]pyridin-6-yl |  | 2.43 | C |
| I.281 |  | C(Me)2 | CMe(OMe) | — | 1,5-naphthyridin-3-yl |  | 2.22 | C |
| I.313 |  | 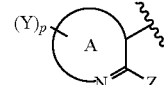 | CF2 | — | quinolin-3-yl |  | 4.10 | C |
| I.314 |  | C(Me)Bn | CF2 | — | quinolin-3-yl |  | 4.29 | C |
| I.315 |  | 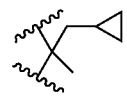 | C=O | — | quinolin-3-yl |  | 3.50 | C |
| I.316 |  | 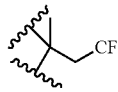 | C=O | — | quinolin-3-yl |  | 3.11 | C |
| I.317 |  | 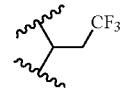 | C=O | — | quinolin-3-yl |  | 3.06 | C |
| I.318 |  |  | CF2 | — | quinolin-3-yl |  | 3.81 | C |
| I.319 |  |  | C=O | — | quinolin-3-yl |  | 3.44 | C |

TABLE 1A-continued

| Example | (X)n | L1 | L2 | L3 | ⟨structure⟩ Z | M + H | logP | log P Method |
|---|---|---|---|---|---|---|---|---|
| I.330 | | C(Me)2 | CMe(OMe) | — | 8-cyano-quinolin-3-yl | | 3.00 | C |
| I.331 | | *CH2C(Me)2CH2CH=CF2 (with F)* | C=O | — | quinolin-3-yl | | 3.89 | C |
| I.332 | | *C(Me)2CH2CH2-phenyl* | CF2 | — | quinolin-3-yl | | 4.55 | C |
| I.333 | | *C(Me)2CH2-(5-CF3-furan-2-yl)* | C=O | — | quinolin-3-yl | | 4.08 | C |
| I.334 | | *C(Me)2CH2-(pyridin-3-yl)* | C=O | — | quinolin-3-yl | | 1.97 | C |
| I.335 | | *CH(cyclopropyl)* | C=O | — | quinolin-3-yl | | 2.90 | C |
| I.336 | | *C(Me)2-cyclopropyl* | CF2 | — | quinolin-3-yl | | 3.47 | C |
| I.337 | | *CH(CH2-cyclopropyl)* | C=O | — | quinolin-3-yl | | 3.26 | C |
| I.338 | | CH2 | S | — | quinoxalin-2-yl | 330 | 2.73 | A |
| I.339 | | *C(Me)2CH2-(pyridin-3-yl)* | CF2 | — | quinolin-3-yl | | 2.11 | C |
| I.340 | | C(Me)2 | CMe(OMe) | — | 5-(ethoxy-carbonyl)quinolin-3-yl | | 3.58 | C |
| I.344 | | CH(Bn) | S | — | quinoxalin-2-yl | 420 | 3.97 | A |
| I.345 | | C(Me)2 | C=O | N(Me) | quinolin-3-yl | | 2.42 | C |
| I.346 | | CH2 | C=O | NH | quinolin-3-yl | | 1.63 | C |
| I.347 | | CH2 | CH2 | CH2 | 7,8-difluoro-quinolin-3-yl | | 2.79 | C |
| I.348 | | C(Me)2 | CH2 | CH2 | quinolin-3-yl | | 2.91 | C |
| I.349 | | CH2 | CH2 | CH2 | quinolin-3-yl | | 2.39 | C |
| I.350 | | CH(Me) | CH2 | CH2 | 7,8-difluoro-quinolin-3-yl | | 3.09 | C |
| I.351 | | CH(Me) | CH2 | CH2 | quinolin-3-yl | | 2.68 | C |
| I.352 | | C(Me)2 | CH2 | CH2 | 7,8-difluoro-quinolin-3-yl | | 3.34 | C |
| I.353 | | CH2 | CH(Ph) | CH2 | 7,8-difluoro-quinolin-3-yl | | 3.92 | C |
| I.354 | | CH2 | CH(Ph) | CH2 | quinolin-3-yl | | 3.62 | C |
| I.355 | | CH(Me) | CH(Ph) | CH2 | quinolin-3-yl | | 3.94 | C |
| I.356 | | CH(Et) | CH(Ph) | CH2 | 7,8-difluoro-quinolin-3-yl | | 4.47 | C |

TABLE 1A-continued

| Example | (X)n | L1 | L2 | L3 | A ring / Z | M + H | logP | log P Method |
|---|---|---|---|---|---|---|---|---|
| I.357 | | CH(Me) | CH(Ph) | CH2 | 7,8-difluoro-quinolin-3-yl | | 4.19 | C |
| I.358 | | CH2 | O | C(Me)2 | quinolin-3-yl | | 2.74 | C |
| I.359 | | CH2 | O | C(Me)2 | 7,8-difluoro-quinolin-3-yl | | 3.12 | C |
| I.360 | | CH2 | O | C(Me)2 | 8-fluoro-quinolin-3-yl | | 2.83 | C |

Note:
Me: methyl; Et: ethyl; i-Pr: isopropyl Ph: phenyl; Bn: benzyl

Note[(1)]:
1.4/1 E/Z mixture

Table 1b illustrates in a non-limiting manner an example of a compound of formula (Im) according to the invention

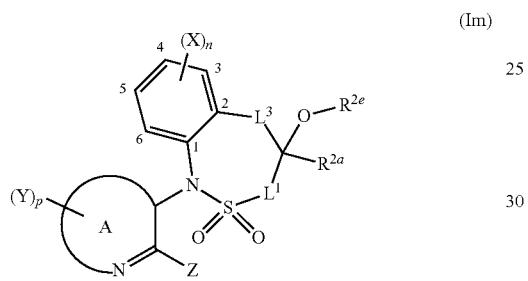

(Im)

In table 1b, M+H (Apcl+) and log P are defined as for table 1a.

In table 1b, the point of attachment of the $(X)_n$ residue to the phenyl ring is based on the above numbering of the phenyl ring.

TABLE 1b

| Example | (X)$_n$ | L$^1$ | R$^{2e}$ | R$^{2a}$ | L$^3$ | A/Z | M + H | logP | logP Method |
|---|---|---|---|---|---|---|---|---|---|
| I.249 | | C(Me)$_2$ | (4-chlorophenyl)methyl | Me | — | quinolin-3-yl | | 4.45 | C |
| I.250 | | C(Me)$_2$ | benzyl | Me | — | quinolin-3-yl | | 4.04 | C |
| I.268 | | C(Me)$_2$ | naphthalen-2-ylmethyl | Me | — | quinolin-3-yl | | 4.68 | C |
| I.272 | | C(Me)$_2$ | (4-phenylphenyl)methyl | Me | — | quinolin-3-yl | | 5.04 | C |
| I.275 | | C(Me)$_2$ | [4-(trifluoromethoxy)phenyl]methyl | Me | — | quinolin-3-yl | | 4.76 | C |
| I.276 | | C(Me)$_2$ | (4-benzoylphenyl)methyl | Me | — | quinolin-3-yl | | 4.43 | C |
| I.279 | | C(Me)$_2$ | (4-tert-butylphenyl)methyl | Me | — | quinolin-3-yl | | 5.50 | C |
| I.280 | | C(Me)$_2$ | (3-cyanophenyl)methyl | Me | — | quinolin-3-yl | | 3.51 | C |
| I.282 | | C(Me)$_2$ | (4-methylsulfonylphenyl)methyl | Me | — | quinolin-3-yl | | 2.95 | C |
| I.283 | | C(Me)$_2$ | (3-methoxyphenyl)methyl | Me | — | quinolin-3-yl | | 4.02 | C |
| I.284 | | C(Me)$_2$ | (4-cyanophenyl)methyl | Me | — | quinolin-3-yl | | 3.58 | C |
| I.285 | | C(Me)$_2$ | (3-methylphenyl)methyl | Me | — | quinolin-3-yl | | 4.47 | C |
| I.286 | | C(Me)$_2$ | (2-methylphenyl)methyl | Me | — | quinolin-3-yl | | 4.42 | C |
| I.287 | | C(Me)$_2$ | (3-chlorophenyl)methyl | Me | — | quinolin-3-yl | | 4.43 | C |
| I.288 | | C(Me)$_2$ | (2-chlorophenyl)methyl | Me | — | quinolin-3-yl | | 4.53 | C |
| I.289 | | C(Me)$_2$ | (4-methoxyphenyl)methyl | Me | — | quinolin-3-yl | | 4.02 | C |
| I.290 | | C(Me)$_2$ | [4-(trifluoromethyl)phenyl]methyl | Me | — | quinolin-3-yl | | 4.55 | C |
| I.291 | | C(Me)$_2$ | (4-fluorophenyl)methyl | Me | — | quinolin-3-yl | | 4.13 | C |
| I.292 | | C(Me)$_2$ | (3-fluorophenyl)methyl | Me | — | quinolin-3-yl | | 4.11 | C |
| I.293 | | C(Me)$_2$ | (2-fluorophenyl)methyl | Me | — | quinolin-3-yl | | 4.21 | C |
| I.294 | | C(Me)$_2$ | (3-phenoxyphenyl)methyl | Me | — | quinolin-3-yl | | 4.95 | C |
| I.295 | | C(Me)$_2$ | (4-methylphenyl)methyl | Me | — | quinolin-3-yl | | 4.51 | C |
| I.296 | | C(Me)$_2$ | (2-cyanophenyl)methyl | Me | — | quinolin-3-yl | | 3.66 | C |

TABLE 1b-continued

| Example | $(X)_n$ | $L^1$ | $R^{2e}$ | $R^{2a}$ | $L^3$ | A | M + H | logP | logP Method |
|---|---|---|---|---|---|---|---|---|---|
| I.297 | | $C(Me)_2$ | (4-phenoxyphenyl)methyl | Me | — | quinolin-3-yl | | 5.04 | C |
| I.298 | | $C(Me)_2$ | pyridin-2-ylmethyl | Me | — | quinolin-3-yl | | 2.08 | C |
| I.299 | | $C(Me)_2$ | 2,1,3-benzothiadiazol-5-ylmethyl | Me | — | quinolin-3-yl | | 3.76 | C |
| I.300 | | $C(Me)_2$ | (4,6-dimethylpyrimidin-2-yl)methyl | Me | — | quinolin-3-yl | | 2.83 | C |
| I.301 | | $C(Me)_2$ | prop-2-yn-1-yl | Me | — | quinolin-3-yl | | 3.09 | C |
| I.302 | | $C(Me)_2$ | [3-(trifluoromethoxy)phenyl]methyl | Me | — | quinolin-3-yl | | 4.66 | C |
| I.303 | | $C(Me)_2$ | [2-(4-chlorophenyl)-1,3-thiazol-4-yl]methyl | Me | — | quinolin-3-yl | | 5.26 | C |
| I.304 | | $C(Me)_2$ | [5-(trifluoromethyl)-2-furyl]methyl | Me | — | quinolin-3-yl | | 4.26 | C |
| I.305 | | $C(Me)_2$ | (1-methyl-1H-indazol-6-yl)methyl | Me | — | quinolin-3-yl | | 3.35 | C |
| I.306 | | $C(Me)_2$ | allyl | Me | — | quinolin-3-yl | | 3.57 | C |
| I.307 | | $C(Me)_2$ | [4-(trifluoromethylthio)phenyl]methyl | Me | — | quinolin-3-yl | | 5.06 | C |
| I.308 | | $C(Me)_2$ | (3-phenylphenyl)methyl | Me | — | quinolin-3-yl | | 4.95 | C |
| I.309 | | $C(Me)_2$ | 1,3-thiazol-2-ylmethyl | Me | — | quinolin-3-yl | | 2.95 | C |
| I.310 | | $C(Me)_2$ | naphthalen-1-ylmethyl | Me | — | quinolin-3-yl | | 4.66 | C |
| I.311 | | $C(Me)_2$ | 1,2-benzoxazol-3-ylmethyl | Me | — | quinolin-3-yl | | 3.77 | C |
| I.312 | | $C(Me)_2$ | 1,3-benzoxazol-2-ylmethyl | Me | — | quinolin-3-yl | | 3.57 | C |
| I.320 | | $C(Me)_2$ | (3-benzoylphenyl)methyl | Me | — | quinolin-3-yl | | 4.41 | C |
| I.321 | | $C(Me)_2$ | (2,4-dichlorophenyl)methyl | Me | — | quinolin-3-yl | | 5.13 | C |
| I.322 | | $C(Me)_2$ | [2-fluoro-4-(trifluoromethyl)phenyl]methyl | Me | — | quinolin-3-yl | | 4.75 | C |
| I.323 | | $C(Me)_2$ | [2-chloro-4-(2-cyanophenyl)phenyl]methyl | Me | — | quinolin-3-yl | | 4.84 | C |
| I.324 | | $C(Me)_2$ | [2-fluoro-4-(trifluoromethoxy)phenyl]methyl | Me | — | quinolin-3-yl | | 4.88 | C |
| I.325 | | $C(Me)_2$ | [2-chloro-4-(trifluoromethyl)phenyl]methyl | Me | — | quinolin-3-yl | | 5.10 | C |
| I.326 | | $C(Me)_2$ | (4-chloro-2-methylphenyl)methyl | Me | — | quinolin-3-yl | | 4.80 | C |
| I.327 | | $C(Me)_2$ | [2-methyl-4-(trifluoromethoxy)phenyl]methyl | Me | — | quinolin-3-yl | | 5.00 | C |
| I.328 | | $C(Me)_2$ | (2-fluoro-4-methoxyphenyl)methyl | Me | — | quinolin-3-yl | | 4.18 | C |
| I.329 | | $C(Me)_2$ | [3,5-bis(trifluoromethyl)phenyl]methyl | Me | — | quinolin-3-yl | | 4.90 | C |
| I.341 | | $C(Me)_2$ | [4-(difluoromethoxy)-2-fluorophenyl]methyl | Me | — | quinolin-3-yl | | 4.27 | C |
| I.342 | | $C(Me)_2$ | (2-chloro-4-methoxyphenyl)methyl | Me | — | quinolin-3-yl | | 4.51 | C |
| I.343 | | $C(Me)_2$ | (4-benzyloxyphenyl)methyl | Me | — | quinolin-3-yl | | 4.96 | C |

Note:
Me: methyl

Table 2 illustrates in a non-limiting manner an example of a compound of formula (IVa) according to the invention:

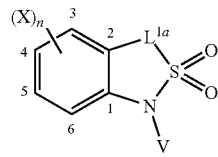

(IVa)

In table 2, M+H (Apcl+) and log P are defined as for table 1a.

In table 2, the point of attachment of the $(X)_n$ residue to the phenyl ring is based on the above numbering of the phenyl ring.

TABLE 2

| Example | $(X)_n$ | $L^{1a}$ | V | M + H | logP | logP Method |
|---|---|---|---|---|---|---|
| IVa.01 | | $C(Me)_2$ | allyl | | 2.75 | A |

Note:
Me: methyl

Table 3 illustrates in a non-limiting manner an example of a compound of formula (IIIb1) or a compound of formula (IVb1) according to the invention:

(IIIb1)

(IVb1)

In table 3, M+H (Apcl+) and log P are defined as for table 1a.

In table 3, the point of attachment of the $(X)_n$ residue to the phenyl ring is based on the above numbering of the phenyl ring.

TABLE 3

| Example | $(X)_n$ | $L^{2a}$ | $L^1$ | V | M + H | logP | logP Method |
|---|---|---|---|---|---|---|---|
| IIIb1.01 | | CH(Me) | $C(Me)_2$ | | | 1.92 | C |
| IIIb1.02 | | C = O | $C(Me)_2$ | | | 1.69 | C |
| IIIb1.03 | | $CF_2$ | $C(Me)_2$ | | | 2.07 | C |
| IIIb1.04 | | CMe(OMe) | $C(Me)_2$ | | | 1.72 | C |
| IVb1.01 | | C = O | $C(Me)_2$ | Bn | | 3.39 | C |
| IVb1.02 | | $CF_2$ | $C(Me)_2$ | Bn | | 3.74 | C |

TABLE 3-continued

| Example | (X)$_n$ | L$^{2a}$ | L$^1$ | V | M + H | logP | logP Method |
|---|---|---|---|---|---|---|---|
| IVb1.03 | | 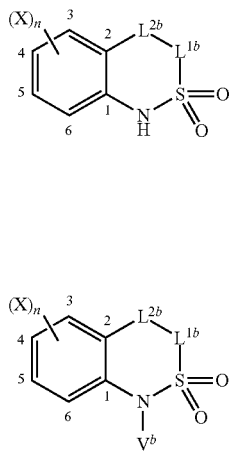 | C(Me)$_2$ | Bn | | 3.60 | C |
| IVb1.04 | | CMe(F) | C(Me)$_2$ | Bn | | 3.89 | C |
| IVb1.05 | | CMe(OH) | C(Me)$_2$ | Bn | | 3.01 | C |
| IVb1.06 | | CMe(OMe) | C(Me)$_2$ | Bn | | 3.42 | C |

Note:
Me: methyl;
Bn: benzyl

Table 4 illustrates in a non-limiting manner an example of a compound of formula (IIIb2) or a compound of formula (IVb2) according to the invention:

(IIIb2)

(IVb2)

In table 4, M+H (Apcl+) and log P are defined as for table 1a.

In table 4, the point of attachment of the (X)$_n$ residue to the phenyl ring is based on the above numbering of the phenyl ring.

TABLE 4

| Example | (X)$_n$ | L$^{2b}$ | L$^{1b}$ | V$^b$ | M + H | logP | logP Method |
|---|---|---|---|---|---|---|---|
| IIIb2.01 | | O | C(Me)$_2$ | | | 1.65 | C |
| IVb2.01 | | O | C(Me)$_2$ | 4-methoxybenzyl | | 3.35 | C |

Note:
Me: methyl

Table 5 illustrates in a non-limiting manner an example of a compound of formula (IIIc) or a compound of formula (IVc) according to the invention:

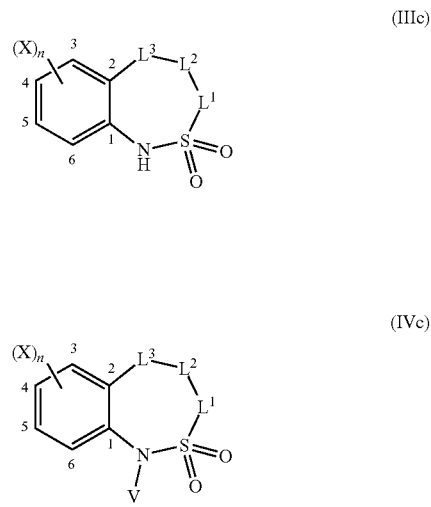

In table 5, M+H (Apcl+) and log P are defined as for table 1a.

In table 5, the point of attachment of the (X)$_n$ residue to the phenyl ring is based on the above numbering of the phenyl ring.

TABLE 5

| Example | (X)$_n$ | L$^3$ | L$^2$ | L$^1$ | V | M + H | logP | logP Method |
|---|---|---|---|---|---|---|---|---|
| IIIc.01 | | CH$_2$ | CH(Ph) | CH$_2$ | | | 2.49 | C |
| IIIc.02 | | CH$_2$ | CH$_2$ | CH$_2$ | | | 1.20 | C |
| IIIc.03 | | C(Me)$_2$ | O | CH$_2$ | | | 1.49 | C |
| IVc.01 | | CH$_2$ | CH(Ph) | CH$_2$ | Bn | | 3.98 | C |
| IVc.02 | | C(Me)$_2$ | O | CH$_2$ | 4-methoxybenzyl | | 3.06 | C |

Note:
Me: methyl; Ph: phenyl; Bn: benzyl

Table 6 illustrates in a non-limiting manner examples of compounds of formula (V) according to the invention:

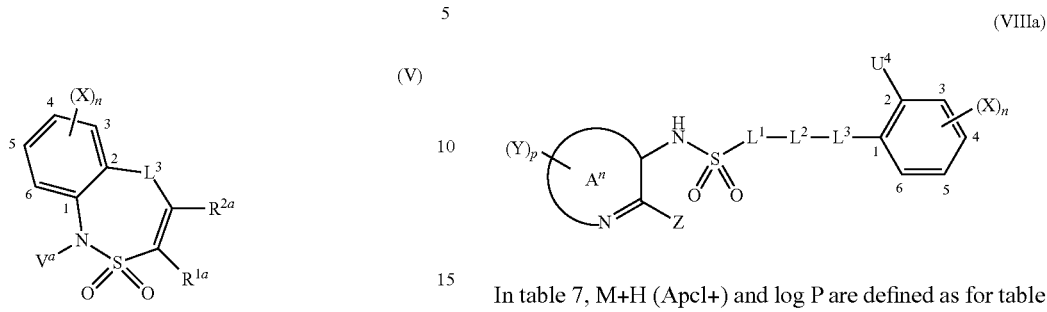

(V)

In table 6, M+H (Apcl+) and log P are defined as for table 1a.

Table 7 illustrates in a non-limiting manner examples of compounds of formula (VIIIa) according to the invention:

(VIIIa)

In table 7, M+H (Apcl+) and log P are defined as for table 1a. In table 7, the point of attachment of the $(X)_n$ residue to the phenyl ring is based on the above numbering of the phenyl ring.

TABLE 7

| Example | $(X)_n$ | $L^1$ | $L^2$ | $L^3$ | $U^4$ | (structure) | M + H | logP | logP Method |
|---|---|---|---|---|---|---|---|---|---|
| VIIIa.01 |  | $CH_2$ | — | — | Br | 2-methylquinolin-3-yl | 391 | 2.08 | A |
| VIIIa.02 |  | $CH_2$ | — | — | Br | 7,8-difluoro-2-methylquinolin-3-yl | 427 | 3.02 | A |
| VIIIa.03 |  | $CH_2$ | — | — | Br | 5,6-difluoro-3-methylquinoxalin-2-yl | 428 | 3.21 | A |
| VIIIa.04 |  | $CH_2$ | — | — | Br | 8-fluoroquinolin-3-yl | 395 | 2.64 | A |
| VIIIa.05 | 5-Me | $CH_2$ | — | — | Br | 7,8-difluoro-2-methylquinolin-3-yl | 441 | 3.35 | A |
| VIIIa.06 | 5-OMe | $CH_2$ | — | — | Br | 7,8-difluoro-2-methylquinolin-3-yl | 457 | 3.13 | A |
| VIIIa.07 | 6-Br | $CH_2$ | — | — | Br | 8-fluoroquinolin-3-yl | 473 | 2.91 | A |
| VIIIa.08 | 4-F | $CH_2$ | — | — | Br | 8-fluoroquinolin-3-yl | 413 | 2.64 | A |
| VIIIa.09 | 5-Me | $CH_2$ | — | — | Br | 8-fluoroquinolin-3-yl | 409 | 2.84 | A |
| VIIIa.10 |  | $CH_2$ | — | — | Br | 2,4-bis(difluoromethyl)quinolin-3-yl | 477 | 3.39 | A |
| VIIIa.11 | 3-Cl | $CH_2$ | — | — | Br | 8-fluoroquinolin-3-yl | 429 | 2.90 | A |
| VIIIa.12 | 3-F | $CH_2$ | — | — | Br | 8-fluoroquinolin-3-yl | 413 | 2.71 | A |
| VIIIa.13 | 5-Cl | $CH_2$ | — | — | Br | 8-fluoroquinolin-3-yl | 429 | 2.94 | A |
| VIIIa.14 | 5-F | $CH_2$ | — | — | Br | 8-fluoroquinolin-3-yl | 413 | 2.68 | A |
| VIIIa.15 | 3-Me | $CH_2$ | — | — | Br | 8-fluoroquinolin-3-yl | 409 | 2.88 | A |
| VIIIa.16 | 5-OMe | $CH_2$ | — | — | Br | 8-fluoroquinolin-3-yl | 425 | 2.71 | A |
| VIIIa.17 | 4-Me | $CH_2$ | — | — | Br | 8-fluoroquinolin-3-yl | 409 | 2.92 | A |
| VIIIa.18 |  | $CH_2$ | $C(Me)_2$ | — | Br |  |  | 2.98 | C |
| VIIIa.19 | 5-F | $CH_2$ | $CH_2$ | — | Br | quinolin-3-yl |  | 2.77 | C |
| VIIIa.20 |  | $CH_2$ | $CH_2$ | — | Br | 7,8-difluoro-2-methylquinolin-3-yl |  | 3.25 | C |
| VIIIa.21 | 5-F | $CH_2$ | $C(Me)_2$ | — | Br | quinolin-3-yl |  | 3.12 | C |
| VIIIa.22 | 5-Cl | $CH_2$ | $CH_2$ | — | Br | quinolin-3-yl |  | 3.53 | C |
| VIIIa.23 |  | $CH_2$ | $CH_2$ | — | Br | quinolin-3-yl |  | 2.69 | C |
| VIIIa.24 |  | $CH_2$ | $CH_2$ | $CH_2$ | Br | quinolin-3-yl |  | 2.89 | C |

Note:
Me: methyl

In table 6, the point of attachment of the $(X)_n$ residue to the phenyl ring is based on the above numbering of the phenyl ring.

TABLE 6

| Example | $(X)_n$ | $L^3$ | $R^{2a}$ | $R^{1a}$ | $V^a$ | M + H | log P | logP Method |
|---|---|---|---|---|---|---|---|---|
| V.01 |  | $CH_2$ | H | H | Bn |  | 6.01 | C |

Note:
Bn: benzyl

Table 8 illustrates in a non-limiting manner examples of compounds of formula (Xa) according to the invention:

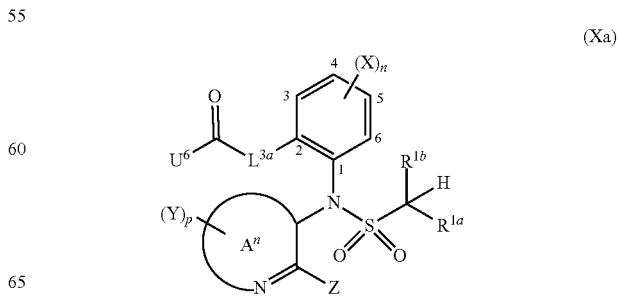

(Xa)

In table 8, M+H (Apcl+) and log P are defined as for table 1a.

In table 8, the point of attachment of the (X)_n residue to the phenyl ring is based on the above numbering of the phenyl ring.

TABLE 8

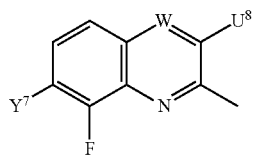

| Example | (X)_n | L^{3a} | U^6 | R^{1a} | R^{1b} | Z | M + H | logP | logP Method |
|---|---|---|---|---|---|---|---|---|---|
| Xa.01 | 4-F | — | OMe | H | H | quinolin-3-yl | | 2.37 | C |
| Xa.02 | | — | OMe | H | H | quinolin-3-yl | | 2.17 | C |
| Xa.03 | | — | OMe | H | H | quinoxalin-2-yl | | 2.42 | C |
| Xa.04 | | — | OMe | H | H | 7,8-difluoroquinolin-3-yl | | 2.58 | C |

Note:
Me: methyl

Table 9 illustrates in a non-limiting manner examples of compounds of formula (IIa) according to the invention:

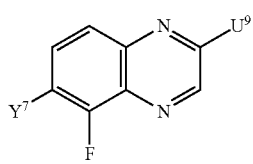

(IIa)

In table 9, M+H (Apcl+) and log P are defined as for table 1a.

TABLE 9

| Example | W | Y^7 | U^8 | M + H | logP | logP Method |
|---|---|---|---|---|---|---|
| IIa.01 | CH | H | I | 288 | 3.06 | A |
| IIa.02 | CH | F | NH_2 | | 1.32 | A |
| IIa.03 | CH | F | I | | 3.39 | B |
| IIa.04 | N | F | OH | 197 | 1.32 | A |
| IIa.05 | N | F | Br | 259 | 2.96 | A |
| IIa.06 | N | F | NH_2 | 196 | 1.29 | A |
| IIa.07 | N | H | Br | 241 | 2.64 | A |

Table 10 illustrates in a non-limiting manner examples of compounds of formula (IIb) according to the invention:

(IIb)

In table 10, M+H (Apcl+) and log P are defined as for table 1a.

TABLE 10

| Example | Y^7 | U^9 | M + H | logP | logP Method |
|---|---|---|---|---|---|
| IIb.01 | F | Br | | 2.62 | A |
| IIb.02 | F | NH_2 | 182 | 1.20 | A |
| IIb.03 | H | Br | | 2.30 | A |

Table 11 illustrates other preferred compounds of formula (II), (III) and (IV), according to the invention.

In table 11, M+H (Apcl+) and log P are defined as for table 1a.

TABLE 11

| Example | Structure | M + H | log P | logP Method |
|---|---|---|---|---|
| II.01A | 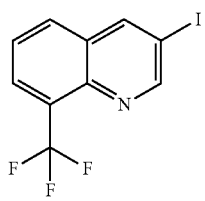 [SMILES: FC(F)(F)c1cccc2cc(I)cnc12] | 324 | 3.11 | A |
| II.02A | 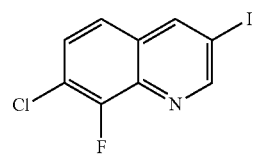 [SMILES: Fc1c(Cl)ccc2cc(I)cnc12] | 308 | 3.37 | A |
| II.03A | 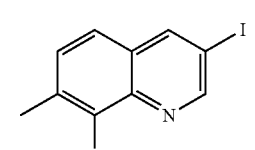 | 288 | 3.11 | A |
| II.04A | 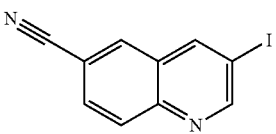 [SMILES: N#Cc1ccc2ncc(I)cc2c1] | 281 | 2.5 | A |

TABLE 11-continued

| Example | Structure | M + H | log P | log P Method |
|---|---|---|---|---|
| II.05A | (6-F, 8-F quinoline, 3-I) | 292 | 2.88 | A |
| II.06A | (5-F, 8-F quinoline, 3-I) | 292 | 2.94 | A |
| II.07A | (7-Cl, 8-Cl quinoline, 3-I) | 324 | 3.83 | A |
| II.08A | (6-F, 7-F quinoline, 3-I) | 292 | 3.15 | A |
| II.09A | (6-Cl, 8-F quinoline, 3-I) | 308 | 3.15 | A |
| II.10A | (5-Me, 8-F quinoline, 3-I) | 288 | 3.06 | A |
| II.11A | (8-CN quinoline, 3-I) | 281 | 2.54 | A |
| II.12A | (5-F, 7-F quinoline, 3-I) | 292 | 3.31 | A |
| III.01A | (4-F benzisothiazoline dioxide) | | 1.34 | A |
| III.02A | (4-CF3 benzisothiazoline dioxide) | | 1.99 | A |
| III.03A | (5-CF3 benzisothiazoline dioxide) | 238 | 1.95 | A |
| III.04A | (4-OCF3 benzisothiazoline dioxide) | 254 | 2.11 | A |
| III.05A | (4-CN benzisothiazoline dioxide) | | 1.08 | A |
| III.06A | (3,3-dimethyl benzothiazine dioxide) | | 1.6 | C |
| III.07A | (spirocyclopropyl benzothiazine dioxide) | | 1.49 | C |
| IV.01A | (N-benzyl spirocyclopropyl benzothiazine dioxide) | | 3.19 | C |

Table 12 provides the NMR data (1H) of some compounds disclosed in tables 1a, 1b, 2 to 11.

The $^1$H-NMR data of selected examples are stated in the form of $^1$H-NMR peak lists. For each signal peak, the δ value in ppm and the signal intensity in brackets are listed.

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

The ¹H-NMR peak lists are similar to classical ¹H-NMR prints and contain therefore usually all peaks, which are listed at classical NMR-interpretation. Additionally they can show like classical ¹H-NMR prints signals of solvents, stereoisomers of the target compounds, which are also object of the invention, and/or peaks of impurities. To show compound signals in the delta-range of solvents and/or water the usual peaks of solvents, for example peaks of DMSO in d6-DMSO and the peak of water are shown in our ¹H-NMR peak lists and have usually on average a high intensity.

The peaks of stereoisomers of the target compounds and/or peaks of impurities have usually on average a lower intensity than the peaks of target compounds (for example with a purity>90%). Such stereoisomers and/or impurities can be typical for the specific preparation process. Therefore their peaks can help to recognize the reproduction of the preparation process via "side-products-fingerprints".

An expert, who calculates the peaks of the target compounds with known methods (MestreC, ACD-simulation, but also with empirically evaluated expectation values), can isolate the peaks of the target compounds as needed optionally using additional intensity filters. This isolation would be similar to relevant peak picking at classical ¹H-NMR interpretation.

Further details of NMR-data description with peak lists can be found in the publication "Citation of NMR Peaklist Data within patent applications" of the Research Disclosure Database Number 564025.

TABLE 12

NMR peak lists

I.001: ¹H-NMR(300.2 MHz, CDCl3):
δ = 9.0841 (3.9); 9.0761 (4.1); 8.4693 (2.5); 8.4630 (3.3); 8.4565 (2.5); 7.7504 (1.7); 7.7235 (2.7); 7.6628 (1.2); 7.6469 (1.3); 7.6371 (2.2); 7.6208 (2.1); 7.6101 (1.3); 7.5938 (1.3); 7.5723 (1.8); 7.5675 (1.8); 7.5470 (1.4); 7.5416 (1.2); 7.5379 (1.9); 7.5334 (2.1); 7.5207 (0.4); 7.5122 (1.1); 7.5075 (1.2); 7.3016 (14.8); 7.2756 (2.7); 7.2713 (2.7); 7.2494 (1.8); 7.2449 (1.8); 7.1582 (1.6); 7.1549 (1.7); 7.1328 (3.1); 7.1295 (3.2); 7.1074 (1.6); 7.1042 (1.7); 6.9542 (2.9); 6.9507 (3.0); 6.9289 (2.3); 6.9253 (2.3); 6.7237 (2.9); 6.6982 (2.6); 5.3397 (1.1); 4.4276 (1.0); 2.2205 (1.2); 2.2167 (1.5); 2.1980 (5.1); 2.1905 (5.3); 2.1868 (3.1); 2.1728 (1.8); 2.1690 (1.5); 1.7278 (1.6); 1.7241 (1.7); 1.7102 (3.0); 1.7063 (5.3); 1.6989 (5.2); 1.6801 (1.5); 1.6764 (1.4); 1.6202 (16.0); 0.0503 (0.4); 0.0394 (12.4); 0.0284 (0.4)

I.002: ¹H-NMR(400.0 MHz, $d_6$-DMSO):
δ = 8.8716 (6.1); 8.8655 (6.3); 8.5506 (5.5); 8.5448 (5.3); 8.1724 (3.5); 8.1533 (7.7); 8.1327 (4.2); 7.9125 (1.9); 7.8921 (3.3); 7.8742 (1.9); 7.7511 (2.4); 7.7314 (3.6); 7.7132 (1.8); 7.5568 (3.5); 7.5380 (3.9); 7.3570 (1.6); 7.3373 (3.7); 7.3180 (2.2); 7.2085 (2.6); 7.1896 (4.3); 7.1708 (1.9); 6.8007 (4.6); 6.7809 (4.2); 5.0148 (0.9); 4.9981 (3.0); 4.9807 (3.0); 4.9632 (0.9); 3.9083 (6.0); 3.3435 (146.7); 3.1753 (1.2); 2.6775 (0.7); 2.5126 (98.9); 2.5086 (122.9); 2.3354 (0.7); 1.7172 (16.0); 1.6998 (15.8)

I.003: ¹H-NMR(400.0 MHz, $d_6$-DMSO):
δ = 8.9251 (6.4); 8.9193 (6.4); 8.6214 (5.7); 8.0094 (2.5); 7.9951 (2.9); 7.9856 (2.9); 7.9749 (0.6); 7.7299 (6.0); 7.7149 (4.8); 7.7063 (3.2); 7.6979 (5.5); 7.5672 (3.8); 7.5482 (4.2); 7.3725 (1.8); 7.3533 (4.0); 7.3339 (2.4); 7.2276 (2.8); 7.2087 (4.6); 7.1900 (2.0); 6.8700 (4.8); 6.8500 (4.4); 5.0329 (1.0); 5.0160 (3.2); 4.9987 (3.2); 4.9812 (1.0); 3.9080 (8.7); 3.3443 (287.3); 3.1809 (0.7); 3.1696 (0.7); 3.1401 (0.4); 2.6776 (1.0); 2.6727 (1.0); 2.5085 (169.4); 2.3352 (1.0); 1.7143 (16.0); 1.6969 (15.8); 0.9176 (0.4)

I.004: ¹H-NMR(400.0 MHz, $d_6$-DMSO):
δ = 8.9320 (6.8); 8.9261 (7.0); 8.6396 (5.6); 8.0167 (0.5); 8.0069 (2.6); 7.9971 (2.6); 7.9928 (2.6); 7.9831 (3.0); 7.9730 (0.5); 7.7327 (6.2); 7.7238 (3.2); 7.7166 (4.6); 7.7099 (3.3); 7.7007 (5.7); 7.5973 (3.9); 7.5796 (4.2); 7.3783 (1.8); 7.3607 (3.9); 7.3416 (2.5); 7.2436 (2.8); 7.2246 (4.6); 7.2058 (2.0); 6.8820 (4.9); 6.8622 (4.6); 5.9478 (0.7); 5.9278 (16.0); 5.9079 (0.6); 3.9077 (11.7); 3.5190 (6.1); 3.4779 (7.2); 3.3489 (225.9); 3.1806 (0.5); 3.1690 (0.5); 3.0100 (6.9); 2.9685 (5.8); 2.6775 (0.8); 2.5129 (120.4); 2.5088 (153.7); 2.5047 (114.6); 2.3353 (0.8)

I.005: ¹H-NMR(400.0 MHz, $d_6$-DMSO):
δ = 8.9560 (4.4); 8.9502 (4.6); 8.6598 (3.7); 8.0197 (0.4); 8.0090 (1.8); 7.9994 (1.8); 7.9961 (1.8); 7.9853 (2.0); 7.9756 (0.4); 7.7334 (4.1); 7.7247 (2.2); 7.7170 (3.3); 7.7110 (2.3); 7.7014 (3.9); 7.6896 (3.0); 7.6701 (2.9); 7.4062 (1.4); 7.3885 (5.3); 7.3813 (3.9); 7.3763 (3.9); 7.3675 (5.9); 7.3068 (1.0); 7.2964 (4.9); 7.2883 (3.7); 7.2828 (3.5); 7.2746 (3.3); 7.2409 (1.9); 7.2219 (3.1); 7.2030 (1.4); 6.9156 (3.3); 6.8956 (3.1); 4.0096 (5.2); 3.9666 (6.7); 3.9079 (16.0); 3.7248 (6.2); 3.6818 (4.6); 3.5138 (0.4); 3.4819 (0.4); 3.4641 (0.5); 3.4283 (0.8); 3.3511 (318.6); 3.2572 (1.2); 3.1752 (2.9); 2.6783 (0.8); 2.5090 (156.6); 2.3355 (0.9)

I.006: ¹H-NMR(400.0 MHz, $d_6$-DMSO):
δ = 8.9200 (9.4); 8.9142 (10.1); 8.6050 (8.7); 7.9952 (3.8); 7.9812 (4.7); 7.9716 (4.5); 7.9615 (1.0); 7.7210 (8.6); 7.7062 (7.4); 7.6972 (5.0); 7.6892 (8.4); 7.6130 (5.9); 7.5938 (6.4); 7.3607 (2.8); 7.3417 (6.1); 7.3222 (3.8); 7.2395 (4.2); 7.2207 (6.7); 7.2018 (2.9); 6.8646 (7.3); 6.8447 (6.8); 3.9075 (16.0); 3.5123 (0.5); 3.4847 (0.4); 3.3550 (656.2); 3.2102 (0.6); 3.1810 (1.3); 3.1691 (1.2); 3.0717 (0.3); 2.6778 (1.4); 2.5091 (256.3); 2.3398 (5.9); 2.3046 (6.7); 2.1423 (2.9); 2.1302 (2.9); 2.1137 (4.0); 2.1032 (5.0); 2.0785 (3.0); 2.0661 (2.6); 1.7878 (11.6); 1.7792 (11.7); 1.7486 (3.6); 1.7210 (0.9); 1.7120 (0.9); 1.5196 (1.8); 1.4981 (1.9); 1.2624 (0.3); 1.2389 (0.4)

I.007: ¹H-NMR(400.0 MHz, $d_6$-DMSO):
δ = 8.8844 (1.7); 8.8781 (1.7); 8.5525 (1.4); 8.5464 (1.4); 8.1668 (0.9); 8.1489 (1.4); 8.1315 (1.1); 7.9082 (0.5); 7.8880 (0.8); 7.8700 (0.5); 7.7478 (0.6); 7.7277 (0.9); 7.7100 (0.5); 7.6190 (1.0); 7.6001 (1.0); 7.3574 (0.4); 7.3378 (1.0); 7.3185 (0.6); 7.2333 (0.7); 7.2142 (1.1); 7.1953 (0.5); 6.8241 (1.2); 6.8046 (1.1); 3.9066 (1.7); 3.3585 (83.3); 3.1744 (0.4); 2.5129 (26.8); 2.5087 (34.1); 2.5045 (25.0); 1.7692 (16.0)

I.008: ¹H-NMR(400.0 MHz, $d_6$-DMSO):
δ = 8.8421 (15.6); 8.8360 (16.0); 8.5475 (14.3); 8.5419 (13.9); 8.1653 (9.7); 8.1481 (13.0); 8.1308 (11.5); 7.9134 (5.1); 7.8941 (8.7); 7.8784 (12.3); 7.8611 (10.7); 7.7499 (6.5); 7.7303 (9.3); 7.7122 (4.8); 7.3636 (4.2); 7.3441 (9.9); 7.3249 (6.6); 7.2709 (7.3); 7.2520 (11.2); 7.2331 (4.7); 6.7657 (12.1); 6.7459 (11.3); 3.9084 (11.8); 3.5140 (0.6); 3.4656 (0.5); 3.3436 (359.7); 3.2553 (0.6); 3.1754 (2.0); 3.0822 (4.0); 3.0665 (4.6); 3.0580 (6.4); 3.0481 (6.7); 3.0419 (6.4); 3.0331 (7.1); 3.0243 (5.8); 3.0092 (4.9); 2.7069 (4.3); 2.6835 (8.9); 2.6734 (7.0); 2.6667 (7.0); 2.6558 (7.0); 2.6331 (4.4); 2.5086 (345.9); 2.4277 (0.4); 2.3629 (0.8); 2.3349 (3.8); 2.3248 (3.5); 2.3186 (3.4); 2.3107 (3.3); 2.3020 (3.0); 2.2957 (4.1); 2.2807 (2.2); 2.2732 (1.9); 2.2569 (1.0); 2.2487 (1.1); 2.2314 (2.3); 2.2243 (2.6); 2.2069 (4.4); 2.1891 (2.6); 2.1826 (3.1); 2.1785 (3.1); 2.1612 (1.6); 2.1547 (1.3); 2.1369 (0.6); 1.3028 (0.4); 1.2641 (0.6); 1.2402 (0.7); 0.9183 (0.3); 0.0051 (0.5)

TABLE 12-continued

NMR peak lists

I.009: ¹H-NMR(400.0 MHz, d₆-DMSO):
δ = 8.8677 (15.7); 8.8617 (16.0); 8.5504 (14.2); 8.5448 (13.9); 8.1672 (9.6); 8.1495 (14.4); 8.1317 (11.4); 7.9106 (5.1); 7.8909 (8.3); 7.8719 (5.3); 7.7483 (6.5); 7.7288 (9.2); 7.7105 (4.8); 7.5877 (9.7); 7.5686 (10.7); 7.3409 (4.4); 7.3215 (10.0); 7.3022 (6.4); 7.2216 (7.1); 7.2026 (11.2); 7.1837 (4.8); 6.7896 (12.0); 6.7698 (11.2); 3.9080 (14.6); 3.5140 (0.7); 3.3452 (425.8); 3.1751 (3.3); 3.0148 (0.3); 2.7144 (6.0); 2.7008 (5.6); 2.6964 (5.8); 2.6823 (8.0); 2.6689 (5.8); 2.5085 (343.8); 2.3351 (1.9); 2.2201 (3.4); 2.2008 (7.4); 2.1834 (7.1); 2.1657 (6.4); 2.1466 (4.4); 2.0696 (1.8); 2.0514 (4.8); 2.0305 (8.2); 2.0187 (5.5); 1.9886 (1.8); 1.9671 (0.7); 1.9481 (2.0); 1.9400 (2.0); 1.9191 (6.1); 1.9085 (7.0); 1.9019 (7.8); 1.8899 (7.2); 1.3044 (0.4); 1.2629 (0.4); 1.2547 (0.6); 1.2400 (0.8); 0.8576 (0.4); 0.8402 (0.4); 0.8158 (0.4); 0.0047 (0.6)

I.010: ¹H-NMR(400.0 MHz, d₆-DMSO):
δ = 8.8726 (6.5); 8.8665 (6.6); 8.5625 (5.9); 8.5567 (5.7); 8.1665 (3.8); 8.1487 (6.2); 8.1305 (4.7); 7.9103 (2.1); 7.8913 (3.4); 7.8718 (2.1); 7.7478 (2.7); 7.7281 (3.8); 7.7102 (2.0); 7.5824 (4.0); 7.5635 (4.4); 7.3580 (1.9); 7.3388 (4.1); 7.3194 (2.6); 7.2189 (2.9); 7.1998 (4.8); 7.1809 (2.1); 6.8085 (5.0); 6.7885 (4.7); 5.9442 (0.6); 5.9243 (16.0); 3.9027 (6.5); 3.5272 (6.1); 3.5085 (0.6); 3.4859 (7.2); 3.4597 (0.5); 3.3505 (250.7); 3.3444 (268.1); 3.2688 (0.7); 3.1701 (0.9); 3.0015 (6.9); 2.9598 (5.9); 2.6732 (0.9); 2.5040 (170.6); 2.3304 (1.0); 1.2354 (2.0); 0.8538 (0.4); 0.0000 (1.1)

I.011: ¹H-NMR(400.0 MHz, d₆-DMSO):
δ = 8.8684 (11.9); 8.8624 (12.1); 8.5373 (10.7); 8.5317 (10.5); 8.1620 (7.3); 8.1487 (8.3); 8.1437 (8.6); 8.1285 (8.8); 7.9050 (3.8); 7.8854 (6.3); 7.8661 (4.0); 7.7443 (4.9); 7.7246 (7.0); 7.7067 (3.7); 7.6043 (7.2); 7.5853 (8.0); 7.3447 (3.4); 7.3252 (7.6); 7.3058 (4.8); 7.2198 (5.2); 7.2007 (8.4); 7.1819 (3.6); 6.7946 (9.1); 6.7748 (8.5); 3.9093 (16.0); 3.5155 (0.4); 3.3446 (261.8); 3.2364 (0.4); 3.1764 (3.6); 2.6784 (1.4); 2.5096 (256.4); 2.3522 (6.0); 2.3167 (7.9); 2.1409 (3.4); 2.1267 (3.2); 2.1134 (4.5); 2.1016 (5.8); 2.0775 (3.5); 2.0643 (3.1); 1.7931 (14.8); 1.7864 (14.6); 1.7583 (4.7); 1.7319 (1.0); 1.7197 (1.0); 1.5655 (0.5); 1.5231 (2.1); 1.5073 (2.2); 1.4825 (1.6); 1.4603 (0.7); 1.2557 (0.4); 1.2407 (0.5); 0.0063 (0.5)

I.012: ¹H-NMR(400.0 MHz, d₆-DMSO):
δ = 8.8239 (6.6); 8.8179 (6.8); 8.4965 (6.0); 8.4907 (5.9); 8.1753 (3.9); 8.1549 (4.5); 8.1449 (4.3); 8.1238 (4.7); 7.9000 (2.2); 7.8800 (3.7); 7.8619 (2.3); 7.7421 (2.7); 7.7228 (4.1); 7.7048 (2.1); 7.5219 (4.0); 7.5030 (4.4); 7.3918 (1.9); 7.3728 (4.2); 7.3534 (2.6); 7.2185 (2.9); 7.1997 (4.8); 7.1809 (2.2); 6.8651 (5.0); 6.8451 (4.6); 4.8476 (5.0); 4.8376 (5.1); 3.9080 (12.1); 3.4405 (0.4); 3.3455 (181.1); 3.2734 (1.1); 3.1750 (2.7); 2.6778 (0.8); 2.5792 (0.5); 2.5614 (1.4); 2.5508 (1.7); 2.5444 (2.3); 2.5086 (160.0); 2.3353 (0.9); 1.2545 (0.4); 1.2406 (0.5); 1.1733 (15.8); 1.1559 (15.4); 1.0258 (16.0); 1.0089 (15.8); 0.9169 (0.4); 0.8989 (0.4); 0.8638 (0.4)

I.013: ¹H-NMR(400.0 MHz, d₆-DMSO):
δ = 8.9054 (12.0); 8.8995 (12.3); 8.6284 (11.2); 8.6230 (10.9); 8.1857 (7.5); 8.1657 (16.0); 8.1447 (8.9); 7.9272 (4.0); 7.9083 (6.8); 7.8894 (4.0); 7.7625 (5.0); 7.7432 (7.4); 7.7249 (3.8); 7.3112 (3.6); 7.2917 (7.9); 7.2719 (4.9); 7.2515 (6.6); 7.2331 (9.7); 7.1620 (6.3); 7.1433 (8.8); 7.1245 (3.4); 6.7937 (9.6); 6.7738 (9.0); 3.9075 (11.0); 3.5132 (0.6); 3.4967 (0.5); 3.3547 (602.0); 3.1752 (2.7); 2.6783 (1.4); 2.5090 (255.0); 2.3354 (1.4); 2.0309 (3.7); 2.0161 (12.8); 2.0090 (14.6); 1.9971 (6.0); 1.9564 (1.0); 1.9244 (0.9); 1.8839 (5.8); 1.8712 (13.9); 1.8644 (13.2); 1.8493 (3.8); 1.2395 (0.4)

I.014: ¹H-NMR(400.0 MHz, d₆-DMSO):
δ = 8.9019 (4.9); 8.8958 (5.0); 8.5865 (4.5); 8.5808 (4.3); 8.2501 (0.4); 8.1723 (3.0); 8.1542 (5.2); 8.1354 (3.5); 7.9151 (1.6); 7.8955 (2.6); 7.8768 (1.6); 7.7521 (2.0); 7.7328 (2.9); 7.7145 (1.6); 7.6783 (3.1); 7.6595 (3.4); 7.4401 (0.4); 7.4253 (0.8); 7.4025 (0.9); 7.3899 (4.7); 7.3768 (4.7); 7.3688 (7.8); 7.3510 (2.3); 7.3058 (1.1); 7.2955 (5.6); 7.2875 (4.2); 7.2821 (4.0); 7.2738 (4.0); 7.2203 (2.2); 7.2013 (3.6); 7.1824 (1.7); 6.8450 (3.8); 6.8250 (3.5); 4.0205 (6.0); 3.9776 (7.6); 3.9064 (16.0); 3.8663 (0.8); 3.7202 (7.0); 3.6773 (5.4); 3.5128 (0.6); 3.3644 (266.5); 3.1749 (3.7); 2.6777 (0.6); 2.5086 (117.0); 2.3353 (0.7)

I.015: ¹H-NMR(400.0 MHz, d₆-DMSO):
δ = 8.9407 (1.5); 8.9350 (1.6); 8.6253 (1.5); 8.0049 (0.6); 7.9907 (0.8); 7.9810 (0.7); 7.7261 (1.5); 7.7117 (1.2); 7.7019 (0.8); 7.6941 (1.4); 7.6316 (1.0); 7.6127 (1.2); 7.3754 (0.5); 7.3559 (1.1); 7.3364 (0.7); 7.2550 (0.8); 7.2363 (1.2); 7.2173 (0.6); 6.8988 (1.3); 6.8789 (1.2); 3.9087 (1.4); 3.3396 (48.4); 2.5086 (41.9); 1.7688 (16.0); 1.2410 (1.1)

I.016: ¹H-NMR(400.0 MHz, d₆-DMSO):
δ = 8.8973 (8.6); 8.8918 (8.8); 8.6220 (8.3); 8.0016 (3.4); 7.9914 (4.0); 7.9783 (4.0); 7.8896 (5.4); 7.8713 (5.7); 7.7313 (7.9); 7.7228 (5.0); 7.7152 (6.8); 7.6995 (7.1); 7.3776 (2.4); 7.3605 (5.4); 7.3412 (3.6); 7.2904 (3.9); 7.2717 (5.9); 7.2530 (2.6); 6.8331 (6.4); 6.8134 (5.9); 3.9081 (16.0); 3.5132 (0.4); 3.4695 (0.3); 3.4620 (0.4); 3.3440 (340.5); 3.2736 (1.4); 3.2003 (0.4); 3.1748 (2.6); 3.0772 (2.2); 3.0530 (3.9); 3.0432 (4.3); 3.0374 (4.2); 3.0277 (4.4); 3.0197 (3.6); 3.0044 (2.8); 2.7090 (2.4); 2.6860 (5.3); 2.6773 (4.8); 2.6686 (4.8); 2.6578 (4.3); 2.6353 (2.5); 2.5085 (238.7); 2.3622 (0.6); 2.3347 (2.6); 2.3251 (2.4); 2.3116 (2.1); 2.2967 (2.5); 2.2818 (1.5); 2.2734 (1.3); 2.2583 (0.6); 2.2485 (0.7); 2.2242 (1.6); 2.2065 (2.5); 2.1824 (2.0); 2.1614 (1.0); 2.1361 (0.4); 1.3041 (0.4); 1.2633 (0.6); 1.2397 (0.6); 0.9175 (0.3); 0.8367 (0.3)

I.017: ¹H-NMR(400.0 MHz, d₆-DMSO):
δ = 8.9212 (12.5); 8.9153 (12.8); 8.6217 (10.5); 8.0133 (0.9); 8.0030 (4.8); 7.9888 (5.0); 7.9794 (5.5); 7.9687 (1.0); 7.7281 (11.2); 7.7189 (5.8); 7.7123 (8.4); 7.7049 (5.8); 7.6961 (10.4); 7.5976 (7.2); 7.5795 (8.0); 7.3586 (3.3); 7.3390 (7.5); 7.3196 (4.8); 7.2421 (5.3); 7.2233 (8.5); 7.2044 (3.6); 6.8594 (9.2); 6.8397 (8.5); 3.9082 (16.0); 3.5134 (0.5); 3.3446 (353.3); 3.1807 (0.7); 3.1694 (0.6); 2.7027 (4.3); 2.6783 (5.2); 2.6719 (5.6); 2.6562 (3.7); 2.5126 (225.7); 2.5088 (284.8); 2.3352 (1.6); 2.2229 (2.6); 2.2038 (5.5); 2.1860 (5.2); 2.1686 (4.7); 2.1493 (3.2); 2.0806 (0.7); 2.0690 (1.3); 2.0509 (3.4); 2.0394 (5.1); 2.0296 (6.0); 2.0154 (3.9); 1.9979 (1.8); 1.9878 (1.3); 1.9790 (0.7); 1.9656 (0.4); 1.9468 (1.4); 1.9389 (1.5); 1.9174 (4.6); 1.9067 (5.1); 1.9000 (5.7); 1.8875 (5.3); 1.3419 (0.3); 1.2635 (0.4); 1.2550 (0.5); 1.2394 (0.6); 0.9177 (0.4); 0.0050 (0.7)

I.018: ¹H-NMR(400.0 MHz, d₆-DMSO):
δ = 8.9145 (6.4); 8.9086 (6.6); 8.6161 (5.6); 8.0248 (0.4); 8.0148 (2.5); 8.0005 (2.7); 7.9911 (2.9); 7.9807 (0.5); 7.7326 (5.8); 7.7230 (3.0); 7.7172 (4.4); 7.7092 (3.0); 7.7007 (5.4); 7.6905 (0.5); 7.5064 (3.3); 7.4876 (3.7); 7.3623 (1.7); 7.3430 (3.6); 7.3237 (2.2); 7.1943 (2.7); 7.1755 (4.5); 7.1567 (2.0); 6.8574 (4.6); 6.8373 (4.3); 5.0235 (16.0); 3.9078 (8.1); 3.3467 (223.6); 3.3048 (1.7); 3.1803 (0.4); 3.1715 (0.4); 2.6776 (0.7); 2.5126 (95.9); 2.5087 (122.2); 2.5050 (91.6); 2.3353 (0.7)

I.019: ¹H-NMR(400.0 MHz, d₆-DMSO):
δ = 8.8618 (6.2); 8.8558 (6.5); 8.5452 (5.7); 8.5397 (5.7); 8.1764 (3.7); 8.1550 (7.4); 8.1330 (4.4); 7.9124 (2.0); 7.8947 (3.5); 7.8766 (2.0); 7.8741 (2.0); 7.7523 (2.4); 7.7331 (3.8); 7.7149 (1.9); 7.4966 (3.4); 7.4780 (3.8);

TABLE 12-continued

NMR peak lists 7.3473 (1.7); 7.3283 (3.7); 7.3086 (2.2); 7.1760 (2.7); 7.1575 (4.4); 7.1386 (2.0); 6.7891 (4.6); 6.7691 (4.3); 5.0073 (16.0); 3.9076 (5.9); 3.3520 (192.5); 3.1752 (0.9); 2.6777 (0.6); 2.5125 (87.2); 2.5088 (109.3); 2.3358 (0.6)

I.020: $^1$H-NMR(400.0 MHz, d$_6$-DMSO):
δ = 8.8760 (7.2); 8.8700 (7.4); 8.5652 (5.8); 8.0111 (2.8); 8.0054 (1.8); 7.9976 (3.2); 7.9874 (3.2); 7.9769 (0.5); 7.9355 (0.4); 7.7373 (0.4); 7.7174 (5.7); 7.7048 (6.0); 7.6919 (3.3); 7.6856 (6.0); 7.6727 (0.8); 7.5318 (4.0); 7.5131 (4.5); 7.4844 (0.4); 7.4095 (2.0); 7.3910 (4.4); 7.3719 (2.7); 7.2398 (3.0); 7.2209 (4.8); 7.2022 (2.2); 7.1578 (0.3); 6.9411 (5.0); 6.9212 (4.7); 4.8671 (5.2); 4.8571 (5.2); 4.2437 (0.4); 4.2273 (0.6); 4.2108 (0.3); 3.9072 (14.8); 3.5136 (0.5); 3.4397 (0.7); 3.3536 (319.2); 3.2731 (0.9); 3.1747 (1.9); 3.1600 (0.6); 2.6821 (0.8); 2.6778 (1.0); 2.5666 (0.6); 2.5496 (1.6); 2.5311 (4.7); 2.5130 (138.4); 2.5088 (177.7); 2.5046 (132.6); 2.3356 (1.0); 2.3317 (0.8); 1.2542 (0.4); 1.2385 (0.6); 1.1647 (16.0); 1.1473 (15.6); 1.0105 (16.0); 0.9935 (15.6); 0.9352 (0.6); 0.9168 (1.2); 0.8985 (0.7); 0.8800 (0.4); 0.8666 (0.4); 0.0041 (0.4)

I.021: $^1$H-NMR(300.2 MHz, CDCl3):
δ = 9.0580 (5.9); 9.0504 (7.7); 9.0391 (2.7); 8.4042 (3.9); 8.3988 (4.9); 8.3918 (3.7); 8.2462 (1.8); 8.2413 (3.0); 8.2362 (1.7); 8.2181 (1.8); 8.2133 (3.3); 8.2084 (1.7); 7.7422 (1.4); 7.7359 (1.3); 7.7256 (1.4); 7.7189 (1.6); 7.7118 (2.3); 7.7052 (2.3); 7.6948 (2.2); 7.6883 (2.2); 7.6795 (1.4); 7.6728 (1.3); 7.6622 (1.4); 7.6554 (1.4); 7.6487 (2.0); 7.6424 (2.0); 7.6317 (1.8); 7.6248 (2.2); 7.6209 (2.4); 7.5980 (2.2); 7.5892 (3.0); 7.5664 (2.9); 7.5580 (1.5); 7.5276 (3.2); 7.5129 (3.2); 7.5080 (2.4); 7.4992 (5.0); 7.4852 (2.8); 7.4762 (2.4); 7.4677 (1.4); 7.4446 (1.6); 7.4337 (2.9); 7.4085 (3.3); 7.3700 (1.6); 7.3438 (3.3); 7.3177 (2.7); 7.3160 (2.7); 7.3133 (2.7); 7.3012 (66.9); 7.1982 (2.8); 7.1951 (2.6); 7.1729 (4.2); 7.1700 (3.9); 7.1477 (1.7); 6.9502 (0.4); 6.6950 (4.1); 6.6682 (3.8); 5.3408 (12.9); 4.6446 (16.0); 4.4333 (1.2); 3.7454 (6.8); 2.0497 (0.5); 1.5992 (43.5); 0.1090 (0.8); 0.0498 (2.2); 0.0391 (63.8); 0.0282 (2.5)

I.022: $^1$H-NMR(300.2 MHz, CDCl3):
δ = 9.0987 (10.7); 9.0910 (10.8); 8.4511 (7.7); 8.4456 (9.9); 8.4388 (7.2); 7.7474 (2.7); 7.7410 (2.7); 7.7306 (2.9); 7.7240 (3.0); 7.7168 (4.3); 7.7103 (4.4); 7.7000 (4.2); 7.6935 (3.9); 7.6160 (4.0); 7.5931 (4.0); 7.5845 (5.6); 7.5617 (5.5); 7.5532 (2.7); 7.5388 (0.6); 7.5303 (2.7); 7.5150 (0.5); 7.3186 (0.5); 7.3011 (17.2); 7.2963 (4.6); 7.2747 (7.8); 7.2706 (8.2); 7.2485 (5.4); 7.2441 (5.1); 7.2236 (1.3); 7.1988 (0.8); 7.1598 (4.9); 7.1566 (4.7); 7.1344 (9.3); 7.1312 (8.4); 7.1091 (4.6); 7.1058 (4.0); 6.9544 (8.1); 6.9513 (8.0); 6.9291 (6.4); 6.9259 (6.0); 6.6994 (8.8); 6.6727 (8.0); 2.3931 (3.7); 2.2652 (0.4); 2.2159 (3.8); 2.2123 (4.2); 2.1938 (14.6); 2.1862 (15.3); 2.1682 (5.4); 2.1646 (4.2); 2.1133 (0.8); 1.7803 (0.8); 1.7288 (5.3); 1.7253 (5.2); 1.7075 (15.4); 1.7001 (16.0); 1.6811 (4.8); 1.6775 (4.1); 1.6285 (0.6); 1.2925 (0.4); 0.0376 (9.8); 0.0266 (0.4)

I.023: $^1$H-NMR(400.1 MHz, CDCl3):
δ = 8.9986 (1.2); 8.9928 (1.2); 8.3379 (0.9); 8.3337 (1.1); 8.3292 (0.8); 7.6691 (0.4); 7.6642 (0.4); 7.6588 (0.5); 7.6540 (0.4); 7.6462 (0.4); 7.6414 (0.4); 7.5544 (0.4); 7.5372 (0.4); 7.5308 (0.6); 7.5135 (0.6); 7.3391 (0.7); 7.3366 (0.7); 7.3201 (0.9); 7.3177 (0.9); 7.2954 (0.4); 7.2923 (0.4); 7.2760 (0.9); 7.2729 (0.8); 7.2597 (3.2); 7.2535 (0.6); 7.1861 (0.6); 7.1842 (0.6); 7.1671 (0.9); 7.1653 (0.9); 7.1481 (0.4); 6.6971 (1.0); 6.6773 (0.9); 1.8284 (16.0); 1.5544 (3.4); −0.0002 (3.0)

I.024: $^1$H-NMR(400.1 MHz, CDCl3):
δ = 8.9817 (15.9); 8.9761 (16.0); 8.3312 (15.5); 7.6788 (4.1); 7.6742 (4.2); 7.6661 (4.6); 7.6613 (4.9); 7.6560 (6.1); 7.6512 (6.0); 7.6433 (5.8); 7.6387 (5.4); 7.6054 (10.3); 7.5867 (11.5); 7.5842 (10.8); 7.5527 (4.9); 7.5353 (5.5); 7.5291 (7.8); 7.5119 (7.7); 7.5057 (4.0); 7.4883 (3.5); 7.2842 (4.6); 7.2811 (4.5); 7.2596 (52.0); 7.2455 (8.3); 7.2423 (7.2); 7.2095 (8.5); 7.2074 (8.1); 7.1905 (12.5); 7.1716 (5.0); 6.6146 (12.6); 6.5947 (11.9); 4.0495 (0.5); 3.3026 (5.1); 3.2854 (5.9); 3.2785 (7.7); 3.2674 (7.2); 3.2617 (6.6); 3.2502 (8.4); 3.2452 (6.8); 3.2340 (2.6); 3.2271 (5.6); 2.6614 (4.7); 2.6434 (7.1); 2.6368 (8.4); 2.6259 (6.0); 2.6211 (7.4); 2.6097 (7.6); 2.6055 (6.0); 2.5867 (5.4); 2.4043 (0.6); 2.3870 (1.1); 2.3746 (2.2); 2.3630 (2.5); 2.3571 (5.3); 2.3512 (4.8); 2.3382 (6.7); 2.3336 (10.0); 2.3155 (9.6); 2.3102 (6.2); 2.2981 (3.9); 2.2924 (4.8); 2.2858 (2.2); 2.2751 (1.6); 2.2688 (0.8); 2.2626 (0.9); 2.2403 (1.0); 1.5501 (58.4); 1.3040 (0.5); 1.2659 (2.2); 0.8985 (1.0); 0.8820 (2.6); 0.8644 (1.1); −0.0002 (44.4)

I.025: $^1$H-NMR(300.2 MHz, CDCl3):
δ = 9.1717 (9.2); 7.8601 (1.7); 7.8533 (1.4); 7.8441 (1.8); 7.8371 (1.6); 7.8287 (2.6); 7.8219 (2.3); 7.8127 (2.5); 7.8059 (2.0); 7.7371 (1.8); 7.7117 (2.6); 7.7049 (2.7); 7.6797 (3.0); 7.6725 (1.8); 7.6636 (3.4); 7.6475 (1.6); 7.6362 (4.6); 7.5077 (1.9); 7.5057 (1.8); 7.5033 (1.6); 7.4826 (3.3); 7.4805 (3.9); 7.4783 (3.2); 7.4576 (4.1); 7.4558 (4.1); 7.4337 (3.8); 7.4322 (3.9); 7.3186 (3.1); 7.3152 (2.4); 7.2972 (11.6); 7.2938 (5.1); 7.2681 (1.7); 7.2648 (1.3); 4.6586 (16.0); 2.0441 (0.5); 1.6014 (4.5); 0.0417 (2.5); 0.0384 (4.0); 0.0352 (9.0)

I.026: $^1$H-NMR(300.2 MHz, CDCl3):
δ = 9.0754 (1.1); 9.0676 (1.1); 9.0344 (0.9); 9.0291 (0.9); 9.0205 (0.9); 9.0153 (0.9); 8.4609 (0.8); 8.4543 (1.0); 8.4481 (0.7); 8.2629 (0.6); 8.2577 (1.0); 8.2524 (0.6); 8.2350 (0.6); 8.2297 (1.1); 8.2246 (0.6); 7.7252 (0.5); 7.6985 (0.8); 7.6839 (0.8); 7.6585 (1.2); 7.6311 (0.4); 7.6147 (0.4); 7.6051 (0.6); 7.5887 (0.7); 7.5781 (0.5); 7.5736 (0.6); 7.5616 (0.5); 7.5571 (0.7); 7.5478 (2.2); 7.5415 (0.7); 7.5332 (1.6); 7.5204 (1.6); 7.5055 (1.8); 7.4951 (0.9); 7.4901 (0.9); 7.4811 (0.4); 7.4766 (0.3); 7.4695 (0.5); 7.4600 (0.9); 7.4554 (0.8); 7.4343 (0.5); 7.4298 (0.5); 7.3017 (12.6); 7.2011 (0.5); 7.1930 (0.4); 7.1836 (0.5); 7.1711 (0.7); 7.1358 (2.5); 7.0414 (1.2); 7.0332 (0.6); 7.0280 (0.9); 7.0241 (0.9); 7.0190 (0.7); 7.0111 (1.2); 6.6159 (0.6); 6.6062 (0.4); 6.6025 (0.5); 6.5933 (0.4); 6.5860 (0.5); 3.4104 (16.0); 3.3755 (1.9); 3.2602 (0.5); 3.2087 (1.0); 2.0483 (0.5); 1.6277 (5.5); 0.0389 (8.9)

I.027: $^1$H-NMR(300.2 MHz, CDCl3):
δ = 9.1874 (2.2); 7.7951 (0.5); 7.7885 (0.5); 7.7790 (0.5); 7.7723 (0.5); 7.7213 (0.4); 7.6964 (0.4); 7.6891 (0.6); 7.6642 (0.6); 7.6115 (0.7); 7.5846 (1.0); 7.4883 (0.4); 7.4823 (0.4); 7.4646 (0.6); 7.4587 (0.7); 7.4376 (0.4); 7.4317 (0.5); 7.4068 (0.5); 7.3871 (1.1); 7.3813 (0.9); 7.3653 (0.9); 7.3618 (0.8); 7.3414 (0.7); 7.3385 (0.7); 7.3014 (7.4); 4.3772 (1.7); 1.8106 (16.0); 1.7295 (0.4); 1.5973 (9.7); 0.0394 (5.3)

I.028: $^1$H-NMR(499.9 MHz, CDCl3):
δ = 8.2986 (3.7); 7.6202 (0.8); 7.6168 (0.8); 7.6100 (0.9); 7.6061 (0.9); 7.6021 (1.1); 7.5987 (1.0); 7.5919 (1.0); 7.4735 (0.7); 7.4593 (0.9); 7.4548 (1.2); 7.4409 (1.2); 7.4362 (0.7); 7.4222 (0.5); 7.3782 (1.7); 7.3631 (1.9); 7.2609 (4.2); 7.2534 (2.0); 7.2377 (1.1); 7.1054 (1.3); 7.0902 (2.3); 7.0750 (1.0); 6.2931 (2.2); 6.2770 (2.1); 5.2978 (1.4); 4.6536 (0.8); 4.6221 (3.3); 4.6031 (3.7); 4.5717 (0.9); 2.7606 (16.0); 2.0432 (0.4); 2.0042 (0.6); 1.5780 (5.3); −0.0002 (3.9)

I.029: $^1$H-NMR(400.0 MHz, d$_6$-DMSO):
δ = 8.6028 (3.3); 8.0547 (0.7); 8.0503 (0.7); 8.0409 (0.7); 8.0364 (0.8); 8.0316 (0.9); 8.0274 (0.9); 8.0179 (0.8); 7.8222 (0.6); 7.8039 (0.8); 7.7970 (0.9); 7.7797 (0.9); 7.7737 (0.6); 7.7552 (0.5); 7.6134 (1.8); 7.5969 (1.9);

TABLE 12-continued

NMR peak lists 7.3011 (0.8); 7.2981 (0.8); 7.2816 (1.8); 7.2788 (1.8); 7.2622 (1.2); 7.2593 (1.1); 7.1893 (1.3); 7.1721 (2.0); 7.1705 (2.1); 7.1531 (0.9); 6.5348 (2.2); 6.5152 (2.1); 3.9025 (2.4); 3.3293 (172.3); 3.1757 (0.8); 3.1628 (0.8); 2.6699 (16.0); 2.5069 (71.4); 2.5026 (90.5); 2.4981 (64.8); 2.3336 (0.4); 2.3292 (0.5); 2.3250 (0.4); 1.8163 (13.9); 1.7694 (13.2); 1.2904 (0.3); −0.0003 (4.3)
I.030: $^1$H-NMR(300.2 MHz, CDCl3):
δ = 8.3963 (2.8); 7.6902 (0.6); 7.6839 (0.6); 7.6729 (0.6); 7.6664 (0.6); 7.6595 (0.8); 7.6534 (0.8); 7.6425 (0.8); 7.6364 (0.8); 7.5381 (0.7); 7.5153 (0.8); 7.5066 (1.1); 7.4840 (1.0); 7.4755 (0.6); 7.4527 (0.5); 7.3045 (13.0); 7.2606 (0.8); 7.2564 (0.7); 7.2348 (1.7); 7.2309 (1.5); 7.2088 (1.2); 7.2045 (1.0); 7.1257 (1.1); 7.1224 (0.9); 7.1004 (2.0); 7.0971 (1.7); 7.0750 (1.0); 7.0717 (0.8); 6.9547 (1.9); 6.9295 (1.4); 6.9266 (1.2); 6.3479 (1.9); 6.3213 (1.8); 5.3439 (0.7); 2.8118 (14.2); 2.2691 (0.3); 2.2333 (1.0); 2.2196 (1.4); 2.2102 (3.6); 2.2037 (1.4); 2.1874 (1.1); 2.1516 (0.4); 1.8063 (1.0); 1.8004 (0.9); 1.7901 (0.8); 1.7739 (0.9); 1.7679 (0.8); 1.7523 (0.7); 1.6706 (0.9); 1.6574 (0.8); 1.6489 (0.8); 1.6354 (0.7); 1.6247 (0.9); 1.6184 (1.0); 1.6047 (16.0); 0.0536 (0.5); 0.0429 (13.2); 0.0320 (0.4)
I.031: $^1$H-NMR(300.2 MHz, CDCl3):
δ = 8.3237 (2.9); 8.3201 (2.8); 7.6688 (0.6); 7.6625 (0.7); 7.6443 (2.1); 7.6320 (1.1); 7.6228 (2.4); 7.6194 (2.3); 7.5268 (0.8); 7.5041 (0.9); 7.4953 (1.2); 7.4725 (1.2); 7.4641 (0.6); 7.4413 (0.6); 7.3044 (7.5); 7.2888 (0.6); 7.2840 (0.7); 7.2633 (1.7); 7.2584 (1.6); 7.2378 (1.4); 7.2326 (1.2); 7.2159 (1.3); 7.2117 (1.4); 7.1908 (1.8); 7.1872 (1.6); 7.1655 (0.7); 7.1620 (0.6); 6.2983 (1.7); 6.2955 (1.8); 6.2718 (1.6); 5.3430 (1.3); 3.3730 (0.5); 3.3669 (0.5); 3.3550 (0.5); 3.3432 (0.7); 3.3353 (0.7); 3.3111 (0.7); 3.3041 (0.7); 3.2920 (0.6); 3.2799 (0.5); 3.2708 (0.6); 3.2478 (0.3); 2.8398 (0.3); 2.8155 (0.7); 2.8108 (0.7); 2.8041 (0.4); 2.7909 (0.5); 2.7863 (0.5); 2.7708 (0.6); 2.7512 (16.0); 2.5868 (0.6); 2.5835 (0.6); 2.5757 (0.4); 2.5533 (0.6); 2.5443 (0.5); 2.5190 (0.4); 2.4379 (0.4); 2.4219 (0.6); 2.4159 (0.7); 2.4075 (0.8); 2.3987 (0.9); 2.3910 (0.9); 2.3847 (1.3); 2.3774 (0.7); 2.3679 (1.2); 2.3613 (0.9); 2.3543 (0.8); 2.3444 (0.7); 2.3372 (0.6); 2.3302 (0.4); 1.6208 (9.0); 0.0419 (7.4)
I.032: $^1$H-NMR(300.2 MHz, CDCl3):
δ = 8.3547 (5.0); 7.6832 (0.4); 7.6769 (0.5); 7.6609 (1.0); 7.6545 (1.1); 7.6456 (1.2); 7.6369 (1.2); 7.6308 (1.5); 7.6141 (0.9); 7.6079 (0.9); 7.5293 (0.7); 7.5243 (0.9); 7.5007 (1.4); 7.4931 (1.4); 7.4700 (1.5); 7.4618 (0.7); 7.4437 (0.5); 7.4389 (0.6); 7.3040 (9.4); 7.2476 (0.6); 7.2430 (1.0); 7.2329 (0.9); 7.2240 (1.5); 7.2171 (1.8); 7.2137 (1.7); 7.2070 (0.9); 7.1985 (1.4); 7.1913 (1.1); 7.1869 (1.2); 7.1332 (1.4); 7.1316 (1.0); 7.1177 (5.5); 7.1082 (3.5); 7.0976 (1.9); 7.0945 (1.7); 7.0870 (2.8); 7.0834 (2.2); 7.0723 (0.4); 7.0633 (0.5); 6.3289 (1.4); 6.3118 (2.4); 6.3020 (1.5); 6.2858 (2.1); 5.3422 (3.2); 2.8228 (16.0); 2.7462 (10.6); 2.6756 (2.2); 2.6576 (3.5); 2.6383 (1.5); 2.0514 (2.7); 1.9766 (1.5); 1.9583 (1.4); 1.8929 (2.3); 1.8757 (2.1); 1.7786 (0.4); 1.7615 (0.9); 1.7457 (1.4); 1.7289 (1.6); 1.7130 (1.2); 1.6966 (0.7); 1.6364 (2.2); 1.4739 (0.9); 1.4514 (0.6); 1.4344 (1.1); 1.4201 (1.2); 1.4038 (1.7); 1.3847 (1.3); 1.3437 (0.9); 1.3271 (1.3); 1.3089 (1.2); 1.2972 (1.7); 1.2785 (1.1); 1.2626 (1.5); 1.2428 (1.4); 1.2307 (1.5); 1.2119 (1.1); 1.1957 (0.4); 1.1336 (0.5); 1.1150 (0.6); 1.1008 (0.6); 1.0828 (0.6); 1.0644 (0.3); 0.0522 (0.4); 0.0414 (9.5); 0.0305 (0.4)
I.033: $^1$H-NMR(300.2 MHz, CDCl3):
δ = 9.0864 (8.8); 9.0787 (9.3); 8.4309 (6.0); 8.4251 (8.2); 8.4186 (6.3); 7.7402 (2.2); 7.7338 (2.3); 7.7234 (2.4); 7.7168 (2.5); 7.7097 (3.5); 7.7032 (3.7); 7.6927 (3.4); 7.6863 (3.5); 7.6140 (3.3); 7.5913 (3.4); 7.5824 (4.8); 7.5596 (4.6); 7.5513 (2.4); 7.5284 (2.2); 7.3372 (0.4); 7.3252 (1.3); 7.3193 (0.8); 7.3041 (31.7); 7.2917 (3.5); 7.2852 (3.9); 7.2767 (4.1); 7.2675 (5.0); 7.2649 (4.5); 7.2614 (5.2); 7.2413 (4.3); 7.2346 (6.7); 7.2301 (5.7); 7.2052 (3.2); 7.1903 (0.7); 7.1734 (3.0); 7.1703 (2.9); 7.1480 (6.8); 7.1452 (6.9); 7.1240 (6.2); 7.1199 (10.3); 7.1130 (8.6); 7.0937 (2.9); 7.0877 (2.0); 6.6768 (7.4); 6.6506 (6.9); 4.0952 (0.3); 2.6546 (7.6); 2.6368 (8.0); 2.3988 (16.0); 2.1177 (0.4); 2.0988 (0.4); 1.9158 (8.0); 1.8979 (7.6); 1.7562 (1.8); 1.7379 (3.2); 1.7218 (3.2); 1.7060 (3.5); 1.6879 (2.4); 1.6320 (10.6); 1.4450 (1.6); 1.4248 (2.5); 1.4168 (2.8); 1.4084 (2.1); 1.3947 (3.7); 1.3775 (2.9); 1.3194 (2.7); 1.3022 (4.0); 1.2840 (3.3); 1.2725 (2.8); 1.2532 (1.9); 1.2230 (2.7); 1.2033 (3.0); 1.1900 (3.2); 1.1715 (2.6); 1.1545 (1.6); 0.0528 (0.9); 0.0421 (28.2); 0.0311 (1.0)
I.034: $^1$H-NMR(300.2 MHz, CDCl3):
δ = 8.3429 (3.7); 8.1666 (1.4); 8.1384 (1.7); 7.8923 (1.3); 7.8686 (2.2); 7.8645 (2.3); 7.8455 (1.3); 7.8407 (1.5); 7.8359 (0.7); 7.8174 (1.0); 7.8127 (0.7); 7.6374 (1.1); 7.6109 (1.6); 7.5871 (0.7); 7.4191 (1.2); 7.3936 (1.4); 7.3034 (20.4); 7.2838 (1.4); 7.2587 (0.8); 7.1412 (1.2); 7.1158 (1.8); 7.0906 (0.8); 6.3594 (1.7); 6.3327 (1.6); 5.3429 (1.6); 4.6572 (3.0); 4.6464 (3.3); 2.7630 (15.5); 1.6045 (16.0); 0.0529 (0.7); 0.0422 (19.4); 0.0312 (0.6)
I.035: $^1$H-NMR(300.2 MHz, CDCl3):
δ = 8.3525 (3.8); 8.1631 (1.4); 8.1351 (1.7); 7.8994 (0.7); 7.8765 (1.6); 7.8613 (1.3); 7.8562 (1.6); 7.8511 (1.4); 7.8380 (1.6); 7.8332 (1.9); 7.8285 (1.0); 7.8098 (1.2); 7.8052 (1.0); 7.6283 (1.1); 7.6245 (0.9); 7.6015 (1.6); 7.5782 (0.7); 7.3042 (22.9); 7.2771 (0.3); 7.2294 (1.0); 7.2247 (0.8); 7.2215 (0.8); 7.2132 (0.6); 7.2074 (1.3); 7.2037 (1.4); 7.1992 (1.4); 7.1873 (0.6); 7.1809 (0.8); 7.1777 (0.8); 7.1731 (1.0); 7.1232 (0.5); 7.1044 (2.5); 7.0993 (2.7); 7.0928 (1.2); 7.0899 (1.2); 7.0805 (2.1); 7.0715 (2.0); 7.0555 (0.6); 6.3424 (1.0); 6.3300 (1.5); 6.3162 (1.0); 6.3037 (1.4); 2.7816 (11.9); 2.7661 (0.6); 2.7031 (8.1); 2.6763 (1.5); 2.6602 (2.1); 2.6442 (1.1); 2.3995 (1.4); 2.0519 (6.1); 1.9707 (1.0); 1.9526 (1.0); 1.8850 (1.5); 1.8680 (1.5); 1.7791 (0.4); 1.7617 (0.7); 1.7462 (0.8); 1.7309 (0.8); 1.7122 (0.5); 1.6204 (16.0); 1.4468 (0.4); 1.4307 (0.7); 1.4154 (0.7); 1.4004 (1.1); 1.3806 (0.8); 1.3348 (0.6); 1.3175 (0.8); 1.2998 (0.9); 1.2892 (0.6); 1.2699 (0.7); 1.2631 (0.6); 1.2502 (0.7); 1.2424 (0.8); 1.2317 (0.8); 1.2110 (0.5); 1.1340 (0.3); 1.1145 (0.4); 1.1006 (0.4); 1.0832 (0.4); 0.0534 (0.7); 0.0426 (22.0); 0.0316 (0.8)
I.036: $^1$H-NMR(300.2 MHz, CDCl3):
δ = 8.3933 (4.0); 8.1699 (1.6); 8.1416 (1.9); 7.9049 (1.4); 7.8780 (1.8); 7.8690 (1.2); 7.8643 (1.0); 7.8457 (1.4); 7.8409 (1.6); 7.8360 (0.8); 7.8175 (1.1); 7.8128 (0.8); 7.6386 (1.2); 7.6120 (1.8); 7.5884 (0.8); 7.3041 (13.5); 7.2452 (0.8); 7.2409 (0.8); 7.2193 (1.8); 7.2154 (1.6); 7.1934 (1.2); 7.1891 (1.1); 7.1058 (1.1); 7.1024 (1.0); 7.0805 (2.2); 7.0771 (1.8); 7.0552 (1.2); 7.0518 (0.9); 6.9447 (2.0); 6.9419 (1.8); 6.9194 (1.5); 6.9166 (1.3); 6.3648 (2.0); 6.3382 (1.9); 2.7693 (16.0); 2.2677 (0.3); 2.2319 (1.1); 2.2185 (1.8); 2.2102 (3.9); 2.1892 (1.2); 2.1533 (0.4); 2.0895 (0.4); 1.7950 (1.1); 1.7792 (0.9); 1.7638 (1.0); 1.7577 (0.9); 1.7428 (0.8); 1.6627 (0.9); 1.6502 (1.0); 1.6417 (1.0); 1.6202 (6.8); 1.3267 (0.5); 1.3031 (1.6); 0.9471 (0.5); 0.9250 (1.5); 0.9021 (0.6); 0.0537 (0.5); 0.0429 (13.3); 0.0352 (0.4); 0.0320 (0.4)
I.037: $^1$H-NMR(300.2 MHz, CDCl3):
δ = 8.3651 (4.4); 8.1662 (2.0); 8.1385 (2.3); 7.8895 (2.0); 7.8623 (3.5); 7.8385 (1.9); 7.8341 (2.0); 7.8106 (1.2); 7.8063 (0.9); 7.6331 (1.6); 7.6069 (2.2); 7.5831 (0.9); 7.3763 (2.0); 7.3729 (2.0); 7.3515 (2.3); 7.3480 (2.1); 7.3259 (0.4); 7.3076 (3.2); 7.2771 (1.0); 7.2730 (1.1); 7.2517 (2.2); 7.2475 (2.0); 7.2258 (1.4); 7.2215 (1.2); 7.1683 (1.7); 7.1649 (1.7); 7.1433 (2.3); 7.1181 (0.9); 6.3725 (2.3); 6.3463 (2.1); 2.7801 (16.0); 2.7360 (0.5); 1.9355 (15.3); 1.8745 (14.9); 1.8450 (0.3); 1.7151 (0.4); 1.6976 (2.0); 0.0459 (3.2)

TABLE 12-continued

NMR peak lists

I.038: $^1$H-NMR(300.2 MHz, CDCl3):
δ = 8.3203 (3.8); 8.1571 (1.4); 8.1293 (1.7); 7.8833 (1.4); 7.8567 (2.6); 7.8335 (1.3); 7.8286 (1.5); 7.8239 (0.8); 7.8053 (1.0); 7.8005 (0.8); 7.6392 (1.4); 7.6353 (1.5); 7.6282 (1.2); 7.6249 (1.2); 7.6148 (1.7); 7.6102 (1.8); 7.6014 (1.7); 7.5777 (0.7); 7.5747 (0.7); 7.3044 (8.1); 7.2733 (0.6); 7.2686 (0.7); 7.2478 (1.6); 7.2429 (1.6); 7.2222 (1.3); 7.2170 (1.2); 7.1965 (1.2); 7.1922 (1.4); 7.1713 (1.7); 7.1675 (1.7); 7.1462 (0.7); 7.1424 (0.6); 6.3169 (1.6); 6.3139 (1.7); 6.2904 (1.5); 6.2882 (1.5); 5.3424 (1.0); 3.3834 (0.4); 3.3798 (0.5); 3.3730 (0.4); 3.3609 (0.5); 3.3574 (0.5); 3.3529 (0.6); 3.3423 (0.6); 3.3351 (0.7); 3.3257 (0.5); 3.3216 (0.6); 3.3127 (0.7); 3.3029 (0.5); 3.2906 (0.4); 3.2868 (0.4); 3.2816 (0.6); 2.8128 (0.6); 2.8085 (0.6); 2.8019 (0.4); 2.7889 (0.5); 2.7830 (0.6); 2.7781 (0.6); 2.7691 (0.5); 2.7651 (0.5); 2.7095 (16.0); 2.5863 (0.5); 2.5828 (0.5); 2.5750 (0.4); 2.5632 (0.4); 2.5565 (0.4); 2.5523 (0.5); 2.5437 (0.5); 2.5184 (0.4); 2.4361 (0.4); 2.4143 (0.7); 2.4055 (0.7); 2.3937 (0.9); 2.3830 (1.3); 2.3756 (0.6); 2.3703 (0.6); 2.3631 (1.2); 2.3528 (0.8); 2.3401 (0.6); 2.3323 (0.6); 2.3246 (0.3); 1.6423 (4.6); 1.3096 (1.0); 0.9466 (0.4); 0.9249 (1.1); 0.9017 (0.4); 0.0429 (7.0)

I.039: $^1$H-NMR(300.2 MHz, CDCl3):
δ = 8.5947 (4.5); 8.5860 (4.6); 7.9856 (2.9); 7.9802 (3.4); 7.9771 (3.2); 7.9718 (2.7); 7.6044 (2.1); 7.5991 (2.2); 7.5789 (2.6); 7.5735 (2.6); 7.5566 (0.4); 7.5288 (2.2); 7.5178 (7.9); 7.5093 (6.4); 7.5001 (3.1); 7.4925 (3.4); 7.4889 (3.0); 7.4004 (1.6); 7.3897 (1.3); 7.3812 (1.4); 7.3653 (2.8); 7.3527 (1.5); 7.3432 (3.0); 7.3392 (2.9); 7.3177 (2.0); 7.3135 (2.2); 7.3046 (41.6); 7.1814 (1.6); 7.1758 (1.6); 7.1553 (2.1); 7.1504 (2.1); 7.1299 (1.1); 7.1242 (1.0); 6.8155 (1.1); 5.3442 (1.0); 4.8076 (16.0); 2.0890 (0.5); 1.6044 (15.0); 1.3030 (0.4); 0.0537 (1.4); 0.0429 (39.2); 0.0319 (1.4)

I.040: $^1$H-NMR(300.2 MHz, CDCl3):
δ = 9.0049 (1.6); 8.9971 (1.6); 8.4199 (1.1); 8.4146 (1.4); 8.4073 (0.9); 7.7505 (0.7); 7.7252 (1.2); 7.6716 (0.5); 7.6555 (0.5); 7.6459 (0.8); 7.6297 (0.8); 7.6189 (0.5); 7.6026 (0.5); 7.5809 (0.7); 7.5760 (0.7); 7.5553 (0.4); 7.5501 (0.6); 7.5465 (0.8); 7.5420 (0.7); 7.5208 (0.4); 7.5163 (0.4); 7.3037 (12.2); 7.2842 (0.5); 7.2758 (0.9); 7.2570 (0.8); 7.2478 (0.6); 7.2290 (0.5); 6.8993 (0.7); 6.8967 (0.6); 6.8707 (0.8); 6.8677 (0.9); 6.8376 (0.6); 6.8351 (0.5); 6.4977 (1.4); 6.4709 (1.3); 1.9849 (16.0); 1.6003 (11.5); 0.0526 (0.4); 0.0418 (11.3); 0.0308 (0.4)

I.041: $^1$H-NMR(300.2 MHz, CDCl3):
δ = 8.8607 (2.9); 8.8528 (3.0); 8.2759 (2.1); 8.2705 (2.6); 8.2634 (1.8); 7.7141 (1.1); 7.6871 (2.3); 7.6507 (1.0); 7.6351 (1.0); 7.6255 (1.6); 7.6094 (1.6); 7.5984 (0.8); 7.5823 (0.8); 7.5573 (1.3); 7.5523 (1.2); 7.5321 (0.8); 7.5229 (1.4); 7.5182 (1.2); 7.4974 (0.8); 7.4926 (0.7); 7.3791 (3.8); 7.3674 (5.0); 7.3577 (5.8); 7.3448 (1.2); 7.3377 (1.0); 7.3039 (30.4); 7.2885 (1.7); 7.2745 (3.0); 7.2623 (2.3); 7.2564 (1.7); 7.2513 (1.7); 7.2425 (1.5); 7.2308 (1.1); 7.2061 (0.6); 7.1023 (1.0); 7.0991 (0.9); 7.0769 (2.4); 7.0738 (2.0); 7.0517 (1.4); 7.0485 (1.2); 6.9966 (2.2); 6.9714 (1.2); 6.7176 (2.2); 6.6908 (2.1); 4.7479 (1.0); 4.7260 (1.4); 4.7004 (1.1); 3.7225 (1.2); 3.7023 (1.1); 3.6752 (1.4); 3.6549 (1.4); 3.3300 (1.6); 3.3033 (1.5); 3.2828 (1.2); 3.2562 (1.2); 2.4001 (3.0); 1.6058 (16.0); 0.0534 (1.0); 0.0426 (26.8); 0.0317 (0.9)

I.042: $^1$H-NMR(300.2 MHz, CDCl3):
δ = 9.1288 (1.4); 8.1743 (0.4); 8.1668 (0.4); 8.0528 (0.4); 8.0279 (0.4); 7.8276 (0.4); 7.8215 (0.4); 7.8114 (0.4); 7.8031 (0.8); 7.7947 (0.3); 7.7851 (0.3); 7.7790 (0.4); 7.6618 (0.4); 7.6348 (0.5); 7.4677 (0.4); 7.4426 (0.4); 7.4195 (0.4); 7.2986 (15.4); 7.2692 (0.5); 5.3385 (0.6); 4.6519 (1.8); 4.4307 (1.0); 1.5875 (16.0); 0.0483 (0.4); 0.0374 (13.0); 0.0266 (0.4)

I.043: $^1$H-NMR(300.2 MHz, CDCl3):
δ = 9.1681 (3.2); 8.1888 (0.7); 8.1840 (0.5); 8.1795 (0.5); 8.1638 (0.9); 8.1564 (0.8); 8.0343 (0.7); 8.0279 (0.9); 8.0117 (0.6); 8.0071 (0.7); 8.0017 (0.9); 7.8258 (0.4); 7.8086 (0.9); 7.8025 (0.8); 7.7908 (1.0); 7.7828 (1.4); 7.7756 (0.8); 7.7643 (0.8); 7.7584 (0.8); 7.7410 (0.3); 7.6679 (0.9); 7.6649 (0.9); 7.6591 (0.9); 7.6541 (0.9); 7.6407 (1.1); 7.6371 (1.3); 7.6299 (1.1); 7.4694 (0.5); 7.4647 (0.5); 7.4441 (0.9); 7.4392 (0.5); 7.4174 (0.6); 7.4123 (0.6); 7.3604 (0.8); 7.3565 (0.8); 7.3351 (1.1); 7.3315 (1.1); 7.3095 (0.5); 7.3062 (0.6); 7.2987 (13.7); 4.3863 (0.5); 3.5863 (0.4); 3.3060 (0.4); 3.2829 (0.5); 3.2743 (0.6); 3.2589 (0.6); 3.2514 (0.5); 3.2348 (0.7); 3.2290 (0.6); 3.2047 (0.6); 2.6879 (0.4); 2.6655 (0.6); 2.6596 (0.7); 2.6414 (0.4); 2.6358 (0.6); 2.6204 (0.6); 2.6154 (0.4); 2.6116 (0.5); 2.5903 (0.4); 2.3834 (0.4); 2.3774 (0.4); 2.3680 (0.6); 2.3593 (0.5); 2.3540 (0.5); 2.3454 (0.8); 2.3383 (0.4); 2.3347 (0.4); 2.3286 (0.7); 2.3220 (0.5); 2.3149 (0.4); 2.3038 (0.3); 2.2979 (0.4); 1.5947 (16.0); 1.3039 (0.5); 0.9195 (0.5); 0.0375 (4.4)

I.044: $^1$H-NMR(300.2 MHz, CDCl3):
δ = 9.1364 (2.5); 8.1913 (0.5); 8.1861 (0.4); 8.1807 (0.3); 8.1669 (0.6); 8.1589 (0.6); 8.0218 (0.5); 8.0140 (0.6); 7.9993 (0.4); 7.9938 (0.5); 7.9893 (0.7); 7.8038 (0.7); 7.7974 (0.6); 7.7895 (0.8); 7.7802 (1.4); 7.7707 (0.6); 7.7632 (0.6); 7.7571 (0.6); 7.6138 (0.6); 7.5869 (0.9); 7.4702 (0.4); 7.4647 (0.5); 7.4460 (0.6); 7.4406 (0.7); 7.4191 (0.4); 7.4136 (0.5); 7.3947 (0.4); 7.3893 (0.5); 7.3689 (1.1); 7.3638 (0.8); 7.3350 (0.8); 7.3315 (0.7); 7.3103 (0.8); 7.3071 (0.7); 7.2983 (2.0); 4.3716 (0.5); 3.1737 (1.6); 1.8130 (16.0); 1.7348 (0.5); 1.7240 (0.4); 1.6385 (2.0); 0.0373 (0.8)

I.045: $^1$H-NMR(300.2 MHz, CDCl3):
δ = 9.1925 (16.0); 8.5526 (0.4); 8.1975 (3.5); 8.1927 (2.7); 8.1886 (2.4); 8.1721 (4.7); 8.1651 (4.0); 8.0706 (3.4); 8.0632 (4.7); 8.0462 (3.0); 8.0419 (3.5); 8.0379 (4.6); 7.9202 (0.4); 7.8476 (1.4); 7.8416 (1.9); 7.8243 (4.5); 7.8183 (3.9); 7.8044 (5.0); 7.7993 (6.0); 7.7966 (5.9); 7.7914 (3.8); 7.7778 (3.8); 7.7721 (4.1); 7.7543 (2.2); 7.7486 (5.9); 7.7211 (5.7); 7.4424 (2.7); 7.4379 (2.8); 7.4169 (4.6); 7.4125 (4.8); 7.3898 (3.1); 7.3853 (3.2); 7.3547 (0.4); 7.2984 (21.8); 7.2818 (0.6); 7.2624 (3.1); 7.2590 (3.1); 7.2369 (5.8); 7.2336 (5.6); 7.2115 (2.9); 7.2082 (2.7); 7.0911 (0.4); 7.0660 (0.6); 6.9690 (4.8); 6.9656 (5.0); 6.9440 (4.0); 6.9400 (4.1); 6.8694 (0.6); 6.8424 (0.6); 6.8213 (0.5); 4.3995 (2.2); 4.0810 (0.8); 4.0564 (1.4); 4.0330 (1.0); 3.6771 (1.5); 3.6506 (1.5); 3.6263 (0.8); 3.3213 (3.4); 2.1890 (2.4); 2.1850 (2.9); 2.1661 (9.7); 2.1590 (10.1); 2.1548 (5.6); 2.1409 (3.4); 2.1369 (2.8); 2.0856 (0.5); 1.8852 (0.5); 1.7581 (0.5); 1.7067 (3.1); 1.7029 (3.2); 1.6890 (5.7); 1.6849 (10.0); 1.6778 (10.0); 1.6586 (2.8); 1.6548 (2.5); 1.6123 (8.9); 1.2924 (1.0); 0.9193 (0.4); 0.0484 (0.5); 0.0376 (13.7); 0.0267 (0.5)

I.046: $^1$H-NMR(300.2 MHz, CDCl3):
δ = 9.1573 (11.7); 7.8606 (2.0); 7.8578 (2.4); 7.8321 (4.0); 7.8295 (4.8); 7.7909 (2.3); 7.7733 (2.4); 7.7651 (2.9); 7.7471 (2.9); 7.7368 (1.5); 7.7189 (1.7); 7.7079 (3.4); 7.6805 (4.4); 7.5095 (1.8); 7.5073 (1.8); 7.4966 (2.7); 7.4919 (3.0); 7.4844 (3.5); 7.4823 (3.5); 7.4709 (2.7); 7.4648 (3.9); 7.4598 (5.1); 7.4552 (4.6); 7.4383 (2.8); 7.4337 (4.0); 7.4299 (3.9); 7.3157 (3.1); 7.3126 (3.0); 7.2982 (23.3); 7.2905 (4.8); 7.2875 (4.1); 7.2653 (1.7); 7.2621 (1.6); 5.3373 (2.4); 4.6592 (16.0); 2.0455 (1.4); 1.5935 (10.3); 0.0474 (0.9); 0.0367 (18.4); 0.0257 (0.7)

I.047: $^1$H-NMR(300.2 MHz, CDCl3):
δ = 9.2374 (4.2); 7.8737 (0.6); 7.8670 (0.6); 7.8579 (0.7); 7.8509 (0.7); 7.8424 (1.0); 7.8355 (1.0); 7.8264 (0.9); 7.8195 (0.9); 7.7489 (1.6); 7.7387 (0.9); 7.7230 (1.9); 7.7136 (1.0); 7.7065 (1.3); 7.6812 (1.2); 7.6746 (0.6);

TABLE 12-continued

| NMR peak lists |
|---|

7.6493 (0.6); 7.4565 (0.8); 7.4519 (0.8); 7.4309 (1.5); 7.4266 (1.5); 7.4039 (1.0); 7.3993 (0.9); 7.2982 (19.2); 7.2916 (1.6); 7.2878 (1.2); 7.2656 (1.9); 7.2623 (1.8); 7.2402 (0.9); 7.2369 (0.8); 6.9843 (1.6); 6.9811 (1.6); 6.9587 (1.3); 6.9554 (1.3); 5.3375 (1.1); 2.2100 (0.8); 1.9927 (0.7); 2.1887 (0.9); 2.1697 (3.0); 2.1626 (3.2); 2.1444 (1.1); 2.1405 (0.9); 2.0464 (2.6); 1.7190 (1.0); 1.7152 (1.1); 1.6970 (3.2); 1.6900 (3.3); 1.6706 (1.0); 1.6667 (1.0); 1.6118 (16.0); 1.3202 (0.4); 1.2905 (0.6); 0.0461 (0.4); 0.0353 (12.7); 0.0244 (0.5)

I.048: $^1$H-NMR(300.2 MHz, CDCl3):
δ = 9.2268 (1.2); 9.2155 (6.3); 7.8339 (1.4); 7.8272 (1.1); 7.8178 (1.4); 7.8110 (1.5); 7.8074 (1.2); 7.8025 (2.1); 7.7958 (2.0); 7.7915 (1.1); 7.7865 (1.8); 7.7797 (1.6); 7.7300 (0.4); 7.7190 (1.4); 7.6937 (1.9); 7.6866 (2.3); 7.6704 (4.5); 7.6675 (5.4); 7.6543 (2.1); 7.6454 (4.5); 7.6410 (5.6); 7.6372 (3.3); 7.6299 (1.0); 7.4819 (1.8); 7.4769 (1.5); 7.4567 (3.2); 7.4521 (2.3); 7.4343 (1.1); 7.4296 (2.2); 7.4248 (1.7); 7.4019 (1.2); 7.3976 (1.3); 7.3869 (3.0); 7.3829 (2.7); 7.3744 (2.3); 7.3615 (3.7); 7.3575 (3.1); 7.3496 (1.4); 7.3366 (1.5); 7.3324 (1.3); 7.3095 (3.5); 7.3022 (9.4); 7.2975 (25.6); 7.2705 (1.7); 7.0688 (1.3); 7.0655 (1.1); 7.0433 (2.1); 7.0402 (1.7); 7.0182 (1.0); 6.9037 (2.0); 6.8766 (1.8); 5.3413 (0.4); 5.3366 (1.1); 4.3854 (7.1); 3.8587 (2.7); 3.8365 (4.6); 3.8253 (0.8); 3.8133 (2.9); 3.7485 (0.3); 3.7254 (0.4); 3.6169 (0.7); 3.6053 (3.3); 3.5967 (1.5); 3.5847 (5.7); 3.5684 (2.0); 3.5638 (3.5); 3.5572 (0.9); 3.5357 (0.3); 3.4662 (0.4); 3.4476 (0.4); 3.2955 (1.2); 3.2722 (1.8); 3.2640 (1.8); 3.2539 (1.4); 3.2483 (1.8); 3.2407 (1.8); 3.2367 (1.5); 3.2237 (2.1); 3.2184 (1.7); 3.2042 (0.9); 3.1969 (1.4); 3.1940 (1.6); 3.1701 (0.5); 2.6890 (1.1); 2.6775 (0.7); 2.6638 (2.0); 2.6578 (2.2); 2.6541 (1.6); 2.6394 (1.7); 2.6345 (1.9); 2.6189 (1.8); 2.6138 (1.4); 2.6096 (1.4); 2.5892 (1.2); 2.5086 (0.3); 2.4302 (0.9); 2.4092 (2.7); 2.4018 (1.4); 2.3878 (4.1); 2.3643 (3.5); 2.3574 (2.0); 2.3534 (1.9); 2.3482 (2.7); 2.3428 (2.0); 2.3381 (1.8); 2.3324 (2.3); 2.3251 (1.8); 2.3181 (1.4); 2.3071 (1.2); 2.3018 (1.2); 2.2942 (1.0); 2.2782 (0.8); 2.2622 (0.6); 2.2506 (0.6); 2.2411 (0.4); 2.2301 (0.5); 2.2191 (0.4); 2.1936 (0.4); 2.0497 (0.4); 2.0450 (1.1); 1.6044 (2.7); 1.5927 (16.0); 1.2913 (0.6); 0.0479 (2.7); 0.0408 (7.0); 0.0360 (19.7); 0.0268 (0.4); 0.0251 (0.6)

I.049: $^1$H-NMR(499.9 MHz, CDCl3):
δ = 7.4671 (0.6); 7.4079 (0.8); 7.3924 (0.9); 7.3865 (0.9); 7.3711 (0.8); 7.3470 (1.4); 7.3450 (1.5); 7.3319 (1.9); 7.3298 (2.2); 7.3258 (1.0); 7.3227 (0.9); 7.3101 (1.9); 7.3072 (1.7); 7.2946 (1.5); 7.2916 (1.4); 7.2605 (93.4); 7.2527 (2.7); 7.2505 (2.4); 7.2372 (0.7); 7.2354 (0.7); 7.0487 (0.5); 6.7695 (1.9); 6.7540 (1.8); 2.9874 (16.0); 2.4863 (10.0); 2.0085 (0.3); 1.7756 (2.7); 1.5461 (10.1); 1.3363 (0.4); 1.2961 (0.5); 1.2846 (0.7); 1.2546 (4.8); 1.2323 (0.7); 0.8935 (0.5); 0.8802 (0.8); 0.8743 (0.5); 0.8665 (0.6); 0.8492 (0.4); 0.8387 (0.5); 0.1164 (0.3); 0.0061 (4.0); −0.0002 (84.4); −0.0065 (4.6); −0.1202 (0.4)

I.050: $^1$H-NMR(300.2 MHz, CDCl3):
δ = 9.1680 (2.5); 7.8221 (0.4); 7.8202 (0.4); 7.8178 (0.4); 7.8155 (0.4); 7.7918 (0.9); 7.7895 (0.8); 7.7870 (0.7); 7.7671 (0.5); 7.7500 (0.5); 7.7418 (0.6); 7.7240 (0.6); 7.6521 (0.7); 7.6507 (0.7); 7.6251 (0.9); 7.6237 (0.9); 7.4862 (0.4); 7.4797 (0.7); 7.4736 (0.5); 7.4623 (0.6); 7.4563 (0.8); 7.4534 (0.8); 7.4469 (0.7); 7.4419 (0.5); 7.4354 (0.4); 7.4294 (0.6); 7.4206 (0.4); 7.4161 (0.4); 7.4050 (0.3); 7.4003 (0.4); 7.3795 (1.0); 7.3747 (0.8); 7.3566 (0.8); 7.3530 (0.8); 7.3325 (0.7); 7.3293 (0.7); 7.2985 (2.8); 1.8103 (16.0); 1.7362 (0.4); 1.6056 (1.4); 0.0366 (2.9)

I.051: $^1$H-NMR(499.9 MHz, d$_6$-DMSO):
δ = 7.9608 (0.5); 7.9417 (1.3); 7.9252 (1.3); 7.9058 (0.7); 7.8525 (1.3); 7.8440 (1.4); 7.8353 (1.0); 7.8256 (0.9); 7.6187 (2.2); 7.6037 (2.5); 7.4040 (1.0); 7.3892 (2.3); 7.3742 (1.6); 7.3391 (1.7); 7.3241 (2.5); 7.3092 (1.0); 7.1215 (2.7); 7.1058 (2.4); 3.3321 (3.0); 2.8669 (16.0); 2.5059 (3.6); 2.0795 (0.4); 1.7040 (1.7); 1.2318 (0.4); −0.0002 (1.0)

I.052: $^1$H-NMR(300.2 MHz, CDCl3):
δ = 8.2947 (2.0); 8.2904 (2.0); 7.6489 (0.4); 7.6425 (0.5); 7.6318 (0.5); 7.6253 (0.5); 7.6185 (0.7); 7.6120 (0.7); 7.6013 (0.6); 7.5949 (0.6); 7.5114 (0.6); 7.4887 (0.6); 7.4797 (0.9); 7.4571 (0.8); 7.4486 (0.5); 7.4258 (0.5); 7.2985 (2.0); 6.9958 (1.3); 6.9912 (1.2); 6.9873 (1.5); 6.8445 (0.8); 6.8356 (0.8); 6.8153 (0.9); 6.8065 (0.8); 6.3013 (2.0); 6.2722 (1.8); 4.7340 (0.3); 4.6702 (0.4); 4.6178 (2.2); 4.5992 (2.4); 4.5469 (0.4); 3.8293 (16.0); 3.8044 (0.8); 2.7908 (11.8); 2.6231 (0.5); 2.0409 (4.5); 1.7081 (1.3); 0.0310 (1.5)

I.053: $^1$H-NMR(300.2 MHz, CDCl3):
δ = 8.3173 (2.7); 8.3130 (2.7); 7.6578 (0.6); 7.6514 (0.6); 7.6407 (0.6); 7.6341 (0.7); 7.6274 (0.9); 7.6209 (0.9); 7.6102 (0.9); 7.6038 (0.9); 7.5176 (0.8); 7.4949 (0.9); 7.4860 (1.2); 7.4634 (1.1); 7.4548 (0.6); 7.4321 (0.6); 7.2983 (3.7); 7.2221 (2.2); 7.1020 (1.1); 7.0749 (1.2); 6.2434 (2.3); 6.2162 (2.2); 5.3354 (1.0); 4.6677 (0.4); 4.6153 (2.8); 4.5964 (3.2); 4.5442 (0.5); 2.7884 (16.0); 2.3802 (12.1); 2.0817 (1.3); 1.6443 (3.4); 1.2950 (0.6); 0.0351 (4.0)

I.054: $^1$H-NMR(499.9 MHz, d$_6$-DMSO):
δ = 8.6697 (5.3); 8.0444 (1.6); 8.0307 (1.7); 8.0260 (1.5); 7.7098 (1.4); 7.6975 (3.5); 7.6829 (2.5); 7.6674 (0.4); 7.5517 (2.2); 7.5366 (2.3); 7.2219 (1.0); 7.2064 (2.2); 7.1911 (1.4); 7.1200 (1.5); 7.1049 (2.4); 7.0899 (1.1); 6.4509 (2.5); 6.4350 (2.4); 3.3239 (7.1); 2.6419 (16.0); 2.4365 (27.1); 2.0098 (1.1); 1.7708 (0.4); 1.7478 (14.5); 1.7332 (14.4); 1.1668 (0.6)

I.055: $^1$H-NMR(499.9 MHz, d$_6$-DMSO):
δ = 8.4869 (4.2); 7.8838 (2.2); 7.8677 (2.4); 7.6472 (0.9); 7.6317 (1.5); 7.6260 (1.1); 7.6100 (1.4); 7.5844 (1.1); 7.5744 (1.3); 7.5685 (1.6); 7.5585 (1.6); 7.5490 (2.6); 7.5337 (2.5); 7.2291 (1.1); 7.2274 (1.0); 7.2136 (2.4); 7.1982 (1.5); 7.1201 (1.6); 7.1051 (2.6); 7.0900 (1.2); 6.4648 (2.7); 6.4490 (2.6); 3.5900 (6.3); 2.5891 (17.7); 2.4395 (31.7); 2.4364 (38.9); 2.0095 (1.4); 1.7523 (16.0); 1.7332 (0.5); 1.7042 (15.4); 1.6901 (0.7); 1.1675 (0.4)

I.056: $^1$H-NMR(499.9 MHz, d$_6$-DMSO):
δ = 7.9419 (3.2); 7.9262 (2.8); 7.6542 (1.6); 7.6390 (2.7); 7.6331 (2.6); 7.6200 (3.7); 7.6071 (2.9); 7.5915 (2.1); 7.5585 (3.5); 7.5437 (3.1); 7.1913 (2.2); 7.1784 (3.3); 7.1662 (1.8); 7.1630 (1.9); 7.0749 (2.6); 7.0616 (3.2); 7.0467 (1.4); 6.3126 (3.5); 6.2974 (2.8); 3.3104 (3.4); 2.5426 (19.5); 2.5346 (12.4); 2.5216 (17.2); 2.4387 (17.4); 2.4355 (17.8); 2.0217 (0.5); 2.0197 (0.5); 2.0120 (1.2); 2.0091 (1.5); 1.7680 (16.0); 1.7279 (16.0); 1.1618 (0.4)

I.057: $^1$H-NMR(499.9 MHz, d$_6$-DMSO):
δ = 7.9142 (2.0); 7.8969 (2.2); 7.6276 (2.2); 7.6258 (2.1); 7.6124 (2.5); 7.6104 (2.4); 7.5918 (1.5); 7.5754 (1.1); 7.5619 (0.3); 7.5454 (0.4); 7.5421 (0.4); 7.5257 (0.4); 7.2780 (0.4); 7.2657 (1.2); 7.2632 (1.4); 7.2502 (2.2); 7.2480 (2.2); 7.2348 (1.4); 7.2324 (1.2); 7.1450 (1.5); 7.1433 (1.5); 7.1298 (2.5); 7.1281 (2.5); 7.1199 (0.5); 7.1146 (1.1); 7.1129 (1.0); 6.3756 (0.5); 6.3598 (0.6); 6.3497 (2.4); 6.3340 (2.3); 3.3972 (12.9); 2.8792 (2.4); 2.7787 (3.6); 2.6465 (0.4); 2.6429 (0.5); 2.6401 (0.5); 2.6258 (0.4); 2.5853 (16.7); 2.5755 (16.8); 2.5627 (1.4); 2.5565 (1.3); 2.5390 (3.9); 2.5297 (0.7); 2.5259 (0.9); 2.5117 (51.1); 2.5082 (67.0); 2.5046 (51.2); 2.5013 (31.5); 2.4543 (0.4); 2.3693 (0.5); 2.3657 (0.4); 1.9951 (0.6); 1.8346 (16.0); 1.8205 (1.4); 1.7953 (15.4); 1.7682 (0.7); 1.7470 (0.4); 1.6714 (0.3); 1.6550 (0.4); 1.2399 (0.8); 1.1805 (0.5); 1.1762 (0.4)

TABLE 12-continued

NMR peak lists

I.058: $^1$H-NMR(300.2 MHz, CDCl3):
δ = 8.9311 (1.1); 8.9232 (1.2); 8.2844 (1.0); 8.2715 (0.7); 7.4678 (1.0); 7.3756 (0.7); 7.3698 (1.1); 7.3659 (0.7); 7.3442 (0.8); 7.3393 (1.4); 7.3331 (0.7); 7.3249 (0.4); 7.3201 (0.4); 7.2987 (1.7); 7.2941 (0.8); 7.2730 (0.7); 7.2680 (0.6); 7.2110 (0.7); 7.2073 (0.7); 7.1857 (0.9); 7.1821 (0.9); 7.1605 (0.3); 7.1569 (0.3); 6.7453 (0.8); 6.7430 (0.8); 6.7186 (0.7); 6.7169 (0.7); 2.5872 (4.9); 2.3872 (0.8); 1.8570 (16.0); 1.7186 (0.6); 0.0344 (0.9)

I.059: $^1$H-NMR(499.9 MHz, d$_6$-DMSO):
δ = 8.7240 (4.2); 8.4823 (0.7); 8.4737 (0.7); 8.4711 (0.7); 8.4656 (0.8); 8.4549 (0.7); 7.9469 (0.5); 7.9274 (0.9); 7.9122 (0.9); 7.8926 (0.4); 7.6188 (1.6); 7.6037 (1.7); 7.3102 (0.8); 7.3080 (0.7); 7.2947 (1.6); 7.2792 (1.0); 7.2771 (0.9); 7.1997 (1.1); 7.1846 (1.8); 7.1694 (0.8); 6.5861 (1.9); 6.5703 (1.8); 3.3212 (17.7); 2.5054 (9.8); 2.5022 (12.0); 2.4990 (8.9); 2.2539 (0.6); 2.2485 (0.6); 2.2368 (1.0); 2.2250 (0.6); 2.2197 (0.6); 1.7945 (16.0); 1.2341 (0.6); 1.2253 (0.4); 1.2215 (0.4); 1.2153 (0.7); 1.2073 (0.7); 1.2039 (0.7); 1.1970 (0.8); 1.1898 (0.5); 1.1861 (0.5); 1.1783 (0.4); 1.1652 (0.4); 1.1561 (0.6); 1.1538 (0.6); 1.1472 (0.8); 1.1385 (0.8); 1.1277 (0.7); 1.1215 (0.4); 0.7940 (0.6); 0.7862 (0.8); 0.7749 (0.9); 0.7672 (0.7); 0.6888 (0.3); 0.6774 (0.7); 0.6688 (0.9); 0.6583 (0.8); 0.6498 (0.5); −0.0002 (3.8)

I.060: $^1$H-NMR(300.2 MHz, CDCl3):
δ = 9.0135 (4.8); 9.0057 (5.0); 8.4180 (3.2); 8.4109 (4.0); 8.4053 (3.2); 7.7481 (2.0); 7.7219 (3.4); 7.6756 (1.5); 7.6597 (1.6); 7.6499 (2.6); 7.6337 (2.6); 7.6230 (1.6); 7.6067 (1.5); 7.5883 (2.2); 7.5834 (2.2); 7.5629 (1.3); 7.5575 (1.4); 7.5542 (2.2); 7.5495 (2.2); 7.5284 (1.2); 7.5239 (1.2); 7.3329 (2.5); 7.3301 (2.8); 7.3055 (5.0); 7.3022 (5.9); 7.2986 (19.6); 7.2437 (2.6); 7.2168 (4.0); 7.1898 (1.7); 6.6174 (3.6); 6.5915 (3.3); 5.3373 (2.0); 4.6369 (16.0); 1.6001 (2.5); 1.2912 (0.5); 0.0477 (0.7); 0.0368 (20.3); 0.0259 (0.8)

I.061: $^1$H-NMR(499.9 MHz, d$_6$-DMSO):
δ = 7.7941 (3.6); 7.3292 (3.4); 7.1360 (3.6); 3.5884 (16.0); 3.4455 (0.8); 2.5068 (4.7); 2.5035 (6.1); 2.5002 (4.6); 2.0864 (0.8); −0.0002 (1.6)

I.062: $^1$H-NMR(300.2 MHz, CDCl3):
δ = 8.3265 (2.0); 8.3222 (2.0); 7.6495 (0.4); 7.6433 (0.5); 7.6323 (0.5); 7.6258 (0.5); 7.6189 (0.7); 7.6126 (0.7); 7.6019 (0.6); 7.5954 (0.6); 7.5135 (0.6); 7.4908 (0.6); 7.4818 (0.8); 7.4591 (0.8); 7.4507 (0.4); 7.4279 (0.4); 7.2986 (9.8); 6.9421 (2.1); 6.9334 (2.4); 6.8016 (1.3); 6.7927 (1.1); 6.7726 (1.4); 6.7637 (1.3); 6.3035 (2.4); 6.2746 (2.1); 3.8466 (16.0); 2.8126 (11.7); 1.8911 (11.2); 1.8536 (10.6); 1.6004 (10.9); 0.1073 (0.8); 0.0371 (9.9); 0.0261 (0.4)

I.063: $^1$H-NMR(300.2 MHz, CDCl3):
δ = 9.0251 (2.1); 9.0173 (2.2); 8.4012 (1.4); 8.3947 (1.8); 8.3885 (1.4); 7.7303 (0.9); 7.7035 (1.6); 7.6500 (0.7); 7.6339 (0.7); 7.6242 (1.2); 7.6079 (1.2); 7.5972 (0.7); 7.5810 (0.7); 7.5588 (1.0); 7.5539 (1.0); 7.5332 (0.6); 7.5281 (0.6); 7.5244 (1.0); 7.5198 (1.0); 7.4986 (0.6); 7.4941 (0.6); 7.3198 (0.9); 7.2989 (9.6); 7.2927 (2.1); 7.2647 (1.0); 6.7049 (2.0); 6.6768 (1.8); 6.3291 (1.9); 6.3022 (1.8); 4.5584 (7.2); 3.9520 (16.0); 1.6010 (10.4); 0.1076 (0.8); 0.0482 (0.3); 0.0374 (9.4); 0.0266 (0.4)

I.064: $^1$H-NMR(300.2 MHz, CDCl3):
δ = 9.0260 (1.7); 9.0181 (1.7); 8.4063 (1.1); 8.4004 (1.4); 8.3934 (1.1); 7.7347 (0.7); 7.7081 (1.2); 7.6554 (0.5); 7.6394 (0.6); 7.6297 (1.0); 7.6135 (0.9); 7.6027 (0.6); 7.5864 (0.6); 7.5646 (0.8); 7.5596 (0.8); 7.5390 (0.5); 7.5339 (0.5); 7.5302 (0.8); 7.5256 (0.8); 7.5044 (0.5); 7.4998 (0.4); 7.2986 (17.0); 7.2612 (0.6); 7.2349 (1.2); 7.2086 (0.7); 7.0024 (1.2); 6.9766 (1.0); 6.5349 (1.1); 6.5082 (1.0); 4.5470 (4.5); 2.3872 (7.2); 1.5884 (16.0); 0.1074 (1.4); 0.0486 (0.5); 0.0378 (16.3); 0.0268 (0.6)

I.065: $^1$H-NMR(300.2 MHz, CDCl3):
δ = 8.3383 (2.8); 8.3341 (2.8); 7.6513 (0.6); 7.6449 (0.6); 7.6342 (0.7); 7.6276 (0.7); 7.6209 (1.0); 7.6145 (1.0); 7.6037 (0.9); 7.5973 (0.9); 7.5098 (0.8); 7.4871 (0.9); 7.4781 (1.2); 7.4554 (1.2); 7.4471 (0.6); 7.4243 (0.6); 7.2984 (2.4); 7.1653 (2.4); 7.1629 (2.5); 7.0666 (1.3); 7.0632 (1.2); 7.0396 (1.3); 7.0362 (1.3); 6.2491 (2.7); 6.2221 (2.5); 5.3333 (0.4); 2.8030 (16.0); 2.3940 (12.8); 1.8992 (15.2); 1.8466 (14.6); 1.6726 (3.8); 0.0350 (1.9)

I.066: $^1$H-NMR(300.2 MHz, CDCl3):
δ = 8.3462 (2.0); 8.3417 (2.0); 7.6629 (0.4); 7.6564 (0.4); 7.6457 (0.5); 7.6392 (0.5); 7.6324 (0.7); 7.6259 (0.7); 7.6153 (0.6); 7.6088 (0.6); 7.5166 (0.6); 7.4939 (0.6); 7.4849 (0.8); 7.4623 (0.8); 7.4539 (0.4); 7.4311 (0.4); 7.2984 (4.2); 6.7742 (1.2); 6.7655 (1.2); 6.7452 (1.3); 6.7365 (1.4); 6.5103 (2.3); 6.5018 (2.2); 6.3059 (2.4); 6.2770 (2.1); 5.3355 (0.6); 3.8134 (16.0); 2.7990 (11.5); 2.2033 (1.8); 2.1877 (0.9); 2.1777 (2.7); 2.1728 (1.2); 2.1666 (1.1); 2.1494 (0.8); 2.1137 (0.3); 2.0430 (1.3); 1.7727 (0.4); 1.7681 (0.5); 1.7619 (0.5); 1.7575 (0.4); 1.7528 (0.7); 1.7357 (0.7); 1.7297 (0.7); 1.7131 (0.6); 1.6446 (0.7); 1.6259 (5.6); 1.6075 (0.7); 1.5987 (0.6); 1.5892 (0.6); 0.1077 (0.4); 0.0361 (4.0)

I.067: $^1$H-NMR(300.2 MHz, CDCl3):
δ = 8.3662 (2.7); 8.3616 (2.7); 7.6693 (0.6); 7.6628 (0.6); 7.6521 (0.6); 7.6454 (0.7); 7.6388 (0.9); 7.6323 (0.9); 7.6216 (0.8); 7.6151 (0.8); 7.5191 (0.8); 7.4965 (0.8); 7.4874 (1.1); 7.4648 (1.1); 7.4564 (0.6); 7.4336 (0.6); 7.2985 (5.9); 7.0400 (1.0); 7.0378 (1.2); 7.0344 (1.2); 7.0323 (1.0); 7.0130 (1.1); 7.0108 (1.2); 7.0074 (1.2); 7.0052 (1.1); 6.7399 (2.3); 6.7382 (2.2); 6.7360 (2.2); 6.7344 (2.2); 6.2498 (2.7); 6.2228 (2.5); 5.3359 (1.9); 2.7950 (16.0); 2.3571 (12.4); 2.2325 (0.4); 2.1966 (1.1); 2.1827 (1.4); 2.1740 (3.8); 2.1643 (1.6); 2.1478 (1.2); 2.1119 (0.5); 2.0820 (0.4); 1.7725 (0.9); 1.7653 (0.9); 1.7559 (1.0); 1.7395 (1.0); 1.7334 (0.9); 1.7175 (0.8); 1.6359 (1.0); 1.6319 (0.4); 1.6242 (8.6); 1.6137 (1.0); 1.6000 (0.9); 1.5898 (1.0); 1.5818 (1.0); 0.1086 (0.6); 0.0369 (5.1)

I.068: $^1$H-NMR(499.9 MHz, CDCl3):
δ = 10.4543 (0.5); 9.0075 (3.8); 9.0028 (3.9); 8.4004 (2.5); 8.3968 (3.3); 8.3934 (2.5); 7.6776 (2.1); 7.6611 (2.8); 7.5840 (1.0); 7.5743 (1.1); 7.5682 (1.8); 7.5585 (1.8); 7.5520 (1.1); 7.5423 (1.0); 7.4980 (1.5); 7.4958 (1.5); 7.4824 (1.2); 7.4800 (1.3); 7.4773 (1.6); 7.4750 (1.6); 7.4617 (1.2); 7.4596 (1.1); 7.2720 (1.0); 7.0914 (1.8); 7.0756 (3.7); 7.0598 (2.2); 6.8274 (2.7); 6.8120 (2.4); 6.4980 (2.7); 6.4820 (2.6); 2.6597 (1.3); 2.2689 (16.0); 2.1126 (1.1); 2.1013 (3.3); 2.0964 (4.2); 2.0852 (1.8); 2.0837 (1.8); 2.0538 (0.6); 2.0484 (0.6); 2.0167 (2.0); 2.0096 (2.6); 2.0056 (4.2); 2.0006 (3.3); 1.9897 (1.1); 1.9882 (0.9); 1.8477 (0.3); −0.0002 (0.4)

I.069: $^1$H-NMR(499.9 MHz, CDCl3):
δ = 8.9720 (2.5); 8.9676 (2.7); 8.3494 (2.4); 7.6524 (1.1); 7.6360 (1.5); 7.5600 (0.4); 7.5505 (0.6); 7.5442 (1.0); 7.5349 (1.0); 7.5283 (0.8); 7.5189 (0.6); 7.4675 (0.8); 7.4471 (1.1); 7.4316 (0.6); 7.1971 (1.0); 7.1805 (2.0); 7.1640 (1.2); 6.6564 (1.9); 6.6395 (1.8); 6.2744 (2.0); 6.2584 (1.9); 3.9012 (9.4); 1.9004 (16.0)

I.070: $^1$H-NMR(400.0 MHz, d$_6$-DMSO):
δ = 9.1750 (2.0); 9.1688 (2.1); 8.7882 (1.9); 8.7841 (2.0); 8.7123 (1.8); 8.7061 (1.8); 8.4631 (1.9); 8.4592 (1.9); 7.6454 (1.0); 7.6287 (1.0); 7.6263 (1.0); 7.4035 (0.4); 7.4006 (0.4); 7.3840 (1.0); 7.3812 (1.0); 7.3647 (0.7);

TABLE 12-continued

NMR peak lists 7.3616 (0.6); 7.2898 (0.7); 7.2709 (1.2); 7.2536 (0.5); 7.2519 (0.5); 7.0242 (1.3); 7.0046 (1.1); 3.3366 (11.3); 2.8935 (1.0); 2.7343 (0.9); 2.6649 (0.6); 2.5149 (4.3); 2.5107 (8.8); 2.5062 (11.7); 2.5018 (8.4); 2.4976 (4.1); 1.7591 (16.0); −0.0002 (1.1)
I.071: $^1$H-NMR(400.0 MHz, $d_6$-DMSO):
δ = 9.2241 (2.0); 9.2195 (2.5); 9.2167 (2.2); 9.2096 (1.9); 9.1582 (2.0); 9.1540 (1.8); 8.5226 (2.0); 8.5158 (1.9); 7.6521 (1.0); 7.6349 (1.1); 7.6333 (1.1); 7.4130 (0.4); 7.4104 (0.4); 7.3936 (1.0); 7.3912 (1.0); 7.3742 (0.7); 7.3714 (0.7); 7.2957 (0.8); 7.2776 (1.2); 7.2589 (0.5); 7.0769 (1.3); 7.0571 (1.2); 3.3434 (6.0); 2.8960 (0.6); 2.7370 (0.5); 2.5147 (4.1); 2.5105 (5.3); 2.5063 (3.9); 1.7721 (16.0); −0.0002 (0.5)
I.072: $^1$H-NMR(400.0 MHz, $d_6$-DMSO):
δ = 12.3844 (0.6); 8.3176 (3.7); 8.0213 (0.8); 7.5675 (0.8); 7.5650 (0.9); 7.5484 (1.0); 7.5459 (1.0); 7.3470 (0.4); 7.3438 (0.4); 7.3275 (0.9); 7.3246 (0.9); 7.3081 (0.6); 7.3049 (0.6); 7.2291 (0.6); 7.2268 (0.7); 7.2101 (1.0); 7.2079 (1.0); 7.1912 (0.5); 7.1889 (0.4); 6.9650 (1.2); 6.9458 (1.0); 6.6744 (1.2); 6.6657 (1.1); 3.3294 (8.8); 2.8910 (2.0); 2.7324 (1.8); 2.5123 (6.2); 2.5080 (12.5); 2.5035 (16.4); 2.4990 (11.7); 2.4946 (5.6); 1.7014 (16.0); −0.0002 (2.4)
I.073: $^1$H-NMR(400.0 MHz, $d_6$-DMSO):
δ = 8.5673 (0.8); 8.4968 (1.7); 8.4911 (1.7); 8.2432 (1.4); 8.2405 (1.4); 7.5813 (0.9); 7.5792 (0.9); 7.5624 (1.0); 7.5604 (1.0); 7.3150 (0.4); 7.3120 (0.5); 7.2954 (2.3); 7.2923 (2.2); 7.2762 (0.7); 7.2731 (0.7); 7.1843 (0.7); 7.1672 (1.1); 7.1653 (1.1); 7.1483 (0.5); 7.1464 (0.5); 6.6868 (1.2); 6.6672 (1.1); 3.3355 (10.0); 2.8918 (1.1); 2.7331 (1.0); 2.5092 (7.8); 2.5049 (10.1); 2.5004 (7.3); 1.7546 (16.0); 1.7082 (0.9); 1.5978 (0.8); −0.0002 (1.3)
I.074: $^1$H-NMR(400.0 MHz, $d_6$-DMSO):
δ = 9.1844 (0.6); 9.1788 (0.6); 9.0713 (1.0); 9.0647 (0.9); 8.6657 (1.6); 8.6588 (1.5); 8.6527 (0.9); 8.6486 (0.8); 8.6319 (0.9); 8.6280 (0.7); 7.7643 (0.6); 7.7538 (0.6); 7.7439 (0.6); 7.7335 (0.6); 7.6310 (1.0); 7.6121 (1.1); 7.3749 (0.4); 7.3555 (1.0); 7.3361 (0.7); 7.2543 (0.8); 7.2354 (1.2); 7.2165 (0.5); 6.9167 (1.3); 6.8968 (1.2); 3.3369 (6.6); 2.8928 (0.5); 2.7343 (0.5); 2.5103 (7.5); 2.5063 (9.2); 2.5023 (6.7); 1.7694 (16.0); −0.0002 (1.2)
I.075: $^1$H-NMR(400.0 MHz, $d_6$-DMSO):
δ = 9.0076 (2.0); 9.0014 (2.0); 8.6406 (1.8); 8.6344 (1.8); 8.1612 (1.0); 8.1424 (1.0); 8.1406 (1.0); 8.0671 (1.0); 8.0484 (1.2); 7.9571 (0.6); 7.7152 (0.9); 7.6956 (1.4); 7.6758 (0.7); 7.6265 (1.0); 7.6095 (1.0); 7.3717 (0.4); 7.3690 (0.4); 7.3523 (1.0); 7.3498 (0.9); 7.3329 (0.6); 7.3301 (0.6); 7.2522 (0.7); 7.2339 (1.1); 7.2153 (0.5); 6.9122 (1.2); 6.8925 (1.1); 3.3426 (10.0); 2.8933 (4.0); 2.7353 (3.6); 2.5163 (2.8); 2.5122 (5.6); 2.5078 (7.4); 2.5033 (5.4); 1.7683 (16.0); −0.0002 (0.6)
I.076: $^1$H-NMR(400.0 MHz, $d_6$-DMSO):
δ = 9.9061 (2.1); 9.8998 (2.2); 8.9290 (2.2); 8.9227 (2.2); 8.8435 (3.6); 7.5950 (1.0); 7.5780 (1.1); 7.5760 (1.1); 7.3434 (0.4); 7.3406 (0.5); 7.3239 (1.0); 7.3214 (1.0); 7.3045 (0.7); 7.3017 (0.6); 7.2148 (0.7); 7.1974 (1.2); 7.1959 (1.2); 7.1786 (0.5); 6.9434 (1.3); 6.9238 (1.2); 3.3342 (5.7); 2.8932 (1.6); 2.7342 (1.5); 2.5099 (6.3); 2.5055 (8.3); 2.5011 (6.0); 1.7863 (16.0); 1.7017 (0.6); 1.5491 (3.3); −0.0002 (1.1)
I.077: $^1$H-NMR(400.0 MHz, $d_6$-DMSO):
δ = 8.5855 (1.7); 8.5796 (1.7); 8.5715 (0.4); 8.5649 (0.4); 8.4226 (1.9); 8.4166 (1.7); 8.0673 (1.5); 8.0525 (1.6); 8.0107 (0.4); 8.0039 (0.4); 7.9679 (0.4); 7.9531 (0.7); 7.5910 (1.0); 7.5756 (2.1); 7.5608 (1.7); 7.4063 (0.4); 7.3914 (0.4); 7.3222 (0.4); 7.3194 (0.4); 7.3029 (1.0); 7.3003 (0.9); 7.2835 (0.6); 7.2806 (0.6); 7.1963 (0.7); 7.1774 (1.1); 7.1585 (0.5); 6.7226 (1.2); 6.7029 (1.1); 3.3324 (29.6); 3.0710 (0.3); 2.8912 (2.0); 2.7387 (0.4); 2.7323 (1.9); 2.5076 (16.8); 2.5033 (21.4); 2.4989 (15.3); 1.7549 (16.0); 1.2390 (0.5); −0.0002 (1.6)
I.078: $^1$H-NMR(400.0 MHz, $d_6$-DMSO):
δ = 9.0458 (1.9); 9.0397 (2.0); 8.6856 (1.7); 8.6794 (1.7); 8.1956 (1.3); 8.1734 (1.5); 7.9308 (1.3); 7.9087 (1.1); 7.6317 (1.0); 7.6130 (1.0); 7.3800 (0.4); 7.3777 (0.4); 7.3606 (1.0); 7.3413 (0.6); 7.2622 (0.7); 7.2433 (1.1); 7.2244 (0.5); 6.9394 (1.2); 6.9196 (1.1); 3.3407 (9.7); 2.8948 (0.6); 2.7364 (0.6); 2.5131 (6.1); 2.5087 (7.9); 2.5043 (5.7); 1.7648 (16.0); −0.0002 (0.6)
I.079: $^1$H-NMR(400.0 MHz, $d_6$-DMSO):
δ = 9.0470 (1.8); 9.0411 (1.8); 8.4503 (1.0); 8.4464 (1.3); 8.4414 (1.1); 7.7524 (0.3); 7.7418 (0.4); 7.7385 (0.4); 7.7305 (0.5); 7.7270 (0.4); 7.7162 (0.4); 7.7048 (0.4); 7.6385 (0.9); 7.6361 (1.0); 7.6199 (1.2); 7.6169 (1.2); 7.5990 (0.6); 7.5901 (0.6); 7.5765 (0.3); 7.3891 (0.4); 7.3859 (0.4); 7.3696 (1.0); 7.3667 (1.0); 7.3501 (0.7); 7.3470 (0.6); 7.2708 (0.7); 7.2536 (1.1); 7.2518 (1.2); 7.2348 (0.5); 7.2329 (0.5); 6.9851 (1.2); 6.9654 (1.1); 3.3379 (14.0); 2.8941 (1.2); 2.7350 (1.0); 2.5113 (8.0); 2.5069 (10.5); 2.5025 (7.6); 1.7678 (16.0); −0.0002 (1.1)
I.080: $^1$H-NMR(400.0 MHz, $d_6$-DMSO):
δ = 8.9191 (1.6); 8.9133 (1.7); 8.5903 (1.4); 7.8681 (1.8); 7.8451 (2.1); 7.8228 (0.4); 7.6346 (1.0); 7.6328 (1.0); 7.6157 (1.2); 7.6138 (1.1); 7.3893 (0.4); 7.3864 (0.4); 7.3698 (1.0); 7.3672 (1.0); 7.3504 (0.7); 7.3475 (0.6); 7.2671 (0.7); 7.2495 (1.2); 7.2306 (0.5); 6.9490 (1.3); 6.9292 (1.2); 3.3383 (8.0); 2.8949 (0.5); 2.7364 (0.5); 2.5126 (5.8); 2.5083 (7.6); 2.5040 (5.6); 1.7591 (16.0); −0.0002 (0.8)
I.081: $^1$H-NMR(400.0 MHz, $d_6$-DMSO):
δ = 10.2153 (3.2); 9.0440 (1.9); 9.0377 (2.0); 8.8026 (1.6); 8.7821 (1.5); 8.7759 (1.4); 8.2821 (0.4); 8.2602 (2.0); 8.2503 (1.6); 8.2466 (1.4); 8.2284 (0.3); 8.2246 (0.3); 7.6354 (0.9); 7.6164 (1.0); 7.3781 (0.4); 7.3751 (0.4); 7.3585 (0.9); 7.3562 (0.9); 7.3393 (0.6); 7.3363 (0.6); 7.2597 (0.7); 7.2408 (1.1); 7.2220 (0.5); 6.9220 (1.2); 6.9022 (1.1); 3.3399 (12.5); 2.8932 (1.3); 2.7349 (1.2); 2.6750 (0.4); 2.5157 (3.2); 2.5115 (6.5); 2.5071 (8.6); 2.5026 (6.2); 2.4983 (3.0); 1.7740 (16.0); −0.0002 (0.7)
I.082: $^1$H-NMR(400.0 MHz, $d_6$-DMSO):
δ = 8.8080 (1.9); 8.8018 (2.0); 8.4859 (1.9); 8.4797 (1.8); 7.9551 (0.7); 7.9227 (1.4); 7.8999 (1.7); 7.6873 (1.7); 7.6645 (1.4); 7.5993 (1.0); 7.5824 (1.1); 7.3346 (0.4); 7.3319 (0.4); 7.3171 (1.0); 7.3126 (1.0); 7.2957 (0.6); 7.2930 (0.6); 7.2050 (0.7); 7.1862 (1.2); 7.1676 (0.5); 6.7454 (1.3); 6.7257 (1.2); 4.0049 (10.1); 3.9833 (11.6); 3.3349 (7.8); 2.8915 (4.5); 2.7333 (4.1); 2.5090 (7.9); 2.5047 (10.5); 2.5003 (7.6); 1.7647 (16.0); −0.0002 (1.4)
I.083: $^1$H-NMR(400.0 MHz, $d_6$-DMSO):
δ = 8.0289 (1.4); 8.0223 (1.4); 7.6190 (1.4); 7.6124 (1.3); 7.5364 (0.9); 7.5342 (1.0); 7.5176 (1.1); 7.5153 (1.1); 7.2967 (0.5); 7.2937 (0.5); 7.2801 (1.0); 7.2744 (1.0); 7.2578 (0.6); 7.2547 (0.6); 7.1395 (0.7); 7.1377 (0.7); 7.1206 (1.2); 7.1187 (1.2); 7.1017 (0.5); 7.0997 (0.5); 6.5645 (1.2); 6.5450 (1.2); 4.3697 (1.4); 4.3571 (1.5); 4.3441 (1.1); 3.3278 (6.9); 2.8905 (1.1); 2.8654 (0.8); 2.8495 (1.6); 2.8337 (0.9); 2.7319 (1.1); 2.5069 (6.8); 2.5025 (9.1); 2.4980 (6.5); 1.9601 (0.8); 1.9466 (1.0); 1.9337 (0.8); 1.7105 (16.0); −0.0002 (1.4)
I.084: $^1$H-NMR(400.0 MHz, $d_6$-DMSO):
δ = 8.3652 (3.9); 8.0516 (1.5); 8.0427 (1.5); 7.5706 (0.9); 7.5686 (0.9); 7.5517 (1.0); 7.5496 (0.9); 7.3488 (0.4); 7.3457 (0.4); 7.3295 (0.9); 7.3266 (0.9); 7.3100 (0.6); 7.3069 (0.6); 7.2337 (0.7); 7.2319 (0.6); 7.2148 (1.1);

| TABLE 12-continued |
|---|
| NMR peak lists |

7.2131 (1.0); 7.1959 (0.5); 6.9639 (1.2); 6.9441 (1.1); 6.6925 (1.9); 6.6835 (1.9); 3.9086 (9.9); 3.3346 (3.8); 2.8911 (0.7); 2.7339 (0.6); 2.5142 (2.4); 2.5099 (4.8); 2.5054 (6.3); 2.5009 (4.5); 2.4966 (2.1); 1.7024 (16.0); −0.0002 (0.8)
I.085: $^1$H-NMR(400.0 MHz, d$_6$-DMSO):
δ = 8.4878 (0.9); 8.0074 (1.7); 7.9985 (1.8); 7.5887 (0.9); 7.5863 (1.0); 7.5696 (1.0); 7.5673 (1.0); 7.3667 (0.4); 7.3636 (0.4); 7.3470 (0.9); 7.3444 (0.9); 7.3278 (0.7); 7.3246 (0.6); 7.2462 (0.7); 7.2293 (1.1); 7.2272 (1.1); 7.2104 (0.5); 7.2083 (0.5); 7.1123 (1.2); 7.0930 (1.1); 6.7767 (1.8); 6.7677 (1.7); 3.7957 (10.0); 3.3395 (14.3); 2.8915 (1.7); 2.7330 (1.6); 2.5096 (6.6); 2.5052 (8.7); 2.5008 (6.3); 1.7214 (16.0); −0.0002 (0.7)
I.086: $^1$H-NMR(400.0 MHz, d$_6$-DMSO):
δ = 9.0662 (1.8); 9.0600 (1.8); 8.8029 (1.7); 8.7996 (1.8); 8.6590 (1.6); 8.6530 (1.5); 8.2903 (1.1); 8.2685 (1.6); 8.1671 (1.1); 8.1631 (1.1); 8.1453 (0.8); 8.1412 (0.8); 7.9556 (1.0); 7.6360 (1.1); 7.6172 (1.1); 7.3840 (0.5); 7.3651 (1.0); 7.3467 (0.7); 7.2685 (0.8); 7.2496 (1.2); 7.2306 (0.5); 6.9478 (1.3); 6.9280 (1.2); 3.3385 (13.8); 2.8931 (6.0); 2.7343 (5.7); 2.5104 (7.6); 2.5065 (9.7); 2.5024 (7.3); 1.7629 (16.0); −0.0002 (0.8)
I.087: $^1$H-NMR(400.0 MHz, d$_6$-DMSO):
δ = 7.6779 (1.4); 7.5539 (0.9); 7.5515 (1.0); 7.5350 (1.0); 7.5326 (1.0); 7.3054 (0.4); 7.3025 (0.4); 7.2859 (0.9); 7.2832 (0.9); 7.2665 (0.6); 7.2636 (0.6); 7.1599 (0.7); 7.1423 (1.1); 7.1410 (1.1); 7.1235 (0.5); 6.6181 (1.1); 6.5982 (1.0); 3.3275 (2.7); 3.0019 (1.0); 2.9837 (1.9); 2.9656 (1.2); 2.5073 (6.4); 2.5029 (8.4); 2.4985 (6.1); 2.1582 (0.6); 2.1404 (0.8); 2.1227 (0.6); 1.7141 (16.0); −0.0002 (1.4)
I.088: $^1$H-NMR(400.0 MHz, d$_6$-DMSO):
δ = 8.3276 (1.1); 8.3224 (1.2); 7.9532 (0.4); 7.5527 (2.2); 7.5339 (1.1); 7.5316 (1.1); 7.3081 (0.4); 7.3051 (0.5); 7.2886 (1.0); 7.2858 (1.0); 7.2692 (0.6); 7.2662 (0.6); 7.1619 (0.7); 7.1448 (1.1); 7.1430 (1.2); 7.1259 (0.5); 7.1241 (0.5); 6.6416 (1.2); 6.6220 (1.2); 3.3320 (13.5); 2.9082 (0.8); 2.8909 (3.9); 2.8765 (1.0); 2.8316 (0.8); 2.8158 (1.6); 2.8007 (0.8); 2.7319 (2.2); 2.5071 (7.3); 2.5027 (9.6); 2.4983 (7.0); 1.8850 (0.6); 1.8714 (1.0); 1.8618 (0.7); 1.8566 (0.9); 1.8459 (0.4); 1.8411 (0.3); 1.7964 (0.4); 1.7920 (0.4); 1.7814 (1.0); 1.7667 (1.0); 1.7534 (0.7); 1.7096 (16.0); −0.0002 (0.9)
I.089: $^1$H-NMR(400.0 MHz, d$_6$-DMSO):
δ = 8.8966 (1.8); 8.8902 (1.9); 8.5077 (1.7); 8.5014 (1.7); 7.9814 (0.9); 7.9602 (1.1); 7.7408 (0.8); 7.7235 (1.0); 7.6209 (0.9); 7.6132 (1.0); 7.6115 (1.0); 7.6017 (1.2); 7.5944 (1.2); 7.5830 (0.7); 7.3471 (0.4); 7.3443 (0.4); 7.3276 (1.0); 7.3253 (1.0); 7.3083 (0.7); 7.3054 (0.6); 7.2245 (0.7); 7.2056 (1.2); 7.1867 (0.5); 6.8067 (1.2); 6.7869 (1.2); 3.3377 (13.2); 2.8914 (3.2); 2.7731 (7.0); 2.7337 (2.9); 2.5095 (7.5); 2.5052 (9.7); 2.5008 (7.0); 1.7670 (16.0); −0.0002 (0.9)
I.090: $^1$H-NMR(400.0 MHz, d$_6$-DMSO):
δ = 9.1137 (0.9); 9.1100 (1.0); 9.1033 (1.0); 9.0996 (0.9); 9.0427 (1.8); 9.0367 (1.8); 8.5695 (0.9); 8.5485 (0.9); 8.4031 (1.4); 8.3973 (1.4); 7.9112 (1.0); 7.9008 (1.0); 7.8899 (0.9); 7.8794 (0.9); 7.6403 (0.9); 7.6381 (1.0); 7.6213 (1.0); 7.6191 (1.0); 7.3894 (0.4); 7.3864 (0.4); 7.3699 (1.0); 7.3671 (1.0); 7.3505 (0.7); 7.3474 (0.6); 7.2702 (0.7); 7.2528 (1.1); 7.2512 (1.1); 7.2339 (0.5); 6.9840 (1.2); 6.9643 (1.1); 3.3387 (5.6); 2.8938 (0.3); 2.5123 (5.6); 2.5080 (7.3); 2.5036 (5.2); 1.7684 (16.0); −0.0002 (1.1)
I.091: $^1$H-NMR(400.0 MHz, d$_6$-DMSO):
δ = 8.2675 (1.9); 8.2618 (2.0); 8.0693 (2.2); 8.0636 (2.1); 7.6950 (1.7); 7.6864 (1.8); 7.5537 (0.9); 7.5513 (1.0); 7.5347 (1.1); 7.5324 (1.1); 7.2707 (0.4); 7.2676 (0.5); 7.2513 (1.0); 7.2484 (1.0); 7.2318 (0.7); 7.2287 (0.6); 7.1351 (0.7); 7.1329 (0.7); 7.1161 (1.2); 7.1140 (1.2); 7.0972 (0.5); 7.0950 (0.5); 6.6013 (2.2); 6.5927 (2.2); 6.5075 (1.2); 6.4881 (1.2); 3.8930 (10.2); 3.7966 (0.7); 3.3368 (7.3); 3.3353 (7.3); 2.8904 (1.2); 2.7328 (1.1); 2.5127 (3.3); 2.5085 (6.7); 2.5041 (8.8); 2.4996 (6.3); 2.4955 (3.0); 1.7504 (16.0); −0.0002 (1.0)
I.092: $^1$H-NMR(400.0 MHz, d$_6$-DMSO):
δ = 8.3265 (1.4); 8.0493 (1.6); 8.0458 (1.6); 7.8222 (1.8); 7.8143 (1.8); 7.5626 (1.1); 7.5437 (1.2); 7.2858 (0.5); 7.2831 (0.5); 7.2661 (1.0); 7.2639 (1.1); 7.2470 (0.7); 7.2442 (0.7); 7.1458 (0.9); 7.1269 (1.3); 7.1080 (0.6); 6.6942 (1.5); 6.6865 (1.4); 6.5553 (1.3); 6.5356 (1.3); 3.8735 (9.6); 3.3607 (1.4); 2.8904 (1.8); 2.7321 (1.7); 2.5219 (0.6); 2.5084 (8.0); 2.5041 (10.4); 2.5001 (7.9); 2.3583 (0.7); 1.7606 (16.0); 1.2377 (0.3); −0.0002 (1.2)
I.093: $^1$H-NMR(400.0 MHz, d$_6$-DMSO):
δ = 9.0856 (1.4); 9.0809 (1.4); 8.0161 (1.8); 8.0102 (1.8); 7.9530 (0.7); 7.6613 (1.0); 7.6583 (1.2); 7.6542 (1.2); 7.6511 (1.1); 7.5713 (1.0); 7.5545 (1.0); 7.5524 (1.0); 7.3277 (0.4); 7.3249 (0.5); 7.3083 (1.0); 7.3056 (1.0); 7.2887 (0.8); 7.2861 (0.7); 7.1791 (0.7); 7.1603 (1.1); 7.1430 (0.5); 7.1167 (1.0); 7.1089 (1.2); 7.1069 (1.3); 7.0993 (1.1); 6.7920 (1.2); 6.7724 (1.2); 6.6835 (1.1); 6.6735 (1.1); 3.7291 (0.4); 3.3316 (11.5); 2.8906 (4.5); 2.7319 (4.1); 2.5070 (13.4); 2.5027 (17.6); 2.4983 (12.8); 1.7539 (16.0); 1.7051 (2.3); 1.5877 (1.7); 1.2398 (0.3); −0.0002 (2.0)
I.094: $^1$H-NMR(300.2 MHz, CDCl3):
δ = 8.9804 (1.1); 8.9725 (1.2); 8.4190 (0.7); 8.4119 (0.9); 8.4062 (0.7); 7.7428 (0.4); 7.7162 (0.8); 7.6405 (0.6); 7.6243 (0.5); 7.5771 (0.4); 7.5724 (0.4); 7.5429 (0.4); 7.5386 (0.4); 7.3377 (0.7); 7.3346 (0.8); 7.3105 (1.0); 7.3074 (1.0); 7.2981 (2.8); 7.1488 (0.8); 7.1219 (1.5); 7.0949 (0.7); 6.6179 (0.9); 6.6147 (1.0); 6.5911 (0.8); 6.5880 (0.8); 2.0451 (16.0); 1.6210 (0.3); 1.5878 (0.6); 0.1089 (1.5); 0.1072 (1.7); 0.0371 (2.9)
I.095: $^1$H-NMR(300.2 MHz, CDCl3):
δ = 9.0248 (2.0); 9.0180 (2.0); 8.4186 (2.1); 8.4128 (2.6); 8.4061 (2.0); 7.7522 (1.2); 7.7263 (2.2); 7.6785 (1.0); 7.6626 (1.1); 7.6529 (1.8); 7.6368 (1.8); 7.6259 (1.1); 7.6097 (1.0); 7.5909 (1.5); 7.5859 (1.5); 7.5655 (0.9); 7.5601 (1.0); 7.5568 (1.6); 7.5521 (1.5); 7.5311 (0.9); 7.5265 (0.8); 7.3967 (1.2); 7.3787 (1.2); 7.3686 (1.3); 7.3507 (1.2); 7.2987 (12.1); 6.8905 (1.1); 6.8825 (1.1); 6.8616 (1.3); 6.8538 (1.8); 6.8330 (1.1); 6.8250 (1.3); 6.4293 (1.6); 6.4214 (1.6); 6.3996 (1.6); 6.3918 (1.6); 4.6129 (6.9); 4.1935 (1.1); 4.1697 (3.3); 4.1459 (3.4); 4.1221 (1.2); 2.6522 (10.3); 2.0811 (16.0); 1.6315 (1.8); 1.3190 (4.2); 1.2952 (8.5); 1.2714 (4.1); 0.1065 (1.9); 0.0466 (0.4); 0.0358 (11.0); 0.0249 (0.4)
I.096: $^1$H-NMR(300.2 MHz, CDCl3):
δ = 9.0073 (1.6); 8.3706 (2.1); 8.3649 (2.9); 8.3590 (2.1); 7.7106 (1.3); 7.6839 (2.2); 7.6328 (0.9); 7.6168 (1.0); 7.6070 (1.7); 7.5909 (1.6); 7.5801 (1.0); 7.5639 (1.0); 7.5387 (1.4); 7.5340 (1.4); 7.5131 (0.9); 7.5043 (1.5); 7.4999 (1.5); 7.4784 (1.1); 7.4744 (1.1); 7.3303 (0.4); 7.3219 (0.4); 7.2995 (2.4); 7.2154 (3.0); 7.1421 (1.5); 7.1147 (1.7); 6.6353 (3.1); 6.6080 (2.8); 4.7195 (0.8); 4.5862 (9.1); 2.6439 (6.7); 2.3855 (16.0); 2.2284 (1.2); 2.0757 (0.3); 1.2896 (0.9); 0.0323 (2.1)
I.097: $^1$H-NMR(300.2 MHz, CDCl3):
δ = 9.0694 (11.6); 9.0615 (11.8); 8.4668 (7.8); 8.4612 (10.0); 8.4540 (7.4); 7.7585 (5.1); 7.7317 (8.3); 7.6761 (3.6); 7.6601 (3.8); 7.6504 (6.7); 7.6342 (6.4); 7.6234 (4.0); 7.6071 (3.8); 7.5882 (5.6); 7.5833 (5.4); 7.5626 (3.2); 7.5573 (3.8); 7.5540 (5.6); 7.5494 (5.3); 7.5282 (3.2); 7.5237 (2.9); 7.2991 (15.5); 6.9111 (4.1); 6.8934

TABLE 12-continued

NMR peak lists (4.7); 6.8829 (9.3); 6.8652 (8.9); 6.8447 (5.7); 6.8371 (5.6); 6.8159 (7.4); 6.8083 (7.3); 6.7875 (2.6); 6.7798 (2.8); 6.4426 (6.8); 6.4351 (6.5); 6.4128 (7.0); 6.4052 (6.5); 2.2576 (5.5); 2.2083 (3.9); 2.2045 (4.6); 2.1855 (15.2); 2.1784 (16.0); 2.1742 (8.6); 2.1602 (5.6); 2.1564 (4.4); 2.1050 (0.8); 2.0417 (0.7); 1.7545 (0.8); 1.7030 (5.1); 1.6992 (5.1); 1.6851 (9.6); 1.6811 (15.6); 1.6741 (15.9); 1.6548 (4.9); 1.6510 (4.6); 1.6020 (0.5); 0.0464 (0.6); 0.0356 (16.6); 0.0246 (0.6)

I.098: $^1$H-NMR(499.9 MHz, CDCl3):
δ = 8.9609 (5.7); 8.9561 (5.4); 8.3550 (4.0); 8.3514 (4.9); 8.3476 (3.5); 7.6954 (3.1); 7.6790 (4.3); 7.6193 (1.7); 7.6097 (1.9); 7.6036 (3.0); 7.5939 (3.0); 7.5874 (1.7); 7.5778 (1.6); 7.5322 (2.7); 7.5298 (2.8); 7.5219 (5.1); 7.5200 (5.3); 7.5179 (5.8); 7.5117 (2.8); 7.5093 (2.5); 7.4961 (1.7); 7.4938 (1.5); 7.4326 (2.9); 7.4286 (2.6); 7.4155 (3.0); 7.4115 (2.6); 7.2610 (13.9); 6.5531 (5.8); 6.5359 (5.5); 4.5879 (16.0); 1.5650 (2.3); 1.2550 (1.0); 0.0061 (0.9); −0.0002 (13.7); −0.0068 (0.5)

I.099: $^1$H-NMR(300.2 MHz, CDCl3):
δ = 9.0066 (1.4); 8.9998 (1.4); 8.4580 (1.5); 7.3911 (2.8); 7.3689 (2.0); 7.3633 (2.0); 7.3430 (1.2); 7.3404 (1.2); 7.3097 (0.5); 7.3058 (0.5); 7.2996 (0.4); 7.2841 (1.0); 7.2806 (0.9); 7.2582 (0.7); 7.2546 (0.6); 7.1970 (0.8); 7.1721 (1.1); 7.1470 (0.4); 6.7193 (1.2); 6.6931 (1.1); 2.6665 (6.0); 1.8586 (16.0)

I.100: $^1$H-NMR(300.2 MHz, CDCl3):
δ = 8.9960 (1.3); 8.9881 (1.3); 8.2728 (0.8); 8.2675 (1.0); 8.2607 (0.8); 7.7104 (0.8); 7.7049 (1.1); 7.6996 (0.8); 7.5204 (0.8); 7.5133 (0.8); 7.4877 (0.8); 7.4806 (0.8); 7.3848 (0.6); 7.3810 (0.6); 7.3597 (0.8); 7.3559 (1.0); 7.3465 (0.4); 7.3254 (0.9); 7.3205 (0.7); 7.2993 (1.4); 7.2945 (0.6); 7.2412 (0.6); 7.2376 (0.7); 7.2160 (0.8); 7.2125 (0.8); 7.1908 (0.3); 6.7996 (0.9); 6.7978 (0.8); 6.7730 (0.8); 2.0376 (1.9); 1.8492 (16.0); 0.0330 (0.6)

I.101: $^1$H-NMR(300.2 MHz, CDCl3):
δ = 8.9752 (0.7); 8.3229 (1.3); 7.5963 (0.8); 7.5683 (1.2); 7.4854 (0.7); 7.4632 (0.7); 7.4358 (0.4); 7.3521 (0.8); 7.3272 (1.1); 7.2997 (0.7); 7.2784 (0.9); 7.2750 (0.8); 7.2526 (0.6); 7.2490 (0.6); 7.1858 (0.7); 7.1622 (1.0); 7.1373 (0.4); 6.7071 (1.1); 6.6809 (1.0); 5.3131 (1.0); 2.5635 (4.0); 2.5564 (4.0); 1.8476 (16.0); 0.0227 (0.3)

I.102: $^1$H-NMR(300.2 MHz, CDCl3):
δ = 9.1239 (1.4); 9.1155 (1.4); 8.4175 (1.4); 8.4091 (1.4); 8.1898 (0.7); 8.1657 (0.8); 8.1287 (0.7); 8.1014 (0.8); 7.7440 (0.5); 7.7180 (0.8); 7.6921 (0.4); 7.3860 (0.6); 7.3824 (0.7); 7.3609 (0.8); 7.3573 (1.0); 7.3461 (0.4); 7.3415 (0.4); 7.3203 (0.8); 7.3157 (0.7); 7.2992 (1.3); 7.2945 (0.7); 7.2896 (0.5); 7.2369 (0.7); 7.2337 (0.7); 7.2117 (0.9); 7.2087 (0.8); 7.1866 (0.3); 6.8277 (0.9); 6.8011 (0.9); 5.3349 (0.7); 1.8604 (16.0); 0.0385 (0.8)

I.103: $^1$H-NMR(300.2 MHz, CDCl3):
δ = 9.1330 (1.5); 9.1247 (1.6); 8.4165 (1.5); 8.4083 (1.5); 8.2188 (0.8); 8.2145 (0.9); 8.1947 (0.9); 8.1905 (0.9); 8.1662 (0.8); 8.1623 (0.7); 8.1384 (0.9); 8.1346 (0.8); 7.7497 (0.8); 7.7251 (0.9); 7.7224 (0.9); 7.6979 (0.6); 7.3914 (0.6); 7.3879 (0.7); 7.3664 (0.9); 7.3629 (1.0); 7.3481 (0.4); 7.3434 (0.4); 7.3224 (0.9); 7.3177 (0.8); 7.2990 (0.8); 7.2965 (0.7); 7.2915 (0.5); 7.2433 (0.7); 7.2398 (0.7); 7.2180 (0.9); 7.2147 (0.9); 7.1928 (0.4); 6.8132 (1.0); 6.8116 (0.9); 6.7867 (0.9); 5.3253 (0.8); 1.8474 (16.0)

I.104: $^1$H-NMR(300.2 MHz, CDCl3):
δ = 9.0179 (1.4); 9.0102 (1.4); 8.3404 (1.0); 8.3351 (1.2); 8.3330 (1.2); 8.3280 (0.9); 7.6507 (0.3); 7.6208 (4.1); 7.6045 (1.2); 7.3695 (0.7); 7.3657 (0.8); 7.3445 (0.9); 7.3406 (1.0); 7.3241 (0.4); 7.3195 (0.4); 7.2986 (1.1); 7.2936 (0.8); 7.2722 (0.7); 7.2675 (0.6); 7.2107 (0.7); 7.2074 (0.7); 7.1855 (0.9); 7.1822 (0.9); 7.1603 (0.4); 7.1570 (0.3); 6.7633 (1.0); 6.7619 (1.0); 6.7368 (0.9); 1.8371 (16.0)

I.105: $^1$H-NMR(300.2 MHz, CDCl3):
δ = 8.9507 (1.0); 8.9432 (1.0); 8.2922 (1.1); 8.2844 (1.1); 7.9870 (0.5); 7.9615 (0.5); 7.9508 (0.5); 7.9253 (0.5); 7.6673 (0.6); 7.6396 (0.7); 7.6339 (0.7); 7.6062 (0.6); 7.3741 (0.6); 7.3704 (0.7); 7.3491 (0.8); 7.3453 (0.9); 7.3285 (0.4); 7.3238 (0.4); 7.3026 (0.9); 7.2991 (1.1); 7.2767 (0.6); 7.2719 (0.5); 7.2153 (0.6); 7.2118 (0.7); 7.1901 (0.9); 7.1867 (0.9); 7.1649 (0.3); 6.7308 (0.9); 6.7290 (0.9); 6.7042 (0.8); 5.3263 (0.4); 1.8551 (16.0)

I.106: $^1$H-NMR(300.2 MHz, CDCl3):
δ = 9.0026 (1.2); 8.9946 (1.2); 8.3516 (0.8); 8.3459 (1.0); 8.3387 (0.7); 7.7142 (0.5); 7.6872 (0.8); 7.6325 (0.4); 7.6165 (0.4); 7.6068 (0.6); 7.5906 (0.6); 7.5798 (0.4); 7.5635 (0.6); 7.5324 (0.5); 7.5276 (0.5); 7.5068 (0.4); 7.5019 (0.4); 7.4978 (0.6); 7.4933 (0.5); 7.4721 (0.3); 7.2993 (2.2); 7.1678 (1.1); 7.1664 (1.1); 7.1382 (0.6); 7.1361 (0.6); 7.1327 (0.5); 7.1111 (0.6); 7.1090 (0.6); 7.1055 (0.6); 6.7031 (1.2); 6.6761 (1.1); 2.4198 (5.7); 1.8394 (16.0); 1.6278 (0.4); 0.0372 (2.4)

I.107: $^1$H-NMR(300.2 MHz, CDCl3):
δ = 9.0166 (1.2); 9.0086 (1.2); 8.4080 (0.8); 8.4022 (1.0); 8.3951 (0.8); 7.7450 (0.5); 7.7183 (0.8); 7.6665 (0.4); 7.6505 (0.4); 7.6408 (0.6); 7.6246 (0.6); 7.6138 (0.4); 7.5975 (0.4); 7.5743 (0.5); 7.5694 (0.5); 7.5436 (0.4); 7.5400 (0.5); 7.5354 (0.5); 7.5142 (0.3); 7.3396 (0.7); 7.3218 (0.7); 7.3114 (0.8); 7.2993 (1.3); 7.2937 (0.8); 6.9136 (0.4); 6.9056 (0.4); 6.8847 (0.7); 6.8768 (0.7); 6.8560 (0.4); 6.8480 (0.4); 6.4629 (0.7); 6.4550 (0.7); 6.4331 (0.7); 6.4252 (0.7); 1.8593 (16.0); 0.0344 (1.3)

I.108: $^1$H-NMR(300.2 MHz, CDCl3):
δ = 9.0623 (3.2); 9.0544 (3.3); 8.4275 (2.1); 8.4216 (2.8); 8.4148 (2.0); 7.7289 (1.4); 7.7020 (2.4); 7.6436 (1.0); 7.6275 (1.0); 7.6178 (1.8); 7.6016 (1.7); 7.5908 (1.0); 7.5745 (1.0); 7.5497 (1.4); 7.5450 (1.4); 7.5241 (0.9); 7.5189 (1.0); 7.5153 (1.5); 7.5108 (1.4); 7.4895 (0.9); 7.4851 (0.8); 7.2992 (4.6); 7.0885 (1.4); 7.0851 (1.5); 7.0613 (1.6); 7.0580 (1.7); 6.7424 (3.0); 6.7410 (3.0); 6.7388 (3.0); 6.6500 (3.4); 6.6228 (3.0); 5.3351 (0.5); 2.3729 (16.0); 2.1813 (1.0); 2.1778 (1.2); 2.1593 (4.2); 2.1516 (4.3); 2.1339 (1.5); 2.1303 (1.2); 1.6949 (1.4); 1.6914 (1.4); 1.6737 (4.2); 1.6662 (4.4); 1.6473 (1.6); 1.6439 (1.5); 0.0371 (4.7)

I.109: $^1$H-NMR(300.2 MHz, CDCl3):
δ = 9.0653 (7.3); 9.0575 (7.5); 8.4397 (4.6); 8.4337 (6.2); 8.4269 (4.6); 7.7334 (3.1); 7.7065 (5.1); 7.6496 (2.2); 7.6336 (2.3); 7.6239 (4.0); 7.6076 (3.9); 7.5970 (2.4); 7.5806 (2.3); 7.5598 (3.3); 7.5550 (3.3); 7.5343 (2.0); 7.5291 (2.1); 7.5254 (3.4); 7.5208 (3.3); 7.4997 (1.9); 7.4952 (1.8); 7.2992 (14.8); 7.2828 (2.1); 7.2763 (2.1); 7.2593 (3.3); 7.2561 (3.0); 7.2528 (3.7); 7.2497 (2.7); 7.2330 (3.2); 7.2204 (1.9); 7.1624 (1.9); 7.1591 (1.9); 7.1371 (5.2); 7.1339 (5.3); 7.1107 (10.2); 7.1050 (6.7); 7.0862 (2.0); 7.0798 (1.2); 6.6950 (5.5); 6.6689 (5.2); 2.6494 (5.7); 2.6316 (6.0); 2.0436 (16.0); 1.9071 (6.0); 1.8894 (5.7); 1.7568 (1.3); 1.7382 (2.2); 1.7219 (2.3); 1.7061 (2.6); 1.6881 (1.7); 1.6266 (1.3); 1.4369 (1.2); 1.4167 (1.9); 1.4065 (2.1); 1.4002 (1.6); 1.3863 (2.8); 1.3695 (2.2); 1.3410 (1.1); 1.2930 (3.2); 1.2747 (2.4); 1.2631 (2.0); 1.2440 (1.5); 1.2172 (2.0); 1.1973 (2.2); 1.1845 (2.4); 1.1660 (1.9); 1.1485 (1.1); 0.0481 (0.6); 0.0373 (16.1); 0.0264 (0.5)

I.110: $^1$H-NMR(400.0 MHz, d$_6$-DMSO):
δ = 8.9047 (3.7); 8.8989 (3.7); 8.5870 (3.3); 7.9976 (1.5); 7.9837 (1.8); 7.9743 (1.6); 7.9636 (0.3); 7.7135 (3.2); 7.6998 (2.9); 7.6888 (1.8); 7.6816 (3.1); 7.6692 (0.3); 7.5169 (2.2); 7.4981 (2.5); 7.3848 (1.0); 7.3654 (2.3); 7.3464 (1.4); 7.2430 (1.6); 7.2243 (2.5); 7.2060 (1.1); 6.9130 (2.8); 6.8931 (2.6); 3.9033 (4.6); 3.3289 (93.7);

TABLE 12-continued

NMR peak lists 2.6712 (0.5); 2.5029 (94.6); 2.3296 (0.6); 2.2802 (0.4); 2.2622 (1.3); 2.2438 (2.1); 2.2260 (2.8); 2.2075 (2.4); 2.1890 (0.8); 2.1676 (0.7); 2.1490 (2.4); 2.1306 (2.9); 2.1127 (2.1); 2.0943 (1.4); 2.0766 (0.4); 1.0485 (7.6); 1.0301 (16.0); 1.0116 (7.1); −0.0002 (5.4)

I.111: $^1$H-NMR(300.2 MHz, CDCl3):
δ = 9.0018 (10.9); 8.9938 (11.1); 8.3781 (7.1); 8.3724 (9.2); 8.3654 (6.7); 7.7327 (4.6); 7.7060 (7.8); 7.6562 (3.4); 7.6402 (3.6); 7.6306 (6.0); 7.6144 (5.7); 7.6035 (3.4); 7.5873 (3.2); 7.5619 (4.9); 7.5571 (4.7); 7.5364 (3.0); 7.5312 (3.4); 7.5275 (5.0); 7.5229 (4.7); 7.5018 (3.0); 7.4973 (2.7); 7.3977 (5.3); 7.3942 (5.8); 7.3725 (7.1); 7.3689 (8.2); 7.3569 (3.2); 7.3523 (3.2); 7.3313 (7.7); 7.3266 (6.3); 7.3051 (6.6); 7.2992 (24.6); 7.2490 (5.9); 7.2453 (5.9); 7.2237 (7.8); 7.2201 (7.4); 7.1984 (2.9); 7.1948 (2.6); 6.7429 (7.6); 6.7407 (7.4); 6.7163 (7.1); 6.7144 (6.7); 5.3358 (6.4); 4.1502 (1.1); 4.1430 (1.2); 4.1304 (2.3); 4.1229 (2.4); 4.1086 (8.8); 4.0998 (14.0); 4.0904 (16.0); 4.0624 (8.6); 4.0549 (8.5); 4.0213 (2.4); 4.0135 (2.0); 2.5569 (5.4); 2.5505 (5.6); 2.5083 (9.5); 2.5018 (9.1); 2.4023 (5.1); 2.3824 (4.9); 2.3664 (5.0); 2.3521 (4.1); 2.3466 (5.3); 2.3330 (3.0); 2.3166 (3.1); 2.2968 (2.8); 1.6362 (1.4); 1.2919 (0.6); 0.0474 (0.9); 0.0366 (24.1); 0.0273 (0.6); 0.0257 (0.8)

I.112: $^1$H-NMR(300.2 MHz, CDCl3):
δ = 9.0209 (5.8); 9.0130 (6.0); 8.4092 (3.7); 8.4028 (4.9); 8.3964 (3.7); 7.7665 (3.2); 7.7627 (3.1); 7.7423 (4.0); 7.7364 (4.2); 7.7037 (4.2); 7.6479 (1.8); 7.6319 (1.9); 7.6222 (3.2); 7.6059 (3.1); 7.5953 (1.9); 7.5789 (1.8); 7.5557 (2.6); 7.5509 (2.7); 7.5301 (1.6); 7.5250 (1.7); 7.5213 (2.7); 7.5167 (2.7); 7.4955 (1.6); 7.4910 (1.5); 7.3378 (1.3); 7.3327 (1.6); 7.3123 (3.9); 7.3071 (4.0); 7.2996 (13.9); 7.2869 (3.4); 7.2812 (3.1); 7.2703 (3.1); 7.2656 (3.6); 7.2451 (4.0); 7.2412 (3.8); 7.2200 (1.5); 7.2160 (1.6); 6.9922 (3.7); 6.6886 (4.1); 6.6658 (3.3); 6.6632 (3.5); 5.3368 (3.3); 3.4850 (7.3); 3.4466 (2.8); 3.4378 (8.4); 2.6618 (8.4); 2.6146 (7.5); 2.0443 (1.4); 1.6348 (0.6); 1.2929 (0.3); 0.8720 (0.4); 0.8635 (0.3); 0.8524 (0.9); 0.8348 (2.0); 0.8231 (6.4); 0.8124 (16.0); 0.8041 (7.1); 0.7928 (2.4); 0.7754 (1.0); 0.7647 (0.4); 0.7559 (0.5); 0.0487 (0.5); 0.0379 (14.4); 0.0287 (0.4); 0.0271 (0.6)

I.113: $^1$H-NMR(300.2 MHz, CDCl3):
δ = 8.9923 (4.1); 8.9844 (4.2); 8.3828 (2.6); 8.3769 (3.4); 8.3701 (2.6); 7.7320 (1.7); 7.7066 (3.0); 7.6590 (1.3); 7.6430 (1.4); 7.6333 (2.3); 7.6171 (2.2); 7.6063 (1.3); 7.5902 (1.3); 7.5678 (2.0); 7.5629 (1.8); 7.5422 (1.1); 7.5334 (1.9); 7.5289 (1.8); 7.5077 (1.6); 7.5032 (1.1); 7.3671 (2.0); 7.3632 (2.3); 7.3430 (3.5); 7.3385 (4.4); 7.3176 (3.1); 7.3127 (2.5); 7.2994 (20.0); 7.2917 (2.6); 7.2868 (1.8); 7.2373 (2.2); 7.2337 (2.4); 7.2120 (2.8); 7.2087 (2.8); 7.1869 (1.0); 7.1834 (1.0); 6.6844 (2.8); 6.6825 (2.8); 6.6577 (2.8); 5.3376 (7.0); 4.9313 (15.6); 4.9251 (16.0); 4.7964 (0.9); 3.5550 (4.5); 3.5447 (1.7); 3.5159 (1.7); 3.5051 (5.3); 2.9970 (0.4); 2.9245 (0.4); 2.9018 (5.3); 2.8910 (1.8); 2.8622 (1.7); 2.8520 (4.5); 2.0453 (7.8); 1.2932 (0.6); 0.0485 (0.7); 0.0378 (21.3); 0.0269 (0.7)

I.114: $^1$H-NMR(300.2 MHz, CDCl3):
δ = 9.0122 (0.6); 9.0043 (0.6); 8.4066 (0.4); 8.4011 (0.5); 8.3940 (0.4); 7.7147 (0.5); 7.6401 (0.3); 7.2985 (4.8); 7.2839 (0.5); 7.2585 (0.5); 7.2502 (0.6); 7.2451 (0.7); 6.6531 (0.4); 6.6483 (0.4); 6.6278 (0.3); 4.6903 (2.1); 1.6132 (2.2); 0.3431 (0.6); 0.3314 (16.0); 0.3220 (0.4); 0.3194 (0.5); 0.0364 (5.7)

I.115: $^1$H-NMR(300.2 MHz, CDCl3):
δ = 9.0034 (2.0); 8.9954 (2.1); 8.3978 (1.4); 8.3923 (1.7); 8.3851 (1.3); 7.7434 (0.8); 7.7181 (1.4); 7.6742 (0.7); 7.6584 (0.7); 7.6486 (1.2); 7.6325 (1.1); 7.6216 (0.7); 7.6054 (0.6); 7.5849 (1.0); 7.5799 (1.0); 7.5594 (0.6); 7.5507 (1.0); 7.5460 (1.0); 7.5251 (0.6); 7.5204 (0.5); 7.4256 (1.5); 7.4221 (1.6); 7.4193 (1.6); 7.3365 (1.0); 7.3337 (0.8); 7.3292 (1.0); 7.3075 (1.4); 7.2995 (18.0); 6.6530 (2.1); 6.6243 (1.9); 5.3386 (5.0); 4.6247 (5.6); 4.1727 (0.4); 4.1488 (0.4); 3.9962 (0.3); 2.0840 (1.9); 1.5884 (16.0); 1.3220 (0.5); 1.2982 (1.0); 1.2744 (0.5); 0.0494 (0.6); 0.0462 (0.4); 0.0385 (17.5); 0.0295 (0.5); 0.0277 (0.6)

I.116: $^1$H-NMR(300.2 MHz, CDCl3):
δ = 8.9864 (1.1); 8.9784 (1.1); 8.3582 (0.7); 8.3525 (0.9); 8.3453 (0.7); 7.7299 (0.5); 7.7047 (0.8); 7.6550 (0.4); 7.6390 (0.4); 7.6293 (0.6); 7.6132 (0.6); 7.6023 (0.4); 7.5861 (0.3); 7.5573 (0.5); 7.5524 (0.5); 7.5317 (0.4); 7.5267 (0.4); 7.5228 (0.5); 7.5182 (0.5); 7.2994 (6.2); 7.1344 (0.6); 7.1256 (0.7); 7.1083 (0.6); 7.0994 (0.7); 7.0718 (0.4); 7.0628 (0.4); 7.0429 (0.9); 7.0339 (0.7); 7.0140 (0.5); 7.0050 (0.4); 6.7610 (0.7); 6.7467 (0.7); 6.7318 (0.6); 6.7175 (0.6); 1.8549 (16.0); 1.7264 (0.4); 1.5971 (5.6); 0.0381 (6.4)

I.117: $^1$H-NMR(300.2 MHz, CDCl3):
δ = 8.9821 (1.2); 8.9741 (1.2); 8.3726 (0.8); 8.3669 (1.0); 8.3598 (0.7); 7.7300 (0.5); 7.7048 (0.9); 7.7033 (0.9); 7.6556 (0.4); 7.6396 (0.4); 7.6300 (0.7); 7.6138 (0.6); 7.6029 (0.4); 7.5867 (0.3); 7.5611 (0.4); 7.5562 (0.5); 7.5356 (0.3); 7.5302 (0.4); 7.5267 (0.6); 7.5221 (0.5); 7.5010 (0.3); 7.3519 (1.3); 7.3447 (1.6); 7.3028 (1.2); 7.2993 (1.8); 7.2958 (0.8); 7.2747 (1.0); 7.2673 (0.8); 6.6993 (1.5); 6.6709 (1.3); 2.0799 (1.2); 1.8608 (16.0); 1.6548 (1.0); 1.2939 (0.6); 0.0350 (1.6)

I.118: $^1$H-NMR(300.2 MHz, CDCl3):
δ = 8.9904 (0.7); 8.9825 (0.7); 8.3933 (0.5); 8.3876 (0.6); 8.3805 (0.4); 7.7045 (0.5); 7.6239 (0.4); 7.6077 (0.4); 7.4481 (0.4); 7.4443 (0.4); 7.4224 (0.6); 7.4187 (0.5); 7.2996 (7.2); 7.2930 (0.7); 7.2665 (0.8); 7.2405 (0.4); 6.7607 (0.5); 6.7569 (0.5); 6.7342 (0.5); 6.7304 (0.5); 5.3389 (0.6); 1.9579 (10.0); 1.5854 (4.2); 0.5417 (0.7); 0.5312 (16.0); 0.5205 (0.6); 0.0391 (7.6)

I.119: $^1$H-NMR(300.2 MHz, CDCl3):
δ = 9.0115 (3.5); 9.0056 (3.4); 8.4112 (4.4); 7.7460 (2.0); 7.7193 (3.5); 7.6720 (1.3); 7.6562 (1.4); 7.6463 (2.4); 7.6302 (2.4); 7.6195 (1.4); 7.6033 (1.3); 7.5836 (2.0); 7.5795 (2.0); 7.5577 (1.4); 7.5498 (2.3); 7.5237 (1.2); 7.3121 (1.8); 7.2989 (6.4); 7.2852 (4.0); 7.2581 (2.6); 7.1727 (4.8); 7.1457 (3.1); 6.5821 (3.9); 6.5554 (3.6); 5.3349 (2.5); 4.6623 (16.0); 1.4677 (0.5); 1.2913 (0.6); 0.0359 (5.8)

I.120: $^1$H-NMR(300.2 MHz, CDCl3):
δ = 9.0242 (3.0); 9.0181 (3.1); 8.4219 (4.2); 7.7525 (1.8); 7.7257 (3.2); 7.6799 (1.3); 7.6641 (1.4); 7.6543 (2.4); 7.6382 (2.4); 7.6274 (1.4); 7.6112 (1.3); 7.5932 (2.0); 7.5884 (1.9); 7.5676 (1.2); 7.5592 (2.1); 7.5548 (2.0); 7.5333 (1.2); 7.5291 (1.1); 7.4088 (1.8); 7.3811 (3.8); 7.3533 (2.3); 7.2984 (10.0); 7.0781 (2.2); 7.0752 (2.2); 7.0498 (1.8); 7.0469 (1.8); 6.6219 (4.1); 6.5948 (3.8); 5.3353 (0.5); 4.6635 (16.0); 1.6921 (0.4); 1.2915 (0.6); 0.0467 (0.4); 0.0359 (9.4); 0.0249 (0.4)

I.121: $^1$H-NMR(300.2 MHz, CDCl3):
δ = 9.0099 (3.3); 8.4299 (6.8); 7.7586 (2.7); 7.7321 (4.7); 7.6871 (2.2); 7.6713 (2.4); 7.6614 (4.0); 7.6454 (4.0); 7.6346 (2.4); 7.6185 (2.2); 7.6009 (3.3); 7.5961 (3.2); 7.5754 (2.0); 7.5670 (3.6); 7.5624 (3.2); 7.5411 (1.9); 7.5368 (1.8); 7.4921 (1.2); 7.4651 (4.3); 7.4385 (12.7); 7.4185 (1.9); 7.4112 (0.8); 7.2985 (15.9); 6.8830 (0.4); 6.8602 (3.5); 6.8536 (4.4); 6.8308 (3.5); 4.7775 (16.0); 1.6817 (0.9); 1.2912 (0.8); 0.0465 (0.5); 0.0358 (13.8); 0.0249 (0.6)

TABLE 12-continued

NMR peak lists

I.122: $^1$H-NMR(300.2 MHz, CDCl3):
δ = 9.0192 (1.1); 9.0110 (1.1); 8.5437 (0.9); 8.5355 (1.0); 7.7092 (0.4); 7.6772 (0.4); 7.3807 (0.6); 7.3768 (0.6); 7.3556 (0.7); 7.3517 (0.9); 7.3434 (0.4); 7.3386 (0.4); 7.3175 (0.8); 7.3126 (0.7); 7.2987 (2.4); 7.2916 (0.7); 7.2866 (0.5); 7.2284 (0.6); 7.2246 (0.8); 7.2143 (0.4); 7.2032 (0.9); 7.1997 (0.9); 7.1916 (0.5); 7.1843 (0.5); 7.1782 (0.4); 7.1745 (0.3); 7.1608 (0.4); 7.1530 (0.3); 6.7325 (0.8); 6.7304 (0.8); 6.7056 (0.7); 2.0445 (1.2); 1.8687 (16.0); 1.6203 (0.5); 0.0375 (2.6)

I.123: $^1$H-NMR(300.2 MHz, CDCl3):
δ = 9.0062 (2.6); 8.9984 (2.6); 8.3763 (1.8); 8.3703 (2.3); 8.3637 (1.7); 7.7287 (1.2); 7.7017 (2.0); 7.6454 (0.8); 7.6294 (0.9); 7.6197 (1.4); 7.6034 (1.4); 7.5927 (0.8); 7.5764 (0.8); 7.5480 (1.2); 7.5434 (1.1); 7.5224 (0.8); 7.5172 (0.9); 7.5136 (1.2); 7.5092 (1.2); 7.4878 (0.7); 7.4835 (0.7); 7.3468 (0.8); 7.3422 (1.0); 7.3294 (1.5); 7.3234 (2.1); 7.3177 (2.1); 7.3042 (2.7); 7.2987 (6.8); 7.2166 (1.4); 7.2133 (1.5); 7.1910 (1.8); 7.1662 (0.7); 7.1630 (0.6); 6.7713 (2.1); 6.7596 (0.4); 6.7460 (1.6); 6.7420 (1.5); 5.9367 (0.6); 5.9274 (0.4); 5.9122 (0.4); 5.9033 (0.9); 5.8801 (1.0); 5.8711 (0.5); 5.8560 (0.4); 5.8466 (0.8); 5.8221 (0.4); 5.3068 (1.5); 5.2729 (1.4); 5.2597 (1.6); 5.2551 (1.4); 5.2032 (1.3); 5.1986 (1.2); 2.9344 (0.3); 2.9116 (1.5); 2.8886 (2.6); 2.8652 (1.5); 2.8431 (0.4); 1.8449 (16.0); 0.0366 (5.1)

I.124: $^1$H-NMR(300.2 MHz, CDCl3):
δ = 8.9905 (8.1); 8.9826 (8.2); 8.3577 (5.2); 8.3519 (6.7); 8.3449 (5.0); 7.7193 (3.4); 7.6924 (5.8); 7.6399 (2.4); 7.6239 (2.6); 7.6142 (4.3); 7.5980 (4.1); 7.5872 (2.5); 7.5709 (2.4); 7.5420 (3.5); 7.5373 (3.5); 7.5165 (2.2); 7.5114 (2.4); 7.5075 (3.6); 7.5030 (3.4); 7.4818 (2.2); 7.4774 (2.0); 7.3519 (2.2); 7.3470 (2.5); 7.3266 (4.2); 7.3220 (5.1); 7.2985 (15.4); 7.2724 (6.7); 7.2690 (5.1); 7.2091 (4.5); 7.2057 (4.5); 7.1840 (5.4); 7.1808 (5.0); 7.1587 (2.0); 7.1553 (1.9); 6.7804 (5.7); 6.7787 (5.5); 6.7537 (5.4); 5.9799 (1.7); 5.9555 (3.5); 5.9459 (2.1); 5.9312 (2.0); 5.9221 (5.1); 5.8988 (5.4); 5.8897 (2.5); 5.8751 (2.3); 5.8653 (4.6); 5.8411 (2.3); 5.3414 (7.3); 5.3364 (9.1); 5.3073 (16.0); 5.3024 (15.1); 5.2509 (7.3); 5.2459 (6.7); 3.0362 (2.3); 3.0127 (2.4); 2.9885 (7.4); 2.9650 (7.3); 2.9476 (7.6); 2.9226 (7.4); 2.8999 (2.6); 2.8749 (2.4); 2.0402 (1.3); 1.6737 (0.6); 0.0357 (10.4); 0.0248 (0.4)

I.125: $^1$H-NMR(300.2 MHz, CDCl3):
δ = 9.0068 (1.2); 8.9989 (1.2); 8.4046 (0.8); 8.3990 (1.0); 8.3920 (0.8); 7.7532 (0.5); 7.7264 (0.9); 7.6709 (0.4); 7.6549 (0.4); 7.6451 (0.7); 7.6290 (0.6); 7.6182 (0.4); 7.6019 (0.4); 7.5790 (0.5); 7.5741 (0.5); 7.5534 (0.3); 7.5480 (0.4); 7.5447 (0.6); 7.5401 (0.5); 7.5189 (0.3); 7.2983 (3.1); 7.2710 (1.7); 7.1796 (1.0); 7.1733 (1.0); 7.1524 (0.7); 7.1461 (0.7); 6.7016 (1.4); 6.6954 (1.4); 2.0421 (1.7); 1.8593 (16.0); 1.6279 (0.5); 0.0352 (2.1)

I.126: $^1$H-NMR(300.2 MHz, CDCl3):
δ = 8.9865 (1.2); 8.9787 (1.2); 8.4100 (0.8); 8.4043 (1.1); 8.3976 (0.8); 7.7360 (0.6); 7.7093 (0.9); 7.6560 (0.4); 7.6400 (0.4); 7.6303 (0.7); 7.6141 (0.6); 7.6033 (0.4); 7.5870 (0.4); 7.5650 (0.6); 7.5603 (0.5); 7.5394 (0.4); 7.5307 (0.6); 7.5262 (0.5); 7.5049 (0.3); 7.3094 (0.5); 7.3052 (0.6); 7.2984 (1.7); 7.2834 (1.2); 7.2792 (1.1); 7.2550 (1.1); 7.2289 (1.4); 7.2027 (0.6); 6.6800 (0.9); 6.6759 (0.8); 6.6539 (0.8); 6.6499 (0.8); 3.5164 (2.7); 2.0655 (16.0); 2.0412 (0.7); 0.0346 (1.2)

I.127: $^1$H-NMR(300.2 MHz, CDCl3):
δ = 8.9794 (0.8); 8.9715 (0.8); 8.4023 (0.5); 8.3962 (0.7); 8.3900 (0.5); 7.7341 (0.3); 7.7075 (0.6); 7.6283 (0.4); 7.6121 (0.4); 7.5626 (0.3); 7.5585 (0.3); 7.5286 (0.4); 7.5244 (0.3); 7.2992 (2.0); 7.2405 (0.8); 7.2356 (0.8); 7.2269 (0.8); 7.2013 (0.8); 6.6408 (0.5); 6.6359 (0.5); 6.6155 (0.5); 6.6107 (0.5); 2.0575 (9.4); 1.6148 (1.9); 0.3540 (0.6); 0.3432 (16.0); 0.3315 (0.7); 0.2777 (0.4); 0.0370 (1.4)

I.128: $^1$H-NMR(300.2 MHz, CDCl3):
δ = 9.0166 (4.3); 9.0087 (4.4); 8.4114 (2.9); 8.4055 (3.8); 8.3988 (2.9); 7.7416 (1.9); 7.7152 (3.3); 7.6667 (1.3); 7.6507 (1.5); 7.6410 (2.4); 7.6249 (2.4); 7.6141 (1.4); 7.5978 (1.4); 7.5775 (2.0); 7.5727 (2.0); 7.5520 (1.2); 7.5433 (2.1); 7.5388 (2.0); 7.5176 (1.2); 7.5131 (1.1); 7.3343 (0.8); 7.3079 (3.4); 7.2986 (10.2); 7.2903 (5.3); 7.2834 (8.1); 7.2643 (1.2); 7.2568 (0.4); 6.6852 (2.4); 6.6777 (2.5); 6.6623 (1.8); 6.6551 (2.2); 4.7114 (16.0); 3.4542 (9.1); 3.1511 (0.8); 1.6270 (1.1); 0.0360 (5.0)

I.129: $^1$H-NMR(300.2 MHz, CDCl3):
δ = 9.0133 (1.3); 9.0055 (1.3); 8.4060 (0.8); 8.3999 (1.1); 8.3935 (0.8); 7.7334 (0.6); 7.7065 (1.0); 7.6489 (0.4); 7.6328 (0.4); 7.6230 (0.7); 7.6068 (0.7); 7.5961 (0.4); 7.5798 (0.4); 7.5544 (0.6); 7.5497 (0.6); 7.5288 (0.4); 7.5236 (0.4); 7.5199 (0.6); 7.5155 (0.6); 7.4941 (0.3); 7.2988 (3.3); 7.2574 (0.7); 7.2310 (1.6); 7.2047 (0.9); 6.9051 (1.0); 6.9018 (1.1); 6.8791 (0.9); 6.8758 (0.9); 6.6293 (1.0); 6.6260 (1.0); 6.6026 (0.9); 6.5993 (0.9); 5.3764 (0.8); 5.3712 (1.2); 5.3660 (0.9); 5.0394 (1.2); 5.0372 (1.2); 2.1974 (4.6); 1.9285 (16.0); 1.6209 (1.5); 0.0366 (2.1)

I.130: $^1$H-NMR(499.9 MHz, CDCl3):
δ = 9.1652 (3.2); 9.1605 (3.1); 8.9793 (10.7); 8.9745 (10.4); 8.9634 (7.3); 8.9587 (6.8); 8.3504 (12.7); 8.3468 (12.6); 8.3430 (8.3); 8.3355 (1.9); 7.7181 (2.0); 7.7000 (4.0); 7.6985 (3.9); 7.6904 (8.1); 7.6822 (3.7); 7.6740 (10.8); 7.6504 (0.4); 7.6471 (0.4); 7.6439 (0.3); 7.6403 (0.3); 7.6184 (1.6); 7.6138 (2.7); 7.6083 (4.6); 7.6037 (3.9); 7.5984 (6.9); 7.5926 (7.5); 7.5884 (4.8); 7.5826 (6.8); 7.5764 (4.3); 7.5724 (2.5); 7.5667 (3.0); 7.5581 (0.6); 7.5532 (0.4); 7.5430 (0.6); 7.5244 (3.7); 7.5219 (3.8); 7.5194 (3.1); 7.5165 (5.6); 7.5139 (4.7); 7.5089 (3.3); 7.5037 (5.2); 7.5011 (7.0); 7.4985 (5.3); 7.4958 (5.7); 7.4933 (4.5); 7.4882 (2.7); 7.4858 (2.6); 7.4803 (3.8); 7.4778 (2.9); 7.4673 (0.6); 7.4425 (0.4); 7.4249 (0.4); 7.4068 (0.4); 7.3687 (6.4); 7.3534 (7.3); 7.3469 (3.8); 7.3314 (7.5); 7.3166 (6.3); 7.3132 (4.8); 7.3085 (5.4); 7.3062 (6.3); 7.3022 (6.6); 7.2967 (3.4); 7.2943 (2.9); 7.2858 (5.1); 7.2801 (1.5); 7.2776 (1.3); 7.2607 (49.3); 7.2527 (1.8); 7.2487 (1.4); 7.2404 (1.2); 7.2367 (2.2); 7.2330 (1.4); 7.2245 (1.1); 7.2207 (1.2); 7.2055 (0.5); 7.2020 (0.6); 7.1971 (0.5); 7.1861 (0.6); 7.1823 (0.6); 7.1596 (7.6); 7.1443 (12.0); 7.1290 (5.3); 7.1007 (5.4); 7.0489 (0.4); 6.7307 (7.5); 6.7147 (7.1); 6.6974 (5.1); 6.6814 (4.8); 6.4460 (16.0); 6.3612 (10.2); 6.1765 (0.4); 4.8349 (1.0); 4.8304 (0.6); 4.8189 (2.6); 4.8066 (6.2); 4.7915 (7.0); 4.7770 (3.6); 4.7658 (1.0); 4.7435 (0.3); 3.4170 (2.4); 3.4149 (2.3); 3.4039 (2.4); 3.4018 (2.2); 3.3873 (2.8); 3.3852 (2.7); 3.3742 (2.7); 3.3721 (2.5); 3.3571 (2.5); 3.3395 (0.7); 3.3277 (9.7); 3.3237 (8.5); 3.3224 (7.9); 3.3140 (10.0); 3.3101 (14.9); 3.2943 (0.7); 3.2927 (0.6); 3.0089 (3.2); 2.9929 (3.2); 2.9792 (2.8); 2.9632 (2.7); 2.0042 (9.5); 1.6237 (2.0); 1.2846 (0.3); 1.2556 (1.4); 0.0062 (2.6); −0.0002 (48.4); −0.0068 (1.7)

I.131: $^1$H-NMR(300.2 MHz, CDCl3):
δ = 8.9823 (1.2); 8.9744 (1.2); 8.3764 (0.8); 8.3709 (1.0); 8.3638 (0.7); 7.7354 (0.5); 7.7088 (0.9); 7.6619 (0.4); 7.6459 (0.4); 7.6362 (0.7); 7.6201 (0.7); 7.6091 (0.4); 7.5930 (0.4); 7.5677 (0.6); 7.5628 (0.6); 7.5422 (0.4); 7.5368 (0.4); 7.5333 (0.6); 7.5288 (0.5); 7.5077 (0.4); 7.5031 (0.3); 7.4881 (1.2); 7.4815 (1.6); 7.4523 (1.0); 7.4454 (0.7); 7.4240 (1.0); 7.4171 (0.9); 7.2982 (8.3); 6.6444 (1.4); 6.6161 (1.3); 2.0446 (1.7); 1.8639 (16.0); 1.6171 (0.4); 0.0370 (8.8)

TABLE 12-continued

NMR peak lists

I.132: ¹H-NMR(499.9 MHz, CDCl3):
δ = 8.9451 (3.2); 8.9404 (3.2); 8.3316 (2.1); 8.3282 (2.7); 8.3251 (2.1); 8.2793 (0.7); 8.2742 (4.9); 8.2706 (1.8); 8.2602 (1.8); 8.2563 (5.3); 8.2514 (0.7); 7.6704 (1.8); 7.6533 (3.1); 7.6476 (5.5); 7.6439 (2.0); 7.6336 (1.8); 7.6297 (5.1); 7.6247 (0.7); 7.5949 (0.9); 7.5852 (0.9); 7.5791 (1.5); 7.5695 (1.5); 7.5629 (0.9); 7.5533 (0.8); 7.5048 (1.2); 7.5028 (1.2); 7.4893 (1.0); 7.4869 (1.1); 7.4843 (1.4); 7.4822 (1.3); 7.4686 (0.9); 7.4667 (0.9); 7.4253 (0.9); 7.4214 (0.9); 7.4113 (1.3); 7.4078 (1.7); 7.4055 (1.3); 7.3955 (1.1); 7.3913 (1.2); 7.2683 (1.5); 7.2569 (0.7); 7.2416 (2.2); 7.2281 (4.8); 7.2248 (3.2); 7.2129 (0.8); 7.2094 (0.5); 6.8239 (2.5); 6.8078 (2.4); 2.2980 (16.0); 2.0026 (10.8); −0.0002 (1.0)

I.133: ¹H-NMR(499.9 MHz, CDCl3):
δ = 8.9501 (3.1); 8.9453 (3.0); 8.4764 (2.7); 8.4657 (2.7); 8.3317 (2.0); 8.3283 (2.3); 8.3244 (1.8); 7.6866 (1.6); 7.6702 (2.2); 7.6125 (0.9); 7.6029 (1.0); 7.5967 (1.5); 7.5871 (1.5); 7.5806 (0.9); 7.5709 (0.8); 7.5248 (1.2); 7.5224 (1.3); 7.5093 (1.0); 7.5068 (1.1); 7.5042 (1.3); 7.5018 (1.3); 7.4887 (0.9); 7.4863 (0.9); 7.4322 (1.1); 7.4292 (1.1); 7.4162 (1.7); 7.4144 (1.8); 7.4013 (1.4); 7.3982 (1.3); 7.3575 (3.3); 7.3551 (3.4); 7.3086 (0.3); 7.2940 (2.5); 7.2905 (2.3); 7.2833 (2.5); 7.2799 (2.3); 7.2665 (1.6); 7.2612 (14.3); 7.2513 (2.2); 7.2496 (2.3); 7.2365 (1.7); 7.2346 (1.6); 7.2192 (2.4); 7.2166 (2.4); 7.2038 (1.7); 7.2013 (1.0); 6.8075 (2.2); 6.7914 (2.0); 2.2353 (16.0); 2.0054 (7.4); 1.5862 (0.8); 1.2551 (0.5); 0.0063 (0.7); −0.0002 (12.8); −0.0068 (0.5)

I.134: ¹H-NMR(300.2 MHz, CDCl3):
δ = 8.9946 (1.1); 8.9867 (1.1); 8.3983 (0.7); 8.3925 (1.0); 8.3857 (0.7); 7.7262 (0.5); 7.6992 (0.8); 7.6418 (0.3); 7.6257 (0.4); 7.6160 (0.6); 7.5998 (0.6); 7.5891 (0.4); 7.5728 (0.4); 7.5475 (0.5); 7.5428 (0.5); 7.5168 (0.4); 7.5131 (0.5); 7.5086 (0.5); 7.4489 (0.4); 7.2986 (2.4); 7.2035 (0.5); 7.1769 (1.2); 7.1502 (0.7); 6.8281 (0.8); 6.8017 (0.7); 6.5548 (0.8); 6.5529 (0.8); 6.5283 (0.8); 2.1130 (0.5); 2.0442 (16.0); 1.6359 (0.5); 1.2918 (1.3); I.1386 (0.3); 1.1236 (0.8); 1.1169 (0.9); 1.1024 (0.5); 1.0952 (0.9); 1.0889 (0.8); 1.0746 (0.4); 0.9426 (0.4); 0.9280 (1.0); 0.9238 (1.1); 0.9101 (0.9); 0.9057 (1.0); 0.8886 (0.4); 0.0362 (2.1)

I.135: ¹H-NMR(300.2 MHz, CDCl3):
δ = 9.0785 (4.8); 9.0706 (4.9); 8.4447 (3.2); 8.4388 (4.2); 8.4321 (3.1); 7.7451 (2.2); 7.7184 (3.6); 7.6621 (1.4); 7.6460 (1.6); 7.6363 (2.7); 7.6200 (2.6); 7.6094 (1.6); 7.5930 (1.5); 7.5722 (2.9); 7.5676 (2.9); 7.5591 (1.1); 7.5421 (6.7); 7.5377 (5.1); 7.5181 (6.5); 7.5076 (2.6); 7.5002 (3.4); 7.4948 (2.5); 7.4862 (1.0); 7.4774 (3.2); 7.4647 (0.7); 7.4572 (0.9); 7.4470 (6.5); 7.4412 (6.8); 7.4338 (1.8); 7.4250 (4.2); 7.4200 (5.1); 7.4153 (3.4); 7.3984 (4.2); 7.3719 (2.5); 7.2986 (4.4); 7.1889 (4.0); 7.1864 (4.0); 7.1628 (3.3); 7.1603 (3.1); 6.6962 (3.6); 6.6699 (3.4); 4.6199 (16.0); 2.0387 (2.0); 1.6820 (0.7); 0.0379 (3.1)

I.136: ¹H-NMR(300.2 MHz, CDCl3):
δ = 9.0562 (2.4); 9.0483 (2.4); 8.5124 (2.1); 8.5041 (2.2); 8.4445 (1.5); 8.4388 (2.0); 8.4318 (1.5); 7.7685 (1.8); 7.7603 (2.2); 7.7410 (2.4); 7.7329 (3.2); 7.6855 (0.7); 7.6696 (0.7); 7.6599 (1.3); 7.6438 (1.3); 7.6329 (0.8); 7.6166 (0.7); 7.5967 (1.0); 7.5918 (1.0); 7.5711 (0.7); 7.5624 (1.1); 7.5579 (1.1); 7.5505 (2.6); 7.5367 (0.7); 7.5323 (0.6); 7.5231 (2.0); 7.4764 (0.9); 7.4499 (1.9); 7.4232 (1.1); 7.2984 (21.6); 7.1568 (1.9); 7.1309 (1.7); 6.7584 (1.8); 6.7318 (1.6); 5.3373 (0.9); 4.5825 (7.4); 1.5944 (16.0); 1.2919 (0.8); 0.0477 (0.8); 0.0369 (20.2); 0.0260 (0.7)

I.137: ¹H-NMR(300.2 MHz, CDCl3):
δ = 9.0305 (3.8); 9.0226 (3.9); 8.4097 (2.6); 8.4040 (3.4); 8.3971 (2.5); 7.7451 (1.7); 7.7181 (2.9); 7.6602 (1.2); 7.6441 (1.4); 7.6344 (2.2); 7.6182 (2.1); 7.6075 (1.3); 7.5911 (1.2); 7.5685 (1.8); 7.5637 (1.8); 7.5429 (1.1); 7.5342 (1.9); 7.5296 (1.8); 7.5084 (1.0); 7.5039 (1.0); 7.2984 (19.3); 7.2670 (2.8); 6.9799 (2.2); 6.9556 (1.9); 6.5101 (4.0); 5.3370 (7.6); 4.5940 (9.4); 2.3178 (16.0); 2.1392 (0.5); 1.6022 (9.7); 1.2918 (0.7); 0.0477 (0.8); 0.0370 (17.2); 0.0261 (0.6)

I.138: ¹H-NMR(300.2 MHz, CDCl3):
δ = 9.0163 (1.2); 9.0084 (1.2); 8.3918 (0.7); 8.3861 (1.0); 8.3790 (0.7); 7.7410 (0.5); 7.7138 (0.8); 7.6499 (0.4); 7.6337 (0.4); 7.6240 (0.6); 7.6077 (0.6); 7.5970 (0.4); 7.5806 (0.4); 7.5520 (0.6); 7.5474 (0.6); 7.5265 (0.3); 7.5214 (0.4); 7.5175 (0.5); 7.5130 (0.6); 7.4918 (0.3); 7.4874 (0.3); 7.2985 (10.0); 7.2511 (1.0); 7.2252 (1.3); 7.0218 (0.7); 7.0196 (0.7); 6.9959 (0.5); 6.9936 (0.5); 6.5632 (1.2); 5.3376 (1.0); 2.6991 (0.6); 2.3441 (0.4); 2.3170 (5.8); 1.8427 (16.0); 1.5916 (9.0); 0.0484 (0.4); 0.0376 (10.3); 0.0267 (0.4)

I.139: ¹H-NMR(499.9 MHz, CDCl3):
δ = 8.9666 (0.4); 8.9602 (0.9); 8.9556 (0.8); 8.3222 (0.8); 7.6735 (0.7); 7.6569 (0.7); 7.5899 (0.3); 7.5802 (0.4); 7.5741 (0.5); 7.5644 (0.5); 7.4949 (0.4); 7.4928 (0.4); 7.4792 (0.4); 7.4767 (0.5); 7.4742 (0.5); 7.4586 (0.4); 7.2967 (0.3); 7.2852 (1.1); 7.2813 (1.4); 7.2656 (1.1); 7.2631 (1.3); 7.2508 (0.4); 6.7209 (0.5); 6.7178 (0.5); 6.7064 (0.5); 6.7032 (0.5); 4.6523 (0.6); 4.5037 (0.6); 4.4893 (0.6); 1.7442 (2.6); 1.7298 (2.6); 0.4197 (16.0); 0.2947 (3.4); −0.0002 (0.8)

I.140: ¹H-NMR(300.2 MHz, CDCl3):
δ = 9.0285 (3.2); 9.0206 (3.2); 8.4605 (2.9); 8.4525 (3.0); 8.4321 (2.2); 8.4265 (2.8); 8.4199 (2.1); 7.7504 (1.5); 7.7234 (2.5); 7.7138 (2.1); 7.7055 (1.8); 7.6866 (2.4); 7.6784 (2.4); 7.6671 (1.0); 7.6510 (1.0); 7.6413 (1.6); 7.6251 (1.6); 7.6144 (1.0); 7.5981 (0.9); 7.5729 (1.4); 7.5683 (1.3); 7.5473 (0.9); 7.5386 (1.5); 7.5343 (1.4); 7.5207 (3.5); 7.5133 (1.2); 7.5087 (1.0); 7.4937 (2.6); 7.3625 (1.7); 7.3362 (3.5); 7.3096 (2.2); 7.2982 (3.0); 6.9431 (2.5); 6.9400 (2.5); 6.9173 (2.3); 6.9142 (2.1); 6.7957 (2.5); 6.7927 (2.4); 6.7688 (2.4); 6.7658 (2.1); 2.0374 (0.7); 1.6078 (16.0); 0.0294 (1.6)

I.141: ¹H-NMR(300.2 MHz, CDCl3):
δ = 8.9845 (1.2); 8.9764 (1.2); 8.3050 (0.8); 8.2992 (1.0); 8.2922 (0.8); 7.7053 (0.5); 7.6785 (0.9); 7.6274 (0.4); 7.6114 (0.4); 7.6017 (0.6); 7.5854 (0.6); 7.5746 (0.4); 7.5584 (0.4); 7.5220 (0.5); 7.5174 (0.5); 7.4966 (0.4); 7.4916 (0.4); 7.4875 (0.6); 7.4830 (0.6); 7.4618 (0.4); 7.4574 (0.3); 7.2986 (6.7); 6.9350 (1.2); 6.9266 (1.5); 6.8857 (0.6); 6.8771 (0.4); 6.8567 (1.1); 6.8480 (0.9); 6.7959 (1.7); 6.7669 (0.9); 4.1707 (0.5); 4.1468 (0.5); 3.8936 (0.4); 3.8743 (9.6); 2.0821 (2.4); 1.8241 (16.0); 1.6106 (5.1); 1.3199 (0.6); 1.2961 (1.3); 1.2723 (0.6); 0.0366 (6.2)

I.142: ¹H-NMR(300.2 MHz, CDCl3):
δ = 8.9999 (1.9); 8.9919 (1.9); 8.3362 (1.2); 8.3304 (1.6); 8.3233 (1.2); 7.7099 (0.8); 7.6833 (1.4); 7.6375 (0.6); 7.6216 (0.6); 7.6119 (1.1); 7.5957 (1.0); 7.5849 (0.6); 7.5686 (0.6); 7.5403 (0.9); 7.5354 (0.8); 7.5149 (0.5); 7.5098 (0.6); 7.5059 (0.9); 7.5013 (0.8); 7.4802 (0.5); 7.4756 (0.5); 7.2984 (4.0); 6.9953 (1.3); 6.9907 (1.2); 6.9869 (1.5); 6.9057 (0.8); 6.8967 (0.7); 6.8763 (1.0); 6.8674 (0.9); 6.7202 (2.2); 6.6909 (1.6); 4.5909 (5.3); 4.1923 (0.3); 4.1684 (1.0); 4.1446 (1.0); 4.1209 (0.4); 3.8519 (16.0); 2.0800 (5.1); 1.6405 (1.4); 1.3177 (1.4); 1.2939 (3.3); 1.2701 (1.4); 0.1073 (4.1); 0.0348 (2.8)

TABLE 12-continued

NMR peak lists

I.143: ¹H-NMR(300.2 MHz, CDCl3):
δ = 8.9846 (1.1); 8.9767 (1.1); 8.4183 (0.7); 8.4125 (1.0); 8.4056 (0.7); 7.7430 (0.5); 7.7164 (0.8); 7.6652 (0.3); 7.6492 (0.4); 7.6395 (0.6); 7.6233 (0.6); 7.6126 (0.4); 7.5963 (0.4); 7.5759 (0.5); 7.5710 (0.5); 7.5450 (0.4); 7.5417 (0.5); 7.5371 (0.5); 7.2983 (2.3); 7.2317 (0.5); 7.2048 (1.3); 7.1782 (1.1); 7.1402 (1.1); 7.1364 (1.2); 7.1129 (0.6); 7.1091 (0.5); 6.5796 (0.9); 6.5758 (0.8); 6.5534 (0.8); 6.5496 (0.8); 2.0359 (16.0); 1.6175 (0.5); 0.0362 (2.5)

I.144: ¹H-NMR(300.2 MHz, CDCl3):
δ = 8.9985 (1.2); 8.9906 (1.2); 8.4231 (0.8); 8.4174 (1.0); 8.4104 (0.8); 7.7479 (0.5); 7.7226 (0.9); 7.6713 (0.4); 7.6553 (0.4); 7.6455 (0.7); 7.6294 (0.6); 7.6186 (0.4); 7.6023 (0.4); 7.5821 (0.6); 7.5772 (0.5); 7.5565 (0.3); 7.5512 (0.4); 7.5478 (0.6); 7.5432 (0.5); 7.5221 (0.3); 7.3410 (0.7); 7.3134 (1.3); 7.2983 (3.0); 7.2854 (0.9); 7.0696 (0.5); 7.0672 (0.5); 7.0632 (0.5); 7.0411 (0.4); 7.0387 (0.4); 7.0346 (0.4); 6.5982 (1.1); 6.5712 (1.0); 1.9678 (16.0); 1.6120 (0.7); 0.0363 (3.2)

I.145: ¹H-NMR(300.2 MHz, CDCl3):
δ = 8.9827 (2.2); 8.9748 (2.3); 8.4270 (1.5); 8.4205 (2.0); 8.4144 (1.5); 7.7552 (1.0); 7.7287 (1.7); 7.6805 (0.7); 7.6645 (0.8); 7.6547 (1.2); 7.6386 (1.2); 7.6278 (0.7); 7.5908 (1.0); 7.5859 (1.0); 7.5652 (0.6); 7.5566 (1.1); 7.5520 (1.1); 7.5309 (1.7); 7.5058 (1.9); 7.4446 (1.0); 7.4178 (1.5); 7.3910 (0.6); 7.2987 (4.2); 6.9161 (1.5); 6.8900 (1.4); 1.9631 (16.0); 1.6163 (1.3); 1.2923 (0.5); 0.0365 (4.6)

I.146: ¹H-NMR(300.2 MHz, CDCl3):
δ = 8.9986 (1.5); 8.9911 (1.6); 8.9845 (0.6); 8.3793 (1.3); 8.3736 (1.5); 8.3671 (1.2); 7.7142 (0.7); 7.6884 (1.2); 7.6296 (0.4); 7.6133 (0.5); 7.6040 (0.8); 7.5876 (0.8); 7.5802 (0.5); 7.5771 (0.5); 7.5606 (0.4); 7.5343 (0.7); 7.5295 (0.7); 7.5085 (0.6); 7.5035 (0.7); 7.4998 (0.8); 7.4954 (0.7); 7.4741 (0.4); 7.4696 (0.4); 7.2980 (0.5); 7.2743 (0.6); 7.2482 (1.5); 7.2414 (0.6); 7.2218 (1.1); 7.2151 (0.4); 7.1433 (1.4); 7.1392 (1.2); 7.1327 (0.5); 7.1174 (1.0); 7.1134 (0.8); 7.1069 (0.3); 6.7323 (1.2); 6.7283 (1.0); 6.7217 (0.5); 6.7056 (1.1); 6.7016 (0.9); 6.6953 (0.4); 5.3226 (0.4); 4.4158 (1.4); 4.4081 (1.8); 4.3715 (1.9); 4.3636 (1.7); 4.0138 (0.6); 4.0067 (0.4); 3.9904 (1.8); 3.9839 (0.9); 3.9670 (1.9); 3.9608 (0.8); 3.9437 (0.6); 1.9285 (0.8); 1.9085 (16.0); 1.9018 (6.3); 1.5021 (2.0); 1.4952 (1.0); 1.4787 (4.1); 1.4720 (1.7); 1.4554 (2.0); 1.4489 (0.8)

I.147: ¹H-NMR(300.2 MHz, CDCl3):
δ = 9.0229 (3.6); 9.0172 (3.6); 8.4406 (3.8); 8.4349 (5.1); 8.4293 (3.7); 7.7613 (2.3); 7.7354 (4.1); 7.6920 (6.7); 7.6766 (2.2); 7.6666 (3.2); 7.6505 (3.0); 7.6397 (1.9); 7.6231 (4.0); 7.6073 (3.0); 7.6022 (3.0); 7.5921 (3.1); 7.5825 (2.4); 7.5733 (2.9); 7.5688 (2.6); 7.5474 (1.5); 7.5431 (1.4); 7.2989 (9.7); 6.7598 (4.4); 6.7317 (4.1); 5.3358 (0.5); 4.7012 (16.0); 1.2908 (0.3); 0.0465 (0.4); 0.0358 (10.3); 0.0250 (0.4)

I.148: ¹H-NMR(300.2 MHz, CDCl3):
δ = 8.9760 (1.5); 8.9685 (1.4); 8.3815 (1.4); 7.7173 (0.7); 7.6902 (1.2); 7.6379 (0.3); 7.6215 (0.4); 7.6123 (0.6); 7.5960 (0.6); 7.5853 (0.4); 7.5690 (0.3); 7.5444 (0.6); 7.5107 (0.7); 7.4845 (0.4); 7.3695 (3.3); 7.3588 (1.7); 7.3497 (1.6); 7.2981 (0.6); 6.8387 (0.9); 6.8279 (0.9); 6.8189 (0.7); 6.8082 (0.8); 2.6912 (9.4); 1.9174 (16.0); 1.3443 (0.4); 0.9654 (0.4); 0.9411 (0.7); 0.9169 (0.3)

I.149: ¹H-NMR(300.2 MHz, CDCl3):
δ = 9.0589 (1.3); 9.0510 (1.4); 8.4400 (0.9); 8.4339 (1.1); 8.4273 (0.8); 7.7451 (0.6); 7.7182 (1.0); 7.6546 (0.4); 7.6385 (0.4); 7.6287 (0.7); 7.6125 (0.7); 7.6019 (0.4); 7.5855 (0.4); 7.5601 (0.6); 7.5555 (0.6); 7.5344 (0.4); 7.5294 (0.5); 7.5256 (0.7); 7.5212 (0.7); 7.5129 (0.5); 7.5040 (1.7); 7.4993 (1.5); 7.4921 (2.4); 7.4827 (2.7); 7.4703 (0.4); 7.3896 (1.3); 7.3855 (0.8); 7.3779 (1.2); 7.3729 (0.8); 7.3665 (1.0); 7.3578 (0.8); 7.3168 (0.8); 7.2986 (1.1); 7.2904 (1.6); 7.2641 (1.0); 6.9899 (1.0); 6.9865 (1.1); 6.9641 (0.9); 6.9606 (0.9); 6.7481 (1.0); 6.7447 (1.0); 6.7213 (1.0); 6.7179 (0.9); 1.5766 (16.0); 0.0363 (0.5)

I.150: ¹H-NMR(300.2 MHz, CDCl3):
δ = 8.6258 (2.4); 8.5989 (2.7); 8.4375 (4.0); 8.4096 (4.6); 8.0568 (2.2); 8.0528 (2.3); 8.0335 (3.2); 8.0292 (4.3); 8.0053 (2.6); 8.0011 (2.5); 7.9008 (2.7); 7.8733 (3.9); 7.8490 (1.9); 7.4375 (3.4); 7.4145 (4.1); 7.3516 (1.8); 7.3251 (4.2); 7.2984 (47.5); 7.2773 (4.1); 7.2482 (4.4); 7.2043 (3.4); 7.2013 (3.4); 7.1788 (5.1); 7.1760 (4.9); 7.1536 (2.1); 7.1058 (4.1); 7.0987 (4.4); 7.0690 (6.7); 6.9273 (4.0); 6.8885 (4.6); 6.3673 (4.6); 6.3403 (4.3); 5.3375 (0.7); 4.7971 (1.5); 4.7443 (8.1); 4.7223 (8.9); 4.6697 (1.6); 3.0245 (0.9); 2.6618 (0.4); 2.1708 (0.3); 2.0834 (0.5); 1.8255 (0.8); 1.7381 (0.7); 1.6135 (6.8); 1.4605 (1.7); 1.3713 (2.1); 1.3219 (3.2); 1.2926 (16.0); 1.1411 (0.7); 1.0983 (0.5); 1.0603 (0.5); 1.0388 (0.5); 1.0246 (0.5); 1.0155 (0.5); 0.9996 (0.5); 0.9764 (0.5); 0.9177 (2.2); 0.8995 (4.8); 0.8780 (5.0); 0.8273 (0.8); 0.8050 (0.4); 0.1075 (2.3); 0.0480 (1.5); 0.0373 (32.8); 0.0264 (1.3)

I.151: ¹H-NMR(300.2 MHz, CDCl3):
δ = 9.0062 (1.2); 8.9983 (1.2); 8.4267 (0.8); 8.4210 (1.0); 8.4141 (0.7); 7.7569 (0.5); 7.7304 (0.8); 7.6832 (0.4); 7.6672 (0.4); 7.6575 (0.7); 7.6414 (0.6); 7.6306 (0.4); 7.6142 (0.4); 7.5960 (1.9); 7.5896 (0.9); 7.5685 (0.9); 7.5633 (0.9); 7.5601 (1.0); 7.5555 (0.6); 7.2986 (2.8); 6.7965 (0.9); 6.7692 (0.8); 1.9150 (16.0); 1.6130 (0.5); 0.0364 (2.9)

I.152: ¹H-NMR(300.2 MHz, CDCl3):
δ = 10.0636 (16.0); 9.8280 (0.4); 9.4749 (0.5); 9.3117 (3.1); 8.7994 (1.2); 8.7912 (1.3); 8.7775 (5.5); 8.7689 (5.6); 8.0543 (0.7); 8.0487 (0.9); 8.0415 (0.8); 7.7926 (0.3); 7.7788 (3.7); 7.7737 (4.4); 7.7533 (4.1); 7.7482 (4.8); 7.7179 (3.8); 7.7133 (3.5); 7.6914 (4.6); 7.6866 (4.0); 7.6565 (1.0); 7.6170 (0.4); 7.6007 (0.6); 7.5915 (0.7); 7.5753 (0.8); 7.5644 (0.4); 7.5480 (0.4); 7.5108 (0.6); 7.5058 (0.7); 7.4983 (0.7); 7.4913 (1.5); 7.4735 (8.4); 7.4634 (9.3); 7.4541 (4.6); 7.4395 (3.5); 7.4265 (1.9); 7.4116 (5.3); 7.4088 (5.2); 7.3934 (1.2); 7.3393 (0.4); 7.3219 (2.3); 7.3117 (2.1); 7.2994 (25.3); 7.2918 (3.2); 7.2868 (3.2); 7.2717 (7.7); 7.2633 (3.2); 7.2567 (2.0); 7.2457 (3.8); 7.2369 (0.8); 7.2327 (0.8); 7.2057 (0.5); 4.6235 (3.2); 4.1946 (0.8); 4.1708 (2.4); 4.1470 (2.5); 4.1232 (0.9); 3.0233 (8.5); 2.4528 (2.0); 2.0821 (11.2); 1.6269 (7.0); 1.4518 (0.8); 1.3200 (3.1); 1.2963 (6.4); 1.2725 (3.0); 1.1449 (2.7); 1.0268 (0.3); 0.0480 (0.8); 0.0372 (24.3); 0.0282 (0.9); 0.0264 (1.0)

I.153: ¹H-NMR(300.2 MHz, d₆-DMSO):
δ = 8.7692 (0.8); 8.7608 (0.8); 8.1365 (0.5); 8.1308 (0.6); 8.1230 (0.5); 7.9030 (0.3); 7.8808 (0.4); 7.8715 (0.4); 7.6787 (0.5); 7.6712 (0.5); 7.6592 (1.1); 7.6360 (0.6); 7.6298 (0.4); 7.4454 (0.4); 7.4334 (0.3); 7.3300 (1.9); 7.3180 (0.6); 7.3117 (0.8); 5.7777 (1.2); 4.9667 (1.9); 3.3400 (16.0); 2.5343 (1.6); 2.5283 (3.2); 2.5223 (4.4); 2.5162 (3.2); 2.5103 (1.5); 2.0097 (0.4); 1.8668 (3.8); 0.0207 (3.6)

I.154: ¹H-NMR(300.2 MHz, d₆-DMSO):
δ = 8.8016 (1.2); 8.7932 (1.2); 8.1478 (0.7); 8.1421 (0.9); 8.1344 (0.7); 7.9252 (0.4); 7.9202 (0.4); 7.9018 (0.6); 7.8934 (0.6); 7.6682 (0.6); 7.6581 (0.6); 7.6476 (1.4); 7.6237 (0.9); 7.6168 (0.6); 7.5459 (0.4); 7.5369 (0.5);

TABLE 12-continued

| NMR peak lists |
|---|

7.5248 (0.4); 7.5226 (0.4); 7.5157 (0.6); 7.3950 (1.2); 7.3816 (0.9); 7.3732 (2.1); 3.3408 (16.0); 2.5342 (1.2); 2.5282 (2.6); 2.5222 (3.5); 2.5161 (2.5); 2.5103 (1.2); 2.0092 (0.4); 1.8746 (5.4); 1.6494 (5.3); 0.0195 (1.9); −0.0399 (0.4)
I.155: $^1$H-NMR(500.1 MHz, CDCl3):
δ = 8.7917 (8.9); 8.7874 (10.1); 8.1960 (9.3); 8.1917 (10.5); 8.1689 (7.4); 7.8797 (6.6); 7.8634 (7.6); 7.8183 (3.7); 7.8041 (6.4); 7.7876 (3.9); 7.6517 (4.6); 7.6371 (6.8); 7.6216 (3.3); 7.3265 (3.8); 7.3160 (4.9); 7.3085 (4.8); 7.2882 (18.5); 7.1665 (1.5); 7.1591 (9.7); 7.1519 (8.9); 7.1475 (9.3); 7.1407 (9.7); 7.1327 (1.6); 6.6255 (0.8); 6.6179 (4.7); 6.6087 (4.5); 6.5992 (4.6); 3.6952 (6.2); 3.6814 (14.3); 3.6678 (9.3); 3.5546 (10.4); 3.5407 (16.0); 3.5269 (7.0); 1.5952 (9.4); 1.2843 (0.4)
I.156: $^1$H-NMR(500.1 MHz, CDCl3):
δ = 8.7693 (1.4); 8.7644 (1.4); 8.2440 (1.3); 8.2393 (1.3); 8.1859 (0.8); 8.1833 (0.9); 8.1700 (0.8); 8.1674 (0.9); 8.1416 (0.9); 8.1246 (1.0); 7.8496 (0.9); 7.8333 (1.0); 7.7864 (0.4); 7.7844 (0.5); 7.7700 (0.9); 7.7556 (0.5); 7.7535 (0.5); 7.6127 (0.6); 7.5983 (0.9); 7.5825 (0.5); 7.4139 (0.4); 7.4110 (0.5); 7.3967 (0.9); 7.3828 (0.5); 7.3799 (0.5); 7.1982 (0.8); 7.1893 (3.7); 7.1839 (1.2); 7.1680 (0.5); 6.5885 (1.1); 6.5719 (1.0); 1.7284 (16.0); 1.4896 (2.1)
I.157: $^1$H-NMR(500.1 MHz, CDCl3):
δ = 8.8152 (1.4); 8.8105 (1.4); 8.2833 (1.4); 8.2789 (1.4); 8.1970 (1.0); 8.1801 (1.1); 7.9065 (0.9); 7.8903 (1.1); 7.8281 (0.5); 7.8125 (0.9); 7.7975 (0.6); 7.6605 (0.7); 7.6453 (1.0); 7.6304 (0.5); 7.2873 (1.4); 7.2502 (0.7); 7.2371 (0.8); 7.2354 (0.8); 7.1113 (0.7); 7.1092 (0.7); 7.0965 (1.4); 7.0930 (1.4); 7.0812 (0.9); 6.4823 (0.9); 6.4670 (0.9); 3.4595 (4.4); 1.6560 (16.0); 1.6301 (0.9)
I.158: $^1$H-NMR(500.1 MHz, CDCl3):
δ = 8.7993 (5.8); 8.7945 (5.9); 8.2200 (5.5); 8.2154 (5.4); 8.1862 (3.9); 8.1692 (4.2); 7.8855 (3.7); 7.8692 (4.2); 7.8171 (2.0); 7.8026 (3.6); 7.7863 (2.1); 7.6516 (2.7); 7.6370 (3.9); 7.6215 (2.0); 7.2873 (14.1); 7.2751 (2.8); 7.2668 (2.7); 7.1478 (0.8); 7.1361 (5.0); 7.1277 (6.1); 7.1184 (5.3); 7.1079 (0.7); 6.5843 (0.4); 6.5770 (3.0); 6.5686 (2.5); 6.5621 (1.7); 6.5582 (2.9); 3.6753 (1.8); 3.6648 (3.3); 3.6520 (2.0); 3.6397 (6.1); 3.6285 (3.0); 3.6167 (1.2); 3.6035 (0.4); 3.4439 (1.8); 3.4220 (2.5); 3.4077 (2.3); 3.3979 (0.4); 3.3850 (1.2); 1.6198 (15.0); 1.6068 (16.0); 1.5956 (4.9); 1.2838 (0.4)
I.159: $^1$H-NMR(500.1 MHz, CDCl3):
δ = 8.7528 (3.6); 8.7479 (3.9); 8.1885 (3.8); 8.1839 (5.7); 8.1659 (2.5); 8.1373 (2.6); 8.1203 (2.8); 7.8287 (2.5); 7.8123 (2.9); 7.7839 (1.4); 7.7696 (2.4); 7.7530 (1.5); 7.6095 (1.8); 7.5950 (2.6); 7.5793 (1.3); 7.4696 (1.2); 7.4550 (2.4); 7.4412 (1.2); 7.4384 (1.4); 7.2530 (1.9); 7.2380 (3.0); 7.2226 (1.6); 7.1893 (10.7); 6.6855 (3.2); 6.6690 (3.1); 4.4678 (16.0); 1.9324 (1.1); 1.4858 (6.8); 1.1839 (0.5); −0.0003 (0.4)
I.160: $^1$H-NMR(500.1 MHz, CDCl3):
δ = 8.8239 (8.9); 8.8195 (9.0); 8.2146 (9.0); 7.6683 (2.3); 7.6651 (2.4); 7.6583 (2.5); 7.6548 (2.7); 7.6502 (3.3); 7.6468 (3.4); 7.6400 (3.1); 7.6369 (3.1); 7.5563 (2.6); 7.5423 (2.9); 7.5374 (4.3); 7.5235 (4.2); 7.5190 (2.3); 7.5049 (1.9); 7.3401 (3.6); 7.3332 (4.1); 7.3295 (4.2); 7.3218 (4.5); 7.2876 (28.4); 7.1899 (1.7); 7.1822 (10.6); 7.1754 (9.1); 7.1703 (8.8); 7.1635 (9.7); 7.1558 (1.4); 6.6086 (0.9); 6.6015 (4.9); 6.5942 (4.0); 6.5899 (4.3); 6.5827 (4.5); 6.5751 (0.8); 3.6958 (6.0); 3.6821 (13.7); 3.6683 (8.8); 3.5519 (10.6); 3.5381 (16.0); 3.5242 (7.2); 3.5131 (0.4); 1.5696 (21.7); 1.2819 (1.0)
I.161: $^1$H-NMR(500.1 MHz, CDCl3):
δ = 8.7826 (0.9); 8.7651 (0.9); 8.4534 (1.4); 7.9572 (0.9); 7.9409 (1.0); 7.9166 (1.3); 7.8652 (0.4); 7.8502 (0.8); 7.8338 (0.5); 7.7610 (0.6); 7.7462 (0.9); 7.7310 (0.4); 7.2877 (10.6); 7.2446 (0.7); 7.2300 (0.8); 7.1507 (0.7); 7.1354 (0.6); 7.1215 (0.8); 7.1070 (0.9); 6.5700 (1.0); 6.5541 (0.9); 3.4347 (4.0); 1.6309 (16.0); 1.5754 (2.3)
I.162: $^1$H-NMR(500.1 MHz, CDCl3):
δ = 8.7275 (7.0); 8.7102 (7.1); 8.3823 (14.8); 8.3786 (14.9); 7.9940 (0.4); 7.9131 (6.4); 7.9121 (6.4); 7.8978 (7.5); 7.8968 (7.6); 7.8957 (7.5); 7.8459 (10.3); 7.8436 (10.2); 7.8228 (3.9); 7.8201 (3.9); 7.8089 (5.5); 7.8059 (7.1); 7.8027 (4.0); 7.7914 (5.3); 7.7886 (4.7); 7.7224 (5.1); 7.7202 (5.2); 7.7081 (4.9); 7.7062 (8.0); 7.7041 (5.0); 7.6922 (3.5); 7.6900 (3.8); 7.3694 (0.4); 7.2607 (48.8); 7.2254 (4.6); 7.2404 (4.9); 7.2351 (5.5); 7.2258 (0.7); 7.1680 (1.1); 7.1638 (1.7); 7.1533 (5.5); 7.1489 (5.4); 7.1454 (8.4); 7.1399 (16.0); 7.1337 (6.1); 7.1310 (7.5); 7.1275 (6.7); 7.1164 (2.1); 7.1127 (1.2); 6.6687 (0.5); 6.6587 (6.6); 6.6540 (5.9); 6.6459 (3.1); 6.6429 (4.2); 6.6399 (6.4); 5.2979 (0.7); 3.6142 (3.0); 3.6037 (4.9); 3.5984 (1.6); 3.5862 (4.7); 3.5746 (10.7); 3.5637 (3.6); 3.5608 (3.9); 3.5502 (2.5); 3.5369 (0.8); 3.4884 (2.0); 3.3845 (2.4); 3.3624 (4.2); 3.3481 (3.8); 3.3348 (1.1); 3.3251 (1.5); 1.5815 (7.5); 1.5735 (37.5); 1.5603 (35.1); 1.2843 (0.5); 1.2539 (2.2); 1.2426 (0.4); 0.0063 (2.6); −0.0003 (77.0); −0.0068 (2.9)
I.163: $^1$H-NMR(500.1 MHz, CDCl3):
δ = 8.7008 (2.1); 8.6959 (2.1); 8.1956 (2.0); 8.1909 (1.8); 8.1232 (1.3); 8.1062 (1.4); 7.8282 (1.3); 7.8117 (1.6); 7.8030 (1.3); 7.7871 (1.3); 7.7701 (0.7); 7.7677 (0.8); 7.7561 (0.9); 7.7535 (1.4); 7.7393 (0.7); 7.7368 (0.8); 7.5961 (1.0); 7.5818 (1.4); 7.5659 (0.7); 7.2843 (0.5); 7.2697 (1.1); 7.2542 (0.7); 7.2135 (1.1); 7.1981 (1.7); 7.1888 (6.4); 6.4920 (1.3); 6.4755 (1.2); 1.7088 (16.0); 1.4811 (3.2); 1.1856 (0.3)
I.164: $^1$H-NMR(500.1 MHz, CDCl3):
δ = 8.7372 (2.2); 8.7322 (2.1); 8.1448 (2.0); 8.1399 (2.0); 8.1326 (1.4); 8.1153 (1.4); 7.8518 (1.1); 7.8457 (1.1); 7.8353 (1.2); 7.8292 (1.2); 7.8200 (1.3); 7.8037 (1.5); 7.7874 (0.7); 7.7850 (0.8); 7.7734 (1.0); 7.7708 (1.4); 7.7567 (0.7); 7.7541 (0.7); 7.6127 (1.0); 7.5984 (1.4); 7.5825 (0.7); 7.2091 (0.8); 7.2028 (1.0); 7.1897 (16.0); 7.1769 (0.7); 7.1707 (0.6); 6.7517 (1.2); 6.7432 (1.2); 6.7336 (1.1); 6.7252 (1.0); 4.4472 (9.0); 1.4692 (12.4); 1.1844 (0.5)
I.165: $^1$H-NMR(500.1 MHz, CDCl3):
δ = 8.8530 (1.3); 8.8488 (1.3); 8.2980 (1.3); 7.6928 (0.4); 7.6860 (0.4); 7.6826 (0.4); 7.6779 (0.5); 7.6747 (0.5); 7.6677 (0.4); 7.6648 (0.4); 7.5668 (0.4); 7.5529 (0.4); 7.5479 (0.6); 7.5341 (0.6); 7.5296 (0.3); 7.2880 (7.6); 7.2670 (0.6); 7.2533 (0.7); 7.2500 (0.7); 7.1370 (0.6); 7.1336 (0.7); 7.1219 (1.4); 7.1109 (0.8); 7.1088 (0.8); 6.4771 (0.8); 6.4739 (0.8); 6.4591 (0.8); 3.4619 (4.2); 1.6451 (16.0); 1.5709 (7.9); 1.2829 (0.4)
I.166: $^1$H-NMR(500.1 MHz, CDCl3):
δ = 8.7482 (1.3); 8.7433 (1.4); 8.1647 (2.2); 8.1467 (1.0); 7.8707 (0.9); 7.8543 (1.0); 7.7980 (0.5); 7.7836 (0.8); 7.7674 (0.5); 7.6416 (0.6); 7.6270 (0.9); 7.6115 (0.5); 7.5155 (0.9); 7.4996 (1.0); 7.2878 (14.7); 7.2581 (0.5); 7.2435 (1.0); 7.2277 (0.6); 7.1785 (0.6); 7.1642 (0.9); 7.1479 (0.4); 6.7109 (1.0); 6.6947 (1.0); 3.4855 (5.6); 1.7299 (16.0); 1.5615 (8.4)
I.167: $^1$H-NMR(500.1 MHz, CDCl3):
δ = 8.7846 (5.5); 8.7797 (5.5); 8.2121 (5.1); 8.2074 (5.0); 8.1648 (3.5); 8.1479 (3.8); 7.8773 (3.3); 7.8610 (3.8); 7.8031 (1.8); 7.7888 (3.4); 7.7738 (1.8); 7.7724 (1.9); 7.6436 (2.4); 7.6291 (3.6); 7.6135 (1.8); 7.2877 (9.3);

TABLE 12-continued

NMR peak lists 7.2500 (1.9); 7.2469 (1.5); 7.2447 (1.5); 7.2395 (2.4); 7.2318 (2.7); 7.1736 (0.8); 7.1635 (3.2); 7.1600 (4.9); 7.1529 (6.2); 7.1452 (4.1); 7.1434 (4.2); 7.1325 (0.6); 6.6805 (0.4); 6.6730 (2.8); 6.6660 (2.0); 6.6543 (2.7); 6.6480 (0.3); 3.5656 (16.0); 1.6012 (5.6); 1.5448 (2.2); 1.5324 (8.8); 1.5208 (2.2); 1.0886 (2.3); 1.0763 (8.8); 1.0639 (2.0)

I.168: $^1$H-NMR(500.1 MHz, CDCl3):
δ = 9.0793 (2.9); 8.2186 (0.7); 8.2154 (0.7); 8.2026 (0.8); 8.1994 (0.8); 8.1387 (0.6); 8.1359 (0.7); 8.1217 (0.6); 8.1194 (0.7); 8.2208 (0.5); 7.8187 (0.6); 7.8176 (0.5); 7.8045 (0.8); 7.8021 (0.8); 7.7769 (0.4); 7.7738 (0.4); 7.7630 (0.7); 7.7600 (0.8); 7.7570 (0.4); 7.7464 (0.7); 7.7431 (0.6); 7.7280 (0.6); 7.7249 (0.7); 7.7141 (0.4); 7.7113 (0.7); 7.7085 (0.5); 7.5434 (0.4); 7.5401 (0.5); 7.5287 (0.6); 7.5270 (0.6); 7.5256 (0.6); 7.5239 (0.6); 7.5125 (0.5); 7.5092 (0.6); 7.3809 (0.5); 7.3788 (0.6); 7.3647 (0.9); 7.3503 (0.5); 7.3483 (0.4); 7.1898 (16.0); 6.9097 (0.8); 6.9081 (0.8); 6.8934 (0.8); 6.8919 (0.8); 4.4231 (6.5); 1.4666 (10.9); 1.1842 (0.7)

I.169: $^1$H-NMR(500.1 MHz, CDCl3):
δ = 8.3569 (1.2); 8.3537 (1.2); 7.8215 (1.2); 7.6927 (0.4); 7.6884 (0.4); 7.6827 (0.4); 7.6785 (0.3); 7.6049 (0.3); 7.5920 (0.3); 7.5864 (0.6); 7.5737 (0.6); 7.2866 (41.2); 7.2514 (0.5); 7.2340 (0.7); 7.1783 (0.6); 7.1626 (0.5); 7.1592 (0.4); 7.1474 (0.6); 7.1447 (0.7); 7.1325 (0.8); 7.1300 (0.8); 6.5797 (0.8); 6.5774 (0.8); 6.5612 (0.7); 3.4240 (3.1); 1.6128 (16.0); 1.5877 (0.8); 1.5596 (5.3); 1.2811 (0.4)

I.170: $^1$H-NMR(500.1 MHz, CDCl3):
δ = 9.1224 (2.7); 8.2841 (0.7); 8.2809 (0.7); 8.2680 (0.7); 8.2648 (0.7); 8.2160 (0.6); 8.2131 (0.6); 8.1991 (0.6); 8.1967 (0.6); 7.9312 (0.5); 7.9290 (0.5); 7.9280 (0.5); 7.9152 (0.7); 7.9124 (0.7); 7.8433 (0.4); 7.8326 (0.7); 7.8296 (0.7); 7.8268 (0.3); 7.8162 (0.6); 7.8128 (0.5); 7.8030 (0.6); 7.7997 (0.6); 7.7890 (0.4); 7.7862 (0.6); 7.7835 (0.5); 7.5407 (0.4); 7.5374 (0.4); 7.5262 (0.5); 7.5232 (0.6); 7.5210 (0.5); 7.5098 (0.5); 7.5064 (0.5); 7.3701 (0.5); 7.3681 (0.5); 7.3539 (0.8); 7.3525 (0.6); 7.3396 (0.4); 7.3377 (0.4); 7.2591 (4.3); 6.7960 (0.8); 6.7946 (0.8); 6.7794 (0.8); 6.7781 (0.8); 1.7395 (16.0); 1.5449 (1.6); 1.4265 (0.5); 0.0698 (1.4); −0.0003 (5.5)

I.171: $^1$H-NMR(500.1 MHz, CDCl3):
δ = 8.7701 (0.7); 8.7651 (0.7); 8.2216 (0.5); 8.2169 (0.5); 8.1785 (0.4); 8.1752 (0.4); 8.1625 (0.4); 8.1593 (0.4); 8.1431 (0.3); 8.1261 (0.4); 7.8249 (0.3); 7.7722 (0.4); 7.5990 (0.4); 7.4260 (0.3); 7.2127 (0.4); 7.1964 (0.3); 7.1899 (16.0); 6.6434 (0.4); 6.6277 (0.4); 4.3474 (0.6); 4.3334 (0.6); 1.7572 (2.2); 1.7430 (2.2); 1.4961 (1.2)

I.172: $^1$H-NMR(500.1 MHz, CDCl3):
δ = 8.6897 (0.6); 8.6859 (0.6); 8.1934 (0.8); 8.1890 (0.8); 8.0872 (0.5); 8.0705 (0.5); 7.8018 (0.6); 7.7856 (0.7); 7.7170 (0.4); 7.7143 (0.4); 7.7031 (0.5); 7.7002 (0.7); 7.6975 (0.4); 7.6862 (0.4); 7.6835 (0.4); 7.5563 (0.4); 7.5544 (0.5); 7.5403 (0.8); 7.5261 (0.4); 7.5242 (0.4); 7.4278 (0.6); 7.4250 (0.7); 7.4119 (0.7); 7.4089 (0.7); 7.1896 (16.0); 7.0758 (0.3); 7.0731 (0.4); 7.0612 (0.6); 7.0589 (0.7); 7.0454 (0.5); 7.0427 (0.5); 7.0097 (0.5); 7.0066 (0.5); 6.9932 (0.7); 6.9904 (0.6); 6.9787 (0.4); 6.9759 (0.4); 6.4208 (0.8); 6.4183 (0.8); 6.4044 (0.7); 6.4020 (0.7); 1.5809 (13.8); 1.5300 (14.4); 1.4721 (1.0); 1.2171 (0.5); 1.2151 (0.5); 1.1861 (1.6); 0.8112 (0.3); −0.0002 (0.4)

I.173: $^1$H-NMR(500.1 MHz, CDCl3):
δ = 8.7634 (2.0); 8.7585 (2.0); 8.1914 (2.0); 8.1867 (2.0); 8.1632 (1.3); 8.1463 (1.4); 7.8718 (1.4); 7.8573 (1.6); 7.8551 (1.6); 7.7954 (1.0); 7.7926 (1.0); 7.7815 (1.2); 7.7786 (1.9); 7.7756 (1.0); 7.7646 (1.1); 7.7618 (1.0); 7.6394 (1.2); 7.6372 (1.2); 7.6255 (1.2); 7.6232 (2.0); 7.6211 (1.1); 7.6092 (0.9); 7.6071 (0.8); 7.5244 (1.6); 7.5215 (1.7); 7.5083 (1.9); 7.5054 (1.9); 7.2866 (28.3); 7.2446 (1.0); 7.2418 (1.2); 7.2300 (1.5); 7.2274 (1.7); 7.2262 (1.2); 7.2140 (1.3); 7.2114 (1.3); 7.1643 (1.2); 7.1614 (1.2); 7.1495 (1.2); 7.1481 (1.6); 7.1452 (1.5); 7.1337 (1.0); 7.1307 (0.9); 6.6789 (2.0); 6.6763 (2.0); 6.6626 (1.9); 6.6600 (1.8); 3.5181 (0.8); 3.5041 (2.7); 3.4899 (2.8); 3.4759 (0.8); 1.6725 (16.0); 1.6251 (15.9); 1.6144 (11.2); 1.6003 (10.5); 1.5750 (1.6); 1.2828 (0.8)

I.174: $^1$H-NMR(500.1 MHz, CDCl3):
δ = 8.7625 (1.4); 8.7575 (1.4); 8.2371 (1.0); 8.2324 (1.0); 8.1730 (0.7); 8.1558 (0.7); 7.8804 (0.6); 7.8647 (0.7); 7.8150 (0.4); 7.8121 (0.4); 7.8011 (0.6); 7.7981 (0.8); 7.7951 (0.4); 7.7841 (0.5); 7.7812 (0.4); 7.6459 (0.5); 7.6438 (0.5); 7.6298 (0.8); 7.6158 (0.4); 7.6136 (0.4); 7.2590 (9.0); 7.2140 (0.9); 7.2093 (1.0); 7.0630 (0.6); 7.0581 (0.5); 7.0454 (0.6); 7.0405 (0.6); 6.4011 (1.3); 6.3835 (1.3); 3.3970 (3.0); 1.6217 (16.0); 1.5499 (1.0); 0.0061 (0.4); −0.0003 (10.6); −0.0070 (0.4)

I.175: $^1$H-NMR(500.1 MHz, CDCl3):
δ = 8.7460 (10.3); 8.7410 (10.2); 8.1599 (5.7); 8.1426 (16.0); 8.1380 (9.1); 7.8494 (5.1); 7.8330 (6.1); 7.8025 (3.3); 7.7997 (2.9); 7.7886 (4.3); 7.7858 (5.9); 7.7831 (3.1); 7.7719 (3.5); 7.7691 (2.9); 7.6341 (3.8); 7.6321 (3.6); 7.6180 (6.1); 7.6035 (2.9); 7.2931 (7.6); 7.2884 (7.8); 7.2591 (25.5); 7.1067 (4.4); 7.1020 (4.1); 7.0892 (4.7); 7.0844 (4.4); 6.5389 (10.3); 6.5213 (9.7); 5.2964 (0.5); 3.6368 (4.6); 3.6230 (10.9); 3.6093 (7.2); 3.5104 (9.8); 3.4966 (14.1); 3.4831 (5.7); 2.0425 (0.5); 1.5745 (11.7); 1.2550 (0.8); 0.0061 (1.0); −0.0003 (29.6); −0.0069 (1.3)

I.176: $^1$H-NMR(500.1 MHz, CDCl3):
δ = 8.7520 (15.0); 8.7470 (15.2); 8.1705 (12.9); 8.1650 (15.6); 8.1448 (9.4); 7.8582 (7.5); 7.8418 (8.7); 7.8036 (5.0); 7.8007 (5.1); 7.7897 (6.8); 7.7868 (9.9); 7.7839 (5.2); 7.7728 (6.0); 7.7700 (5.0); 7.6361 (5.8); 7.6343 (6.0); 7.6201 (9.6); 7.6060 (4.3); 7.6040 (4.4); 7.4653 (0.5); 7.3596 (0.4); 7.2590 (104.7); 7.2497 (12.3); 7.2450 (12.3); 7.0882 (6.9); 7.0834 (6.6); 7.0706 (7.3); 7.0658 (6.9); 7.0474 (0.6); 6.8062 (0.4); 6.4951 (16.0); 6.4775 (15.2); 5.2975 (0.4); 3.6319 (0.8); 3.6188 (4.7); 3.6084 (11.0); 3.5973 (6.0); 3.5955 (5.8); 3.5838 (11.1); 3.5732 (5.2); 3.5605 (0.9); 3.4906 (0.8); 3.3830 (4.6); 3.3728 (0.8); 3.3613 (5.6); 3.3465 (4.7); 3.3253 (3.4); 2.0330 (0.9); 1.5861 (41.9); 1.5732 (42.6); 1.5478 (24.1); 1.3329 (0.4); 1.2840 (0.9); 1.2534 (9.9); 1.2297 (0.6); 0.8929 (0.4); 0.8796 (0.6); 0.1162 (0.5); 0.0061 (5.2); −0.0003 (121.6); −0.0070 (5.1); −0.1203 (0.5)

I.177: $^1$H-NMR(500.1 MHz, CDCl3):
δ = 9.0577 (5.4); 8.1933 (1.1); 8.1903 (1.3); 8.1764 (1.2); 8.1739 (1.3); 7.9090 (1.1); 7.9051 (1.8); 7.9006 (0.8); 7.8927 (1.7); 7.8899 (2.7); 7.8852 (1.1); 7.8263 (0.6); 7.8231 (0.7); 7.8124 (1.4); 7.8094 (1.4); 7.8066 (0.6); 7.7961 (1.4); 7.7926 (1.1); 7.7847 (1.2); 7.7814 (1.3); 7.7708 (0.7); 7.7680 (1.2); 7.7652 (1.1); 7.7544 (0.5); 7.7513 (0.5); 7.4009 (0.8); 7.3995 (0.8); 7.3971 (0.8); 7.3896 (1.3); 7.3852 (2.2); 7.3815 (0.9); 7.3746 (1.2); 7.3713 (1.3); 7.3598 (0.4); 7.3567 (0.3); 7.2586 (17.3); 6.7125 (0.8); 6.7093 (1.0); 6.6986 (0.6); 6.6961 (0.9); 6.6942 (1.0); 1.7145 (16.0); 1.5353 (6.2); 0.0061 (0.7); −0.0003 (22.5); −0.0071 (0.7)

I.178: $^1$H-NMR(500.1 MHz, CDCl3):
δ = 8.7501 (2.8); 8.7450 (2.8); 8.2421 (1.8); 8.2375 (1.8); 8.1887 (1.2); 8.1717 (1.3); 7.8941 (1.1); 7.8777 (1.3); 7.8435 (0.9); 7.8408 (0.8); 7.8296 (1.2); 7.8267 (1.6); 7.8238 (0.8); 7.8126 (1.0); 7.8099 (0.8); 7.6731 (1.0); 7.6709 (1.0); 7.6591 (0.9); 7.6569 (1.6); 7.6546 (0.9); 7.6429 (0.7); 7.6406 (0.7); 7.5765 (1.0); 7.5706 (1.0); 7.5597 (1.0); 7.5538 (1.0); 7.2587 (36.2); 7.2527 (0.4); 7.0940 (0.4); 7.0882 (0.4); 7.0756 (0.7); 7.0737 (0.7); 7.0701 (0.5); 7.0612 (0.5); 7.0553 (0.4); 6.5945 (0.7); 6.5857 (0.8); 6.5763 (0.7); 6.5674 (0.7); 3.4195 (0.4);

TABLE 12-continued

NMR peak lists 1.7629 (16.0); 1.5370 (4.9); 1.2856 (0.6); 1.2542 (0.9); 0.8439 (0.4); 0.8372 (0.4); 0.0687 (0.5); 0.0061 (1.5); −0.0003 (48.4); −0.0071 (2.0)
I.179: $^1$H-NMR(500.1 MHz, CDCl3):
δ = 8.8221 (1.3); 8.8170 (1.3); 8.2965 (0.9); 8.2917 (0.9); 8.2087 (0.6); 8.1916 (0.7); 7.9242 (0.7); 7.9180 (1.2); 7.9072 (0.7); 7.9011 (1.3); 7.8609 (0.4); 7.8581 (0.4); 7.8470 (0.5); 7.8441 (0.8); 7.8411 (0.4); 7.8300 (0.5); 7.8272 (0.4); 7.6904 (0.4); 7.6883 (0.5); 7.6763 (0.4); 7.6743 (0.8); 7.6720 (0.4); 7.6602 (0.3); 7.6580 (0.3); 7.2593 (7.1); 7.2160 (0.4); 7.2098 (0.4); 7.2017 (0.4); 7.1978 (0.5); 7.1956 (0.4); 7.1916 (0.4); 7.1836 (0.4); 7.1775 (0.4); 6.6942 (0.7); 6.6858 (0.7); 6.6761 (0.6); 6.6676 (0.6); 1.7860 (16.0); −0.0003 (9.7)
I.180: $^1$H-NMR(500.1 MHz, CDCl3):
δ = 8.7942 (11.8); 8.7891 (12.1); 8.2279 (5.6); 8.2247 (6.0); 8.2124 (12.7); 8.2088 (13.8); 8.1800 (5.4); 8.1627 (5.8); 7.8785 (4.9); 7.8624 (5.4); 7.8286 (3.5); 7.8258 (3.6); 7.8147 (4.4); 7.8118 (6.7); 7.8088 (3.6); 7.7977 (3.9); 7.7949 (3.7); 7.6616 (3.8); 7.6594 (4.0); 7.6474 (3.7); 7.6454 (6.5); 7.6432 (3.8); 7.6313 (2.9); 7.6292 (2.9); 7.5610 (3.5); 7.5577 (3.4); 7.5464 (4.5); 7.5434 (4.9); 7.5412 (4.1); 7.5300 (4.1); 7.5266 (4.2); 7.4653 (1.3); 7.3626 (4.2); 7.3607 (4.5); 7.3465 (7.0); 7.3322 (3.9); 7.3302 (3.5); 7.2587 (207.0); 7.0471 (1.0); 6.8827 (6.7); 6.8814 (6.7); 6.8663 (6.6); 6.8648 (6.4); 3.4910 (0.4); 2.2334 (0.3); 2.2188 (0.4); 2.2034 (0.5); 2.0186 (0.4); 2.0051 (0.4); 1.9916 (3.6); 1.9830 (5.6); 1.9807 (11.1); 1.9737 (16.0); 1.9655 (6.1); 1.9352 (1.3); 1.9245 (1.2); 1.8936 (6.2); 1.8859 (15.6); 1.8789 (11.8); 1.8765 (6.2); 1.8684 (3.6); 1.5343 (45.9); 1.4801 (0.3); 1.4218 (0.6); 1.3701 (1.4); 1.3329 (1.3); 1.3137 (1.0); 1.2852 (3.0); 1.2537 (4.6); 0.8935 (0.6); 0.8808 (1.5); 0.8664 (0.9); 0.8449 (2.0); 0.8383 (2.0); 0.8104 (0.9); 0.1162 (0.9); 0.0687 (4.1); 0.0061 (7.9); −0.0003 (243.9); −0.0070 (9.6); −0.1201 (1.0)
I.181: $^1$H-NMR(500.1 MHz, CDCl3):
δ = 8.1050 (1.6); 8.0884 (1.7); 7.9373 (1.5); 7.9205 (1.7); 7.7990 (0.8); 7.7963 (0.8); 7.7850 (1.3); 7.7823 (1.6); 7.7682 (1.1); 7.7655 (1.0); 7.7071 (1.1); 7.6907 (1.5); 7.6767 (0.7); 7.4654 (0.6); 7.2590 (118.0); 7.2345 (1.1); 7.2267 (1.2); 7.2158 (1.2); 7.0844 (0.4); 7.0737 (2.4); 7.0635 (2.6); 7.0558 (2.1); 7.0474 (0.8); 6.1842 (1.4); 6.1800 (0.8); 6.1733 (1.1); 6.1705 (0.9); 6.1655 (1.2); 3.6026 (0.5); 3.5684 (0.6); 3.3108 (0.6); 3.2733 (0.4); 2.9931 (16.0); 1.7003 (3.2); 1.6507 (3.1); 1.5338 (64.8); 1.3329 (0.5); 1.2841 (0.9); 1.2552 (2.8); 0.8802 (0.4); 0.1164 (0.7); −0.0003 (133.0); −0.0069 (4.7); −0.1201 (0.5)
I.182: $^1$H-NMR(500.1 MHz, CDCl3):
δ = 9.0432 (14.2); 8.1670 (3.0); 8.1637 (3.5); 8.1500 (3.0); 8.1477 (3.4); 7.9252 (2.9); 7.9226 (2.7); 7.9213 (2.4); 7.9093 (4.2); 7.9060 (3.7); 7.7909 (1.4); 7.7877 (1.7); 7.7770 (3.4); 7.7739 (3.3); 7.7713 (1.7); 7.7612 (3.7); 7.7571 (4.5); 7.7524 (3.6); 7.7420 (1.8); 7.7396 (3.0); 7.7366 (2.8); 7.7258 (1.4); 7.7227 (1.2); 7.2587 (21.0); 7.2514 (2.7); 7.2422 (2.2); 7.2402 (2.7); 7.2374 (3.0); 7.1677 (1.1); 7.1644 (1.4); 7.1531 (3.7); 7.1498 (3.9); 7.1429 (2.8); 7.1394 (5.0); 7.1351 (3.3); 7.1274 (2.7); 7.1236 (2.6); 7.1127 (1.0); 7.1090 (0.8); 6.5962 (3.4); 6.5935 (2.5); 6.5813 (3.6); 6.5775 (3.2); 3.4288 (16.0); 1.5888 (78.6); 1.5513 (7.9); 1.2540 (0.8); 0.0063 (0.8); −0.0003 (22.8); −0.0069 (0.9)
I.183: $^1$H-NMR(500.1 MHz, CDCl3):
δ = 8.8384 (3.5); 8.8335 (3.6); 8.2520 (1.9); 8.2489 (2.0); 8.2360 (5.9); 8.2312 (4.4); 7.5789 (1.3); 7.5686 (1.5); 7.5607 (2.2); 7.5504 (2.1); 7.5467 (1.3); 7.5433 (1.2); 7.5320 (1.4); 7.5296 (1.7); 7.5289 (1.8); 7.5268 (1.4); 7.5154 (1.4); 7.5122 (1.4); 7.5049 (2.3); 7.4868 (1.6); 7.4831 (2.4); 7.4650 (1.5); 7.3287 (1.4); 7.3269 (1.5); 7.3126 (2.4); 7.2984 (1.3); 7.2964 (1.2); 7.2610 (10.6); 6.7311 (2.3); 6.7300 (2.3); 6.7146 (2.2); 4.5367 (16.0); 4.2928 (13.9); 4.2885 (14.5); 2.0034 (0.9); 1.2562 (0.3); 0.0063 (0.4); −0.0003 (13.1); −0.0068 (0.5)
I.184: $^1$H-NMR(500.1 MHz, CDCl3):
δ = 8.7989 (3.4); 8.7941 (3.5); 8.2446 (1.8); 8.2414 (1.9); 8.2286 (2.0); 8.2250 (2.5); 8.2200 (2.4); 8.2159 (2.0); 7.6633 (1.5); 7.6598 (1.5); 7.6451 (1.9); 7.6416 (1.9); 7.5442 (1.0); 7.5407 (1.1); 7.5295 (1.3); 7.5270 (1.6); 7.5242 (1.3); 7.5129 (1.3); 7.5096 (1.3); 7.5010 (1.7); 7.4863 (1.8); 7.4829 (1.5); 7.4682 (1.4); 7.3198 (1.4); 7.3180 (1.4); 7.3036 (2.3); 7.2894 (1.2); 7.2875 (1.1); 7.2630 (5.4); 6.7322 (2.2); 6.7312 (2.2); 6.7157 (2.1); 4.5395 (15.4); 4.1198 (16.0); 2.0026 (0.4); 1.6280 (0.4); 1.2545 (0.9); −0.0003 (6.4)
I.185: $^1$H-NMR(500.1 MHz, CDCl3):
δ = 8.1917 (2.7); 8.1895 (2.7); 7.5980 (0.6); 7.5941 (0.6); 7.5878 (0.6); 7.5839 (0.7); 7.5798 (0.8); 7.5759 (0.8); 7.5696 (0.8); 7.5657 (0.7); 7.4609 (0.7); 7.4472 (0.7); 7.4419 (1.0); 7.4283 (1.0); 7.4233 (0.6); 7.4096 (0.5); 7.2935 (1.0); 7.2901 (0.9); 7.2881 (0.7); 7.2801 (1.1); 7.2754 (1.2); 7.2593 (17.5); 7.1008 (0.4); 7.0900 (1.2); 7.0860 (1.1); 7.0799 (1.6); 7.0752 (2.7); 7.0705 (1.2); 7.0655 (1.6); 7.0623 (1.5); 7.0509 (0.5); 7.0476 (0.4); 6.2343 (1.4); 6.2302 (1.5); 6.2206 (0.7); 6.2183 (1.0); 6.2155 (1.4); 3.6956 (0.4); 3.6829 (0.5); 3.6772 (0.6); 3.6647 (0.6); 3.6578 (0.5); 3.6460 (0.9); 3.6348 (0.7); 3.5989 (3.4); 3.5878 (2.0); 3.5754 (0.9); 3.5686 (0.8); 3.4956 (0.5); 3.4850 (0.5); 2.6836 (16.0); 1.7842 (0.4); 1.5437 (9.6); 0.0061 (0.8); −0.0003 (24.0); −0.0070 (0.6)
I.186: $^1$H-NMR(500.1 MHz, CDCl3):
δ = 8.8660 (3.0); 8.8612 (3.1); 8.2804 (1.9); 8.2775 (2.2); 8.2759 (2.2); 8.2731 (2.0); 8.2673 (1.9); 8.2640 (2.0); 8.2513 (2.0); 8.2481 (2.0); 7.6959 (0.7); 7.6921 (0.7); 7.6859 (0.7); 7.6820 (0.8); 7.6776 (1.0); 7.6737 (1.0); 7.6676 (0.9); 7.6638 (0.9); 7.5888 (0.9); 7.5751 (1.0); 7.5697 (1.5); 7.5678 (1.5); 7.5643 (1.2); 7.5562 (1.4); 7.5530 (1.7); 7.5509 (2.2); 7.5477 (1.4); 7.5366 (1.6); 7.5331 (1.4); 7.3541 (1.3); 7.3522 (1.4); 7.3380 (2.2); 7.3237 (1.2); 7.3218 (1.1); 7.2597 (18.5); 6.7346 (2.2); 6.7192 (2.1); 6.7181 (2.1); 4.5386 (16.0); 2.0042 (1.2); 1.5405 (10.7); 1.2536 (0.5); 0.0063 (0.7); −0.0003 (22.7); −0.0068 (0.8)
I.187: $^1$H-NMR(500.1 MHz, CDCl3):
δ = 8.4493 (4.3); 8.4468 (4.4); 7.6897 (0.8); 7.6859 (0.9); 7.6798 (0.9); 7.6759 (0.9); 7.6715 (1.1); 7.6676 (1.2); 7.6616 (1.1); 7.6577 (1.0); 7.5546 (1.1); 7.5410 (1.1); 7.5356 (1.6); 7.5300 (0.4); 7.5222 (1.7); 7.5170 (1.9); 7.5075 (0.4); 7.5035 (0.9); 7.2590 (36.5); 7.2307 (1.5); 7.2166 (1.8); 7.1100 (0.6); 7.1070 (0.7); 7.0947 (1.6); 7.0921 (1.5); 7.0795 (1.4); 7.0761 (1.2); 7.0668 (1.7); 7.0641 (2.0); 7.0520 (2.3); 7.0495 (2.3); 7.0372 (0.8); 7.0348 (0.8); 6.1607 (2.2); 6.1583 (2.4); 6.1444 (2.0); 6.1422 (2.2); 3.6392 (1.5); 3.6055 (1.9); 3.2736 (2.6); 3.2399 (2.1); 3.2138 (1.3); 2.0433 (0.8); 1.7263 (14.6); 1.6701 (3.8); 1.5378 (1.7); 1.4318 (1.6); 1.4269 (0.3); 1.4036 (0.3); 1.3409 (1.1); 1.3331 (0.7); 1.2971 (0.7); 1.2842 (1.4); 1.2728 (1.4); 1.2556 (7.4); 1.2446 (1.4); 1.2227 (0.7); 1.1897 (4.3); 0.8938 (0.8); 0.8802 (1.5); 0.8729 (0.9); 0.8662 (1.0); 0.8594 (0.8); 0.8518 (0.9); 0.8385 (0.9); 0.0695 (0.5); 0.0062 (1.3); −0.0003 (42.6); −0.0068 (1.7)
I.188: $^1$H-NMR(500.1 MHz, CDCl3):
δ = 8.8892 (6.5); 8.1462 (0.9); 8.1421 (1.0); 8.1363 (1.0); 8.1321 (1.0); 8.1273 (1.0); 8.1232 (1.1); 8.1174 (1.0); 8.1132 (1.0); 7.6416 (0.9); 7.6276 (0.9); 7.6226 (1.7); 7.6087 (1.7); 7.6037 (0.9); 7.5898 (0.8); 7.4655 (0.6); 7.2590 (113.3); 7.2476 (1.8); 7.2443 (1.5); 7.2336 (1.7); 7.2292 (1.6); 7.1015 (0.4); 7.0979 (0.5); 7.0869 (1.5); 7.0830 (1.4); 7.0742 (2.4); 7.0726 (2.4); 7.0702 (2.8); 7.0675 (1.7); 7.0599 (2.0); 7.0569 (1.8); 7.0472 (0.8); 7.0454 (0.7); 7.0422 (0.5); 6.1814 (1.9); 6.1777 (2.1); 6.1653 (1.4); 6.1627 (1.9); 3.4633 (8.8); 1.7050 (16.0);

| TABLE 12-continued |
|---|
| NMR peak lists |

1.6539 (15.9); 1.6171 (0.4); 1.5302 (60.9); 1.2548 (0.5); 1.1896 (0.4); 0.1163 (0.5); 0.0061 (5.0); −0.0003 (135.0); −0.0068 (4.8); −0.1201 (0.5)
I.189: $^1$H-NMR(500.1 MHz, CDCl3):
δ = 8.8813 (1.1); 8.8765 (1.1); 8.3364 (0.7); 8.3336 (0.8); 8.3320 (0.8); 8.3292 (0.7); 8.2696 (0.7); 8.2665 (0.7); 8.2537 (0.7); 8.2505 (0.7); 7.6976 (0.4); 7.6937 (0.4); 7.6876 (0.3); 7.6838 (0.3); 7.5917 (0.3); 7.5779 (0.3); 7.5727 (0.5); 7.5590 (0.5); 7.5110 (0.4); 7.5078 (0.4); 7.4965 (0.5); 7.4935 (0.6); 7.4911 (0.5); 7.4800 (0.5); 7.4765 (0.5); 7.3012 (0.5); 7.2993 (0.5); 7.2851 (0.8); 7.2837 (0.7); 7.2708 (0.5); 7.2690 (0.5); 7.2604 (3.9); 6.6455 (0.8); 6.6444 (0.8); 6.6291 (0.8); 6.6279 (0.8); 1.7873 (16.0); 1.5522 (3.1); −0.0003 (5.2)
I.190: $^1$H-NMR(500.1 MHz, CDCl3):
δ = 8.7741 (10.6); 8.7689 (11.0); 8.1733 (5.6); 8.1606 (9.5); 8.1564 (16.0); 7.8913 (5.6); 7.8852 (5.8); 7.8746 (6.0); 7.8685 (10.1); 7.8528 (5.5); 7.8508 (6.3); 7.8287 (3.3); 7.8260 (3.0); 7.8148 (4.1); 7.8120 (6.1); 7.8091 (3.1); 7.7979 (3.6); 7.7950 (3.2); 7.6629 (4.0); 7.6608 (4.0); 7.6469 (6.4); 7.6327 (2.8); 7.6310 (2.8); 7.4660 (0.3); 7.2955 (3.2); 7.2893 (3.2); 7.2811 (3.6); 7.2775 (4.1); 7.2749 (3.7); 7.2714 (3.7); 7.2626 (5.9); 7.2595 (57.6); 7.0479 (0.3); 6.9478 (5.8); 6.9392 (5.9); 6.9299 (5.3); 6.9212 (5.2); 3.4900 (0.3); 1.9905 (3.8); 1.9798 (11.4); 1.9727 (15.3); 1.9644 (5.9); 1.9336 (1.1); 1.9118 (1.1); 1.8807 (6.0); 1.8727 (15.5); 1.8656 (11.7); 1.8551 (3.8); 1.5527 (47.0); 1.2551 (0.6); 0.0694 (0.4); 0.0061 (2.5); −0.0003 (68.9); −0.0070 (2.4)
I.191: $^1$H-NMR(500.1 MHz, CDCl3):
δ = 8.2236 (2.6); 8.2213 (2.6); 7.5971 (0.5); 7.5930 (0.6); 7.5868 (0.6); 7.5830 (0.6); 7.5787 (0.8); 7.5750 (0.8); 7.5686 (0.7); 7.5646 (0.7); 7.4656 (0.4); 7.4540 (0.6); 7.4403 (0.7); 7.4349 (1.0); 7.4214 (1.0); 7.4162 (0.6); 7.4025 (0.5); 7.2591 (75.6); 7.2229 (1.0); 7.2088 (1.2); 7.2054 (1.2); 7.0745 (0.4); 7.0712 (0.4); 7.0596 (1.1); 7.0564 (1.0); 7.0475 (0.6); 7.0440 (1.1); 7.0402 (0.9); 7.0350 (1.3); 7.0319 (1.6); 7.0201 (1.6); 7.0174 (1.6); 7.0054 (0.6); 7.0028 (0.5); 6.0858 (1.4); 6.0832 (1.7); 6.0695 (1.3); 6.0672 (1.4); 3.5619 (1.1); 3.5282 (1.6); 3.3622 (1.8); 3.3286 (1.2); 2.7586 (16.0); 1.6772 (11.0); 1.6656 (11.8); 1.5339 (48.1); 1.2540 (1.0); 1.2443 (0.3); 0.1164 (0.3); 0.0063 (2.6); −0.0003 (94.7); −0.0068 (3.1); −0.1200 (0.4)
I.192: $^1$H-NMR(500.1 MHz, CDCl3):
δ = 8.7126 (3.4); 8.7075 (3.3); 8.1272 (1.6); 8.1099 (4.7); 8.1051 (2.6); 7.8372 (1.4); 7.8349 (1.6); 7.8211 (1.6); 7.8184 (2.0); 7.7684 (1.2); 7.7654 (1.1); 7.7545 (1.4); 7.7515 (2.1); 7.7488 (1.0); 7.7377 (1.2); 7.7348 (1.0); 7.6145 (1.2); 7.6123 (1.2); 7.5983 (2.0); 7.5960 (1.2); 7.5839 (0.9); 7.5820 (0.8); 7.2591 (38.9); 7.1999 (1.7); 7.1942 (1.7); 7.1796 (1.7); 7.1739 (1.7); 6.8809 (1.0); 6.8752 (1.0); 6.8664 (1.1); 6.8631 (1.3); 6.8608 (1.1); 6.8573 (1.1); 6.8486 (1.2); 6.8428 (1.0); 6.6914 (2.0); 6.6810 (2.0); 6.6735 (1.7); 6.6631 (1.6); 3.4501 (0.8); 3.4360 (2.9); 3.4219 (2.7); 3.4077 (0.8); 1.6265 (16.0); 1.5819 (16.2); 1.5682 (11.1); 1.5542 (10.8); 1.5437 (18.6); 0.0061 (1.4); −0.0003 (40.6); −0.0070 (1.7)
I.193: $^1$H-NMR(500.1 MHz, CDCl3):
δ = 8.6985 (1.6); 8.6934 (1.5); 8.1290 (0.7); 8.1120 (0.8); 8.0755 (1.0); 8.0706 (1.0); 7.8334 (0.6); 7.8313 (0.6); 7.8170 (0.7); 7.8149 (0.7); 7.7714 (0.4); 7.7686 (0.5); 7.7575 (0.6); 7.7547 (0.9); 7.7517 (0.5); 7.7407 (0.5); 7.7378 (0.5); 7.6163 (0.5); 7.6142 (0.5); 7.6022 (0.5); 7.6002 (0.8); 7.5979 (0.5); 7.5861 (0.4); 7.5840 (0.4); 7.2593 (4.6); 7.1911 (0.7); 7.1853 (0.7); 7.1713 (0.7); 7.1656 (0.7); 6.8949 (0.4); 6.8892 (0.4); 6.8802 (0.4); 6.8769 (0.5); 6.8744 (0.4); 6.8712 (0.5); 6.8623 (0.5); 6.8565 (0.5); 6.7308 (0.8); 6.7204 (0.8); 6.7129 (0.7); 6.7026 (0.7); 3.4111 (5.7); 1.6962 (0.3); 1.6871 (16.0); 1.6810 (0.7); 1.5694 (2.5); −0.0003 (4.8)
I.194: $^1$H-NMR(500.1 MHz, CDCl3):
δ = 8.7659 (1.4); 8.7609 (1.4); 8.2336 (1.0); 8.2289 (0.9); 8.1634 (0.7); 8.1463 (0.7); 7.8763 (0.6); 7.8598 (0.7); 7.8048 (0.4); 7.8021 (0.4); 7.7910 (0.5); 7.7880 (0.8); 7.7852 (0.4); 7.7740 (0.5); 7.7712 (0.4); 7.6402 (0.5); 7.6380 (0.5); 7.6240 (0.8); 7.6100 (0.4); 7.6078 (0.4); 7.2590 (29.5); 6.9569 (0.4); 6.9512 (0.5); 6.9395 (0.4); 6.9336 (0.5); 6.8128 (0.4); 6.4691 (0.6); 6.4595 (0.6); 6.4510 (0.6); 6.4413 (0.6); 3.4048 (2.8); 1.6172 (16.0); 1.5366 (9.4); 0.0061 (1.2); −0.0003 (34.5); −0.0068 (1.4)
I.195: $^1$H-NMR(500.1 MHz, CDCl3):
δ = 8.7437 (8.0); 8.7388 (8.1); 8.1507 (5.9); 8.1337 (6.4); 8.1104 (8.6); 8.1058 (8.6); 7.8407 (5.3); 7.8244 (6.0); 7.7902 (3.4); 7.7874 (3.5); 7.7763 (4.5); 7.7734 (6.6); 7.7707 (3.8); 7.7594 (3.9); 7.7566 (3.5); 7.6263 (4.1); 7.6243 (4.1); 7.6103 (6.6); 7.5962 (3.1); 7.5942 (2.9); 7.2592 (42.1); 7.0473 (0.5); 7.0314 (3.9); 7.0258 (4.2); 7.0140 (3.9); 7.0083 (4.0); 6.8836 (2.3); 6.8778 (2.3); 6.8657 (3.7); 6.8626 (3.4); 6.8504 (2.6); 6.8445 (2.4); 6.6396 (5.2); 6.6298 (5.5); 6.6215 (4.7); 6.6117 (4.4); 3.6435 (5.3); 3.6297 (11.6); 3.6159 (7.4); 3.4882 (10.5); 3.4744 (16.0); 3.4605 (6.8); 3.3925 (0.3); 2.9821 (0.6); 1.5600 (19.9); 1.2553 (0.5); 0.0059 (3.2); −0.0003 (48.4)
I.196: $^1$H-NMR(500.1 MHz, CDCl3):
δ = 8.8899 (1.1); 8.8852 (1.1); 8.2883 (0.7); 8.2853 (0.9); 8.2843 (0.8); 8.2812 (0.7); 7.6620 (0.4); 7.6581 (0.4); 7.6519 (0.4); 7.6481 (0.3); 7.5599 (0.3); 7.5461 (0.3); 7.5410 (0.5); 7.5272 (0.5); 7.2595 (4.8); 7.1161 (1.7); 7.1123 (1.4); 7.1033 (0.8); 7.1006 (0.7); 6.9596 (0.4); 6.9546 (0.4); 6.9471 (0.4); 6.9430 (0.6); 6.9385 (0.5); 6.9302 (0.4); 6.9257 (0.4); 6.5138 (0.8); 6.4983 (0.7); 6.4959 (0.7); 1.8907 (16.0); 1.5443 (3.7); 0.0062 (0.4); −0.0003 (9.3); −0.0069 (0.5)
I.197: $^1$H-NMR(500.1 MHz, CDCl3):
δ = 8.8424 (1.3); 8.8374 (1.3); 8.2755 (0.9); 8.2708 (0.9); 8.1847 (0.6); 8.1676 (0.6); 7.8894 (0.5); 7.8730 (0.6); 7.8250 (0.4); 7.8222 (0.4); 7.8111 (0.5); 7.8081 (0.7); 7.8053 (0.4); 7.7941 (0.4); 7.7914 (0.4); 7.6555 (0.4); 7.6534 (0.4); 7.6415 (0.4); 7.6394 (0.7); 7.6372 (0.4); 7.6253 (0.3); 7.2590 (5.2); 7.1154 (0.4); 7.1023 (1.0); 7.0989 (1.0); 7.0909 (0.6); 7.0882 (0.6); 7.0769 (0.6); 7.0742 (0.8); 6.9371 (0.4); 6.9336 (0.4); 6.9230 (0.4); 6.9203 (0.6); 6.9173 (0.5); 6.9066 (0.4); 6.9032 (0.4); 6.5216 (0.7); 6.5191 (0.7); 6.5053 (0.7); 6.5026 (0.7); 1.9024 (16.0); 1.5540 (0.9); −0.0003 (10.2); −0.0068 (0.4)
I.198: $^1$H-NMR(500.1 MHz, CDCl3):
δ = 8.8326 (4.9); 8.8276 (5.0); 8.1927 (3.3); 8.1877 (3.3); 8.1740 (2.2); 8.1562 (2.5); 7.8641 (1.9); 7.8478 (2.3); 7.8143 (1.6); 7.8116 (1.5); 7.8004 (2.0); 7.7975 (2.9); 7.7946 (1.4); 7.7835 (1.8); 7.7807 (1.5); 7.6441 (1.7); 7.6420 (1.6); 7.6301 (1.6); 7.6279 (2.7); 7.6258 (1.6); 7.6139 (1.2); 7.6118 (1.3); 7.2590 (16.4); 7.1581 (0.9); 7.1544 (1.4); 7.1415 (3.7); 7.1379 (3.9); 7.1335 (2.7); 7.1308 (2.5); 7.1197 (2.6); 7.1170 (2.9); 7.1145 (0.8); 7.1032 (1.1); 7.1003 (1.0); 6.9729 (1.6); 6.9691 (1.7); 6.9592 (1.4); 6.9562 (2.4); 6.9529 (1.8); 6.9426 (1.6); 6.9390 (1.4); 6.6137 (2.6); 6.6113 (2.7); 6.5975 (2.5); 6.5948 (2.5); 5.2234 (1.2); 5.2108 (4.2); 5.1980 (4.1); 5.1852 (1.2); 1.8752 (15.6); 1.8625 (16.0); 1.5598 (6.4); 1.2545 (0.5); 0.0061 (0.9); −0.0003 (31.2); −0.0070 (0.9)
I.199: $^1$H-NMR(500.1 MHz, CDCl3):
δ = 8.8294 (3.3); 8.8244 (3.4); 8.1759 (4.6); 8.1708 (2.9); 8.1608 (2.0); 7.8656 (1.6); 7.8636 (1.6); 7.8494 (1.9); 7.8471 (1.9); 7.8204 (1.1); 7.8175 (1.0); 7.8065 (1.4); 7.8034 (2.0); 7.8004 (1.1); 7.7892 (1.2); 7.7866 (1.0); 7.6488 (1.3); 7.6467 (1.3); 7.6326 (2.0); 7.6186 (1.0); 7.6164 (0.9); 7.2592 (10.8); 7.2024 (1.2); 7.1993 (1.4); 7.1859 (2.8); 7.1828 (2.7); 7.1642 (1.6); 7.1613 (1.5); 7.1499 (1.8); 7.1472 (2.1); 7.1450 (1.0); 7.1334 (1.0);

| TABLE 12-continued |
|---|
| NMR peak lists |

7.1304 (0.9); 7.0032 (1.2); 7.0000 (1.2); 6.9889 (1.3); 6.9864 (1.9); 6.9837 (1.5); 6.9726 (1.2); 6.9694 (1.1);
6.6576 (2.1); 6.6549 (2.1); 6.6412 (2.0); 6.6384 (1.9); 5.2970 (0.4); 5.1536 (16.0); 4.9321 (0.5); 1.5667 (3.7);
1.2546 (0.5); 0.0699 (0.4); 0.0062 (0.6); −0.0003 (13.2); −0.0067 (0.6)
I.200: $^1$H-NMR(500.1 MHz, CDCl3):
δ = 8.7779 (2.5); 8.7730 (2.6); 8.2384 (2.8); 8.2334 (2.8); 7.8766 (1.0); 7.8739 (1.1); 7.8609 (1.1); 7.8580 (1.1);
7.5791 (1.0); 7.5688 (1.1); 7.5609 (1.5); 7.5506 (1.4); 7.4922 (1.6); 7.4741 (1.2); 7.4704 (1.7); 7.4522 (1.1);
7.3620 (0.4); 7.3472 (1.0); 7.3327 (0.6); 7.2939 (0.9); 7.2920 (1.0); 7.2778 (1.3); 7.2596 (36.9); 6.5477 (1.2);
6.5312 (1.2); 4.2889 (10.2); 4.2847 (9.9); 1.7676 (16.0); 1.5416 (55.0); 0.0690 (0.9); 0.0062 (1.3); −0.0003 (40.8); −0.0070
(1.5)
I.201: $^1$H-NMR(500.1 MHz, CDCl3):
δ = 8.7427 (2.5); 8.7378 (2.6); 8.2290 (1.4); 8.2250 (1.7); 8.2214 (1.4); 7.8732 (1.0); 7.8705 (1.1); 7.8574 (1.1);
7.8546 (1.1); 7.6682 (1.1); 7.6647 (1.1); 7.6500 (1.4); 7.6465 (1.4); 7.4934 (1.2); 7.4786 (1.3); 7.4752 (1.1);
7.4605 (1.0); 7.3614 (0.4); 7.3470 (1.0); 7.3321 (0.6); 7.2880 (0.9); 7.2861 (0.9); 7.2713 (1.3); 7.2602 (13.0);
6.5476 (1.2); 6.5310 (1.2); 4.1176 (11.7); 1.7698 (16.0); 1.5550 (16.2); 0.0697 (0.4); 0.0061 (0.5); −0.0003 (15.0); −0.0071
(0.5)
I.202: $^1$H-NMR(500.1 MHz, CDCl3):
δ = 8.8014 (2.6); 8.7967 (2.7); 8.2602 (1.7); 8.2571 (2.0); 8.2530 (1.7); 7.6777 (0.7); 7.6709 (1.4); 7.6678 (1.0);
7.6628 (1.6); 7.6559 (1.6); 7.6520 (1.6); 7.6457 (1.0); 7.5564 (0.8); 7.5426 (0.8); 7.5374 (1.2); 7.5237 (1.2);
7.5187 (0.6); 7.5049 (0.6); 7.2596 (28.4); 7.2243 (0.5); 7.2141 (2.6); 7.2098 (1.9); 7.2042 (2.5); 7.1992 (1.6);
7.1960 (2.2); 7.1942 (2.0); 7.1847 (0.4); 6.4681 (1.6); 6.4637 (0.9); 6.4580 (1.3); 6.4545 (1.0); 6.4492 (1.5);
4.9071 (2.2); 4.8840 (2.3); 3.2648 (2.6); 3.2416 (2.5); 2.0050 (0.4); 1.6921 (15.8); 1.6350 (16.0); 1.5448 (31.2);
1.2536 (0.3); 0.0692 (0.5); 0.0063 (1.0); −0.0003 (32.7); −0.0068 (1.1)
I.203: $^1$H-NMR(500.1 MHz, CDCl3):
δ = 8.8483 (1.3); 8.8434 (1.3); 8.2874 (1.4); 8.2824 (1.4); 8.2568 (0.7); 8.2536 (0.8); 8.2408 (0.8); 8.2377 (0.8);
7.5998 (0.5); 7.5895 (0.6); 7.5816 (0.8); 7.5714 (0.7); 7.5081 (0.8); 7.4913 (0.6); 7.4899 (0.8); 7.4884 (0.7);
7.4863 (0.9); 7.4770 (0.6); 7.4742 (0.7); 7.4716 (0.6); 7.4682 (0.7); 7.4605 (0.5); 7.4571 (0.5); 7.2786 (0.5);
7.2768 (0.6); 7.2610 (4.7); 7.2483 (0.5); 7.2464 (0.5); 6.6441 (0.8); 6.6287 (0.8); 6.6275 (0.8); 4.3000 (5.4);
4.2958 (5.6); 1.7877 (16.0); 1.5621 (2.0); 0.0703 (0.5); −0.0003 (5.0)
I.204: $^1$H-NMR(500.1 MHz, CDCl3):
δ = 8.8138 (1.3); 8.8090 (1.3); 8.2750 (0.7); 8.2718 (0.9); 8.2675 (0.7); 8.2542 (0.7); 8.2511 (0.8); 8.2383 (0.8);
8.2352 (0.7); 7.6900 (0.6); 7.6865 (0.6); 7.6718 (0.7); 7.6683 (0.7); 7.5099 (0.6); 7.4952 (0.7); 7.4917 (1.0);
7.4884 (0.5); 7.4771 (1.1); 7.4746 (0.7); 7.4717 (0.5); 7.4605 (0.5); 7.4571 (0.5); 7.2737 (0.5); 7.2718 (0.6);
7.2598 (10.0); 7.2433 (0.5); 7.2414 (0.5); 6.6476 (0.8); 6.6464 (0.8); 6.6309 (0.8); 6.6296 (0.8); 4.1265 (6.1);
1.7899 (16.0); 1.5467 (7.5); 0.0061 (0.4); −0.0003 (10.8); −0.0070 (0.4)
I.205: $^1$H-NMR(500.1 MHz, CDCl3):
δ = 8.8173 (14.8); 8.8123 (15.3); 8.2970 (10.0); 8.2922 (9.8); 8.2593 (7.9); 8.2562 (8.2); 8.2435 (8.1); 8.2402
(7.8); 8.2030 (6.8); 8.1869 (7.5); 8.1860 (7.5); 7.9166 (5.9); 7.9143 (6.3); 7.9001 (6.7); 7.8979 (7.2); 7.8490
(4.7); 7.8461 (5.1); 7.8351 (5.9); 7.8322 (9.4); 7.8291 (5.0); 7.8181 (5.2); 7.8152 (5.2); 7.6794 (5.0); 7.6772
(5.3); 7.6653 (4.8); 7.6632 (8.7); 7.6609 (5.3); 7.6492 (3.9); 7.6469 (4.0); 7.4792 (4.8); 7.4760 (4.7); 7.4647
(6.3); 7.4617 (7.0); 7.4593 (5.5); 7.4482 (5.7); 7.4448 (5.4); 7.2713 (5.8); 7.2694 (6.7); 7.2598 (121.1); 7.2553
(11.8); 7.2538 (8.4); 7.2410 (5.4); 7.2390 (5.1); 7.0481 (0.7); 6.6685 (8.6); 6.6671 (8.6); 6.6517 (8.4); 6.6504
(8.3); 2.4924 (12.7); 2.0042 (4.1); 1.9229 (0.6); 1.9136 (1.7); 1.9027 (8.1); 1.8950 (8.5); 1.8890 (16.0); 1.8753
(6.9); 1.8629 (1.4); 1.5571 (68.0); 1.3704 (0.5); 1.3330 (0.6); 1.2851 (1.2); 1.2564 (1.6); 0.8805 (0.6); 0.8664
(0.4); 0.8436 (0.7); 0.8377 (0.7); 0.1164 (0.5); 0.0693 (3.5); 0.0062 (4.6); −0.0003 (116.8); −0.0069 (4.2); −0.1201
(0.4)
I.206: $^1$H-NMR(500.1 MHz, CDCl3):
δ = 8.8094 (2.2); 8.8047 (2.3); 8.2858 (1.4); 8.2830 (1.6); 8.2815 (1.6); 8.2785 (1.4); 7.8896 (1.0); 7.8868 (1.0);
7.8738 (1.1); 7.8710 (1.1); 7.6930 (0.5); 7.6891 (0.5); 7.6830 (0.6); 7.6791 (0.6); 7.6747 (0.7); 7.6708 (0.7);
7.6646 (0.7); 7.6608 (0.6); 7.5742 (0.6); 7.5605 (0.7); 7.5553 (1.0); 7.5416 (1.0); 7.5367 (0.5); 7.5229 (0.5);
7.3814 (0.4); 7.3673 (1.0); 7.3527 (0.7); 7.3161 (0.9); 7.3140 (1.0); 7.3003 (1.3); 7.2856 (0.6); 7.2837 (0.6);
7.2597 (9.9); 6.5510 (1.2); 6.5345 (1.1); 1.7664 (16.0); 1.5484 (9.5); 0.0061 (0.3); −0.0003 (12.5); −0.0069 (0.4)
I.207: $^1$H-NMR(500.1 MHz, CDCl3):
δ = 8.7308 (1.4); 8.7258 (1.4); 8.2382 (1.0); 8.2333 (1.0); 8.1488 (0.7); 8.1317 (0.8); 7.8673 (0.6); 7.8520 (0.7);
7.7881 (0.4); 7.7855 (0.4); 7.7744 (0.6); 7.7715 (0.8); 7.7575 (0.5); 7.7547 (0.5); 7.6299 (0.5); 7.6139 (0.8);
7.5977 (0.4); 7.4656 (0.7); 7.2590 (124.8); 7.2022 (0.7); 7.1964 (0.7); 7.1815 (0.7); 7.1757 (0.7); 7.0474 (0.7);
6.8166 (0.4); 6.8110 (0.4); 6.8024 (0.4); 6.7984 (0.6); 6.7928 (0.5); 6.7842 (0.4); 6.7785 (0.4); 6.5066 (0.8);
6.4963 (0.8); 6.4885 (0.7); 6.4782 (0.6); 1.8134 (0.5); 1.6352 (16.0); 1.5816 (16.6); 1.5334 (61.3); 1.3129 (0.4);
1.2846 (0.5); 1.2539 (1.5); 0.8808 (0.5); 0.1163 (0.6); 0.0866 (0.3); 0.0759 (0.6); 0.0689 (13.4); 0.0615 (0.5);
0.0062 (4.7); −0.0003 (145.0); −0.0069 (4.4); −0.1201 (0.5)
I.208: $^1$H-NMR(500.1 MHz, CDCl3):
δ = 8.7507 (15.6); 8.7457 (16.0); 8.1492 (8.5); 8.1431 (12.8); 8.1377 (13.2); 8.1335 (9.7); 7.8473 (7.2); 7.8311
(8.3); 7.7902 (5.2); 7.7873 (5.1); 7.7763 (6.8); 7.7732 (9.7); 7.7702 (5.1); 7.7592 (5.8); 7.7563 (5.2); 7.6271
(5.9); 7.6250 (6.0); 7.6130 (5.8); 7.6110 (9.8); 7.6088 (5.8); 7.5970 (4.5); 7.5948 (4.5); 7.4657 (0.7); 7.2593
(135.3); 7.0476 (0.8); 6.9878 (5.4); 6.9820 (5.7); 6.9703 (5.3); 6.9646 (5.7); 6.8622 (3.1); 6.8565 (3.0); 6.8440
(4.5); 6.8404 (4.0); 6.8289 (3.6); 6.8231 (3.3); 6.5912 (8.3); 6.5814 (8.4); 6.5731 (7.2); 6.5634 (7.1); 3.6163
(3.3); 3.6056 (5.4); 3.6007 (2.0); 3.5882 (5.8); 3.5768 (13.1); 3.5636 (4.3); 3.5630 (4.8); 3.5522 (3.2); 3.5390
(1.0); 3.3858 (2.7); 3.3636 (4.4); 3.3488 (3.8); 3.3359 (1.1); 1.5846 (1.8); 1.5765 (40.2); 1.5633
(41.4); 1.5486 (55.9); 1.3455 (1.0); 1.3332 (0.4); 1.2843 (0.7); 1.2552 (2.0); 0.8804 (0.4); 0.1164 (0.5); 0.0063
(4.9); −0.0003 (156.1); −0.0068 (5.4); −0.1200 (0.5)
I.209: $^1$H-NMR(500.1 MHz, CDCl3):
δ = 8.8027 (1.5); 8.7978 (1.5); 8.2809 (1.1); 8.2763 (1.0); 8.1880 (0.7); 8.1707 (0.8); 7.8912 (0.6); 7.8745 (0.7);
7.8221 (0.4); 7.8193 (0.5); 7.8082 (0.6); 7.8053 (0.9); 7.8024 (0.4); 7.7912 (0.5); 7.7885 (0.5); 7.7282 (0.7);
7.7251 (0.7); 7.7126 (0.8); 7.7093 (0.8); 7.6480 (0.5); 7.6460 (0.5); 7.6320 (0.8); 7.6298 (0.5); 7.6179 (0.4);
7.6159 (0.4); 7.2598 (31.7); 7.1544 (0.6); 7.1515 (0.6); 7.1384 (0.6); 7.1351 (0.6); 7.1170 (0.6); 7.1143 (0.6);
7.1013 (0.7); 7.0991 (0.8); 7.0867 (0.4); 7.0842 (0.3); 6.4460 (0.8); 6.4435 (0.9); 6.4296 (0.8); 6.4272 (0.8);
5.9197 (2.3); 5.5629 (2.2); 1.7752 (16.0); 1.5516 (66.4); 1.2858 (0.4); 1.2534 (1.4); 0.0690 (1.2); 0.0061 (0.9); −0.0003
(28.2); −0.0070 (1.0)

TABLE 12-continued

NMR peak lists

I.210: ¹H-NMR(500.1 MHz, d₆-DMSO):
δ = 12.3166 (3.6); 8.8368 (7.4); 8.8318 (7.7); 8.4189 (4.9); 8.4141 (4.9); 8.1333 (3.2); 8.1303 (3.4); 8.1173 (3.6); 8.1142 (3.6); 8.1020 (3.3); 8.0849 (3.8); 8.0732 (3.2); 8.0566 (3.2); 7.8678 (2.0); 7.8649 (2.1); 7.8540 (2.6); 7.8510 (3.9); 7.8480 (2.1); 7.8370 (2.3); 7.8342 (2.1); 7.7069 (2.2); 7.7048 (2.3); 7.6908 (3.8); 7.6768 (1.8); 7.6746 (1.8); 7.3719 (1.6); 7.3688 (1.7); 7.3573 (2.6); 7.3546 (2.9); 7.3411 (2.5); 7.3379 (2.5); 7.2864 (2.3); 7.2841 (2.6); 7.2699 (3.6); 7.2558 (1.9); 7.2534 (1.9); 6.8202 (3.7); 6.8183 (3.9); 6.8038 (3.7); 6.8019 (3.6); 4.9456 (16.0); 3.3074 (73.8); 2.6349 (0.4); 2.5072 (24.1); 2.5036 (52.1); 2.5000 (72.5); 2.4963 (52.1); 2.4928 (24.8); 2.3611 (0.4); 1.2363 (0.4); 1.1467 (0.4); 0.0061 (0.8); −0.0003 (24.1); −0.0071 (0.8)

I.211: ¹H-NMR(500.1 MHz, CDCl3):
δ = 8.7624 (3.5); 8.7574 (3.6); 8.2500 (2.5); 8.2452 (2.5); 8.1831 (1.8); 8.1656 (1.9); 7.8857 (1.6); 7.8694 (1.8); 7.8221 (1.1); 7.8193 (1.1); 7.8082 (1.4); 7.8053 (2.1); 7.8023 (1.1); 7.7912 (1.2); 7.7884 (1.1); 7.6970 (1.7); 7.6920 (1.3); 7.6851 (1.0); 7.6818 (1.2); 7.6779 (1.8); 7.6503 (1.2); 7.6482 (1.2); 7.6342 (2.0); 7.6322 (1.2); 7.6201 (0.9); 7.6180 (0.9); 7.2598 (23.1); 7.2208 (0.4); 7.2172 (0.6); 7.2064 (1.8); 7.2023 (2.3); 7.1941 (3.8); 7.1876 (2.1); 7.1818 (1.3); 7.1702 (0.4); 6.4654 (1.3); 6.4617 (1.0); 6.4583 (0.5); 6.4526 (1.2); 6.4480 (1.2); 2.0489 (9.2); 2.0016 (9.2); 1.7298 (16.0); 1.7023 (8.4); 1.6963 (8.4); 1.5630 (53.5); 1.5235 (0.4); 1.2551 (0.5); 0.0694 (0.9); 0.0061 (0.6); −0.0003 (20.3); −0.0068 (0.8)

I.212: ¹H-NMR(500.1 MHz, CDCl3):
δ = 8.6939 (2.2); 8.6889 (2.3); 8.3034 (1.5); 8.2988 (1.4); 8.1356 (1.0); 8.1193 (1.1); 7.8673 (0.9); 7.8651 (0.9); 7.8487 (1.0); 7.7741 (0.7); 7.7712 (0.7); 7.7602 (0.9); 7.7572 (1.3); 7.7543 (0.6); 7.7432 (0.8); 7.7404 (0.7); 7.6183 (0.7); 7.6161 (0.7); 7.6044 (0.7); 7.6021 (1.2); 7.5999 (0.7); 7.5881 (0.6); 7.5859 (0.5); 7.5289 (1.0); 7.5255 (0.7); 7.5235 (0.7); 7.5144 (1.2); 7.5100 (1.1); 7.2601 (12.2); 7.2145 (0.4); 7.2037 (1.2); 7.1998 (1.1); 7.1910 (1.2); 7.1893 (1.5); 7.1867 (1.5); 7.1843 (1.2); 7.1763 (1.1); 7.1728 (1.1); 7.1615 (0.4); 6.6177 (1.1); 6.6138 (1.2); 6.6037 (0.7); 6.6018 (0.8); 6.5990 (1.1); 3.3661 (16.0); 1.8232 (10.7); 1.6942 (9.9); 1.5703 (23.8); 1.5555 (10.0); 0.0693 (0.5); 0.0061 (0.4); −0.0003 (11.0); −0.0071 (0.4)

I.213: ¹H-NMR(500.1 MHz, CDCl3):
δ = 8.7756 (2.1); 8.7706 (2.2); 8.2330 (1.9); 8.2285 (1.8); 8.1730 (1.5); 8.1550 (1.6); 7.8819 (1.3); 7.8655 (1.5); 7.8136 (1.0); 7.8107 (1.0); 7.7997 (2.8); 7.7966 (3.6); 7.7937 (1.2); 7.7831 (2.2); 7.7803 (2.4); 7.6486 (1.1); 7.6465 (1.1); 7.6346 (1.1); 7.6324 (1.8); 7.6303 (1.1); 7.6184 (0.8); 7.6162 (0.8); 7.2598 (37.1); 7.2251 (0.7); 7.2225 (0.9); 7.2105 (1.5); 7.2080 (1.6); 7.1949 (1.3); 7.1921 (1.3); 7.1784 (1.3); 7.1751 (1.4); 7.1637 (0.9); 7.1620 (1.4); 7.1607 (1.1); 7.1589 (1.5); 7.1477 (0.8); 7.1444 (0.7); 6.5198 (1.7); 6.5172 (1.6); 6.5036 (1.8); 6.5009 (1.7); 4.0538 (2.2); 1.7837 (9.4); 1.7816 (9.3); 1.7306 (16.0); 1.6205 (13.8); 1.5591 (59.4); 1.3009 (0.4); 1.2869 (0.3); 1.2532 (1.0); 0.0691 (1.4); 0.0060 (1.1); −0.0003 (34.7); −0.0071 (1.2)

I.214: ¹H-NMR(500.1 MHz, CDCl3):
δ = 8.7505 (2.3); 8.7455 (2.4); 8.2316 (1.5); 8.2267 (1.5); 8.1687 (1.0); 8.1517 (1.1); 7.8764 (0.8); 7.8740 (0.9); 7.8600 (1.0); 7.8577 (1.0); 7.8063 (0.7); 7.8035 (0.8); 7.7924 (0.9); 7.7895 (1.4); 7.7865 (0.7); 7.7755 (0.8); 7.7726 (0.8); 7.6364 (0.8); 7.6342 (0.8); 7.6225 (0.7); 7.6202 (1.3); 7.6180 (0.8); 7.6063 (0.6); 7.6041 (0.6); 7.5787 (0.6); 7.5771 (0.6); 7.5726 (0.4); 7.5710 (0.7); 7.5680 (0.7); 7.5652 (0.5); 7.5627 (0.5); 7.5599 (0.7); 7.5583 (0.7); 7.2595 (18.9); 7.1636 (2.0); 7.1589 (1.2); 7.1531 (1.6); 7.1496 (0.9); 7.1487 (0.9); 7.1453 (1.8); 6.4703 (1.1); 6.4655 (0.5); 6.4607 (0.8); 6.4570 (0.7); 6.4515 (1.1); 4.7476 (2.4); 3.9030 (16.0); 1.7348 (10.4); 1.5576 (19.9); 1.4833 (11.2); 1.2554 (0.4); 0.0695 (0.6); 0.0064 (0.6); −0.0003 (17.9); −0.0068 (0.6)

I.215: ¹H-NMR(500.1 MHz, CDCl3):
δ = 8.7565 (3.1); 8.7515 (3.2); 8.2420 (2.2); 8.2373 (2.2); 8.1803 (1.6); 8.1640 (1.7); 7.8866 (1.4); 7.8705 (1.6); 7.8227 (1.0); 7.8200 (1.0); 7.8088 (1.3); 7.8059 (1.9); 7.8030 (1.0); 7.7918 (1.2); 7.7891 (1.0); 7.6549 (1.4); 7.6528 (1.4); 7.6497 (1.7); 7.6446 (1.0); 7.6431 (0.9); 7.6410 (0.9); 7.6364 (3.2); 7.6224 (0.9); 7.6203 (0.9); 7.2595 (23.9); 7.1959 (0.4); 7.1872 (3.9); 7.1813 (2.2); 7.1797 (2.2); 7.1759 (2.2); 7.1742 (1.9); 7.1683 (3.5); 7.1613 (0.4); 7.1595 (0.4); 6.4774 (1.6); 6.4719 (0.8); 6.4688 (0.9); 6.4651 (1.2); 6.4585 (1.5); 4.8997 (2.3); 4.8764 (2.4); 3.3564 (3.0); 3.3331 (3.0); 1.7035 (15.6); 1.6495 (16.0); 1.5573 (40.7); 1.2535 (1.0); 0.0692 (0.8); 0.0061 (0.9); −0.0003 (26.3); −0.0070 (1.0)

I.216: ¹H-NMR(500.1 MHz, CDCl3):
δ = 8.7747 (3.8); 8.7697 (4.0); 8.2400 (2.7); 8.2353 (2.6); 8.1837 (1.8); 8.1667 (2.0); 7.8874 (1.7); 7.8710 (1.9); 7.8258 (1.2); 7.8230 (1.2); 7.8119 (1.5); 7.8090 (2.4); 7.8060 (1.2); 7.7950 (1.4); 7.7921 (1.3); 7.6526 (2.6); 7.6481 (1.4); 7.6459 (1.0); 7.6387 (3.6); 7.6246 (1.1); 7.6225 (1.1); 7.2596 (37.8); 7.2450 (0.4); 7.2412 (0.5); 7.2304 (1.2); 7.2265 (1.2); 7.2192 (1.9); 7.2148 (3.2); 7.2109 (1.4); 7.2045 (1.9); 7.2013 (1.8); 7.1897 (0.6); 7.1865 (0.4); 6.5152 (1.4); 6.5028 (1.1); 6.5005 (1.6); 5.8503 (2.3); 5.7488 (2.3); 2.0045 (0.5); 1.7654 (16.0); 1.6059 (10.4); 1.6028 (10.6); 1.5526 (81.3); 1.2563 (0.5); 0.0692 (1.2); 0.0063 (1.4); −0.0003 (38.8); −0.0068 (1.7)

I.217: ¹H-NMR(500.1 MHz, CDCl3):
δ = 8.7462 (0.6); 8.7286 (0.7); 8.4637 (1.4); 8.4600 (1.4); 7.9285 (0.6); 7.9121 (0.7); 7.8508 (1.3); 7.8474 (1.0); 7.8396 (0.5); 7.8366 (0.7); 7.8334 (0.4); 7.8220 (0.5); 7.8194 (0.4); 7.7518 (0.5); 7.7497 (0.5); 7.7356 (0.7); 7.7216 (0.3); 7.2596 (9.4); 6.8566 (0.6); 6.8511 (0.7); 6.8386 (0.7); 6.8331 (0.7); 6.7131 (0.4); 6.7098 (0.5); 6.7077 (0.4); 6.7043 (0.4); 6.6950 (0.5); 6.6895 (0.4); 6.6148 (0.7); 6.6043 (0.8); 6.5967 (0.5); 6.5862 (0.5); 1.8642 (16.0); 1.5469 (6.2); 0.0061 (0.6); −0.0003 (17.8); −0.0070 (0.6)

I.218: ¹H-NMR(500.1 MHz, CDCl3):
δ = 9.0640 (0.5); 9.0592 (6.6); 9.0535 (0.4); 8.1825 (1.4); 8.1793 (1.6); 8.1666 (1.3); 8.1655 (1.4); 8.1630 (1.6); 7.9226 (1.3); 7.9219 (1.3); 7.9196 (1.3); 7.9180 (1.2); 7.9060 (2.0); 7.9025 (1.7); 7.8196 (1.7); 7.8164 (0.9); 7.8057 (1.7); 7.8026 (1.6); 7.8000 (0.9); 7.7897 (1.8); 7.7860 (1.6); 7.7824 (1.6); 7.7789 (1.6); 7.7685 (1.6); 7.7657 (1.4); 7.7629 (1.3); 7.7521 (0.7); 7.7490 (0.6); 7.2636 (0.5); 7.2587 (7.3); 7.2548 (0.8); 7.2435 (0.9); 7.2409 (2.1); 7.2379 (1.5); 7.2319 (0.3); 7.2269 (1.8); 7.2240 (1.8); 7.2115 (2.5); 7.2083 (2.7); 7.1948 (1.2); 7.1915 (1.0); 7.0278 (1.2); 7.0245 (1.0); 7.0138 (1.2); 7.0113 (1.7); 7.0081 (1.3); 6.9975 (1.3); 6.9941 (1.1); 6.7838 (2.0); 6.7810 (2.0); 6.7675 (1.7); 6.7647 (1.8); 5.1600 (1.2); 5.1551 (16.0); 5.1494 (0.9); 5.1461 (0.5); 1.5554 (0.8); 1.5505 (9.6); 1.5448 (0.5); 0.0060 (0.8); 0.0047 (1.0); −0.0003 (13.5); −0.0063 (0.8); −0.0094 (0.4)

I.219: ¹H-NMR(500.1 MHz, CDCl3):
δ = 8.8462 (1.3); 8.8415 (1.3); 8.2966 (0.8); 8.2930 (1.1); 8.2897 (0.9); 7.7413 (0.7); 7.7382 (0.7); 7.7257 (0.8); 7.7225 (0.8); 7.6764 (0.3); 7.6701 (0.3); 7.6663 (0.4); 7.6619 (0.4); 7.6581 (0.4); 7.6518 (0.4); 7.6481 (0.4); 7.5517 (0.4); 7.5379 (0.4); 7.5327 (0.6); 7.5190 (0.6); 7.2599 (29.0); 7.1891 (0.4); 7.1772 (0.6); 7.1746 (0.7); 7.1615 (0.6); 7.1582 (0.6); 7.1441 (0.6); 7.1414 (0.7); 7.1285 (0.8); 7.1263 (0.8); 7.1139 (0.4); 7.1114 (0.3);

TABLE 12-continued

| NMR peak lists |
| --- |

6.4306 (0.8); 6.4283 (0.9); 6.4143 (0.8); 6.4120 (0.8); 5.9315 (2.3); 5.5727 (2.2); 1.7875 (0.4); 1.7640 (16.0); 1.5546 (24.1); 1.5074 (0.4); 1.4118 (0.6); 1.2850 (0.8); 1.2770 (0.4); 1.2554 (1.8); 0.8803 (0.5); 0.8665 (0.4); 0.8438 (0.4); 0.8380 (0.4); 0.0061 (2.0); −0.0003 (59.4); −0.0068 (2.3)

I.220: $^1$H-NMR(500.1 MHz, CDCl3):
δ = 8.8256 (1.3); 8.8206 (1.3); 8.2423 (0.9); 8.2374 (0.8); 8.1767 (0.6); 8.1597 (0.6); 7.8830 (0.5); 7.8664 (0.6); 7.8241 (0.4); 7.8213 (0.4); 7.8102 (0.5); 7.8073 (0.7); 7.8044 (0.4); 7.7932 (0.4); 7.7904 (0.4); 7.6581 (0.4); 7.6561 (0.4); 7.6441 (0.4); 7.6420 (0.7); 7.6399 (0.4); 7.2591 (7.2); 6.8638 (0.6); 6.8583 (0.6); 6.8457 (0.6); 6.8401 (0.6); 6.6875 (0.3); 6.6726 (0.4); 6.6694 (0.5); 6.6671 (0.4); 6.6639 (0.4); 6.6545 (0.4); 6.6489 (0.4); 6.5324 (0.7); 6.5217 (0.7); 6.5142 (0.5); 6.5036 (0.5); 1.8903 (16.0); 1.5475 (5.3); 0.0061 (0.4); −0.0003 (13.0); −0.0070 (0.5)

I.221: $^1$H-NMR(500.1 MHz, CDCl3):
δ = 8.8155 (3.5); 8.8104 (3.7); 8.1682 (1.8); 8.1512 (1.9); 8.1014 (2.5); 8.0966 (2.6); 7.8505 (1.6); 7.8341 (1.9); 7.8165 (1.1); 7.8137 (1.1); 7.8026 (1.4); 7.7997 (2.1); 7.7967 (1.1); 7.7857 (1.2); 7.7828 (1.1); 7.6490 (1.2); 7.6469 (1.3); 7.6350 (1.2); 7.6329 (2.0); 7.6309 (1.3); 7.6188 (0.9); 7.6167 (0.9); 7.2595 (8.8); 6.9453 (1.7); 6.9398 (1.8); 6.9274 (1.7); 6.9220 (1.8); 6.7664 (0.8); 6.7609 (0.7); 6.7515 (0.8); 6.7482 (1.6); 6.7465 (1.0); 6.7428 (1.4); 6.7335 (1.4); 6.7281 (1.4); 6.7060 (2.2); 6.6952 (2.3); 6.6879 (1.2); 6.6770 (1.1); 5.1227 (16.0); 1.5637 (12.4); 0.0061 (0.4); −0.0003 (16.9); −0.0066 (0.6)

I.222: $^1$H-NMR(500.1 MHz, CDCl3):
δ = 8.7135 (5.6); 8.6960 (5.8); 8.3494 (11.6); 8.3456 (11.8); 8.0071 (0.6); 7.9213 (0.4); 7.9005 (5.1); 7.8838 (6.0); 7.8219 (3.2); 7.8193 (3.4); 7.8080 (4.6); 7.8051 (5.8); 7.8018 (3.5); 7.7905 (4.3); 7.7879 (4.2); 7.7781 (8.2); 7.7755 (8.2); 7.7246 (4.4); 7.7223 (4.4); 7.7083 (6.6); 7.7061 (4.1); 7.6943 (2.9); 7.6921 (2.7); 7.4666 (0.4); 7.3994 (0.3); 7.3838 (0.6); 7.2601 (74.7); 7.0484 (0.4); 7.0306 (3.7); 7.0249 (4.0); 7.0133 (3.7); 7.0076 (4.0); 6.9310 (2.2); 6.9253 (2.0); 6.9129 (3.4); 6.9073 (2.9); 6.8977 (2.8); 6.8920 (2.4); 6.7479 (5.7); 6.7382 (5.8); 6.7299 (4.8); 6.7202 (4.6); 5.2984 (2.3); 3.7290 (0.7); 3.7150 (0.7); 3.6170 (4.6); 3.6031 (11.0); 3.5893 (6.9); 3.4899 (0.5); 3.4721 (10.3); 3.4584 (16.0); 3.4444 (6.5); 1.5597 (5.9); 1.4217 (0.4); 1.3331 (0.4); 1.2842 (0.8); 1.2800 (0.9); 1.2576 (4.1); 1.2552 (4.2); 1.2437 (2.2); 1.2296 (1.2); 0.8938 (0.4); 0.8801 (0.8); 0.8662 (0.4); 0.8461 (0.4); 0.1163 (0.5); 0.0063 (4.0); −0.0003 (145.8); −0.0068 (4.6); −0.1199 (0.5)

I.223: $^1$H-NMR(500.1 MHz, CDCl3):
δ = 8.7222 (1.7); 8.7048 (1.8); 8.4264 (3.8); 8.4226 (3.7); 7.9036 (1.5); 7.8874 (1.8); 7.8413 (1.0); 7.8386 (1.0); 7.8273 (1.5); 7.8243 (1.7); 7.8211 (1.0); 7.8098 (1.4); 7.8071 (1.2); 7.7416 (1.4); 7.7394 (1.3); 7.7254 (4.7); 7.7232 (3.6); 7.7114 (1.0); 7.7092 (0.8); 7.2601 (17.4); 6.9387 (1.3); 6.9367 (1.4); 6.9348 (1.4); 6.9326 (1.3); 6.9210 (1.3); 6.9177 (1.7); 6.9148 (1.3); 6.7930 (2.5); 6.7886 (3.7); 6.7789 (3.6); 6.7757 (4.2); 5.2983 (0.6); 5.1077 (16.0); 1.5580 (4.9); 1.2573 (0.9); 1.2434 (0.7); 1.2294 (0.3); 0.0060 (1.2); −0.0003 (34.5); −0.0071 (1.0); −0.0095 (0.4)

I.224: $^1$H-NMR(500.1 MHz, CDCl3):
δ = 8.8766 (3.0); 8.8718 (3.0); 8.1914 (1.9); 8.1882 (2.3); 8.1841 (1.9); 7.6576 (0.7); 7.6537 (0.7); 7.6475 (0.7); 7.6437 (0.7); 7.6393 (1.0); 7.6354 (1.0); 7.6292 (1.0); 7.6254 (0.9); 7.5552 (0.9); 7.5415 (0.9); 7.5362 (1.4); 7.5226 (1.4); 7.5176 (0.7); 7.5039 (0.6); 7.2592 (26.4); 7.2163 (0.8); 7.2128 (1.1); 7.1997 (2.8); 7.1962 (2.8); 7.1902 (1.6); 7.1875 (1.6); 7.1763 (1.7); 7.1735 (2.0); 7.1597 (0.7); 7.1569 (0.7); 7.0257 (1.1); 7.0221 (1.1); 7.0117 (1.1); 7.0088 (1.7); 7.0058 (1.3); 6.9953 (1.0); 6.9918 (1.0); 6.6459 (2.0); 6.6434 (2.0); 6.6295 (1.9); 6.6269 (1.8); 5.1524 (16.0); 1.5359 (31.1); 0.0061 (1.6); −0.0003 (49.4); −0.0070 (1.6)

I.225: $^1$H-NMR(500.1 MHz, CDCl3):
δ = 8.8029 (2.9); 8.7982 (3.0); 8.2639 (1.9); 8.2607 (2.2); 8.2567 (1.8); 7.7116 (1.7); 7.7068 (1.5); 7.6988 (1.0); 7.6961 (1.2); 7.6925 (1.8); 7.6754 (0.7); 7.6715 (0.8); 7.6654 (0.7); 7.6615 (0.8); 7.6571 (1.0); 7.6533 (1.0); 7.6471 (0.9); 7.6433 (0.9); 7.5542 (0.9); 7.5404 (0.9); 7.5353 (1.3); 7.5215 (1.3); 7.5166 (0.7); 7.5028 (0.6); 7.4665 (0.5); 7.2599 (88.3); 7.2505 (0.8); 7.2469 (0.8); 7.2357 (1.7); 7.2322 (1.8); 7.2282 (1.2); 7.2223 (3.4); 7.2172 (1.7); 7.2129 (1.2); 7.2087 (1.2); 7.1969 (0.5); 7.0482 (0.4); 6.4567 (1.4); 6.4537 (1.1); 6.4509 (0.6); 6.4435 (1.3); 6.4396 (1.2); 2.0405 (9.3); 2.0051 (0.6); 1.9933 (9.3); 1.7238 (16.0); 1.6798 (8.4); 1.6737 (8.3); 1.5896 (0.4); 1.5488 (207.7); 1.4218 (0.6); 1.3327 (0.4); 1.2849 (0.8); 1.2770 (0.6); 1.2540 (1.9); 0.8802 (0.4); 0.8440 (0.4); 0.8378 (0.4); 0.8089 (0.3); 0.1162 (0.7); 0.0688 (0.7); 0.0062 (5.4); −0.0003 (167.8); −0.0070 (6.6); −0.1202 (0.7)

I.226: $^1$H-NMR(500.1 MHz, CDCl3):
δ = 8.6935 (1.9); 8.6888 (1.9); 8.3209 (1.2); 8.3180 (1.4); 8.3136 (1.1); 7.6459 (0.4); 7.6420 (0.4); 7.6359 (0.5); 7.6320 (0.5); 7.6276 (0.6); 7.6238 (0.6); 7.6176 (0.6); 7.6137 (0.5); 7.5335 (1.0); 7.5301 (0.8); 7.5284 (0.7); 7.5189 (1.3); 7.5147 (1.7); 7.5009 (0.6); 7.4958 (0.8); 7.4819 (0.8); 7.4770 (0.4); 7.4665 (0.4); 7.4631 (0.4); 7.2599 (74.7); 7.2476 (1.2); 7.2436 (1.1); 7.2344 (1.5); 7.2334 (1.6); 7.2302 (1.5); 7.2284 (1.2); 7.2197 (1.2); 7.2164 (1.1); 7.2049 (0.4); 7.0482 (0.4); 6.6534 (1.2); 6.6497 (1.4); 6.6395 (0.8); 6.6377 (0.8); 6.6348 (1.1); 3.3547 (0.4); 3.3305 (16.0); 1.8141 (0.5); 1.8058 (11.0); 1.6811 (10.4); 1.5469 (232.2); 1.5217 (10.5); 1.4218 (0.4); 1.2853 (0.9); 1.2550 (1.1); 0.8437 (0.4); 0.8378 (0.4); 0.1162 (0.5); 0.0688 (0.6); 0.0062 (4.6); −0.0003 (130.0); −0.0069 (5.0); −0.1202 (0.5)

I.227: $^1$H-NMR(500.1 MHz, CDCl3):
δ = 8.8167 (2.1); 8.8120 (2.2); 8.2533 (1.4); 8.2502 (1.8); 8.2462 (1.4); 7.8120 (1.5); 7.8088 (1.7); 7.7961 (1.6); 7.7928 (1.7); 7.6724 (0.6); 7.6686 (0.6); 7.6624 (0.6); 7.6585 (0.6); 7.6541 (0.8); 7.6503 (0.8); 7.6441 (0.7); 7.6403 (0.7); 7.5524 (0.8); 7.5386 (0.8); 7.5334 (1.1); 7.5197 (1.1); 7.5148 (0.6); 7.5010 (0.6); 7.2602 (34.6); 7.2524 (1.0); 7.2496 (0.8); 7.2378 (1.5); 7.2351 (1.5); 7.2220 (1.3); 7.2192 (1.3); 7.2020 (1.2); 7.1985 (1.4); 7.1856 (1.4); 7.1840 (1.1); 7.1825 (1.4); 7.1712 (0.8); 7.1680 (0.8); 6.5076 (1.7); 6.5051 (1.7); 6.4915 (1.8); 6.4888 (1.6); 3.9883 (1.4); 3.4905 (1.1); 1.7823 (11.6); 1.7249 (16.0); 1.5952 (13.7); 1.5540 (23.2); 1.3330 (0.4); 1.2844 (0.6); 1.2547 (1.0); 0.0691 (1.4); 0.0063 (1.9); −0.0003 (67.0); −0.0068 (2.3)

I.228: $^1$H-NMR(500.1 MHz, CDCl3):
δ = 8.8174 (3.2); 8.8126 (3.2); 8.2569 (2.0); 8.2540 (2.4); 8.2497 (2.0); 7.6788 (0.8); 7.6750 (0.9); 7.6681 (1.8); 7.6650 (1.8); 7.6602 (1.6); 7.6561 (1.5); 7.6541 (1.5); 7.6496 (2.0); 7.5591 (1.0); 7.5454 (1.0); 7.5402 (1.4); 7.5264 (1.4); 7.5215 (0.8); 7.5077 (0.7); 7.2595 (31.8); 7.2520 (1.4); 7.2477 (2.0); 7.2424 (4.1); 7.2364 (1.4); 7.2330 (1.9); 7.2295 (1.9); 7.2182 (0.5); 7.2148 (0.4); 6.5081 (1.2); 6.5045 (1.3); 6.4976 (0.5); 6.4945 (1.0); 6.4917 (1.4); 5.8401 (2.2); 5.7389 (2.3); 2.0048 (0.4); 1.7616 (16.0); 1.5856 (10.4); 1.5825 (10.4); 1.5420 (53.6); 1.2854 (0.5); 1.2559 (0.5); 0.0063 (1.7); −0.0003 (58.0); −0.0068 (2.0)

I.229: $^1$H-NMR(500.1 MHz, CDCl3):
δ = 8.7878 (1.9); 8.7831 (2.0); 8.2461 (1.2); 8.2429 (1.5); 8.2388 (1.2); 7.6615 (0.4); 7.6576 (0.5); 7.6514 (0.5); 7.6476 (0.5); 7.6432 (0.6); 7.6393 (0.6); 7.6331 (0.6); 7.6293 (0.6); 7.5882 (0.7); 7.5841 (0.5); 7.5807 (0.8);

TABLE 12-continued

| NMR peak lists |
|---|

7.5779 (0.5); 7.5757 (0.5); 7.5733 (0.5); 7.5708 (0.8); 7.5693 (0.7); 7.5384 (0.6); 7.5247 (0.6); 7.5194 (0.8); 7.5057 (0.8); 7.5008 (0.5); 7.4870 (0.4); 7.2596 (21.0); 7.2029 (0.3); 7.1927 (1.6); 7.1907 (1.4); 7.1884 (1.4); 7.1821 (2.3); 7.1744 (1.6); 7.1717 (1.1); 6.4680 (1.1); 6.4641 (0.6); 6.4573 (0.7); 6.4542 (0.7); 6.4493 (1.1); 4.7267 (2.6); 3.8963 (16.0); 2.0048 (0.4); 1.7287 (10.9); 1.5433 (36.2); 1.4625 (11.6); 1.2855 (0.6); 1.2555 (0.6); 0.8448 (0.4); 0.8386 (0.4); 0.0061 (1.2); −0.0003 (40.0); −0.0070 (1.2)

I.230: $^1$H-NMR(500.1 MHz, CDCl3):
δ = 9.0245 (2.0); 7.5815 (0.5); 7.5783 (0.5); 7.5718 (0.4); 7.5682 (0.5); 7.5613 (0.4); 7.5466 (0.4); 7.5420 (0.5); 7.5271 (0.5); 7.4794 (0.6); 7.4770 (0.6); 7.4642 (0.7); 7.4616 (0.6); 7.2594 (6.5); 6.9531 (0.7); 6.9505 (0.8); 6.9379 (0.7); 6.9352 (0.6); 6.9203 (0.5); 6.9173 (0.6); 6.9050 (0.8); 6.9021 (0.8); 6.8569 (0.8); 6.8542 (0.8); 6.8417 (0.5); 6.8392 (0.5); 2.0057 (16.0); 1.5427 (8.9); 0.0063 (0.4); −0.0003 (10.8); −0.0068 (0.4)

I.231: $^1$H-NMR(500.1 MHz, CDCl3):
δ = 9.0935 (12.5); 7.7252 (1.5); 7.7213 (1.5); 7.7156 (1.6); 7.7115 (1.6); 7.7063 (2.2); 7.7024 (2.4); 7.6967 (2.2); 7.6927 (2.1); 7.6473 (2.0); 7.6324 (2.0); 7.6280 (3.0); 7.6130 (2.9); 7.6089 (1.4); 7.5939 (1.2); 7.2675 (2.1); 7.2637 (3.0); 7.2594 (33.2); 7.2537 (2.8); 7.2520 (3.1); 7.2495 (3.3); 7.1948 (1.4); 7.1918 (1.8); 7.1802 (4.1); 7.1771 (4.0); 7.1658 (5.5); 7.1619 (4.6); 7.1496 (2.7); 7.1460 (2.7); 7.1350 (1.1); 7.1314 (0.9); 6.6034 (3.6); 6.6008 (2.9); 6.5880 (4.1); 6.5847 (3.4); 3.4265 (16.0); 1.5693 (82.9); 1.5407 (34.9); 1.4377 (0.3); 1.2545 (0.5); 0.0063 (2.0); −0.0003 (56.1); −0.0069 (2.3)

I.232: $^1$H-NMR(500.1 MHz, CDCl3):
δ = 8.9820 (2.3); 7.9880 (0.6); 7.9854 (0.6); 7.9715 (0.6); 7.9689 (0.6); 7.8282 (0.5); 7.8261 (0.6); 7.8112 (0.7); 7.8092 (0.6); 7.6839 (0.4); 7.6811 (0.4); 7.6700 (0.5); 7.6672 (0.7); 7.6644 (0.3); 7.6534 (0.4); 7.6505 (0.4); 7.5540 (0.5); 7.5513 (0.5); 7.5401 (0.4); 7.5375 (0.8); 7.5349 (0.5); 7.5236 (0.4); 7.5210 (0.4); 7.4747 (0.6); 7.4721 (0.5); 7.4703 (0.4); 7.4604 (0.7); 7.4569 (0.6); 7.2582 (2.7); 6.9204 (0.6); 6.9176 (0.6); 6.9069 (1.3); 6.9027 (1.5); 6.8920 (0.7); 6.8889 (0.7); 6.8420 (0.8); 6.8383 (0.9); 6.8288 (0.4); 6.8270 (0.4); 6.8242 (0.5); 2.0207 (16.0); 1.5607 (3.9); −0.0003 (4.7)

I.233: $^1$H-NMR(500.1 MHz, CDCl3):
δ = 8.8174 (5.1); 8.8123 (5.2); 8.1642 (2.4); 8.1482 (2.6); 8.1472 (2.6); 8.1261 (3.5); 8.1212 (3.5); 7.8532 (2.0); 7.8511 (2.2); 7.8347 (2.6); 7.8103 (1.6); 7.8074 (1.6); 7.7965 (2.1); 7.7935 (3.1); 7.7905 (1.6); 7.7795 (1.8); 7.7766 (1.7); 7.6441 (1.8); 7.6418 (1.8); 7.6301 (1.8); 7.6278 (3.0); 7.6257 (1.7); 7.6139 (1.4); 7.6116 (1.3); 7.2597 (11.2); 6.8996 (2.5); 6.8941 (2.6); 6.8816 (2.6); 6.8761 (2.6); 6.7334 (1.2); 6.7279 (1.1); 6.7186 (1.4); 6.7153 (2.1); 6.7131 (1.5); 6.7099 (2.0); 6.7005 (2.1); 6.6949 (1.9); 6.6573 (3.1); 6.6464 (3.1); 6.6392 (1.9); 6.6283 (1.8); 5.2003 (1.3); 5.1876 (4.6); 5.1749 (4.6); 5.1623 (1.3); 3.4893 (0.4); 1.8521 (16.0); 1.8394 (16.0); 1.5751 (11.0); 1.2536 (0.5); 0.0060 (0.7); −0.0003 (21.4); −0.0070 (0.8)

I.234: $^1$H-NMR(500.1 MHz, CDCl3):
δ = 8.7123 (6.9); 8.6951 (7.2); 8.3615 (15.3); 8.3578 (16.0); 8.0249 (0.6); 8.0207 (0.4); 7.9371 (0.3); 7.9217 (0.4); 7.9034 (6.1); 7.8871 (7.4); 7.8219 (4.0); 7.8192 (4.0); 7.8080 (6.0); 7.8018 (14.6); 7.7904 (6.0); 7.7878 (5.3); 7.7243 (5.2); 7.7220 (5.6); 7.7102 (4.5); 7.7080 (8.2); 7.7060 (5.1); 7.6941 (3.5); 7.6918 (3.5); 7.5609 (0.3); 7.5453 (0.4); 7.4663 (1.0); 7.4110 (0.5); 7.3956 (0.7); 7.3798 (0.3); 7.2597 (193.5); 7.0480 (1.0); 6.9843 (4.2); 6.9786 (4.9); 6.9669 (4.4); 6.9612 (4.8); 6.9086 (2.6); 6.9029 (2.3); 6.8907 (3.8); 6.8755 (3.2); 6.8697 (2.7); 6.6954 (6.9); 6.6857 (7.0); 6.6774 (5.9); 6.6677 (5.9); 5.2984 (0.5); 3.7152 (0.4); 3.5815 (2.9); 3.5707 (4.6); 3.5553 (4.8); 3.5434 (11.7); 3.5325 (4.0); 3.5298 (4.3); 3.5190 (2.6); 3.3551 (0.5); 3.3551 (2.4); 3.3333 (3.6); 3.3194 (3.3); 3.3072 (0.8); 3.3022 (0.6); 3.2950 (1.6); 1.6918 (0.4); 1.6779 (0.5); 1.6306 (0.7); 1.5623 (45.0); 1.5495 (92.4); 1.4701 (0.3); 1.4217 (0.8); 1.3702 (0.3); 1.3331 (0.4); 1.2826 (1.1); 1.2538 (3.0); 1.2438 (1.1); 1.2297 (0.5); 0.8799 (0.6); 0.8432 (0.5); 0.8091 (0.4); 0.1162 (1.3); 0.0797 (0.5); 0.0061 (12.2); −0.0003 (353.7); −0.0071 (9.4); −0.1202 (1.2)

I.235: $^1$H-NMR(500.1 MHz, CDCl3):
δ = 8.7454 (3.9); 8.7278 (4.0); 8.4118 (7.7); 8.4082 (7.8); 7.9255 (3.6); 7.9098 (4.2); 7.8667 (5.7); 7.8642 (5.8); 7.8411 (2.2); 7.8385 (2.2); 7.8271 (3.1); 7.8241 (4.0); 7.8210 (2.3); 7.8096 (3.0); 7.8070 (2.6); 7.7381 (2.9); 7.7359 (3.0); 7.7219 (4.6); 7.7198 (2.8); 7.7079 (2.0); 7.7057 (1.9); 7.2600 (61.3); 6.9522 (2.4); 6.9465 (2.8); 6.9348 (2.5); 6.9291 (2.8); 6.8718 (1.5); 6.8660 (1.3); 6.8536 (2.2); 6.8385 (1.8); 6.8327 (1.5); 6.5551 (3.6); 6.5457 (3.8); 6.5370 (3.3); 6.5275 (3.3); 5.2983 (0.6); 3.3806 (16.0); 1.7216 (0.4); 1.6330 (0.3); 1.6239 (0.3); 1.5935 (95.4); 1.5576 (9.5); 1.4617 (0.5); 1.2797 (1.1); 1.2547 (1.2); 0.1165 (0.4); 0.0063 (3.1); −0.0003 (99.6); −0.0068 (4.1); −0.1201 (0.4)

I.236: $^1$H-NMR(500.1 MHz, CDCl3):
δ = 8.7409 (5.0); 8.7356 (5.1); 8.1456 (2.6); 8.1308 (6.5); 8.1269 (6.3); 7.8466 (2.2); 7.8443 (2.5); 7.8304 (2.5); 7.8281 (2.9); 7.7850 (1.5); 7.7824 (1.5); 7.7712 (1.9); 7.7684 (2.9); 7.7654 (1.6); 7.7544 (1.7); 7.7516 (1.5); 7.6231 (1.8); 7.6210 (1.9); 7.6070 (3.0); 7.6048 (1.9); 7.5929 (1.3); 7.5912 (1.3); 7.2598 (9.7); 7.0038 (1.8); 6.9981 (1.9); 6.9862 (1.8); 6.9805 (1.8); 6.8621 (1.0); 6.8563 (1.0); 6.8441 (1.5); 6.8407 (1.3); 6.8386 (1.3); 6.8288 (1.2); 6.8230 (1.1); 6.6006 (2.5); 6.5909 (2.6); 6.5826 (2.2); 6.5728 (2.2); 3.6216 (1.6); 3.6037 (0.4); 3.5975 (2.1); 3.5771 (0.4); 3.3758 (0.9); 3.3551 (2.1); 3.3385 (1.6); 3.3308 (3.3); 3.3275 (2.5); 3.3237 (2.0); 3.3142 (1.0); 3.3101 (0.4); 3.3031 (0.4); 3.2936 (0.4); 2.2489 (0.7); 2.2395 (0.8); 2.2338 (0.9); 2.2244 (0.9); 2.2205 (1.0); 2.2115 (0.9); 2.2054 (0.9); 2.1964 (0.8); 2.1903 (0.3); 1.7997 (0.8); 1.7845 (1.2); 1.7709 (1.1); 1.7689 (1.1); 1.7561 (1.1); 1.7407 (0.8); 1.5937 (6.5); 1.1625 (7.7); 1.1475 (16.0); 1.1325 (7.3); 0.0061 (0.6); −0.0003 (17.1); −0.0070 (0.6)

I.237: $^1$H-NMR(500.1 MHz, CDCl3):
δ = 8.7122 (2.4); 8.6945 (2.5); 8.3343 (5.5); 8.3306 (5.6); 7.9056 (2.2); 7.9046 (2.2); 7.8892 (2.6); 7.8179 (1.5); 7.8153 (1.4); 7.8040 (2.3); 7.7978 (5.2); 7.7865 (2.1); 7.7838 (1.8); 7.7217 (1.8); 7.7196 (1.9); 7.7076 (1.7); 7.7055 (2.8); 7.7034 (1.8); 7.6915 (1.2); 7.6893 (1.1); 7.2602 (29.9); 7.0009 (1.6); 6.9952 (1.8); 6.9835 (1.7); 6.9778 (1.8); 6.9108 (1.0); 6.9050 (0.9); 6.8949 (1.3); 6.8927 (1.4); 6.8895 (1.2); 6.8872 (1.2); 6.8775 (1.2); 6.8718 (1.0); 6.7080 (2.5); 6.6990 (2.1); 6.6803 (2.0); 6.5867 (1.5); 6.5693 (0.4); 6.5628 (2.0); 3.5419 (0.4); 3.3430 (0.8); 3.3220 (2.0); 3.3060 (1.5); 3.2983 (3.3); 3.2950 (2.4); 3.2916 (2.4); 3.2820 (0.9); 3.2774 (0.4); 3.2705 (0.3); 3.2611 (0.3); 2.2314 (0.7); 2.2220 (0.7); 2.2163 (0.8); 2.2069 (0.8); 2.2030 (0.9); 2.1939 (0.9); 2.1879 (0.8); 2.1789 (0.8); 1.7782 (0.8); 1.7693 (0.3); 1.7630 (1.2); 1.7548 (0.4); 1.7494 (1.0); 1.7477 (1.0); 1.7346 (1.2); 1.7194 (0.7); 1.5610 (21.8); 1.2570 (1.0); 1.2548 (1.0); 1.2434 (0.6); 1.1613 (7.7); 1.1463 (16.0); 1.1312 (7.0); 1.0288 (0.4); 1.0156 (0.4); 1.0111 (0.7); 0.8533 (0.4); 0.8404 (0.4); 0.8059 (0.6); 0.8033 (0.4); 0.7907 (0.4); 0.6993 (0.7); 0.0063 (1.8); −0.0003 (52.7); −0.0068 (1.8)

I.238: $^1$H-NMR(500.1 MHz, CDCl3):
δ = 8.7224 (2.4); 8.7050 (2.5); 8.4328 (5.4); 8.4290 (5.5); 7.9023 (2.1); 7.8859 (2.6); 7.8367 (1.3); 7.8341 (1.4); 7.8228 (1.9); 7.8198 (2.5); 7.8165 (1.4); 7.8053 (1.8); 7.8026 (1.7); 7.7464 (3.6); 7.7432 (3.6); 7.7374 (2.0);

TABLE 12-continued

| NMR peak lists |
|---|

7.7351 (2.0); 7.7210 (2.8); 7.7188 (1.8); 7.7071 (1.2); 7.7048 (1.2); 7.2597 (44.0); 6.8924 (2.1); 6.8874 (2.2); 6.8749 (1.9); 6.8699 (2.0); 6.7774 (0.7); 6.7724 (0.5); 6.7631 (0.7); 6.7593 (2.5); 6.7543 (2.4); 6.7453 (5.4); 6.7401 (2.7); 6.7350 (3.3); 6.7282 (0.9); 6.7173 (0.6); 5.1624 (1.2); 5.1497 (4.3); 5.1370 (4.2); 5.1243 (1.2); 1.8428 (16.0); 1.8302 (15.8); 1.5499 (28.2); 1.2577 (0.7); 1.2438 (0.5); 0.0061 (2.6); −0.0003 (82.4); −0.0070 (2.7)

I.239: $^1$H-NMR(500.1 MHz, CDCl3):
δ = 14.2030 (0.4); 10.9572 (0.4); 8.8409 (15.8); 8.8358 (16.0); 8.3687 (11.8); 8.3656 (12.4); 8.3527 (12.7); 8.3495 (12.1); 8.3117 (14.2); 8.3069 (14.0); 8.2000 (10.6); 8.1835 (11.7); 7.9173 (9.4); 7.9009 (10.8); 7.8669 (7.0); 7.8641 (7.3); 7.8530 (9.2); 7.8501 (14.0); 7.8471 (7.3); 7.8360 (8.0); 7.8332 (7.4); 7.6970 (7.8); 7.6949 (8.0); 7.6830 (7.9); 7.6808 (13.0); 7.6788 (7.7); 7.6668 (5.9); 7.6647 (5.6); 7.6156 (7.0); 7.6123 (7.0); 7.6010 (9.0); 7.5982 (9.8); 7.5957 (8.0); 7.5844 (8.3); 7.5811 (8.6); 7.4661 (1.5); 7.4296 (9.2); 7.4276 (8.6); 7.4133 (14.7); 7.4117 (10.6); 7.3989 (7.7); 7.3970 (7.6); 7.2994 (0.6); 7.2595 (289.0); 7.0479 (1.2); 6.8749 (0.4); 6.8521 (13.5); 6.8506 (13.4); 6.8355 (12.9); 6.8340 (12.6); 4.2345 (0.4); 3.6782 (0.4); 2.3111 (0.4); 2.2777 (0.4); 2.1699 (0.7); 2.0048 (3.5); 1.7142 (0.4); 1.6893 (0.5); 1.6548 (0.5); 1.6238 (0.7); 1.5837 (2.2); 1.5438 (291.8); 1.4954 (0.5); 1.4793 (0.5); 1.4355 (0.4); 1.4221 (1.7); 1.3702 (1.0); 1.3436 (1.5); 1.3330 (1.1); 1.2855 (3.2); 1.2559 (5.6); 1.2257 (0.7); 1.1391 (0.5); 1.1165 (0.4); 1.1097 (0.4); 1.0918 (0.6); 1.0726 (0.6); 1.0353 (0.6); 1.0087 (0.7); 0.9038 (0.6); 0.8802 (1.6); 0.8664 (1.4); 0.8442 (3.4); 0.8386 (3.3); 0.8088 (2.1); 0.1163 (2.1); 0.0793 (0.7); 0.0690 (2.7); 0.0396 (1.6); 0.0063 (16.0); −0.0003 (527.9); −0.0068 (17.5); −0.1200 (1.7); −2.1322 (0.5); −2.7962 (0.4)

I.240: $^1$H-NMR(500.1 MHz, CDCl3):
δ = 8.7750 (4.2); 8.7699 (4.2); 8.2240 (2.0); 8.2209 (2.0); 8.2080 (2.1); 8.2048 (2.1); 8.1523 (1.9); 8.1353 (2.1); 8.1136 (2.8); 8.1086 (2.8); 7.8378 (1.8); 7.8214 (2.0); 7.7910 (1.3); 7.7882 (1.2); 7.7771 (1.7); 7.7742 (2.4); 7.7713 (1.2); 7.7602 (1.5); 7.7574 (1.3); 7.6269 (1.4); 7.6247 (1.4); 7.6129 (1.4); 7.6107 (2.4); 7.6084 (1.4); 7.5967 (1.1); 7.5945 (1.0); 7.3220 (1.0); 7.3188 (1.1); 7.3074 (1.8); 7.3055 (1.5); 7.3043 (1.8); 7.3027 (1.4); 7.2912 (1.7); 7.2879 (1.7); 7.2595 (18.5); 7.2560 (2.2); 7.2534 (2.0); 7.2398 (2.1); 7.2376 (2.0); 7.2253 (1.1); 7.2229 (1.0); 6.7819 (2.3); 6.7797 (2.3); 6.7655 (2.1); 6.7634 (2.1); 4.5872 (16.0); 4.3941 (2.2); 4.3800 (7.0); 4.3657 (7.1); 4.3516 (2.3); 2.0035 (1.4); 1.5586 (32.5); 1.3997 (7.6); 1.3855 (14.8); 1.3714 (7.6); 1.2856 (0.4); 1.2555 (0.8); 0.8453 (0.3); 0.8382 (0.3); 0.0693 (0.5); 0.0061 (1.1); −0.0003 (33.4); −0.0069 (1.0)

I.241: $^1$H-NMR(500.1 MHz, CDCl3):
δ = 8.7657 (4.2); 8.7606 (4.3); 8.2090 (2.0); 8.2060 (2.0); 8.1929 (2.2); 8.1899 (2.1); 8.1499 (2.0); 8.1330 (2.1); 8.1025 (2.9); 8.0976 (2.9); 7.8304 (1.8); 7.8138 (2.1); 7.7898 (1.3); 7.7870 (1.2); 7.7759 (1.7); 7.7729 (2.4); 7.7700 (1.2); 7.7589 (1.5); 7.7561 (1.3); 7.6247 (1.4); 7.6226 (1.4); 7.6106 (1.4); 7.6086 (2.4); 7.6064 (1.4); 7.5946 (1.1); 7.5924 (1.0); 7.4382 (1.0); 7.4343 (1.6); 7.4298 (0.8); 7.4213 (4.9); 7.4182 (6.9); 7.4123 (1.0); 7.4031 (5.0); 7.3993 (1.4); 7.3913 (1.2); 7.3876 (1.8); 7.3791 (1.2); 7.3752 (1.8); 7.3709 (0.9); 7.3681 (0.8); 7.3616 (1.6); 7.3552 (0.5); 7.3517 (0.4); 7.3483 (0.6); 7.3251 (1.0); 7.3219 (1.1); 7.3104 (1.8); 7.3086 (1.7); 7.3074 (1.8); 7.3058 (1.4); 7.2942 (1.8); 7.2910 (1.7); 7.2590 (37.7); 7.2497 (1.9); 7.2360 (2.2); 7.2339 (1.9); 7.2216 (1.1); 7.2190 (1.0); 6.7733 (2.3); 6.7712 (2.3); 6.7569 (2.2); 6.7548 (2.1); 5.3371 (13.7); 4.6081 (16.0); 2.0037 (1.2); 1.5880 (0.5); 1.5485 (99.2); 1.4219 (0.4); 1.3703 (0.4); 1.2856 (0.8); 1.2554 (1.1); 0.8802 (0.4); 0.8445 (0.6); 0.8387 (0.6); 0.8101 (0.3); 0.0691 (1.1); 0.0062 (1.8); −0.0003 (67.5); −0.0069 (2.2)

I.242: $^1$H-NMR(500.1 MHz, CDCl3):
δ = 8.7511 (4.4); 8.7460 (4.4); 8.1433 (1.9); 8.1264 (2.1); 8.0441 (3.0); 8.0392 (2.9); 7.8966 (2.0); 7.8906 (1.9); 7.8777 (2.0); 7.8717 (1.8); 7.8191 (1.8); 7.8028 (2.1); 7.7896 (1.4); 7.7867 (1.3); 7.7757 (1.9); 7.7727 (2.5); 7.7697 (1.2); 7.7587 (1.5); 7.7558 (1.3); 7.6262 (1.5); 7.6240 (1.5); 7.6100 (2.4); 7.5960 (1.1); 7.5938 (1.1); 7.4658 (0.6); 7.4296 (0.7); 7.4188 (8.4); 7.4132 (6.4); 7.4093 (6.3); 7.4084 (6.3); 7.3974 (1.1); 7.3941 (1.1); 7.3920 (1.3); 7.3887 (1.5); 7.3830 (1.4); 7.3795 (1.0); 7.3748 (0.9); 7.3712 (1.5); 7.3633 (0.8); 7.3542 (0.4); 7.2792 (0.4); 7.2717 (0.8); 7.2646 (3.0); 7.2594 (95.0); 7.2498 (1.9); 7.0589 (1.1); 7.0529 (1.1); 7.0477 (0.7); 7.0441 (1.2); 7.0408 (1.5); 7.0382 (1.2); 7.0349 (1.3); 7.0262 (1.3); 7.0201 (1.2); 6.8275 (2.1); 6.8178 (2.2); 6.8094 (1.8); 6.7999 (1.8); 5.3551 (0.4); 5.3413 (16.0); 5.3315 (0.4); 4.6982 (4.3); 4.5469 (15.2); 4.5373 (0.5); 1.5825 (0.5); 1.5752 (0.4); 1.5693 (0.5); 1.5622 (1.0); 1.5544 (2.0); 1.5471 (8.2); 1.5421 (208.9); 1.5326 (5.5); 1.5238 (0.7); 1.5200 (0.5); 1.5177 (0.7); 1.5161 (0.7); 1.5140 (0.7); 1.5062 (0.6); 1.4219 (0.9); 1.3702 (0.8); 1.3328 (0.5); 1.2856 (1.7); 1.2543 (2.3); 0.8803 (0.6); 0.8662 (0.4); 0.8447 (1.1); 0.8380 (1.1); 0.8093 (0.6); 0.1163 (0.6); 0.0689 (2.9); 0.0209 (0.4); 0.0198 (0.6); 0.0120 (1.2); 0.0060 (7.1); −0.0003 (180.5); −0.0069 (5.6); −0.0098 (4.1); −0.0187 (0.5); −0.0224 (0.4); −0.0245 (0.6); −0.0263 (0.5); −0.0283 (0.4); −0.0361 (0.3); −0.1200 (0.6)

I.243: $^1$H-NMR(500.1 MHz, CDCl3):
δ = 9.0939 (5.5); 7.7210 (0.7); 7.7171 (0.7); 7.7114 (0.7); 7.7073 (0.7); 7.7022 (1.0); 7.6982 (1.1); 7.6926 (1.0); 7.6885 (1.0); 7.6386 (0.9); 7.6236 (0.9); 7.6193 (1.4); 7.6043 (1.3); 7.6002 (0.7); 7.5852 (0.6); 7.4699 (1.5); 7.4539 (1.7); 7.2594 (17.1); 7.2490 (0.9); 7.2464 (1.0); 7.2342 (1.5); 7.2319 (1.7); 7.2186 (1.2); 7.2160 (1.2); 7.1781 (0.8); 7.1770 (0.9); 7.1754 (0.9); 7.1740 (0.8); 7.1623 (1.4); 7.1606 (1.4); 7.1594 (1.5); 7.1461 (0.7); 7.1448 (0.6); 7.1432 (0.6); 6.6280 (1.8); 6.6256 (1.9); 6.6118 (1.8); 6.6093 (1.7); 3.5806 (0.4); 3.5664 (1.3); 3.5521 (1.3); 3.5379 (0.4); 1.5972 (17.2); 1.5879 (10.1); 1.5736 (10.1); 1.5399 (18.4); 1.3806 (16.0); 1.2542 (0.6); 0.0063 (1.0); −0.0003 (36.5); −0.0068 (1.1)

I.244: $^1$H-NMR(500.1 MHz, CDCl3):
δ = 8.8107 (2.6); 8.8060 (2.6); 8.2713 (1.6); 8.2680 (2.0); 8.2639 (1.6); 7.6621 (0.6); 7.6582 (0.6); 7.6520 (0.6); 7.6481 (0.7); 7.6437 (0.8); 7.6399 (0.8); 7.6337 (0.8); 7.6299 (0.8); 7.5335 (0.8); 7.5197 (0.8); 7.5145 (1.1); 7.5008 (1.1); 7.4958 (0.6); 7.4820 (0.6); 7.4340 (0.6); 7.4321 (1.2); 7.4304 (1.1); 7.4200 (1.1); 7.4175 (1.2); 7.2594 (32.3); 7.1509 (0.5); 7.1478 (0.6); 7.1363 (1.7); 7.1330 (1.6); 7.1218 (2.5); 7.1177 (2.5); 7.1066 (1.1); 7.1030 (1.2); 7.0908 (0.4); 7.0885 (0.4); 6.4681 (1.6); 6.4651 (1.2); 6.4527 (1.8); 6.4492 (1.5); 3.6047 (0.4); 3.5904 (1.2); 3.5762 (1.2); 3.5619 (0.4); 1.6386 (16.0); 1.6022 (9.3); 1.5880 (9.4); 1.5389 (30.5); 1.4607 (15.6); 1.2554 (0.7); 0.0063 (1.9); −0.0003 (65.9); −0.0068 (2.2)

I.245: $^1$H-NMR(500.1 MHz, CDCl3):
δ = 15.6169 (0.3); 13.8612 (0.4); 13.1112 (0.4); 12.4544 (0.4); 8.7590 (4.3); 8.7540 (4.4); 8.1769 (2.1); 8.1739 (2.1); 8.1608 (2.4); 8.1578 (2.2); 8.1525 (2.0); 8.1350 (2.3); 8.1058 (3.0); 8.1005 (3.1); 7.8319 (1.9); 7.8156 (2.2); 7.7947 (1.4); 7.7920 (1.2); 7.7808 (1.6); 7.7779 (2.4); 7.7638 (1.7); 7.7611 (1.2); 7.6301 (1.5); 7.6139 (2.5); 7.5979 (1.1); 7.4661 (1.6); 7.3879 (1.6); 7.3828 (0.7); 7.3757 (1.3); 7.3702 (12.6); 7.3644 (11.0); 7.3522 (0.9); 7.3468 (1.4); 7.3314 (1.0); 7.3282 (1.1); 7.3136 (1.9); 7.3004 (1.5); 7.2971 (1.6); 7.2596 (282.6); 7.2508 (2.9); 7.2484 (2.5); 7.2343 (2.4); 7.2198 (1.3); 7.2175 (1.2); 7.0479 (1.4); 6.7728 (2.4); 6.7565 (2.4); 5.2904 (14.6); 4.5946 (16.0); 3.6999 (0.3); 2.1699 (0.7); 2.0435 (0.4); 1.6231 (1.2); 1.6216 (1.0); 1.6033 (0.6); 1.5818 (1.7); 1.5751 (1.2); 1.5424 (815.9); 1.5201 (1.0); 1.5016 (0.7); 1.4955 (0.5); 1.4809 (0.4); 1.4629 (0.4); 1.4435

| TABLE 12-continued |
|---|
| NMR peak lists |

(0.4); 1.4272 (1.8); 1.4218 (2.6); 1.3701 (2.0); 1.3328 (1.0); 1.3272 (0.7); 1.3084 (0.7); 1.2855 (3.6); 1.2565 (4.9); 1.1886 (0.6); 1.1826 (0.5); 1.0886 (0.5); 1.0631 (0.6); 1.0079 (0.6); 0.9987 (0.5); 0.9370 (0.4); 0.9268 (0.4); 0.9165 (0.4); 0.8920 (0.9); 0.8804 (1.7); 0.8676 (1.1); 0.8439 (3.2); 0.8379 (3.2); 0.8086 (1.8); 0.7961 (1.2); 0.1163 (2.0); 0.0804 (0.8); 0.0791 (0.6); 0.0688 (8.6); 0.0388 (0.6); 0.0062 (14.2); −0.0003 (469.8); −0.0069 (14.2); −0.1202 (1.9)

I.246: $^1$H-NMR(500.1 MHz, CDCl3):
δ = 8.7750 (4.3); 8.7699 (4.2); 8.2132 (2.0); 8.2101 (2.0); 8.1972 (2.1); 8.1940 (2.0); 8.1530 (1.9); 8.1360 (2.0); 8.1136 (2.8); 8.1086 (2.8); 7.8384 (1.7); 7.8242 (1.8); 7.8219 (2.0); 7.7931 (1.3); 7.7903 (1.3); 7.7792 (1.7); 7.7763 (2.4); 7.7733 (1.3); 7.7622 (1.4); 7.7595 (1.3); 7.6285 (1.4); 7.6264 (1.4); 7.6146 (1.3); 7.6124 (2.3); 7.6101 (1.4); 7.5984 (1.0); 7.5962 (1.0); 7.3282 (1.0); 7.3250 (1.1); 7.3136 (1.7); 7.3118 (1.6); 7.3104 (1.7); 7.3089 (1.4); 7.2973 (1.7); 7.2940 (1.5); 7.2641 (1.2); 7.2585 (28.8); 7.2546 (2.7); 7.2521 (1.9); 7.2444 (0.4); 7.2398 (1.6); 7.2382 (2.1); 7.2363 (1.9); 7.2239 (1.1); 7.2215 (1.1); 6.7809 (2.2); 6.7787 (2.3); 6.7644 (2.0); 7.7624 (2.0); 6.1035 (0.6); 6.0916 (1.2); 6.0826 (0.6); 6.0797 (0.6); 6.0707 (1.4); 6.0690 (0.8); 6.0586 (0.8); 6.0570 (1.4); 6.0481 (0.7); 6.0453 (0.6); 6.0362 (1.4); 6.0244 (0.6); 5.4033 (0.8); 5.4005 (2.1); 5.3975 (2.3); 5.3945 (0.8); 5.3689 (0.7); 5.3660 (2.0); 5.3629 (2.1); 5.3599 (0.8); 5.3260 (0.8); 5.3236 (2.0); 5.3209 (1.9); 5.3187 (0.8); 5.3050 (0.8); 5.3028 (1.9); 5.3000 (1.9); 5.2977 (0.8); 4.8220 (3.0); 4.8195 (4.7); 4.8170 (3.1); 4.8102 (2.8); 4.8077 (4.6); 4.8051 (3.0); 4.6128 (0.9); 4.6073 (16.0); 1.5440 (0.7); 1.5388 (13.2); 1.4218 (0.5); 1.3702 (0.9); 1.3329 (0.4); 1.2854 (1.6); 1.2554 (1.3); 0.8807 (0.5); 0.8669 (0.4); 0.8564 (0.6); 0.8444 (1.2); 0.8379 (1.1); 0.8327 (1.1); 0.8090 (0.5); 0.0058 (2.2); −0.0003 (56.9); −0.0071 (1.7); −0.0098 (0.4); −0.0109 (0.5); −0.0129 (0.3); −0.0148 (0.4); −0.0161 (0.4)

I.247: $^1$H-NMR(500.1 MHz, CDCl3):
δ = 8.7733 (2.1); 8.7683 (2.2); 8.2176 (1.0); 8.2145 (1.1); 8.2015 (1.1); 8.1985 (1.1); 8.1527 (1.0); 8.1358 (1.1); 8.1091 (1.5); 8.1043 (1.5); 7.8377 (0.9); 7.8213 (1.1); 7.7928 (0.7); 7.7899 (0.7); 7.7789 (0.9); 7.7759 (1.3); 7.7729 (0.7); 7.7619 (0.8); 7.7590 (0.7); 7.6280 (0.7); 7.6259 (0.8); 7.6138 (0.7); 7.6119 (1.2); 7.6097 (0.8); 7.5979 (0.6); 7.5957 (0.6); 7.3294 (0.5); 7.3261 (0.5); 7.3145 (0.9); 7.3130 (0.9); 7.3115 (1.0); 7.3102 (0.8); 7.2985 (0.9); 7.2952 (0.8); 7.2586 (14.9); 7.2424 (1.2); 7.2403 (1.1); 7.2280 (0.6); 7.2256 (0.6); 6.7813 (1.2); 6.7792 (1.2); 6.7649 (1.1); 6.7628 (1.1); 4.5699 (8.6); 4.1192 (16.0); 1.5386 (8.8); 1.2855 (0.4); 1.2547 (0.4); 0.8446 (0.4); 0.8381 (0.3); 0.8331 (0.3); 0.0061 (1.1); −0.0003 (28.3); −0.0070 (1.0)

I.248: $^1$H-NMR(500.1 MHz, CDCl3):
δ = 8.7628 (4.4); 8.7577 (4.5); 8.1677 (2.0); 8.1647 (2.2); 8.1519 (3.2); 8.1487 (2.3); 8.1371 (2.2); 8.1150 (2.9); 8.1102 (2.9); 7.8353 (1.9); 7.8189 (2.2); 7.7983 (1.4); 7.7954 (1.3); 7.7845 (1.7); 7.7815 (2.6); 7.7785 (1.4); 7.7675 (1.6); 7.7646 (1.4); 7.6739 (3.4); 7.6578 (4.3); 7.6325 (1.5); 7.6303 (1.5); 7.6184 (1.4); 7.6163 (2.5); 7.6140 (1.5); 7.6023 (1.1); 7.6001 (1.1); 7.5408 (3.9); 7.5248 (3.1); 7.3361 (1.1); 7.3329 (1.2); 7.3213 (1.8); 7.3183 (2.0); 7.3166 (1.5); 7.3050 (1.7); 7.3019 (1.7); 7.2584 (36.7); 7.2483 (1.9); 7.2459 (1.9); 7.2335 (1.7); 7.2319 (2.2); 7.2300 (2.0); 7.2176 (1.2); 7.2153 (1.2); 6.7744 (2.4); 6.7724 (2.4); 6.7580 (2.3); 6.7560 (2.2); 5.3847 (9.4); 4.6224 (16.0); 1.5370 (23.2); 1.3704 (0.8); 1.3330 (0.4); 1.2932 (0.4); 1.2855 (1.4); 1.2568 (1.3); 0.8919 (0.3); 0.8807 (0.7); 0.8671 (0.5); 0.8449 (1.0); 0.8380 (1.0); 0.8330 (0.9); 0.8253 (0.7); 0.8110 (0.5); 0.0062 (2.0); −0.0003 (72.6); −0.0068 (2.2)

I.249: $^1$H-NMR(500.1 MHz, CDCl3):
δ = 8.6403 (3.4); 8.6353 (3.5); 8.2090 (2.4); 8.2042 (2.5); 8.1264 (1.6); 8.1103 (1.8); 7.7803 (1.8); 7.7765 (1.5); 7.7735 (1.0); 7.7624 (3.2); 7.7596 (1.7); 7.7456 (1.3); 7.7428 (0.9); 7.6058 (1.3); 7.5920 (2.0); 7.5755 (1.0); 7.5618 (1.8); 7.5586 (1.7); 7.5465 (1.9); 7.5431 (1.8); 7.4652 (0.6); 7.3258 (0.4); 7.3154 (2.5); 7.2983 (5.7); 7.2694 (7.0); 7.2588 (133.0); 7.2529 (5.1); 7.2172 (0.8); 7.2137 (0.7); 7.2021 (1.6); 7.1988 (1.6); 7.1867 (1.5); 7.1830 (1.5); 7.1775 (1.7); 7.1744 (1.7); 7.1622 (2.0); 7.1594 (1.9); 7.1477 (1.0); 7.1448 (0.6); 7.0472 (0.7); 6.5710 (1.9); 6.5682 (2.1); 6.5549 (1.6); 6.5524 (1.8); 4.5706 (1.9); 4.5468 (2.8); 4.4475 (2.6); 4.4237 (1.8); 2.2782 (0.6); 1.9056 (15.4); 1.8605 (0.6); 1.7821 (16.0); 1.7424 (0.7); 1.5788 (15.8); 1.5320 (64.2); 1.2851 (0.4); 1.2580 (0.8); 0.8453 (0.4); 0.8386 (0.4); 0.1163 (1.0); 0.0687 (0.9); 0.0388 (0.8); 0.0061 (7.0); −0.0003 (236.3); −0.0068 (9.3); −0.0414 (0.4); −0.1201 (1.0)

I.250: $^1$H-NMR(500.1 MHz, CDCl3):
δ = 8.6746 (3.6); 8.6696 (3.8); 8.2236 (2.4); 8.2189 (2.3); 8.1272 (1.6); 8.1104 (1.8); 8.1089 (1.8); 7.7760 (1.6); 7.7688 (1.4); 7.7658 (1.1); 7.7599 (2.1); 7.7547 (1.9); 7.7518 (1.9); 7.7490 (1.0); 7.7379 (1.4); 7.7350 (1.0); 7.5966 (1.3); 7.5943 (1.4); 7.5908 (1.8); 7.5873 (1.4); 7.5861 (1.4); 7.5805 (2.2); 7.5777 (1.6); 7.5760 (2.3); 7.5719 (2.0); 7.5664 (1.0); 7.5641 (0.9); 7.4650 (0.3); 7.3886 (2.3); 7.3746 (3.5); 7.3320 (2.1); 7.3283 (0.8); 7.3176 (4.2); 7.3147 (1.8); 7.3024 (2.1); 7.2718 (1.3); 7.2587 (60.6); 7.2429 (0.7); 7.2019 (0.6); 7.1983 (0.8); 7.1872 (1.8); 7.1836 (1.6); 7.1724 (3.4); 7.1680 (3.6); 7.1570 (1.8); 7.1537 (1.9); 7.1422 (0.8); 7.1391 (0.6); 7.0470 (0.3); 6.5561 (1.8); 6.5527 (2.1); 6.5414 (1.2); 6.5402 (1.4); 6.5374 (1.8); 4.6407 (1.6); 4.6176 (2.7); 4.5501 (2.5); 4.5268 (1.5); 1.9340 (16.0); 1.7861 (16.0); 1.6072 (16.0); 1.5367 (11.0); 0.1163 (0.4); 0.0689 (0.5); 0.0063 (2.9); −0.0003 (108.0); −0.0068 (4.1); −0.1200 (0.4)

I.251: $^1$H-NMR(500.1 MHz, CDCl3):
δ = 8.4483 (1.5); 8.4434 (1.5); 7.9222 (0.7); 7.9175 (0.7); 7.9053 (0.9); 7.9007 (0.8); 7.7283 (1.9); 7.7114 (1.6); 7.5143 (1.0); 7.5110 (1.0); 7.4991 (1.3); 7.4957 (1.3); 7.3352 (0.4); 7.3319 (0.5); 7.3203 (1.2); 7.3169 (1.1); 7.3050 (1.1); 7.3013 (1.0); 7.2943 (1.0); 7.2912 (1.1); 7.2791 (1.2); 7.2762 (1.2); 7.2591 (21.9); 6.8022 (1.2); 6.7994 (1.3); 6.7864 (1.1); 6.7838 (1.2); 5.2983 (0.4); 3.2580 (16.0); 1.7588 (11.8); 1.7196 (0.4); 1.6356 (10.8); 1.5340 (4.6); 1.4445 (10.9); 1.2853 (0.4); 1.2553 (0.6); 0.0062 (1.3); −0.0003 (35.4); −0.0067 (1.4)

I.252: $^1$H-NMR(500.1 MHz, CDCl3):
δ = 8.2760 (2.2); 8.2714 (2.3); 8.0021 (2.7); 7.9975 (2.6); 7.4867 (1.1); 7.4834 (1.1); 7.4713 (1.3); 7.4679 (1.2); 7.2593 (13.9); 7.2539 (2.4); 7.1232 (0.5); 7.1197 (0.6); 7.1084 (1.1); 7.1052 (1.1); 7.0926 (1.1); 7.0890 (1.0); 7.0782 (1.0); 7.0754 (1.1); 7.0629 (1.2); 7.0603 (1.2); 7.0482 (0.6); 7.0455 (0.5); 6.5008 (2.7); 6.4939 (2.6); 6.4613 (1.3); 6.4586 (1.4); 6.4452 (1.2); 6.4426 (1.2); 3.9364 (0.7); 3.9333 (0.5); 3.9236 (15.2); 3.8596 (0.8); 3.3795 (16.0); 2.2764 (0.6); 1.8306 (11.5); 1.7611 (0.3); 1.7262 (0.6); 1.7072 (10.9); 1.6470 (0.4); 1.5894 (11.4); 1.5584 (1.6); 1.3405 (0.3); 1.2849 (2.5); 1.2560 (1.6); 0.8803 (0.5); 0.8676 (0.3); 0.0061 (1.5); −0.0003 (27.6); −0.0068 (0.8)

I.253: $^1$H-NMR(500.1 MHz, CDCl3):
δ = 8.4566 (1.9); 8.4519 (2.0); 8.1953 (2.4); 8.1906 (2.3); 7.6312 (2.0); 7.6193 (2.1); 7.5094 (1.0); 7.5060 (0.9); 7.4941 (1.2); 7.4906 (1.1); 7.3037 (2.6); 7.2918 (2.4); 7.2592 (19.1); 7.1954 (0.4); 7.1920 (0.5); 7.1807 (1.0); 7.1772 (1.0); 7.1650 (1.0); 7.1613 (0.9); 7.1535 (0.9); 7.1505 (1.0); 7.1382 (1.1); 7.1354 (1.2); 7.1234 (0.5); 7.1206 (0.4); 6.5374 (1.1); 6.5346 (1.2); 6.5213 (1.0); 6.5187 (1.1); 5.2981 (0.7); 3.3629 (16.0); 1.8190 (11.0); 1.6936 (9.9); 1.5617 (10.2); 1.5422 (11.2); 1.2852 (0.5); 1.2550 (0.7); 0.0061 (1.3); −0.0003 (36.6); −0.0070 (1.5)

TABLE 12-continued

NMR peak lists

I.254: $^1$H-NMR(500.1 MHz, CDCl3):
δ = 8.7121 (2.2); 8.7070 (2.2); 8.2785 (2.1); 8.2733 (2.1); 7.7060 (0.8); 7.6898 (1.0); 7.6044 (0.8); 7.6022 (0.7); 7.5924 (0.8); 7.5905 (1.0); 7.5884 (0.8); 7.5224 (1.0); 7.5190 (0.7); 7.5172 (0.7); 7.5079 (1.2); 7.5032 (2.1); 7.4869 (1.2); 7.4724 (0.8); 7.2591 (10.2); 7.2023 (0.4); 7.1915 (1.1); 7.1876 (1.0); 7.1783 (1.3); 7.1772 (1.5); 7.1742 (1.4); 7.1722 (1.2); 7.1637 (1.1); 7.1603 (1.1); 7.1489 (0.4); 6.6147 (1.1); 6.6110 (1.2); 6.6006 (0.7); 6.5988 (0.8); 6.5960 (1.1); 5.8085 (0.6); 5.4752 (0.6); 3.3659 (16.0); 2.8099 (7.6); 1.8213 (10.5); 1.6923 (9.8); 1.6322 (5.4); 1.5552 (10.6); 1.5499 (10.1); 0.0061 (0.7); −0.0003 (19.0); −0.0070 (0.8)

I.255: $^1$H-NMR(500.1 MHz, CDCl3):
δ = 11.8798 (0.3); 8.8689 (1.6); 8.8672 (1.6); 8.8641 (1.6); 8.8625 (1.4); 8.3781 (2.4); 8.3734 (2.3); 8.2059 (2.3); 8.2012 (2.2); 7.5139 (1.0); 7.5108 (1.0); 7.4983 (1.2); 7.4952 (1.1); 7.4658 (0.4); 7.2724 (0.7); 7.2693 (0.8); 7.2592 (62.6); 7.2416 (0.9); 7.2384 (0.8); 7.1993 (0.8); 7.1968 (0.9); 7.1840 (1.1); 7.1817 (1.1); 7.1726 (1.4); 7.1689 (0.6); 7.1665 (0.5); 7.0477 (0.3); 6.7880 (1.4); 6.7864 (1.5); 6.7833 (1.4); 6.7819 (1.4); 6.6709 (1.2); 6.6686 (1.2); 6.6548 (1.2); 6.6525 (1.1); 3.8841 (0.9); 3.3093 (16.0); 1.8004 (10.8); 1.7027 (10.0); 1.5385 (84.7); 1.5346 (16.3); 1.4218 (0.5); 1.3701 (0.3); 1.3328 (0.6); 1.2843 (1.0); 1.2549 (1.7); 0.8803 (0.4); 0.8439 (0.3); 0.8380 (0.3); 0.1163 (0.5); 0.0061 (4.0); −0.0003 (124.0); −0.0070 (4.4); −0.1202 (0.5)

I.256: $^1$H-NMR(500.1 MHz, CDCl3):
δ = 8.6108 (2.9); 8.6056 (2.7); 8.4668 (0.4); 8.4615 (0.4); 8.2850 (0.4); 8.2799 (0.4); 8.2588 (2.6); 8.2535 (2.4); 7.6766 (0.4); 7.5051 (1.4); 7.5022 (1.3); 7.4894 (1.4); 7.4865 (1.3); 7.4661 (0.4); 7.3639 (2.7); 7.3628 (2.5); 7.2596 (63.0); 7.2427 (1.1); 7.2397 (1.0); 7.2267 (0.8); 7.2236 (1.5); 7.1879 (1.2); 7.1855 (1.1); 7.1726 (1.4); 7.1704 (1.2); 7.1577 (0.6); 7.1553 (0.5); 7.0480 (0.3); 6.6114 (1.6); 6.6093 (1.5); 6.5953 (1.3); 6.5931 (1.2); 3.3377 (0.8); 3.3120 (3.0); 3.2970 (16.0); 3.2669 (1.0); 3.2100 (1.4); 2.5621 (1.1); 2.5374 (9.4); 2.5362 (9.3); 2.5314 (2.0); 2.4243 (0.7); 1.8556 (0.7); 1.8115 (1.2); 1.8047 (2.5); 1.7903 (11.8); 1.7812 (0.8); 1.7707 (1.1); 1.7684 (1.2); 1.7463 (0.5); 1.7163 (1.8); 1.7054 (2.6); 1.6899 (11.5); 1.6785 (1.0); 1.6678 (1.0); 1.6566 (1.0); 1.6387 (1.1); 1.6296 (1.7); 1.6114 (2.8); 1.5670 (5.6); 1.5558 (5.6); 1.5389 (4.8); 1.5210 (12.5); 1.4952 (1.6); 1.4731 (0.7); 1.4268 (1.0); 1.4220 (1.0); 1.3985 (1.5); 1.3702 (1.0); 1.3328 (2.2); 1.2843 (3.8); 1.2559 (14.0); 1.1577 (0.5); 1.0847 (0.5); 1.0767 (0.5); 0.9411 (0.4); 0.8937 (1.6); 0.8802 (2.9); 0.8725 (1.6); 0.8663 (2.0); 0.8592 (1.6); 0.8517 (1.8); 0.8385 (1.9); 0.8101 (0.6); 0.1164 (0.6); 0.0691 (0.5); 0.0061 (6.6); −0.0002 (119.7); −0.0069 (3.3); −0.1201 (0.4)

I.257: $^1$H-NMR(500.1 MHz, CDCl3):
δ = 8.2833 (0.8); 7.9989 (0.5); 7.6681 (0.6); 7.6653 (0.6); 7.6519 (0.6); 7.6492 (0.6); 7.5035 (1.2); 7.4885 (1.7); 7.4662 (0.7); 7.4346 (0.4); 7.4321 (0.4); 7.4164 (0.4); 7.3065 (0.4); 7.3036 (0.4); 7.2725 (0.4); 7.2598 (51.9); 7.2449 (0.6); 7.2421 (0.6); 7.2061 (0.3); 7.1931 (0.8); 7.1778 (1.8); 7.1617 (2.4); 7.1469 (1.5); 7.1330 (0.5); 6.9251 (0.5); 6.9118 (0.5); 6.8848 (0.5); 6.7530 (0.6); 6.7507 (0.6); 6.7371 (0.6); 6.7348 (0.6); 6.5219 (1.1); 6.5071 (1.0); 3.9276 (0.8); 3.8915 (5.1); 3.7436 (0.4); 3.7296 (1.1); 3.7156 (1.1); 3.7015 (0.4); 3.6640 (0.3); 3.3497 (9.3); 3.2098 (5.1); 2.2767 (0.4); 1.8119 (9.9); 1.7738 (0.4); 1.7157 (4.8); 1.6990 (16.0); 1.6722 (5.4); 1.6415 (6.9); 1.6317 (1.7); 1.6277 (1.2); 1.6103 (4.5); 1.5524 (9.0); 1.4932 (6.4); 1.4772 (0.6); 1.4509 (0.4); 1.4219 (0.7); 1.3979 (3.7); 1.3702 (0.4); 1.3391 (0.3); 1.2955 (0.5); 1.2851 (1.9); 1.2580 (3.3); 1.2441 (3.5); 1.2300 (1.7); 0.8803 (0.6); 0.8661 (0.4); 0.8577 (0.4); 0.8398 (0.4); 0.1163 (0.5); 0.0062 (4.5); −0.0002 (95.2); −0.0069 (2.2)

I.258: $^1$H-NMR(500.1 MHz, CDCl3):
δ = 10.2593 (0.4); 8.9189 (2.4); 8.9137 (2.5); 8.5315 (2.0); 8.5262 (1.9); 7.5242 (1.1); 7.5207 (1.0); 7.5092 (1.4); 7.5054 (1.3); 7.3360 (0.5); 7.3256 (0.6); 7.3217 (0.7); 7.3114 (0.6); 7.2603 (10.6); 7.2541 (0.6); 7.2427 (1.2); 7.2392 (1.1); 7.2277 (1.3); 7.2239 (1.9); 7.2207 (1.3); 7.2091 (1.2); 7.2060 (1.2); 7.1942 (0.5); 7.1913 (0.4); 6.8394 (1.6); 6.8245 (1.5); 6.6689 (1.3); 6.6658 (1.4); 6.6532 (1.0); 6.6504 (1.2); 3.3447 (16.0); 1.8002 (11.0); 1.6674 (10.8); 1.5806 (3.9); 1.5232 (11.0); 1.2579 (0.5); 1.2440 (0.6); 0.0061 (0.7); −0.0003 (20.0); −0.0071 (0.6)

I.259: $^1$H-NMR(500.1 MHz, CDCl3):
δ = 8.5872 (3.2); 7.7306 (0.7); 7.7273 (0.7); 7.7150 (0.8); 7.7117 (0.8); 7.5511 (1.6); 7.5439 (1.6); 7.2594 (5.2); 7.1355 (0.7); 7.1323 (0.6); 7.1198 (0.7); 7.1161 (0.6); 7.1093 (0.6); 7.1063 (0.7); 7.0938 (0.7); 7.0911 (0.8); 7.0791 (0.3); 6.7736 (1.8); 6.7663 (1.8); 6.3679 (0.8); 6.3652 (0.9); 6.3516 (0.7); 6.3492 (0.8); 5.9084 (2.3); 5.5407 (2.3); 3.8160 (9.8); 1.7815 (16.0); 1.5555 (8.5); 0.0061 (0.4); −0.0003 (10.0); −0.0070 (0.4)

I.260: $^1$H-NMR(500.1 MHz, CDCl3):
δ = 9.0031 (0.6); 8.9991 (0.6); 8.6060 (1.9); 8.6012 (2.0); 8.4747 (0.4); 8.4713 (0.7); 8.4679 (0.4); 8.2259 (1.2); 8.2222 (1.6); 8.2184 (1.1); 7.5256 (1.1); 7.5221 (0.8); 7.5201 (0.7); 7.5114 (1.2); 7.5068 (1.2); 7.4096 (1.7); 7.2878 (1.0); 7.2844 (1.1); 7.2792 (0.5); 7.2653 (1.9); 7.2597 (25.2); 7.2347 (0.4); 7.2239 (1.1); 7.2199 (1.2); 7.2130 (1.2); 7.2098 (1.7); 7.2087 (1.6); 7.2047 (1.2); 7.1981 (1.2); 7.1947 (1.1); 7.1834 (0.9); 6.6443 (1.2); 6.6403 (1.2); 6.6307 (0.7); 6.6287 (0.8); 6.6257 (1.2); 3.3416 (16.0); 2.5421 (8.1); 2.5297 (3.0); 1.8083 (11.3); 1.6786 (10.8); 1.5456 (11.7); 1.5305 (11.5); 1.2851 (0.6); 1.2549 (0.7); 0.0061 (1.4); −0.0003 (45.8); −0.0070 (1.8)

I.261: $^1$H-NMR(500.1 MHz, CDCl3):
δ = 8.3989 (4.0); 7.5189 (0.9); 7.5142 (0.6); 7.5090 (1.0); 7.5054 (0.6); 7.5005 (2.7); 7.4935 (2.0); 7.2594 (12.1); 7.1700 (1.2); 7.1679 (1.4); 7.1650 (1.1); 7.1594 (1.7); 7.1539 (1.1); 7.1508 (1.4); 7.1492 (1.4); 6.6385 (2.7); 6.6314 (2.7); 6.5585 (1.1); 6.5533 (0.6); 6.5492 (0.7); 6.5440 (0.6); 6.5397 (1.0); 3.9265 (14.1); 3.3782 (16.0); 1.8216 (10.3); 1.6902 (9.3); 1.5760 (9.4); 1.5473 (13.4); 0.0063 (0.8); −0.0003 (21.4); −0.0069 (0.8)

I.262: $^1$H-NMR(500.1 MHz, CDCl3):
δ = 8.7796 (2.1); 8.7746 (2.1); 8.2775 (1.5); 8.2727 (1.5); 8.2334 (1.8); 8.2299 (1.8); 8.1983 (1.4); 8.1808 (1.5); 7.8726 (1.4); 7.8691 (1.4); 7.8553 (1.3); 7.8516 (1.3); 7.5453 (1.0); 7.5416 (0.7); 7.5389 (0.6); 7.5315 (0.9); 7.5265 (1.1); 7.2878 (0.4); 7.2772 (1.1); 7.2730 (1.3); 7.2692 (1.3); 7.2637 (3.0); 7.2596 (29.6); 7.2546 (1.6); 7.2509 (1.3); 7.2396 (0.4); 6.7125 (1.1); 6.7080 (0.9); 6.6999 (0.6); 6.6971 (0.7); 6.6939 (1.0); 3.4310 (0.4); 3.3225 (16.0); 1.8023 (10.2); 1.6737 (9.7); 1.5438 (20.4); 1.5067 (9.9); 1.2580 (0.6); 1.2441 (0.6); 0.0061 (1.9); −0.0003 (52.7); −0.0071 (1.8)

I.263: $^1$H-NMR(500.1 MHz, CDCl3):
δ = 8.8049 (2.5); 8.7998 (2.6); 8.3286 (2.3); 8.3235 (2.3); 8.1558 (2.3); 8.1525 (2.4); 7.9675 (2.8); 7.9642 (2.8); 7.5473 (1.0); 7.5431 (0.7); 7.5389 (0.6); 7.5361 (0.6); 7.5337 (0.7); 7.5286 (1.1); 7.3247 (0.3); 7.3145 (1.3); 7.3104 (2.0); 7.3034 (2.6); 7.2959 (1.9); 7.2923 (1.3); 7.2817 (0.3); 7.2599 (23.8); 6.7903 (1.2); 6.7855 (0.7); 6.7833 (0.6); 6.7797 (0.6); 6.7755 (0.7); 6.7717 (1.1); 5.2985 (0.6); 3.2801 (16.0); 1.7831 (10.3); 1.7460 (1.0); 1.6610 (10.1); 1.5429 (13.6); 1.4709 (10.3); 1.2551 (0.4); 0.0063 (1.5); −0.0003 (45.6); −0.0068 (1.6)

TABLE 12-continued

NMR peak lists

I.264: ¹H-NMR(500.1 MHz, CDCl3):
δ = 8.5170 (4.3); 7.5220 (1.0); 7.5157 (0.7); 7.5144 (0.6); 7.5100 (1.1); 7.5030 (1.1); 7.4807 (2.3); 7.4735 (2.4); 7.2596 (16.3); 7.2067 (0.3); 7.1987 (2.7); 7.1919 (1.8); 7.1867 (1.7); 7.1798 (2.7); 6.7260 (2.6); 6.7189 (2.6); 6.6255 (1.1); 6.6187 (1.1); 6.6145 (0.6); 6.6126 (0.7); 6.6067 (1.0); 3.7870 (15.2); 3.3813 (16.0); 1.8221 (10.9); 1.6998 (10.0); 1.5578 (10.5); 1.5483 (17.9); 1.2552 (0.5); 0.0062 (1.1); −0.0003 (30.8); −0.0070 (1.2)

I.265: ¹H-NMR(500.1 MHz, CDCl3):
δ = 8.7173 (1.7); 8.7147 (2.0); 8.7107 (1.3); 8.3006 (2.3); 8.2962 (2.1); 8.0944 (2.1); 8.0874 (2.0); 7.5161 (1.3); 7.5133 (1.2); 7.5006 (1.4); 7.4977 (1.3); 7.2924 (0.7); 7.2894 (0.6); 7.2773 (1.4); 7.2745 (1.3); 7.2597 (29.8); 7.2187 (1.1); 7.2164 (1.0); 7.2034 (1.4); 7.2013 (1.3); 7.1884 (0.7); 7.1861 (0.6); 6.6834 (1.6); 6.6813 (1.4); 6.6672 (1.5); 6.6653 (1.2); 3.2941 (16.0); 3.2896 (1.2); 1.7926 (12.0); 1.7581 (0.4); 1.7116 (1.0); 1.6956 (11.5); 1.6505 (0.7); 1.6337 (0.3); 1.6206 (1.0); 1.6149 (1.0); 1.6056 (0.4); 1.5737 (1.5); 1.5476 (16.9); 1.5186 (11.9); 1.4763 (0.7); 1.4382 (0.6); 1.2852 (1.1); 1.2561 (1.7); 1.2443 (0.4); 0.8803 (0.4); 0.8444 (0.4); 0.0059 (3.7); −0.0003 (51.0); −0.0070 (1.4)

I.266: ¹H-NMR(500.1 MHz, CDCl3):
δ = 9.1497 (0.9); 9.1451 (0.9); 8.8263 (1.6); 8.8208 (1.7); 8.3662 (2.0); 8.3607 (2.0); 8.2517 (1.0); 8.2480 (1.1); 8.2354 (1.1); 8.2316 (1.2); 7.6008 (0.6); 7.5982 (0.7); 7.5848 (0.7); 7.5823 (0.8); 7.5633 (0.9); 7.5549 (1.0); 7.5471 (1.0); 7.5393 (1.7); 7.5258 (1.2); 7.5213 (1.2); 7.2833 (0.3); 7.2807 (0.4); 7.2724 (0.4); 7.2684 (1.1); 7.2600 (17.9); 7.2538 (1.9); 7.2463 (1.4); 7.2436 (1.8); 7.2419 (1.9); 7.2387 (1.4); 7.2315 (1.2); 7.2282 (1.2); 7.2167 (0.4); 7.2135 (0.3); 7.0963 (0.4); 7.0940 (0.5); 7.0791 (0.7); 7.0657 (0.4); 7.0634 (0.4); 6.7720 (0.8); 6.7560 (0.7); 6.6954 (1.2); 6.6915 (1.3); 6.6817 (0.7); 6.6798 (0.9); 6.6769 (1.2); 5.8085 (2.1); 5.4748 (2.1); 3.3415 (15.4); 1.8093 (11.4); 1.7704 (0.6); 1.6826 (11.0); 1.6439 (0.6); 1.6333 (16.0); 1.6109 (0.4); 1.5682 (3.1); 1.5221 (11.2); 1.4951 (0.3); 1.2855 (0.7); 1.2581 (1.0); 1.2442 (1.2); 1.2301 (0.6); 0.0062 (1.4); −0.0003 (32.5); −0.0067 (1.6)

I.267: ¹H-NMR(500.1 MHz, CDCl3):
δ = 8.2702 (1.3); 8.2657 (1.3); 7.5610 (1.2); 7.5589 (1.2); 7.5566 (1.3); 7.4798 (1.0); 7.4767 (1.0); 7.4642 (1.2); 7.4610 (1.2); 7.2596 (21.4); 7.1929 (0.5); 7.1897 (0.6); 7.1782 (1.0); 7.1751 (1.0); 7.1735 (0.7); 7.1620 (0.9); 7.1588 (0.9); 7.1279 (0.9); 7.1254 (1.0); 7.1126 (1.0); 7.1101 (1.0); 7.0977 (0.6); 7.0952 (0.5); 6.5353 (1.2); 6.5328 (1.2); 6.5191 (1.1); 6.5166 (1.1); 3.3390 (16.0); 3.0659 (1.3); 3.0504 (2.3); 3.0350 (1.3); 3.0014 (1.0); 2.9865 (1.8); 2.9715 (1.0); 2.2332 (0.5); 2.2178 (1.5); 2.2026 (2.0); 2.1875 (1.4); 2.1722 (0.4); 1.7945 (11.3); 1.6640 (10.2); 1.5509 (4.7); 1.5393 (11.3); 1.2546 (0.4); 0.0061 (1.3); −0.0003 (42.6); −0.0071 (1.3)

I.268: ¹H-NMR(500.1 MHz, CDCl3):
δ = 8.7244 (3.8); 8.7194 (3.8); 8.1599 (2.5); 8.1553 (2.4); 8.0869 (1.7); 8.0699 (1.9); 7.8370 (2.6); 7.8158 (1.2); 7.8118 (1.3); 7.8031 (2.7); 7.7977 (1.5); 7.7864 (2.4); 7.7504 (1.3); 7.7344 (2.0); 7.7319 (2.4); 7.7208 (1.4); 7.7178 (2.3); 7.7147 (1.2); 7.7039 (1.2); 7.7009 (1.3); 7.6371 (1.4); 7.6279 (1.8); 7.6229 (3.0); 7.6132 (2.1); 7.6091 (1.8); 7.5338 (1.3); 7.5317 (1.3); 7.5200 (1.3); 7.5177 (2.0); 7.5155 (1.2); 7.5037 (0.8); 7.5016 (0.9); 7.4832 (1.7); 7.4799 (1.7); 7.4660 (1.7); 7.4628 (1.9); 7.4589 (0.8); 7.4485 (1.3); 7.4451 (1.6); 7.4394 (1.8); 7.4345 (3.8); 7.4296 (1.6); 7.4239 (1.4); 7.4206 (1.7); 7.4102 (0.6); 7.4070 (0.4); 7.2586 (65.2); 7.2142 (0.6); 7.2105 (0.8); 7.1995 (1.8); 7.1958 (1.6); 7.1846 (3.7); 7.1803 (3.6); 7.1694 (1.9); 7.1662 (1.8); 7.1546 (0.7); 7.1515 (0.6); 7.0471 (0.4); 6.5764 (2.0); 6.5729 (2.1); 6.5617 (1.3); 6.5605 (1.4); 6.5577 (1.9); 5.2978 (0.6); 4.7986 (1.5); 4.7749 (2.5); 4.7054 (2.4); 4.6816 (1.4); 2.2779 (0.3); 2.1694 (0.8); 1.9733 (15.3); 1.8238 (15.8); 1.6293 (16.0); 1.5367 (79.7); 1.2852 (0.4); 1.2534 (1.2); 0.1163 (0.4); 0.0687 (0.4); 0.0061 (3.8); −0.0003 (121.6); −0.0071 (4.0); −0.1202 (0.4)

I.269: ¹H-NMR(500.1 MHz, CDCl3):
δ = 8.4425 (1.7); 8.4382 (1.7); 8.1199 (2.0); 7.6698 (0.4); 7.6671 (0.4); 7.6538 (0.4); 7.6510 (0.4); 7.6016 (0.6); 7.5990 (0.6); 7.5857 (0.6); 7.5830 (0.6); 7.4982 (0.8); 7.4948 (0.8); 7.4830 (1.0); 7.4794 (0.9); 7.2848 (0.4); 7.2821 (0.4); 7.2670 (0.7); 7.2599 (24.4); 7.2544 (0.8); 7.2515 (0.6); 7.2463 (0.4); 7.1628 (0.4); 7.1527 (0.4); 7.1491 (0.5); 7.1381 (0.8); 7.1346 (0.8); 7.1226 (0.9); 7.1187 (0.8); 7.1154 (0.8); 7.1120 (0.9); 7.1000 (1.0); 7.0974 (1.2); 7.0852 (0.5); 7.0823 (0.9); 7.0672 (0.4); 6.7574 (0.6); 6.7555 (0.6); 6.7466 (0.4); 6.7416 (0.7); 6.7395 (0.6); 6.7307 (0.4); 6.7284 (0.3); 6.4691 (1.0); 6.4661 (1.0); 6.4532 (0.8); 6.4504 (0.9); 5.8095 (1.8); 5.4762 (1.8); 3.9772 (0.4); 3.9691 (0.4); 3.9584 (10.2); 3.9270 (0.4); 3.3669 (12.3); 3.2100 (1.6); 1.8238 (8.7); 1.7650 (0.6); 1.7161 (1.4); 1.7025 (8.1); 1.6737 (2.8); 1.6442 (4.0); 1.6334 (16.0); 1.6113 (1.4); 1.5744 (9.4); 1.5591 (2.0); 1.4952 (3.6); 1.3989 (1.1); 1.2582 (0.8); 1.2548 (0.6); 1.2443 (0.8); 1.2302 (0.4); 0.0063 (1.7); −0.0003 (44.8); −0.0068 (1.7)

I.270: ¹H-NMR(500.1 MHz, CDCl3):
δ = 8.4953 (2.4); 8.4918 (2.2); 7.9323 (2.9); 7.9279 (2.7); 7.9110 (2.4); 7.5032 (1.5); 7.4879 (1.6); 7.4851 (1.4); 7.2595 (29.6); 7.1969 (0.6); 7.1940 (0.6); 7.1820 (1.4); 7.1666 (1.2); 7.1633 (1.0); 7.1522 (1.2); 7.1501 (1.2); 7.1370 (1.6); 7.1221 (0.6); 7.0438 (2.4); 7.0407 (2.2); 6.5360 (1.7); 6.5199 (1.6); 3.6610 (0.4); 3.3559 (16.0); 1.8136 (13.5); 1.6919 (13.2); 1.6207 (0.4); 1.5549 (18.3); 1.5451 (14.0); 1.4221 (0.4); 1.2853 (0.4); 1.2553 (1.1); −0.0003 (56.8); −0.0066 (1.8)

I.271: ¹H-NMR(500.1 MHz, CDCl3):
δ = 9.0385 (2.8); 9.0349 (2.9); 9.0115 (2.3); 9.0060 (2.3); 8.9411 (2.2); 8.9376 (2.2); 8.4063 (2.3); 8.4008 (2.2); 7.5531 (0.9); 7.5496 (0.7); 7.5472 (0.6); 7.5391 (1.0); 7.5343 (1.1); 7.3384 (0.4); 7.3276 (1.0); 7.3234 (1.2); 7.3179 (1.1); 7.3137 (1.9); 7.3084 (1.1); 7.3031 (1.2); 7.2995 (1.1); 7.2882 (0.4); 7.2599 (18.9); 6.8632 (1.1); 6.8590 (1.1); 6.8501 (0.6); 6.8477 (0.7); 6.8447 (1.1); 5.2985 (1.1); 3.3028 (16.0); 1.7919 (10.6); 1.6698 (9.7); 1.5517 (7.0); 1.5209 (0.6); 1.4821 (9.8); 1.2549 (0.4); 0.0061 (1.4); −0.0003 (42.6); −0.0071 (1.4)

I.272: ¹H-NMR(500.1 MHz, CDCl3):
δ = 8.7020 (3.8); 8.6971 (3.9); 8.2038 (2.6); 8.1990 (2.5); 8.1152 (1.9); 8.1046 (0.3); 8.0975 (1.9); 7.7529 (0.9); 7.7500 (1.6); 7.7455 (1.8); 7.7424 (1.7); 7.7392 (1.2); 7.7361 (2.6); 7.7328 (1.2); 7.7292 (2.1); 7.7261 (2.2); 7.7215 (1.9); 7.7188 (0.7); 7.6130 (1.7); 7.6096 (1.3); 7.6078 (1.2); 7.5985 (2.0); 7.5941 (1.9); 7.5686 (2.8); 7.5658 (3.7); 7.5627 (2.2); 7.5517 (4.6); 7.5496 (5.5); 7.5461 (6.5); 7.5329 (2.7); 7.5296 (6.4); 7.4648 (0.4); 7.4564 (4.7); 7.4426 (3.8); 7.4397 (3.9); 7.4279 (4.5); 7.4152 (1.1); 7.4122 (2.6); 7.3540 (0.9); 7.3516 (1.6); 7.3492 (0.9); 7.3406 (0.8); 7.3370 (2.2); 7.3332 (0.6); 7.3246 (0.5); 7.3223 (0.8); 7.3199 (0.6); 7.2583 (33.9); 7.2179 (0.5); 7.2142 (0.7); 7.2033 (1.9); 7.1994 (1.7); 7.1907 (2.0); 7.1890 (2.5); 7.1864 (2.4); 7.1840 (2.0); 7.1760 (1.9); 7.1725 (1.8); 7.1611 (0.7); 7.1579 (0.5); 6.5806 (1.9); 6.5768 (2.1); 6.5666 (1.2); 6.5648 (1.4); 6.5619 (1.9); 4.6830 (1.8); 4.6595 (2.7); 4.5761 (2.6); 4.5527 (1.7); 1.9519 (14.9); 1.8108 (16.0); 1.6158 (16.0); 1.5435 (18.7); 0.0063 (1.7); −0.0003 (54.1); −0.0068 (2.0)

TABLE 12-continued

NMR peak lists

I.273: ¹H-NMR(500.1 MHz, CDCl3):
δ = 8.7373 (1.6); 8.7357 (1.6); 8.7327 (1.7); 8.7311 (1.6); 8.3195 (2.6); 8.3147 (2.4); 7.5014 (1.0); 7.4984 (1.1);
7.4858 (1.2); 7.4828 (1.2); 7.2596 (28.8); 7.2543 (1.1); 7.2510 (0.8); 7.2392 (0.9); 7.2378 (0.9); 7.2363 (1.0);
7.2232 (0.9); 7.2200 (0.9); 7.1790 (0.9); 7.1765 (0.9); 7.1636 (1.2); 7.1613 (1.1); 7.1487 (0.6); 7.1463 (0.6);
6.6479 (1.3); 6.6456 (1.3); 6.6317 (1.2); 6.6294 (1.2); 6.5606 (2.6); 3.3029 (16.0); 2.5431 (11.6); 1.7941 (11.0);
1.6949 (10.3); 1.6338 (0.8); 1.6046 (0.3); 1.5464 (5.7); 1.5305 (11.8); 1.4961 (0.4); 1.2853 (0.8); 1.2549 (1.2);
0.0062 (2.2); −0.0003 (53.7); −0.0070 (2.0)
I.274: ¹H-NMR(500.1 MHz, CDCl3):
δ = 8.2554 (2.1); 8.2510 (2.0); 7.4791 (1.5); 7.4765 (1.4); 7.4631 (2.0); 7.4600 (2.8); 7.2597 (15.5); 7.1993 (0.7);
7.1966 (0.6); 7.1844 (1.4); 7.1686 (1.1); 7.1658 (0.9); 7.1349 (1.1); 7.1331 (1.1); 7.1197 (1.6); 7.1047 (0.7);
6.5632 (1.7); 6.5470 (1.5); 5.2982 (0.6); 3.3335 (16.0); 2.9686 (1.7); 2.9558 (3.2); 2.9429 (1.7); 2.8267 (1.5);
2.8141 (2.8); 2.8017 (1.5); 1.9520 (0.5); 1.9394 (1.2); 1.9284 (1.8); 1.9161 (1.8); 1.9080 (0.5); 1.9034 (0.6);
1.8537 (0.9); 1.8486 (0.7); 1.8415 (1.8); 1.8294 (1.8); 1.8185 (1.2); 1.8057 (0.6); 1.7906 (13.3); 1.6580 (13.2);
1.5830 (2.2); 1.5327 (13.3); 1.2551 (0.5); −0.0002 (29.2)
I.275: ¹H-NMR(500.1 MHz, CDCl3):
δ = 8.6420 (3.9); 8.6370 (4.0); 8.2244 (2.5); 8.2202 (2.5); 8.1221 (1.8); 8.1062 (1.4); 8.1042 (1.9); 7.7723 (4.5);
7.7697 (1.4); 7.7567 (3.8); 7.7538 (2.3); 7.7432 (1.7); 7.7402 (1.0); 7.6017 (1.3); 7.5995 (1.3); 7.5877 (1.1);
7.5855 (2.1); 7.5833 (1.3); 7.5714 (2.6); 7.5686 (2.1); 7.5560 (2.1); 7.5525 (1.9); 7.4166 (3.6); 7.3991 (4.2);
7.2589 (37.2); 7.2206 (0.7); 7.2174 (0.8); 7.2100 (1.8); 7.2026 (1.9); 7.1904 (1.8); 7.1866 (1.7); 7.1822 (1.7);
7.1790 (1.9); 7.1670 (1.8); 7.1640 (2.1); 7.1522 (3.7); 7.1363 (2.6); 6.5752 (2.0); 6.5723 (2.2); 6.5594 (1.7);
6.5565 (1.9); 4.6010 (1.8); 4.5774 (2.6); 4.4728 (2.4); 4.4491 (1.7); 1.9138 (15.3); 1.7941 (16.0); 1.5850 (16.2);
1.5404 (54.2); 0.0061 (2.0); −0.0003 (65.8); −0.0071 (2.6)
I.276: ¹H-NMR(500.1 MHz, CDCl3):
δ = 8.5983 (4.0); 8.5933 (4.2); 8.2245 (2.6); 8.2196 (2.6); 8.1083 (1.7); 8.0917 (2.0); 8.0903 (2.0); 7.7660 (1.8);
7.7609 (2.0); 7.7582 (4.0); 7.7559 (4.2); 7.7504 (3.6); 7.7468 (7.7); 7.7421 (5.8); 7.7391 (4.4); 7.7339 (2.1);
7.7303 (7.2); 7.7272 (2.2); 7.5898 (2.7); 7.5795 (0.9); 7.5745 (4.8); 7.5714 (2.7); 7.5659 (1.0); 7.5623 (2.8);
7.5587 (1.8); 7.5499 (1.0); 7.5474 (1.7); 7.5449 (0.9); 7.4992 (4.2); 7.4825 (3.7); 7.4654 (0.5); 7.4587 (3.1);
7.4555 (1.3); 7.4429 (4.4); 7.4312 (0.9); 7.4279 (2.1); 7.2590 (52.7); 7.2385 (0.8); 7.2352 (0.9); 7.2237 (1.9);
7.2203 (1.7); 7.2083 (1.8); 7.2045 (1.8); 7.2015 (1.7); 7.1982 (1.7); 7.1862 (1.9); 7.1833 (2.0); 7.1714 (0.8);
7.1685 (0.7); 7.0474 (0.4); 6.6011 (2.1); 6.5981 (2.4); 6.5853 (1.7); 6.5824 (2.1); 5.2979 (0.5); 4.7094 (1.8);
4.6842 (2.5); 4.5484 (2.4); 4.5231 (1.8); 1.9358 (14.8); 1.8233 (16.0); 1.5860 (16.3); 1.5402 (47.9); 0.1164 (0.3);
0.0689 (0.4); 0.0062 (3.0); −0.0003 (85.0); −0.0069 (3.2)
I.277: ¹H-NMR(500.1 MHz, CDCl3):
δ = 8.4498 (1.7); 8.4481 (1.7); 8.4452 (1.7); 8.4436 (1.6); 7.8896 (2.2); 7.8848 (2.2); 7.4969 (1.1); 7.4940 (1.2);
7.4813 (1.3); 7.4784 (1.3); 7.2781 (1.3); 7.2755 (1.4); 7.2723 (1.5); 7.2698 (1.4); 7.2593 (28.1); 7.2407 (0.7);
7.2377 (0.7); 7.2257 (1.1); 7.2232 (1.1); 7.2097 (1.0); 7.2067 (0.8); 7.1537 (0.9); 7.1514 (0.9); 7.1383 (1.3);
7.1363 (1.2); 7.1234 (0.6); 7.1211 (0.6); 7.0598 (1.3); 7.0536 (1.5); 7.0518 (1.5); 7.0457 (1.3); 6.7249 (1.3);
6.7168 (1.2); 6.6841 (1.4); 6.6819 (1.4); 6.6678 (1.4); 6.6657 (1.2); 3.3169 (16.0); 1.7992 (11.7); 1.6966 (11.1);
1.5449 (18.7); 1.2855 (0.7); 1.2576 (1.0); 1.2440 (0.6); 0.0061 (2.5); −0.0002 (49.4); −0.0069 (1.3)
I.278: ¹H-NMR(500.1 MHz, CDCl3):
δ = 8.0177 (1.8); 8.0127 (2.0); 7.4928 (1.8); 7.4901 (1.6); 7.4877 (2.0); 7.4691 (1.2); 7.4662 (1.6); 7.4534 (1.4);
7.4505 (1.6); 7.2597 (20.7); 7.1905 (0.6); 7.1875 (0.7); 7.1730 (1.3); 7.1597 (1.0); 7.1566 (1.0); 7.1096 (0.9);
7.1074 (1.1); 7.0922 (1.5); 7.0795 (0.6); 7.0771 (0.7); 6.5255 (1.4); 6.5234 (1.6); 6.5091 (1.4); 6.5071 (1.5);
5.2984 (0.4); 4.4107 (1.8); 4.3999 (2.3); 4.3898 (1.9); 3.6410 (0.4); 3.3256 (16.0); 2.8683 (1.4); 2.8555 (2.7);
2.8427 (1.5); 2.0709 (0.6); 2.0582 (1.5); 2.0459 (1.6); 2.0369 (1.4); 2.0241 (0.6); 1.7880 (12.5); 1.7009 (0.4);
1.6638 (12.1); 1.6501 (0.5); 1.6333 (0.6); 1.5824 (0.6); 1.5468 (10.6); 1.5377 (15.1); 1.4977 (0.4); 1.4216 (0.4);
1.2852 (0.4); 1.2547 (1.0); 0.0061 (1.6); −0.0003 (41.0)
I.279: ¹H-NMR(500.1 MHz, CDCl3):
δ = 8.6952 (0.8); 8.6902 (0.8); 8.2207 (0.5); 8.2163 (0.5); 8.1209 (0.4); 8.1032 (0.4); 7.7597 (0.3); 7.7551 (0.4);
7.7519 (0.4); 7.7458 (0.6); 7.7387 (0.4); 7.7356 (0.5); 7.7312 (0.4); 7.5976 (0.4); 7.5834 (0.6); 7.5788 (0.4);
7.5679 (0.5); 7.3537 (0.4); 7.3365 (1.8); 7.3235 (1.4); 7.3064 (0.4); 7.2587 (12.7); 7.1821 (0.4); 7.1780 (0.4);
7.1717 (0.4); 7.1674 (0.6); 7.1628 (0.4); 7.1569 (0.6); 7.1533 (0.4); 6.5605 (0.4); 6.5564 (0.4); 6.5418 (0.4);
4.6249 (0.4); 4.6021 (0.6); 4.5410 (0.6); 4.5181 (0.4); 1.9354 (3.2); 1.7767 (3.4); 1.6131 (3.4); 1.5374 (19.0);
1.3038 (16.0); 1.2530 (0.5); 0.0061 (0.7); −0.0003 (21.8); −0.0070 (0.8)
I.280: ¹H-NMR(500.1 MHz, CDCl3):
δ = 8.5970 (3.7); 8.5919 (3.8); 8.2557 (2.6); 8.2509 (2.4); 8.1238 (1.7); 8.1069 (1.9); 7.8142 (1.6); 7.7979 (1.9);
7.7824 (1.2); 7.7795 (1.2); 7.7685 (1.5); 7.7656 (2.1); 7.7626 (1.1); 7.7516 (1.3); 7.7487 (1.1); 7.6711 (1.3);
7.6553 (1.5); 7.6179 (3.8); 7.6036 (1.2); 7.6017 (2.1); 7.5877 (1.0); 7.5854 (0.9); 7.5643 (1.7); 7.5610 (1.6);
7.5488 (2.0); 7.5455 (1.9); 7.5262 (1.3); 7.5106 (1.7); 7.4010 (1.8); 7.3855 (2.9); 7.3700 (1.3); 7.2593 (33.9);
7.2355 (0.7); 7.2322 (0.8); 7.2207 (1.7); 7.2175 (1.5); 7.2050 (1.6); 7.2014 (1.5); 7.1902 (1.4); 7.1874 (1.6);
7.1749 (1.8); 7.1722 (1.8); 7.1600 (0.8); 7.1573 (0.7); 6.5800 (2.0); 6.5773 (2.2); 6.5640 (1.8); 6.5613 (1.9);
5.2981 (1.4); 4.5941 (1.7); 4.5695 (2.5); 4.4756 (2.3); 4.4511 (1.6); 1.9122 (15.3); 1.8020 (16.0); 1.5839 (16.0);
1.5436 (26.4); 0.0063 (1.6); −0.0003 (51.2); −0.0068 (2.0)
I.281: ¹H-NMR(500.1 MHz, CDCl3):
δ = 8.9867 (1.1); 8.9835 (1.1); 8.9783 (1.1); 8.9751 (1.1); 8.9330 (2.2); 8.9280 (2.2); 8.4279 (0.9); 8.4267 (0.9);
8.4249 (0.8); 8.4109 (1.0); 8.4097 (0.9); 8.4079 (0.8); 8.2967 (1.5); 8.2952 (1.5); 8.2917 (1.6); 8.2902 (1.5);
7.6559 (1.5); 7.6476 (1.4); 7.6389 (1.4); 7.6305 (1.4); 7.5369 (1.0); 7.5335 (0.8); 7.5310 (0.7); 7.5229 (1.0);
7.5182 (1.2); 7.2833 (0.3); 7.2794 (0.5); 7.2687 (1.4); 7.2644 (1.6); 7.2599 (23.2); 7.2548 (2.5); 7.2494 (1.3);
7.2442 (1.3); 7.2407 (1.1); 7.2295 (0.4); 6.7817 (1.2); 6.7775 (1.1); 6.7685 (0.6); 6.7661 (0.7); 6.7631 (1.1);
3.3319 (16.0); 1.8012 (11.2); 1.6755 (10.4); 1.6336 (2.8); 1.5511 (11.1); 1.5102 (10.4); 0.0063 (1.5); −0.0003
(39.4); −0.0068 (1.6)
I.282: ¹H-NMR(500.1 MHz, CDCl3):
δ = 8.4857 (2.2); 8.4806 (2.4); 8.2658 (1.5); 8.2609 (1.5); 8.0835 (1.0); 8.0659 (1.1); 7.8587 (2.7); 7.8553 (1.0);
7.8454 (1.0); 7.8419 (3.2); 7.7982 (0.9); 7.7819 (1.1); 7.7691 (0.7); 7.7664 (0.7); 7.7552 (0.9); 7.7524 (1.3);
7.7494 (0.7); 7.7383 (0.8); 7.7355 (0.7); 7.6093 (0.8); 7.6071 (0.8); 7.5931 (1.4); 7.5907 (1.0); 7.5855 (2.4);
7.5794 (0.9); 7.5769 (0.8); 7.5683 (3.0); 7.5648 (1.4); 7.5523 (1.2); 7.5490 (1.1); 7.2593 (32.2); 7.2438 (0.5);
7.2407 (0.6); 7.2290 (1.0); 7.2258 (1.0); 7.2133 (1.0); 7.2098 (0.9); 7.1975 (0.8); 7.1947 (1.0); 7.1822 (1.1);
7.1795 (1.2); 7.1673 (0.5); 7.1646 (0.5); 6.5905 (1.2); 6.5878 (1.3); 6.5744 (1.1); 6.5718 (1.2); 5.2981 (1.9);

TABLE 12-continued

NMR peak lists 4.6751 (1.0); 4.6494 (1.4); 4.4927 (1.4); 4.4670 (1.0); 3.0186 (16.0); 1.9132 (8.6); 1.8204 (9.2); 1.7751 (0.4); 1.5669 (9.5); 1.5422 (38.4); 1.2534 (0.6); 0.0060 (1.8); −0.0003 (57.7); −0.0071 (1.9)

I.283: $^1$H-NMR(500.1 MHz, CDCl3):
δ = 8.6718 (2.3); 8.6668 (2.3); 8.2141 (1.5); 8.2094 (1.5); 8.1220 (1.1); 8.1060 (0.8); 8.1041 (1.1); 7.7633 (2.7); 7.7604 (0.9); 7.7475 (2.1); 7.7343 (1.0); 7.7314 (0.6); 7.5917 (0.8); 7.5895 (0.8); 7.5781 (1.7); 7.5753 (2.1); 7.5632 (1.4); 7.5595 (1.7); 7.2589 (14.6); 7.2252 (1.0); 7.2094 (1.7); 7.2036 (0.6); 7.1929 (1.8); 7.1889 (1.1); 7.1772 (1.2); 7.1733 (1.9); 7.1701 (1.2); 7.1584 (1.1); 7.1553 (1.2); 7.1436 (0.5); 7.1406 (0.4); 7.0465 (1.2); 6.9007 (1.0); 6.8999 (1.0); 6.8856 (0.9); 6.7860 (0.7); 6.7814 (0.7); 6.7698 (0.6); 6.7651 (0.6); 6.5694 (1.2); 6.5662 (1.4); 6.5536 (0.9); 6.5507 (1.2); 5.2973 (1.3); 4.6183 (1.1); 4.5946 (1.6); 4.4893 (1.4); 4.4656 (1.0); 3.8132 (0.7); 3.6701 (16.0); 1.9173 (9.6); 1.7960 (9.7); 1.5826 (10.0); 1.5510 (11.7); 0.0061 (0.7); −0.0003 (23.6); −0.0070 (0.8)

I.284: $^1$H-NMR(500.1 MHz, CDCl3):
δ = 8.5429 (3.8); 8.5379 (4.0); 8.2299 (2.5); 8.2251 (2.5); 8.1131 (1.9); 8.0952 (1.9); 7.7789 (4.1); 7.7755 (1.4); 7.7650 (2.9); 7.7621 (3.2); 7.7593 (2.0); 7.7503 (1.6); 7.7475 (0.9); 7.6135 (1.3); 7.6114 (1.3); 7.5998 (1.2); 7.5971 (2.1); 7.5834 (1.5); 7.5812 (0.9); 7.5643 (3.6); 7.5609 (1.5); 7.5555 (1.9); 7.5517 (3.1); 7.5476 (6.2); 7.5401 (2.2); 7.5368 (2.0); 7.4926 (4.6); 7.4755 (2.9); 7.4658 (0.3); 7.2592 (41.0); 7.2408 (0.8); 7.2377 (0.9); 7.2261 (1.7); 7.2230 (1.6); 7.2103 (1.6); 7.2068 (1.5); 7.1914 (1.5); 7.1885 (1.7); 7.1760 (1.8); 7.1734 (2.0); 7.1612 (0.9); 7.1585 (0.7); 6.5958 (2.1); 6.5932 (2.2); 6.5797 (1.9); 6.5771 (2.0); 5.2980 (2.1); 4.6356 (1.8); 4.6097 (2.5); 4.4609 (2.3); 4.4351 (1.8); 1.9031 (15.1); 1.8087 (16.0); 1.5618 (16.3); 1.5422 (66.9); 1.2534 (0.6); 0.0689 (0.4); 0.0061 (2.0); −0.0003 (67.0); −0.0070 (2.3)

I.285: $^1$H-NMR(500.1 MHz, CDCl3):
δ = 8.6869 (3.0); 8.6819 (3.0); 8.2142 (2.4); 8.2094 (2.3); 8.1312 (1.4); 8.1141 (1.5); 7.7733 (1.7); 7.7683 (1.5); 7.7655 (0.9); 7.7574 (2.4); 7.7545 (2.4); 7.7514 (1.7); 7.7487 (1.0); 7.7381 (1.4); 7.7348 (1.0); 7.5963 (1.3); 7.5943 (1.4); 7.5906 (1.8); 7.5872 (1.4); 7.5854 (1.3); 7.5805 (2.2); 7.5762 (2.2); 7.5717 (1.9); 7.5663 (1.0); 7.5641 (0.9); 7.2587 (21.5); 7.2237 (0.8); 7.2075 (2.0); 7.2007 (0.6); 7.1971 (0.9); 7.1930 (2.6); 7.1861 (2.1); 7.1814 (4.0); 7.1788 (4.0); 7.1737 (3.4); 7.1721 (3.4); 7.1691 (2.9); 7.1669 (2.6); 7.1586 (1.8); 7.1552 (1.6); 7.1438 (0.6); 7.1406 (0.5); 7.0705 (1.3); 7.0564 (1.1); 6.5636 (1.7); 6.5599 (1.8); 6.5478 (1.2); 6.5449 (1.6); 5.2973 (1.7); 4.6137 (1.6); 4.5906 (2.8); 4.5302 (2.5); 4.5071 (1.5); 2.2848 (13.2); 1.9323 (15.8); 1.7796 (16.0); 1.6082 (15.8); 1.5526 (5.4); 1.2534 (0.3); 0.0061 (0.9); −0.0003 (34.7); −0.0070 (1.0)

I.286: $^1$H-NMR(500.1 MHz, CDCl3):
δ = 8.6455 (2.7); 8.6406 (2.8); 8.1759 (2.2); 8.1713 (2.2); 8.1275 (1.2); 8.1101 (1.3); 7.7665 (3.3); 7.7517 (4.9); 7.7470 (1.2); 7.7357 (1.3); 7.7330 (0.9); 7.5936 (1.2); 7.5914 (1.2); 7.5863 (1.8); 7.5827 (1.7); 7.5784 (2.1); 7.5753 (1.4); 7.5712 (2.1); 7.5674 (1.9); 7.5635 (1.0); 7.5614 (0.9); 7.4653 (1.3); 7.4519 (1.4); 7.2588 (50.1); 7.2018 (0.7); 7.1983 (0.8); 7.1872 (2.1); 7.1835 (1.7); 7.1783 (1.7); 7.1750 (1.6); 7.1720 (2.0); 7.1681 (2.7); 7.1650 (2.4); 7.1621 (1.8); 7.1538 (3.1); 7.1502 (3.0); 7.1388 (1.3); 7.1357 (1.0); 6.5493 (1.7); 6.5461 (1.9); 6.5335 (1.4); 6.5307 (1.6); 5.2979 (1.7); 4.6444 (1.9); 4.6205 (2.6); 4.4974 (2.3); 4.4736 (1.7); 2.2646 (14.6); 1.9528 (15.6); 1.7819 (16.0); 1.6090 (15.7); 1.5404 (34.1); 1.2533 (1.8); 0.0061 (2.7); −0.0003 (90.8); −0.0071 (2.5)

I.287: $^1$H-NMR(500.1 MHz, CDCl3):
δ = 8.6607 (2.2); 8.6559 (2.3); 8.2355 (2.0); 8.2310 (2.0); 8.1364 (1.2); 8.1195 (1.3); 7.7991 (1.4); 7.7829 (1.7); 7.7782 (1.2); 7.7754 (1.0); 7.7641 (1.3); 7.7613 (1.7); 7.7584 (1.0); 7.7473 (1.0); 7.7445 (1.0); 7.6087 (1.1); 7.6070 (1.1); 7.5928 (1.8); 7.5786 (0.8); 7.5768 (0.8); 7.5648 (1.6); 7.5613 (1.6); 7.5496 (2.0); 7.5460 (1.9); 7.3545 (2.4); 7.2740 (0.7); 7.2590 (45.8); 7.2416 (1.0); 7.2265 (2.9); 7.2194 (1.7); 7.2144 (4.5); 7.2022 (1.8); 7.1989 (1.7); 7.1867 (1.6); 7.1829 (1.5); 7.1794 (1.4); 7.1761 (1.6); 7.1612 (1.7); 7.1492 (0.7); 7.1465 (0.6); 6.5685 (1.6); 6.5657 (1.7); 6.5526 (1.4); 6.5500 (1.6); 5.2979 (1.1); 4.5820 (1.8); 4.5580 (2.8); 4.4807 (2.5); 4.4567 (1.6); 1.9138 (15.7); 1.7922 (16.0); 1.5904 (15.4); 1.5414 (18.5); 1.2531 (1.8); 0.0061 (2.4); −0.0003 (74.0); −0.0070 (2.4)

I.288: $^1$H-NMR(500.1 MHz, CDCl3):
δ = 8.6604 (1.9); 8.6558 (1.9); 8.2366 (2.2); 8.2320 (2.1); 8.1378 (1.3); 8.1209 (1.4); 7.7994 (1.3); 7.7830 (1.6); 7.7783 (1.2); 7.7754 (1.0); 7.7642 (1.3); 7.7613 (1.7); 7.7585 (0.9); 7.7473 (1.1); 7.7445 (0.9); 7.6086 (1.2); 7.6069 (1.2); 7.5927 (1.8); 7.5784 (0.9); 7.5767 (0.9); 7.5649 (1.7); 7.5614 (1.5); 7.5496 (2.0); 7.5461 (1.9); 7.3542 (2.5); 7.2784 (0.6); 7.2735 (0.9); 7.2659 (0.9); 7.2590 (18.8); 7.2417 (0.9); 7.2409 (0.9); 7.2260 (3.0); 7.2185 (1.9); 7.2138 (5.0); 7.2024 (1.9); 7.1990 (1.9); 7.1870 (1.7); 7.1832 (1.6); 7.1797 (1.5); 7.1764 (1.7); 7.1644 (1.7); 7.1615 (1.8); 7.1496 (0.7); 7.1468 (0.6); 6.5691 (1.8); 6.5662 (2.0); 6.5531 (1.5); 6.5505 (1.7); 5.2972 (1.2); 4.5821 (1.7); 4.5580 (2.8); 4.4798 (2.6); 4.4557 (1.6); 1.9133 (15.8); 1.7921 (16.0); 1.5896 (16.2); 1.5631 (1.2); 1.2535 (0.4); 0.0061 (0.7); −0.0003 (27.1); −0.0070 (0.8)

I.289: $^1$H-NMR(500.1 MHz, CDCl3):
δ = 8.6844 (1.9); 8.6794 (1.9); 8.1997 (1.3); 8.1950 (1.3); 8.1276 (0.8); 8.1111 (0.9); 7.7783 (0.9); 7.7683 (0.7); 7.7653 (1.0); 7.7621 (1.1); 7.7543 (1.0); 7.7515 (1.1); 7.7486 (0.6); 7.7376 (0.7); 7.7347 (0.6); 7.5976 (0.7); 7.5955 (0.7); 7.5868 (1.0); 7.5834 (1.4); 7.5815 (1.7); 7.5724 (1.0); 7.5678 (1.5); 7.2954 (2.0); 7.2781 (2.2); 7.2591 (24.1); 7.1954 (0.4); 7.1846 (0.9); 7.1806 (0.9); 7.1726 (1.1); 7.1704 (1.3); 7.1682 (1.5); 7.1654 (1.0); 7.1578 (1.0); 7.1544 (0.9); 7.1430 (0.4); 6.8604 (0.3); 6.8547 (2.8); 6.8506 (0.9); 6.8415 (0.8); 6.8373 (2.6); 6.5585 (1.0); 6.5547 (1.1); 6.5446 (0.6); 6.5427 (0.7); 6.5398 (1.0); 4.5735 (1.0); 4.5514 (1.6); 4.4892 (1.5); 4.4670 (0.9); 3.7786 (16.0); 1.9234 (8.4); 1.7646 (8.7); 1.5999 (8.6); 1.5437 (17.4); 0.0063 (1.1); −0.0003 (38.3); −0.0068 (1.3)

I.290: $^1$H-NMR(500.1 MHz, CDCl3):
δ = 8.6220 (2.6); 8.6170 (2.7); 8.2079 (1.9); 8.2033 (1.9); 8.1199 (1.1); 8.1027 (1.3); 7.7727 (0.9); 7.7698 (1.2); 7.7588 (1.2); 7.7557 (2.6); 7.7539 (4.0); 7.7395 (3.3); 7.5995 (1.1); 7.5975 (1.1); 7.5856 (1.1); 7.5833 (1.7); 7.5702 (2.2); 7.5672 (2.6); 7.5551 (2.1); 7.5514 (2.6); 7.5485 (2.6); 7.5317 (3.9); 7.4981 (3.5); 7.4819 (1.8); 7.2590 (51.0); 7.2344 (0.6); 7.2312 (0.7); 7.2195 (1.4); 7.2163 (1.4); 7.2040 (1.3); 7.2004 (1.2); 7.1919 (1.2); 7.1890 (1.3); 7.1765 (1.4); 7.1739 (1.5); 7.1617 (0.6); 7.1590 (0.6); 6.5930 (1.5); 6.5905 (1.5); 6.5771 (1.4); 6.5747 (1.4); 4.6538 (1.3); 4.6288 (1.9); 4.5095 (1.7); 4.4846 (1.2); 1.9161 (15.6); 1.8048 (16.0); 1.5793 (15.3); 1.5425 (10.9); 0.0689 (0.4); 0.0061 (2.5); −0.0003 (77.5); −0.0071 (2.3)

I.291: $^1$H-NMR(500.1 MHz, CDCl3):
δ = 8.6383 (3.5); 8.6333 (3.6); 8.2306 (2.3); 8.2260 (2.2); 8.1280 (1.5); 8.1113 (1.6); 7.7887 (1.6); 7.7757 (2.3); 7.7730 (2.8); 7.7620 (1.7); 7.7590 (2.0); 7.7562 (1.0); 7.7451 (1.4); 7.7423 (1.0); 7.6078 (1.2); 7.6056 (1.3); 7.5936 (1.3); 7.5917 (2.0); 7.5894 (1.2); 7.5776 (1.0); 7.5753 (1.1); 7.5724 (1.8); 7.5690 (1.5); 7.5572 (2.1); 7.5536 (1.8); 7.4658 (0.3); 7.3533 (1.8); 7.3422 (2.0); 7.3358 (2.1); 7.3291 (0.8); 7.3248 (2.0); 7.2591 (50.5);

| TABLE 12-continued |
|---|
| NMR peak lists |

7.2142 (0.6); 7.2108 (0.7); 7.1996 (1.8); 7.1960 (1.5); 7.1842 (1.8); 7.1799 (2.2); 7.1757 (1.8); 7.1639 (1.7); 7.1608 (1.9); 7.1490 (0.7); 7.1462 (0.6); 7.0027 (2.6); 6.9986 (0.8); 6.9893 (0.9); 6.9852 (4.8); 6.9811 (0.9); 6.9718 (0.7); 6.9678 (2.3); 6.5673 (1.8); 6.5642 (2.0); 6.5513 (1.5); 6.5486 (1.8); 4.5752 (1.5); 4.5523 (2.2); 4.5042 (0.3); 4.4575 (2.0); 4.4347 (1.3); 1.9128 (16.0); 1.7814 (16.0); 1.5850 (16.1); 1.5455 (34.3); 0.0061 (1.9); −0.0003 (75.1); −0.0071 (2.4)

I.292: $^{1}$H-NMR(500.1 MHz, CDCl3):
δ = 8.6554 (3.4); 8.6504 (3.6); 8.2500 (2.4); 8.2452 (2.4); 8.1311 (1.6); 8.1144 (1.8); 7.7994 (1.6); 7.7831 (1.9); 7.7764 (1.2); 7.7737 (1.0); 7.7625 (1.5); 7.7596 (1.9); 7.7568 (1.0); 7.7456 (1.2); 7.7428 (1.0); 7.6074 (1.2); 7.6054 (1.2); 7.5913 (2.0); 7.5893 (1.2); 7.5772 (1.0); 7.5752 (0.9); 7.5692 (1.7); 7.5657 (1.5); 7.5539 (2.0); 7.5504 (1.8); 7.2812 (0.6); 7.2694 (0.8); 7.2653 (1.4); 7.2590 (18.1); 7.2539 (1.7); 7.2498 (1.1); 7.2378 (1.0); 7.2138 (0.6); 7.2104 (0.8); 7.1989 (1.7); 7.1956 (1.6); 7.1836 (1.7); 7.1797 (1.6); 7.1764 (1.6); 7.1731 (1.7); 7.1612 (1.8); 7.1582 (1.9); 7.1462 (2.4); 7.1294 (2.1); 7.1046 (1.0); 6.9505 (0.6); 6.9458 (0.6); 6.9335 (1.0); 6.9289 (1.0); 6.9168 (0.5); 6.9124 (0.5); 6.5634 (1.9); 6.5604 (2.1); 6.5475 (1.6); 6.5447 (1.8); 5.2975 (1.2); 4.6029 (1.6); 4.5787 (2.6); 4.5036 (2.4); 4.4794 (1.5); 1.9175 (15.6); 1.7948 (16.0); 1.5944 (16.2); 1.5578 (6.3); 0.0062 (0.9); −0.0003 (25.9); −0.0068 (0.9)

I.293: $^{1}$H-NMR(500.1 MHz, CDCl3):
δ = 8.6572 (3.6); 8.6522 (3.7); 8.2295 (2.5); 8.2247 (2.4); 8.1220 (1.6); 8.1053 (1.7); 7.7798 (1.6); 7.7668 (2.2); 7.7643 (2.9); 7.7532 (1.6); 7.7504 (2.0); 7.7474 (1.1); 7.7364 (1.3); 7.7335 (1.1); 7.6212 (0.7); 7.6058 (2.9); 7.6023 (1.5); 7.5996 (1.2); 7.5959 (1.8); 7.5919 (2.4); 7.5869 (2.0); 7.5820 (1.4); 7.5800 (2.1); 7.5778 (1.3); 7.5659 (1.0); 7.5638 (0.9); 7.2592 (43.8); 7.2493 (0.6); 7.2454 (1.0); 7.2337 (0.7); 7.2295 (0.9); 7.2256 (0.5); 7.2183 (0.4); 7.2147 (0.5); 7.2061 (0.4); 7.2021 (0.7); 7.1914 (1.8); 7.1874 (1.8); 7.1825 (1.9); 7.1776 (3.6); 7.1722 (1.9); 7.1678 (1.9); 7.1642 (1.8); 7.1530 (0.7); 7.1496 (0.5); 7.1004 (1.1); 7.0983 (1.2); 7.0853 (1.9); 7.0833 (2.0); 7.0703 (0.9); 7.0684 (0.9); 7.0363 (1.1); 7.0344 (1.0); 7.0199 (1.3); 6.9997 (0.9); 6.9972 (0.9); 6.5559 (1.9); 6.5516 (1.6); 6.5427 (1.0); 6.5402 (1.2); 6.5371 (1.8); 5.2980 (0.3); 4.7535 (1.5); 4.7296 (1.9); 4.5557 (1.8); 4.5317 (1.5); 1.9599 (15.6); 1.7797 (15.8); 1.6153 (16.0); 1.5971 (0.6); 1.5437 (42.9); 1.5159 (0.3); 0.9674 (0.4); 0.0689 (0.4); 0.0063 (2.1); −0.0003 (60.5); −0.0068 (2.2)

I.294: $^{1}$H-NMR(500.1 MHz, CDCl3):
δ = 8.6671 (3.9); 8.6621 (4.0); 8.2339 (2.5); 8.2293 (2.4); 8.1322 (1.7); 8.1166 (1.9); 7.7961 (1.6); 7.7797 (1.9); 7.7747 (1.3); 7.7719 (1.2); 7.7607 (1.6); 7.7579 (2.1); 7.7550 (1.2); 7.7439 (1.4); 7.7411 (1.2); 7.6032 (1.3); 7.6010 (1.3); 7.5891 (1.3); 7.5870 (2.1); 7.5848 (1.3); 7.5730 (1.0); 7.5708 (0.9); 7.5549 (1.7); 7.5516 (1.6); 7.5395 (2.0); 7.5361 (1.9); 7.4655 (0.3); 7.3251 (0.4); 7.3206 (2.7); 7.3164 (1.0); 7.3105 (0.5); 7.3057 (3.6); 7.3035 (3.5); 7.2989 (0.6); 7.2925 (1.1); 7.2885 (3.5); 7.2836 (1.9); 7.2678 (3.3); 7.2589 (62.2); 7.2520 (2.3); 7.1977 (0.7); 7.1945 (0.8); 7.1830 (1.8); 7.1797 (1.5); 7.1674 (1.8); 7.1637 (1.7); 7.1561 (1.6); 7.1530 (1.9); 7.1409 (3.4); 7.1381 (2.7); 7.1259 (2.2); 7.1236 (1.5); 7.1007 (0.8); 7.0987 (1.6); 7.0965 (0.9); 7.0839 (2.4); 7.0712 (0.6); 7.0691 (1.2); 7.0669 (0.6); 7.0472 (0.3); 7.0076 (2.2); 6.9991 (0.7); 6.9978 (0.7); 6.9952 (3.4); 6.9929 (4.3); 6.9887 (1.1); 6.9815 (1.1); 6.9796 (1.9); 6.9777 (3.8); 6.9737 (3.4); 6.9708 (0.3); 6.8954 (1.2); 6.8917 (1.1); 6.8795 (1.0); 6.8758 (1.0); 6.5569 (2.0); 6.5541 (2.3); 6.5409 (1.7); 6.5382 (1.9); 5.2979 (0.3); 4.5971 (1.5); 4.5731 (2.7); 4.5201 (2.6); 4.4961 (1.4); 1.9026 (15.3); 1.7487 (16.0); 1.5854 (16.0); 1.5397 (74.1); 1.3013 (0.5); 1.2836 (0.6); 1.2533 (2.3); 0.1164 (0.3); 0.0689 (0.6); 0.0064 (2.9); −0.0003 (95.3); −0.0068 (2.8)

I.295: $^{1}$H-NMR(500.1 MHz, CDCl3):
δ = 8.6854 (3.6); 8.6804 (3.7); 8.2111 (2.5); 8.2063 (2.4); 8.1275 (1.6); 8.1107 (1.9); 8.1095 (1.8); 7.7724 (1.8); 7.7678 (1.5); 7.7648 (1.0); 7.7565 (2.5); 7.7538 (2.7); 7.7508 (1.7); 7.7481 (1.0); 7.7369 (1.4); 7.7340 (1.0); 7.5956 (1.3); 7.5934 (1.3); 7.5878 (1.8); 7.5843 (1.4); 7.5817 (1.9); 7.5797 (2.2); 7.5773 (1.3); 7.5732 (2.0); 7.5689 (1.9); 7.5655 (1.1); 7.5632 (1.0); 7.2682 (3.3); 7.2588 (26.2); 7.1961 (0.5); 7.1923 (0.7); 7.1815 (1.8); 7.1777 (1.7); 7.1672 (2.6); 7.1643 (2.3); 7.1622 (2.0); 7.1537 (1.9); 7.1503 (1.7); 7.1388 (0.7); 7.1355 (0.8); 7.1291 (3.7); 7.1134 (3.0); 6.5558 (2.0); 6.5521 (2.0); 6.5416 (1.2); 6.5399 (1.3); 6.5371 (1.8); 4.6022 (1.4); 4.5795 (2.6); 4.5250 (2.4); 4.5024 (1.4); 4.1285 (0.9); 4.1142 (0.9); 4.0999 (0.3); 2.3270 (12.7); 2.0433 (4.3); 2.0333 (0.8); 1.9269 (15.6); 1.7661 (16.0); 1.6050 (1.5); 1.5497 (34.3); 1.4317 (0.4); 1.2861 (1.3); 1.2726 (2.0); 1.2582 (6.2); 1.2535 (8.1); 1.2442 (2.2); 1.2215 (0.4); 0.8935 (0.5); 0.8885 (0.5); 0.8800 (0.9); 0.8660 (0.6); 0.8546 (0.3); 0.8416 (0.4); 0.8382 (0.3); 0.0061 (1.4); −0.0003 (37.5); −0.0071 (1.0)

I.296: $^{1}$H-NMR(500.1 MHz, CDCl3):
δ = 8.5778 (3.7); 8.5728 (3.8); 8.2419 (2.5); 8.2370 (2.5); 8.1096 (1.7); 8.0935 (1.9); 7.8170 (1.7); 7.8013 (1.8); 7.7850 (1.6); 7.7684 (3.1); 7.7544 (1.6); 7.7515 (2.0); 7.7487 (1.1); 7.7375 (1.3); 7.7347 (1.1); 7.6333 (1.6); 7.6298 (1.2); 7.6280 (1.2); 7.6188 (1.9); 7.6143 (3.4); 7.5975 (2.9); 7.5836 (2.1); 7.5695 (0.9); 7.5673 (1.0); 7.5207 (1.0); 7.5182 (1.0); 7.5054 (1.9); 7.5029 (1.8); 7.4898 (1.1); 7.4873 (1.0); 7.3385 (1.1); 7.3217 (1.8); 7.3081 (0.8); 7.2594 (50.8); 7.2407 (0.6); 7.2369 (0.7); 7.2261 (1.8); 7.2222 (1.7); 7.2140 (1.9); 7.2117 (2.5); 7.2095 (2.4); 7.2068 (2.0); 7.1991 (1.9); 7.1956 (1.8); 7.1843 (0.7); 7.1810 (0.5); 6.5778 (1.9); 6.5739 (2.0); 6.5637 (1.2); 6.5619 (1.3); 6.5590 (1.8); 4.8460 (2.1); 4.8211 (2.4); 4.5361 (2.3); 4.5110 (2.0); 4.1286 (0.8); 4.1144 (0.8); 4.1002 (0.3); 2.0435 (3.6); 2.0334 (1.1); 1.9633 (15.4); 1.8113 (16.0); 1.5811 (16.4); 1.5434 (88.4); 1.4318 (0.6); 1.2858 (1.3); 1.2729 (1.9); 1.2584 (6.4); 1.2532 (11.4); 1.2446 (2.3); 0.8935 (0.6); 0.8800 (1.0); 0.8659 (0.6); 0.8382 (0.3); 0.8305 (0.3); 0.0061 (2.4); −0.0003 (75.3); −0.0070 (2.1)

I.297: $^{1}$H-NMR(500.1 MHz, CDCl3):
δ = 8.6450 (3.7); 8.6401 (3.8); 8.2420 (2.7); 8.2372 (2.6); 8.1295 (1.8); 8.1130 (2.0); 7.7996 (1.7); 7.7834 (2.0); 7.7754 (1.2); 7.7725 (1.1); 7.7614 (1.5); 7.7586 (2.0); 7.7557 (1.0); 7.7445 (1.3); 7.7418 (1.1); 7.6056 (1.2); 7.6037 (1.3); 7.5914 (3.0); 7.5765 (2.4); 7.5730 (2.6); 7.4654 (0.3); 7.3441 (4.0); 7.3316 (3.6); 7.3271 (5.2); 7.3218 (1.1); 7.3168 (3.9); 7.3147 (3.7); 7.3035 (1.2); 7.2998 (3.4); 7.2951 (0.4); 7.2589 (55.6); 7.2105 (0.5); 7.2069 (0.7); 7.1959 (1.8); 7.1921 (1.7); 7.1815 (3.2); 7.1772 (3.0); 7.1667 (1.8); 7.1634 (1.7); 7.1519 (0.7); 7.1488 (0.5); 7.1009 (1.4); 7.0861 (2.4); 7.0714 (1.1); 7.0059 (3.4); 7.0038 (4.0); 6.9997 (1.2); 6.9884 (3.6); 6.9866 (3.4); 6.9690 (0.4); 6.9641 (0.6); 6.9587 (5.5); 6.9548 (1.7); 6.9453 (1.6); 6.9415 (0.5); 6.9361 (0.6); 6.5673 (2.0); 6.5637 (2.1); 6.5515 (1.4); 6.5485 (1.9); 4.6049 (1.9); 4.5823 (2.8); 4.4973 (2.7); 4.4746 (1.9); 3.7956 (0.6); 2.0332 (0.4); 1.9304 (14.9); 1.7854 (16.0); 1.5986 (16.1); 1.5404 (59.2); 1.2844 (0.4); 1.2532 (3.4); 0.1163 (0.4); 0.0062 (2.7); −0.0003 (95.2); −0.0069 (3.8); −0.1200 (0.4)

I.298: $^{1}$H-NMR(500.1 MHz, CDCl3):
δ = 8.5946 (3.7); 8.5896 (3.8); 8.4848 (1.3); 8.4834 (1.4); 8.4817 (1.3); 8.4769 (1.2); 8.4752 (1.4); 8.4739 (1.4); 8.4722 (1.2); 8.1906 (2.5); 8.1860 (2.5); 8.1005 (1.8); 8.0837 (1.7); 7.7519 (0.9); 7.7490 (1.4); 7.7383 (2.2); 7.7352 (4.0); 7.7225 (1.6); 7.7200 (4.9); 7.6708 (1.4); 7.6551 (2.0); 7.5950 (1.2); 7.5914 (2.8); 7.5880 (1.6); 7.5788 (2.7); 7.5763 (5.0); 7.5726 (2.1); 7.5646 (2.1); 7.5612 (3.0); 7.5483 (0.9); 7.5461 (0.9); 7.2597 (20.7); 7.2129 (0.6); 7.2095 (0.8); 7.1981 (1.8); 7.1947 (1.6); 7.1829 (1.9); 7.1782 (2.2); 7.1742 (1.9); 7.1625 (1.8);

| NMR peak lists |
|---|

7.1595 (2.0); 7.1476 (0.8); 7.1446 (0.6); 7.1290 (1.0); 7.1190 (1.0); 7.1161 (1.0); 7.1044 (0.9); 6.5737 (2.0); 6.5707 (2.2); 6.5578 (1.6); 6.5551 (1.9); 4.7601 (2.0); 4.7337 (2.6); 4.5340 (2.4); 4.5077 (2.0); 2.0334 (0.4); 2.0038 (0.5); 1.9285 (15.5); 1.8324 (16.0); 1.5742 (16.9); 1.5676 (30.5); 1.2534 (3.8); 0.0062 (1.0); −0.0003 (30.0); −0.0070 (1.0)

I.299: $^1$H-NMR(500.1 MHz, CDCl3):
δ = 8.6566 (3.7); 8.6516 (3.8); 8.2446 (2.6); 8.2402 (2.6); 8.0827 (1.8); 8.0647 (1.8); 8.0029 (2.8); 7.9252 (2.4); 7.9069 (2.6); 7.7490 (4.3); 7.7336 (4.8); 7.7304 (2.4); 7.7192 (1.4); 7.7163 (0.9); 7.6171 (1.7); 7.6138 (1.6); 7.6017 (2.0); 7.5976 (3.3); 7.5940 (2.1); 7.5788 (1.9); 7.5757 (1.9); 7.5729 (1.5); 7.5706 (1.4); 7.5567 (2.1); 7.5426 (0.9); 7.5404 (0.9); 7.4657 (0.4); 7.2592 (87.0); 7.2417 (0.7); 7.2384 (0.8); 7.2269 (1.7); 7.2236 (1.6); 7.2113 (1.6); 7.2076 (1.5); 7.2019 (1.5); 7.1988 (1.7); 7.1866 (1.7); 7.1838 (1.8); 7.1717 (0.7); 7.1689 (0.7); 7.0475 (0.5); 6.6056 (1.9); 6.6028 (2.1); 6.5896 (1.8); 6.5869 (1.9); 4.8169 (0.4); 4.7529 (1.4); 4.7276 (2.3); 4.6571 (2.2); 4.6551 (2.2); 4.6317 (1.3); 4.6294 (1.3); 2.0331 (0.6); 1.9644 (15.1); 1.8380 (16.0); 1.6151 (15.9); 1.5385 (132.3); 1.4219 (0.4); 1.3329 (0.3); 1.2855 (0.9); 1.2532 (5.1); 0.8803 (0.5); 0.8438 (0.4); 0.8096 (0.4); 0.1162 (0.6); 0.0061 (4.8); −0.0003 (149.5); −0.0070 (5.0); −0.1202 (0.6)

I.300: $^1$H-NMR(500.1 MHz, CDCl3):
δ = 8.7996 (1.5); 8.7946 (1.5); 8.2751 (1.0); 8.2702 (1.0); 8.1461 (0.7); 8.1290 (0.8); 8.0086 (0.7); 8.0032 (0.4); 7.9993 (0.5); 7.9940 (0.4); 7.9895 (0.7); 7.8562 (0.6); 7.8397 (0.7); 7.7795 (0.4); 7.7767 (0.4); 7.7656 (0.6); 7.7627 (0.8); 7.7598 (0.4); 7.7487 (0.5); 7.7459 (0.4); 7.6166 (0.5); 7.6145 (0.5); 7.6005 (0.8); 7.5865 (0.4); 7.5843 (0.4); 7.2596 (11.4); 7.1500 (0.9); 7.1482 (0.9); 7.1457 (0.9); 7.1396 (1.3); 7.1337 (0.8); 7.1315 (0.9); 7.1289 (0.8); 6.9445 (1.7); 6.5193 (0.7); 6.5152 (0.4); 6.5101 (0.4); 6.5089 (0.4); 6.5055 (0.4); 6.5005 (0.7); 5.2980 (0.6); 4.9401 (0.7); 4.9142 (1.6); 4.8771 (1.6); 4.8511 (0.7); 2.5025 (16.0); 2.4932 (0.4); 2.4333 (0.5); 2.0199 (6.1); 1.7754 (6.0); 1.7385 (6.0); 1.5672 (6.6); 1.2535 (0.3); 0.0062 (0.6); −0.0003 (20.2); −0.0068 (0.6)

I.301: $^1$H-NMR(500.1 MHz, CDCl3):
δ = 8.7609 (3.3); 8.7559 (3.4); 8.3045 (2.4); 8.2997 (2.3); 8.1543 (1.6); 8.1374 (1.8); 7.8713 (1.5); 7.8550 (1.6); 7.7901 (1.0); 7.7873 (1.0); 7.7762 (1.3); 7.7733 (1.9); 7.7704 (1.0); 7.7593 (1.1); 7.7565 (1.0); 7.6311 (1.6); 7.6269 (2.0); 7.6213 (1.4); 7.6175 (1.1); 7.6117 (3.2); 7.5973 (0.9); 7.5951 (0.8); 7.2594 (26.1); 7.2135 (0.4); 7.2037 (1.9); 7.2010 (2.2); 7.1991 (1.9); 7.1930 (3.2); 7.1869 (1.9); 7.1846 (2.2); 7.1826 (1.9); 7.1724 (0.4); 6.5731 (1.7); 6.5681 (1.0); 6.5634 (1.0); 6.5584 (1.0); 6.5543 (1.6); 4.2986 (1.2); 4.2938 (1.2); 4.2671 (2.7); 4.2623 (2.8); 4.2241 (2.7); 4.2193 (2.7); 4.1925 (1.2); 4.1878 (1.2); 2.4659 (1.9); 2.4611 (3.8); 2.4563 (1.9); 2.0333 (0.5); 2.0043 (4.4); 1.9267 (16.0); 1.7215 (15.3); 1.5909 (15.2); 1.5466 (41.9); 1.2535 (6.0); 0.8800 (0.5); 0.0061 (1.4); −0.0003 (42.4); −0.0070 (1.4)

I.302: $^1$H-NMR(500.1 MHz, CDCl3):
δ = 8.6535 (3.7); 8.6485 (3.8); 8.2363 (2.5); 8.2318 (2.4); 8.1281 (1.7); 8.1112 (1.8); 8.1101 (1.8); 7.7893 (1.6); 7.7752 (2.7); 7.7727 (3.0); 7.7614 (1.7); 7.7585 (2.0); 7.7557 (1.1); 7.7445 (1.4); 7.7418 (1.1); 7.6044 (1.3); 7.6023 (1.3); 7.5903 (1.3); 7.5884 (2.1); 7.5862 (1.2); 7.5743 (1.0); 7.5721 (1.0); 7.5665 (1.7); 7.5632 (1.6); 7.5511 (2.0); 7.5476 (1.9); 7.3389 (0.4); 7.3281 (4.2); 7.3268 (4.5); 7.3141 (2.8); 7.2987 (0.7); 7.2590 (34.8); 7.2430 (1.9); 7.2414 (2.0); 7.2189 (0.7); 7.2155 (0.9); 7.2040 (1.8); 7.2009 (1.6); 7.1884 (1.8); 7.1848 (1.5); 7.1776 (1.6); 7.1745 (1.8); 7.1622 (1.8); 7.1594 (2.0); 7.1474 (0.8); 7.1447 (0.7); 7.0969 (0.9); 7.0821 (0.9); 6.5688 (2.0); 6.5660 (2.2); 6.5528 (1.7); 6.5501 (1.9); 5.2979 (1.7); 4.6110 (1.7); 4.5866 (2.9); 4.5141 (2.7); 4.4897 (1.6); 1.9140 (15.7); 1.7972 (16.0); 1.5922 (16.2); 1.5441 (39.0); 1.2533 (1.3); 0.0061 (1.7); −0.0003 (62.4); −0.0070 (1.7)

I.303: $^1$H-NMR(500.1 MHz, CDCl3):
δ = 8.6288 (4.1); 8.6237 (4.1); 8.1764 (2.8); 8.1716 (2.7); 8.0989 (1.8); 8.0833 (2.0); 7.8259 (0.7); 7.8210 (6.0); 7.8170 (1.9); 7.8076 (2.7); 7.8037 (6.7); 7.7987 (0.8); 7.7441 (1.1); 7.7413 (1.4); 7.7303 (1.3); 7.7274 (2.3); 7.7243 (1.6); 7.7196 (1.9); 7.7135 (1.1); 7.7107 (1.7); 7.7030 (2.2); 7.6014 (1.8); 7.5980 (1.6); 7.5863 (2.1); 7.5826 (1.9); 7.5413 (1.4); 7.5391 (1.4); 7.5274 (1.4); 7.5251 (2.2); 7.5227 (1.3); 7.5111 (1.0); 7.5089 (1.0); 7.4657 (0.3); 7.4177 (2.5); 7.4154 (5.0); 7.4130 (2.4); 7.4048 (0.9); 7.3999 (6.7); 7.3959 (2.1); 7.3865 (1.9); 7.3827 (6.3); 7.3777 (0.7); 7.2591 (54.2); 7.2229 (0.6); 7.2195 (2.0); 7.2080 (2.0); 7.2046 (1.8); 7.2029 (1.9); 7.1890 (3.2); 7.1857 (2.0); 7.1740 (2.0); 7.1709 (2.0); 7.1592 (0.8); 7.1563 (0.6); 6.5937 (2.1); 6.5906 (2.3); 6.5778 (1.7); 6.5751 (2.0); 5.2980 (2.9); 4.8711 (2.0); 4.8688 (2.0); 4.8460 (2.3); 4.8436 (2.3); 4.5788 (2.3); 4.5762 (2.2); 4.5536 (2.0); 4.5510 (2.0); 1.9338 (14.6); 1.8389 (16.0); 1.5636 (17.0); 1.5429 (38.9); 1.3329 (0.4); 1.2845 (0.6); 1.2531 (2.1); 0.8362 (0.3); 0.8224 (0.3); 0.8088 (0.4); 0.1162 (0.4); 0.0061 (2.6); −0.0003 (96.8); −0.0070 (3.2); −0.1201 (0.4)

I.304: $^1$H-NMR(500.1 MHz, CDCl3):
δ = 8.7085 (3.5); 8.7035 (3.6); 8.2749 (2.6); 8.2702 (2.6); 8.1529 (1.8); 8.1360 (1.9); 7.8511 (1.6); 7.8347 (1.8); 7.7944 (1.0); 7.7916 (1.1); 7.7806 (1.4); 7.7777 (2.1); 7.7747 (1.1); 7.7608 (1.2); 7.7608 (1.1); 7.6286 (1.2); 7.6266 (1.2); 7.6125 (2.1); 7.6019 (1.7); 7.5985 (2.1); 7.5964 (2.0); 7.5875 (1.8); 7.5830 (1.8); 7.2591 (44.6); 7.2200 (0.3); 7.2161 (0.7); 7.2053 (1.7); 7.2013 (1.7); 7.1940 (1.8); 7.1908 (2.5); 7.1897 (2.5); 7.1859 (1.8); 7.1790 (1.8); 7.1757 (1.7); 7.1643 (0.6); 7.1611 (0.5); 6.7210 (1.5); 6.7188 (1.6); 6.7144 (1.7); 6.7123 (1.6); 6.5661 (1.8); 6.5622 (1.9); 6.5522 (1.1); 6.5503 (1.3); 6.5473 (1.8); 6.4126 (1.9); 6.4064 (1.8); 4.5560 (7.4); 1.9169 (15.6); 1.7465 (16.0); 1.6040 (15.8); 1.5402 (70.6); 1.4219 (1.0); 1.3361 (0.6); 1.3329 (0.5); 1.2844 (0.8); 1.2543 (4.2); 0.8803 (0.5); 0.8380 (0.4); 0.0061 (2.3); −0.0003 (80.0); −0.0069 (3.2); −0.1202 (0.3)

I.305: $^1$H-NMR(500.1 MHz, CDCl3):
δ = 8.6132 (2.4); 8.6082 (2.4); 8.0762 (1.6); 8.0716 (1.6); 8.0282 (1.1); 8.0269 (1.1); 8.0112 (1.2); 8.0102 (1.2); 7.8739 (3.0); 7.8721 (3.0); 7.7096 (0.7); 7.7058 (0.7); 7.6968 (0.8); 7.6929 (1.3); 7.6888 (0.7); 7.6798 (0.7); 7.6760 (0.8); 7.6210 (1.7); 7.6195 (1.8); 7.6148 (2.0); 7.5966 (2.4); 7.5926 (1.0); 7.5809 (1.3); 7.5772 (1.2); 7.5247 (0.4); 7.5212 (0.5); 7.5084 (1.5); 7.5050 (1.4); 7.5000 (1.3); 7.4979 (1.2); 7.4871 (1.0); 7.4850 (1.0); 7.4816 (0.4); 7.4707 (0.4); 7.4687 (0.4); 7.2591 (13.8); 7.2381 (0.4); 7.2347 (0.5); 7.2233 (1.2); 7.2197 (1.0); 7.2083 (1.2); 7.2044 (1.8); 7.2012 (1.2); 7.1895 (1.2); 7.1864 (1.2); 7.1747 (0.5); 7.1718 (0.4); 6.9686 (1.2); 6.9664 (1.2); 6.9521 (1.1); 6.9498 (1.1); 6.6378 (1.2); 6.6347 (1.4); 6.6222 (1.2); 6.6192 (1.2); 5.2975 (0.6); 4.8166 (1.1); 4.7922 (1.3); 4.5678 (1.2); 4.5435 (1.0); 3.6813 (16.0); 1.9457 (9.0); 1.8536 (9.6); 1.5619 (10.4); 1.5552 (13.0); 1.3705 (0.4); 1.2855 (0.6); 1.2553 (0.7); 0.8449 (0.4); 0.8382 (0.3); 0.8330 (0.3); 0.0063 (0.7); −0.0003 (23.0); −0.0069 (0.8)

I.306: $^1$H-NMR(500.1 MHz, CDCl3):
δ = 8.6958 (3.3); 8.6907 (3.5); 8.3250 (2.2); 8.3201 (2.2); 8.1417 (1.5); 8.1247 (1.7); 7.8644 (1.4); 7.8477 (1.6); 7.7795 (1.0); 7.7766 (1.0); 7.7656 (1.3); 7.7626 (2.0); 7.7597 (1.0); 7.7487 (1.2); 7.7458 (1.1); 7.6200 (1.1); 7.6178 (1.1); 7.6061 (1.1); 7.6038 (1.9); 7.6017 (1.1); 7.5898 (0.9); 7.5876 (0.8); 7.5384 (1.5); 7.5350 (1.2); 7.5333 (1.1); 7.5238 (1.8); 7.5196 (1.7); 7.2594 (52.3); 7.1987 (0.5); 7.1950 (0.6); 7.1840 (1.7); 7.1801 (1.6);

TABLE 12-continued

NMR peak lists 7.1698 (2.6); 7.1661 (2.4); 7.1555 (1.8); 7.1522 (1.7); 7.1407 (0.6); 7.1376 (0.5); 6.5710 (1.8); 6.5674 (2.0);
6.5567 (1.1); 6.5551 (1.2); 6.5523 (1.7); 5.9627 (0.4); 5.9532 (0.8); 5.9434 (0.4); 5.9415 (0.5); 5.9320 (0.9);
5.9282 (0.5); 5.9225 (0.5); 5.9188 (1.0); 5.9092 (0.5); 5.9072 (0.5); 5.8976 (1.0); 5.8881 (0.5); 5.4042 (0.6);
5.4006 (1.6); 5.3970 (1.6); 5.3934 (0.6); 5.3697 (0.5); 5.3662 (1.4); 5.3626 (1.4); 5.3590 (0.5); 5.1715 (0.5);
5.1683 (1.5); 5.1649 (1.6); 5.1617 (0.6); 5.1503 (0.5); 5.1471 (1.5); 5.1438 (1.5); 5.1405 (0.5); 4.1185 (0.4);
4.1151 (0.7); 4.1117 (0.4); 4.1088 (0.4); 4.1054 (0.7); 4.1021 (0.4); 4.0927 (0.6); 4.0894 (1.2); 4.0859 (0.6);
4.0831 (0.7); 4.0796 (1.1); 4.0763 (0.6); 4.0124 (0.6); 4.0088 (1.1); 4.0051 (0.7); 4.0031 (0.7); 3.9995 (1.1);
3.9960 (0.6); 3.9867 (0.4); 3.9830 (0.7); 3.9795 (0.4); 3.9773 (0.4); 3.9738 (0.7); 3.9703 (0.4); 2.0333 (0.8);
2.0047 (0.6); 1.8661 (16.0); 1.7311 (15.1); 1.5687 (15.3); 1.5412 (76.9); 1.4318 (0.4); 1.2533 (7.8); 0.8929 (0.4);
0.8801 (0.6); 0.1163 (0.3); 0.0063 (2.5); −0.0003 (84.4); −0.0068 (2.3)
I.307: $^1$H-NMR(500.1 MHz, CDCl3):
δ = 8.6255 (3.8); 8.6205 (3.9); 8.2212 (2.6); 8.2163 (2.6); 8.1160 (1.9); 8.0982 (1.8); 7.7729 (0.9); 7.7701 (1.4);
7.7639 (1.6); 7.7603 (2.0); 7.7561 (2.6); 7.7529 (1.0); 7.7476 (2.0); 7.7445 (2.4); 7.7415 (2.0); 7.5986 (1.3);
7.5965 (1.4); 7.5817 (5.5); 7.5652 (6.4); 7.5525 (2.0); 7.5491 (1.9); 7.4656 (0.4); 7.4499 (4.3); 7.4333 (3.2);
7.2591 (71.2); 7.2254 (0.7); 7.2220 (0.8); 7.2193 (0.4); 7.2104 (0.7); 7.2073 (1.7); 7.1949 (1.6); 7.1914 (1.5);
7.1838 (1.5); 7.1808 (1.7); 7.1685 (1.8); 7.1657 (2.0); 7.1536 (0.8); 7.1509 (0.7); 7.0474 (0.4); 6.5803 (2.0);
6.5775 (2.2); 6.5643 (1.8); 6.5617 (1.9); 4.6381 (1.8); 4.6132 (2.6); 4.4959 (2.4); 4.4709 (1.7); 3.6531 (0.4);
1.9148 (15.2); 1.8065 (16.0); 1.5818 (16.2); 1.5381 (105.3); 1.4980 (0.4); 1.2849 (0.4); 1.2532 (2.4); 0.8410
(0.4); 0.1163 (0.5); 0.0061 (3.8); −0.0003 (128.4); −0.0069 (3.8); −0.0403 (0.4); −0.1201 (0.5)
I.308: $^1$H-NMR(500.1 MHz, CDCl3):
δ = 8.6848 (3.8); 8.6798 (3.8); 8.2065 (2.6); 8.2018 (2.4); 8.0882 (1.7); 8.0704 (1.9); 7.7417 (1.1); 7.7388 (1.2);
7.7279 (1.2); 7.7250 (2.1); 7.7220 (1.3); 7.7114 (2.2); 7.7083 (1.7); 7.6973 (2.0); 7.6348 (2.6); 7.6067 (1.7);
7.6034 (1.3); 7.6019 (1.3); 7.5920 (2.0); 7.5878 (2.0); 7.5627 (1.3); 7.5513 (1.1); 7.5489 (1.3); 7.5467 (2.0);
7.5443 (1.2); 7.5326 (1.0); 7.5305 (1.0); 7.5243 (2.8); 7.5216 (3.8); 7.5177 (1.0); 7.5075 (3.7); 7.5055 (3.6);
7.5011 (0.5); 7.4880 (1.4); 7.4732 (1.7); 7.4655 (0.6); 7.3961 (1.2); 7.3810 (2.9); 7.3700 (2.3); 7.3664 (2.9);
7.3553 (6.6); 7.3427 (1.6); 7.3398 (3.4); 7.2953 (1.0); 7.2929 (1.8); 7.2904 (1.0); 7.2821 (0.8); 7.2782 (2.2);
7.2741 (0.8); 7.2589 (90.3); 7.2096 (0.5); 7.2059 (0.7); 7.1950 (1.3); 7.1912 (1.6); 7.1805 (3.4); 7.1761 (3.0);
7.1656 (1.8); 7.1623 (1.8); 7.1508 (0.6); 7.1477 (0.5); 7.0473 (0.4); 6.5794 (1.9); 6.5758 (2.1); 6.5636 (1.4);
6.5607 (1.9); 4.7044 (1.8); 4.6811 (2.6); 4.5902 (2.4); 4.5669 (1.6); 2.0331 (0.4); 1.9481 (14.9); 1.8116 (15.6);
1.6057 (16.0); 1.5376 (112.7); 1.4219 (0.7); 1.3702 (0.4); 1.3363 (0.5); 1.3330 (0.4); 1.2854 (0.9); 1.2539 (5.2);
1.2229 (0.4); 0.8934 (0.4); 0.8801 (0.6); 0.8663 (0.4); 0.8408 (0.6); 0.8309 (0.4); 0.1163 (0.6); 0.0063 (4.7); −0.0003
(150.4); −0.0068 (5.1); −0.1201 (0.6)
I.309: $^1$H-NMR(500.1 MHz, CDCl3):
δ = 8.6970 (3.6); 8.6920 (3.7); 8.2616 (2.4); 8.2567 (2.4); 8.1426 (1.6); 8.1250 (1.8); 7.8346 (1.5); 7.8182 (1.7);
7.7839 (1.1); 7.7810 (1.1); 7.7700 (1.4); 7.7670 (2.2); 7.7641 (1.2); 7.7531 (1.3); 7.7502 (1.2); 7.7390 (3.8);
7.7325 (4.1); 7.7221 (0.4); 7.7155 (0.4); 7.6202 (1.7); 7.6169 (2.7); 7.6049 (2.2); 7.6011 (3.6); 7.5868 (0.9);
7.5846 (0.9); 7.4658 (0.4); 7.2900 (4.6); 7.2836 (4.5); 7.2592 (65.1); 7.2280 (0.7); 7.2246 (0.8); 7.2132 (1.7);
7.2098 (1.6); 7.1978 (1.8); 7.1940 (1.6); 7.1909 (1.6); 7.1875 (1.7); 7.1755 (1.7); 7.1726 (1.9); 7.1607 (0.8);
7.1578 (0.6); 7.0475 (0.3); 6.5767 (1.9); 6.5737 (2.1); 6.5607 (1.6); 6.5579 (1.9); 4.9864 (0.5); 4.9042 (2.9);
4.8783 (4.8); 4.7991 (4.4); 4.7731 (2.8); 4.1372 (1.8); 2.7277 (0.4); 2.7121 (0.5); 2.6991 (0.5); 2.2787 (0.6);
2.0332 (0.4); 1.9463 (16.0); 1.8139 (16.0); 1.6184 (16.0); 1.5573 (7.9); 1.5158 (0.9); 1.5003 (0.7); 1.4862 (0.4);
1.4218 (0.5); 1.3933 (0.5); 1.3777 (0.7); 1.3628 (0.7); 1.3482 (0.5); 1.3332 (0.4); 1.2862 (2.8); 1.2769 (0.9);
1.2537 (4.9); 1.2131 (0.4); 0.9331 (1.5); 0.9184 (2.8); 0.9037 (1.4); 0.8935 (0.5); 0.8801 (0.9); 0.8676 (0.6);
0.8551 (0.4); 0.8431 (0.5); 0.8293 (0.4); 0.1162 (0.4); 0.0061 (4.1); −0.0003 (115.0); −0.0071 (3.5); −0.1201 (0.4)
I.310: $^1$H-NMR(500.1 MHz, CDCl3):
δ = 8.6865 (3.5); 8.6815 (3.6); 8.1588 (2.7); 8.1540 (2.7); 8.1084 (1.8); 8.0915 (2.0); 7.9118 (1.2); 7.9054 (1.1);
7.8967 (0.8); 7.8924 (1.4); 7.8823 (1.4); 7.8772 (0.9); 7.8741 (0.9); 7.8697 (1.5); 7.8632 (1.5); 7.7794 (1.8);
7.7629 (1.9); 7.7530 (1.1); 7.7502 (1.1); 7.7392 (1.2); 7.7363 (2.1); 7.7333 (1.2); 7.7222 (1.1); 7.7195 (1.2);
7.6943 (2.6); 7.6814 (2.0); 7.6769 (2.3); 7.6413 (1.7); 7.6376 (1.4); 7.6265 (1.9); 7.6225 (1.8); 7.5672 (1.3);
7.5654 (1.3); 7.5513 (2.0); 7.5372 (0.9); 7.5353 (0.9); 7.5069 (0.5); 7.4990 (3.7); 7.4931 (2.1); 7.4917 (2.2);
7.4868 (2.2); 7.4797 (3.5); 7.4721 (0.5); 7.4184 (1.8); 7.4036 (2.0); 7.4022 (2.1); 7.3877 (1.5); 7.2583 (19.5);
7.2148 (0.5); 7.2113 (0.6); 7.2002 (1.7); 7.1964 (1.6); 7.1851 (3.1); 7.1809 (3.3); 7.1697 (1.8); 7.1665 (1.7);
7.1549 (0.6); 7.1519 (0.5); 6.5739 (1.9); 6.5706 (2.0); 6.5581 (1.4); 6.5553 (1.8); 5.2968 (5.0); 5.1246 (1.7);
5.1001 (2.5); 5.0002 (2.4); 4.9757 (1.7); 2.1688 (0.4); 2.0333 (0.3); 2.0102 (15.0); 2.0025 (6.6); 1.8147 (15.7);
1.6229 (16.0); 1.5489 (29.6); 1.4219 (0.4); 1.3706 (0.5); 1.3332 (0.4); 1.2924 (0.4); 1.2853 (1.1); 1.2543 (4.4);
0.8932 (0.4); 0.8802 (0.7); 0.8664 (0.5); 0.8446 (1.0); 0.8383 (1.0); 0.8110 (0.5); 0.0061 (1.1); −0.0003 (35.0); −0.0067
(1.6)
I.311: $^1$H-NMR(500.1 MHz, CDCl3):
δ = 8.7522 (3.6); 8.7471 (3.8); 8.2653 (2.4); 8.2606 (2.4); 8.1401 (1.6); 8.1229 (1.8); 7.9925 (1.3); 7.9907 (2.2);
7.9763 (1.4); 7.9747 (2.2); 7.9728 (1.5); 7.8461 (1.5); 7.8297 (1.7); 7.7879 (1.1); 7.7851 (1.1); 7.7740 (1.5);
7.7710 (2.1); 7.7681 (1.1); 7.7570 (1.3); 7.7542 (1.1); 7.6592 (1.7); 7.6558 (1.6); 7.6439 (2.0); 7.6404 (1.8);
7.6243 (1.2); 7.6221 (1.3); 7.6104 (1.2); 7.6081 (2.1); 7.6058 (1.3); 7.5941 (0.9); 7.5919 (0.9); 7.5647 (0.3);
7.5616 (0.7); 7.5602 (0.6); 7.5477 (2.3); 7.5444 (2.9); 7.5432 (4.2); 7.5409 (2.5); 7.5305 (2.0); 7.5282 (2.0);
7.5136 (0.7); 7.5112 (0.7); 7.4657 (0.4); 7.3025 (1.4); 7.2994 (1.4); 7.2899 (1.2); 7.2867 (2.5); 7.2836 (1.5);
7.2739 (1.2); 7.2709 (1.2); 7.2591 (74.4); 7.2516 (1.7); 7.2400 (1.2); 7.2368 (1.6); 7.2245 (1.8); 7.2207 (1.6);
7.2154 (1.6); 7.2123 (1.8); 7.2000 (1.7); 7.1972 (1.9); 7.1852 (0.8); 7.1824 (0.6); 7.0474 (0.4); 6.6043 (1.9);
6.6015 (2.2); 6.5884 (1.6); 6.5856 (1.8); 4.9558 (3.1); 4.9313 (4.9); 4.8568 (5.0); 4.8323 (3.1); 2.1696 (0.6);
2.0332 (1.1); 2.0045 (0.8); 1.9337 (15.6); 1.7611 (16.0); 1.6058 (15.8); 1.5381 (76.8); 1.4988 (0.3); 1.4318 (1.3);
1.4219 (0.7); 1.3702 (0.4); 1.3360 (0.6); 1.3329 (1.0); 1.2842 (1.8); 1.2534 (14.0); 1.1056 (0.3); 0.8935 (0.8);
0.8800 (1.6); 0.8661 (0.9); 0.8439 (1.0); 0.1162 (0.5); 0.0689 (0.6); 0.0061 (4.1); −0.0003 (136.5); −0.0070 (4.6); −0.1202
(0.4)
I.312: $^1$H-NMR(500.1 MHz, CDCl3):
δ = 8.8213 (0.6); 8.8163 (0.6); 8.3121 (0.4); 8.3074 (0.4); 7.8540 (0.3); 7.7831 (0.3); 7.6174 (0.3); 7.3634 (0.4);
7.3601 (0.5); 7.3529 (0.6); 7.3453 (0.4); 7.2591 (30.8); 7.1739 (0.4); 4.9240 (0.4); 4.8975 (0.7); 4.8193 (0.7);
4.7928 (0.4); 2.2812 (0.8); 2.0433 (0.4); 2.0333 (0.8); 1.9992 (2.6); 1.7903 (2.7); 1.6767 (0.5); 1.6566 (2.7);
1.5984 (0.3); 1.5389 (17.6); 1.4319 (0.6); 1.4221 (0.6); 1.4087 (0.4); 1.3949 (0.4); 1.3702 (0.5); 1.3495 (0.6);
1.3430 (0.9); 1.3328 (1.1); 1.2857 (4.6); 1.2548 (16.0); 1.1584 (0.6); 1.1415 (0.5); 1.1047 (0.6); 1.0745 (0.5);
1.0214 (0.3); 1.0093 (0.3); 0.9628 (0.4); 0.9478 (0.3); 0.9397 (0.3); 0.8936 (1.6); 0.8803 (2.7); 0.8740 (1.6);

TABLE 12-continued

| NMR peak lists |
| --- |

0.8670 (2.0); 0.8596 (1.4); 0.8547 (1.5); 0.8430 (1.7); 0.8301 (1.5); 0.7147 (0.3); 0.0688 (0.6); 0.0059 (1.2); −0.0003 (53.4); −0.0067 (2.9); −0.0134 (0.5)

I.313: $^1$H-NMR(500.1 MHz, CDCl3):
δ = 8.7785 (5.5); 8.7735 (5.6); 8.7635 (0.3); 8.2652 (3.6); 8.2604 (3.7); 8.1870 (2.6); 8.1700 (2.8); 7.8950 (2.4); 7.8785 (2.8); 7.8671 (2.2); 7.8515 (2.3); 7.8352 (1.7); 7.8325 (1.8); 7.8213 (2.1); 7.8185 (3.3); 7.8155 (1.8); 7.8044 (1.9); 7.8016 (1.8); 7.6638 (1.8); 7.6617 (2.0); 7.6499 (1.8); 7.6477 (3.2); 7.6454 (2.0); 7.6337 (1.4); 7.6314 (1.4); 7.4656 (0.5); 7.3514 (0.8); 7.3364 (2.0); 7.3209 (1.4); 7.2986 (0.4); 7.2829 (1.8); 7.2810 (2.0); 7.2671 (3.1); 7.2589 (91.7); 7.2530 (2.2); 7.0473 (0.5); 6.5635 (2.5); 6.5470 (2.3); 2.2760 (1.0); 2.2627 (1.1); 2.2464 (2.4); 2.2329 (2.4); 2.2073 (1.5); 2.2049 (1.5); 1.9315 (1.5); 2.1751 (0.7); 2.1610 (0.8); 2.0332 (1.8); 2.0047 (1.1); 1.9479 (1.2); 1.9047 (0.6); 1.8992 (0.6); 1.8590 (11.6); 1.8549 (11.6); 1.5353 (62.7); 1.5059 (0.5); 1.4936 (0.3); 1.3330 (0.6); 1.2998 (0.6); 1.2843 (1.2); 1.2533 (16.0); 1.1815 (0.3); 1.0996 (0.5); 1.0888 (0.8); 1.0745 (1.1); 1.0601 (0.8); 1.0507 (0.4); 0.9073 (0.3); 0.8924 (0.8); 0.8881 (0.7); 0.8802 (1.3); 0.8658 (0.7); 0.8422 (0.5); 0.6382 (0.9); 0.6355 (0.8); 0.6259 (3.7); 0.6191 (1.5); 0.6159 (1.4); 0.6121 (3.5); 0.6098 (3.9); 0.6027 (0.9); 0.6000 (1.0); 0.2530 (1.0); 0.2430 (4.0); 0.2324 (3.8); 0.2228 (0.9); 0.1163 (0.6); 0.0689 (1.6); 0.0393 (0.5); 0.0063 (4.2); −0.0003 (156.3); −0.0068 (5.9); −0.1200 (0.6)

I.314: $^1$H-NMR(500.1 MHz, CDCl3):
δ = 8.7519 (7.4); 8.7469 (7.7); 8.2528 (5.0); 8.2480 (5.0); 8.1727 (3.5); 8.1558 (3.9); 7.8767 (3.2); 7.8627 (6.7); 7.8605 (6.0); 7.8469 (3.6); 7.8275 (2.4); 7.8246 (2.6); 7.8136 (3.0); 7.8106 (4.8); 7.8076 (2.4); 7.7966 (2.8); 7.7937 (2.6); 7.6555 (2.7); 7.6533 (2.7); 7.6416 (2.6); 7.6393 (4.5); 7.6370 (2.7); 7.6253 (2.0); 7.6230 (2.0); 7.4652 (0.8); 7.3780 (4.2); 7.3629 (7.2); 7.3430 (2.8); 7.3359 (3.0); 7.3323 (3.9); 7.3283 (3.2); 7.3238 (2.4); 7.3189 (8.8); 7.3156 (3.3); 7.3069 (2.7); 7.3042 (5.0); 7.2976 (2.8); 7.2944 (4.8); 7.2909 (4.3); 7.2883 (3.2); 7.2805 (4.1); 7.2737 (4.6); 7.2660 (1.6); 7.2586 (140.2); 7.0471 (0.8); 6.5654 (3.5); 6.5489 (3.4); 5.2980 (1.0); 3.6818 (2.2); 3.6530 (6.4); 3.6265 (4.3); 3.6234 (4.4); 3.5979 (1.5); 3.5945 (1.6); 2.9547 (1.6); 2.8828 (1.3); 2.6127 (0.8); 2.1695 (1.4); 2.1009 (0.7); 2.0330 (0.9); 2.0044 (9.7); 1.7581 (0.4); 1.6765 (0.4); 1.6424 (16.0); 1.6386 (15.9); 1.5352 (39.0); 1.4317 (0.5); 1.4220 (0.4); 1.3328 (0.9); 1.2840 (1.7); 1.2533 (9.5); 0.8932 (0.6); 0.8800 (1.1); 0.8660 (0.6); 0.8435 (0.5); 0.1162 (0.8); 0.0687 (2.4); 0.0061 (7.0); −0.0003 (224.0); −0.0070 (9.4); −0.1203 (0.9)

I.315: $^1$H-NMR(500.1 MHz, CDCl3):
δ = 8.8493 (6.2); 8.8442 (6.1); 8.3170 (4.6); 8.3123 (4.4); 8.2486 (3.4); 8.2454 (3.4); 8.2326 (6.7); 8.2298 (4.3); 8.2166 (3.5); 7.9316 (2.9); 7.9156 (3.3); 7.8844 (2.2); 7.8817 (1.9); 7.8705 (2.9); 7.8675 (3.8); 7.8647 (1.9); 7.8535 (2.4); 7.8507 (1.9); 7.7059 (2.4); 7.7037 (2.2); 7.6897 (3.8); 7.6756 (1.8); 7.6735 (1.6); 7.5137 (2.0); 7.5105 (2.0); 7.4992 (2.8); 7.4963 (3.2); 7.4938 (2.2); 7.4826 (2.3); 7.4792 (2.2); 7.3049 (2.5); 7.3030 (2.3); 7.2887 (4.2); 7.2743 (2.2); 7.2724 (2.2); 7.2595 (16.0); 6.6401 (4.0); 6.6236 (4.0); 3.3233 (0.3); 3.3022 (1.1); 3.2972 (0.5); 3.2920 (0.6); 3.2810 (1.2); 3.2709 (1.4); 3.2599 (0.5); 3.2498 (1.4); 3.2287 (0.5); 3.0685 (0.6); 3.0478 (2.0); 3.0373 (0.6); 3.0270 (2.1); 3.0166 (1.6); 3.0063 (0.8); 2.9959 (1.6); 2.9751 (0.6); 2.0333 (0.7); 1.9618 (16.0); 1.9604 (15.6); 1.5616 (10.8); 1.2864 (0.5); 1.2538 (6.7); 0.8800 (0.5); 0.0060 (1.1); −0.0003 (27.7); −0.0071 (1.0)

I.316: $^1$H-NMR(500.1 MHz, CDCl3):
δ = 8.8550 (15.7); 8.8500 (16.0); 8.2924 (11.4); 8.2877 (11.2); 8.2664 (8.7); 8.2633 (8.5); 8.2505 (9.0); 8.2473 (8.6); 8.2274 (7.9); 8.2105 (8.7); 7.9198 (7.3); 7.9035 (8.3); 7.8778 (5.6); 7.8750 (5.0); 7.8639 (7.2); 7.8609 (10.0); 7.8579 (4.9); 7.8469 (6.2); 7.8440 (5.1); 7.6994 (6.0); 7.6974 (5.7); 7.6854 (6.0); 7.6832 (9.7); 7.6812 (5.6); 7.6692 (4.5); 7.6671 (4.1); 7.5523 (4.7); 7.5489 (5.1); 7.5376 (6.5); 7.5353 (7.9); 7.5346 (7.9); 7.5324 (6.0); 7.5210 (6.4); 7.5178 (5.9); 7.4660 (0.6); 7.3412 (6.6); 7.3393 (6.2); 7.3250 (10.8); 7.3106 (5.6); 7.3087 (5.4); 7.2595 (101.4); 7.0478 (0.5); 6.7329 (10.3); 6.7320 (10.1); 6.7162 (9.9); 5.2980 (0.6); 4.5645 (5.0); 4.5551 (6.6); 4.5531 (6.3); 4.5437 (5.3); 3.5121 (0.9); 3.4999 (0.9); 3.4912 (2.7); 3.4792 (3.1); 3.4703 (3.2); 3.4594 (4.2); 3.4477 (3.2); 3.4388 (3.6); 3.4267 (3.0); 3.4180 (1.1); 3.4059 (1.0); 3.0487 (1.0); 3.0399 (0.9); 3.0284 (3.1); 3.0197 (3.2); 3.0082 (4.0); 2.9993 (3.8); 2.9971 (3.2); 2.9881 (3.7); 2.9767 (3.0); 2.9679 (2.8); 2.9564 (1.0); 2.9476 (0.9); 2.2782 (0.5); 2.0432 (0.5); 2.0333 (1.3); 1.5555 (17.4); 1.4271 (0.4); 1.4219 (0.4); 1.3332 (1.2); 1.2843 (2.2); 1.2538 (14.0); 1.1897 (0.6); 0.8938 (1.0); 0.8802 (1.8); 0.8661 (1.0); 0.8409 (0.6); 0.1163 (0.6); 0.0694 (0.9); 0.0063 (5.2); −0.0003 (156.3); −0.0068 (4.9); −0.1200 (0.6)

I.317: $^1$H-NMR(500.1 MHz, CDCl3):
δ = 8.8603 (2.7); 8.8552 (2.7); 8.3191 (1.8); 8.3143 (1.8); 8.2546 (1.4); 8.2515 (1.4); 8.2388 (1.5); 8.2356 (1.4); 8.2162 (1.3); 8.1993 (1.4); 7.9187 (1.2); 7.9025 (1.4); 7.8655 (0.9); 7.8627 (0.8); 7.8516 (1.1); 7.8486 (1.6); 7.8458 (0.8); 7.8346 (1.0); 7.8318 (0.9); 7.6901 (0.9); 7.6879 (1.0); 7.6760 (0.9); 7.6738 (1.6); 7.6718 (0.9); 7.6598 (0.7); 7.6576 (0.7); 7.4941 (0.8); 7.4909 (0.8); 7.4796 (1.1); 7.4766 (1.3); 7.4742 (1.0); 7.4631 (1.0); 7.4596 (0.9); 7.2828 (1.0); 7.2808 (1.0); 7.2665 (1.8); 7.2590 (22.6); 7.2503 (1.1); 7.2503 (1.0); 6.6473 (1.6); 6.6464 (1.6); 6.6310 (1.6); 6.6299 (1.5); 3.3094 (0.9); 3.3039 (1.0); 3.2746 (1.3); 3.2692 (1.3); 3.1117 (1.7); 3.1062 (1.8); 3.0770 (1.2); 3.0714 (1.3); 2.1776 (1.6); 2.1720 (3.3); 2.1666 (1.4); 2.0042 (1.4); 1.9256 (16.0); 1.8977 (0.4); 1.5420 (2.1); 1.2535 (2.9); 0.8803 (0.4); 0.0690 (8.0); 0.0061 (1.1); −0.0003 (41.3); −0.0070 (1.3)

I.318: $^1$H-NMR(500.1 MHz, CDCl3):
δ = 8.7719 (7.3); 8.7669 (7.2); 8.2578 (5.2); 8.2529 (5.0); 8.1886 (3.5); 8.1716 (3.7); 7.8939 (3.3); 7.8776 (3.8); 7.8653 (3.0); 7.8502 (3.1); 7.8382 (2.3); 7.8355 (2.1); 7.8243 (3.0); 7.8214 (4.1); 7.8185 (2.0); 7.8073 (2.4); 7.8045 (2.1); 7.6666 (2.7); 7.6645 (2.5); 7.6504 (4.3); 7.6364 (2.0); 7.6342 (1.8); 7.4655 (0.7); 7.3610 (1.3); 7.3461 (2.9); 7.3303 (2.0); 7.2935 (2.7); 7.2777 (4.2); 7.2589 (120.4); 7.0473 (0.6); 6.5764 (3.4); 6.5600 (3.2); 6.0303 (0.4); 6.0151 (0.9); 5.9960 (1.2); 5.9811 (1.2); 5.9612 (0.9); 5.9469 (0.5); 5.2880 (2.9); 5.2853 (3.0); 5.2601 (3.5); 5.2576 (3.7); 5.2546 (3.3); 5.2515 (2.9); 5.2404 (3.3); 3.0751 (2.9); 3.0601 (0.9); 3.0457 (2.5); 3.0315 (2.6); 3.0175 (2.3); 3.0031 (2.2); 2.9882 (0.7); 2.9738 (0.8); 2.9550 (0.5); 2.8834 (0.4); 2.1696 (1.1); 2.0331 (0.6); 2.0046 (0.6); 1.6989 (16.0); 1.6949 (15.3); 1.6319 (0.5); 1.6261 (0.5); 1.5621 (0.4); 1.5347 (72.5); 1.3327 (0.3); 1.2840 (0.7); 1.2535 (6.2); 1.2044 (0.3); 0.8933 (0.4); 0.8804 (0.7); 0.8667 (0.4); 0.8455 (0.5); 0.1163 (0.9); 0.0688 (2.0); 0.0061 (6.1); −0.0003 (211.1); −0.0069 (6.8); −0.1201 (0.8)

I.319: $^1$H-NMR(500.1 MHz, CDCl3):
δ = 8.8509 (2.2); 8.8459 (2.5); 8.8406 (0.4); 8.3189 (1.7); 8.3143 (2.0); 8.2398 (1.5); 8.2366 (1.6); 8.2238 (1.6); 8.2207 (1.6); 8.2152 (1.6); 8.1984 (1.5); 7.9212 (1.3); 7.9050 (1.4); 7.8609 (0.9); 7.8580 (0.9); 7.8470 (1.2); 7.8440 (1.8); 7.8410 (1.0); 7.8300 (1.0); 7.8271 (0.9); 7.6867 (1.0); 7.6846 (1.0); 7.6724 (1.0); 7.6705 (1.7); 7.6683 (1.1); 7.6565 (0.8); 7.6543 (0.7); 7.4819 (0.8); 7.4785 (0.9); 7.4672 (1.1); 7.4649 (1.5); 7.4620 (1.2); 7.4507 (1.1); 7.4474 (1.0); 7.2685 (0.4); 7.2664 (1.1); 7.2638 (0.9); 7.2590 (14.9); 7.2531 (2.0); 7.2502 (2.1); 7.2486 (1.6); 7.2446 (0.4); 7.2358 (1.0); 7.2339 (1.0); 6.6469 (1.8); 6.6458 (1.8); 6.6304 (1.7); 5.7970 (0.4); 5.7773 (0.6); 5.7628 (0.6); 5.7579 (0.4); 5.7432 (0.5); 5.2290 (1.3); 5.2268 (1.4); 5.2089 (1.2); 5.2066 (1.3);

TABLE 12-continued

| NMR peak lists |
| --- |

5.1906 (1.4); 5.1878 (1.3); 5.1853 (0.7); 5.1568 (1.2); 5.1541 (1.2); 3.0216 (0.5); 3.0076 (0.5); 2.9931 (0.9); 2.9789 (0.8); 2.9228 (1.0); 2.9076 (1.0); 2.8943 (0.6); 2.8791 (0.5); 2.0038 (0.5); 1.7684 (0.4); 1.7581 (16.0); 1.7529 (2.5); 1.5442 (2.3); 1.2536 (2.0); 0.0691 (0.4); 0.0118 (0.3); 0.0096 (0.5); −0.0003 (26.5); −0.0060 (3.1); −0.0115 (0.5)

I.320: $^1$H-NMR(500.1 MHz, CDCl3):
δ = 8.6405 (4.0); 8.6355 (4.0); 8.2324 (2.7); 8.2275 (2.5); 8.1216 (1.8); 8.1047 (1.9); 7.8053 (0.5); 7.7890 (4.1); 7.7865 (4.1); 7.7727 (5.4); 7.7699 (4.2); 7.7570 (1.8); 7.7541 (2.4); 7.7510 (2.5); 7.7471 (2.8); 7.7403 (1.6); 7.7373 (1.2); 7.6982 (1.4); 7.6821 (2.9); 7.6662 (1.6); 7.6000 (1.4); 7.5979 (1.4); 7.5838 (2.5); 7.5801 (2.8); 7.5769 (2.3); 7.5647 (4.4); 7.5614 (2.7); 7.5523 (0.9); 7.5497 (1.6); 7.5471 (0.8); 7.4694 (3.0); 7.4659 (1.5); 7.4536 (4.2); 7.4419 (0.9); 7.4373 (2.8); 7.4212 (3.1); 7.4060 (1.4); 7.2590 (76.0); 7.2160 (0.7); 7.2127 (0.8); 7.2012 (1.7); 7.1978 (1.6); 7.1857 (1.8); 7.1820 (1.6); 7.1758 (1.6); 7.1727 (1.8); 7.1606 (1.8); 7.1576 (1.9); 7.1456 (0.8); 7.1429 (0.7); 7.0474 (0.4); 6.5699 (2.1); 6.5670 (2.2); 6.5539 (1.7); 6.5512 (2.0); 5.2982 (1.3); 4.6731 (1.8); 4.6493 (2.6); 4.5540 (2.4); 4.5302 (1.7); 2.1697 (0.8); 2.0332 (0.5); 2.0046 (0.9); 1.9219 (14.8); 1.7807 (16.0); 1.7349 (0.5); 1.5906 (16.2); 1.5365 (60.2); 1.2854 (0.5); 1.2533 (5.2); 0.8803 (0.5); 0.8436 (0.4); 0.8385 (0.4); 0.1163 (0.5); 0.0689 (1.3); 0.0063 (3.9); −0.0003 (133.4); −0.0068 (4.6); −0.1201 (0.5)

I.321: $^1$H-NMR(500.1 MHz, CDCl3):
δ = 8.5775 (3.9); 8.5725 (4.0); 8.1718 (2.6); 8.1668 (2.5); 8.1080 (1.8); 8.0915 (1.7); 7.7649 (1.0); 7.7620 (1.4); 7.7512 (2.1); 7.7483 (3.8); 7.7449 (0.8); 7.7359 (1.6); 7.7331 (4.8); 7.6561 (2.3); 7.6394 (2.5); 7.5945 (1.4); 7.5923 (1.4); 7.5828 (1.9); 7.5802 (2.4); 7.5779 (2.9); 7.5678 (2.1); 7.5642 (2.8); 7.4655 (0.4); 7.3155 (3.8); 7.3113 (3.9); 7.2589 (75.5); 7.2373 (0.7); 7.2338 (0.8); 7.2224 (1.8); 7.2190 (1.6); 7.2072 (1.8); 7.2032 (1.8); 7.2014 (1.8); 7.1978 (1.9); 7.1860 (1.8); 7.1830 (2.0); 7.1711 (0.8); 7.1682 (0.7); 7.1349 (1.9); 7.1308 (1.9); 7.1182 (1.9); 7.1140 (1.7); 7.0472 (0.4); 6.5958 (2.0); 6.5927 (2.3); 6.5801 (1.6); 6.5771 (1.9); 5.2982 (0.9); 4.6936 (2.0); 4.6675 (2.4); 4.4005 (2.2); 4.3743 (1.9); 2.0332 (0.6); 2.0046 (0.6); 1.9390 (15.3); 1.8037 (16.0); 1.7413 (0.5); 1.5689 (16.5); 1.5603 (1.0); 1.5338 (59.0); 1.5029 (0.4); 1.4674 (0.9); 1.4494 (0.9); 1.2855 (0.4); 1.2740 (0.6); 1.2533 (4.9); 0.8802 (0.4); 0.1164 (0.4); 0.0688 (1.2); 0.0063 (3.5); −0.0003 (124.9); −0.0068 (4.9); −0.1201 (0.5)

I.322: $^1$H-NMR(500.1 MHz, CDCl3):
δ = 8.6015 (3.8); 8.5964 (3.9); 8.1939 (2.5); 8.1895 (2.5); 8.1061 (1.9); 8.0883 (1.8); 7.8044 (0.7); 7.7894 (1.5); 7.7740 (0.8); 7.7668 (1.0); 7.7638 (1.5); 7.7562 (1.6); 7.7531 (2.8); 7.7499 (2.8); 7.7467 (1.0); 7.7400 (1.9); 7.7369 (2.9); 7.7354 (2.6); 7.5943 (1.3); 7.5922 (1.3); 7.5844 (1.8); 7.5807 (2.7); 7.5777 (2.4); 7.5692 (2.1); 7.5653 (2.2); 7.5621 (1.1); 7.3190 (1.4); 7.3029 (1.3); 7.2691 (1.4); 7.2589 (37.2); 7.2494 (1.5); 7.2409 (0.8); 7.2375 (0.9); 7.2260 (1.8); 7.2227 (1.7); 7.2108 (1.8); 7.2069 (1.6); 7.2036 (1.7); 7.2003 (1.9); 7.1883 (1.9); 7.1853 (2.0); 7.1735 (0.8); 7.1706 (0.7); 6.5968 (2.0); 6.5938 (2.3); 6.5808 (1.7); 6.5781 (2.0); 5.2979 (0.4); 4.7587 (1.3); 4.7326 (1.6); 4.4842 (1.5); 4.4583 (1.3); 2.0043 (0.5); 1.9353 (15.5); 1.8014 (16.0); 1.7558 (0.5); 1.5793 (16.6); 1.5484 (0.8); 1.5389 (30.1); 1.2538 (1.5); 0.0690 (0.6); 0.0063 (1.8); −0.0003 (62.5); −0.0068 (2.2)

I.323: $^1$H-NMR(500.1 MHz, CDCl3):
δ = 8.6518 (3.7); 8.6468 (3.8); 8.1782 (2.8); 8.1735 (2.7); 8.0974 (1.8); 8.0807 (2.0); 7.8530 (2.3); 7.8370 (2.5); 7.7652 (1.8); 7.7631 (1.9); 7.7497 (3.8); 7.7393 (1.6); 7.7361 (2.4); 7.7341 (2.4); 7.7254 (1.9); 7.7225 (2.0); 7.7198 (1.2); 7.7085 (1.4); 7.7058 (1.1); 7.6502 (1.1); 7.6475 (1.0); 7.6347 (2.5); 7.6318 (3.1); 7.6271 (1.5); 7.6247 (1.4); 7.6193 (1.9); 7.6166 (3.0); 7.6119 (2.0); 7.5691 (1.4); 7.5532 (2.2); 7.5391 (1.5); 7.5370 (1.0); 7.5206 (3.9); 7.5170 (3.9); 7.4713 (1.4); 7.4690 (1.5); 7.4560 (2.3); 7.4538 (2.5); 7.4407 (1.0); 7.4384 (1.1); 7.4233 (2.4); 7.4077 (2.1); 7.3556 (2.0); 7.3520 (1.9); 7.3396 (1.9); 7.3360 (1.8); 7.2589 (40.4); 7.2449 (0.6); 7.2409 (0.7); 7.2301 (1.8); 7.2261 (1.8); 7.2209 (1.8); 7.2162 (3.6); 7.2109 (1.9); 7.2061 (2.0); 7.2026 (1.7); 7.1914 (0.7); 7.1879 (0.4); 6.6049 (2.0); 6.6027 (1.7); 6.5916 (1.1); 6.5892 (1.3); 6.5862 (1.9); 5.2979 (1.3); 4.8086 (2.0); 4.7821 (2.5); 4.5584 (2.4); 4.5318 (1.9); 2.1695 (0.4); 2.0333 (0.5); 2.0043 (6.6); 1.9870 (14.1); 1.8422 (15.7); 1.7899 (0.5); 1.6097 (16.0); 1.5988 (0.8); 1.5406 (21.9); 1.3703 (0.5); 1.3330 (0.3); 1.2855 (1.1); 1.2535 (4.6); 0.8935 (0.4); 0.8803 (0.7); 0.8665 (0.4); 0.8438 (0.8); 0.8377 (0.8); 0.8106 (0.4); 0.0690 (0.7); 0.0060 (3.0); −0.0003 (71.4); −0.0070 (1.9)

I.324: $^1$H-NMR(500.1 MHz, CDCl3):
δ = 8.6231 (3.9); 8.6180 (3.9); 8.2224 (2.6); 8.2176 (2.5); 8.1179 (1.7); 8.1011 (1.9); 8.0998 (1.8); 7.7774 (1.9); 7.7726 (1.7); 7.7697 (1.0); 7.7612 (2.6); 7.7587 (2.9); 7.7557 (1.8); 7.7529 (1.1); 7.7418 (1.5); 7.7389 (1.0); 7.6851 (1.0); 7.6687 (2.2); 7.6518 (1.1); 7.6017 (1.4); 7.5995 (1.4); 7.5862 (3.5); 7.5834 (2.6); 7.5716 (1.4); 7.5682 (2.1); 7.5631 (0.4); 7.2589 (49.2); 7.2267 (0.6); 7.2231 (0.8); 7.2118 (1.8); 7.2084 (1.7); 7.1968 (2.0); 7.1939 (2.2); 7.1927 (2.3); 7.1905 (2.0); 7.1790 (1.8); 7.1758 (1.9); 7.1642 (0.7); 7.1612 (0.6); 6.9499 (1.1); 6.9278 (1.4); 6.9060 (1.1); 6.5778 (2.0); 6.5745 (2.2); 6.5627 (1.5); 6.5618 (1.6); 6.5591 (1.9); 4.7090 (1.6); 4.6846 (2.0); 4.4581 (2.0); 4.4335 (1.6); 3.9390 (0.3); 3.4363 (0.4); 2.1695 (0.4); 2.0332 (0.4); 1.9355 (15.2); 1.7862 (16.0); 1.7547 (0.4); 1.5891 (16.2); 1.5372 (37.0); 1.5269 (0.9); 1.2534 (4.0); 1.2037 (1.1); 0.0690 (0.8); 0.0063 (2.1); −0.0003 (85.8); −0.0068 (3.0); −0.1200 (0.3)

I.325: $^1$H-NMR(500.1 MHz, CDCl3):
δ = 8.5638 (3.8); 8.5587 (4.0); 8.1420 (2.6); 8.1371 (2.6); 8.0879 (1.7); 8.0719 (1.9); 7.8800 (1.6); 7.8636 (1.7); 7.7537 (1.1); 7.7509 (1.2); 7.7399 (1.3); 7.7370 (2.2); 7.7340 (1.3); 7.7230 (1.7); 7.7200 (2.4); 7.7021 (2.0); 7.5904 (1.8); 7.5869 (1.6); 7.5790 (1.5); 7.5754 (2.5); 7.5717 (2.0); 7.5651 (1.4); 7.5630 (2.2); 7.5605 (1.3); 7.5492 (3.5); 7.4655 (0.3); 7.3940 (1.4); 7.3777 (1.3); 7.2588 (59.6); 7.2508 (1.3); 7.2392 (1.9); 7.2359 (1.7); 7.2239 (1.8); 7.2200 (1.6); 7.2159 (1.7); 7.2127 (1.8); 7.2007 (1.9); 7.1977 (2.1); 7.1857 (0.8); 7.1830 (0.7); 6.6179 (2.0); 6.6150 (2.2); 6.6021 (1.7); 6.5993 (2.0); 5.2982 (0.8); 4.7597 (1.5); 4.7319 (1.8); 4.4469 (1.6); 4.4194 (1.4); 1.9490 (15.2); 1.8259 (16.0); 1.5678 (16.7); 1.5350 (46.3); 1.2753 (0.4); 1.2535 (3.5); 0.1163 (0.4); 0.0689 (1.0); 0.0063 (3.0); −0.0003 (97.9); −0.0068 (4.0); −0.1202 (0.4)

I.326: $^1$H-NMR(500.1 MHz, CDCl3):
δ = 8.6309 (3.7); 8.6259 (3.8); 8.1470 (2.6); 8.1420 (2.5); 8.1245 (1.8); 8.1066 (1.8); 7.7710 (4.2); 7.7678 (1.4); 7.7597 (0.7); 7.7566 (2.9); 7.7546 (3.1); 7.7516 (2.0); 7.7422 (1.6); 7.7393 (0.9); 7.6038 (1.3); 7.6017 (1.3); 7.5900 (1.2); 7.5875 (2.1); 7.5737 (1.0); 7.5715 (0.9); 7.5575 (1.7); 7.5541 (1.6); 7.5422 (2.0); 7.5387 (1.9); 7.4030 (2.2); 7.3866 (2.4); 7.2588 (38.1); 7.2159 (0.7); 7.2127 (0.8); 7.2012 (1.8); 7.1980 (1.6); 7.1856 (1.7); 7.1819 (1.5); 7.1734 (1.5); 7.1704 (1.7); 7.1581 (1.8); 7.1553 (2.0); 7.1432 (0.9); 7.1405 (0.8); 7.1324 (2.1); 7.1285 (2.5); 7.0983 (1.5); 7.0940 (1.2); 7.0819 (1.3); 7.0777 (1.1); 6.5647 (2.0); 6.5619 (2.2); 6.5486 (1.8); 6.5460 (1.9); 4.5659 (2.0); 4.5417 (2.6); 4.3888 (2.5); 4.3646 (1.9); 2.2294 (0.5); 2.2151 (14.8); 2.0331 (0.4); 2.0041 (0.8); 1.9242 (15.3); 1.7780 (16.0); 1.7334 (0.4); 1.5819 (16.3); 1.5395 (29.3); 1.2934 (0.6); 1.2855 (0.8); 1.2796 (0.7); 1.2534 (5.1); 1.2073 (0.5); 1.1939 (0.4); 0.8802 (0.6); 0.8449 (0.4); 0.8374 (0.4); 0.0689 (0.6); 0.0063 (2.0); −0.0003 (58.8); −0.0069 (2.2)

TABLE 12-continued

NMR peak lists

I.327: $^1$H-NMR(500.1 MHz, CDCl3):
δ = 8.6257 (3.8); 8.6207 (3.8); 8.1835 (2.6); 8.1787 (2.6); 8.1182 (1.9); 8.1002 (1.8); 7.7702 (1.0); 7.7673 (1.4); 7.7559 (2.7); 7.7535 (3.0); 7.7425 (1.8); 7.7391 (3.7); 7.5965 (1.2); 7.5945 (1.3); 7.5830 (1.2); 7.5798 (2.2); 7.5668 (2.5); 7.5641 (2.5); 7.5518 (2.1); 7.5480 (3.4); 7.5305 (2.2); 7.2587 (42.2); 7.2209 (0.7); 7.2176 (0.8); 7.2061 (1.7); 7.2028 (1.6); 7.1905 (1.6); 7.1869 (1.5); 7.1799 (1.4); 7.1769 (1.7); 7.1647 (1.8); 7.1619 (1.9); 7.1498 (0.8); 7.1471 (0.7); 6.9887 (3.4); 6.9704 (1.1); 6.5748 (2.0); 6.5721 (2.2); 6.5589 (1.8); 6.5562 (2.0); 4.5886 (2.0); 4.5643 (2.6); 4.4083 (2.4); 4.3839 (1.9); 2.2412 (15.0); 2.2151 (0.6); 2.1695 (0.4); 2.0332 (0.5); 1.9347 (15.0); 1.9244 (0.8); 1.7910 (16.0); 1.7781 (0.7); 1.5898 (16.3); 1.5369 (33.4); 1.2850 (0.3); 1.2534 (4.2); 0.8802 (0.4); 0.0689 (0.8); 0.0061 (2.5); −0.0003 (75.1); −0.0070 (2.5)

I.328: $^1$H-NMR(500.1 MHz, CDCl3):
δ = 8.6815 (2.2); 8.6765 (2.2); 8.2123 (1.5); 8.2077 (1.4); 8.1256 (1.0); 8.1090 (1.1); 7.7874 (0.9); 7.7714 (1.1); 7.7670 (0.8); 7.7641 (0.6); 7.7531 (1.0); 7.7501 (1.2); 7.7472 (0.6); 7.7361 (0.8); 7.7333 (0.6); 7.6064 (1.0); 7.6023 (0.7); 7.5979 (1.3); 7.5950 (1.3); 7.5925 (0.8); 7.5875 (1.1); 7.5835 (0.8); 7.5814 (1.3); 7.5793 (0.8); 7.5673 (0.6); 7.5652 (0.5); 7.4478 (0.6); 7.4308 (1.3); 7.4137 (0.7); 7.2588 (11.3); 7.1944 (0.3); 7.1843 (1.1); 7.1797 (2.1); 7.1726 (2.5); 7.1651 (2.1); 7.1613 (1.2); 6.6322 (1.0); 6.6271 (1.0); 6.6157 (0.6); 6.6103 (2.5); 6.6059 (0.6); 6.5867 (1.1); 6.5818 (0.9); 6.5560 (1.1); 6.5514 (0.7); 6.5492 (0.6); 6.5448 (0.6); 6.5409 (0.7); 6.5372 (1.1); 4.6735 (1.0); 4.6511 (1.2); 4.5100 (1.2); 4.4876 (0.9); 3.7987 (0.4); 3.7621 (16.0); 1.9539 (8.8); 1.7492 (9.3); 1.6175 (9.4); 1.5478 (4.4); 1.2536 (2.3); 0.0062 (0.6); −0.0003 (21.6); −0.0068 (0.7)

I.329: $^1$H-NMR(500.1 MHz, CDCl3):
δ = 8.5980 (3.7); 8.5930 (3.8); 8.2250 (2.6); 8.2202 (2.6); 8.1175 (1.7); 8.1008 (1.8); 7.8525 (5.1); 7.7921 (1.6); 7.7777 (2.7); 7.7753 (2.8); 7.7639 (1.6); 7.7610 (2.0); 7.7581 (1.1); 7.7470 (1.3); 7.7441 (1.1); 7.7189 (2.2); 7.6085 (1.2); 7.6065 (1.2); 7.5924 (2.0); 7.5904 (1.2); 7.5784 (1.0); 7.5763 (0.9); 7.5650 (1.7); 7.5618 (1.7); 7.5494 (1.9); 7.5462 (1.9); 7.4653 (0.4); 7.2588 (71.8); 7.2378 (0.9); 7.2347 (0.9); 7.2231 (1.6); 7.2201 (1.6); 7.2071 (1.5); 7.2038 (1.4); 7.1858 (1.4); 7.1830 (1.6); 7.1703 (1.7); 7.1678 (1.8); 7.1554 (0.9); 7.1529 (0.8); 7.0473 (0.4); 6.5899 (2.0); 6.5874 (2.2); 6.5738 (1.9); 6.5712 (1.9); 4.6777 (1.6); 4.6524 (2.3); 4.5432 (2.1); 4.5179 (1.5); 2.1697 (0.4); 2.0332 (0.5); 2.0046 (0.8); 1.9171 (15.2); 1.8191 (16.0); 1.5852 (16.1); 1.5334 (54.7); 1.5028 (0.4); 1.4219 (0.4); 1.3702 (0.4); 1.3327 (0.4); 1.2854 (1.0); 1.2533 (5.0); 0.8938 (0.4); 0.8803 (0.7); 0.8661 (0.4); 0.8446 (0.8); 0.1162 (0.5); 0.0688 (1.4); 0.0396 (0.4); 0.0062 (4.2); −0.0003 (120.8); −0.0069 (4.8); −0.1201 (0.5)

I.330: $^1$H-NMR(500.1 MHz, CDCl3):
δ = 8.7472 (2.5); 8.7421 (2.5); 8.3989 (2.5); 8.3939 (2.4); 8.1385 (1.4); 8.1360 (1.6); 8.1241 (1.6); 8.1215 (1.6); 8.1082 (1.4); 8.1058 (1.2); 8.0915 (1.6); 8.0891 (1.3); 7.6783 (1.4); 7.6637 (1.6); 7.6620 (1.5); 7.6473 (1.2); 7.5410 (1.1); 7.5372 (0.8); 7.5341 (0.7); 7.5274 (1.0); 7.5222 (1.2); 7.2882 (0.4); 7.2775 (1.3); 7.2732 (1.5); 7.2707 (1.4); 7.2648 (3.1); 7.2600 (8.4); 7.2562 (1.6); 7.2523 (1.3); 7.2413 (0.4); 6.7292 (1.3); 6.7246 (1.0); 6.7170 (0.7); 6.7139 (0.8); 6.7107 (1.2); 3.3135 (16.0); 1.7966 (11.6); 1.6741 (11.2); 1.5474 (4.9); 1.4983 (11.3); 1.2540 (1.4); 0.0061 (0.7); −0.0003 (13.5); −0.0069 (0.4)

I.331: $^1$H-NMR(500.1 MHz, CDCl3):
δ = 8.8448 (2.4); 8.8398 (2.4); 8.3042 (2.0); 8.2995 (1.9); 8.2498 (1.5); 8.2466 (1.5); 8.2338 (1.6); 8.2306 (1.7); 8.2251 (1.4); 8.2079 (1.5); 7.9232 (1.3); 7.9073 (1.5); 7.8704 (0.9); 7.8677 (0.9); 7.8565 (1.2); 7.8536 (1.6); 7.8508 (0.9); 7.8395 (1.0); 7.8368 (0.9); 7.6952 (1.0); 7.6923 (1.0); 7.6798 (1.6); 7.6771 (1.0); 7.6650 (0.8); 7.6630 (0.8); 7.5036 (0.8); 7.5004 (0.9); 7.4890 (1.1); 7.4862 (1.4); 7.4839 (1.0); 7.4725 (1.0); 7.4693 (1.0); 7.2873 (1.1); 7.2855 (1.1); 7.2713 (1.9); 7.2595 (10.6); 7.2553 (1.2); 6.6577 (1.8); 6.6417 (1.7); 2.4767 (1.8); 2.4654 (2.2); 2.4474 (0.7); 2.0336 (0.4); 1.8252 (16.0); 1.5800 (0.4); 1.3334 (0.3); 1.3042 (0.4); 1.2843 (0.6); 1.2539 (3.9); 0.8801 (0.4); 0.0062 (0.7); −0.0003 (18.4); −0.0068 (0.6)

I.332: $^1$H-NMR(500.1 MHz, CDCl3):
δ = 8.7845 (7.9); 8.7795 (8.1); 8.2617 (5.3); 8.2569 (5.2); 8.1953 (3.6); 8.1782 (4.0); 7.8908 (3.4); 7.8772 (6.2); 7.8645 (3.2); 7.8623 (3.2); 7.8421 (2.5); 7.8394 (2.4); 7.8282 (3.2); 7.8253 (4.5); 7.8224 (2.4); 7.8112 (2.8); 7.8085 (2.5); 7.6695 (2.6); 7.6674 (2.8); 7.6554 (2.6); 7.6534 (4.5); 7.6512 (2.7); 7.6393 (2.0); 7.6372 (2.0); 7.3621 (1.3); 7.3469 (2.8); 7.3308 (2.0); 7.3190 (3.4); 7.3158 (1.4); 7.3100 (1.1); 7.3028 (7.0); 7.2943 (4.6); 7.2892 (6.8); 7.2806 (4.0); 7.2659 (2.0); 7.2639 (2.1); 7.2583 (43.5); 7.2343 (12.4); 7.2196 (9.1); 7.2067 (1.1); 7.2041 (1.5); 7.2017 (0.8); 6.5759 (3.5); 6.5594 (3.4); 5.2972 (1.2); 3.0102 (0.5); 2.9968 (1.8); 2.9890 (2.4); 2.9776 (3.2); 2.9611 (2.8); 2.9541 (1.9); 2.9398 (0.4); 2.6094 (0.4); 2.5905 (0.6); 2.5804 (2.4); 2.5698 (3.0); 2.5599 (2.7); 2.5559 (2.3); 2.5456 (3.0); 2.5355 (1.5); 2.5210 (0.4); 2.0432 (0.5); 2.0333 (0.9); 1.8858 (0.5); 1.8448 (16.0); 1.8414 (15.1); 1.5459 (28.0); 1.4318 (0.6); 1.3333 (0.4); 1.2843 (0.9); 1.2726 (1.2); 1.2536 (10.5); 1.2290 (0.6); 1.2214 (0.5); 0.8931 (0.6); 0.8881 (0.5); 0.8801 (1.0); 0.8659 (0.5); 0.0062 (2.0); −0.0003 (76.8); −0.0069 (2.3)

I.333: $^1$H-NMR(500.1 MHz, CDCl3):
δ = 8.8381 (2.9); 8.8330 (3.0); 8.3154 (2.2); 8.3106 (2.2); 8.2467 (1.5); 8.2435 (1.6); 8.2307 (1.6); 8.2276 (1.6); 8.2149 (1.5); 8.1979 (1.6); 7.9123 (1.4); 7.8959 (1.6); 7.8637 (0.9); 7.8610 (0.9); 7.8498 (1.2); 7.8469 (1.7); 7.8440 (1.0); 7.8328 (1.0); 7.8301 (1.0); 7.6867 (1.0); 7.6847 (1.1); 7.6706 (1.8); 7.6565 (0.8); 7.6545 (0.8); 7.5048 (0.9); 7.5015 (0.9); 7.4902 (1.1); 7.4873 (1.5); 7.4849 (1.0); 7.4735 (1.0); 7.4703 (1.1); 7.2968 (1.1); 7.2951 (1.2); 7.2807 (2.0); 7.2665 (1.0); 7.2647 (1.0); 7.2591 (5.0); 6.7112 (1.3); 6.7092 (1.4); 6.7046 (1.4); 6.7026 (1.4); 6.6471 (2.0); 6.6307 (1.8); 6.3079 (1.6); 6.3014 (1.5); 3.7620 (1.3); 3.7312 (1.8); 3.5673 (2.1); 3.5366 (1.6); 1.7956 (16.0); 1.6334 (0.7); 1.5776 (0.6); 1.2541 (1.8); −0.0003 (8.9); −0.0070 (0.3)

I.334: $^1$H-NMR(500.1 MHz, $d_6$-DMSO):
δ = 9.0744 (1.6); 9.0708 (1.7); 8.7859 (1.9); 8.7820 (1.9); 8.4878 (2.1); 8.4847 (2.2); 8.4782 (2.2); 8.4750 (2.2); 8.2978 (2.7); 8.2938 (2.8); 8.1781 (2.1); 8.1617 (4.0); 8.1560 (2.6); 8.1528 (2.6); 8.1460 (1.7); 8.1401 (2.6); 8.1369 (2.4); 7.9414 (1.3); 7.9385 (1.2); 7.9275 (1.6); 7.9246 (2.3); 7.9217 (1.3); 7.9106 (1.4); 7.9077 (1.3); 7.7688 (1.3); 7.7669 (1.4); 7.7528 (2.2); 7.7388 (1.0); 7.7367 (1.1); 7.6969 (1.2); 7.6937 (1.2); 7.6823 (1.5); 7.6796 (2.0); 7.6771 (1.5); 7.6658 (1.4); 7.6625 (1.4); 7.5524 (0.9); 7.5486 (1.4); 7.5449 (1.4); 7.5367 (1.1); 7.5329 (1.7); 7.5292 (1.1); 7.4233 (1.4); 7.4218 (1.5); 7.4074 (2.6); 7.3931 (1.3); 7.3914 (1.4); 7.3510 (1.6); 7.3414 (1.6); 7.3353 (1.5); 7.3257 (1.4); 6.8308 (2.7); 6.8145 (2.6); 5.7537 (0.5); 3.8080 (1.9); 3.7804 (2.2); 3.3945 (2.9); 3.3669 (2.8); 3.3273 (1.6); 2.5146 (0.4); 2.5079 (5.9); 2.5043 (13.2); 2.5007 (18.6); 2.4970 (13.7); 2.4934 (6.6); 2.0728 (6.4); 1.9927 (0.4); 1.9880 (0.8); 1.5732 (16.0); 1.2352 (0.4); 1.1744 (0.5); −0.0003 (4.7)

I.335: $^1$H-NMR(500.1 MHz, CDCl3):
δ = 8.8262 (15.8); 8.8212 (16.0); 8.3066 (11.8); 8.3018 (11.4); 8.2466 (8.3); 8.2434 (8.3); 8.2307 (8.7); 8.2275 (8.4); 8.2033 (8.0); 8.1864 (8.7); 7.9144 (7.3); 7.8981 (8.3); 7.8531 (4.9); 7.8504 (4.8); 7.8392 (6.4); 7.8363 (9.4); 7.8334 (4.7); 7.8222 (5.5); 7.8195 (5.0); 7.6819 (5.8); 7.6798 (5.6); 7.6657 (9.4); 7.6516 (4.4); 7.6496

TABLE 12-continued

NMR peak lists (4.0); 7.5030 (4.7); 7.4997 (4.6); 7.4884 (6.4); 7.4857 (7.8); 7.4832 (5.4); 7.4719 (5.6); 7.4685 (5.4); 7.2874 (6.1); 7.2856 (6.0); 7.2713 (10.4); 7.2604 (24.6); 7.2571 (6.1); 7.2553 (5.3); 6.7041 (10.1); 6.6878 (9.9); 5.2970 (0.5); 4.0664 (0.4); 3.7142 (15.5); 3.6960 (15.8); 2.9120 (0.4); 1.5933 (8.1); 1.5418 (0.5); 1.4610 (0.9); 1.4514 (1.9); 1.4445 (2.3); 1.4424 (2.1); 1.4350 (4.4); 1.4260 (3.8); 1.4170 (4.4); 1.4093 (2.3); 1.4075 (2.4); 1.4006 (2.1); 1.3910 (1.1); 1.2891 (0.5); 1.2844 (0.4); 1.2753 (0.6); 1.2541 (4.4); 1.2406 (0.5); 0.8882 (0.9); 0.8795 (0.6); 0.8691 (5.6); 0.8628 (11.1); 0.8587 (5.8); 0.8567 (5.5); 0.8528 (5.6); 0.8467 (9.7); 0.8423 (6.0); 0.8408 (6.2); 0.8245 (1.6); 0.8226 (1.5); 0.8104 (0.9); 0.8002 (0.9); 0.7901 (1.9); 0.7872 (2.4); 0.7854 (2.4); 0.7820 (2.6); 0.7749 (3.9); 0.7666 (3.6); 0.7587 (3.4); 0.7507 (1.7); 0.7429 (0.4); 0.6759 (0.4); 0.6660 (0.5); 0.6555 (2.1); 0.6508 (2.8); 0.6479 (3.2); 0.6464 (3.2); 0.6440 (3.3); 0.6417 (3.1); 0.6388 (2.9); 0.6351 (2.9); 0.6321 (2.6); 0.6298 (2.5); 0.6265 (2.8); 0.6227 (2.5); 0.6206 (2.1); 0.6164 (1.5); 0.6082 (0.4); 0.5992 (0.3); 0.0061 (1.3); −0.0003 (38.4); −0.0070 (1.3)

I.336: $^1$H-NMR(500.1 MHz, CDCl3):
δ = 8.7567 (5.4); 8.7517 (5.6); 8.2718 (3.8); 8.2670 (3.8); 8.1806 (2.6); 8.1636 (2.8); 7.8952 (2.4); 7.8795 (4.9); 7.8666 (2.4); 7.8637 (2.4); 7.8327 (1.6); 7.8300 (1.7); 7.8188 (2.1); 7.8159 (3.1); 7.8130 (1.7); 7.8018 (1.8); 7.7991 (1.7); 7.6631 (1.8); 7.6610 (1.9); 7.6490 (1.8); 7.6469 (3.0); 7.6449 (1.2); 7.6329 (1.4); 7.6308 (1.4); 7.3565 (0.9); 7.3418 (2.0); 7.3267 (1.3); 7.2902 (1.8); 7.2882 (2.0); 7.2731 (2.8); 7.2591 (15.9); 6.5903 (2.5); 6.5738 (2.4); 2.0434 (0.4); 1.6654 (0.5); 1.6519 (1.0); 1.6437 (0.8); 1.6375 (1.8); 1.6325 (0.7); 1.6230 (1.1); 1.6097 (0.6); 1.5597 (4.6); 1.4267 (0.4); 1.3912 (16.0); 1.2537 (1.4); 0.7970 (0.6); 0.7892 (1.1); 0.7877 (1.1); 0.7830 (0.5); 0.7801 (0.6); 0.7754 (1.4); 0.7720 (1.6); 0.7704 (1.4); 0.7649 (0.6); 0.7581 (1.5); 0.7472 (0.9); 0.7409 (1.0); 0.7385 (1.0); 0.7358 (0.9); 0.7290 (1.5); 0.7270 (1.8); 0.7228 (1.1); 0.7206 (1.2); 0.7129 (3.1); 0.7049 (3.4); 0.6989 (2.2); 0.6947 (2.2); 0.6927 (2.2); 0.6848 (1.2); 0.6767 (1.0); 0.0061 (0.8); −0.0003 (28.0); −0.0069 (0.9)

I.337: $^1$H-NMR(500.1 MHz, CDCl3):
δ = 8.8543 (1.5); 8.8495 (1.5); 8.3386 (1.5); 8.3341 (1.5); 8.2180 (1.4); 8.2148 (1.4); 8.2018 (2.2); 8.1989 (2.6); 8.1824 (1.2); 8.0178 (0.5); 7.9246 (1.2); 7.9086 (1.3); 7.8498 (0.9); 7.8470 (0.8); 7.8359 (1.1); 7.8329 (1.6); 7.8300 (0.8); 7.8189 (1.0); 7.8161 (0.9); 7.6822 (1.0); 7.6802 (0.9); 7.6681 (1.0); 7.6660 (1.6); 7.6640 (0.9); 7.6520 (0.7); 7.6500 (0.7); 7.4810 (0.8); 7.4777 (0.8); 7.4664 (1.2); 7.4638 (1.3); 7.4611 (0.9); 7.4499 (1.0); 7.4465 (0.9); 7.2598 (23.8); 7.2423 (1.8); 7.2281 (0.9); 7.2260 (0.8); 6.6887 (1.6); 6.6723 (1.6); 5.2982 (2.6); 4.0669 (1.6); 2.9552 (4.5); 2.8836 (3.9); 2.0437 (0.5); 2.0335 (0.8); 1.6459 (16.0); 1.5890 (0.4); 1.5782 (0.7); 1.5720 (0.8); 1.5675 (0.7); 1.5611 (2.0); 1.5525 (29.1); 1.5449 (2.2); 1.5337 (0.6); 1.2912 (0.4); 1.2842 (0.6); 1.2726 (0.6); 1.2534 (6.4); 0.8800 (0.6); 0.6969 (0.8); 0.6937 (1.1); 0.6890 (1.9); 0.6857 (1.0); 0.6827 (0.8); 0.6798 (0.8); 0.6770 (1.0); 0.6721 (1.8); 0.6686 (1.0); 0.6661 (1.0); 0.6490 (0.5); 0.6382 (0.4); 0.6346 (0.4); 0.6271 (0.5); 0.6238 (0.4); 0.6187 (0.5); 0.6154 (0.6); 0.6134 (0.5); 0.6085 (0.5); 0.6044 (0.5); 0.6026 (0.5); 0.5390 (0.5); 0.5356 (0.7); 0.5282 (0.6); 0.5248 (0.7); 0.5197 (0.4); 0.5177 (0.4); 0.5153 (0.4); 0.5123 (0.3); 0.5090 (0.4); 0.0061 (1.2); −0.0003 (35.6); −0.0070 (1.3)

I.338: $^1$H-NMR(300.2 MHz, CDCl3):
δ = 9.0589 (5.4); 8.1984 (1.3); 8.1901 (1.2); 8.1779 (0.8); 8.1711 (1.1); 8.1659 (1.6); 7.9943 (1.2); 7.9880 (1.0); 7.9813 (0.8); 7.9693 (1.3); 7.9615 (1.8); 7.8523 (0.4); 7.8452 (0.7); 7.8291 (2.0); 7.8219 (1.9); 7.8185 (2.3); 7.8073 (4.0); 7.7956 (2.0); 7.7927 (1.5); 7.7858 (1.4); 7.7691 (0.5); 7.4839 (1.5); 7.4785 (1.7); 7.4581 (1.8); 7.4527 (2.1); 7.3087 (0.9); 7.3036 (1.2); 7.2985 (7.0); 7.2840 (1.7); 7.2604 (1.9); 7.2772 (1.9); 7.2583 (1.3); 7.2531 (1.3); 7.2347 (1.3); 7.2291 (1.4); 7.2080 (1.7); 7.2029 (1.7); 7.1834 (0.9); 7.1782 (0.8); 6.9568 (1.9); 6.9522 (1.9); 6.9302 (1.7); 6.9255 (1.6); 5.3365 (7.1); 4.5287 (16.0); 4.1715 (0.5); 4.1477 (0.5); 2.0829 (2.5); 1.6091 (1.5); 1.3440 (0.4); 1.3207 (1.2); 1.2970 (3.4); 1.2732 (0.8); 0.9414 (0.7); 0.9197 (2.2); 0.8964 (0.9); 0.0379 (7.4)

I.339: $^1$H-NMR(500.1 MHz, CDCl3):
δ = 8.7568 (7.3); 8.7518 (7.5); 8.6610 (0.3); 8.6052 (4.4); 8.6011 (4.4); 8.5468 (3.3); 8.5437 (3.5); 8.5372 (3.6); 8.5341 (3.4); 8.2524 (5.1); 8.2476 (5.0); 8.1814 (3.5); 8.1645 (3.9); 7.8864 (3.3); 7.8700 (3.8); 7.8593 (3.4); 7.8435 (3.7); 7.8386 (3.0); 7.8357 (2.6); 7.8245 (3.1); 7.8216 (4.4); 7.8187 (2.4); 7.8075 (2.8); 7.8048 (2.4); 7.7569 (2.5); 7.7447 (2.8); 7.7411 (2.8); 7.7311 (0.3); 7.6659 (2.5); 7.6638 (2.7); 7.6518 (2.5); 7.6497 (4.4); 7.6475 (2.7); 7.6357 (2.0); 7.6335 (2.0); 7.4658 (0.6); 7.3753 (1.3); 7.3604 (2.7); 7.3444 (2.0); 7.3067 (2.5); 7.3050 (2.6); 7.2905 (3.8); 7.2769 (4.0); 7.2675 (3.2); 7.2593 (88.4); 7.2533 (3.4); 7.0477 (0.5); 6.5771 (3.4); 6.5607 (3.3); 3.6963 (2.7); 3.6671 (5.6); 3.6195 (3.7); 3.6162 (3.7); 3.5905 (1.8); 3.5868 (1.8); 3.5334 (0.4); 3.1378 (0.5); 2.0983 (0.4); 2.0436 (1.1); 2.0332 (0.6); 1.7272 (0.6); 1.6531 (16.0); 1.6493 (15.6); 1.5505 (41.4); 1.5202 (0.5); 1.3329 (0.6); 1.3066 (0.9); 1.2995 (0.9); 1.2842 (0.9); 1.2729 (0.8); 1.2534 (6.8); 0.8933 (0.4); 0.8800 (0.7); 0.8659 (0.4); 0.1161 (0.6); 0.0061 (4.7); −0.0003 (169.5); −0.0071 (6.0); −0.1202 (0.6)

I.340: $^1$H-NMR(500.1 MHz, CDCl3):
δ = 9.4009 (1.5); 9.3998 (1.6); 9.3961 (1.6); 9.3948 (1.6); 8.8410 (2.4); 8.8360 (2.4); 8.3496 (1.2); 8.3472 (1.4); 8.3350 (1.3); 8.3325 (1.5); 8.3117 (1.2); 8.2948 (1.3); 7.7736 (1.5); 7.7588 (1.6); 7.7569 (1.5); 7.7420 (1.4); 7.5304 (1.1); 7.5269 (0.9); 7.5155 (1.4); 7.5116 (1.2); 7.2603 (5.4); 7.2460 (0.4); 7.2425 (0.5); 7.2313 (1.2); 7.2276 (1.1); 7.2162 (1.4); 7.2147 (1.3); 7.2114 (1.6); 7.1995 (1.2); 7.1962 (1.2); 7.1846 (0.5); 7.1816 (0.4); 6.7012 (1.2); 6.6979 (1.4); 6.6864 (0.9); 6.6854 (0.9); 6.6826 (1.2); 4.4511 (0.7); 4.4489 (0.7); 4.4368 (2.2); 4.4347 (2.1); 4.4224 (2.2); 4.4205 (2.2); 4.4080 (0.7); 4.4062 (0.7); 3.7276 (0.4); 3.7134 (0.9); 3.3611 (16.0); 1.8156 (10.9); 1.6857 (10.5); 1.5793 (0.5); 1.5395 (10.7); 1.4703 (0.4); 1.4334 (4.0); 1.4192 (8.4); 1.4049 (4.1); 1.2559 (1.4); 1.2540 (1.3); 1.2422 (1.1); 1.2281 (0.5); 0.0061 (0.3); −0.0003 (9.1)

I.341: $^1$H-NMR(500.1 MHz, CDCl3):
δ = 8.5871 (3.7); 8.5821 (3.9); 8.2147 (2.6); 8.2099 (2.5); 8.1115 (1.6); 8.0948 (1.8); 8.0937 (1.9); 7.7773 (1.7); 7.7687 (1.4); 7.7655 (1.4); 7.7613 (2.2); 7.7546 (1.8); 7.7518 (2.0); 7.7489 (1.1); 7.7378 (1.4); 7.7349 (1.1); 7.6098 (1.1); 7.5992 (1.4); 7.5968 (1.7); 7.5934 (2.2); 7.5864 (2.4); 7.5833 (3.7); 7.5755 (1.4); 7.5723 (2.3); 7.5684 (2.7); 7.2590 (14.7); 7.2260 (0.6); 7.2224 (0.7); 7.2114 (1.8); 7.2077 (1.7); 7.1963 (3.3); 7.1920 (3.6); 7.1808 (1.9); 7.1776 (1.9); 7.1661 (0.7); 7.1630 (0.6); 6.8330 (1.1); 6.8224 (1.9); 6.8161 (1.5); 6.8115 (1.6); 6.8077 (1.7); 6.8027 (0.9); 6.5952 (2.0); 6.5817 (2.0); 6.5782 (2.2); 6.5657 (1.4); 6.5630 (1.9); 6.4483 (4.2); 6.3015 (2.0); 4.6953 (1.7); 4.6713 (2.0); 4.4532 (2.0); 4.4292 (1.6); 2.0336 (0.4); 1.9341 (15.2); 1.7781 (16.0); 1.7501 (0.5); 1.5828 (16.4); 1.5577 (3.3); 1.5142 (0.6); 1.2843 (0.4); 1.2539 (3.4); 0.8802 (0.4); 0.0696 (0.4); 0.0063 (1.0); −0.0003 (26.0); −0.0068 (0.9)

I.342: $^1$H-NMR(500.1 MHz, CDCl3):
δ = 8.6426 (2.2); 8.6376 (2.3); 8.1666 (1.5); 8.1619 (1.5); 8.1099 (1.0); 8.0922 (1.1); 7.7522 (1.9); 7.7483 (0.9); 7.7416 (0.5); 7.7385 (1.6); 7.7351 (2.0); 7.7321 (1.3); 7.7239 (1.0); 7.7210 (0.5); 7.6140 (1.0); 7.6104 (0.7); 7.6077 (0.7); 7.6000 (0.9); 7.5951 (1.1); 7.5829 (0.8); 7.5808 (0.8); 7.5693 (0.7); 7.5666 (1.2); 7.5649 (0.8); 7.5525 (0.7); 7.5494 (1.6); 7.5319 (1.5); 7.2709 (0.4); 7.2676 (0.3); 7.2590 (26.9); 7.2531 (1.2); 7.2470 (0.4);

| TABLE 12-continued |
|---|
| NMR peak lists |

7.2121 (0.4); 7.2014 (1.0); 7.1972 (1.1); 7.1926 (1.1); 7.1875 (2.2); 7.1820 (1.2); 7.1777 (1.2); 7.1742 (1.1); 7.1630 (0.4); 6.8845 (2.2); 6.8794 (2.4); 6.7179 (1.1); 6.7127 (1.1); 6.7007 (1.1); 6.6955 (1.1); 6.5806 (1.1); 6.5763 (1.0); 6.5675 (0.6); 6.5649 (0.8); 6.5619 (1.1); 4.7008 (1.3); 4.6770 (1.6); 4.4739 (1.4); 4.4501 (1.2); 3.8382 (0.4); 3.7417 (16.0); 3.7358 (0.9); 2.0333 (0.6); 1.9653 (0.4); 1.9574 (8.7); 1.7929 (0.4); 1.7846 (9.2); 1.6065 (0.4); 1.5982 (9.5); 1.5528 (0.6); 1.5494 (0.7); 1.5411 (22.6); 1.5354 (1.7); 1.5293 (0.5); 1.5235 (0.4); 1.4270 (0.7); 1.2843 (0.5); 1.2534 (5.6); 0.8926 (0.3); 0.8802 (0.5); 0.0690 (0.5); 0.0115 (0.8); 0.0067 (1.2); −0.0003 (50.1); −0.0066 (2.7); −0.0123 (0.6)

I.343: $^1$H-NMR(500.1 MHz, CDCl3):
δ = 8.6845 (3.6); 8.6795 (3.8); 8.1961 (2.6); 8.1914 (2.6); 8.1272 (1.7); 8.1109 (1.9); 7.7789 (1.7); 7.7656 (2.3); 7.7631 (3.0); 7.7520 (1.6); 7.7492 (2.0); 7.7463 (1.1); 7.7352 (1.3); 7.7323 (1.1); 7.5909 (1.3); 7.5888 (1.4); 7.5844 (1.8); 7.5809 (1.4); 7.5790 (1.5); 7.5748 (2.3); 7.5724 (1.6); 7.5701 (2.1); 7.5656 (2.0); 7.5608 (1.1); 7.5587 (1.0); 7.4346 (1.5); 7.4316 (2.2); 7.4175 (4.0); 7.3947 (2.6); 7.3908 (0.8); 7.3803 (4.4); 7.3774 (1.8); 7.3650 (2.1); 7.3338 (1.4); 7.3240 (0.6); 7.3194 (1.8); 7.3146 (0.5); 7.3050 (0.6); 7.2929 (3.9); 7.2756 (4.4); 7.2586 (38.2); 7.1975 (0.5); 7.1938 (0.7); 7.1828 (1.7); 7.1789 (1.7); 7.1704 (2.0); 7.1686 (2.5); 7.1662 (2.4); 7.1636 (2.0); 7.1556 (1.9); 7.1523 (1.8); 7.1409 (0.7); 7.1377 (0.5); 6.9325 (0.6); 6.9267 (5.3); 6.9227 (1.7); 6.9133 (1.5); 6.9093 (4.9); 6.9036 (0.6); 6.5556 (2.0); 6.5519 (2.1); 6.5415 (1.2); 6.5398 (1.3); 6.5370 (1.9); 5.0307 (9.2); 4.5727 (1.8); 4.5504 (2.9); 4.4864 (2.8); 4.4642 (1.7); 4.1286 (0.4); 4.1143 (0.4); 2.2783 (0.8); 2.0434 (1.9); 2.0333 (1.0); 1.9216 (14.8); 1.7645 (16.0); 1.5983 (16.1); 1.5420 (19.3); 1.5131 (0.5); 1.4221 (0.3); 1.3500 (0.4); 1.3329 (0.5); 1.2859 (3.8); 1.2728 (1.9); 1.2535 (12.4); 0.8936 (1.0); 0.8802 (1.7); 0.8663 (1.2); 0.8549 (0.8); 0.8425 (0.9); 0.8294 (0.8); 0.0690 (0.7); 0.0063 (2.0); −0.0003 (72.6); −0.0068 (2.6)

I.344: $^1$H-NMR(300.2 MHz, CDCl3):
δ = 9.1270 (16.0); 9.1103 (0.9); 8.2168 (4.5); 8.2097 (5.1); 8.1931 (3.5); 8.1882 (4.5); 8.1845 (5.4); 8.1685 (0.4); 7.9945 (0.4); 7.9789 (4.1); 7.9739 (3.6); 7.9694 (3.0); 7.9538 (6.3); 7.9468 (6.1); 7.9284 (0.7); 7.8613 (1.6); 7.8551 (2.5); 7.8382 (6.0); 7.8319 (5.2); 7.8200 (6.4); 7.8134 (9.7); 7.8052 (5.2); 7.7935 (4.4); 7.7877 (4.7); 7.7702 (1.8); 7.7645 (1.4); 7.4188 (7.9); 7.4043 (10.4); 7.3955 (9.9); 7.3851 (4.7); 7.3703 (19.0); 7.3623 (12.6); 7.3559 (7.8); 7.3495 (6.8); 7.3350 (8.7); 7.3299 (9.4); 7.3138 (12.8); 7.3070 (11.8); 7.2983 (31.6); 7.2881 (8.3); 7.2729 (1.6); 7.2528 (3.4); 7.2481 (3.6); 7.2283 (6.4); 7.2236 (6.2); 7.2026 (4.3); 7.1974 (4.2); 7.1845 (4.5); 7.1788 (4.5); 7.1578 (5.8); 7.1528 (5.6); 7.1334 (2.9); 7.1282 (2.6); 6.8808 (6.6); 6.8768 (6.3); 6.8545 (5.8); 6.8500 (5.3); 5.3369 (3.6); 4.9129 (5.2); 4.9002 (5.8); 4.8761 (6.0); 4.8634 (5.5); 4.7460 (7.6); 4.1691 (0.3); 3.8289 (0.5); 3.7812 (0.6); 3.7581 (3.8); 3.7455 (3.9); 3.7114 (4.7); 3.6988 (4.5); 3.2551 (0.9); 3.2463 (5.2); 3.2093 (5.6); 3.1996 (4.7); 3.1627 (4.2); 2.3934 (0.4); 2.3146 (0.8); 1.6232 (2.0); 1.4694 (0.4); 1.4443 (0.7); 1.4154 (0.5); 1.2953 (10.2); 0.9417 (0.7); 0.9197 (1.8); 0.8952 (2.0); 0.8727 (1.4); 0.1114 (2.4); 0.0504 (1.2); 0.0396 (28.8); 0.0289 (1.4)

I.345: $^1$H-NMR(500.1 MHz, d$_6$-DMSO):
δ = 8.6074 (2.8); 8.6022 (2.8); 8.2778 (1.8); 8.2728 (1.7); 8.0821 (1.0); 8.0800 (1.1); 8.0656 (1.2); 8.0634 (1.2); 8.0385 (1.2); 8.0212 (1.3); 7.8173 (0.8); 7.8144 (0.8); 7.8035 (1.0); 7.8005 (1.5); 7.7975 (0.9); 7.7866 (0.9); 7.7837 (0.8); 7.7349 (1.0); 7.7321 (1.1); 7.7185 (1.6); 7.7157 (1.6); 7.6874 (0.8); 7.6851 (0.9); 7.6735 (0.8); 7.6712 (1.4); 7.6688 (0.9); 7.6650 (1.0); 7.6621 (1.0); 7.6572 (0.8); 7.6549 (0.8); 7.6504 (1.1); 7.6476 (1.3); 7.6341 (0.7); 7.6311 (0.8); 7.5824 (1.2); 7.5795 (1.2); 7.5662 (1.7); 7.5634 (1.5); 7.4564 (0.9); 7.4535 (0.9); 7.4417 (1.0); 7.4391 (1.1); 7.4376 (1.0); 7.4257 (0.7); 7.4229 (0.7); 3.5270 (16.0); 3.3094 (36.4); 2.5082 (4.6); 2.5046 (10.4); 2.5009 (14.8); 2.4972 (10.7); 2.4936 (5.0); 2.0855 (0.4); 1.3810 (0.7); 1.3290 (0.4); −0.0003 (3.3)

I.346: $^1$H-NMR(500.1 MHz, d$_6$-DMSO):
δ = 10.8149 (4.2); 8.5200 (6.2); 8.5148 (6.8); 8.3300 (4.4); 8.3248 (4.3); 8.0694 (2.6); 8.0540 (2.9); 8.0373 (3.0); 8.0203 (3.3); 7.8163 (1.8); 7.8135 (1.8); 7.8024 (2.3); 7.7995 (3.4); 7.7966 (1.8); 7.7856 (0.8); 7.7828 (1.9); 7.6915 (2.0); 7.6894 (2.0); 7.6754 (3.3); 7.6733 (2.2); 7.6614 (1.6); 7.6593 (1.6); 7.5448 (1.3); 7.5421 (1.6); 7.5274 (2.8); 7.5141 (2.0); 7.5112 (2.4); 7.4968 (2.9); 7.4942 (2.9); 7.4807 (3.9); 7.4781 (3.4); 7.3821 (3.0); 7.3794 (3.8); 7.3660 (2.8); 7.3632 (3.0); 7.3565 (2.4); 7.3535 (2.0); 7.3404 (2.8); 7.3258 (1.8); 7.3228 (1.4); 4.6275 (16.0); 3.3472 (0.4); 3.3078 (128.2); 2.6387 (0.4); 2.6350 (0.4); 2.6313 (0.3); 2.5363 (0.4); 2.5074 (26.0); 2.5038 (54.9); 2.5002 (76.2); 2.4966 (55.1); 2.4930 (25.8); 2.3613 (0.4); 1.2343 (0.5); 1.2148 (0.4); 1.1474 (0.4); 0.0061 (0.7); −0.0003 (17.5); −0.0070 (0.6)

I.347: $^1$H-NMR(500.1 MHz, CDCl3):
δ = 8.7727 (8.1); 8.7679 (8.2); 8.3036 (7.3); 7.6020 (2.1); 7.5983 (2.2); 7.5920 (2.3); 7.5882 (2.4); 7.5837 (3.0); 7.5800 (3.0); 7.5737 (2.8); 7.5700 (2.7); 7.4846 (2.3); 7.4706 (2.7); 7.4656 (3.9); 7.4517 (3.8); 7.4469 (2.1); 7.4328 (1.7); 7.3590 (0.7); 7.3569 (0.7); 7.3439 (3.8); 7.3417 (4.4); 7.3355 (6.8); 7.3301 (16.0); 7.3214 (2.6); 7.3128 (3.4); 7.3067 (2.5); 7.2973 (4.3); 7.2910 (3.1); 7.2857 (2.4); 7.2793 (2.2); 7.2615 (41.9); 7.2291 (6.6); 7.2137 (4.7); 3.4604 (6.4); 3.4487 (7.6); 3.4369 (6.5); 3.1057 (7.5); 3.0947 (5.5); 3.0837 (8.0); 2.3594 (2.3); 2.3473 (4.6); 2.3367 (6.5); 2.3263 (4.3); 2.3141 (2.1); 2.0363 (0.4); 1.5592 (99.6); 1.2855 (0.4); 1.2524 (4.1); 1.2315 (0.4); 1.1909 (0.8); 0.1161 (0.4); −0.0002 (78.3); −0.1200 (0.4)

I.348: $^1$H-NMR(500.1 MHz, CDCl3):
δ = 8.7828 (2.5); 8.7778 (2.5); 8.3397 (2.2); 8.3348 (2.1); 8.0656 (1.5); 8.0488 (1.6); 7.8311 (1.4); 7.8149 (1.6); 7.7131 (0.8); 7.7106 (0.8); 7.6991 (1.1); 7.6965 (1.5); 7.6824 (0.9); 7.6799 (0.8); 7.5829 (1.0); 7.5684 (1.6); 7.5541 (0.8); 7.3013 (0.8); 7.2984 (0.9); 7.2863 (1.7); 7.2834 (1.8); 7.2612 (9.2); 7.2511 (1.7); 7.2489 (1.6); 7.2363 (0.8); 7.2338 (0.8); 7.2188 (0.9); 7.2153 (0.8); 7.2033 (1.3); 7.2002 (1.3); 7.1886 (0.7); 7.1854 (0.6); 7.1012 (1.5); 7.0859 (1.2); 5.3002 (0.3); 1.5740 (16.0); 1.4925 (4.9); 1.2537 (0.4); −0.0002 (16.4)

I.349: $^1$H-NMR(500.1 MHz, CDCl3):
δ = 8.7724 (10.0); 8.7672 (10.3); 8.2529 (8.0); 8.2480 (8.0); 8.0710 (5.4); 8.0541 (6.0); 7.8165 (5.0); 7.8008 (5.8); 7.7138 (3.1); 7.7110 (3.1); 7.6999 (4.3); 7.6971 (6.0); 7.6942 (3.4); 7.6831 (3.6); 7.6803 (3.3); 7.5828 (3.8); 7.5807 (3.8); 7.5666 (6.1); 7.5525 (2.8); 7.5506 (2.8); 7.3221 (9.2); 7.3201 (10.6); 7.3127 (16.0); 7.3009 (1.7); 7.2941 (3.7); 7.2851 (3.0); 7.2785 (5.2); 7.2686 (5.0); 7.2611 (42.2); 7.2474 (9.0); 7.2326 (3.8); 3.4609 (7.2); 3.4491 (8.2); 3.4373 (7.5); 3.1354 (8.0); 3.1244 (5.8); 3.1133 (8.6); 2.3608 (2.4); 2.3485 (4.7); 2.3379 (6.8); 2.3273 (4.6); 2.3150 (2.3); 1.5726 (75.1); 1.2849 (0.3); 1.2526 (3.0); 1.2311 (0.3); 1.1908 (0.7); 0.0061 (4.0); −0.0002 (74.1); −0.0066 (4.6); −0.1199 (0.3)

I.350: $^1$H-NMR(400.1 MHz, CDCl3):
δ = 8.7815 (5.0); 8.7753 (5.1); 8.3271 (3.4); 8.3231 (4.1); 8.3174 (3.3); 7.5972 (1.2); 7.5923 (1.3); 7.5846 (1.4); 7.5797 (1.4); 7.5743 (1.9); 7.5694 (1.9); 7.5617 (1.8); 7.5569 (1.7); 7.4785 (1.6); 7.4611 (1.8); 7.4546 (2.4); 7.4374 (2.3); 7.4311 (1.4); 7.4139 (1.1); 7.3397 (0.3); 7.3213 (2.1); 7.3174 (3.7); 7.3071 (9.7); 7.3048 (10.1); 7.2951 (3.4); 7.2856 (1.8); 7.2761 (3.0); 7.2574 (51.0); 7.2061 (3.4); 7.1876 (2.4); 3.5016 (0.7); 3.4927 (0.9); 3.4842 (1.0); 3.4759 (1.3); 3.4669 (1.0); 3.4586 (1.0); 3.4503 (0.7); 3.1110 (2.4); 3.1001 (3.3); 3.0884 (2.7);

TABLE 12-continued

NMR peak lists 2.3202 (0.7); 2.3101 (0.7); 2.2855 (1.1); 2.2771 (1.0); 2.2107 (0.8); 2.1848 (1.0); 2.1789 (1.1); 2.1734 (1.0); 2.1535 (1.0); 2.1470 (0.6); 2.1417 (0.6); 2.1323 (0.6); 2.1161 (0.5); 2.0298 (0.8); 1.5271 (81.4); 1.5039 (16.6); 1.4866 (16.0); 1.4211 (0.5); 1.2848 (0.8); 1.2551 (8.1); 0.8806 (0.6); 0.8626 (0.4); 0.8546 (0.4); 0.8425 (0.4); 0.8280 (0.4); 0.1460 (0.4); 0.0079 (4.6); −0.0002 (100.9); −0.0083 (5.6); −0.1494 (0.4)
I.351: $^1$H-NMR(500.1 MHz, CDCl3):
δ = 8.7824 (4.6); 8.7772 (4.7); 8.2784 (3.8); 8.2735 (3.8); 8.0650 (2.6); 8.0482 (2.9); 7.8155 (2.6); 7.7992 (2.9); 7.7075 (1.4); 7.7049 (1.5); 7.6937 (2.0); 7.6909 (2.9); 7.6882 (1.6); 7.6769 (1.7); 7.6742 (1.6); 7.5780 (1.8); 7.5762 (1.9); 7.5620 (2.9); 7.5479 (1.4); 7.5461 (1.4); 7.3016 (5.0); 7.2952 (5.1); 7.2935 (5.0); 7.2902 (4.0); 7.2762 (2.0); 7.2690 (1.5); 7.2611 (15.8); 7.2553 (2.3); 7.2497 (1.6); 7.2433 (1.4); 7.2267 (3.1); 7.2121 (1.5); 3.4945 (1.1); 3.4868 (1.0); 3.1929 (0.4); 3.1639 (1.0); 3.1419 (1.2); 3.1277 (0.9); 3.1141 (0.9); 2.2911 (0.8); 2.2079 (0.7); 2.1870 (1.1); 2.1830 (1.2); 2.1620 (0.9); 2.1577 (0.8); 2.1532 (0.8); 2.1324 (0.5); 1.5811 (16.0); 1.5045 (13.0); 1.4907 (13.0); 1.2525 (2.0); −0.0002 (25.3)
I.352: $^1$H-NMR(400.1 MHz, CDCl3):
δ = 8.7902 (6.0); 8.7840 (6.1); 8.3855 (3.9); 8.3815 (4.6); 8.3798 (4.5); 8.3757 (3.8); 7.6098 (1.4); 7.6049 (1.5); 7.5971 (1.5); 7.5922 (1.6); 7.5868 (2.1); 7.5819 (2.1); 7.5741 (2.0); 7.5693 (2.0); 7.4833 (2.0); 7.4660 (2.1); 7.4593 (2.8); 7.4420 (2.7); 7.4359 (1.6); 7.4186 (1.4); 7.3124 (1.1); 7.3072 (1.6); 7.2936 (4.2); 7.2877 (7.0); 7.2843 (3.6); 7.2701 (4.7); 7.2666 (4.6); 7.2575 (54.0); 7.2516 (2.7); 7.2479 (2.2); 7.2380 (2.6); 7.2325 (2.1); 7.2187 (3.2); 7.2136 (2.8); 7.2011 (1.7); 7.1959 (1.4); 7.0817 (3.7); 7.0794 (3.4); 7.0627 (3.0); 7.0597 (2.7); 2.2202 (0.4); 2.2023 (0.4); 2.1783 (0.4); 2.1497 (0.3); 2.0405 (0.4); 2.0298 (0.8); 1.5294 (72.5); 1.4803 (16.0); 1.4214 (0.5); 1.3334 (0.3); 1.2845 (0.7); 1.2551 (5.8); 1.2247 (0.4); 0.8805 (0.5); 0.1460 (0.4); 0.0080 (3.4); −0.0001 (107.6); −0.0085 (3.6); −0.1494 (0.4)
I.353: $^1$H-NMR(500.1 MHz, CDCl3):
δ = 8.8455 (10.8); 8.8405 (11.1); 8.3523 (6.7); 8.3494 (7.8); 8.3477 (7.6); 8.3448 (6.5); 7.6262 (2.4); 7.6224 (2.6); 7.6162 (2.6); 7.6124 (2.7); 7.6078 (3.3); 7.6040 (3.4); 7.5978 (3.2); 7.5941 (3.1); 7.5014 (3.0); 7.4875 (3.2); 7.4823 (4.5); 7.4685 (4.5); 7.4636 (2.5); 7.4497 (2.3); 7.3904 (5.4); 7.3872 (2.4); 7.3838 (2.0); 7.3762 (14.7); 7.3693 (5.6); 7.3610 (12.0); 7.3556 (10.6); 7.3518 (9.4); 7.3498 (8.1); 7.3364 (16.0); 7.3244 (8.3); 7.3226 (9.0); 7.3197 (7.3); 7.3118 (2.4); 7.3077 (7.6); 7.3032 (2.1); 7.2954 (1.6); 7.2930 (2.6); 7.2905 (1.5); 7.2590 (51.9); 7.2548 (12.1); 7.2519 (14.9); 7.2478 (6.8); 7.2440 (6.4); 7.2378 (10.7); 5.2972 (1.5); 3.6676 (1.2); 3.6556 (2.0); 3.6506 (4.8); 3.6481 (5.5); 3.6279 (8.4); 3.6250 (9.4); 3.5980 (11.4); 3.5735 (5.0); 3.5701 (5.2); 3.5551 (4.3); 3.5457 (2.5); 3.5339 (2.8); 3.5265 (4.8); 3.5054 (3.5); 3.4396 (0.6); 3.1968 (5.4); 3.1681 (4.5); 1.5510 (72.9); 1.3243 (0.4); 1.3116 (1.1); 1.2979 (1.4); 1.2845 (1.0); 1.2704 (0.7); 1.2659 (0.6); 1.2536 (1.6); 1.2396 (0.5); 0.8962 (2.6); 0.8822 (6.0); 0.8677 (2.9); 0.1163 (0.3); 0.0061 (2.6); −0.0003 (86.7); −0.0069 (2.6); −0.1201 (0.3)
I.354: $^1$H-NMR(500.1 MHz, CDCl3):
δ = 8.8408 (11.3); 8.8355 (11.8); 8.3025 (7.8); 8.2975 (7.7); 8.0980 (5.2); 8.0812 (5.7); 7.8462 (4.7); 7.8443 (4.8); 7.8299 (5.4); 7.8277 (5.4); 7.7337 (3.5); 7.7310 (3.4); 7.7198 (4.5); 7.7170 (6.5); 7.7140 (3.4); 7.7029 (3.9); 7.7002 (3.8); 7.6021 (3.9); 7.6000 (4.0); 7.5881 (3.7); 7.5860 (6.4); 7.5837 (3.4); 7.5720 (3.0); 7.5708 (2.9); 7.5268 (2.9); 7.4652 (0.5); 7.3905 (4.6); 7.3873 (2.0); 7.3762 (12.7); 7.3609 (10.3); 7.3464 (2.9); 7.3416 (2.1); 7.3367 (4.5); 7.3339 (8.9); 7.3301 (11.4); 7.3248 (7.0); 7.3215 (13.8); 7.3191 (16.0); 7.3112 (4.3); 7.3046 (7.7); 7.3020 (4.1); 7.2923 (1.7); 7.2898 (2.6); 7.2872 (1.7); 7.2817 (5.0); 7.2777 (5.7); 7.2672 (11.4); 7.2647 (14.9); 7.2587 (70.4); 7.2507 (9.6); 7.0471 (0.4); 3.6818 (0.7); 3.6758 (0.8); 3.6591 (2.6); 3.6488 (1.9); 3.6380 (3.7); 3.6329 (4.3); 3.6218 (6.1); 3.6127 (14.8); 3.5949 (2.1); 3.5895 (3.2); 3.5845 (6.7); 3.5635 (2.4); 3.1949 (4.4); 3.1672 (3.9); 2.0329 (0.4); 1.5489 (114.7); 1.4219 (0.5); 1.3259 (0.4); 1.3119 (1.2); 1.2980 (1.5); 1.2847 (1.4); 1.2534 (5.2); 1.2316 (0.5); 1.2237 (0.4); 0.8964 (2.7); 0.8823 (6.3); 0.8678 (3.1); 0.1163 (0.6); 0.0061 (4.9); −0.0003 (161.1); −0.0070 (4.5); −0.1201 (0.5)
I.355: $^1$H-NMR(500.1 MHz, CDCl3):
δ = 8.8743 (6.2); 8.8690 (6.4); 8.3345 (4.5); 8.3294 (4.4); 8.0987 (3.1); 8.0818 (3.3); 7.8469 (2.8); 7.8315 (3.1); 7.7308 (1.9); 7.7280 (1.9); 7.7170 (2.6); 7.7141 (3.8); 7.7111 (1.9); 7.7001 (2.3); 7.6973 (2.0); 7.6004 (2.4); 7.5983 (2.2); 7.5842 (3.7); 7.5702 (1.7); 7.5681 (1.5); 7.3860 (2.7); 7.3829 (1.2); 7.3716 (7.0); 7.3563 (5.0); 7.3346 (0.4); 7.3248 (3.1); 7.3198 (3.0); 7.3152 (6.4); 7.3075 (6.9); 7.3046 (7.0); 7.3005 (5.5); 7.2961 (3.8); 7.2888 (7.3); 7.2835 (4.9); 7.2770 (2.7); 7.2703 (2.3); 7.2589 (33.2); 7.1938 (5.2); 7.1912 (6.7); 7.1771 (5.5); 3.6970 (1.8); 3.6751 (2.1); 3.6677 (2.2); 3.6460 (2.7); 3.6333 (1.9); 3.6249 (0.8); 3.6196 (2.0); 3.6114 (2.2); 3.6060 (0.7); 3.5977 (2.2); 3.5840 (0.6); 3.2804 (1.6); 3.2590 (2.9); 3.2375 (1.3); 3.0863 (2.9); 3.0581 (2.7); 1.5539 (35.3); 1.3119 (0.7); 1.2980 (0.9); 1.2813 (1.3); 1.2673 (1.1); 1.2539 (0.7); 1.2354 (15.8); 1.2217 (16.0); 0.8964 (1.6); 0.8823 (3.6); 0.8678 (1.8); 0.0062 (1.9); −0.0003 (65.9); −0.0068 (2.4)
I.356: $^1$H-NMR(500.1 MHz, CDCl3):
δ = 8.8926 (5.1); 8.8876 (5.2); 8.3581 (3.1); 8.3552 (3.6); 8.3536 (3.6); 8.3507 (3.1); 7.6237 (1.1); 7.6200 (1.2); 7.6137 (1.2); 7.6099 (1.3); 7.6054 (1.6); 7.6016 (1.6); 7.5953 (1.5); 7.5917 (1.4); 7.4972 (1.4); 7.4833 (1.5); 7.4781 (2.1); 7.4644 (2.1); 7.4594 (1.2); 7.4455 (1.0); 7.3884 (2.4); 7.3742 (6.5); 7.3588 (5.0); 7.3444 (2.4); 7.3407 (3.9); 7.3334 (7.1); 7.3269 (6.2); 7.3214 (5.4); 7.3117 (1.6); 7.3099 (1.5); 7.3058 (4.2); 7.2990 (3.7); 7.2920 (2.8); 7.2888 (1.8); 7.2853 (1.3); 7.2806 (1.7); 7.2591 (23.1); 7.2522 (1.6); 7.2460 (2.0); 7.2408 (2.2); 7.2039 (4.5); 7.2013 (5.8); 7.1871 (4.8); 3.5554 (1.4); 3.5486 (1.1); 3.5423 (1.2); 3.5373 (1.3); 3.5335 (2.5); 3.5262 (3.0); 3.5201 (1.8); 3.5151 (1.8); 3.5087 (1.8); 3.5046 (2.5); 3.4299 (2.0); 3.4078 (2.6); 3.3864 (1.0); 3.0582 (2.7); 3.0292 (2.7); 1.8473 (0.6); 1.8411 (0.7); 1.8321 (1.0); 1.8260 (1.0); 1.8168 (1.3); 1.8106 (1.3); 1.8017 (1.1); 1.7955 (1.1); 1.7867 (0.4); 1.7805 (0.4); 1.7571 (0.3); 1.7421 (1.1); 1.7308 (1.2); 1.7270 (1.4); 1.7157 (1.4); 1.7116 (1.1); 1.7004 (1.0); 1.6965 (0.8); 1.6851 (0.7); 1.5515 (33.4); 1.2572 (0.8); 1.2548 (0.8); 1.2435 (0.5); 0.8794 (7.4); 0.8645 (16.0); 0.8494 (7.0); 0.0061 (1.1); −0.0003 (36.9); −0.0070 (1.3)
I.357: $^1$H-NMR(500.1 MHz, CDCl3):
δ = 8.8787 (5.3); 8.8737 (5.5); 8.3834 (3.2); 8.3805 (3.7); 8.3787 (3.8); 8.3759 (3.3); 7.6278 (1.2); 7.6240 (1.3); 7.6178 (1.4); 7.6140 (1.4); 7.6095 (1.7); 7.6057 (1.8); 7.5994 (1.6); 7.5957 (1.5); 7.4999 (1.5); 7.4860 (1.6); 7.4809 (2.3); 7.4670 (2.2); 7.4621 (1.3); 7.4482 (1.2); 7.3860 (2.6); 7.3827 (1.2); 7.3717 (7.0); 7.3564 (5.2); 7.3475 (2.6); 7.3434 (4.3); 7.3362 (7.5); 7.3299 (5.7); 7.3239 (4.5); 7.3212 (2.2); 7.3184 (3.3); 7.3158 (2.3); 7.3082 (1.6); 7.3032 (6.3); 7.2962 (3.0); 7.2915 (2.3); 7.2889 (2.8); 7.2840 (2.1); 7.2718 (3.4); 7.2685 (2.2); 7.2652 (1.9); 7.2593 (29.6); 7.2536 (2.6); 7.1793 (5.0); 7.1765 (6.7); 7.1728 (1.8); 7.1624 (5.4); 3.7240 (0.3); 3.7200 (0.3); 3.7100 (0.3); 3.6339 (1.7); 3.6284 (0.7); 3.6142 (2.6); 3.6047 (2.4); 3.6010 (2.4); 3.5926 (2.4); 3.5871 (0.9); 3.5827 (2.4); 3.5790 (2.6); 3.5653 (0.6); 3.2714 (1.6); 3.2497 (2.8); 3.2284 (1.2); 3.0886 (2.8); 3.0604 (2.5); 1.5492 (49.1); 1.2601 (1.2); 1.2578 (2.0); 1.2437 (3.3); 1.2378 (16.0); 1.2295 (2.6); 1.2242 (15.9); 0.0062 (1.6); −0.0003 (59.0); −0.0069 (1.9)

TABLE 12-continued

NMR peak lists

I.358: ¹H-NMR(500.1 MHz, CDCl3):
δ = 8.8729 (4.8); 8.8679 (4.9); 8.3460 (5.4); 8.3411 (5.3); 8.0761 (3.6); 8.0592 (3.9); 7.8347 (3.4); 7.8183 (3.8); 7.7202 (2.3); 7.7173 (2.4); 7.7063 (3.0); 7.7034 (4.6); 7.7004 (2.3); 7.6894 (2.7); 7.6865 (2.5); 7.5865 (2.7); 7.5843 (2.8); 7.5703 (4.4); 7.5680 (2.6); 7.5563 (2.0); 7.5541 (1.9); 7.3854 (0.3); 7.3828 (0.3); 7.3692 (3.8); 7.3665 (5.5); 7.3585 (9.2); 7.3575 (9.1); 7.3498 (0.9); 7.3219 (2.3); 7.3142 (1.3); 7.3121 (1.4); 7.3059 (3.6); 7.2970 (3.1); 7.2886 (2.3); 7.2590 (25.9); 7.2440 (2.6); 5.2967 (0.5); 4.9421 (1.2); 3.0777 (0.3); 1.8167 (16.0); 1.7015 (0.6); 1.5636 (16.4); 1.2537 (0.9); 0.0061 (1.3); −0.0003 (38.0); −0.0070 (1.0)

I.359: ¹H-NMR(500.1 MHz, CDCl3):
δ = 8.8858 (11.8); 8.8811 (12.1); 8.3785 (11.7); 8.3754 (13.6); 8.3741 (13.6); 8.3709 (11.8); 7.6187 (4.4); 7.6148 (4.7); 7.6087 (4.8); 7.6047 (4.9); 7.6004 (6.0); 7.5964 (6.2); 7.5902 (5.7); 7.5864 (5.7); 7.4870 (5.6); 7.4731 (5.9); 7.4679 (8.2); 7.4540 (8.1); 7.4491 (4.7); 7.4352 (4.3); 7.4141 (2.9); 7.4114 (3.1); 7.4006 (4.2); 7.3981 (10.3); 7.3953 (8.9); 7.3846 (12.8); 7.3819 (14.4); 7.3779 (10.5); 7.3739 (13.1); 7.3619 (4.4); 7.3580 (2.9); 7.3469 (7.8); 7.3428 (5.0); 7.3333 (5.2); 7.3310 (10.8); 7.3270 (7.0); 7.3178 (6.0); 7.3136 (6.2); 7.2993 (0.4); 7.2595 (119.3); 7.2482 (10.9); 7.2326 (7.5); 7.0478 (0.7); 6.8521 (0.4); 6.8345 (0.4); 5.2980 (2.9); 4.9506 (2.4); 4.8333 (0.4); 3.8002 (2.4); 3.7963 (0.8); 3.4959 (0.6); 3.4850 (0.6); 1.9102 (0.3); 1.7987 (16.0); 1.7198 (0.9); 1.6800 (0.4); 1.5612 (0.8); 1.5403 (133.3); 1.4218 (0.4); 1.2846 (0.5); 1.2538 (2.1); 0.8803 (0.4); 0.1163 (0.7); 0.0061 (6.5); −0.0003 (222.2); −0.0070 (6.8); −0.1201 (0.7)

I.360: ¹H-NMR(500.1 MHz, CDCl3):
δ = 8.8626 (7.1); 8.8577 (7.1); 8.3884 (6.7); 8.3850 (8.0); 8.3840 (7.9); 8.3805 (6.6); 7.6298 (5.6); 7.6131 (7.5); 7.5305 (3.4); 7.5208 (3.5); 7.5148 (5.2); 7.5050 (5.2); 7.4985 (3.2); 7.4888 (3.2); 7.4661 (0.4); 7.4103 (1.5); 7.4076 (1.7); 7.4012 (4.7); 7.3987 (5.2); 7.3943 (6.0); 7.3916 (5.4); 7.3857 (4.9); 7.3805 (13.1); 7.3785 (16.0); 7.3746 (8.5); 7.3648 (4.6); 7.3626 (5.4); 7.3439 (4.5); 7.3394 (2.6); 7.3309 (2.6); 7.3281 (6.4); 7.3236 (3.6); 7.3154 (3.3); 7.3106 (3.6); 7.2597 (62.6); 7.2422 (4.3); 7.0481 (0.3); 5.2980 (3.7); 4.9426 (1.5); 3.7962 (0.5); 2.0433 (1.0); 1.8015 (10.8); 1.7089 (0.4); 1.7032 (0.4); 1.5478 (105.1); 1.4220 (0.5); 1.2854 (0.5); 1.2728 (0.4); 1.2584 (1.1); 1.2552 (1.0); 1.2443 (0.4); 0.1163 (0.5); 0.0063 (4.4); −0.0003 (117.9); −0.0069 (5.3); −0.1202 (0.5)

IVa.01: ¹H-NMR(300.2 MHz, CDCl3):
δ = 7.3231 (0.3); 7.3187 (0.4); 7.3044 (0.8); 7.2972 (0.7); 7.2932 (0.8); 7.2714 (0.4); 7.2669 (0.5); 7.2438 (0.6); 7.2404 (0.6); 7.2186 (0.8); 7.2154 (0.7); 7.0891 (0.6); 7.0859 (0.5); 7.0638 (0.9); 7.0607 (0.8); 7.0386 (0.4); 6.8140 (0.8); 6.7874 (0.8); 6.0047 (0.3); 5.9818 (0.4); 5.9475 (0.4); 5.4776 (0.6); 5.4739 (0.6); 5.4205 (0.5); 5.4167 (0.5); 5.3630 (0.7); 5.3591 (0.6); 5.3287 (0.6); 5.3249 (0.6); 4.2820 (0.8); 4.2767 (1.4); 4.2712 (0.9); 4.2642 (0.9); 4.2589 (1.4); 4.2535 (0.8); 1.7500 (0.6); 1.7337 (16.0); 1.6218 (0.7); 0.0441 (0.7)

IIIb1.01: ¹H-NMR(500.1 MHz, CDCl3):
δ = 7.3014 (1.3); 7.2856 (1.5); 7.2592 (8.4); 7.2073 (0.5); 7.2053 (0.6); 7.1902 (1.4); 7.1753 (0.8); 7.0842 (1.0); 7.0817 (1.0); 7.0687 (1.5); 7.0667 (1.4); 7.0537 (0.7); 7.0513 (0.7); 6.7159 (1.6); 6.7137 (1.6); 6.7000 (1.6); 6.6978 (1.5); 6.3074 (0.8); 3.4411 (0.4); 3.4267 (1.2); 3.4124 (1.2); 3.3981 (0.4); 1.5488 (13.8); 1.5380 (16.1); 1.4853 (9.8); 1.4710 (9.5); 1.3464 (16.0); 1.2534 (0.5); 0.0062 (0.7); −0.0003 (15.8); −0.0069 (0.6)

IIIb1.02: ¹H-NMR(500.1 MHz, CDCl3):
δ = 8.0991 (0.6); 8.0961 (0.6); 8.0831 (0.6); 8.0801 (0.6); 7.5726 (0.4); 7.5695 (0.4); 7.5563 (0.5); 7.5549 (0.5); 7.5418 (0.4); 7.5387 (0.4); 7.2604 (1.2); 7.2203 (0.4); 7.2184 (0.5); 7.2041 (0.8); 7.1898 (0.4); 7.1878 (0.4); 6.9459 (0.7); 6.9449 (0.7); 6.9297 (0.7); 1.6814 (16.0); 1.4318 (1.5); −0.0003 (2.3)

IIIb1.03: ¹H-NMR(500.1 MHz, CDCl3):
δ = 7.7494 (1.1); 7.7340 (1.2); 7.4529 (0.5); 7.4512 (0.5); 7.4367 (1.0); 7.4220 (0.6); 7.2589 (2.5); 7.2470 (0.8); 7.2320 (1.4); 7.2170 (0.6); 7.2161 (0.6); 6.9780 (0.5); 6.8643 (1.2); 6.8480 (1.1); 5.0038 (0.4); 2.2707 (0.9); 2.1780 (2.2); 1.6527 (16.0); 1.4317 (8.2); −0.0003 (4.2)

IIIb1.04: ¹H-NMR(500.1 MHz, CDCl3):
δ = 7.4345 (1.2); 7.4322 (1.2); 7.4188 (1.4); 7.4165 (1.4); 7.3212 (0.6); 7.3186 (0.6); 7.3060 (1.3); 7.3034 (1.3); 7.2908 (0.9); 7.2880 (0.8); 7.2596 (4.4); 7.2063 (0.9); 7.2040 (0.9); 7.1908 (1.3); 7.1889 (1.3); 7.1758 (0.6); 7.1736 (0.6); 6.9257 (1.4); 6.9242 (1.4); 6.9100 (1.3); 6.9085 (1.3); 6.2151 (0.8); 5.2981 (0.7); 3.2106 (16.0); 1.7158 (13.7); 1.6117 (12.3); 1.5519 (5.5); 1.4271 (9.5); 1.4004 (12.3); −0.0003 (7.4); −0.0066 (0.4)

IVb1.01: ¹H-NMR(500.1 MHz, CDCl3):
δ = 8.1869 (0.7); 8.1838 (0.8); 8.1710 (0.7); 8.1680 (0.8); 7.5145 (0.4); 7.5113 (0.4); 7.4947 (1.6); 7.4796 (2.1); 7.4389 (1.0); 7.4242 (1.7); 7.4085 (0.9); 7.3632 (0.6); 7.3485 (0.8); 7.2877 (2.6); 7.2078 (0.6); 7.1931 (1.0); 7.1775 (0.5); 7.0395 (1.0); 7.0229 (1.0); 5.2024 (3.6); 1.7175 (16.0); 1.5634 (3.1)

IVb1.02: ¹H-NMR(500.1 MHz, CDCl3):
δ = 7.7670 (0.9); 7.7643 (1.0); 7.7512 (1.0); 7.7485 (1.0); 7.4449 (1.4); 7.4307 (2.4); 7.4297 (2.4); 7.4002 (1.6); 7.3962 (0.5); 7.3855 (2.7); 7.3827 (1.2); 7.3728 (0.6); 7.3698 (1.3); 7.3566 (0.4); 7.3541 (0.4); 7.3419 (0.7); 7.3399 (0.9); 7.3226 (1.3); 7.3081 (1.1); 7.2936 (0.4); 7.2582 (7.6); 7.2045 (0.7); 7.2031 (0.8); 7.1886 (1.3); 7.1742 (0.6); 7.1727 (0.6); 6.9013 (1.1); 6.8999 (1.1); 6.8845 (1.0); 6.8832 (1.0); 5.0608 (5.3); 1.6677 (16.0); 1.6660 (9.4); 1.5344 (13.2); 0.0063 (0.5); −0.0003 (15.5); −0.0068 (0.5)

IVb1.03: ¹H-NMR(500.1 MHz, CDCl3):
δ = 7.6265 (0.7); 7.6235 (0.7); 7.6107 (0.7); 7.6077 (0.7); 7.4630 (0.9); 7.4484 (1.3); 7.4474 (1.3); 7.3817 (0.8); 7.3668 (1.5); 7.3511 (0.8); 7.2954 (0.4); 7.2808 (0.6); 7.2568 (2.0); 7.1839 (0.4); 7.1808 (0.4); 7.1692 (0.5); 7.1667 (0.6); 7.1643 (0.5); 7.1527 (0.5); 7.1497 (0.5); 7.0385 (0.5); 7.0363 (0.5); 7.0221 (0.7); 7.0080 (0.4); 7.0059 (0.4); 6.8062 (0.8); 6.8043 (0.8); 6.7896 (0.7); 6.7877 (0.7); 5.8128 (2.2); 5.4737 (2.1); 5.2947 (0.5); 5.0845 (2.9); 1.6646 (16.0); 1.5397 (4.0); −0.0003 (3.7)

IVb1.04: ¹H-NMR(500.1 MHz, CDCl3):
δ = 7.5864 (1.7); 7.5831 (1.7); 7.5707 (1.8); 7.5674 (1.8); 7.4460 (2.1); 7.4315 (3.4); 7.4306 (3.4); 7.3908 (2.2); 7.3869 (0.8); 7.3759 (3.8); 7.3602 (1.9); 7.3063 (1.1); 7.2917 (1.6); 7.2771 (0.6); 7.2570 (5.0); 7.2104 (0.5); 7.2076 (0.6); 7.2055 (0.5); 7.1957 (0.8); 7.1939 (1.3); 7.1930 (1.3); 7.1910 (1.2); 7.1794 (0.8); 7.1772 (0.9); 7.1743 (0.7); 7.1380 (1.1); 7.1360 (1.2); 7.1225 (1.6); 7.1212 (1.6); 7.1077 (0.8); 7.1058 (0.7); 6.8025 (1.9); 6.7860 (1.8); 5.2953 (1.6); 5.2622 (1.7); 5.2277 (2.0); 4.8299 (2.2); 4.7954 (1.9); 1.9776 (9.3); 1.9300 (9.5); 1.6917 (16.0); 1.5381 (10.6); 1.5291 (8.2); 1.5231 (8.3); 1.4267 (0.3); −0.0003 (9.9); −0.0070 (0.4)

IVb1.05: ¹H-NMR(400.1 MHz, CDCl3):
δ = 7.6927 (1.5); 7.6884 (1.2); 7.6869 (1.1); 7.6737 (1.8); 7.6687 (1.6); 7.4515 (1.2); 7.4482 (1.7); 7.4305 (3.1); 7.4292 (3.1); 7.3996 (2.1); 7.3947 (0.7); 7.3814 (3.5); 7.3777 (1.5); 7.3658 (0.9); 7.3620 (1.6); 7.3142 (1.0); 7.3014 (0.5); 7.2963 (1.4); 7.2781 (0.5); 7.2561 (6.7); 7.1789 (0.5); 7.1743 (0.6); 7.1607 (1.5); 7.1561 (1.4); 7.1417 (2.0); 7.1395 (1.8); 7.1360 (2.2); 7.1349 (2.1); 7.1201 (1.4); 7.1163 (1.7); 7.1019 (0.7); 7.0981 (0.5); 6.8266 (1.7); 6.8223 (1.9); 6.8078 (1.1); 6.8062 (1.2); 6.8029 (1.5); 5.2931 (3.0); 5.2709 (1.4); 5.2280 (1.7);

TABLE 12-continued

NMR peak lists 4.8343 (2.0); 4.7914 (1.6); 4.1117 (2.8); 4.1088 (2.5); 2.0392 (1.4); 1.6925 (16.0); 1.6715 (9.7); 1.6687 (9.5); 1.5330 (10.3); 1.4613 (14.0); 1.4279 (0.4); 1.2742 (0.4); 1.2563 (1.5); 1.2385 (0.4); 0.0080 (0.4); −0.0001 (13.1); −0.0084 (0.5)

IVb1.06: $^1$H-NMR(500.1 MHz, CDCl3):
δ = 7.4633 (1.6); 7.4482 (2.0); 7.3963 (1.1); 7.3933 (1.1); 7.3807 (1.2); 7.3776 (1.2); 7.3471 (1.2); 7.3435 (0.5); 7.3324 (2.5); 7.3168 (1.4); 7.2678 (0.8); 7.2577 (9.9); 7.2533 (1.3); 7.2384 (0.4); 7.1916 (0.6); 7.1885 (0.6); 7.1768 (0.9); 7.1753 (0.9); 7.1739 (1.0); 7.1606 (0.9); 7.1575 (0.8); 7.0805 (0.8); 7.0781 (0.9); 7.0651 (1.2); 7.0631 (1.2); 7.0502 (0.6); 7.0478 (0.6); 6.8675 (1.3); 6.8654 (1.3); 6.8512 (1.2); 6.8491 (1.1); 5.2962 (0.9); 5.0449 (1.1); 5.0116 (1.6); 4.8904 (1.6); 4.8569 (1.0); 3.1777 (16.0); 1.7313 (12.2); 1.6379 (10.8); 1.5287 (9.3); 1.4641 (10.9); 0.0061 (0.4); −0.0003 (17.4); −0.0069 (0.6)

IIIb2.01: $^1$H-NMR(500.1 MHz, CDCl3):
δ = 7.2595 (5.0); 7.0640 (0.6); 7.0590 (0.4); 7.0489 (0.7); 7.0456 (0.6); 7.0306 (0.8); 7.0248 (0.8); 7.0218 (1.0); 7.0194 (0.5); 7.0170 (0.8); 7.0089 (0.5); 7.0053 (0.4); 7.0037 (0.4); 6.8094 (0.6); 6.8054 (0.6); 6.7923 (0.5); 6.7899 (0.6); 1.7636 (16.0); −0.0002 (9.1); −0.0067 (0.3)

IVb2.01: $^1$H-NMR(500.1 MHz, CDCl3):
δ = 7.3809 (1.3); 7.3768 (0.4); 7.3673 (0.4); 7.3633 (1.4); 7.2576 (1.9); 6.9805 (0.7); 6.9782 (1.5); 6.9706 (2.0); 6.9317 (0.5); 6.9235 (0.4); 6.9223 (0.4); 6.9153 (0.7); 6.9115 (1.9); 6.9067 (1.3); 6.8980 (0.8); 6.8941 (1.7); 6.8341 (0.8); 6.8180 (0.6); 5.2952 (2.7); 4.9601 (2.9); 3.8030 (0.6); 3.7990 (9.3); 3.7943 (0.4); 3.7728 (0.4); 1.7644 (0.5); 1.7587 (16.0); 1.7539 (0.9); 1.7506 (0.3); 1.7025 (0.7); 1.5439 (2.9); −0.0003 (3.3)

IIIc.01: $^1$H-NMR(500.1 MHz, CDCl3):
δ = 7.4000 (2.4); 7.3967 (1.1); 7.3886 (1.6); 7.3855 (6.5); 7.3730 (1.9); 7.3701 (4.7); 7.3233 (1.2); 7.3209 (2.5); 7.3184 (1.7); 7.3100 (1.0); 7.3061 (3.3); 7.3020 (1.1); 7.2943 (1.5); 7.2914 (2.3); 7.2768 (7.5); 7.2742 (6.9); 7.2703 (1.7); 7.2578 (20.3); 7.2285 (1.3); 7.2259 (1.4); 7.2135 (3.0); 7.2110 (3.3); 7.1989 (2.1); 7.1964 (2.1); 7.1857 (3.2); 7.1825 (3.2); 7.1707 (1.5); 7.1675 (1.2); 7.1392 (3.0); 7.1374 (3.0); 7.1237 (2.4); 7.1222 (2.4); 6.3278 (2.5); 3.6157 (1.2); 3.6127 (0.5); 3.5919 (1.9); 3.5888 (2.2); 3.5843 (0.7); 3.5688 (1.0); 3.5651 (3.3); 3.5317 (1.1); 3.5288 (2.0); 3.5263 (2.5); 3.5235 (3.6); 3.5205 (1.6); 3.5019 (3.6); 3.4968 (1.6); 3.4782 (3.8); 3.4587 (1.7); 3.4536 (1.4); 3.4370 (0.5); 3.4315 (0.4); 3.0287 (2.3); 3.0044 (2.2); 1.5461 (19.8); 1.4269 (16.0); 0.0061 (0.9); −0.0003 (33.0); −0.0071 (1.1)

IIIc.02: $^1$H-NMR(500.1 MHz, CDCl3):
δ = 7.2590 (46.2); 7.2527 (2.8); 7.2468 (3.3); 7.2401 (2.8); 7.2376 (3.1); 7.2344 (4.6); 7.2312 (4.0); 7.2255 (3.4); 7.2192 (5.6); 7.2111 (0.9); 7.2063 (1.9); 7.2036 (2.2); 7.1913 (9.5); 7.1888 (10.8); 7.1840 (10.2); 7.1788 (16.0); 7.1771 (14.9); 7.1693 (1.8); 7.1636 (0.6); 7.1003 (7.3); 7.0856 (6.6); 6.2049 (3.2); 5.2977 (0.4); 3.3927 (9.3); 3.3918 (9.5); 3.3803 (9.8); 3.3687 (10.2); 3.3679 (9.9); 2.9868 (11.2); 2.9756 (6.1); 2.9647 (12.2); 2.2508 (3.6); 2.2486 (2.2); 2.2430 (2.2); 2.2386 (6.0); 2.2278 (7.8); 2.2209 (2.7); 2.2167 (5.6); 2.2124 (2.2); 2.2069 (2.1); 2.2045 (3.3); 1.5458 (90.9); 1.2533 (1.9); 1.1897 (0.6); 0.0063 (2.5); −0.0003 (86.6); −0.0068 (3.0)

IIIc.03: $^1$H-NMR(500.1 MHz, CDCl3):
δ = 7.3666 (0.7); 7.3580 (1.6); 7.3532 (3.6); 7.3472 (12.5); 7.3422 (2.6); 7.3377 (1.2); 7.3333 (2.2); 7.3295 (1.2); 7.3263 (0.9); 7.3237 (1.3); 7.3192 (0.5); 7.3167 (0.7); 7.3130 (0.6); 7.2593 (9.9); 6.3635 (1.1); 4.7182 (4.0); 4.6666 (0.5); 3.8000 (0.9); 1.7241 (2.0); 1.7106 (16.0); 1.5439 (12.4); 0.0063 (0.6); −0.0003 (15.7); −0.0068 (0.6)

IVc.01: $^1$H-NMR(500.1 MHz, CDCl3):
δ = 7.4000 (2.4); 7.3967 (1.1); 7.3886 (1.6); 7.3855 (6.5); 7.3730 (1.9); 7.3701 (4.7); 7.3233 (1.2); 7.3209 (2.5); 7.3184 (1.7); 7.3100 (1.0); 7.3061 (3.3); 7.3020 (1.1); 7.2943 (1.5); 7.2914 (2.3); 7.2768 (7.5); 7.2742 (6.9); 7.2703 (1.7); 7.2578 (20.3); 7.2285 (1.3); 7.2259 (1.4); 7.2135 (3.0); 7.2110 (3.3); 7.1989 (2.1); 7.1964 (2.1); 7.1857 (3.2); 7.1825 (3.2); 7.1707 (1.5); 7.1675 (1.2); 7.1392 (3.0); 7.1374 (3.0); 7.1237 (2.4); 7.1222 (2.4); 6.3278 (2.5); 3.6157 (1.2); 3.6127 (0.5); 3.5919 (1.9); 3.5888 (2.2); 3.5843 (0.7); 3.5688 (1.0); 3.5651 (3.3); 3.5317 (1.1); 3.5288 (2.0); 3.5263 (2.5); 3.5235 (3.6); 3.5205 (1.6); 3.5019 (3.6); 3.4968 (1.6); 3.4782 (3.8); 3.4587 (1.7); 3.4536 (1.4); 3.4370 (0.5); 3.4315 (0.4); 3.0287 (2.3); 3.0044 (2.2); 1.5461 (19.8); 1.4269 (16.0); 0.0061 (0.9); −0.0003 (33.0); −0.0071 (1.1)

IVc.02: $^1$H-NMR(500.1 MHz, CDCl3):
δ = 7.3010 (0.4); 7.2984 (0.4); 7.2848 (1.1); 7.2823 (1.0); 7.2708 (1.1); 7.2682 (1.1); 7.2588 (2.7); 7.2443 (3.0); 7.2268 (2.7); 7.1756 (0.8); 7.1723 (0.6); 7.1598 (1.1); 7.1580 (0.9); 7.1568 (0.8); 7.1457 (0.6); 7.1422 (0.7); 6.9368 (1.1); 6.9345 (1.1); 6.9209 (1.0); 6.9188 (0.9); 6.8572 (0.6); 6.8513 (3.3); 6.8472 (1.1); 6.8381 (1.0); 6.8340 (3.0); 6.8282 (0.4); 5.1778 (0.5); 5.1483 (0.5); 4.8287 (0.9); 4.7705 (3.3); 4.6606 (0.5); 4.4757 (0.5); 4.4462 (0.5); 4.1418 (0.5); 4.1275 (1.4); 4.1132 (1.4); 4.0989 (0.5); 3.7984 (16.0); 2.0418 (6.5); 1.7178 (3.8); 1.5613 (2.9); 1.5534 (3.9); 1.2718 (1.7); 1.2576 (3.4); 1.2433 (1.7); −0.0003 (4.1)

V.01: $^1$H-NMR(500.1 MHz, CDCl3):
δ = 7.3017 (0.4); 7.2851 (35.8); 7.2572 (7.6); 7.2479 (0.6); 7.2376 (2.0); 7.2340 (3.2); 7.2267 (5.8); 7.2197 (4.4); 7.2158 (3.6); 7.2057 (1.0); 7.2010 (0.4); 7.1827 (0.4); 7.1747 (2.7); 7.1694 (1.7); 7.1677 (1.6); 7.1646 (1.2); 7.1606 (1.2); 7.1563 (1.6); 7.1083 (1.9); 7.1046 (1.2); 7.1029 (1.0); 7.1005 (1.0); 7.0968 (1.4); 7.0904 (1.4); 6.5018 (1.1); 6.4983 (2.3); 6.4948 (1.1); 6.4793 (1.5); 6.4757 (3.0); 6.4722 (1.5); 6.3344 (1.4); 6.3228 (3.0); 6.3114 (2.2); 6.3002 (2.4); 6.2885 (1.1); 5.2948 (4.2); 4.8640 (16.0); 3.3751 (3.6); 3.3720 (3.6); 3.3635 (3.6); 3.3604 (3.5); 1.5390 (8.0); 1.4268 (1.2); 0.0061 (0.5); −0.0003 (12.7); −0.0070 (0.5)

VIIIa.01: $^1$H-NMR(300.2 MHz, CDCl3):
δ = 8.0713 (3.9); 8.0131 (1.4); 7.9855 (1.7); 7.7261 (1.3); 7.6979 (2.0); 7.6901 (0.9); 7.6717 (1.4); 7.6669 (1.5); 7.6620 (0.8); 7.6438 (1.1); 7.6388 (0.8); 7.5875 (1.3); 7.5821 (1.4); 7.5745 (1.6); 7.5707 (1.6); 7.5620 (1.8); 7.5557 (2.5); 7.5488 (2.4); 7.5441 (1.9); 7.5274 (1.6); 7.5040 (0.7); 7.5007 (0.6); 7.4138 (0.9); 7.4099 (0.8); 7.3888 (1.7); 7.3849 (1.6); 7.3635 (0.9); 7.3594 (0.8); 7.3012 (5.7); 7.2616 (1.0); 7.2559 (1.0); 7.2360 (1.3); 7.2310 (1.3); 7.2100 (0.6); 7.2045 (0.6); 6.4555 (1.5); 4.7902 (9.6); 2.6012 (16.0); 2.0851 (0.4); 1.6679 (0.7); 0.0391 (5.7)

VIIIa.02: $^1$H-NMR(300.2 MHz, CDCl3):
δ = 8.0231 (2.9); 8.0187 (2.8); 7.6293 (1.3); 7.6240 (1.3); 7.6037 (1.6); 7.5983 (1.6); 7.5550 (1.5); 7.5516 (1.5); 7.5283 (1.8); 7.5247 (1.8); 7.4639 (0.4); 7.4451 (0.5); 7.4323 (4.2); 7.4129 (2.7); 7.4072 (2.2); 7.4027 (2.7); 7.3819 (2.1); 7.3509 (0.4); 7.3014 (18.5); 7.2601 (1.0); 7.2546 (1.0); 7.2343 (1.4); 7.2289 (1.3); 7.2086 (0.6); 7.2031 (0.6); 6.3831 (0.6); 4.8028 (9.8); 2.6273 (16.0); 1.6007 (2.3); 0.0504 (0.5); 0.0395 (17.1); 0.0290 (0.6)

VIIIa.03: $^1$H-NMR(300.2 MHz, CDCl3):
δ = 11.5776 (0.7); 7.6799 (1.6); 7.6586 (1.9); 7.5788 (1.9); 7.5518 (2.1); 7.4344 (0.7); 7.4033 (1.4); 7.3780 (1.6); 7.3496 (1.4); 7.3276 (2.3); 7.3036 (42.0); 7.1563 (1.1); 7.1346 (1.7); 7.1094 (0.8); 6.9385 (0.9); 6.9248 (1.0);

TABLE 12-continued

NMR peak lists 6.9191 (1.0); 6.9006 (0.9); 6.8947 (0.9); 4.7564 (9.9); 2.7250 (0.4); 2.6682 (16.0); 1.5990 (44.6); 0.1113 (0.9); 0.0527 (1.3); 0.0418 (38.8); 0.0309 (1.4)

VIIIa.04: $^1$H-NMR(400.1 MHz, d$_6$-DMSO):
δ = 10.7567 (5.7); 8.7288 (5.7); 8.7226 (5.8); 8.0218 (4.9); 7.7028 (3.2); 7.6823 (4.3); 7.5911 (3.8); 7.5805 (1.7); 7.5706 (4.8); 7.5609 (2.9); 7.5478 (5.3); 7.5410 (2.1); 7.5281 (5.0); 7.4775 (2.3); 7.4578 (1.8); 7.4502 (2.4); 7.4312 (3.6); 7.4138 (3.8); 7.3955 (1.9); 7.2691 (2.0); 7.2653 (2.0); 7.2493 (3.1); 7.2465 (3.0); 7.2306 (1.5); 7.2268 (1.4); 4.8386 (16.0); 3.3121 (8.8); 2.5134 (8.4); 2.5093 (11.0); 2.5053 (8.2); 1.2423 (0.4)

VIIIa.05: $^1$H-NMR(300.2 MHz, CDCl3):
δ = 8.0542 (2.8); 8.0495 (2.6); 7.4632 (0.4); 7.4452 (0.5); 7.4316 (3.3); 7.4118 (2.6); 7.4056 (2.8); 7.4012 (1.8); 7.3926 (2.1); 7.3793 (3.5); 7.3501 (0.4); 7.3074 (0.5); 7.2984 (25.1); 7.0315 (1.1); 7.0258 (1.1); 7.0055 (1.0); 6.9984 (1.0); 6.3756 (0.5); 5.3380 (0.6); 4.7509 (9.8); 4.1711 (1.0); 4.1473 (1.0); 4.1235 (0.3); 2.7084 (0.4); 2.6239 (16.0); 2.3400 (12.2); 2.0833 (4.5); 2.0464 (0.9); 1.5972 (5.6); 1.3207 (1.2); 1.2969 (2.4); 1.2730 (1.2); 0.0475 (0.8); 0.0367 (25.6); 0.0290 (0.7); 0.0258 (0.9)

VIIIa.06: $^1$H-NMR(300.2 MHz, CDCl3):
δ = 8.6459 (0.4); 8.6400 (0.5); 8.6261 (0.4); 8.0807 (2.2); 8.0761 (2.1); 7.7177 (0.3); 7.4719 (0.4); 7.4544 (0.4); 7.4495 (0.4); 7.4410 (1.0); 7.4378 (1.2); 7.4257 (1.4); 7.4190 (1.0); 7.4056 (0.9); 7.3951 (1.2); 7.3897 (2.5); 7.3738 (1.0); 7.3601 (2.7); 7.3441 (0.7); 7.3397 (0.4); 7.3249 (0.5); 7.3188 (0.4); 7.3045 (0.3); 7.2985 (2.8); 7.1373 (2.2); 7.1272 (2.3); 6.7550 (1.4); 6.7448 (1.3); 6.7254 (1.3); 6.7152 (1.2); 4.7323 (7.4); 3.8184 (0.4); 3.7912 (16.0); 2.6957 (0.4); 2.6446 (12.2); 2.0779 (1.2); 1.2910 (0.6); 0.0319 (2.4)

VIIIa.07: $^1$H-NMR(300.2 MHz, CDCl3):
δ = 8.6567 (4.3); 8.6479 (4.4); 8.0883 (2.8); 8.0829 (3.0); 8.0795 (3.0); 8.0744 (2.6); 7.5469 (0.7); 7.5323 (4.7); 7.5264 (3.6); 7.5240 (3.7); 7.5179 (12.3); 7.5018 (2.4); 7.4908 (9.9); 7.4742 (0.7); 7.3921 (1.5); 7.3790 (1.3); 7.3752 (1.1); 7.3619 (1.2); 7.3572 (1.6); 7.3493 (1.4); 7.3349 (1.1); 7.3271 (1.1); 7.2985 (20.0); 7.1666 (2.5); 6.9764 (2.8); 6.9497 (4.5); 6.9227 (2.3); 5.1434 (16.0); 1.6198 (11.9); 0.0472 (0.7); 0.0364 (20.6); 0.0255 (0.7)

VIIIa.08: $^1$H-NMR(300.2 MHz, CDCl3):
δ = 8.6530 (5.1); 8.6445 (6.2); 8.6263 (2.4); 8.6211 (1.8); 8.0414 (3.1); 8.0361 (3.5); 8.0328 (3.4); 8.0276 (3.0); 7.7597 (0.4); 7.7536 (0.7); 7.7476 (0.4); 7.7342 (0.7); 7.7281 (1.5); 7.7223 (0.7); 7.7086 (0.5); 7.7026 (0.9); 7.6967 (0.5); 7.5992 (2.4); 7.5798 (2.6); 7.5703 (2.7); 7.5499 (4.3); 7.5442 (3.3); 7.5399 (5.9); 7.5314 (7.5); 7.5203 (2.9); 7.4925 (0.5); 7.4261 (0.4); 7.4106 (1.8); 7.3975 (1.4); 7.3937 (1.6); 7.3805 (1.4); 7.3758 (1.9); 7.3655 (1.6); 7.3527 (2.5); 7.3473 (2.0); 7.3380 (1.5); 7.3333 (2.4); 7.3273 (2.2); 7.3220 (1.3); 7.3129 (1.4); 7.3078 (2.4); 7.2984 (35.8); 7.2643 (2.7); 7.2556 (2.9); 7.2375 (2.7); 7.2288 (2.8); 7.0946 (1.6); 7.0858 (1.4); 7.0685 (1.9); 7.0598 (1.7); 7.0401 (1.4); 7.0313 (1.2); 5.3372 (1.5); 5.2019 (0.4); 4.7460 (16.0); 4.1710 (0.5); 4.1471 (0.6); 2.0824 (2.6); 2.0451 (0.6); 1.6219 (1.2); 1.3205 (0.7); 1.2968 (1.4); 1.2730 (0.7); 0.1068 (2.2); 0.0480 (1.0); 0.0371 (35.6); 0.0261 (1.2)

VIIIa.09: $^1$H-NMR(300.2 MHz, CDCl3):
δ = 8.5943 (3.6); 8.5856 (3.7); 7.9987 (2.3); 7.9934 (2.7); 7.9902 (2.6); 7.9848 (2.3); 7.5213 (1.8); 7.5104 (4.7); 7.5020 (5.0); 7.4926 (2.4); 7.4855 (0.5); 7.3917 (1.4); 7.3807 (1.1); 7.3724 (1.5); 7.3567 (4.3); 7.3539 (4.3); 7.3445 (1.3); 7.3391 (1.1); 7.3261 (4.3); 7.3111 (0.4); 7.2988 (18.9); 6.9262 (2.0); 6.9203 (1.8); 6.8986 (1.4); 6.8930 (1.3); 4.7526 (12.9); 4.1713 (0.7); 4.1476 (0.7); 2.2680 (16.0); 2.0823 (3.2); 1.6075 (2.9); 1.3208 (1.0); 1.2971 (2.2); 1.2733 (0.9); 0.9196 (0.6); 0.1073 (1.8); 0.0484 (0.6); 0.0376 (19.0); 0.0266 (0.7)

VIIIa.10: $^1$H-NMR(300.2 MHz, CDCl3):
δ = 8.5933 (0.9); 8.5697 (1.0); 8.2578 (1.4); 8.2290 (1.7); 7.9509 (0.8); 7.9239 (1.6); 7.9002 (1.0); 7.8963 (0.9); 7.8478 (1.0); 7.8239 (1.4); 7.8004 (0.6); 7.6808 (1.6); 7.6767 (1.5); 7.6544 (1.8); 7.6503 (1.8); 7.6093 (1.3); 7.5819 (1.3); 7.5762 (1.4); 7.5563 (1.7); 7.5508 (1.7); 7.4344 (2.8); 7.4022 (0.8); 7.3986 (0.8); 7.3775 (1.8); 7.3733 (1.7); 7.3523 (1.1); 7.3480 (1.0); 7.3127 (1.4); 7.3053 (2.3); 7.2989 (35.7); 7.2870 (1.7); 7.2812 (1.6); 7.2594 (1.8); 7.2240 (1.5); 7.0428 (2.9); 6.8617 (2.1); 4.7569 (9.6); 2.0843 (0.3); 1.5807 (16.0); 1.2949 (0.6); 0.0484 (1.3); 0.0388 (34.6); 0.0282 (1.3)

VIIIa.11: $^1$H-NMR(300.2 MHz, CDCl3):
δ = 8.6564 (4.3); 8.6477 (4.5); 8.0202 (2.9); 8.0149 (3.2); 8.0116 (3.2); 8.0064 (2.7); 7.5578 (0.5); 7.5448 (3.1); 7.5390 (5.1); 7.5305 (6.6); 7.5179 (2.5); 7.4904 (0.5); 7.4735 (2.1); 7.4680 (2.4); 7.4482 (2.6); 7.4427 (3.0); 7.4308 (0.4); 7.4158 (1.6); 7.4008 (2.1); 7.3925 (2.2); 7.3866 (3.0); 7.3811 (1.9); 7.3717 (1.7); 7.3657 (3.7); 7.3602 (3.9); 7.3511 (1.2); 7.2985 (39.9); 7.2862 (3.8); 7.2604 (4.1); 7.2342 (1.7); 6.9473 (0.4); 6.9045 (0.8); 4.8643 (16.0); 4.1952 (0.4); 4.1715 (1.2); 4.1475 (1.2); 4.1238 (0.4); 2.0828 (5.4); 1.5960 (6.6); 1.3211 (1.7); 1.2973 (3.6); 1.2736 (1.5); 0.9409 (0.4); 0.9197 (1.2); 0.8963 (0.4); 0.0483 (1.4); 0.0376 (41.6); 0.0266 (1.6)

VIIIa.12: $^1$H-NMR(300.2 MHz, CDCl3):
δ = 8.6731 (3.5); 8.6646 (3.5); 8.0711 (2.5); 8.0657 (2.9); 8.0628 (2.9); 8.0576 (2.4); 7.6024 (0.7); 7.5957 (1.1); 7.5745 (5.1); 7.5681 (3.9); 7.5600 (2.1); 7.5506 (2.4); 7.5446 (1.4); 7.5357 (2.3); 7.5225 (1.8); 7.5174 (2.4); 7.5123 (1.6); 7.5082 (1.1); 7.4955 (1.3); 7.4902 (1.4); 7.4346 (2.6); 7.4269 (1.8); 7.4124 (2.4); 7.4085 (2.5); 7.4044 (2.5); 7.3999 (2.0); 7.3940 (1.7); 7.3873 (1.4); 7.3821 (1.3); 7.3756 (1.3); 7.3698 (1.1); 7.2986 (52.8); 7.0930 (1.7); 7.0901 (1.6); 7.0667 (2.8); 7.0642 (2.8); 7.0404 (1.3); 7.0375 (1.3); 6.9475 (0.4); 6.8376 (0.8); 4.5863 (10.2); 4.1952 (0.4); 4.1716 (1.1); 4.1477 (1.1); 4.1240 (0.4); 2.0828 (5.2); 1.5935 (16.0); 1.3212 (1.6); 1.2975 (3.4); 1.2737 (1.4); 0.9415 (0.3); 0.9199 (1.1); 0.8972 (0.4); 0.0486 (1.7); 0.0377 (53.2); 0.0268 (1.9)

VIIIa.13: $^1$H-NMR(300.2 MHz, CDCl3):
δ = 8.6283 (4.4); 8.6196 (4.4); 8.0605 (2.8); 8.0551 (3.1); 8.0518 (3.1); 8.0468 (2.6); 7.6056 (4.4); 7.5972 (4.5); 7.5770 (0.3); 7.5702 (0.9); 7.5534 (5.0); 7.5498 (3.0); 7.5430 (5.9); 7.5348 (2.7); 7.5207 (2.1); 7.5066 (0.4); 7.4931 (0.7); 7.4210 (4.5); 7.4135 (1.7); 7.4024 (1.4); 7.3925 (5.7); 7.3834 (1.7); 7.3786 (1.6); 7.3717 (1.4); 7.3555 (1.2); 7.3486 (1.1); 7.2993 (39.5); 7.1087 (2.7); 7.1001 (2.7); 7.0800 (2.3); 7.0716 (2.5); 6.9483 (0.3); 6.9063 (0.4); 5.3386 (0.6); 4.7495 (16.0); 4.1723 (1.0); 4.1486 (0.9); 4.1246 (0.4); 2.0840 (4.3); 1.5980 (3.7); 1.3220 (1.4); 1.2982 (3.0); 1.2744 (1.2); 0.9205 (1.0); 0.8970 (0.4); 0.1078 (2.1); 0.0491 (1.3); 0.0383 (39.5); 0.0273 (1.4)

VIIIa.14: $^1$H-NMR(300.2 MHz, CDCl3):
δ = 8.6560 (4.6); 8.6473 (4.8); 8.0714 (2.9); 8.0660 (3.3); 8.0628 (3.3); 8.0577 (2.7); 7.6415 (1.0); 7.6240 (1.1); 7.6119 (1.2); 7.5945 (1.2); 7.5716 (0.4); 7.5646 (0.9); 7.5478 (5.2); 7.5443 (3.3); 7.5373 (6.2); 7.5292 (2.9); 7.5152 (2.2); 7.5015 (0.5); 7.4875 (0.8); 7.4690 (2.4); 7.4515 (2.5); 7.4394 (2.7); 7.4219 (2.8); 7.4043 (1.8); 7.3926 (1.9); 7.3851 (1.8); 7.3803 (3.8); 7.3699 (4.2); 7.3620 (2.8); 7.3511 (3.9); 7.3463 (2.3); 7.3409 (3.5); 7.2997 (13.4); 7.0528 (0.6); 7.0427 (0.6); 7.0271 (0.7); 7.0234 (0.7); 7.0169 (0.7); 7.0133 (0.6); 6.9977 (0.6); 6.9876 (0.5); 6.9032 (1.4); 6.8931 (1.3); 6.8776 (1.6); 6.8738 (1.5); 6.8675 (1.5); 6.8637 (1.4); 6.8481 (1.2);

TABLE 12-continued

NMR peak lists 6.8380 (1.2); 5.3376 (0.4); 4.7979 (1.2); 4.7560 (16.0); 4.6172 (7.9); 1.6559 (0.6); 1.3043 (1.7); 0.9409 (0.6); 0.9191 (2.0); 0.8958 (0.7); 0.1079 (0.6); 0.0483 (0.4); 0.0373 (12.3); 0.0265 (0.5)

VIIIa.15: $^1$H-NMR(300.2 MHz, CDCl3):
δ = 8.5811 (3.4); 8.5724 (3.5); 7.9591 (2.1); 7.9538 (2.6); 7.9507 (2.4); 7.9453 (2.1); 7.5100 (1.4); 7.4934 (3.7); 7.4882 (3.2); 7.4853 (3.1); 7.4800 (4.2); 7.4659 (0.7); 7.3989 (1.4); 7.3946 (1.4); 7.3840 (1.5); 7.3753 (2.6); 7.3695 (1.9); 7.3628 (1.3); 7.3539 (1.0); 7.3491 (1.4); 7.3340 (1.3); 7.3190 (1.0); 7.2987 (15.3); 7.2138 (1.5); 7.1887 (3.2); 7.1634 (1.9); 7.0984 (1.8); 7.0950 (1.9); 7.0732 (1.2); 6.9734 (1.8); 4.8603 (12.4); 4.1710 (0.6); 4.1473 (0.6); 2.2586 (16.0); 2.0822 (2.5); 1.6153 (13.1); 1.3205 (0.8); 1.2968 (1.8); 1.2729 (0.7); 0.9192 (0.7); 0.0480 (0.7); 0.0372 (14.8); 0.0262 (0.5)

VIIIa.16: $^1$H-NMR(300.2 MHz, CDCl3):
δ = 8.5971 (2.2); 8.5884 (2.2); 8.0216 (1.4); 8.0162 (1.6); 8.0131 (1.5); 8.0077 (1.3); 7.5235 (1.4); 7.5205 (1.5); 7.5153 (2.6); 7.5068 (3.4); 7.4948 (1.3); 7.3904 (0.8); 7.3752 (0.8); 7.3602 (0.7); 7.3533 (2.7); 7.3459 (0.8); 7.3352 (0.6); 7.3238 (2.8); 7.2987 (14.2); 7.1243 (2.2); 7.1142 (2.2); 6.9193 (1.0); 6.6642 (1.3); 6.6540 (1.2); 6.6346 (1.2); 6.6244 (1.1); 4.7512 (7.9); 3.7501 (16.0); 2.0825 (1.0); 1.6056 (10.5); 1.3207 (0.4); 1.2970 (0.8); 0.0481 (0.5); 0.0373 (14.2); 0.0282 (0.4); 0.0264 (0.5)

VIIIa.17: $^1$H-NMR(300.2 MHz, CDCl3):
δ = 8.6103 (3.7); 8.6016 (3.8); 7.9558 (2.2); 7.9503 (2.8); 7.9474 (2.5); 7.9420 (2.2); 7.5430 (0.4); 7.5153 (1.4); 7.5013 (2.0); 7.4949 (4.5); 7.4835 (4.6); 7.4676 (0.8); 7.4403 (3.0); 7.4141 (3.5); 7.3750 (1.3); 7.3674 (1.1); 7.3526 (1.0); 7.3448 (1.0); 7.3400 (1.3); 7.3278 (1.0); 7.3223 (1.0); 7.3099 (0.9); 7.2983 (9.2); 7.2343 (3.2); 7.2323 (3.2); 7.1667 (1.1); 7.0868 (1.8); 7.0607 (1.6); 7.0577 (1.5); 4.7529 (11.7); 4.1696 (0.5); 4.1459 (0.5); 2.1589 (16.0); 2.0808 (2.1); 1.6485 (3.2); 1.3192 (0.7); 1.2954 (1.6); 1.2716 (0.6); 0.9179 (0.7); 0.0359 (7.8)

VIIIa.18: $^1$H-NMR(500.1 MHz, CDCl3):
δ = 8.3563 (1.4); 8.3512 (1.4); 8.0843 (1.0); 8.0674 (1.1); 8.0279 (1.4); 8.0229 (1.3); 7.7928 (0.9); 7.7765 (1.0); 7.6966 (0.5); 7.6822 (0.9); 7.6676 (0.6); 7.6029 (0.7); 7.5879 (1.0); 7.5749 (1.2); 7.5619 (1.0); 7.5597 (1.0); 7.4638 (1.0); 7.4481 (1.0); 7.3616 (0.5); 7.3472 (1.0); 7.3325 (0.5); 7.2873 (3.3); 7.1216 (0.5); 7.1192 (0.5); 7.1059 (0.9); 7.0914 (0.4); 7.0890 (0.4); 4.1182 (5.3); 1.7934 (16.0); 1.6626 (0.3); 1.6498 (0.4); 1.4554 (12.7)

VIIIa.19: $^1$H-NMR(500.1 MHz, CDCl3):
δ = 8.6717 (3.8); 8.6664 (3.9); 8.1341 (2.6); 8.1291 (2.6); 8.0930 (1.8); 8.0760 (2.0); 7.8081 (1.6); 7.8063 (1.6); 7.7917 (1.9); 7.7897 (1.9); 7.7021 (1.0); 7.6994 (1.1); 7.6884 (1.5); 7.6854 (2.2); 7.6824 (1.2); 7.6715 (1.4); 7.6686 (1.3); 7.5940 (1.4); 7.5918 (1.4); 7.5800 (1.3); 7.5778 (2.1); 7.5758 (1.3); 7.5638 (1.0); 7.5618 (0.9); 7.4427 (1.8); 7.4321 (1.9); 7.4251 (2.0); 7.4145 (2.1); 7.4005 (1.5); 7.2601 (5.1); 7.0091 (1.6); 7.0031 (1.7); 6.9914 (1.6); 6.9854 (1.7); 6.8584 (1.0); 6.8524 (0.9); 6.8426 (1.3); 6.8410 (1.2); 6.8366 (1.2); 6.8353 (1.1); 6.8252 (1.0); 6.8193 (0.9); 3.5007 (2.2); 3.4891 (1.8); 3.4853 (2.7); 3.4792 (1.8); 3.4689 (3.0); 3.2874 (2.7); 3.2771 (1.8); 3.2710 (2.5); 3.2673 (1.8); 3.2556 (2.0); 1.6967 (0.3); 1.4260 (16.0); −0.0003 (5.8)

VIIIa.20: $^1$H-NMR(500.1 MHz, CDCl3):
δ = 8.2115 (2.6); 8.2097 (2.6); 7.5404 (0.6); 7.5366 (0.6); 7.5303 (0.6); 7.5264 (0.6); 7.5222 (0.8); 7.5183 (0.8); 7.5120 (0.8); 7.5083 (0.8); 7.4840 (1.8); 7.4687 (1.7); 7.4668 (1.7); 7.4189 (0.7); 7.4050 (0.8); 7.3998 (1.0); 7.3860 (1.0); 7.3812 (0.6); 7.3672 (0.5); 7.2677 (0.6); 7.2597 (12.6); 7.2526 (2.5); 7.2453 (2.0); 7.2431 (1.7); 7.2301 (0.4); 7.2278 (0.4); 7.1269 (1.0); 7.1212 (0.8); 7.1143 (0.9); 7.1109 (1.0); 7.1087 (0.9); 7.1055 (0.8); 7.0980 (0.8); 7.0927 (0.7); 6.4059 (1.9); 3.5459 (2.0); 3.5344 (1.3); 3.5303 (2.2); 3.5241 (1.3); 3.5139 (2.5); 3.3063 (2.3); 3.2961 (1.4); 3.2899 (2.0); 3.2857 (1.4); 3.2744 (1.8); 2.7257 (16.0); 1.5683 (6.1); 1.4265 (9.0); 0.0061 (0.4); −0.0003 (12.2); −0.0070 (0.5)

VIIIa.21: $^1$H-NMR(500.1 MHz, CDCl3):
δ = 8.4372 (1.7); 8.4318 (1.7); 8.0653 (0.8); 8.0483 (0.9); 8.0176 (1.1); 8.0123 (1.1); 7.7712 (0.7); 7.7567 (0.8); 7.7546 (0.8); 7.6846 (0.5); 7.6819 (0.5); 7.6709 (0.6); 7.6680 (1.0); 7.6650 (0.5); 7.6541 (0.6); 7.6512 (0.6); 7.5869 (0.6); 7.5847 (0.6); 7.5729 (0.5); 7.5708 (0.9); 7.5686 (0.6); 7.5569 (0.4); 7.5546 (0.4); 7.3963 (0.9); 7.3847 (0.9); 7.3788 (1.0); 7.3673 (0.9); 7.2639 (0.8); 7.2592 (7.0); 7.2419 (0.8); 7.2359 (0.8); 6.8096 (0.5); 6.8036 (0.5); 6.7957 (0.5); 6.7921 (0.5); 6.7897 (0.5); 6.7862 (0.5); 6.7782 (0.5); 6.7723 (0.4); 6.5305 (0.8); 4.0740 (5.2); 1.7366 (16.0); 1.5749 (1.4); 1.4268 (0.3); −0.0003 (8.9)

VIIIa.22: $^1$H-NMR(500.1 MHz, CDCl3):
δ = 8.6207 (13.3); 8.6154 (13.9); 8.1245 (9.8); 8.1189 (15.7); 8.1006 (7.1); 7.8396 (5.9); 7.8370 (5.9); 7.8232 (6.7); 7.8208 (6.6); 7.7397 (4.0); 7.7370 (4.4); 7.7260 (5.6); 7.7232 (8.8); 7.7202 (4.6); 7.7093 (5.4); 7.7063 (5.2); 7.6298 (4.8); 7.6276 (5.1); 7.6159 (4.6); 7.6135 (8.1); 7.6112 (5.0); 7.5996 (3.6); 7.5973 (3.4); 7.4932 (0.6); 7.4601 (14.3); 7.4430 (16.0); 7.2956 (13.0); 7.2904 (15.4); 7.2866 (98.3); 7.1466 (8.5); 7.1415 (8.2); 7.1295 (7.8); 7.1245 (7.4); 7.0751 (0.5); 6.6355 (7.0); 5.3254 (3.2); 3.5162 (8.9); 3.5044 (7.0); 3.5009 (10.7); 3.4950 (6.9); 3.4845 (11.5); 3.3102 (10.3); 3.2998 (6.5); 3.2939 (9.4); 3.2904 (6.6); 3.2786 (7.6); 1.5833 (30.6); 1.4544 (3.2)

VIIIa.23: $^1$H-NMR(500.1 MHz, CDCl3):
δ = 8.4955 (8.0); 8.4902 (8.3); 8.0807 (3.7); 8.0639 (4.0); 8.0464 (5.4); 8.0412 (5.4); 7.7933 (3.1); 7.7912 (3.2); 7.7770 (3.8); 7.7747 (3.8); 7.6980 (2.3); 7.6952 (2.5); 7.6842 (3.1); 7.6813 (4.8); 7.6783 (2.4); 7.6673 (2.9); 7.6644 (2.8); 7.5887 (2.9); 7.5865 (2.9); 7.5748 (2.5); 7.5725 (4.5); 7.5703 (2.7); 7.5586 (1.9); 7.5564 (1.9); 7.5245 (4.0); 7.5225 (4.1); 7.5086 (4.5); 7.5064 (4.5); 7.3133 (1.8); 7.3094 (2.2); 7.2981 (5.3); 7.2942 (5.2); 7.2859 (3.6); 7.2836 (3.5); 7.2715 (4.4); 7.2692 (4.3); 7.2597 (20.6); 7.2566 (2.5); 7.2541 (2.0); 7.1610 (2.5); 7.1570 (2.5); 7.1451 (3.0); 7.1424 (2.7); 7.1414 (2.8); 7.1308 (1.9); 7.1268 (1.8); 6.6735 (2.6); 3.5129 (4.9); 3.4980 (6.7); 3.4932 (3.7); 3.4819 (6.3); 3.3239 (5.8); 3.3128 (3.6); 3.3077 (5.8); 3.2930 (4.3); 1.6016 (16.0); 1.4266 (5.6); 1.2538 (0.4); 0.0061 (1.1); −0.0003 (37.6); −0.0071 (1.4)

VIIIa.24: $^1$H-NMR(500.1 MHz, CDCl3):
δ = 8.7200 (3.7); 8.7146 (3.8); 8.0904 (1.8); 8.0784 (3.0); 8.0738 (5.2); 7.7956 (1.5); 7.7931 (1.8); 7.7794 (1.8); 7.7767 (2.1); 7.7049 (1.0); 7.7022 (1.0); 7.6912 (1.4); 7.6883 (2.2); 7.6853 (1.1); 7.6743 (1.3); 7.6713 (1.2); 7.5957 (1.4); 7.5935 (1.4); 7.5796 (2.1); 7.5773 (1.4); 7.5657 (0.9); 7.5636 (0.9); 7.4545 (2.0); 7.4524 (2.1); 7.4384 (2.1); 7.4366 (2.2); 7.2595 (7.3); 7.1550 (0.6); 7.1526 (0.1); 7.1397 (0.2); 7.1375 (0.7); 7.1260 (2.7); 7.1237 (3.4); 7.1218 (3.5); 7.1173 (4.3); 7.1066 (1.3); 7.1022 (0.8); 6.9998 (1.2); 6.9953 (1.2); 6.9858 (1.1); 6.9838 (1.4); 6.9816 (1.2); 6.9793 (1.2); 6.9702 (0.9); 6.9657 (0.9); 5.2966 (1.0); 3.2071 (2.8); 3.1950 (1.4); 3.1916 (2.4); 3.1870 (1.5); 3.1758 (3.0); 2.8559 (2.4); 2.8409 (4.2); 2.8258 (2.6); 2.2361 (0.7); 2.2204 (1.6); 2.2158 (0.7); 2.2108 (1.1); 2.2053 (2.6); 2.2003 (1.1); 2.1952 (0.7); 2.1897 (1.4); 2.1745 (0.7); 2.0452 (0.3); 1.6390 (2.4); 1.4264 (16.0); 1.2536 (0.3); 0.0063 (0.4); −0.0003 (14.0); −0.0068 (0.4)

TABLE 12-continued

NMR peak lists

Xa.01: $^1$H-NMR(500.1 MHz, CDCl3):
δ = 8.8092 (1.1); 8.8041 (1.1); 8.2229 (1.0); 8.2180 (1.0); 8.0132 (0.7); 7.9962 (0.8); 7.7407 (0.7); 7.7245 (0.8); 7.6544 (0.4); 7.6402 (0.7); 7.6234 (0.5); 7.6204 (0.7); 7.6140 (0.6); 7.6030 (0.6); 7.5969 (0.6); 7.5336 (0.6); 7.5237 (0.6); 7.5163 (1.1); 7.5055 (0.9); 7.5030 (0.9); 7.4868 (0.4); 7.2545 (0.3); 7.2483 (0.4); 7.2397 (0.4); 7.2372 (0.4); 7.2339 (0.4); 7.2311 (0.4); 7.2223 (0.3); 7.1900 (13.5); 3.7971 (7.9); 3.1946 (7.7); 1.9736 (1.0); 1.4744 (16.0); 1.1890 (0.7); −0.0003 (0.6)

Xa.02: $^1$H-NMR(500.1 MHz, CDCl3):
δ = 8.8186 (2.3); 8.8135 (2.5); 8.2341 (2.2); 8.2293 (2.2); 8.0896 (0.3); 8.0048 (1.5); 7.9878 (1.7); 7.9100 (1.5); 7.8954 (1.8); 7.7355 (1.5); 7.7191 (1.7); 7.6432 (0.7); 7.6410 (0.8); 7.6269 (1.5); 7.6126 (0.8); 7.6103 (0.9); 7.5435 (1.2); 7.5409 (1.5); 7.5355 (2.2); 7.5297 (4.4); 7.5198 (0.5); 7.5044 (1.1); 7.4900 (1.6); 7.4743 (0.8); 7.4203 (0.8); 7.4149 (0.9); 7.4083 (0.7); 7.4037 (1.1); 7.3988 (0.8); 7.3935 (0.7); 7.3874 (0.6); 7.1894 (7.0); 4.0584 (0.3); 4.0441 (0.3); 3.7825 (16.0); 3.5495 (1.4); 3.2090 (1.9); 3.2034 (15.9); 2.0324 (0.5); 1.9726 (1.4); 1.5095 (0.8); 1.3570 (1.3); 1.2024 (0.5); 1.1880 (1.1); 1.1739 (0.4)

Xa.03: $^1$H-NMR(500.1 MHz, CDCl3):
δ = 8.0783 (0.6); 8.0751 (0.6); 8.0641 (2.3); 8.0595 (0.6); 7.9457 (0.5); 7.9431 (0.5); 7.9363 (0.5); 7.9334 (0.5); 7.9296 (0.5); 7.9266 (0.5); 7.9201 (0.6); 7.9192 (0.6); 7.9173 (0.6); 7.6870 (0.4); 7.6844 (0.6); 7.6702 (0.4); 7.6675 (0.3); 7.6303 (0.6); 7.6269 (0.6); 7.6150 (0.5); 7.6115 (0.5); 7.6079 (0.4); 7.6052 (0.4); 7.5938 (0.4); 7.5912 (0.7); 7.5886 (0.4); 7.5774 (0.3); 7.5561 (0.4); 7.5535 (0.5); 7.5407 (0.6); 7.5382 (0.6); 7.4668 (0.7); 7.4645 (0.6); 7.4511 (0.5); 7.4488 (0.5); 7.1898 (16.0); 5.2287 (0.4); 3.7012 (8.9); 3.6836 (8.2); 2.1001 (2.0); 1.9740 (0.4); 1.4691 (9.9); 1.3579 (1.2); 1.1892 (0.4)

Xa.04: $^1$H-NMR(500.1 MHz, CDCl3):
δ = 8.9151 (1.6); 8.9101 (1.6); 8.2774 (1.0); 8.2743 (1.2); 8.2697 (1.1); 8.0132 (1.0); 8.0102 (1.0); 7.9977 (1.0); 7.9948 (1.0); 7.6617 (0.4); 7.6586 (0.4); 7.6468 (0.9); 7.6426 (0.9); 7.6316 (1.1); 7.6284 (1.1); 7.6211 (1.4); 7.6180 (1.6); 7.6053 (0.6); 7.6023 (0.4); 7.5754 (0.4); 7.5716 (0.4); 7.5655 (0.4); 7.5614 (0.4); 7.5571 (0.6); 7.5532 (0.6); 7.5470 (0.5); 7.5432 (0.6); 7.5261 (0.8); 7.5228 (0.7); 7.5104 (0.9); 7.5084 (0.8); 7.5073 (0.8); 7.4964 (0.6); 7.4929 (0.5); 7.4696 (0.5); 7.4656 (0.4); 7.4558 (0.5); 7.4506 (0.8); 7.4368 (0.7); 7.4318 (0.4); 7.4179 (0.4); 7.2590 (60.0); 7.0475 (0.3); 3.8372 (16.0); 3.4022 (0.5); 3.2771 (14.0); 1.5312 (34.3); 0.0688 (0.4); 0.0063 (2.2); −0.0003 (75.3); −0.0068 (2.4)

IIa.01: $^1$H-NMR(400.1 MHz, d$_6$-DMSO):
δ = 8.9624 (2.8); 8.9587 (2.9); 7.7278 (1.1); 7.7229 (1.4); 7.7107 (1.0); 7.7045 (1.6); 7.6023 (0.4); 7.5981 (0.5); 7.5830 (1.4); 7.5788 (1.2); 7.5699 (1.5); 7.5574 (2.0); 7.5548 (2.2); 7.5514 (2.3); 7.5370 (1.1); 7.5311 (0.5); 3.3605 (0.8); 2.8496 (16.0); 2.5220 (0.7); 2.5176 (0.9); 2.5132 (0.7); −0.0002 (0.4)

IIa.02: $^1$H-NMR(300.1 MHz, d$_6$-DMSO):
δ = 7.4844 (1.9); 7.4654 (2.4); 7.4619 (2.2); 7.4524 (10.0); 7.4475 (7.6); 7.4309 (7.2); 7.4274 (6.5); 7.4152 (5.8); 7.3929 (4.7); 7.3847 (1.4); 7.3620 (1.8); 7.2313 (13.5); 7.2255 (13.2); 5.5943 (16.0); 3.3281 (26.8); 2.7377 (0.5); 2.5277 (76.7); 2.5145 (11.6); 2.5084 (14.2); 2.5025 (9.8); 2.4968 (4.6); 2.3141 (0.4); 0.0019 (0.4)

IIa.03: $^1$H-NMR(400.1 MHz, d$_6$-DMSO):
δ = 8.9894 (3.0); 8.9861 (3.1); 7.8107 (0.6); 7.8063 (0.7); 7.7970 (0.7); 7.7923 (0.8); 7.7877 (1.0); 7.7832 (1.1); 7.7739 (0.9); 7.7696 (0.9); 7.7199 (0.8); 7.7020 (0.9); 7.6942 (1.0); 7.6763 (1.0); 7.6711 (0.6); 7.6531 (0.5); 3.3584 (57.2); 2.8471 (16.0); 2.5114 (9.6); 2.5070 (12.5); 2.5027 (9.2)

IIa.04: $^1$H-NMR(400.1 MHz, d$_6$-DMSO):
δ = 12.4554 (11.9); 12.2312 (0.5); 12.2159 (0.4); 12.2104 (0.4); 7.5482 (13.7); 7.4048 (0.7); 7.3637 (0.6); 7.3410 (0.5); 7.2541 (0.5); 7.2471 (0.5); 7.2298 (0.5); 7.2160 (0.6); 7.0371 (16.0); 3.5880 (0.4); 3.3369 (19.2); 3.1138 (0.5); 3.0378 (0.4); 2.9809 (0.4); 2.9168 (0.5); 2.8976 (0.5); 2.5076 (39.1); 2.4241 (62.5); 2.0409 (0.4); 1.9894 (0.4); 1.2845 (0.4)

IIa.05: $^1$H-NMR(400.1 MHz, d$_6$-DMSO):
δ = 8.0014 (0.4); 7.9775 (1.2); 7.9602 (1.4); 7.9510 (2.3); 7.9352 (3.1); 7.9245 (0.5); 7.9109 (0.4); 3.3241 (15.6); 2.8219 (16.0); 2.5120 (6.0); 2.5078 (7.7); 2.5037 (5.7)

IIa.06: $^1$H-NMR(400.1 MHz, d$_6$-DMSO):
δ = 7.6025 (3.3); 7.5793 (6.2); 7.5579 (5.7); 7.5540 (6.2); 7.5319 (4.1); 7.3538 (4.8); 7.3489 (5.2); 7.3414 (5.3); 7.3365 (5.5); 7.3306 (4.8); 7.3256 (4.7); 7.3181 (4.4); 7.3133 (4.3); 7.2231 (0.5); 7.0953 (0.6); 6.9766 (16.0); 6.9030 (0.5); 6.8813 (0.4); 3.7408 (0.6); 3.3482 (3.9); 2.6978 (0.5); 2.5395 (87.3); 2.5246 (6.8); 2.5200 (7.0); 2.5159 (5.4); 2.5046 (1.9); 2.4448 (0.4); 2.3777 (0.5); 1.9991 (0.4); 1.2192 (0.4); 1.1924 (0.4); −0.0002 (3.0)

IIa.07: $^1$H-NMR(400.1 MHz, d$_6$-DMSO):
δ = 7.8581 (0.8); 7.8540 (0.9); 7.8369 (3.0); 7.8323 (3.3); 7.8193 (1.2); 7.8134 (1.4); 7.8002 (1.3); 7.7924 (0.5); 7.7792 (0.5); 7.7291 (1.0); 7.7243 (0.9); 7.7111 (0.8); 7.7035 (1.3); 7.6997 (1.1); 7.6841 (0.8); 7.6807 (0.7); 3.3296 (5.3); 2.8010 (16.0); 2.5117 (3.5); 2.5078 (4.4)

IIb.01: $^1$H-NMR(400.1 MHz, d$_6$-DMSO):
δ = 9.1622 (0.4); 9.1497 (16.0); 8.1065 (2.0); 8.0867 (2.4); 8.0825 (4.2); 8.0630 (4.3); 8.0568 (3.8); 8.0375 (3.5); 8.0116 (4.0); 8.0069 (4.0); 7.9989 (4.4); 7.9944 (4.2); 7.9880 (2.4); 7.9832 (2.5); 7.9752 (2.0); 7.9707 (2.2); 3.3138 (6.3); 2.5176 (2.8); 2.5133 (3.8); 2.5089 (2.8); −0.0002 (1.9)

IIb.02: $^1$H-NMR(400.1 MHz, d$_6$-DMSO):
δ = 8.3847 (16.0); 7.6775 (2.3); 7.6543 (4.0); 7.6328 (3.6); 7.6298 (3.9); 7.6283 (3.8); 7.6067 (2.6); 7.3628 (3.0); 7.3577 (3.2); 7.3505 (3.2); 7.3454 (3.3); 7.3394 (2.9); 7.3343 (2.8); 7.3270 (2.7); 7.3221 (2.6); 7.2017 (10.8); 7.1462 (0.4); 3.3380 (8.8); 2.5221 (2.7); 2.5178 (3.6); 2.5135 (2.7); 1.9976 (0.5); 1.2249 (0.6); −0.0002 (2.5)

IIb.03: $^1$H-NMR(499.9 MHz, d$_6$-DMSO):
δ = 9.1001 (13.5); 7.9495 (2.3); 7.9386 (2.4); 7.9334 (5.4); 7.9220 (6.1); 7.9177 (6.9); 7.9088 (16.0); 7.8949 (2.8); 7.8187 (0.4); 7.7949 (4.2); 7.7767 (5.1); 7.7709 (3.1); 7.7619 (2.5); 7.7577 (2.4); 3.8785 (0.5); 2.5387 (1.3); 1.1997 (0.3); −0.0002 (1.0)

II.01A: $^1$H-NMR(400.1 MHz, CDCl3):
δ = 9.1807 (14.6); 9.1754 (14.8); 8.5964 (16.0); 8.5911 (15.7); 8.0918 (7.9); 8.0738 (8.4); 7.9040 (7.8); 7.8835 (9.1); 7.6289 (5.8); 7.6095 (9.2); 7.5900 (4.6); 7.2603 (4.4); 1.5972 (1.5); −0.0002 (6.6)

II.02A: $^1$H-NMR(400.1 MHz, CDCl3):
δ = 9.0903 (14.7); 9.0856 (15.1); 8.5484 (10.4); 8.5445 (16.0); 8.5406 (10.4); 7.5546 (6.3); 7.5387 (6.2); 7.5324 (10.5); 7.5165 (10.8); 7.4676 (12.1); 7.4643 (11.8); 7.4453 (6.7); 7.4420 (7.1); 7.2669 (5.9); 1.6340 (1.6); 0.0077 (0.4); −0.0002 (8.7); −0.0082 (0.4)

TABLE 12-continued

NMR peak lists

II.03A: ¹H-NMR(400.1 MHz, CDCl3):
δ = 9.0334 (4.8); 9.0287 (4.8); 8.4950 (3.4); 8.4907 (5.3); 8.4866 (3.2); 7.4030 (1.6); 3.3817 (9.0); 7.3779 (5.6); 7.3634 (3.4); 7.3568 (0.6); 7.3423 (1.0); 7.2694 (1.5); 2.4850 (16.0); 2.4788 (15.0); −0.0002 (2.2)

II.04A: ¹H-NMR(499.9 MHz, CDCl3):
δ = 9.1654 (16.0); 9.1613 (15.4); 8.5995 (13.4); 8.5960 (12.6); 8.1685 (11.2); 8.1511 (12.5); 8.1174 (15.3); 8.1140 (14.4); 7.8794 (11.5); 7.8758 (10.6); 7.8620 (10.2); 7.8584 (9.4); 7.2630 (19.2); 5.2975 (0.8); 1.5991 (11.4); 0.0063 (0.6); −0.0002 (12.9); −0.0068 (0.5)

II.05A: ¹H-NMR(400.1 MHz, CDCl3):
δ = 8.9676 (14.1); 8.9632 (14.4); 8.4586 (10.7); 8.4550 (16.0); 8.4515 (10.8); 7.2061 (4.4); 7.1996 (5.1); 7.1912 (13.3); 7.1842 (5.6); 7.1812 (5.9); 7.1777 (6.5); 7.1748 (6.1); 7.1593 (4.3); 7.1527 (5.0); 7.1101 (5.3); 7.1061 (6.2); 7.1002 (4.8); 7.0891 (5.4); 7.0851 (6.3); 7.0792 (4.7); 1.5163 (2.6); 1.2211 (3.2); 1.2105 (0.5); 1.1986 (0.6); 1.1925 (0.6); 1.1801 (0.4); 1.1752 (0.4); 1.1555 (0.5)

II.06A: ¹H-NMR(400.1 MHz, CDCl3):
δ = 9.1294 (15.0); 9.1247 (15.1); 8.8008 (11.0); 8.7970 (16.0); 8.7931 (10.4); 7.3869 (3.7); 7.3755 (3.9); 7.3650 (5.8); 7.3537 (5.8); 7.3408 (4.8); 7.3295 (4.6); 7.2637 (10.4); 7.2020 (4.4); 7.1931 (4.6); 7.1799 (7.6); 7.1710 (7.6); 7.1580 (3.7); 7.1490 (3.5); 1.5916 (2.0)

II.07A: ¹H-NMR(400.1 MHz, CDCl3):
δ = 9.1573 (10.6); 9.1524 (10.8); 8.5455 (11.4); 8.5407 (11.3); 8.2487 (0.4); 7.6275 (4.8); 7.6054 (16.0); 7.5873 (15.7); 7.5652 (5.1); 7.2619 (9.5); 5.2980 (0.5); 1.5620 (3.3)

II.08A: ¹H-NMR(400.1 MHz, CDCl3):
δ = 9.0025 (14.2); 8.9983 (14.5); 8.4612 (16.0); 8.4566 (15.9); 7.8258 (6.8); 7.8067 (7.1); 7.7987 (7.1); 7.7796 (6.8); 7.4560 (8.0); 7.4352 (9.2); 7.4312 (9.3); 7.4104 (8.1); 7.2658 (4.9); 1.2529 (1.2); 0.0763 (0.3); −0.0002 (7.1)

II.09A: ¹H-NMR(400.1 MHz, CDCl3):
δ = 9.0566 (15.0); 9.0519 (15.4); 8.4765 (10.5); 8.4728 (16.0); 8.4692 (10.5); 7.4995 (9.9); 7.4956 (14.5); 7.4920 (11.2); 7.4296 (9.8); 7.4244 (8.6); 7.4052 (9.6); 7.3999 (8.8); 7.2692 (4.4); 1.6650 (0.8); 1.2523 (0.5); −0.0002 (6.5)

II.10A: ¹H-NMR(400.1 MHz, CDCl3):
δ = 9.0747 (4.2); 9.0701 (4.4); 8.6653 (3.0); 8.6609 (5.0); 8.6566 (3.0); 7.3048 (6.8); 7.2849 (8.3); 7.2682 (1.5); 2.5966 (15.5); 2.5946 (16.0); 1.6849 (0.5); 1.6658 (0.5); 1.2728 (0.4); 1.2572 (0.3); 1.2212 (0.3); 0.8807 (0.4); −0.0002 (1.9)

II.11A: ¹H-NMR(400.1 MHz, CDCl3):
δ = 9.2054 (15.3); 9.2004 (15.6); 8.6354 (16.0); 8.6304 (15.9); 8.1566 (9.0); 8.1538 (9.3); 8.1386 (9.8); 8.1358 (10.0); 7.9837 (8.7); 7.9812 (8.6); 7.9629 (10.0); 7.9605 (9.7); 7.6695 (8.3); 7.6506 (10.7); 7.6307 (6.9); 7.2685 (5.7); 6.7085 (0.4); 6.7058 (0.4); 3.7569 (2.6); 1.2543 (0.4); −0.0002 (8.5)

II.12A: ¹H-NMR(400.1 MHz, CDCl3):
δ = 9.0572 (0.4); 9.0522 (0.4); 8.9784 (16.0); 8.9736 (15.2); 8.6379 (15.6); 8.6339 (14.7); 8.6087 (1.0); 8.6045 (0.9); 7.4937 (0.5); 7.4912 (0.5); 7.4687 (0.7); 7.4536 (6.9); 7.4297 (6.9); 7.1887 (3.5); 7.0112 (4.5); 7.0054 (4.3); 6.9877 (7.2); 6.9828 (6.8); 6.9650 (4.5); 6.9592 (4.2); 1.6611 (2.9); 1.2068 (0.4); 1.1719 (0.8); −0.0002 (1.3)

III.01A: ¹H-NMR(499.9 MHz, d$_6$-DMSO):
δ = 10.8377 (0.5); 7.3240 (1.4); 7.3090 (3.2); 7.2954 (3.3); 7.2808 (1.7); 6.8429 (2.4); 6.8254 (4.3); 6.8081 (2.4); 6.6817 (4.5); 6.6661 (4.5); 4.6209 (16.0); 2.5020 (1.3); 1.2980 (0.4); 1.2673 (0.4); 1.2412 (0.4); −0.0002 (0.6)

III.02A: ¹H-NMR(499.9 MHz, d$_6$-DMSO):
δ = 7.5061 (2.6); 7.4902 (5.3); 7.4742 (3.0); 7.3247 (6.2); 7.3088 (5.0); 7.1372 (5.8); 7.1212 (5.1); 4.6975 (16.0); 3.3509 (0.4); 2.5063 (10.0); 0.9402 (0.4)

III.03A: ¹H-NMR(499.9 MHz, d$_6$-DMSO):
δ = 11.1685 (3.4); 7.6614 (6.0); 7.6258 (3.2); 7.6091 (3.3); 6.9915 (4.7); 6.9749 (4.5); 4.6645 (16.0); 2.5125 (1.1); 2.5093 (1.4); 2.5061 (1.0); 1.9917 (0.6); 1.1772 (0.3); −0.0002 (0.9)

III.04A: ¹H-NMR(499.9 MHz, d$_6$-DMSO):
δ = 11.0137 (2.9); 7.4162 (2.2); 7.3997 (4.3); 7.3833 (2.4); 6.9928 (2.8); 6.9759 (2.6); 6.8685 (4.6); 6.8525 (4.3); 4.6285 (16.0); 2.5063 (1.6); −0.0002 (1.2)

III.05A: ¹H-NMR(499.9 MHz, d$_6$-DMSO):
δ = 7.3643 (2.1); 7.3485 (4.2); 7.3326 (2.4); 7.1336 (4.3); 7.1182 (3.7); 6.9844 (4.1); 6.9683 (3.8); 4.4700 (14.7); 3.5737 (0.4); 3.5241 (0.5); 3.5137 (0.4); 3.5024 (0.9); 3.4921 (0.7); 3.4474 (0.8); 3.4359 (0.7); 3.4258 (0.5); 3.4142 (0.4); 2.6421 (6.7); 2.3017 (0.5); 2.0464 (16.0); 1.8992 (3.1); 1.6980 (0.3); 1.4469 (0.4); 1.4322 (0.4); 1.0782 (0.7); 1.0636 (1.3); 1.0489 (0.6)

III.06A: ¹H-NMR(500.1 MHz, CDCl3):
δ = 8.1197 (0.4); 8.1037 (0.4); 7.5802 (0.4); 7.2877 (3.3); 7.2419 (0.3); 7.2295 (1.7); 7.2150 (3.3); 7.1997 (1.9); 7.1518 (2.6); 7.1367 (3.6); 7.0660 (2.5); 7.0512 (3.7); 7.0362 (1.5); 6.9882 (0.5); 6.9721 (0.4); 6.7848 (4.0); 6.7688 (3.6); 6.5313 (2.4); 3.2705 (16.0); 1.7032 (7.1); 1.6555 (0.3); 1.6324 (2.2); 1.5280 (63.7); 1.5069 (0.3); 1.4553 (0.9)

III.07A: ¹H-NMR(500.1 MHz, CDCl3):
δ = 7.2877 (36.0); 7.2519 (1.4); 7.2372 (3.1); 7.2214 (1.9); 7.1395 (2.2); 7.1246 (3.9); 7.0918 (2.9); 7.0769 (3.9); 7.0620 (1.4); 6.8214 (4.0); 6.8054 (3.7); 6.3227 (2.0); 5.3266 (0.6); 3.3780 (16.0); 2.0719 (0.4); 1.6425 (0.3); 1.6113 (2.5); 1.5989 (9.5); 1.5866 (3.1); 1.5665 (19.7); 1.4560 (0.5); 1.2824 (1.6); 1.0282 (2.4); 1.0159 (9.1); 1.0036 (2.0)

IV.01A: ¹H-NMR(500.1 MHz, CDCl3):
δ = 7.4248 (4.1); 7.4097 (8.0); 7.3869 (4.5); 7.3721 (7.0); 7.3568 (3.3); 7.3115 (2.3); 7.2971 (3.2); 7.2873 (8.4); 7.1501 (1.5); 7.1347 (3.1); 7.1183 (4.6); 7.1028 (3.7); 7.0324 (2.8); 7.0175 (3.9); 7.0026 (1.6); 6.8542 (4.2); 6.8377 (3.8); 5.3256 (1.4); 5.0423 (16.0); 3.4303 (15.3); 3.2620 (0.8); 2.3887 (0.4); 1.6105 (2.2); 1.5981 (9.1); 1.5860 (2.3); 1.3259 (0.4); 1.2869 (3.1); 1.2337 (2.6); 1.2327 (2.6); 1.0419 (0.6); 1.0265 (0.4); 1.0097 (2.4); 0.9974 (9.1); 0.9851 (2.2); 0.9107 (0.5); 0.9023 (0.3)

The following examples illustrate in a non-limiting manner the preparation and efficacy of the compounds of formula (I) according to the invention.

Preparation Example 1: Preparation of 3-(2,2-dioxido-2,1-benzothiazol-1(3H)-yl)-8-fluoroquinoline (Compound I.018)

In a first 20 mL microwave vial, 605 mg (2.22 mmol) of 8-fluoro-3-iodoquinoline and 250 mg (1.48 mmol) of 1,3-dihydro-2,1-benzothiazole 2,2-dioxide were dissolved in 12.5 mL of 1,4-dioxane. 963 mg (2.96 mmol) of cesium carbonate were added, followed by 281 mg (1.48 mmol) of copper(I) iodide and 42 mg (0.30 mmol) of (1 S,2S)-N,N'-dimethylcyclohexane-1,2-diamine. The tube was sealed and the mixture was heated at 100° C. for 28 hours. The same reaction was repeated in a second 20 mL microwave vial. The cooled two reaction mixtures were combined, diluted by ethyl acetate and filtered through a plug of Celite® 545. The filtrate was dried over magnesium sulfate. The organic phase was concentrated under reduced pressure and the residue was purified by column chromatography on silica gel (dichloromethane) to yield 630 mg (74% purity, 50% yield) of 3-(2,2-dioxido-2,1-benzothiazol-1(3H)-yl)-8-fluoroquinoline as a viscous oil used as such in the next step. Log P=2.52 [Method A]. (M+H)=315.

Preparation Example 2: Preparation of 3-(3,3-dimethyl-2,2-dioxido-2,1-benzothiazol-1(3H)-yl)-8-fluoroquinoline (Compound I.015)

To a solution of 280 mg (74% purity, 0.66 mmol) of 3-(2,2-dioxido-2,1-benzothiazol-1(3H)-yl)-8-fluoroquinoline and 214 mg (1.51 mmol) of iodomethane in 20 mL of DMSO was added 101 mg (1.51 mmol) of sodium hydroxide. The reaction mixture was stirred at room temperature for 17 hours. The reaction mixture was diluted by water and extracted by ethyl acetate (2×150 mL). The organic extracts were washed by water then brine and dried over magnesium sulfate. The organic phase was concentrated under reduced pressure and the residue was purified by column chromatography on silica gel (dichloromethane) to yield 135 mg (95% purity, 57% yield) of 3-(3,3-dimethyl-2,2-dioxido-2,1-benzothiazol-1(3H)-yl)-8-fluoroquinoline 30 as a viscous oil. Log P=3.12 [Method A]. (M+H)=343.

Preparation Example 3: Preparation of 3-methyl-1-(quinolin-3-yl)-3,4-dihydro-1H-2,1-benzothiazine 2,2-dioxide (compound I.158)

Step 1: Preparation of 3-methyl-3,4-dihydro-1H-2,1-benzothiazine 2,2-dioxide

To a solution of 380 mg (1.32 mmol) of 1-benzyl-3-methyl-3,4-dihydro-1H-2,1-benzothiazine 2,2-dioxide in 5.3 mL of MeOH was added 141 mg (10% Pd basis, 0.132 mmol) of palladium on activated charcoal. The reaction was stirred at room temperature under an atmosphere of $H_2$ for 5 hours. The black suspension was filtered over Celite® 545 and the filtrate was concentrated under reduced pressure. The residue was purified by column chromatography on silica gel (gradient dichloromethane/methyl tert-butyl ether) to yield 240 mg (100% purity, 57% yield) of 3-methyl-3,4-dihydro-1H-2,1-benzothiazine 2,2-dioxide as a white solid. Log P=1.33 [Method C].

Step 2: Preparation of 3-methyl-1-(quinolin-3-yl)-3,4-dihydro-1H-2,1-benzothiazine 2,2-dioxide (Compound 1.158)

A microwave vial was charged with 113 mg (0.573 mmol) of 3-methyl-3,4-dihydro-1H-2,1-benzothiazine 2,2-dioxide, 164 mg (0.859 mmol) of copper(I) iodide and 560 mg (1.72 mmol) of cesium carbonate. The vial was purged with argon. To the reaction mixture were successively added 2.3 mL of dioxane, 156 µL (1.15 mmol) of 3-bromoquinoline and 90 µL (0.57 mmol) of trans-N,N'-dimethylcyclohexane-1,2-diamine. The vial was sealed and the reaction mixture was stirred at 100° C. for 16 hours. After cooling down to room temperature, the reaction mixture was diluted with ethyl acetate and filtered through a plug of Celite® 545. The filtrate was concentrated under reduced pressure and the residue was purified by column chromatography on silica gel (gradient ethyl acetate/cyclohexane) to yield 168 mg (100% purity, 90% yield) 3-methyl-1-(quinolin-3-yl)-3,4-dihydro-1H-2,1-benzothiazine 2,2-dioxide as a yellow solid. Log P=2.58 [Method C]. (M+H)=325.

Preparation Example 4: Preparation of 3-methyl-1-(1-oxidoquinolin-3-yl)-3,4-dihydro-1H-2,1-benzothiazine 2,2-dioxide (Compound I.162)

To a solution of 61 mg (0.19 mmol) of 3-methyl-1-(quinolin-3-yl)-3,4-dihydro-1H-2,1-benzothiazine 2,2-dioxide in 0.4 mL of chloroform at 0° C. was added 70 mg (70% purity, 0.28 mmol) of m-chloroperbenzoic acid. The reaction was stirred at room temperature for 2 hours. The reaction mixture was diluted with ethyl acetate, washed with a saturated aqueous sodium bicarbonate solution, water and brine, dried over sodium sulfate, filtered and concentrated under reduced pressure. The residue was purified by column chromatography on silica gel (gradient ethyl acetate/dichloromethane) to yield 61 mg (100% purity, 97% yield) of 3-methyl-1-(1-oxidoquinolin-3-yl)-3,4-dihydro-1H-2,1-benzothiazine 2,2-dioxide as a white solid. Log P=1.81 [Method C].

Preparation Example 5: Preparation of 1,3,4,5-tetrahydro-2,1-benzothiazepine 2,2-dioxide (Compound IIIc.02)

Step 1: Preparation of 1-benzyl-1,5-dihydro-2,1-benzothiazepine 2,2-dioxide (Compound V.01)

To a solution of 5.43 g (13.9 mmol) of (E)-N-(2-allylphenyl)-N-benzyl-2-phenylethene-1-sulfonamide in 560 mL of dichloromethane was added 296 mg (349 µmol) of (1,3-bis (2,4,6-trimethylphenyl)-2-imidazolidinylidene)dichloro (phenylmethylene)(tricyclohexylphosphine)ruthenium. The reaction mixture was stirred at reflux for 20 hours. The cooled reaction mixture was concentrated under reduced pressure and the residue was purified by column chromatography on silica gel (gradient cyclohexane/ethyl acetate) to yield 3.42 g (95% purity, 85% yield) of 1-benzyl-1,5-dihydro-2,1-benzothiazepine 2,2-dioxide. Log P=6.01 [Method C]. (M+H)=286.

Step 2: Preparation of 1,3,4,5-tetrahydro-2,1-benzothiazepine 2,2-dioxide (Compound IIIc.02)

To a solution of 1.55 g (5.43 mmol) of 1-benzyl-1,5-dihydro-2,1-benzothiazepine 2,2-dioxide in 27 mL of THF/

MeOH (1/1) was added 1.52 g of palladium hydroxide on carbon (5 wt. % on carbon, 543 µmol). The reaction mixture was stirred at reflux under an $H_2$ atmosphere for 6 hours. The cooled reaction mixture was filtered through a plug of Celite®545 and the filtrate was concentrated under reduced pressure. The residue was purified by column chromatography on silica gel (gradient dichloromethane/ethyl acetate) to yield 868 mg (100% purity, 81% yield) of 1,3,4,5-tetrahydro-2,1-benzothiazepine 2,2-dioxide. Log P=1.20 [Method C].

Preparation Example 6: Preparation of 3,3,4,4-tetramethyl-1-(quinolin-3-yl)-3,4-dihydro-1H-2,1-benzothiazine 2,2-dioxide (Compound I.172) and 3,4,4-trimethyl-1-(quinolin-3-yl)-3,4-dihydro-1H-2,1-benzothiazine 2,2-dioxide (I.173)

Step 1: Preparation of 2-(2-bromophenyl)-2-methyl-N-(quinolin-3-yl)propane-1-sulfonamide (compound VIIIa.18)

To a solution of 376 mg (2.61 mmol) of 3-aminoquinoline in 8.7 mL of N,N-dimethylformamide was added dropwise 542 mg (1.74 mmol) of 2-(2-bromophenyl)-2-methylpropane-1-sulfonyl chloride. The reaction was stirred at room temperature for 18 hours. The reaction mixture was diluted with ethyl acetate, washed with a saturated aqueous sodium bicarbonate solution, water and brine, dried over sodium sulfate, filtered and concentrated under reduced pressure. The residue was purified by column chromatography on silica gel (gradient dichloromethane/ethyl acetate) to yield 281 mg (100% purity, 39% yield) of 2-(2-bromophenyl)-2-methyl-N-(quinolin-3-yl)propane-1-sulfonamide as a beige foam. Log P=2.98 [Method C]. (M+H)=419.

Step 2: Preparation of 4,4-dimethyl-1-(quinolin-3-yl)-3,4-dihydro-1H-2,1-benzothiazine 2,2-dioxide (Compound I.166)

To a solution of 161 mg (0.384 mmol) of 2-(2-bromophenyl)-2-methyl-N-(quinolin-3-yl)propane-1-sulfonamide in 3.8 mL of DMSO, were added 368 mg (1.92 mmol) of cesium acetate and 146 mg (0.768 mmol) of copper(I) iodide. The reaction mixture was diluted with ethyl acetate, washed three times with water, once with brine, dried over sodium sulfate, filtered and concentrated under reduced pressure. The residue was purified by column chromatography on silica gel (gradient cyclohexane/ethyl acetate) to yield 94 mg (100% purity, 72% yield) of 4,4-dimethyl-1-(quinolin-3-yl)-3,4-dihydro-1H-2,1-benzothiazine 2,2-dioxide as a white solid. Log P=2.88 [Method C]. (M+H)=339.

Step 3: Preparation of 3,3,4,4-tetramethyl-1-(quinolin-3-yl)-3,4-dihydro-1H-2,1-benzothiazine 2,2-dioxide (Compound I.172) and 3,4,4-trimethyl-1-(quinolin-3-yl)-3,4-dihydro-1H-2,1-benzothiazine 2,2-dioxide (I.173)

To a solution of 71 mg (0.21 mmol) of 4,4-dimethyl-1-(quinolin-3-yl)-3,4-dihydro-1H-2,1-benzothiazine 2,2-dioxide in 2.1 mL of THF at 0° C. were successively added 65 µL (1.05 mmol) of iodomethane and 524 µL (1 M solution in THF, 0.524 mmol) of lithium bis(trimethylsilyl)amide. The reaction was stirred at room temperature for 60 hours and quenched by a saturated aqueous ammonium chloride solution. The mixture was extracted three times with dichloromethane. The combined organic layers were dried over sodium sulfate, filtered and concentrated under reduced pressure. The residue was purified by preparative thin layer chromatography (gradient cyclohexane/ethyl acetate) to yield 6 mg (100% purity, 8% yield) of 3,3,4,4-tetramethyl-1-(quinolin-3-yl)-3,4-dihydro-1H-2,1-benzothiazine 2,2-dioxide as a white solid and 57 mg (100% purity, 77% yield) of 3,4,4-trimethyl-1-(quinolin-3-yl)-3,4-dihydro-1H-2,1-benzothiazine 2,2-dioxide. Log P=3.85 [Method C]. (M+H)=367 & Log P=3.53 [Method C]. (M+H)=353.

Preparation Example 7: Preparation of 4,4-difluoro-3,3-dimethyl-1-(quinolin-3-yl)-3,4-dihydro-1H-2,1-benzothiazine 2,2-dioxide (Compound I.163)

Step 1: Preparation of methyl 2-(quinolin-3-ylamino)benzoate

In a first 20 mL microwave vial, 59 mg (0.08 mmol) of chloro(2-dicyclohexylphosphino-2',4',6'-triisopropyl-1,1'-biphenyl)[2-(2'-amino-1,1'-biphenyl)]palladium(II) and 1.45 g (10.5 mmol) of potassium carbonate were added under argon atmosphere. 15 mL of tert-butanol were added followed by 1.02 mL (7.50 mmol) of 3-bromoquinoline and 1.16 mL (1.16 mmol) of methyl anthranilate. The reaction mixture was stirred for 4 hours at 110° C. under microwave irradiation. The same reaction was repeated in a four more 20 mL microwave vials. The cooled five reaction mixtures were combined, diluted with ethyl acetate and concentrated under reduced pressure. The residue was purified by column chromatography on silica gel (gradient cyclohexane/ethyl acetate) to yield 9.6 g (99% purity, 92% yield) of methyl 2-(quinolin-3-ylamino)benzoate as a pale yellow solid Log P=2.96 [Method C]. (M+H)=279.

Step 2: Preparation of methyl 2-[(methylsulfonyl)(quinolin-3-yl)amino]benzoate (Xa.02)

A solution of lithium bis(trimethylsilyl)amide (1.0 M in tetrahydrofuran, 34.49 mmol) was added to a solution of 9.6 g (34.49 mmol) of methyl 2-(quinolin-3-ylamino)benzoate in 85 mL tetrahydrofuran at 0° C. The mixture was stirred for 10 min resulting in an orange solution. This solution was slowly added to a solution of 4.0 mL (51.68 mmol) of mesyl chloride in 85 mL of tetrahydrofuran at 0° C. The resulting pale yellow solution was stirred at 0° C. for 5 min and quenched by a saturated aqueous ammonium chloride solution. The crude mixture was extracted with three times with ethyl acetate. The combined organic layers were washed with brine, dried over sodium sulfate, filtered and concentrated under reduced pressure. The residue was purified by column chromatography on silica gel (gradient cyclohexane/ethyl acetate) to yield 5.98 g (98% purity, 49% yield) of methyl 2-[(methylsulfonyl)(quinolin-3-yl)amino]benzoate as a yellow solid. Log P=2.17 [Method C]. (M+H)=357.

Step 3: Preparation of 1-(quinolin-3-yl)-1H-2,1-benzothiazin-4(3H)-one 2,2-dioxide (Compound 1.159)

To a suspension of 960 mg (60% (w/w) dispersion in mineral oil, 24.0 mmol) of sodium hydride in 25 mL of N,N-dimethylformamide at 0° C. was added dropwise a solution of 5.98 g (16.8 mmol) of 2-[(methylsulfonyl)(quinolin-3-yl)amino]benzoate in 25 mL of N,N-dimethylformamide. The reaction mixture was allowed to warm up to room temperature and stirred for 1.5 hours. The reaction mixture was quenched with a 1 M aqueous hydrochloric acid solution and diluted with ethyl acetate. The layers were separated. The aqueous phase was neutralized to pH 7 with a saturated aqueous sodium bicarbonate solution and extracted twice with ethyl acetate. The combined organic layers were washed with water, brine, dried over magnesium sulfate, filtered and concentrated under reduced pressure. The residue was purified by column chromatography on silica gel (gradient cyclohexane/ethyl acetate) to yield 3.80 g (98% purity, 70% yield) of 1-(quinolin-3-yl)-1H-2,1-benzothiazin-4(3H)-one 2,2-dioxide as a yellow solid. Log P=2.28 [Method C]. (M+H)=325.

Step 4: Preparation of 3,3-dimethyl-1-(quinolin-3-yl)-1H-2,1-benzothiazin-4(3H)-one 2,2-dioxide (Compound I.156)

To solution of 1.90 g (5.86 mmol) of 1-(quinolin-3-yl)-1H-2,1-benzothiazin-4(3H)-one 2,2-dioxide in 24 mL of N,N-dimethylformamide were added 4.05 g (29.3 mmol) of potassium carbonate and 1.55 mL (17.57 mmol) of iodomethane. The resulting suspension was stirred at room temperature for 1.5 hours. The reaction mixture was concentrated under reduced pressure, then diluted with ethyl acetate and water. The aqueous layer was extracted twice with ethyl acetate. The combined organic layers were washed with brine, dried over magnesium sulfate and concentrated under reduced pressure. The residue was purified by column chromatography on silica gel (gradient cyclohexane/ethyl acetate) to yield 1.47 g (96% purity, 71% yield) of 3,3-dimethyl-1-(quinolin-3-yl)-1H-2,1-benzothiazin-4(3H)-one 2,2-dioxide as a yellow solid. Log P=2.93 [Method C]. (M+H)=353.

Step 5: Preparation of 4,4-difluoro-3,3-dimethyl-1-(quinolin-3-yl)-3,4-dihydro-1H-2,1-benzothiazine 2,2-dioxide (Compound I.163)

To 100 mg (0.28 mmol) of 3,3-dimethyl-1-(quinolin-3-yl)-1H-2,1-benzothiazin-4(3H)-one 2,2-dioxide was added 0.36 mL (2.94 mmol) of 2,2-difluoro-1,3-dimethylimidazolidine at room temperature. The reaction mixture was stirred at 110° C. for 24 hours. The reaction mixture was cooled to room temperature, diluted with dichloromethane and poured onto an aqueous saturated solution of sodium bicarbonate. The aqueous phase was extracted three times with dichloromethane. The combined organic extracts were washed with water, brine, dried over magnesium sulfate and concentrated under reduced pressure. The residue was purified by column chromatography on silica gel (gradient cyclohexane/ethyl acetate) then by preparative thin layer chromatography (gradient dichloromethane/ethyl acetate) to yield 65 mg (99% purity, 61% yield) of 4,4-difluoro-3,3-dimethyl-1-(quinolin-3-yl)-3,4-dihydro-1H-2,1-benzothiazine 2,2-dioxide as a white solid. Log P=3.25 [Method C]. (M+H)=375.

Preparation Example 8: Preparation of 3,3-dichloro-1-(quinolin-3-yl)-1H-2,1-benzothiazin-4(3H)-one 2,2-dioxide (Compound I.239)

To a solution of 365 mg (2.77 mmol) of N-chlorosuccinimide in 4 mL of methanol was added 14 mg (0.19 mmol) of thiourea were added under an argon atmosphere. After five minutes, 200 mg (0.62 mmol) of 1-(quinolin-3-yl)-1H-2,1-benzothiazin-4(3H)-one 2,2-dioxide were added. The reaction mixture was stirred at room temperature for 16 hours. The reaction was quenched with water and diluted with ethyl acetate. The layers were separated and the aqueous phase was extracted with twice with ethyl acetate. The combined organic layers were washed with brine, dried over sodium sulfate, filtered and concentrated under reduced pressure. The residue was purified by column chromatography on silica gel (gradient cyclohexane/ethyl acetate) to yield 200 mg (100% purity, 82% yield) of 3,3-dichloro-1-(quinolin-3-yl)-1H-2,1-benzothiazin-4(3H)-one 2,2-dioxide as a white solid. Log P=3.49 [Method C]. (M+H)=393.

Preparation Example 9: Preparation of N-(benzyloxy)-1-(quinolin-3-yl)-1H-2,1-benzothiazin-4(3H)-imine 2,2-dioxide (Compound I.241)

A suspension of 75 mg (0.23 mmol) of 1-(quinolin-3-yl)-1H-2,1-benzothiazin-4(3H)-one 2,2-dioxide, 76 mg (0.92 mmol) of sodium acetate and 148 mg (0.92 mmol) of O-benzyl hydroxylamine hydrochloride in 2 mL of methanol was stirred at 65° C. for 72 hours. The reaction mixture was quenched with a saturated aqueous ammonium chloride solution and diluted with ethyl acetate. The phases were separated and the aqueous layer was extracted twice with ethyl acetate. The combined organic layers were washed with brine, dried over sodium sulfate, filtered and concentrated under reduced pressure. The residue was purified by column chromatography on silica gel (gradient cyclohexane/ethyl acetate) to yield 78 mg (97% purity, 79% yield) of N-(benzyloxy)-1-(quinolin-3-yl)-1H-2,1-benzothiazin-4(3H)-imine 2,2-dioxide as a white solid. Log P=3.94 [Method C]. (M+H)=430.

Preparation Example 10: Preparation of 4-(benzyloxy)-3,3,4-trimethyl-1-(quinolin-3-yl)-3,4-dihydro-1H-2,1-benzothiazine 2,2-dioxide (Compound I.250)

Step 1: Preparation of 3,3,4-trimethyl-1-(quinolin-3-yl)-3,4-dihydro-1H-2,1-benzothiazin-4-ol 2,2-dioxide (Compound I.213)

To solution of 3.00 g (8.51 mmol) of 3,3-dimethyl-1-(quinolin-3-yl)-1H-2,1-benzothiazin-4(3H)-one 2,2-dioxide in 90 mL of tetrahydrofuran at 0° C. was added dropwise a solution of 9.93 mL methyl magnesium chloride (3 M in tetrahydrofuran). The reaction mixture was allowed to warm up to room temperature and was stirred for 4 hours. The reaction mixture was cooled to 0° C. and quenched by slow addition of a saturated aqueous ammonium chloride solution. The layers were separated and the aqueous layer was extracted twice with ethyl acetate. The combined organic layers were washed with brine, dried over sodium sulfate and concentrated under reduced pressure. The residue was purified by column chromatography on silica gel (gradient cyclohexane/ethyl acetate) to yield 2.25 g (100% purity, 72% yield) of 3,3,4-trimethyl-1-(quinolin-3-yl)-3,4-dihydro-1H-2,1-benzothiazin-4-ol 2,2-dioxide as a yellow solid. Log P=2.46 [Method C]. (M+H)=369.

Step 2 Preparation of 4-(benzyloxy)-3,3,4-trimethyl-1-(quinolin-3-yl)-3,4-dihydro-1H-2,1-benzothiazine 2,2-dioxide (Compound I.250)

To a solution of 75 mg (0.20 mmol) 3,3,4-trimethyl-1-(quinolin-3-yl)-3,4-dihydro-1H-2,1-benzothiazin-4-ol 2,2-dioxide in 1 mL of N,N-dimethylformamide were added 20 mg (60% (w/w) dispersion in mineral oil, 0.48 mmol) of sodium hydride and 72 µL (0.61 mmol) of benzyl bromide at 0° C. The reaction mixture was allowed to warm up to room temperature and stirred for 2 hours. The reaction was quenched with 0.12 mL of n-butylamine (1.2 mmol) and stirred for 20 min. A saturated aqueous ammonium chloride solution was added and the mixture was extracted three times with ethyl acetate. The combined organic extracts were washed with brine, dried over sodium sulfate, filtered and concentrated under reduced pressure. The residue was purified by column chromatography on silica gel (gradient cyclohexane/ethyl acetate) to yield 77 mg (99% purity, 82% yield) of 4-(benzyloxy)-3,3,4-trimethyl-1-(quinolin-3-yl)-3,4-dihydro-1H-2,1-benzothiazine 2,2-dioxide as a white solid. Log P=4.04 [Method C]. (M+H)=459.

Preparation Example 10: Preparation of 1-(7,8-difluoroquinolin-3-yl)-4-fluoro-3,3,4-trimethyl-3,4-dihydro-1H-2,1-benzothiazine 2,2-dioxide (Compound I.225) and 1-(7,8-difluoroquinolin-3-yl)-3,3-dimethyl-4-methylene-3,4-dihydro-1H-2,1-benzothiazine 2,2-dioxide (Compound I.219)

To 613 mg (50% w/w in toluene, 1.38 mmol) of a solution of bis(2-methoxyethyl)aminosulfur trifluoride was added a suspension of 40 mg (0.10 mmol) of 1-(7,8-difluoroquinolin-3-yl)-3,3,4-trimethyl-3,4-dihydro-1H-2,1-benzothiazin-4-ol 2,2-dioxide in 2 mL of dichloromethane at 0° C. The reaction was allowed to warm up to room temperature and stirred for 1 hour. The reaction mixture was poured into a saturated aqueous sodium bicarbonate solution. After gas formation had ceased, dichloromethane was added and the layers were separated. The aqueous layer was extracted twice with dichloromethane and the combined organic layers were dried over sodium sulfate, filtered and concentrated under reduced pressure. The residue was purified by preparative thin layer chromatography (gradient cyclohexane/ethyl acetate) to yield 28 mg (96% purity, 70% yield) of 1-(7,8-difluoroquinolin-3-yl)-4-fluoro-3,3,4-trimethyl-3,4-dihydro-1H-2,1-benzothiazine 2,2-dioxide as a white solid [Log P=3.60 [Method C]. (M+H)=407] and 10 mg (96% purity, 26% yield) of 1-(7,8-difluoroquinolin-3-yl)-3,3-dimethyl-4-methylene-3,4-dihydro-1H-2,1-benzothiazine 2,2-dioxide as a white solid [Log P=3.34 [Method C]. (M+H)=387].

In the following:
CMP1 designates 8-fluoro-3-(2-methoxy-3,3-dimethyl-2,3-dihydro-1H-indol-1-yl)quinoline (prepared in accordance with the teaching of JP2014/221747).
CMP2 3-(3,3-dimethyl-2,3-dihydro-1H-indol-1-yl)-8-fluoroquinoline (prepared in accordance with the teaching of JP2014/221747).

Example A: In Vivo Preventive Test on *Botrytis cinerea* (Grey Mould)

| Solvent: | 5% | by volume of dimethyl sulfoxide |
| | 10% | by volume of acetone |
| Emulsifier: | 1 µL | of Tween ® 80 per mg of active ingredient |

The active ingredients were made soluble and homogenized in a mixture of dimethyl sulfoxide/acetone/Tween®80 and then diluted in water to the desired concentration.

The young plants of gherkin were treated by spraying the active ingredient prepared as described above. Control plants were treated only with an aqueous solution of acetone/dimethyl sulfoxide/Tween®80. After 24 hours, the plants were contaminated by spraying the leaves with an aqueous suspension of *Botrytis cinerea* spores. The contaminated gherkin plants were incubated for 4 to 5 days at 17° C. and at 90% relative humidity.

The test was evaluated 4 to 5 days after the inoculation. 0% means an efficacy which corresponds to that of the control plants while an efficacy of 100% means that no disease is observed.

In this test, the following compounds according to the invention showed efficacy between 70% and 79% at a concentration of 500 ppm of active ingredient: I.017; I.022; I.173; I.177; I.228; I.274; I.355.

In this test, the following compounds according to the invention showed efficacy between 80% and 89% at a concentration of 500 ppm of active ingredient: I.006; I.041; I.052; I.058; I.233; I.287; I.290; I.292.

In this test, the following compounds according to the invention showed efficacy between 90% and 100% at a concentration of 500 ppm of active ingredient: I.001; I.003; I.004; I.007; I.012; I.015; I.016; I.020; I.023; I.024; I.027; I.029; I.030; I.031; I.032; I.033; I.035; I.038; I.040; I.044; I.050; I.051; I.062; I.163; I.165; I.172; I.178; I.192; I.206; I.207; I.208; I.209; I.211; I.212; I.214; I.225; I.226; I.229; I.231; I.243; I.244; I.249; I.250; I.253; I.254; I.281; I.288; I.289; I.291; I.293.

In this test, compound I.015 showed efficacy of at least 90% when tested at a dose of 500 ppm whereas CMP1 (structurally close compound, not according to the invention) showed much lower efficacy at the same dose as shown in table A1.

TABLE A1

| Compound | dose (ppm) | Efficacy |
|---|---|---|
| I.015 | 500 | 100 |
| CMP1 | 500 | 50 |

Example B: In Vivo Preventive Test on *Venturia* (Apples)

| Solvent: | 24.5 | parts by weight of acetone |
| | 24.5 | parts by weight of dimethylacetamide |
| Emulsifier: | 1 | part by weight of alkylaryl polyglycol ether |

To produce a suitable preparation of active ingredient, 1 part by weight of active ingredient was mixed with the stated amounts of solvent and emulsifier, and the concentrate was diluted with water to the desired concentration.

To test for preventive activity, young plants were sprayed with the preparation of active ingredient at the stated rate of application. After the spray coating had dried on, the plants were inoculated with an aqueous conidia suspension of the causal agent of apple scab (*Venturia inaequalis*) and then remained for 1 day in an incubation cabinet at approximately 20° C. and a relative atmospheric humidity of 100%.

The plants were then placed in a greenhouse at approximately 21° C. and a relative atmospheric humidity of approximately 90%.

The test was evaluated 10 days after the inoculation. 0% means an efficacy which corresponds to that of the untreated control, while an efficacy of 100% means that no disease is observed.

In this test, the following compounds according to the invention showed efficacy between 90% and 100% at a concentration of 250 ppm of active ingredient: I.001; I.007; I.015; I.016; I.023; I.024; I.027; I.029; I.031; I.206; I.207; I.211; I.212.

In this test, compound I.015 showed efficacy of at least 90% when tested at a dose of 10 ppm whereas CMP1 and CMP2 (structurally close compounds, not according to the invention) showed much lower efficacy at a dose of 10 ppm as shown in table A2.

TABLE A2

| Compound | dose (ppm) | Efficacy |
|---|---|---|
| I.015 | 10 | 95 |
| CMP1 | 10 | 15 |
| CMP2 | 10 | 4 |

Example C: *Leptnosphaeria nodorum* In Vitro Cell Test

Solvent: dimethyl sulfoxide (DMSO)
Culture medium: 14.6 g anhydrous D-glucose (VWR), 7.1 g Mycological Peptone (Oxoid), 1.4 g granulated Yeast Extract (Merck), QSP 1 liter
Inoculum: spore suspension Active ingredients were solubilized in DMSO and the solution used to prepare the required range of concentrations. The final concentration of DMSO used in the assay was 1%.

A spore suspension of *L. nodorum* was prepared and diluted to the desired spore density.

Active ingredients were evaluated for their ability to inhibit spore germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the active ingredients with the absorbance in control wells without fungicides.

In this test, the following compounds according to the invention showed efficacy between 70% and 79% at a concentration of 20 ppm of active ingredient: I.156; I.190; I.191; I.196; I.198; I.200; I.206; I.261; I.272; I.273; I.276; I.310.

In this test, the following compounds according to the invention showed efficacy between 80% and 89% at a concentration of 20 ppm of active ingredient: I.005; I.022; I.036; I.040; I.077; I.078; I.091; I.114; I.177; I.179; I.188; I.213; I.216; I.220; I.232; I.233; I.249; I.268; I.275; I.280; I.284; I.287; I.290; I.294; I.295; I.296; I.306; I.309; I.352.

In this test, the following compounds according to the invention showed efficacy between 90% and 100% at a concentration of 20 ppm of active ingredient: I.001; I.002; I.003; I.004; I.006; I.007; I.008; I.009; I.010; I.012; I.013; I.015; I.016; I.017; I.018; I.020; I.023; I.024; I.027; I.028; I.029; I.030; I.031; I.032; I.033; I.035; I.037; I.038; I.041; I.043; I.044; I.050; I.051; I.052; I.053; I.054; I.055; I.056; I.058; I.060; I.061; I.062; I.063; I.064; I.066; I.067; I.068; I.069; I.075; I.079; I.080; I.087; I.088; I.089; I.090; I.094; I.096; I.097; I.099; I.100; I.101; I.102; I.103; I.104; I.105; I.106; I.107; I.108; I.109; I.110; I.111; I.112; I.113; I.115; I.116; I.117; I.119; I.120; I.121; I.162; I.163; I.165; I.172; I.173; I.174; I.175; I.176; I.178; I.182; I.189; I.192; I.207; I.209; I.211; I.212; I.214; I.219; I.225; I.226; I.227; I.228; I.229; I.230; I.250; I.252; I.253; I.254; I.260; I.262; I.267; I.270; I.274; I.281; I.283; I.285; I.286; I.288; I.289; I.291; I.292; I.293; I.298; I.301; I.311; I.358; I.359; I.360.

In this test, compound I.015 showed efficacy of at least 80% when tested at a dose of 20 ppm or 4 ppm whereas CMP1 (structurally close compound, not according to the invention) showed much lower efficacy at the same doses as shown in table A3.

TABLE A3

| Compound | dose (ppm) | Efficacy |
|---|---|---|
| I.015 | 20 | 99 |
|  | 4 | 93 |
| CMP1 | 20 | 5 |
|  | 4 | 0 |

Example D: *Pyricularia oryzae* In Vitro Cell Test

Solvent: dimethyl sulfoxide (DMSO)
Culture medium: 14.6 g anhydrous D-glucose (VWR), 7.1 g Mycological Peptone (Oxoid), 1.4 g granulated Yeast Extract (Merck), QSP 1 liter
Inoculum: spore suspension Active ingredients were solubilized in DMSO and the solution used to prepare the required range of concentrations. The final concentration of DMSO used in the assay was ≤1%.

A spore suspension of *P. oryzae* was prepared and diluted to the desired spore density.

Active ingredients were evaluated for their ability to inhibit spore germination and mycelium growth in liquid culture assay. The compounds were added in the desired concentration to the culture medium with spores. After 5 days incubation, fungi-toxicity of compounds was determined by spectrometric measurement of mycelium growth. Inhibition of fungal growth was determined by comparing the absorbance values in wells containing the active ingredients with the absorbance in control wells without fungicides.

In this test, the following compounds according to the invention showed efficacy between 70% and 79% at a concentration of 20 ppm of active ingredient: I.004; I.009; I.011; I.051; I.052; I.056; I.068; I.167; I.176; I.187; I.231; I.241; I.270; I.353; I.357.

In this test, the following compounds according to the invention showed efficacy between 80% and 89% at a concentration of 20 ppm of active ingredient: I.001; I.006; I.008; I.010; I.013; I.025; I.041; I.047; I.062; I.063; I.066; I.067; I.163; I.171; I.174; I.175; I.189; I.191; I.198; I.206; I.212; I.213; I.214; I.227; I.229; I.233; I.240; I.246; I.250; I.261; I.263; I.271; I.278; I.281; I.282; I.294; I.298; I.304; I.306; I.307; I.309; I.354; I.355. In this test, the following compounds according to the invention showed efficacy between 90% and 100% at a concentration of 20 ppm of active ingredient: I.007; I.012; I.015; I.016; I.017; I.020; I.022; I.023; I.024; I.027; I.029; I.030; I.031; I.032; I.033; I.035; I.036; I.037; I.038; I.043; I.044; I.045; I.046; I.050; I.053; I.054; I.055; I.058; I.061; I.069; I.156; I.157; I.162; I.165; I.166; I.172; I.173; I.177; I.178; I.192; I.196; I.197; I.207; I.209; I.211; I.216; I.219; I.220; I.225; I.226; I.228; I.243; I.244; I.249; I.252; I.253; I.254; I.260; I.264; I.267; I.268; I.272; I.274; I.275; I.276; I.279; I.280; I.283; I.284;

I.285; I.286; I.287; I.288; I.289; I.290; I.291; I.292; I.293; I.295; I.296; I.301; I.358; I.359.

In this test, compound I.015 showed efficacy of at least 90% when tested at a dose of 20 ppm whereas CMP1 (structurally close compound, not according to the invention) showed much lower efficacy at the same doses as shown in table A4.

TABLE A4

| Compound | dose (ppm) | Efficacy |
| --- | --- | --- |
| I.015 | 20 | 100 |
| CMP1 | 20 | 7 |

Example E: *Colletotrichum lindemuthianum* In Vitro Cell Test

Solvent: dimethyl sulfoxide (DMSO)
Culture medium: 14.6 g anhydrous D-glucose (VWR), 7.1 g Mycological Peptone (Oxoid), 1.4 g granulated Yeast Extract (Merck), QSP 1 liter
Inoculum: spore suspension Active ingredients were solubilized in DMSO and the solution used to prepare the required range of concentrations. The final concentration of DMSO used in the assay was ≤1%.

A spore suspension of *C. lindemuthianum* was prepared and diluted to the desired spore density.

Active ingredients were evaluated for their ability to inhibit spore germination and mycelium growth in liquid culture assay. The compounds were added in the desired concentration to the culture medium with spores. After 6 days incubation, fungi-toxicity of compounds was determined by spectrometric measurement of mycelium growth. Inhibition of fungal growth was determined by comparing the absorbance values in wells containing the active ingredients with the absorbance in control wells without fungicides.

In this test, the following compounds according to the invention showed efficacy between 70% and 79% at a concentration of 20 ppm of active ingredient: I.052; I.066; I.069; I.070; I.100; I.104; I.160; I.166; I.185; I.187; I.195; I.205; I.240; I.253; I.269; I.270; I.288; I.294; I.296; I.299.

In this test, the following compounds according to the invention showed efficacy between 80% and 89% at a concentration of 20 ppm of active ingredient: I.025; I.029; I.030; I.033; I.036; I.040; I.041; I.042; I.044; I.045; I.053; I.060; I.073; I.079; I.083; I.084; I.085; I.086; I.095; I.097; I.099; I.101; I.102; I.106; I.108; I.112; I.115; I.157; I.163; I.167; I.189; I.191; I.192; I.194; I.203; I.207; I.208; I.233; I.243; I.244; I.249; I.250; I.254; I.260; I.263; I.264; I.267; I.268; I.272; I.275; I.276; I.279; I.280; I.286; I.290; I.301; I.308; I.311; I.360.

In this test, the following compounds according to the invention showed efficacy between 90% and 100% at a concentration of 20 ppm of active ingredient: I.015; I.031; I.035; I.037; I.038; I.043; I.046; I.050; I.054; I.055; I.056; I.058; I.062; I.064; I.068; I.074; I.075; I.077; I.080; I.087; I.088; I.089; I.090; I.091; I.094; I.096; I.103; I.105; I.107; I.109; I.110; I.111; I.113; I.114; I.116; I.117; I.119; I.121; I.162; I.165; I.172; I.196; I.197; I.198; I.199; I.204; I.230; I.232; I.239; I.274; I.283; I.285; I.287; I.289; I.291; I.292; I.293; I.295; I.297; I.298; I.306; I.309; I.358; I.359.

Example F: In Vivo Preventive Test on *Botrytis* Test (Beans)

| | | |
| --- | --- | --- |
| Solvent: | 24.5 | parts by weight of acetone |
| | 24.5 | parts by weight of dimethylacetamide |
| Emulsifier: | 1 | part by weight of alkylaryl polyglycol ether |

To produce a suitable preparation of active compound, 1 part by weight of active compound was mixed with the stated amounts of solvent and emulsifier, and the concentrate was diluted with water to the desired concentration.

To test for preventive activity, young plants were sprayed with the preparation of active compound. After the spray coating had dried on, 2 small pieces of agar covered with growth of *Botrytis cinerea* were placed on each leaf. The inoculated plants were placed in a darkened chamber at 20° C. and a relative atmospheric humidity of 100%.

2 days after the inoculation, the size of the lesions on the leaves was evaluated. 0% means an efficacy which corresponds to that of the untreated control, while an efficacy of 100% means that no disease is observed.

In this test, compound I.015 showed efficacy of at least 90% when tested at a dose of 10 ppm whereas CMP1 and CMP2 (structurally close compounds, not according to the invention) showed much lower efficacy at a dose of 10 ppm as shown in table A5.

TABLE A5

| Compound | dose (ppm) | Efficacy |
| --- | --- | --- |
| I.015 | 10 | 100 |
| CMP1 | 10 | 0 |
| CMP2 | 10 | 0 |

The invention claimed is:
1. A compound selected from the group consisting of: compounds of formula (IIa) and/or salts thereof:

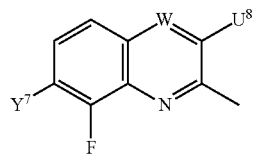

(IIa)

wherein:
W is CH or N;
$Y^7$ is a hydrogen atom or a fluorine atom; and
$U^8$ is a fluorine atom, a bromine atom, a chlorine atom, an iodine atom, a hydroxyl group, an amino group, a mesyl group, a tosyl group or a triflyl group, wherein the compound of formula (IIa) does not represent:
3-bromo-8-fluoro-2-methylquinoline [1259519-95-3],
8-fluoro-2-methylquinolin-3-ol [1314012-55-9],
8-fluoro-2-methylquinolin-3-amine [1259519-93-1],
7,8-difluoro-2-methylquinolin-3-ol [1314012-50-4],
5-fluoro-3-methylquinoxalin-2(1H)-one [1426822-07-2],
2-chloro-5-fluoro-3-methylquinoxaline [1426822-08-3], and/or
2-chloro-5,6-difluoro-3-methylquinoxaline [1415018-73-3], and compounds of formula (IIb) and/or salts thereof:

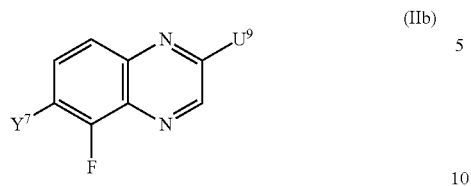

(IIb)

wherein:
Y$^7$ is a hydrogen atom or a fluorine atom; and
U$^9$ is a fluorine atom, a bromine atom, a chlorine atom, an iodine atom, a hydroxyl group, an amino group, a mesyl group, a tosyl group or a triflyl group, wherein the compound of formula (IIb) does not represent:
   5-fluoroquinoxalin-2(1H)-one [55687-16-6],
   5-fluoroquinoxalin-2-amine [1895170-02-1],
   2-chloro-5-fluoroquinoxaline [55687-09-7],
   5,6-difluoroquinoxalin-2(1H)-one [917343-50-1], and/or
   2-chloro-5,6-difluoroquinoxaline [1384067-26-8].

\* \* \* \* \*